United States Patent
Wipf et al.

(10) Patent No.: US 11,766,433 B2
(45) Date of Patent: *Sep. 26, 2023

(54) SMALL MOLECULE INHIBITORS OF THE NUCLEAR TRANSLOCATION OF ANDROGEN RECEPTOR FOR THE TREATMENT OF CASTRATION-RESISTANT PROSTATE CANCER

(71) Applicant: University of Pittsburgh - Of the Commonwealth System of Higher Education, Pittsburgh, PA (US)

(72) Inventors: Peter Wipf, Pittsburgh, PA (US); James K. Johnson, Silver Spring, MD (US); Erin M. Skoda, Silver Spring, MD (US); Joel B. Nelson, Pittsburgh, PA (US); Zhou Wang, Pittsburgh, PA (US); Serene Tai, Pittsburgh, PA (US); Keita Takubo, Pittsburgh, PA (US); John Milligan, Philadelphia, PA (US)

(73) Assignee: University of Pittsburgh - Of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/089,519

(22) Filed: Nov. 4, 2020

(65) Prior Publication Data
US 2021/0186963 A1     Jun. 24, 2021

Related U.S. Application Data

(63) Continuation of application No. 16/139,950, filed on Sep. 24, 2018, now Pat. No. 10,980,806, which is a continuation-in-part of application No. PCT/US2017/024105, filed on Mar. 24, 2017, which
(Continued)

(51) Int. Cl.
| | |
|---|---|
| A61K 31/495 | (2006.01) |
| A61K 31/504 | (2006.01) |
| A61K 31/4985 | (2006.01) |
| A61K 31/497 | (2006.01) |
| A61K 31/4439 | (2006.01) |
| A61K 31/401 | (2006.01) |
| A61K 31/407 | (2006.01) |
| A61K 31/122 | (2006.01) |
| A61K 31/47 | (2006.01) |
| A61K 9/00 | (2006.01) |
| A61P 35/00 | (2006.01) |
| A61K 31/167 | (2006.01) |

(Continued)

(52) U.S. Cl.
CPC .......... *A61K 31/504* (2013.01); *A61K 9/0053* (2013.01); *A61K 31/122* (2013.01); *A61K 31/167* (2013.01); *A61K 31/401* (2013.01); *A61K 31/407* (2013.01); *A61K 31/4439* (2013.01); *A61K 31/47* (2013.01); *A61K 31/497* (2013.01); *A61K 31/4985* (2013.01); *A61P 35/00* (2018.01); *A61K 31/4166* (2013.01); *A61K 31/58* (2013.01); *A61K 2300/00* (2013.01)

(58) Field of Classification Search
CPC .................................................. A61K 31/495
See application file for complete search history.

(56) References Cited

U.S. PATENT DOCUMENTS

| | | | |
|---|---|---|---|
| 4,186,205 | A | 1/1980 | Bender |
| 5,292,758 | A | 3/1994 | Yoshino et al. |
| 5,317,019 | A | 5/1994 | Bender et al. |

(Continued)

FOREIGN PATENT DOCUMENTS

| | | |
|---|---|---|
| EP | 1 340 749 | 9/2003 |
| EP | 1 437 349 | 7/2004 |

(Continued)

OTHER PUBLICATIONS

Dahl, Kenneth, et al. "Palladium-Mediated [11C]Carbonylation at Atmospheric Pressure: A General Method Using Xantphos as Supporting Ligand." European Journal of Organic Chemistry. (2013), pp. 1228-1231. (Year: 2013).*

(Continued)

*Primary Examiner* — John S Kenyon
(74) *Attorney, Agent, or Firm* — Klarquist Sparkman, LLP

(57) ABSTRACT

A compound, or a pharmaceutically acceptable salt or ester thereof, according to formula I:

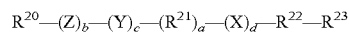

wherein $R^{20}$ is aryl, substituted aryl, heteroaryl, substituted heteroaryl, cycloalkyl, substituted cycloalkyl, heterocycloalkyl, substituted heterocycloalkyl, alkoxy, aryloxy, a thio-containing group, or a seleno-containing group; Z is alkanediyl, substituted alkanediyl, cycloalkanediyl, or substituted cycloalkanediyl; Y is S, O, S(=O), —S(=O)(=O)—, or $NR^{10}$, wherein $R^{10}$ is H or alkyl; $R^{21}$ is alkanediyl, substituted alkanediyl, cycloalkanediyl, substituted cycloalkanediyl, alkadienyl, substituted alkadienyl, cycloalkenediyl, substituted cycloalkenediyl, alkatrienyl, substituted alkatrienyl; X is —C(=O)—, —S(=O)(=O)—, or —N(H)C(=O)—; $R^{22}$ includes at least one divalent amino radical; $R^{23}$ is aryl, substituted aryl, heteroaryl, substituted heteroaryl, cycloalkyl, substituted cycloalkyl, heterocycloalkyl, substituted heterocycloalkyl, alkoxy, aryloxy, a thio-containing group, or a seleno-containing group; a, b, c, and d independently are 0 or 1.

16 Claims, 49 Drawing Sheets

Related U.S. Application Data is a continuation-in-part of application No. 15/080,237, filed on Mar. 24, 2016, now abandoned.

(60) Provisional application No. 62/671,254, filed on May 14, 2018.

(51) Int. Cl.
    *A61K 31/4166*     (2006.01)
    *A61K 31/58*     (2006.01)

(56) References Cited

U.S. PATENT DOCUMENTS

| | | | |
|---|---|---|---|
| 5,929,097 | A | 7/1999 | Levin et al. |
| 6,586,617 | B1 | 7/2003 | Tabuchi et al. |
| 6,680,342 | B2 | 1/2004 | Young et al. |
| 10,544,110 | B2 * | 1/2020 | Wipf ............. A61K 31/58 |
| 10,882,834 | B2 * | 1/2021 | Wipf ............. C07D 295/26 |
| 10,980,806 | B2 * | 4/2021 | Wipf ............. A61P 35/00 |
| 2002/0022630 | A1 | 2/2002 | Zhang et al. |
| 2004/0092529 | A1 | 5/2004 | Blumberg et al. |
| 2007/0142394 | A1 | 6/2007 | Solomon et al. |
| 2009/0163545 | A1 | 6/2009 | Goldfarb |
| 2010/0094006 | A1 | 4/2010 | Nam et al. |
| 2011/0003839 | A1 | 1/2011 | Jung et al. |
| 2012/0264744 | A1 | 10/2012 | Dasgupta et al. |
| 2013/0211075 | A1 | 8/2013 | Ushio et al. |
| 2014/0371235 | A1 | 12/2014 | Wang et al. |
| 2017/0246164 | A1 | 8/2017 | Wang et al. |
| 2018/0237403 | A1 | 8/2018 | Wipf et al. |
| 2019/0022093 | A1 | 1/2019 | Wipf et al. |
| 2021/0061779 | A1 * | 3/2021 | Wipf ............. C07D 413/12 |

FOREIGN PATENT DOCUMENTS

| | | | |
|---|---|---|---|
| EP | 1 992 618 | A1 | 11/2008 |
| JP | 2001 261657 | | 9/2001 |
| WO | WO 99/02502 | | 1/1999 |
| WO | WO 00/40572 | A1 | 7/2000 |
| WO | WO 00/54759 | | 9/2000 |
| WO | WO 2001/029038 | | 4/2001 |
| WO | WO 02/30879 | | 4/2002 |
| WO | WO 2004/014300 | | 2/2004 |
| WO | WO 2004/073634 | | 9/2004 |
| WO | WO 2005/040114 | | 5/2005 |
| WO | WO 2005/079270 | | 9/2005 |
| WO | WO 2005/121130 | | 12/2005 |
| WO | WO 2006/030977 | | 3/2006 |
| WO | WO 2006/044504 | | 4/2006 |
| WO | WO 2007/001701 | | 1/2007 |
| WO | WO 2007/061360 | | 5/2007 |
| WO | WO 2007/071440 | | 6/2007 |
| WO | WO 2007/071443 | | 6/2007 |
| WO | WO 2007/076055 | | 7/2007 |
| WO | WO 2008/011130 | | 1/2008 |
| WO | WO 2008/027584 | | 3/2008 |
| WO | WO 2008/060998 | | 5/2008 |
| WO | WO 2008/114022 | | 9/2008 |
| WO | WO-2009024823 | A2 * | 2/2009 ........... A61K 31/495 |
| WO | WO 2009/092585 | | 7/2009 |
| WO | WO 2009/125923 | | 10/2009 |
| WO | WO 2011/032169 | | 3/2011 |
| WO | WO 2011/050353 | | 4/2011 |
| WO | WO 2013/055793 | | 4/2013 |
| WO | WO 2013/117963 | | 8/2013 |
| WO | WO 2015/042297 | | 3/2015 |

OTHER PUBLICATIONS

Vachal, Petr, et al. "1-Sulfonyl-4-acylpiperazines as Selective Cannabinoid-1 Receptor (CB1R) Inverse Agonists for the Treatment of Obesity." J. Med. Chem. (2009), vol. 52, pp. 2550-2558. (Year: 2009).*

Ai et al., "HDAC6 Regulates Androgen Receptor Hypersensitivity and Nuclear Localization via Modulating Hsp90 Acetylation in Castration-resistant Prostate Cancer," *Mol. Endocrinol.*, 23(12): 1963-1972, 2009.

Bravo-Altamirano et al. "Synthesis and Structure—Activity Relationships of Benzothienothiazepinone Inhibitors of Protein Kinase D," *ACS Med. Chem. Lett.*. vol. 2, pp. 154-159, 2011.

CAS RN 312929-26-3, STN Entry Date: Jan. 5, 2001.
CAS RN 321981-09-3, STN Entry Date: Feb. 19, 2001.
CAS RN 326014-86-2, STN Entry Date: Mar. 7, 2001.
CAS RN 344565-06-6, STN Entry Date: Jul. 5, 2001.
CAS RN 345293-88-1, STN Entry Date: Jul. 11, 2001.
CAS RN 475196-08-8, STN Entry Date: Dec. 5, 2002.
CAS RN 790203-53-1, STN Entry Date: Nov. 29, 2004.
CAS RN 893704-98-8, STN Entry Date: Jul. 17, 2006.
CAS RN 1172844-15-3, STN Entry Date: Aug. 5, 2009.
CAS RN 1179384-26-9, STN Entry Date: Sep. 2, 2009.
CAS RN 1179381-92-0, STN Entry Date: Sep. 2, 2009.
CAS RN 1179402-21-1, STN Entry Date: Sep. 2, 2009.
CAS RN 1624152-83-5, STN Entry Date: Sep. 22, 2014.
CAS RN 1624387-89-8, STN Entry Date: Sep. 23, 2014.
CAS RN 1646734-73-7, STN Entry Date: Feb. 12, 2015.
CAS RN 1647452-68-3, STN Entry Date: Feb. 15, 2015.
CAS RN 2180239-98-7, STN Entry Date: Mar. 1, 2018.

Clausen et al. "In Vitro Cytoxicity and In Vivo Efficacy, Pharmacokinetics, and Metabolism of 10074-G5, a Novel Small-MoleculeInhibitor of c-Myc/Max Dimerization," *The Journal of Pharmacology and Experimental Therapeutics*, vol. 335, No. 3, pp. 715-727, 2010.

Claxton et al., "Cyclization of Lactamimide Ketones to Imidazo[1,2-a]-azacycloalkanes with Hypoglycemic Activity," *Journal of Medicinal Chemistry*, vol. 17, No. 3, pp. 364-367, 1974.

Demchenko et al., "Synthesis and Antifungal Activity of 3-aryl-6,7-dihydro-5H-pyrrolo[1,2-a imidazoles," translated from *Khimiko-Farmatsevticheskii Zhurnal*, vol. 21, No. 22, pp. 1335-1338, 1978.

Extended European Search Report issued by the European Patent Office for EPC Application No. 14846330 dated Jun. 14, 2017.

Extended European Search Report and Written Opinion, dated Mar. 18, 2020, issued in related Application No. EP 17771272.6.

[(1R,2S)-2-(4-Fluorophenyl)cyclopropyl]-(4-pyrimidin-2-ylpiperazin-1-yl)methanone, CID 33811901, PubChem Compound Database, May 29, 2009.

[(1S,2R)-2-(4-Fluorophenyl)cyclopropyl]-(4-pyrimidin-2-ylpiperazin-1-yl)methanone, CID33811888, PubChem Compound Database, May 29, 2009.

Frantz et al. "Large-Scale asymmetric Synthesis of Bioprotective Agent JP4-039 and Analogs," *Organic Letters*, 2011.

Frutos et al. "Expedient synthesis of substituted imidazoles from nitriles," *Tetrahedrom Letters*, vol. 46, pp. 8369-8372, 2005.

Graczyk et al., "The neuroprotective action of JNK3 inhibitors based on the 6,7-dihydro-5H-pyrrolo[1,2-a]imidazole scaffold," *Bioorganic & Medical Chemistry Letters*, vol. 15, pp. 4666-4670, 2005.

International Search Report and Written Opinion issued in International Application No. PCT/US2012/059558, dated Jan. 18, 2013, 20 pages.

International Search Report and Written Opinion issued in International Application No. PCT/US2014/056369 dated Jan. 14, 2015, 12 pages.

International Search Report and Written Opinion for corresponding International Application No. PCT/US2017/024105, dated Jun. 29, 2017.

International Search Report and Written Opinion, dated Jul. 8, 2019, issued in related Application No. PCT/US2019/032033.

Johnson et al., "Small Molecule Antagonists of the Nuclear Androgen Receptor for the Treatment of Castration-Resistant Prostate Cancer," *ACS Medicinal Chemistry Letters*, vol. 7. No. 8, May 27, 2016, pp. 785-790.

Kovtunenko et al., "Derivatives of 1,2-tetramethyleneimidazole," *Ukrainskii Khimicheskii Zhurna* (Russian Edition), vol. 62(3-4), pp. 111-117, 1996 (translated abstract only).

Kovtunenko et al., "Derivatives of 2a,4a-diazacyclopent[c,d]azulene," *Khimiya Geterotsiklicheskikh Soedinenii*, vol. 8, pp. 1072-1077, 1996 (translated abstract only).

(56) References Cited

OTHER PUBLICATIONS

Liu et al., "A general and convenient synthesis of N-aryl piperazines," *Tetrahedron Letters*, vol. 46, pp. 7921-7922, 2005.
Non-Final Office Action issued for U.S. Appl. No. 15/023,349 dated Feb. 27, 2017.
Office Action (Notice of Reasons for Refusal), dated May 15, 2020, issued in corresponding JP Application No. 2018-549435.
O'Shaughnessy et al, "Synthesis of Pyrrolo- and Pyrido-[1,2-a]benzimidazolequinone Anti-tumor Agents Containing a Fused Cyclopropane Ring," *Synthesis*, vol. 7, pp. 1069-1076, 2005.
Paone et al., "Orally Bioavailable Imidazoazepanes as Calcitonin Gene-Related Peptide (CGRP) Receptor Antagonists: Discovery of MK-2918," *Bioorganic and Medicinal Chemistry Letters*, vol. 21, pp. 2683-2686, 2011.
PubChem CID 55564470, create date Jan. 25, 2012, also published as CAS RN 1293729-94-8, STN Entry Date: May 12, 2011.
PubChem CID 55492389, create date Jan. 25, 2012, also published as CAS RN 1316002-05-07, STN Entry Date: Aug. 11, 2011.
PubChem CID 86903336, create date Feb. 7, 2015, also published as CAS RN 1623249-86-4, STN Entry Date: Sep. 19, 2014.
PubChem entry for SCHEMBL 18061526—alleged "create date" of May 29, 2009.
PubChem entry for ST50917073 entered Sep. 13, 2005.
PubChem entry for ACILTCGH entered Jul. 11, 2005.
PubChem entry for CID24884553 entered Sep. 8, 2008.
PubChem database entry for SCH EM BL 18061517 created May 29, 2009.
Ren et al., "Pharmacophore Modeling and Virtual Screening for the Discovery of New Transforming Growth Factor-Beta Type I Receptor (ALK5) Inhibitors," *European Journal of Medicinal Chemistry*, 2009, vol. 44, pp. 4259-4265.
Saporita et al, "The Hsp90 Inhibitor, 17-AAG, Prevents the Ligand-Independent Nuclear Localization of Androgen Receptor in Refractory Prostate Cancer Cells," *The Prostate*, 67:509-520, 2007.
Sasaki et al., "Ring Transformation of Oxazoles to Fused Imidazoles. New Synthetic Route for 6-methyl-2,3-diphenyl-7,8-dihydroimidazo[1m2-b]pyridazine and 5-methyl-2,3-diphenyl-6,7-dihydro-5H-pyrrolo[1,2-a]imidazole, and their perhydrobenzo analogs," *Journal of Chemical Society, Perkins Transactions 1: Organic and Bio-Organic Chemistry*, 1983, vol. 12, pp. 3027-3030.

Valade et al., "Discovery of novel selective Sigma-1 ligands as cognitive enhancers," *MedChemComm*, 2(7): 655-660, Jun. 10, 2011.
Whitlock et al., "Potent and selective $\alpha_{1A}$ adrenoceptor partial agonists—Novel imidazole frameworks," *Bioorganic & Medicinal Chemistry Letters*, 19: 3118-3121, 2009.
Yamaguchi et al., "Construction of a cis-Cyclopropane via Reductive Radical Decarboxylation. Enantioselective Synthesis of cis- and trans-1-Arylpiperazyl-2-phenylcyclopropanes Designed as Antidopaminergic Agents," *J. Org. Chem.*, vol. 68, pp. 9255-9262, 2003.
ZINC17074676 added Sep. 13, 2008.
ZINC2562103 added Oct. 27, 2004.
ZINC25951622 added Feb. 2, 2009.
ZINC25951626 added Feb. 2, 2009.
ZINC25951633 added Feb. 2, 2009.
ZINC25958726 added Feb. 2, 2009.
ZINC25958734 added Feb. 2, 2009.
ZINC303410047 added Mar. 11, 2016.
ZINC303692363 added Mar. 11, 2016.
ZINC303878919 added Mar. 11, 2016.
ZINC30778696 added Apr. 2, 2009.
ZINC30778703 added Apr. 2, 2009.
ZINC3135710 added Nov. 6, 2004.
ZINC38946613 added Feb. 1, 2010.
ZINC38946614 added Feb. 1, 2010.
ZINC38946616 added Feb. 1, 2010.
ZINC39755011 added Mar. 7, 2010.
ZINC54116237 added Nov. 30, 2010.
ZINC54116241 added Nov. 30, 2010.
ZINC58469525 added Feb. 7, 2011.
ZINC72011928 added Feb. 23, 2012.
ZINC92210938 added Jun. 14, 2013.
ZINC92210944 added Jun. 14, 2013.
CAS RN 1623461-69-7, STN Entry Date: Sep. 18, 2014.
CAS RN 1793934-53-8, STN Entry Date: Jul. 5, 2015.
Examiner's Report, dated Apr. 11, 2023, issued in corresponding EPC Application No. 17771272.6, 10 pages.
PubChem entry for CID36925618, created May 29, 2009, 11 pages.

* cited by examiner

| Compound Name | Short # | Structure | MW (exact) | Formula |
|---|---|---|---|---|
| PW9-09 | 909 | 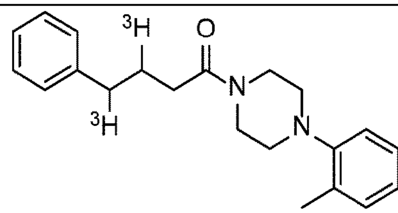 | 236.22 | $C_{21}H_{24}T_2N_2O$ |
| MK504-92 | 492 | 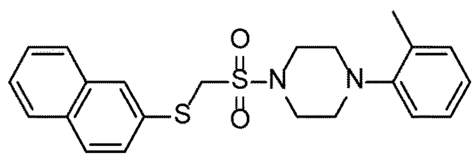 | 412.13 | $C_{22}H_{24}N_2O_2S_2$ |
| MK504-91 | 491 | 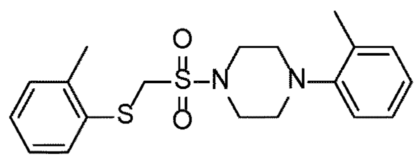 | 376.13 | $C_{19}H_{24}N_2O_2S_2$ |
| MK504-90 | 490 | 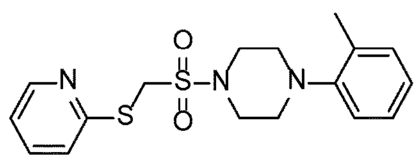 | 363.11 | $C_{17}H_{21}N_3O_2S_2$ |
| EMS386-73 | 673 | 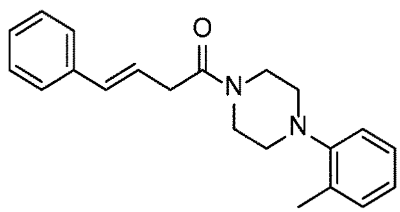 | 320.43 | $C_{21}H_{24}N_2O$ |
| MK504-63 | 463 | 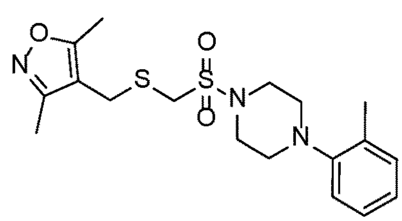 | 395.13 | $C_{18}H_{25}N_3O_3S_2$ |
| MK504-37 | 437 | 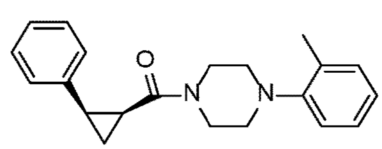 | 320.19 | $C_{21}H_{24}N_2O$ |

| Compound Name | Short # | Structure | MW (exact) | Formula |
|---|---|---|---|---|
| EMS386-23 | 623 | 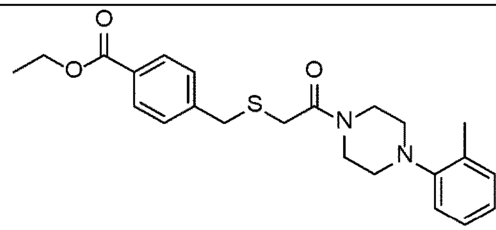 | 412.18 | $C_{23}H_{28}N_2O_3S$ |
| EMS386-15 | 615 | 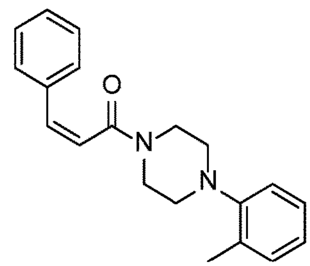 | 306.17 | $C_{20}H_{22}N_2O$ |
| EMS386-08 | 608 | 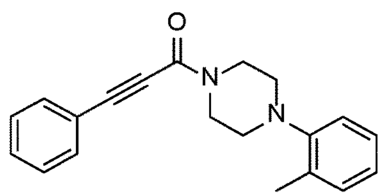 | 308.16 | $C_{20}H_{20}N_2O$ |
| EMS386-07 | 607 | 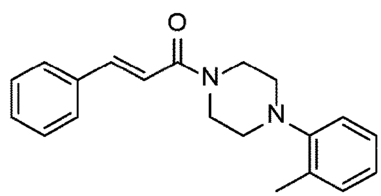 | 306.17 | $C_{20}H_{22}N_2O$ |
| BRE490-17 | 17 | 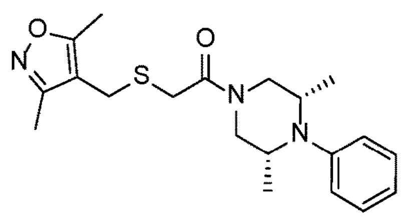 | 373.18 | $C_{20}H_{27}N_3O_2S$ |
| BRE490-18 | 18 | 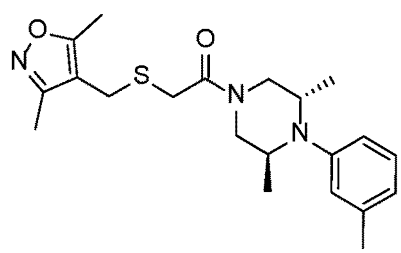 | 387.2 | $C_{21}H_{29}N_3O_2S$ |

FIG. 1C

| Compound Name | Short # | Structure | MW (exact) | Formula |
|---|---|---|---|---|
| BRE490-22 | 22 | 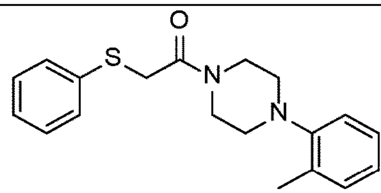 | 326.15 | $C_{19}H_{22}N_2OS$ |
| BRE454-84 | 484 | 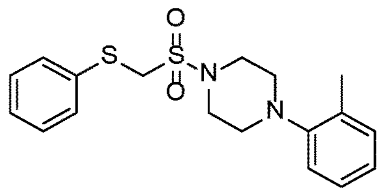 | 362.11 | $C_{18}H_{22}N_2O_2S_2$ |
| MK415-59 | 559 | 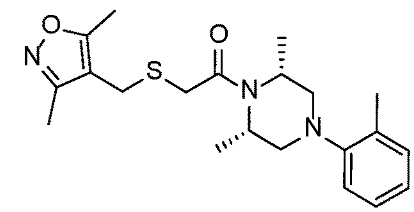 | 387.54 | $C_{21}H_{29}N_3O_2S$ |
| MK415-62 | 562 | 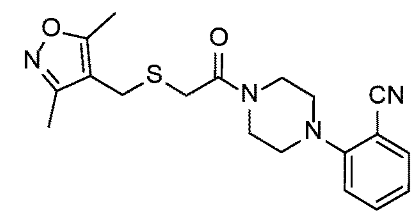 | 370.47 | $C_{19}H_{22}N_4O_2S$ |
| MK415-63 | 563 | 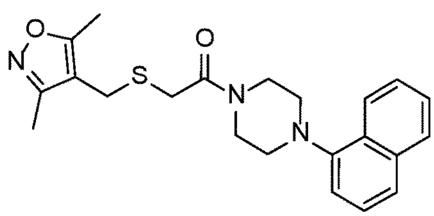 | 395.52 | $C_{22}H_{25}N_3O_2S$ |
| MK415-48 | 548 | 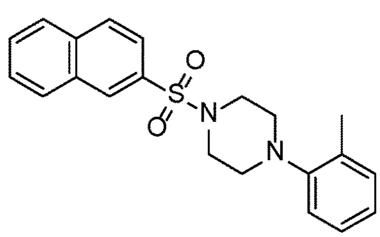 | 366.48 | $C_{21}H_{22}N_2O_2S$ |

FIG. 1D

| Compound Name | Short # | Structure | MW (exact) | Formula |
|---|---|---|---|---|
| MK415-53 | 553 | 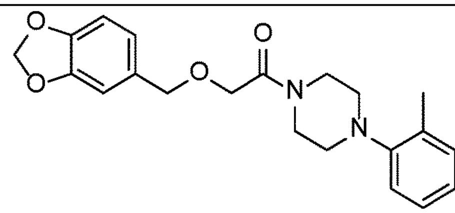 | 368.43 | $C_{21}H_{24}N_2O_4$ |
| MK415-47 | 547 | 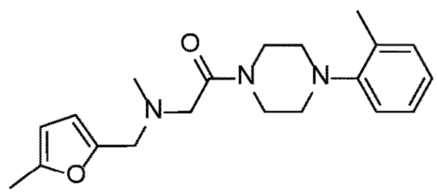 | 341.45 | $C_{20}H_{27}N_3O_2$ |
| BRE454-62 | 462 | 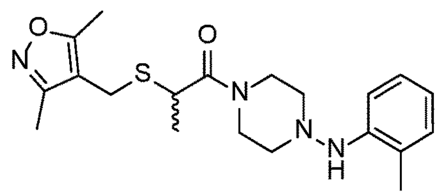 | 387.54 | $C_{21}H_{29}N_3O_2S$ |
| BRE454-75 | 475 | 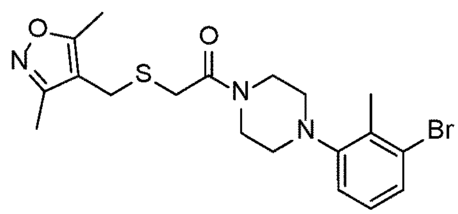 | 438.38 | $C_{19}H_{24}BrN_3O_2$ |
| BRE454-76 | 476 | 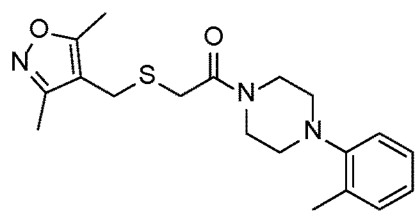 | 373.41 | $C_{20}H_{27}N_3O_2S$ |
| BRE454-71 | 471 | 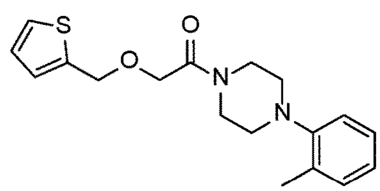 | 330.14 | $C_{18}H_{22}N_2O_2S$ |
| BRE454-78 | 478 | 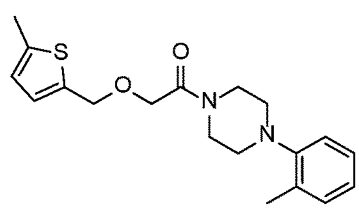 | 344.16 | $C_{19}H_{24}N_2O_2S$ |

FIG. 1E

| Compound Name | Short # | Structure | MW (exact) | Formula |
|---|---|---|---|---|
| BRE454-58 | 458 | 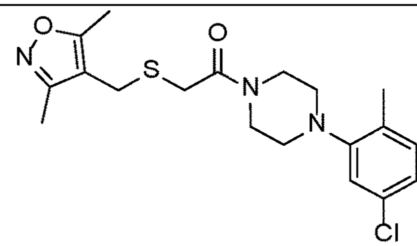 | 393.93 | $C_{19}H_{24}ClN_3O_2S$ |
| BRE454-56 | 456 | 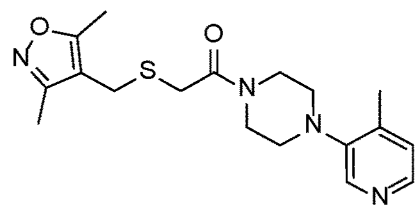 | 360.47 | $C_{18}H_{24}N_4O_2S$ |
| BRE454-46 | 446 | 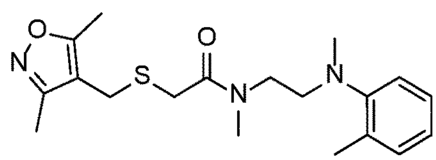 | 361.5 | $C_{19}H_{27}N_3O_2S$ |
| MK415-43-2 | 543 | 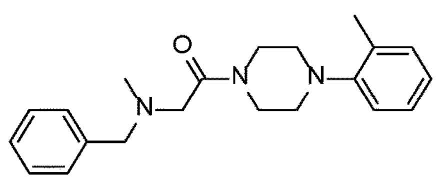 | 337.46 | $C_{21}H_{27}N_3O$ |
| BRE454-43 | 443 | 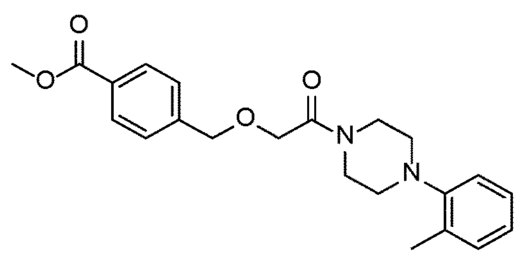 | 382.45 | $C_{22}H_{26}N_2O_4$ |
| BRE454-54 | 454 | 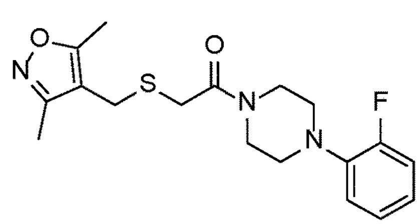 | 363.45 | $C_{18}H_{22}FN_3O_2S$ |

| Compound Name | Short # | Structure | MW (exact) | Formula |
|---|---|---|---|---|
| BRE454-47 | 447 | 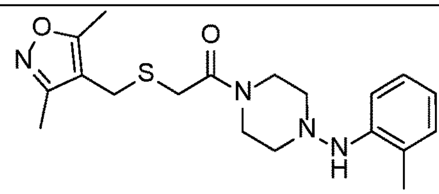 | 373.51 | $C_{20}H_{27}N_3O_2S$ |
|  | 5i |  | 362.19 | $C_{19}H_{28}N_3O_2S$ |
|  | 6 |  | 346.19 | $C_{19}H_{28}ON_3S$ |
|  | 7 |  | 341.17 | $C_{20}H_{25}N_2OS$ |
|  | 12 |  | 376.17 | $C_{19}H_{26}N_3O_3S$ |
|  | 13 |  | 392.16 | $C_{19}H_{26}N_3O_4S$ |
|  | 16 |  | 321.20 | $C_{21}H_{25}ON_2$ |

FIG. 1G

| Compound Name | Short # | Structure | MW (exact) | Formula |
|---|---|---|---|---|
| | 18a | | 344.20 | $C_{19}H_{26}N_3O_3$ |
| | 20a | | 375.18 | $C_{19}H_{27}N_4O_2S$ |
| | 20b | | 390.18 | $C_{20}H_{28}N_3O_3S$ |
| | 26a | | 385.19 | $C_{22}H_{29}O_2N_2S$ |
| | 26b | | 385.19 | $C_{22}H_{29}O_2N_2S$ |

| Compound Name | Short # | Structure | MW (exact) | Formula |
|---|---|---|---|---|
| JJ-450 | | 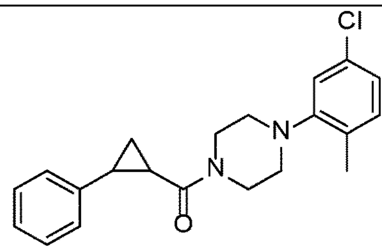 | 373.15 | $C_{21}H_{23}ClFON_2$ |
| JJ-450A | | 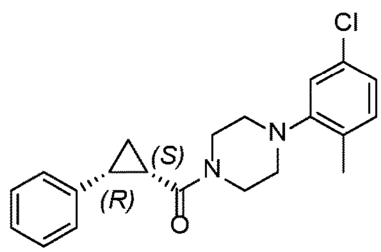 | 373.15 | $C_{21}H_{23}ClFON_2$ |
| JJ-450B | | 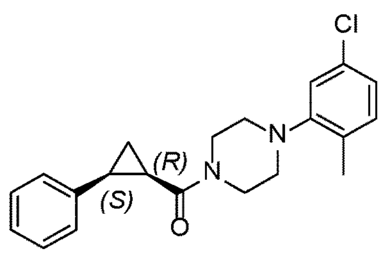 | 373.15 | $C_{21}H_{23}ClFON_2$ |

(+)-JJ-74-134

(±)-ST-73-933

(−)-ST-73-933

(+)-ST-73-933

(±)-KT-73-454

(−)-KT-73-454

(+)-KT-73-454

(±)-KT-73-411

JM-75-845

(±)-ST-73-972

(±)-JJ-74-184

(±)-JJ-74-185

(±)-KT-76-614

(±)-JJ-75-935

KT-75-049

(±)-ST-73-934

(±)-JJ-72-188

(±)-JJ-72-196

(±)-JJ-74-147

(±)-JJ-74-136

(±)-JJ-74-137

Scheme 1

Scheme 2

Scheme 3

Scheme 4

571 + 0.1 nM R1881

SMALL MOLECULE INHIBITORS OF THE NUCLEAR TRANSLOCATION OF ANDROGEN RECEPTOR FOR THE TREATMENT OF CASTRATION-RESISTANT PROSTATE CANCER

CROSS REFERENCE TO RELATED APPLICATIONS

This application is a continuation of application Ser. No. 16/139,950, filed Sep. 24, 2018, issued as U.S. Pat. No. 10,980,806, which is a continuation-in-part of PCT Application No. PCT/US2017/024105, filed Mar. 24, 2017, which is a continuation-in-part of U.S. application Ser. No. 15/080,237, filed Mar. 24, 2016, now abandoned, and this application further claims the benefit of the earlier filing date of U.S. Provisional Application No. 62/671,254, filed May 14, 2018, each of which is incorporated in its entirety herein by reference.

ACKNOWLEDGMENT OF GOVERNMENT SUPPORT

This invention was made with government support under grant #s GM067082, CA186780, CA180995, CA047904, and CA211242, awarded by the National Institutes of Health, and grant #W81XWH-16-1-0659, awarded by the Department of Defense. The government has certain rights in the invention.

BACKGROUND

Castration-resistant prostate cancer (CRPC) is currently incurable and makes prostate cancer the second most common cause of cancer death among men in the United States. The androgen receptor (AR) is activated via multiple mechanisms including AR overexpression, mutation, hypersensitization, and/or intratumoral androgen synthesis in patients relapsed after androgen deprivation therapy (ADT). The steroidal hormones testosterone and dihydrotestosterone are the major endogenous androgens that cause nuclear translocation and subsequent activation of androgen receptor (AR). Overexpression and knockdown studies have demonstrated that AR is a key molecular determinant and an excellent therapeutic target for CRPC. Clinical use of abiraterone, a potent inhibitor of testosterone synthesis, and MDV3100 (enzalutamide) and bicalutamide, AR antagonists, indicates that AR remains a viable target in a significant number of CRPC patients.

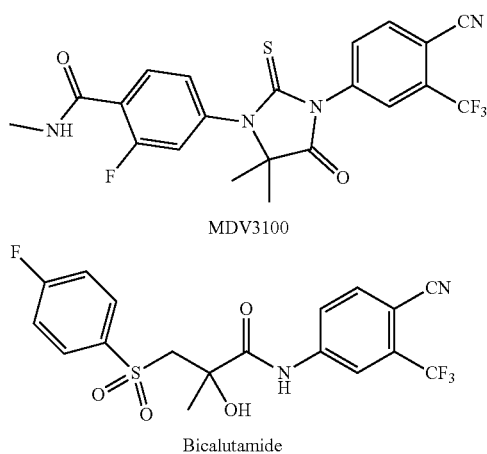

MDV3100

Bicalutamide

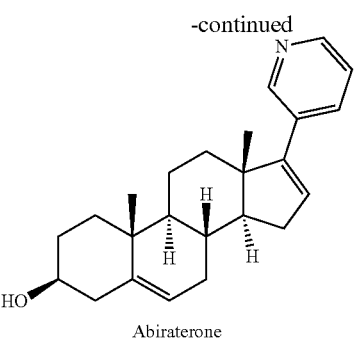

Abiraterone

Androgen receptor (AR), a member of the steroid receptor superfamily, is a ligand-dependent transcription factor that controls the expression of androgen-responsive genes. Intracellular trafficking is an important mechanism in the regulation of many transcription factors, including AR. In order to access its target genes, a transcription factor requires localization to the nucleus. Retention of a transcription factor in the cytoplasm prevents its activity. Thus, a key regulatory step in the action of AR is its nuclear translocation. In androgen-sensitive cells, AR is localized to the cytoplasm in the absence of ligand. Upon addition of androgens, AR translocates to the nucleus and transactivates target genes. However, in CRPC cells, AR remains in the nucleus even in the absence of androgen and transactivates androgen-responsive genes, leading to uncontrolled growth of prostate tumors. Therefore, novel approaches that can block the nuclear localization of AR, degrade nuclear AR, and/or suppress nuclear AR activity may provide an effective therapy against CRPC.

SUMMARY

Disclosed herein is a compound, or a pharmaceutically acceptable salt or ester thereof, having a formula I of:

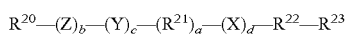

$R^{20}-(Z)_b-(Y)_c-(R^{21})_a-(X)_d-R^{22}-R^{23}$ wherein $R^{20}$ is an aryl, substituted aryl, heteroaryl, substituted heteroaryl, cycloalkyl, substituted cycloalkyl, heterocycloalkyl, substituted heterocycloalkyl, alkoxy, aryloxy, amino, a thio-containing group, or a seleno-containing group; Z is alkanediyl, substituted alkanediyl, cycloalkanediyl, or substituted cycloalkanediyl; Y is S, O, S(=O), —S(=O)(=O)—, or $NR^{10}$, wherein $R^{10}$ is H or alkyl; $R^{21}$ is alkanediyl, substituted alkanediyl, cycloalkanediyl, substituted cycloalkanediyl, alkadienyl, substituted alkadienyl, cycloalkenediyl, substituted cycloalkenediyl, alkatrienyl, substituted alkatrienyl; X is —C(=O)—, —S(=O)(=O)—, or —N(H)C(=O)—; $R^{22}$ is a moiety that includes at least one divalent amino radical; $R^{23}$ is an aryl, substituted aryl, heteroaryl, substituted heteroaryl, cycloalkyl, substituted cycloalkyl, heterocycloalkyl, substituted heterocycloalkyl, alkoxy, aryloxy, amino, a thio-containing group, a seleno-containing group; a is 0 or 1; b is 0 or 1; c is 0 or 1; and d is 0 or 1. In some embodiments, if X is —C(=O)— then Y is not S. In certain embodiments, $R^{21}$ is cycloalkanediyl. When $R^{21}$ is cycloalkanediyl, $R^{20}$ may be a phenyl optionally substituted with at least one halogen and/or $R^{23}$ may be a phenyl substituted with at least one halogen and/or at least one alkyl.

Also disclosed herein is a method for treating prostate cancer in a subject, comprising administering a therapeutically effective amount of an agent to the subject, wherein the agent is a compound, or a pharmaceutically acceptable salt or ester thereof, of formula I or formula II.

The foregoing will become more apparent from the following detailed description, which proceeds with reference to the accompanying figures.

BRIEF DESCRIPTION OF THE DRAWINGS

FIGS. 1A through 1H are a table showing compound structures.

DETAILED DESCRIPTION

Figure 1A:
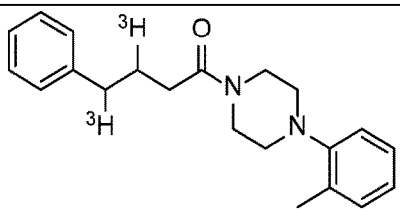
Figure 1A:
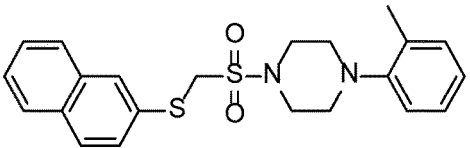
Figure 1A:
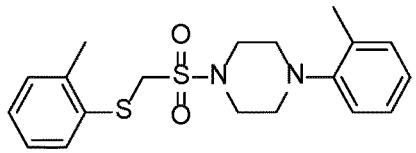
Figure 1A:
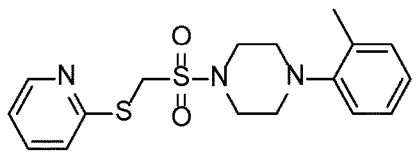
Figure 1A:
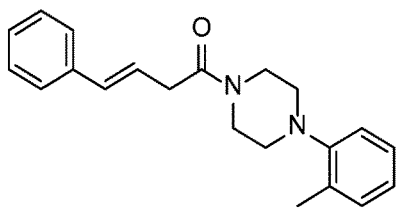
Figure 1A:
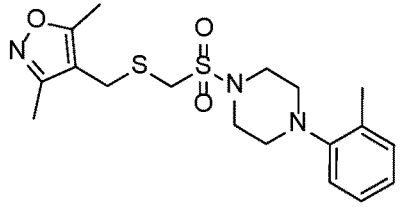
Figure 1A:
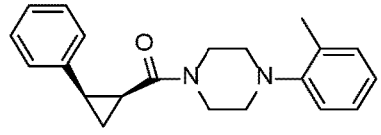
Figure 1B:
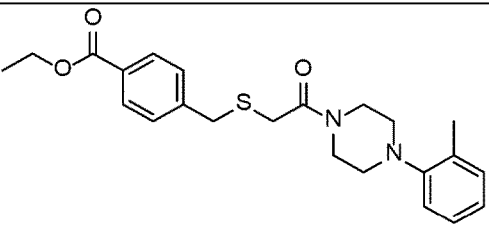
Figure 1B:
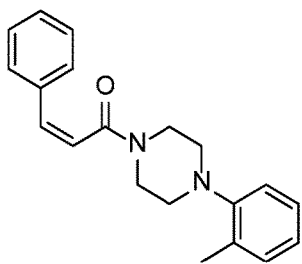
Figure 1B:
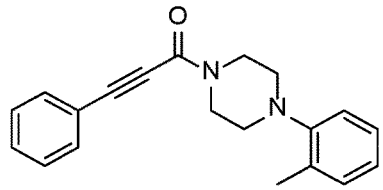
Figure 1B:
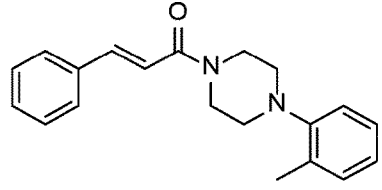
Figure 1B:
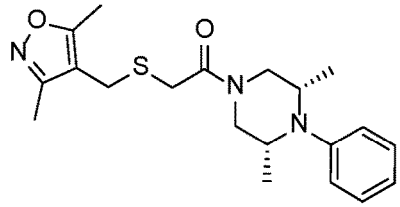
Figure 1B:
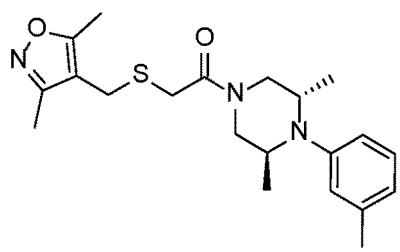
Figure 1F:
Figure 1F:
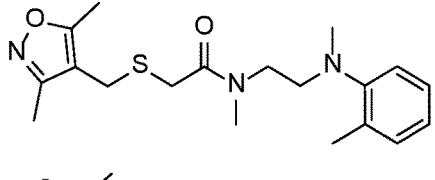
Figure 1F:
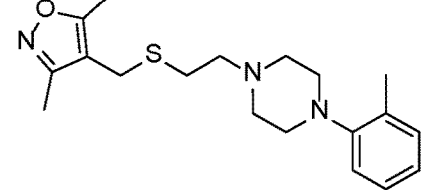
Figure 1F:
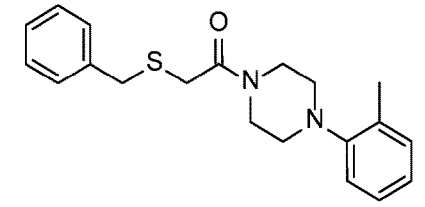
Figure 1F:
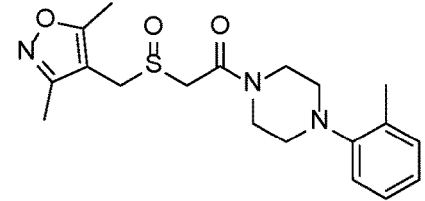
Figure 1F:
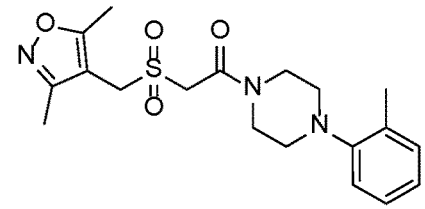
Figure 1F:
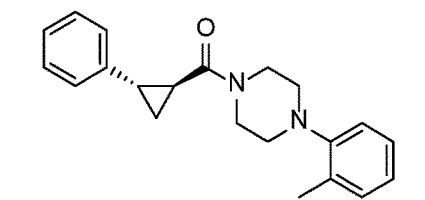
Figure 1H:
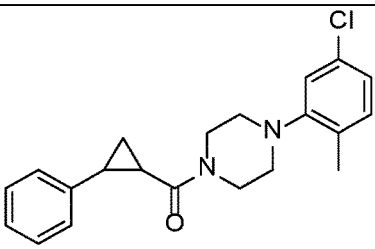
Figure 1H:
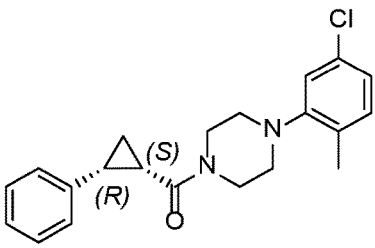
Figure 1H:
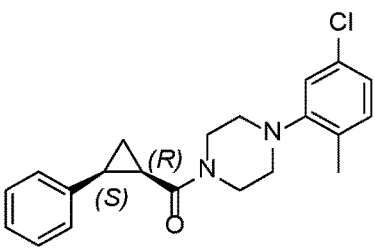
Figure 2A:
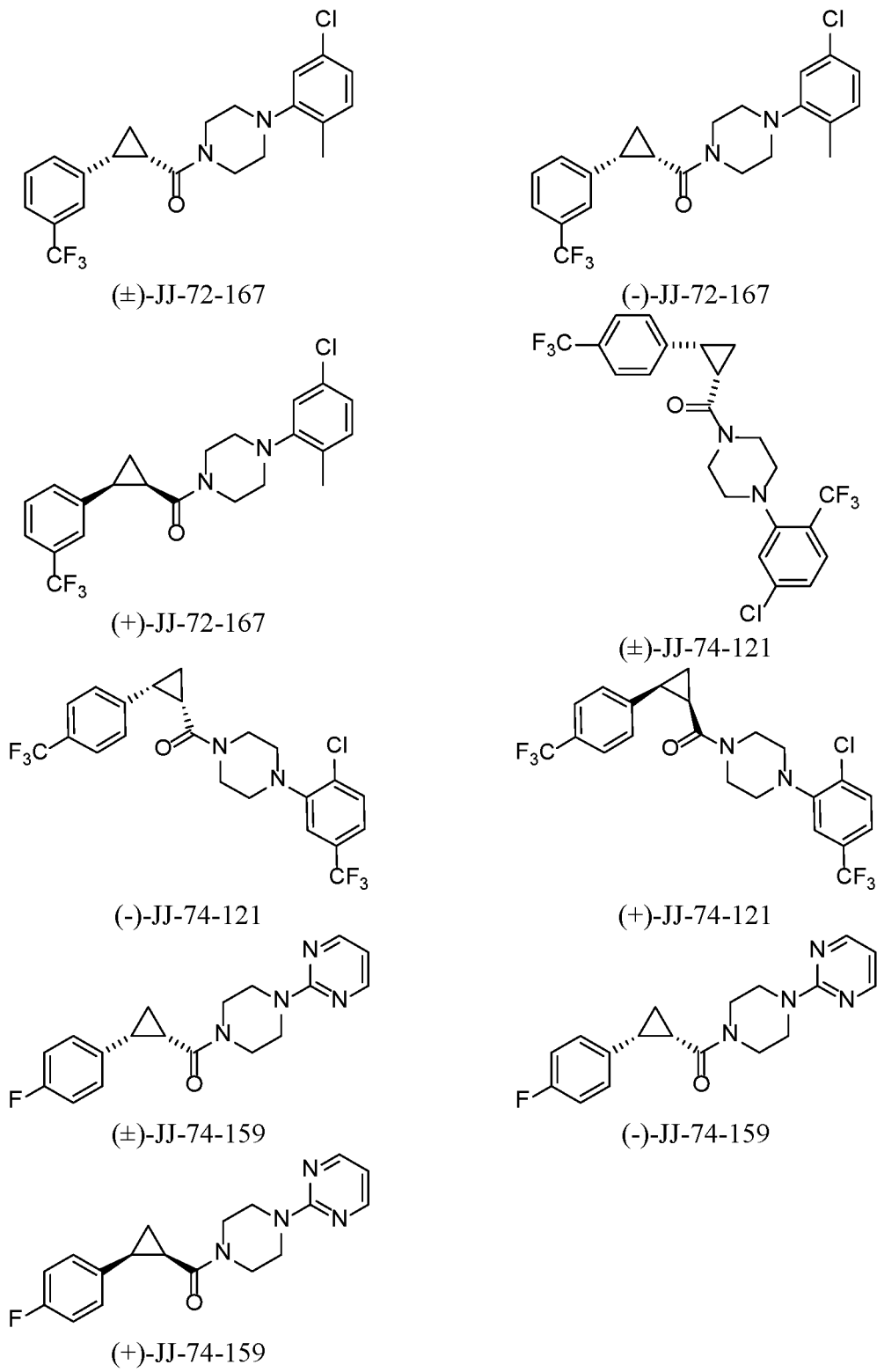
FIGS. 2A through 2L show additional compound structures.
Figure 2B:
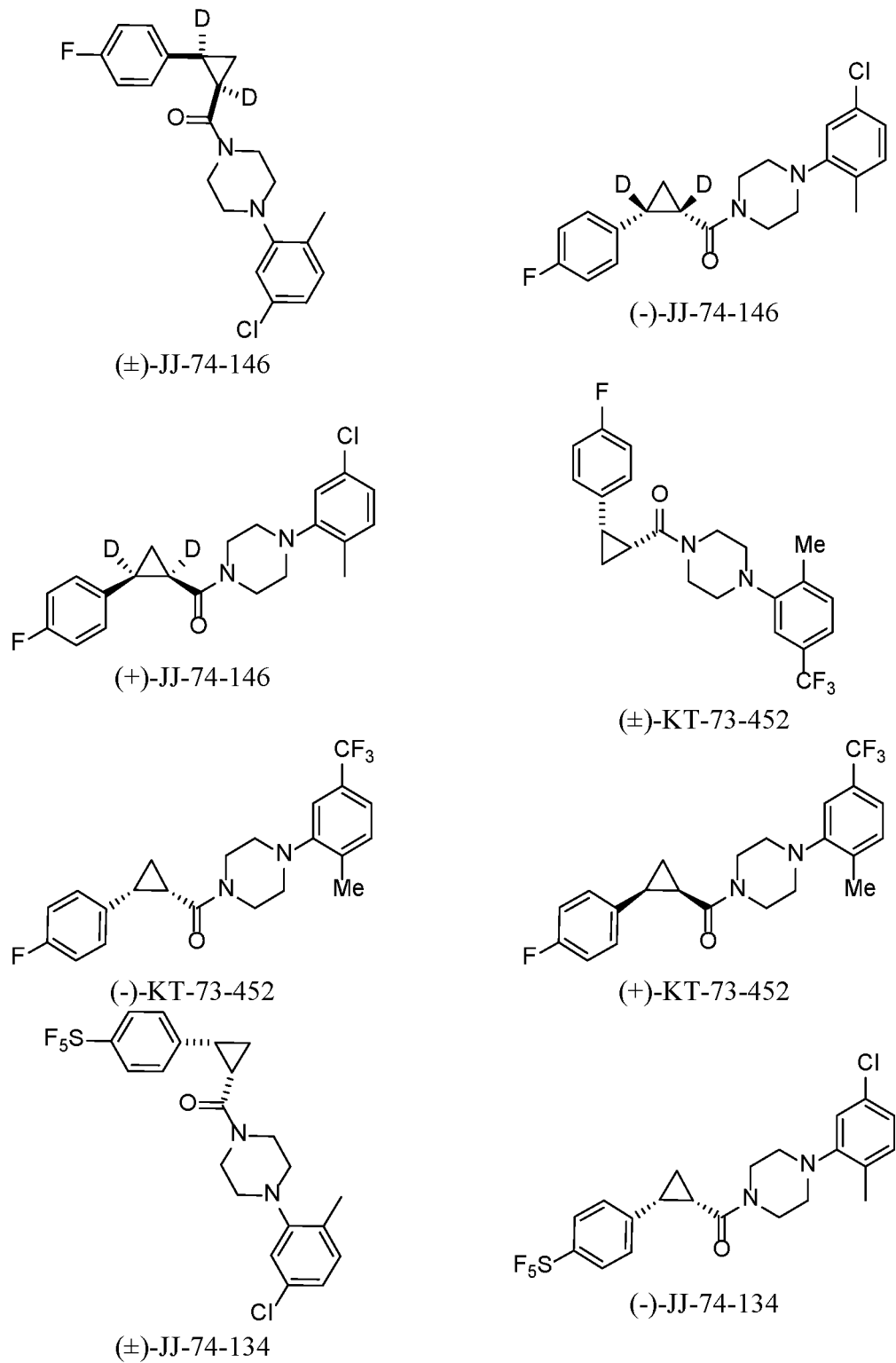
Figure 2C:
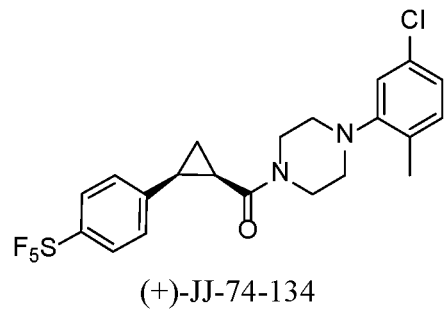
Figure 2C:
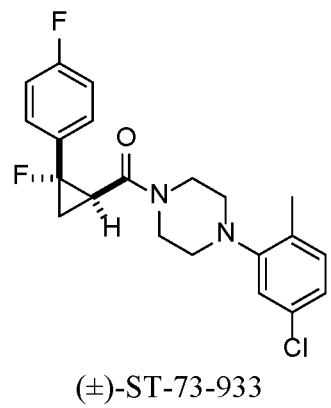
Figure 2C:
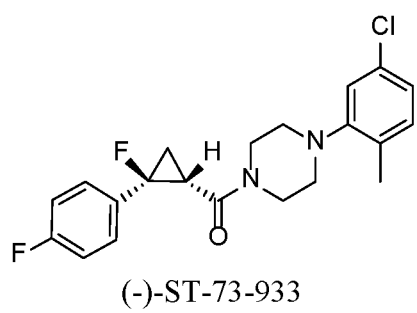
Figure 2C:
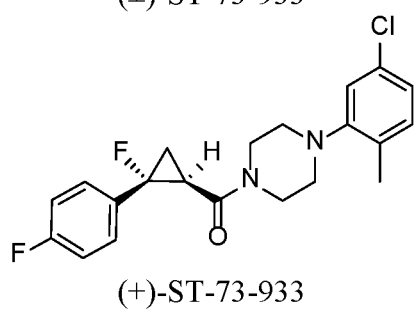
Figure 2C:
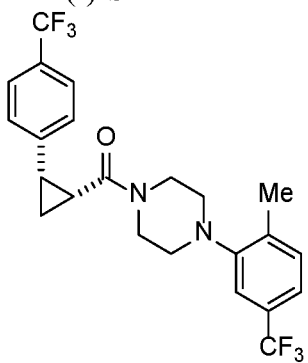
Figure 2C:
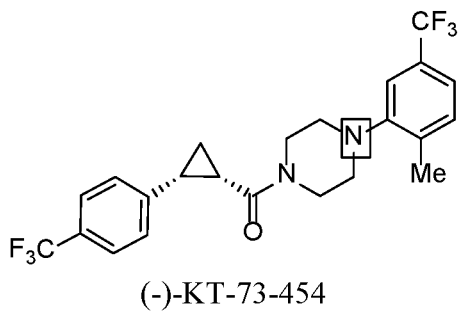
Figure 2C:
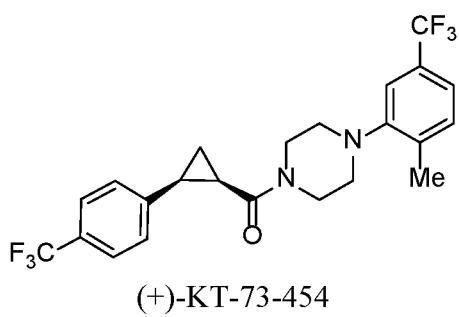
Figure 2C:
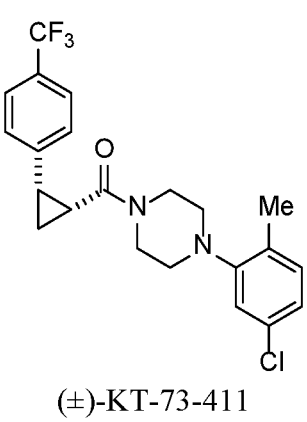
Figure 2D:
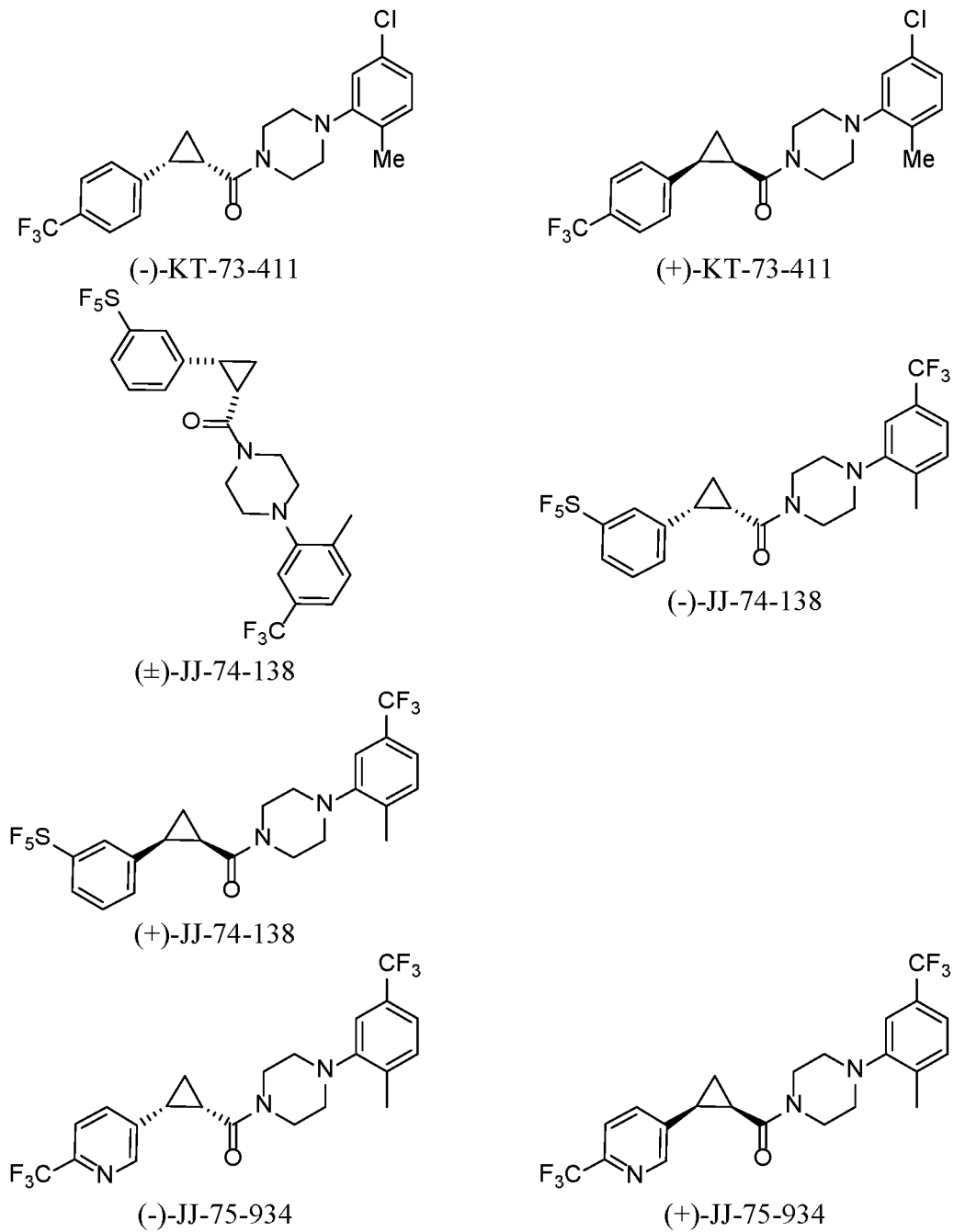
Figure 2E:
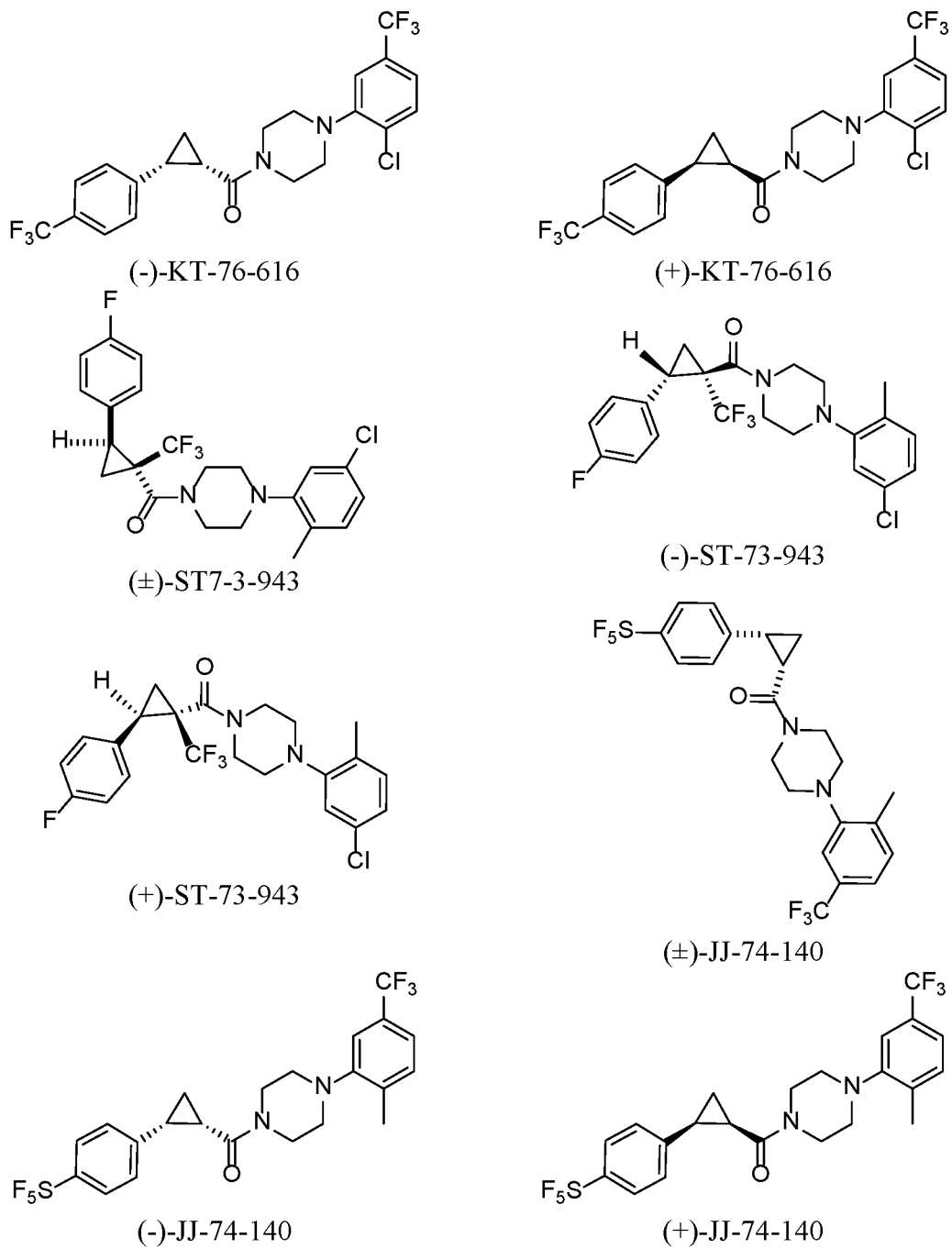
Figure 2F:
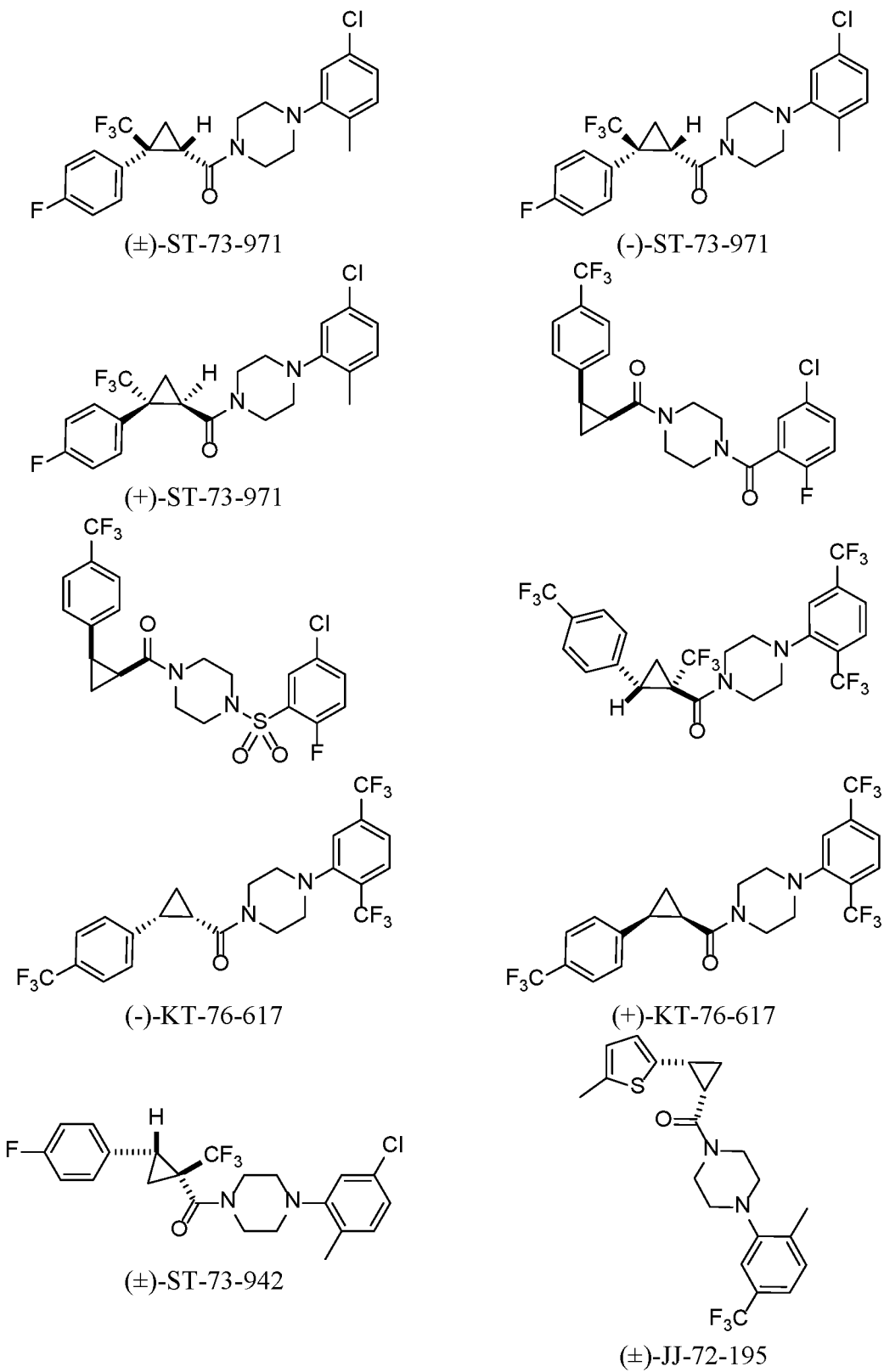
Figure 2G:
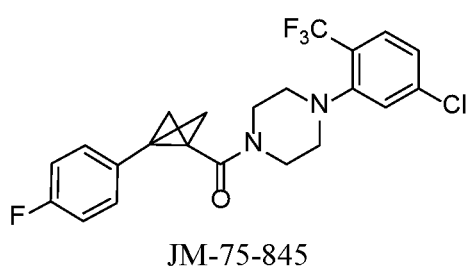
Figure 2G:
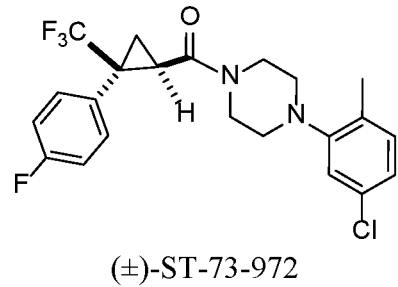
Figure 2G:
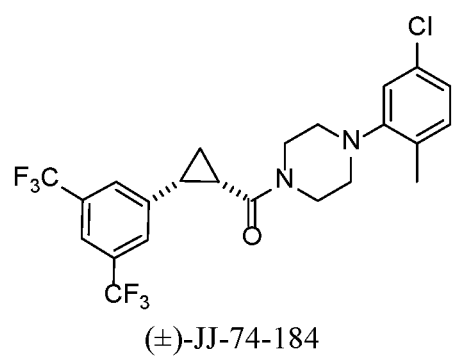
Figure 2G:
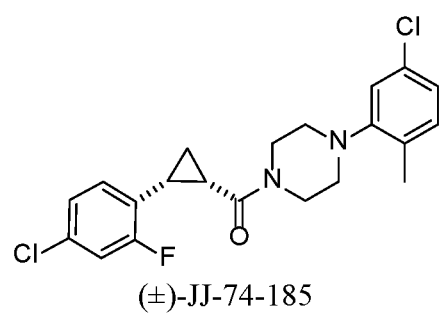
Figure 2G:
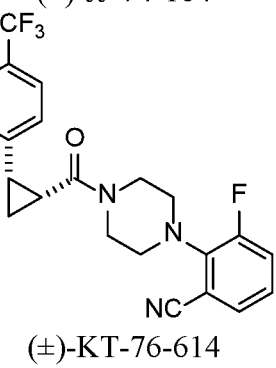
Figure 2G:
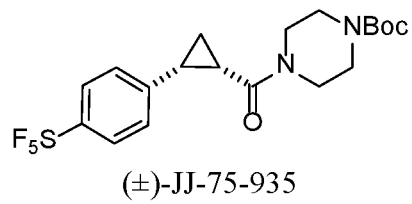
Figure 2G:
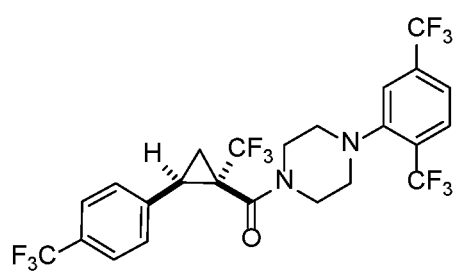
Figure 2G:
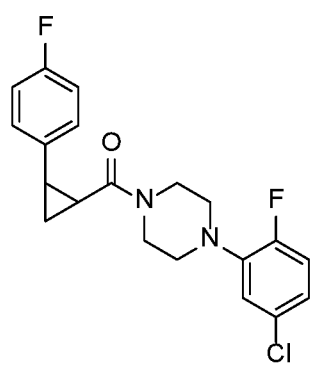
Figure 2H:
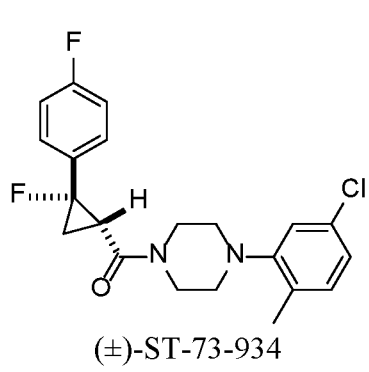
Figure 2H:
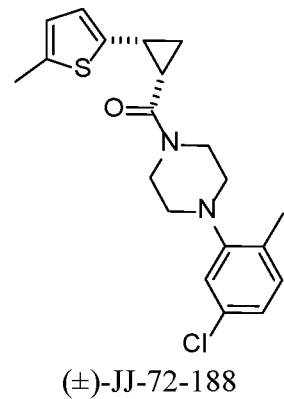
Figure 2H:
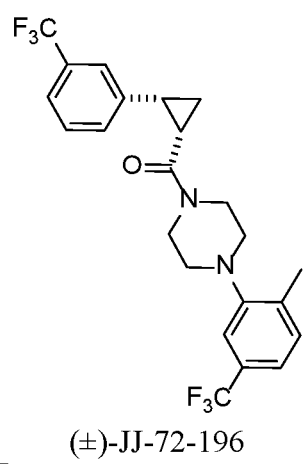
Figure 2H:
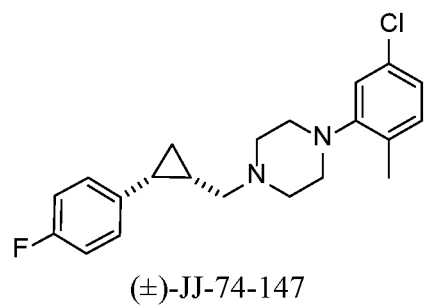
Figure 2H:
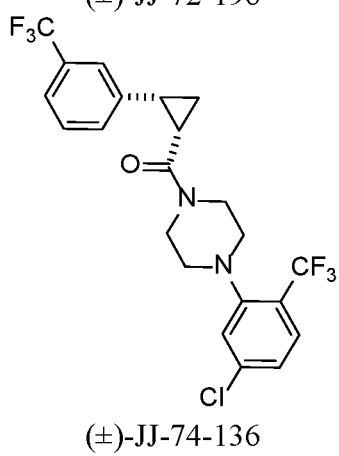
Figure 2H:
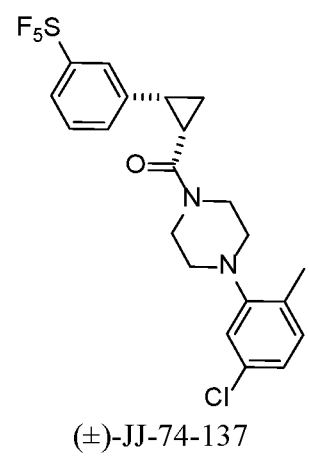
Figure 2I:
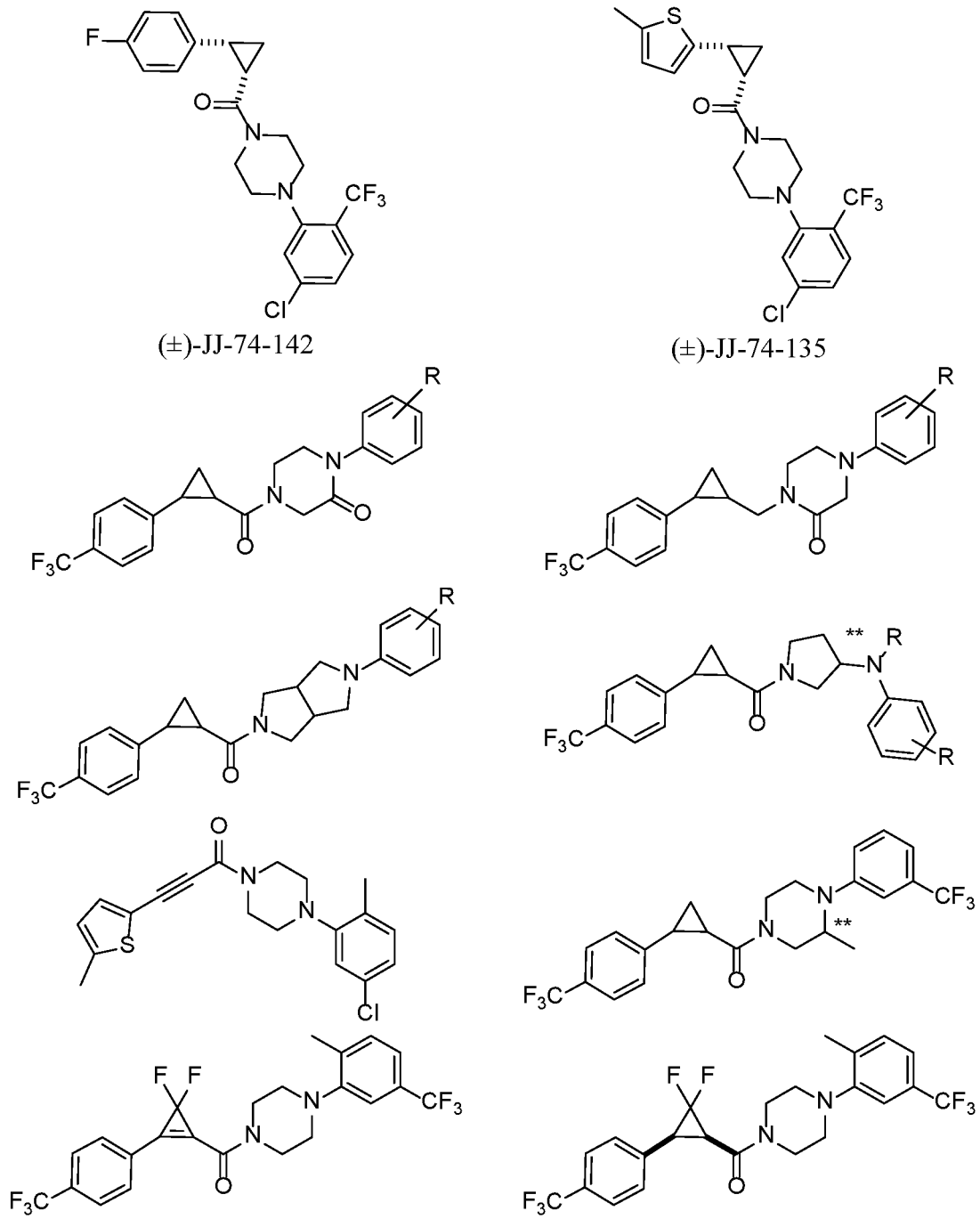
Figure 2J:
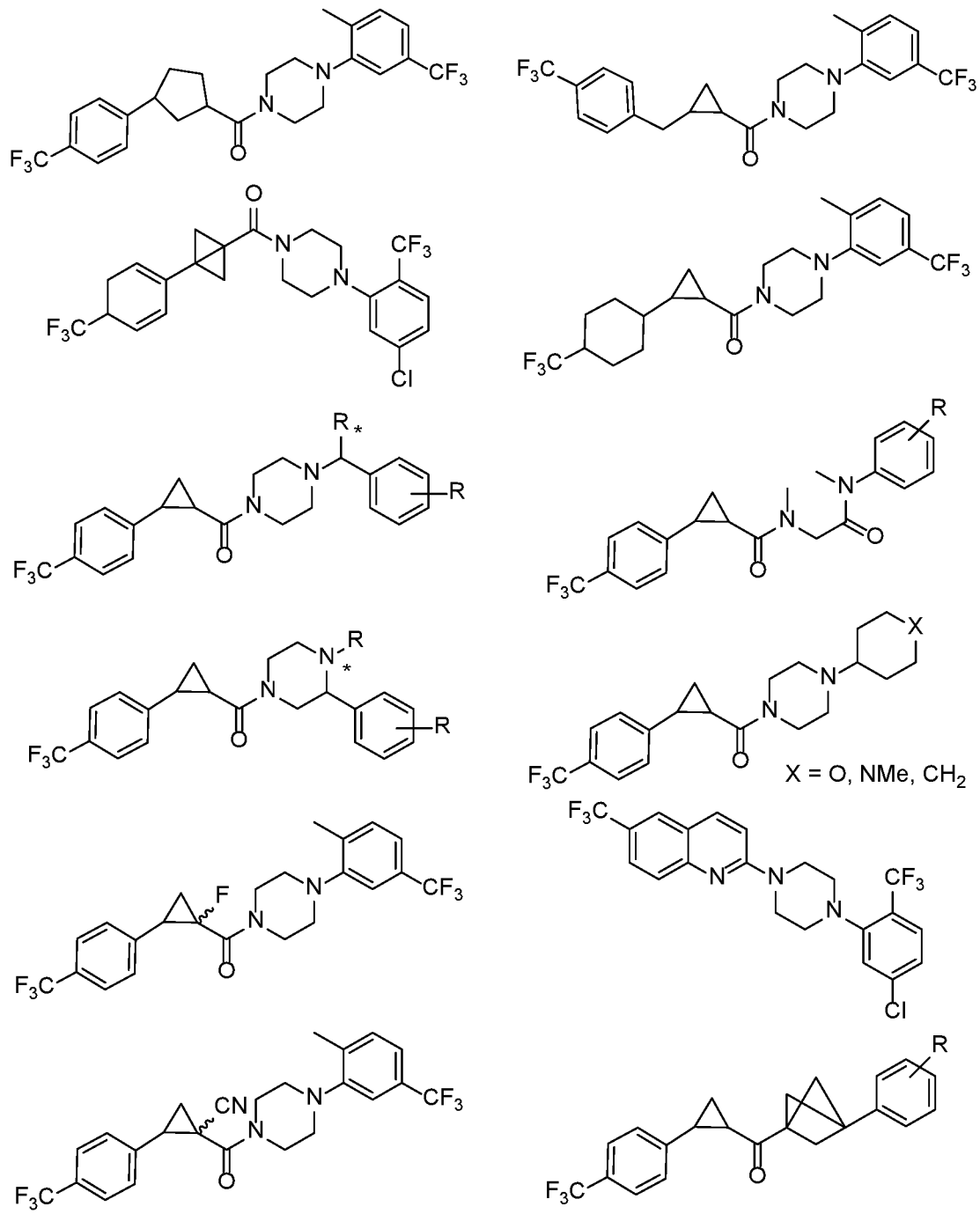
Figure 2K:
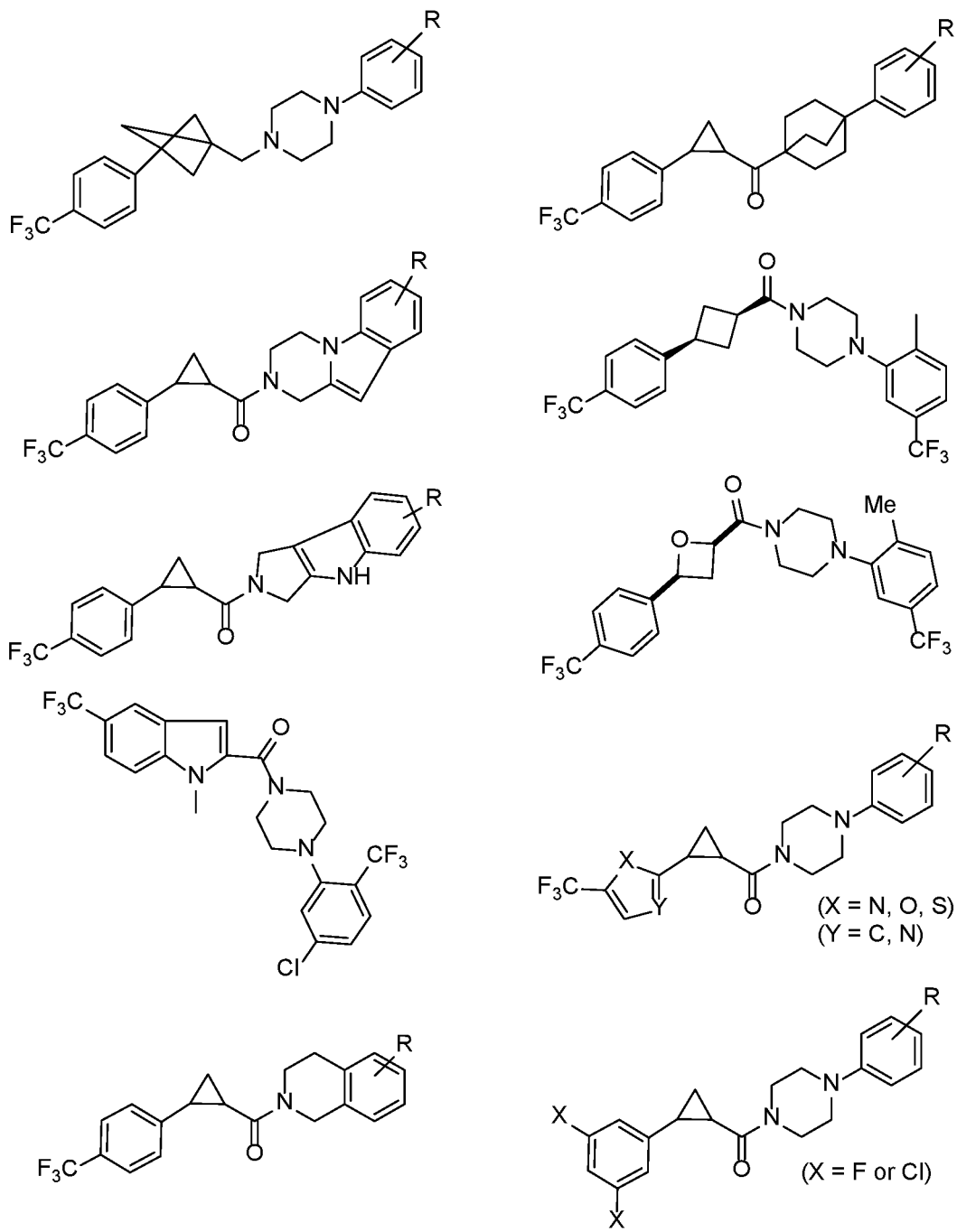
Figure 2L:
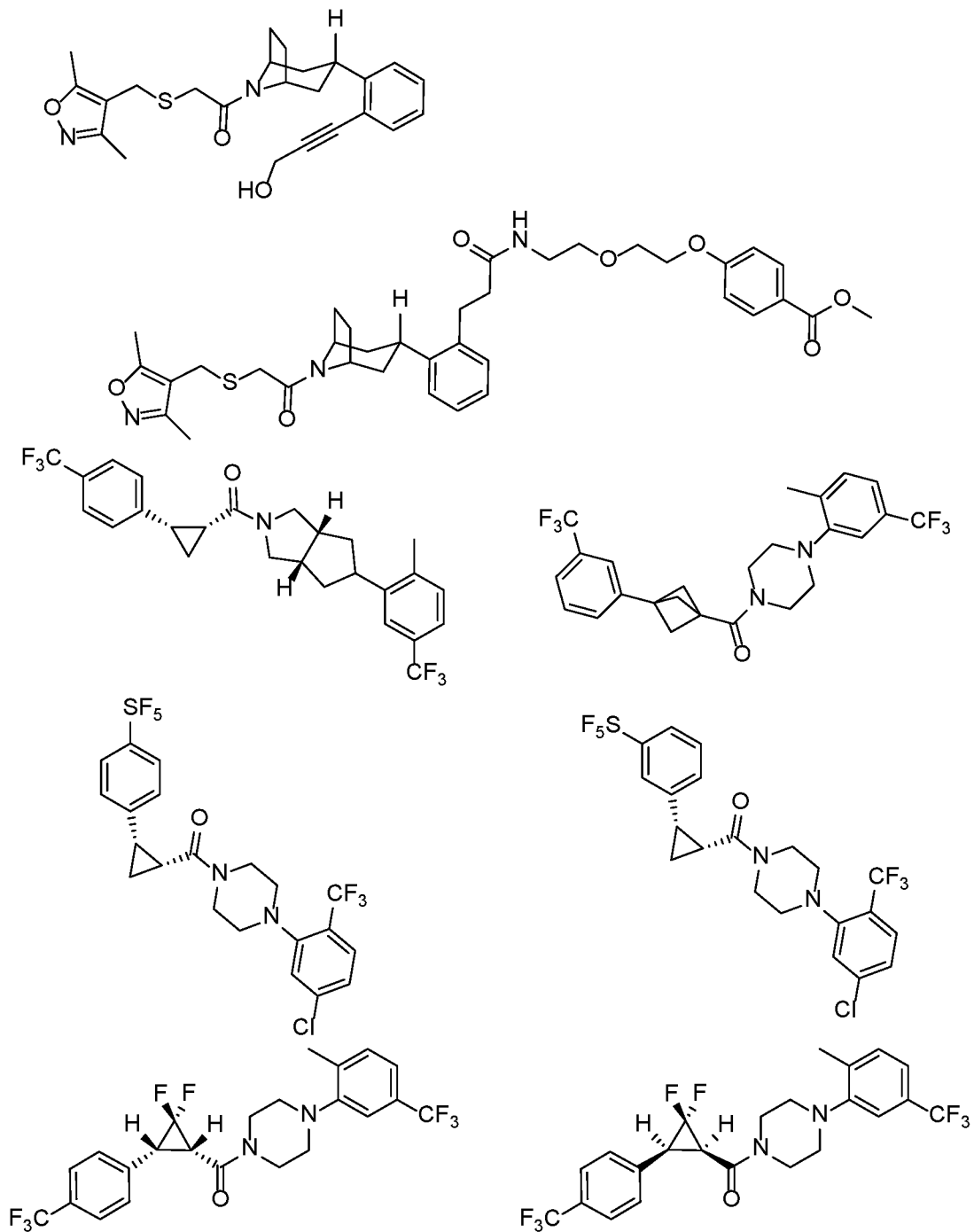
Figure 3A:
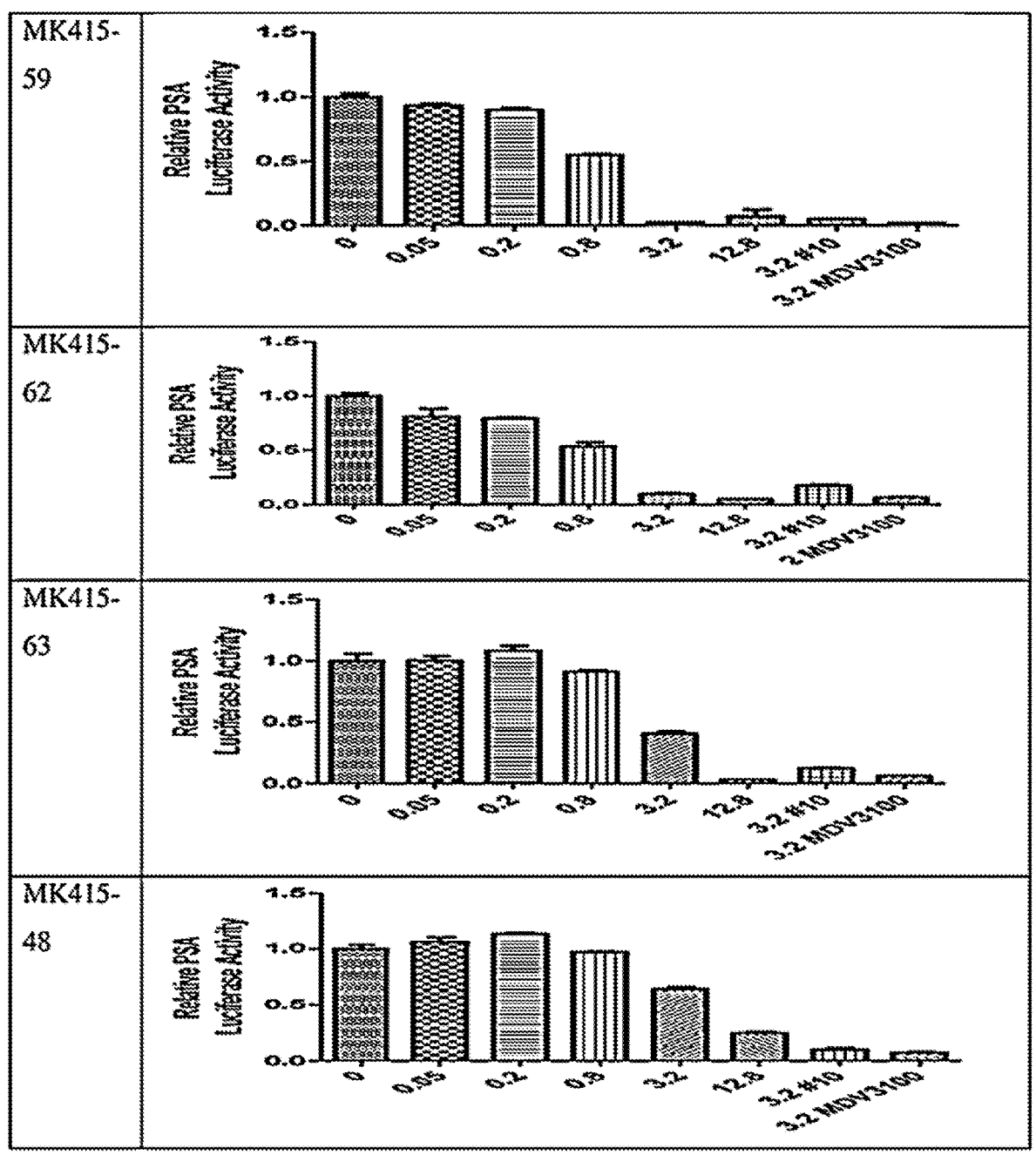
FIGS. 3A through 3E show assay results for several of the compounds. C4-2 cells were transfected with PSA6.1-Luc, GFP-AR, and pRL-CMV and then treated with indicated doses for 24 hours. For luciferase assays, cells were lysed with passive lysis buffer (Promega) and both Firefly and Renilla luciferase activities were read using a Dual-Luciferase Reporter Assay kit (Promega) on a LmaxII384 luminometer (Molecular Devices). Firefly luciferase values were normalized to Renilla (pRL-CMV). Plotted values represent averaged normalized Firefly luciferase activities, each performed in triplicate, relative to DMSO control. This assay is described in more detail in PCT Patent Application Publication WO 2013055793, which is incorporated herein by reference.
Figure 3B:
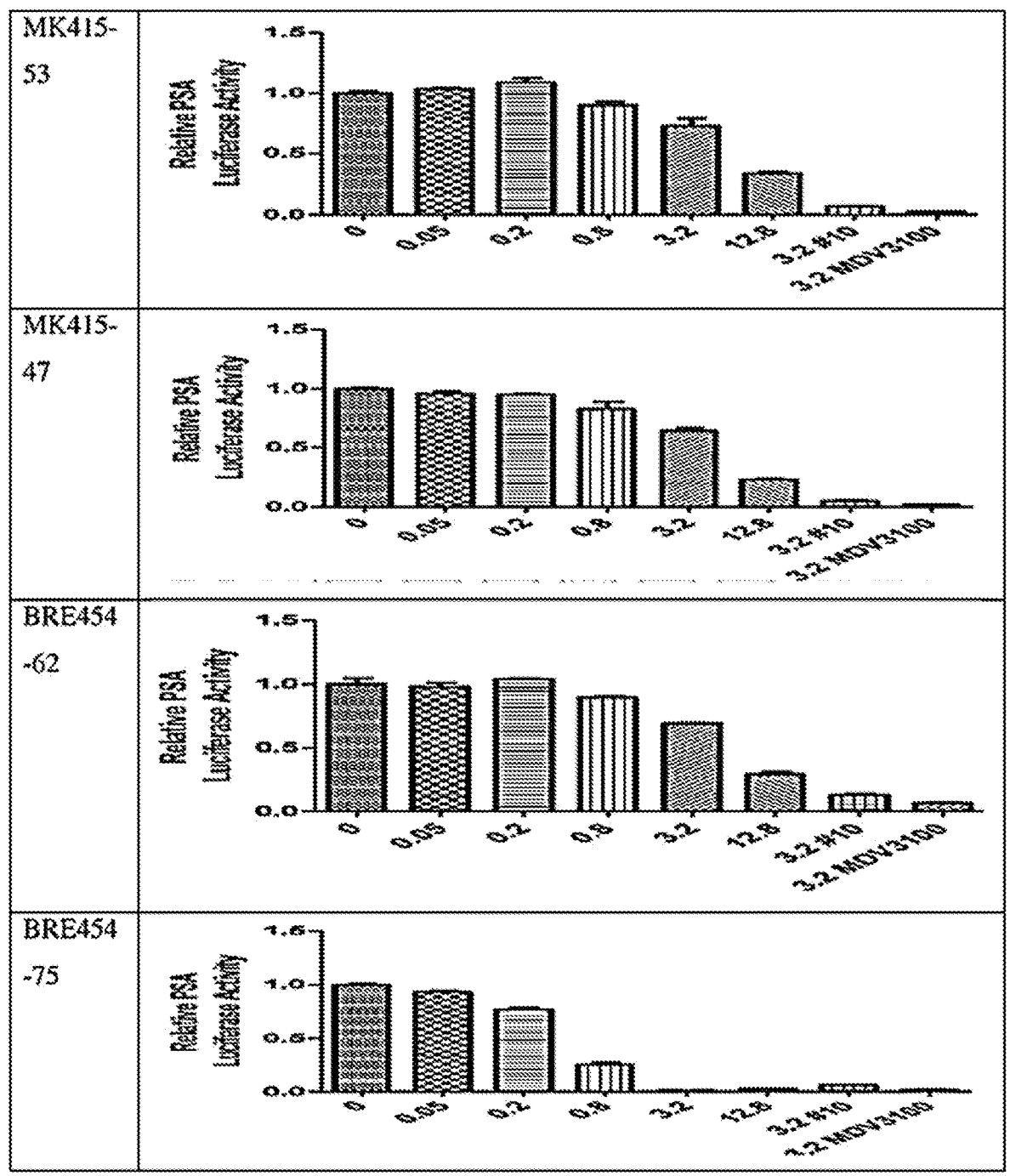
Figure 3C:
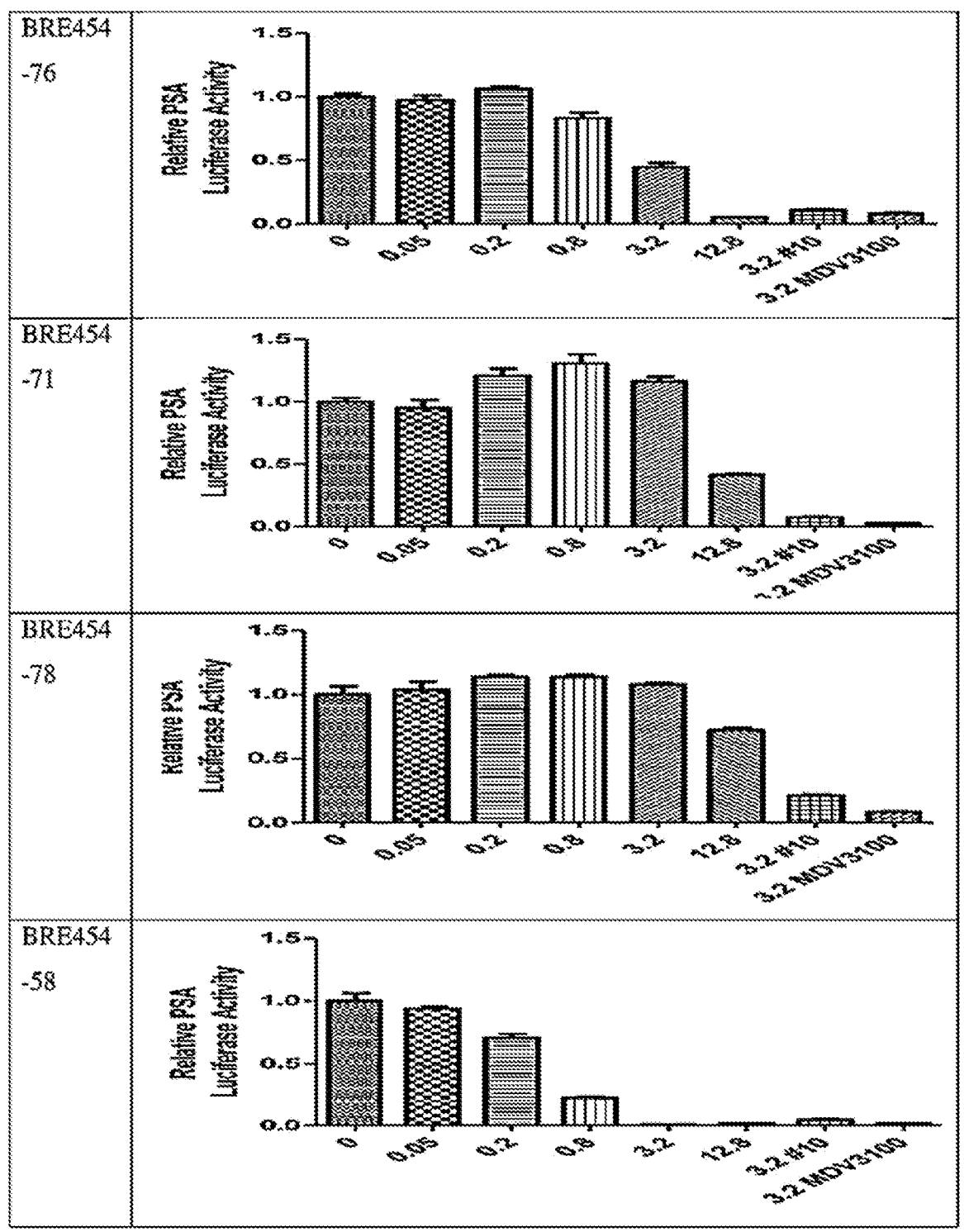
Figure 3D:
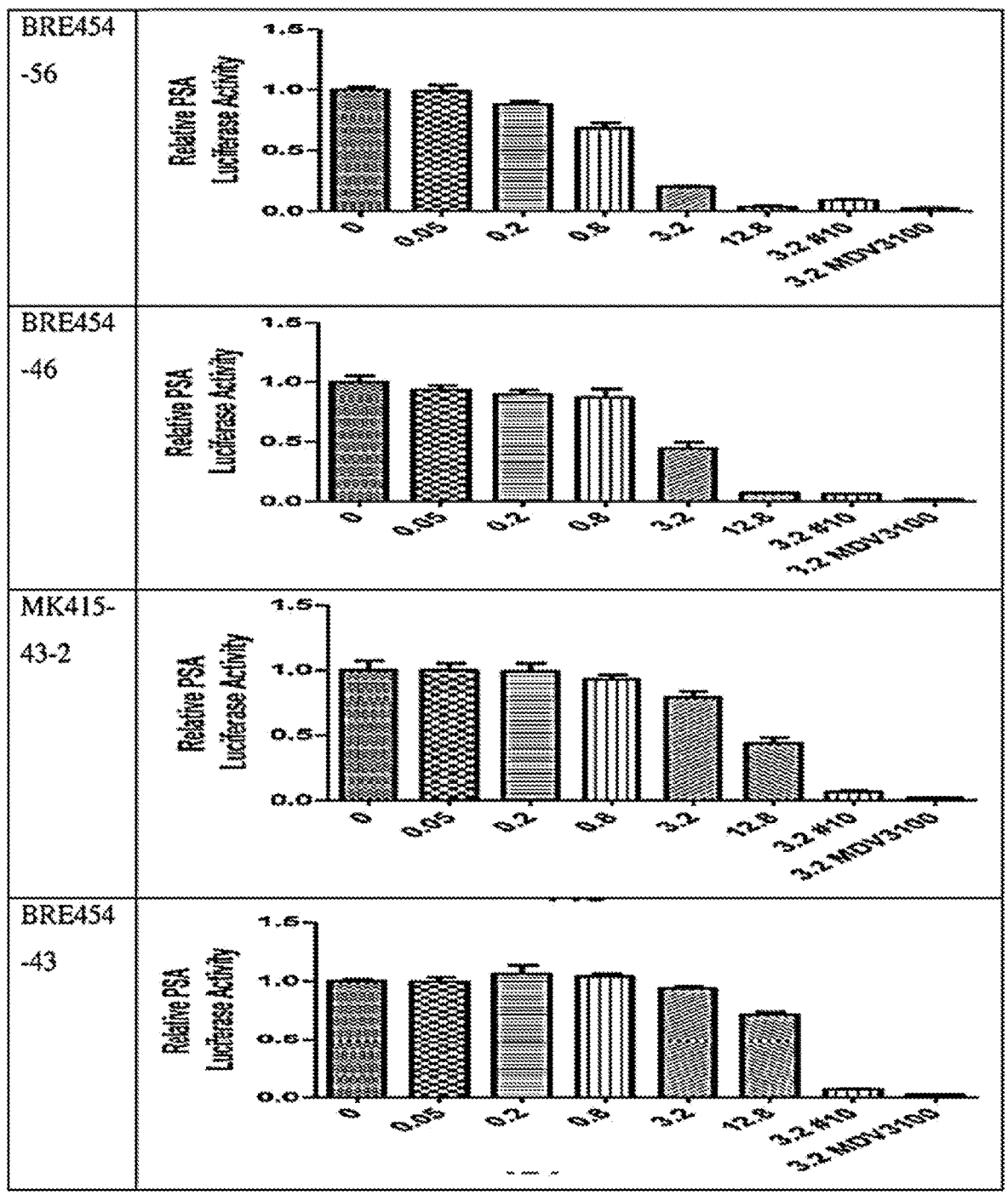
Figure 3E:
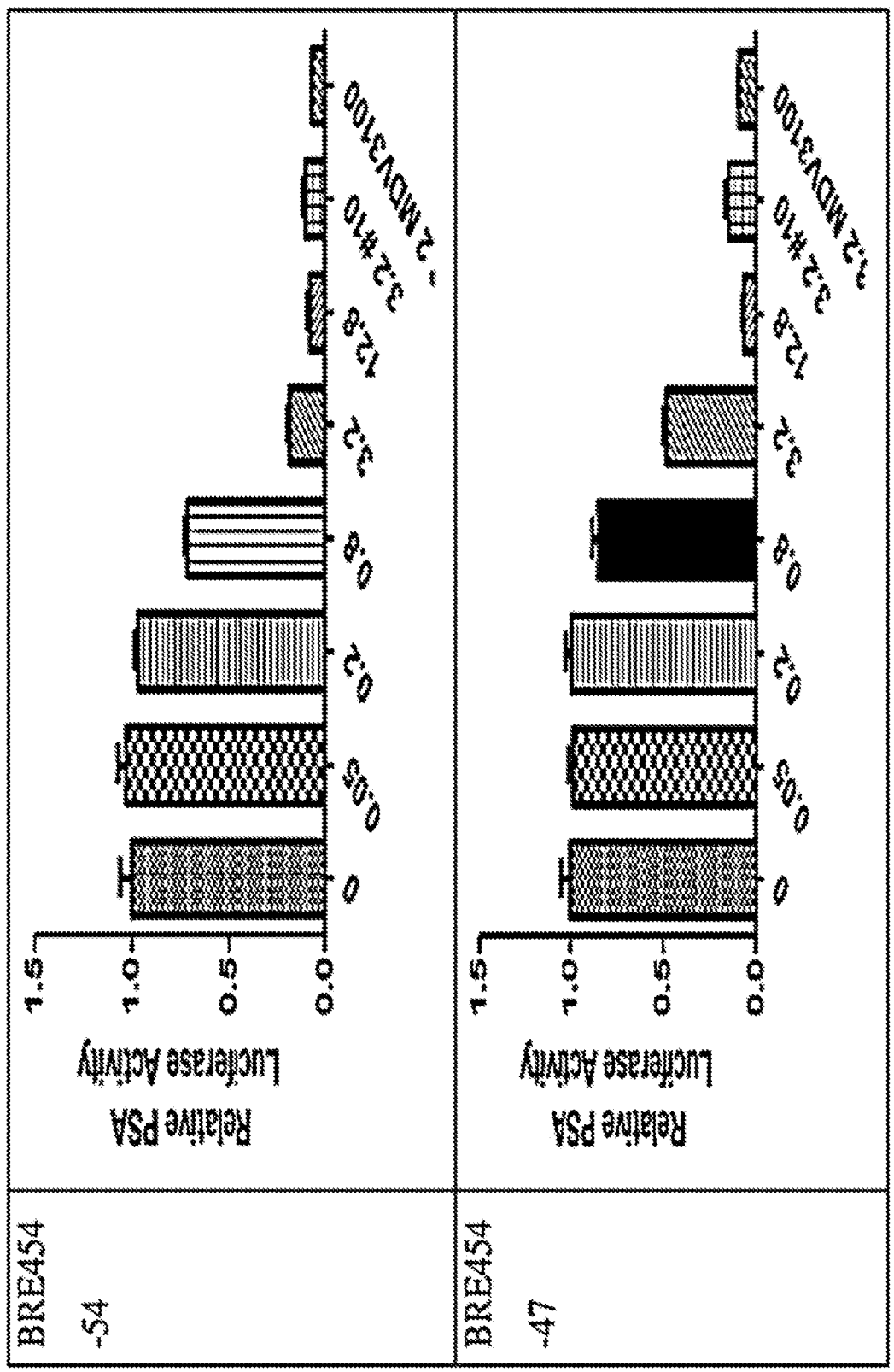

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Administration of" and "administering a" compound should be understood to mean providing a compound, a prodrug of a compound, or a pharmaceutical composition as described herein. The compound or composition can be administered by another person to the subject (e.g., intravenously) or it can be self-administered by the subject (e.g., tablets).

"Alkanediyl" or "cycloalkanediyl" refers to a divalent radical of the general formula —C$_n$H$_{2n}$— or —C$_n$H$_{2n-2}$—, respectively, derived from aliphatic or cycloaliphatic hydrocarbons. "Cycloalkenediyl" refers to a divalent radical of the general formula —C$_n$H$_{2n-4}$— derived from a cycloalkene.

The term "aliphatic" is defined as including alkyl, alkenyl, alkynyl, halogenated alkyl and cycloalkyl groups as described above. A "lower aliphatic" group is a branched or unbranched aliphatic group having from 1 to 10 carbon atoms.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or (C$_1$-C$_6$)alkyl can be methyl, ethyl, propyl, isopropyl, butyl, isobutyl, sec-butyl, pentyl, 3-pentyl, or hexyl; (C$_3$-C$_6$)cycloalkyl can be cyclopropyl, cyclobutyl, cyclopentyl, or cyclohexyl; (C$_3$-C$_6$)cycloalkyl(C$_1$-C$_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; (C$_1$-C$_6$)alkoxy can be methoxy, ethoxy, propoxy, isopropoxy, butoxy, isobutoxy, sec-butoxy, pentoxy, 3-pentoxy, or hexyloxy; (C$_2$-C$_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; (C$_2$-C$_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$) alkanoyl can be acetyl, propanoyl or butanoyl; halo($C_1$-$C_6$) alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$) alkanoyloxy can be acetoxy, propanoyloxy, butanoyloxy, isobutanoyloxy, pentanoyloxy, or hexanoyloxy.

The term "alkylaryl" refers to a group in which an alkyl group is substituted for a hydrogen atom of an aryl group. An example is —Ar—R, wherein Ar is an arylene group and R is an alkyl group.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

"Alkynyl" refers to a cyclic, branched or straight chain group containing only carbon and hydrogen, and unless otherwise mentioned typically contains one to twelve carbon atoms, and contains one or more triple bonds. Alkynyl groups may be unsubstituted or substituted. "Lower alkynyl" groups are those that contain one to six carbon atoms.

The term "amide" or "amido" is represented by the formula —C(O)NRR', where R and R' independently can be a hydrogen, alkyl, alkenyl, alkynyl, aryl, arylalkyl, cycloalkyl, halogenated alkyl, or heterocycloalkyl group described above. A suitable amido group is acetamido.

The term "amine" or "amino" refers to a group of the formula —NRR', where R and R' can be, independently, hydrogen or an alkyl, alkenyl, alkynyl, aryl, arylalkyl, carbonyl (e.g., —C(O)R", where R" can be hydrogen, an alkyl, alkenyl, alkynyl, aryl, or an arylalkyl), cycloalkyl, halogenated alkyl, or heterocycloalkyl group. For example, an "alkylamino" or "alkylated amino" refers to —NRR', wherein at least one of R or R' is an alkyl.

"Aminocarbonyl" alone or in combination, means an amino substituted carbonyl (carbamoyl) radical, wherein the amino radical may optionally be mono- or di-substituted, such as with alkyl, aryl, arylalkyl, cycloalkyl, cycloalkylalkyl, alkanoyl, alkoxycarbonyl, aralkoxycarbonyl and the like. An aminocarbonyl group may be —C(O)—N(R) (wherein R is a substituted group or H). An "aminocarbonyl" is inclusive of an amido group. A suitable aminocarbonyl group is acetamido.

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. Structural analogs are often found using quantitative structure activity relationships (QSAR), with techniques such as those disclosed in Remington (*The Science and Practice of Pharmacology*, 19th Edition (1995), chapter 28). A derivative is a molecule derived from the base structure.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "aryl" refers to any carbon-based aromatic group including, but not limited to, phenyl, naphthyl, etc. The term "aryl" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

The term "arylalkyl" refers to an alkyl group where at least one hydrogen atom is substituted by an aryl group. An example of an arylalkyl group is a benzyl group.

"Carbonyl" refers to a group of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

"Carboxyl" refers to a —COO group. Substituted carboxyl refers to —COOR where R is aliphatic, heteroaliphatic, alkyl, heteroalkyl, or a carboxylic acid or ester.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "co-administration" or "co-administering" refers to administration of a first agent with a second agent within the same general time period, and does not require administration at the same exact moment in time (although co-administration is inclusive of administering at the same exact moment in time). Thus, co-administration may be on the same day or on different days, or in the same week or in different weeks. The first agent and the second agent may be included in the same composition or they may each individually be included in separate compositions. In certain embodiments, the two agents may be administered during a time frame wherein their respective periods of biological activity overlap. Thus, the term includes sequential as well as coextensive administration of two or more agents.

"Derivative" refers to a compound or portion of a compound that is derived from or is theoretically derivable from a parent compound.

The terms "halogenated alkyl" or "haloalkyl group" refer to an alkyl group as defined above with one or more hydrogen atoms present on these groups substituted with a halogen (F, Cl, Br, I).

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Inhibiting" refers to inhibiting the full development of a disease or condition. "Inhibiting" also refers to any quantitative or qualitative reduction in biological activity or binding, relative to a control.

"N-heterocyclic" refers to mono or bicyclic rings or ring systems that include at least one nitrogen heteroatom. The rings or ring systems generally include 1 to 9 carbon atoms in addition to the heteroatom(s) and may be saturated, unsaturated or aromatic (including pseudoaromatic). The term "pseudoaromatic" refers to a ring system which is not strictly aromatic, but which is stabilized by means of delocalization of electrons and behaves in a similar manner to aromatic rings. Aromatic includes pseudoaromatic ring systems, such as pyrrolyl rings.

Examples of 5-membered monocyclic N-heterocycles include pyrrolyl, H-pyrrolyl, pyrrolinyl, pyrrolidinyl, oxazolyl, oxadiazolyl, (including 1,2,3 and 1,2,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), and dithiazolyl. Examples of 6-membered monocyclic N-heterocycles include pyridyl, pyrimidinyl, pyridazinyl, pyrazinyl, piperidinyl, morpholinyl, thiomorpholinyl, piperazinyl, and triazinyl. The heterocycles may be optionally substituted with a broad range of substituents, and preferably with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino. The N-heterocyclic group may be fused to a carbocyclic ring such as phenyl, naphthyl, indenyl, azulenyl, fluorenyl, and anthracenyl.

Examples of 8, 9 and 10-membered bicyclic heterocycles include 1H thieno[2,3-c]pyrazolyl, indolyl, isoindolyl, benzoxazolyl, benzothiazolyl, benzisoxazolyl, benzisothiazolyl, benzimidazolyl, indazolyl, isoquinolinyl, quinolinyl, quinoxalinyl, purinyl, cinnolinyl, phthalazinyl, quinazolinyl, quinoxalinyl, benzotriazinyl, and the like. These heterocycles may be optionally substituted, for example with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino. Unless otherwise defined optionally substituted N-heterocyclics includes pyridinium salts and the N-oxide form of suitable ring nitrogens.

Examples of N-heterocycles also include bridged groups such as, for example, azabicyclo (for example, azabicyclooctane).

"Stereoisomers" are isomers that have the same molecular formula and sequence of bonded atoms, but which differ only in the three-dimensional orientation of the atoms in space. By convention, bold wedge bonds are used to indicate bonds coming out of the page toward the reader, and hashed wedge bonds are used to indicate bonds going behind the page away from the reader. Pairs of bold and hashed bonds that are not wedged are used to indicate bonds of the same orientation, i.e., a pair of bonds that are both coming out of the page or going behind the page.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like.

"Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), arylalkyl (for example benzyl), aryloxyalkyl (for example, phenoxymethyl), aryl (for example, phenyl, optionally substituted by, for example, halogen, C.sub.1-4 alkyl, or C.sub.1-4 alkoxy) or amino); sulphonate esters, such as alkyl- or arylalkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

It will be appreciated that the compounds described herein may have metal binding, chelating, complex forming properties and therefore may exist as metal complexes or metal chelates.

Some of the compounds described herein may also exist in their tautomeric form.

The term "subject" includes both human and veterinary subjects.

A "therapeutically effective amount" or "diagnostically effective amount" refers to a quantity of a specified agent sufficient to achieve a desired effect in a subject being treated with that agent. Ideally, a therapeutically effective amount or diagnostically effective amount of an agent is an amount sufficient to inhibit or treat the disease without causing a substantial cytotoxic effect in the subject. The therapeutically effective amount or diagnostically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" is inclusive of inhibiting the full development of a disease or condition, for example, in a subject who is at risk for a disease, or who has a disease, such as cancer or a disease associated with a compromised immune system. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. For a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions which will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

Groups which are substituted (e.g. substituted alkyl), may in some embodiments be substituted with a group which is substituted (e.g. substituted aryl). In some embodiments, the number of substituted groups linked together is limited to two (e.g. substituted alkyl is substituted with substituted aryl, wherein the substituent present on the aryl is not further substituted). In some embodiments, a substituted group is not substituted with another substituted group (e.g. substituted alkyl is substituted with unsubstituted aryl).

Overview

CRPC is responsible for all prostate cancer deaths, and eventually all prostate cancer will develop into CRPC. The current best treatment for CRPC is MDV3100 (enzalutamide), which binds to androgen receptor. It is effective against a number of androgen-dependent prostate cancer cell lines. However, it is ineffective against the androgen-dependent prostate cancer cell line 22Rv1. Compounds disclosed herein are effective against all androgen-dependent cell lines tested including 22Rv1, a promising and unique property.

Several of the compounds show sub-micromolar inhibition of PSA-luciferase expression in C4-2 cells. Further, cell proliferation in androgen-dependent cell lines is significantly decreased while proliferation in androgen-independent cell lines is unaffected.

Agents

Disclosed herein are agents that can be used for treating prostate cancer, particularly castration-resistant prostate cancer. The agents may inhibit AR nuclear localization and/or reduce AR levels in castration-resistant prostate cancer.

In one embodiment, the agent is a compound, or a pharmaceutically acceptable salt or ester thereof, having a formula I of:

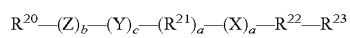

wherein $R^{20}$ is an aryl, substituted aryl, heteroaryl, substituted heteroaryl, cycloalkyl, substituted cycloalkyl, heterocycloalkyl, substituted heterocycloalkyl, alkoxy, aryloxy, a thio-containing group, a seleno-containing group, halide, or a nitro-containing group;

Z is alkanediyl, substituted alkanediyl, cycloalkanediyl, or substituted cycloalkanediyl;

Y is S, O, S(=O), —S(=O)(=O)—, or $NR^{10}$, wherein $R^{10}$ is H or alkyl (preferably methyl);

$R^{21}$ is alkanediyl, substituted alkanediyl, cycloalkanediyl, substituted cycloalkanediyl, alkadienyl, substituted alkadienyl, cycloalkenediyl, substituted cycloalkenediyl, alkatrienyl, or substituted alkatrienyl;

X is —C(=O)—, —S(=O)(=O)—, or —N(H)C(=O)—;

$R^{22}$ is a moiety that includes at least one divalent amino radical;

$R^{23}$ is an aryl, substituted aryl, heteroaryl, substituted heteroaryl, cycloalkyl, substituted cycloalkyl, heterocycloalkyl, substituted heterocycloalkyl, alkoxy, aryloxy, amino, a thio-containing group, or a seleno-containing group;

a is 0 or 1;

b is 0 or 1;

c is 0 or 1; and d is 0 or 1.

In some embodiments, if X is —C(=O)— then Y is not S. In certain embodiments, $R^{21}$ is cycloalkanediyl, such as cyclopropanediyl. When $R^{21}$ is cycloalkanediyl, $R^{20}$ may be a phenyl optionally substituted with at least one halogen and/or $R^{23}$ may be a phenyl substituted with at least one halogen and or at least one alkyl.

In certain embodiments, $R^{20}$ is selected from isoxazolyl, substituted isoxazolyl (e.g, dialkyl-substituted such as dimethyl, hydroxy-substituted, hydroxyalkyl-substituted, or a combination thereof), oxazolyl, substituted oxazolyl (e.g., dialkyl-substituted such as dimethyl, hydroxy-substituted, hydroxyalkyl-substituted, or a combination thereof) cyclohexyl, substituted cyclohexyl (e.g., hydroxy-substituted cyclohexyl), piperidinyl, substituted piperidinyl (e.g., hydroxy-substituted piperidinyl), oxacyclopentyl, substituted oxacyclopentyl (e.g., hydroxyalkyl-substituted), oxacyclohexanyl, substituted oxacyclopentyl (e.g., hydroxyalkyl-substituted), thiophenyl, substituted thiophenyl (e.g., hydroxyalkyl-substituted), phenyl, substituted phenyl (e.g., hydroxyalkyl-substituted or halogen-substituted), pyridinyl, substituted pyridinyl (e.g., hydroxyalkyl-substituted), indolyl, substituted indolyl (e.g., hydroxyalkyl-substituted), furanyl, substituted furanyl (e.g., hydroxyalkyl-substituted), imidazolyl, substituted imidazolyl (e.g., hydroxyalkyl-substituted). In preferred embodiments, $R^{20}$ is substituted isoxazolyl, particularly dialkyl (e.g., dimethyl)-substituted isooxazolyl, phenyl, or substituted phenyl, particularly halogen-substituted phenyl (e.g., fluorophenyl).

In certain embodiments, $R^{21}$ is selected from $C_1$-$C_3$ alkanediyl or substituted $C_1$-$C_3$ alkanediyl (e.g., alkyl-substituted such as methyl or dimethyl), preferably $C_1$ alkanediyl (—CH$_2$—), $C_3$ alkanediyl (—(CH$_2$)$_3$—), or cycloalkanediyl, preferably cyclopropanediyl. In certain embodiments, $R^{21}$ is:

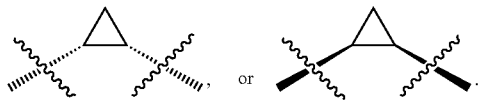

In certain embodiments, $R^{22}$ is selected from:

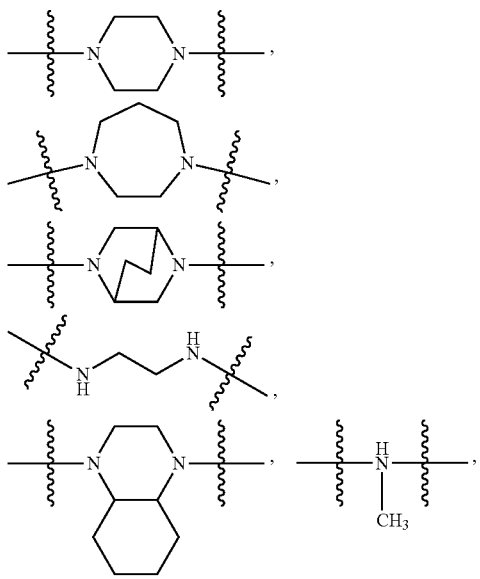

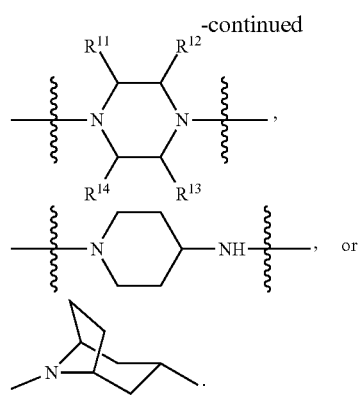

wherein $R^{11}$ to $R^{14}$ are each individually H or alkyl, provided that at least one of $R^{11}$ to $R^{14}$ is alkyl. In certain embodiments, $R^{12}$ and $R^{13}$ are each alkyl (e.g., methyl) and $R^{11}$ and $R^{14}$ are each H. In certain embodiments, $R^{11}$ and $R^{14}$ are each alkyl (e.g., methyl) and $R^{12}$ and $R^{13}$ are each H.

In certain embodiments, $R^{22}$ is a divalent radical of a N-heterocyclic group. Illustrative N-heterocylic groups include piperazinyl, substituted piperazinyl, azabicyclo (for example, azabicyclooctane), and substituted azabicyclo.

In certain embodiments, $R^{23}$ is selected from phenyl, substituted phenyl (e.g., alkyl-substituted phenyl such as dimethyl-substituted, or halogen substituted, such as chloro- or fluoro-substituted, or amino-substituted, or aminoalkyl-substituted; alkynyl-substituted phenyl), piperidinyl, substituted piperidinyl (e.g., amino-substituted), furanyl, substituted furanyl (e.g., aminoalkyl-substituted or amino-substituted), pyridinyl, substituted pyridinyl (e.g., aminoalkyl-substituted or amino-substituted), pyrimidinyl, substituted pyrimidinyl (e.g., aminoalkyl-substituted or amino-substituted), naphthenyl, substituted naphthenyl, (e.g., aminoalkyl-substituted or amino-substituted), thiazole, substituted thiazole (e.g., aminoalkyl-substituted or amino-substituted); isoindazolyl, substituted isoindazolyl (e.g., aminoalkyl-substituted or amino-substituted); triazolyl, or substituted triazolyl (e.g., aminoalkyl-substituted or amino-substituted). $R^{23}$ may have two or more substituents, such as an alkyl substituent and a halogen substituent. Preferably, $R^{23}$ is a substituted phenyl having a structure of:

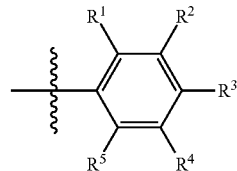

wherein each of $R^1$-$R^5$ is individually H, alkyl, substituted alkyl, alkynyl, substituted alkynyl, halogen, or cyano, provided that at least one of $R^1$-$R^5$ is not H. In certain embodiments, at least one of $R^1$-$R^5$ is alkyl (such as methyl), halogen or cyano. In certain embodiments, $R^1$ is alkyl, halogen or cyano. In certain embodiments, $R^1$ is alkyl and $R^4$ is halogen. In certain embodiments, at least one of $R^1$-$R^5$ is hydroxy-substituted alkynyl.

In certain embodiments, Z is selected from $C_1$-$C_3$ alkanediyl, preferably —CH$_2$—.

In certain embodiments, $R^{20}$ is phenyl or substituted isoxazolyl, b is 0; c is 1; a is 1; $R^{21}$ is —CH$_2$—, Y is S; X is —S(=O)(=O)—, $R^{22}$ is:

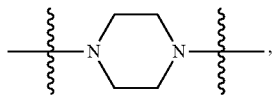

and $R^{23}$ is substituted phenyl.

In certain embodiments, $R^{20}$ is substituted phenyl, b is 0, c is 0, $R^{21}$ is cyclopropanediyl, a is 1, X is —C(=O)—, d is 1, $R^{22}$ is

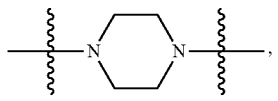

and $R^{23}$ is substituted phenyl. In one such embodiment, $R^{20}$ is halophenyl and $R^{23}$ is halo- and alkyl-substituted phenyl.

In certain embodiments, $R^{21}$ is —CH$_2$—, Y is S; and X is —S(=O)(=O)—.

In certain embodiments, $R^{22}$ is:

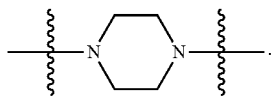 [SMILES: *N1CCN(*)CC1]

In certain embodiments, Y is S, O, S(=O), —S(=O)(=O)—; and X is —C(=O)—.

In certain embodiments, b is 0; c is 0; a is 1; and X is —C(=O)—.

In certain embodiments, b is 0; c is 0; a is 1; X is —C(=O)—; and $R^{21}$ is alkanediyl (particularly —CH$_2$CH$_2$—),

In certain embodiments, b is 0; c is 0; a is 1; X is —C(=O)—; $R^{21}$ is alkanediyl (particularly —CH$_2$CH$_2$—),

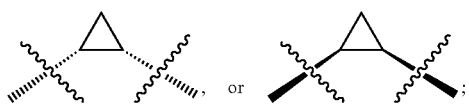

and $R^{22}$ is

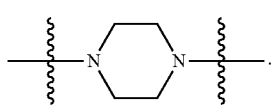

In certain embodiments, b is 0; c is 0; a is 1; X is —C(=O)—; $R^{21}$ is alkanediyl (particularly —CH$_2$CH$_2$—),

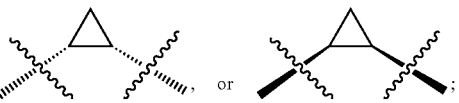

$R^{22}$ is

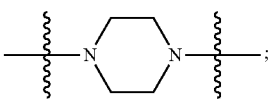

$R^{20}$ is phenyl, substituted phenyl, or substituted isoxazolyl; and $R^{23}$ is substituted phenyl.

In a further embodiment, the agent is a compound, or a pharmaceutically acceptable salt or ester thereof, having a formula II of:

$$R^{30}—(Z')_b—(Y')—(R^{31})_a—X'—R^{32}—R^{33}$$

wherein $R^{30}$ is an aryl, substituted aryl, heteroaryl, substituted heteroaryl, heterocycloalkyl, substituted heterocycloalkyl, alkoxy, aryloxy, amino, a thio-containing group, or a seleno-containing group;

Z' is alkanediyl, or substituted alkanediyl;

Y' is S;

$R^{31}$ is alkanediyl or substituted alkanediyl;

X is —C(=O)—;

$R^{32}$ is a moiety that includes at least one divalent amino radical;

$R^{33}$ is a phenyl substituted with at least one halogen or cyano;

a is 0 or 1; and b is 0 or 1.

In certain embodiments, $R^{30}$ is selected from isoxazolyl, substituted isoxazolyl (e.g, dialkyl-substituted such as dimethyl, hydroxy-substituted, hydroxyalkyl-substituted, or a combination thereof), oxazolyl, substituted oxazolyl (e.g, dialkyl-substituted such as dimethyl, hydroxy-substituted, hydroxyalkyl-substituted, or a combination thereof) cyclohexyl, substituted cyclohexyl (e.g., hydroxy-substituted cyclohexyl), piperidinyl, substituted piperidinyl (e.g., hydroxy-substituted piperidinyl), oxacyclopentyl, substituted oxacyclopentyl (e.g., hydroxyalkyl-substituted), oxacyclohexanyl, substituted oxacyclopentyl (e.g., hydroxyalkyl-substituted), thiophenyl, substituted thiophenyl (e.g., hydroxyalkyl-substituted), phenyl, substituted phenyl (e.g., hydroxyalkyl-substituted), pyridinyl, substituted pyridinyl (e.g., hydroxyalkyl-substituted), indolyl, substituted indolyl (e.g., hydroxyalkyl-substituted), furanyl, substituted furanyl (e.g., hydroxyalkyl-substituted), imidazolyl, substituted imidazolyl (e.g., hydroxyalkyl-substituted). In preferred embodiments, $R^{30}$ is substituted isoxazolyl, particularly dialkyl (e.g., dimethyl)-substituted isooxazolyl, or phenyl.

In certain embodiments, Z' is selected from $C_1$-$C_3$ alkanediyl, preferably —CH$_2$—.

In certain embodiments, $R^{31}$ is selected from $C_1$-$C_3$ alkanediyl or substituted $C_1$-$C_3$ alkanediyl (e.g., alkyl-substituted such as methyl or dimethyl), preferably $C_1$ alkanediyl.

In certain embodiments, $R^{32}$ is selected from:

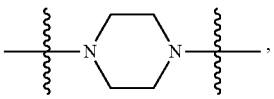

-continued

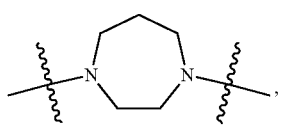

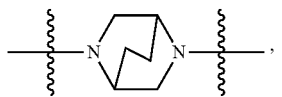

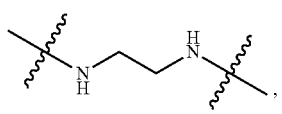

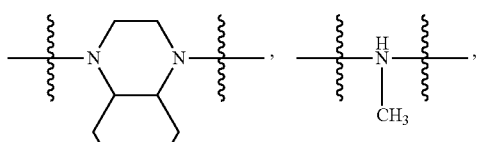

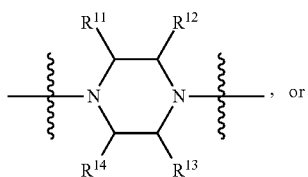

Preferably, $R^{33}$ is a substituted phenyl having a structure of:

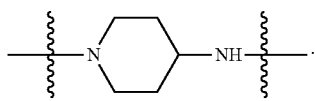

wherein each of $R^1$-$R^5$ is individually H, alkyl, halogen, or cyano, provided that at least one of $R^1$-$R^5$ is halogen or cyano. In certain embodiments, $R^1$ is alkyl, halogen or cyano.

In certain embodiments, $R^{30}$ is substituted isoxazolyl, b is 1; a is 1; $R^{21}$ is —CH$_2$—; and $R^{32}$ is:

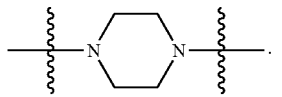

In a further embodiment, the agent is a compound, or stereoisomer, pharmaceutically acceptable salt, or an ester thereof according to formula III:

formula III

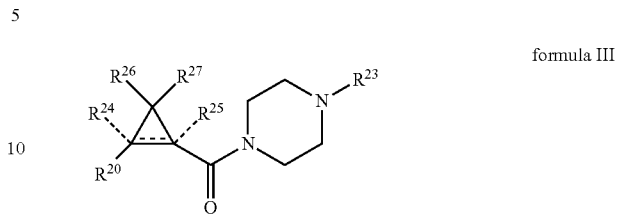

where the bond represented by "----" is a single or double bond. $R^{20}$ is (a) phenyl substituted with $C_1$-$C_3$ perfluoroalkyl, halo, or pentafluorosulfanyl, (b) thiophenyl substituted with $C_1$-$C_3$ alkyl, or (c) cycloalkyl substituted with $C_1$-$C_3$ perfluoroalkyl. $R^{23}$ is (a) phenyl mono- or di-substituted with substituents selected from halo, $C_1$-$C_3$ alkyl, $C_1$-$C_3$ perfluoroalkyl, pentafluorosulfanyl (—SF$_5$), cyano, —C(O)Oalkyl, or —C(O)N(H)alkyl (b) pyrimidinyl, (c) cycloalkyl, or (d) heterocycloalkyl. $R^{24}$ and $R^{25}$ are absent if the bond represented by ---- is a double bond, or $R^{24}$ and $R^{25}$ independently are hydrogen, deuterium, $C_1$-$C_3$ perhaloalkyl, halo, or cyano, or $R^{24}$ and $R^{25}$ together form —CH$_2$—. $R^{26}$ and $R^{27}$ independently are hydrogen, deuterium, or halo. In some embodiments, when $R^{24}$-$R^{27}$ are hydrogen, then $R^{20}$ is not halo-substituted phenyl.

In some examples, $R^{20}$ is phenyl substituted with —CF$_3$, —SF$_5$, or —F; thiophenyl substituted with —CH$_3$; or cyclohexyl substituted with —CF$_3$. In certain examples, $R^{20}$ is phenyl or cyclohexyl and is substituted at the C4 position. In other examples, $R^{20}$ is phenyl substituted at the C3 position.

In any of the foregoing examples, $R^{23}$ may be phenyl substituted with —CF$_3$; phenyl disubstituted with two halo substituents, halo and —CF$_3$, halo and —CH$_3$, or halo and cyano; pyrimidinyl; cyclohexyl; or heterocyclohexyl (e.g., containing a heteroatom or group selected from O, N(H), or N(CH$_3$)). In some examples, $R^{23}$ is a disubstituted phenyl and the two substituents are para to one another.

In certain embodiments, the compound, or a stereoisomer, pharmaceutically acceptable salt, or ester thereof, has a formula according to any one of formulas IV-XVII:

formula IV

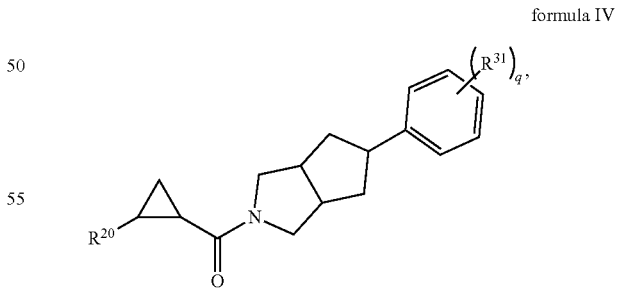

formula V

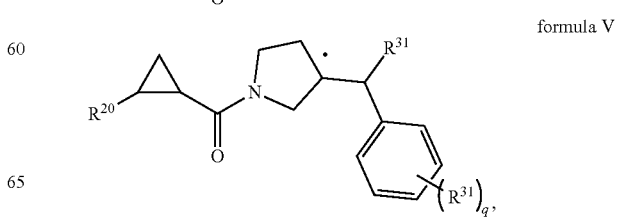

-continued formula VI
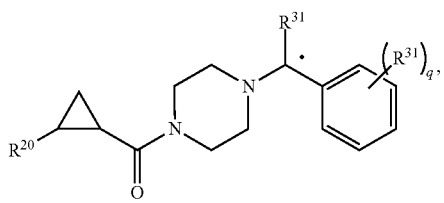

formula VII
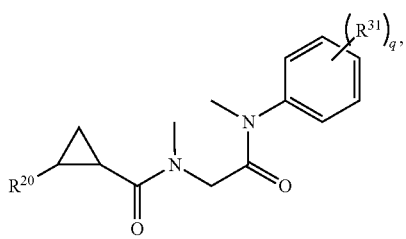

formula VIII
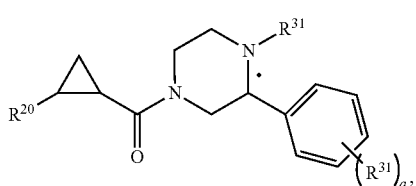

formula IX
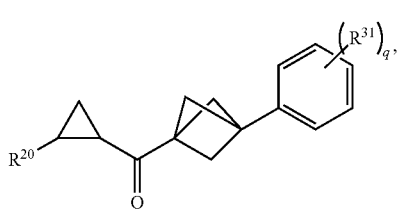

formula X
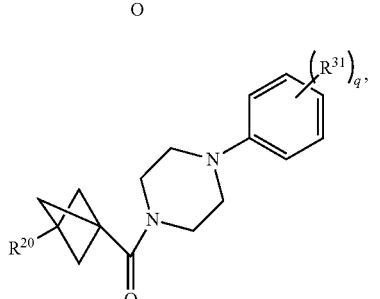

formula XI
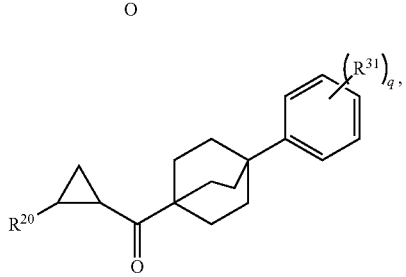

formula XII
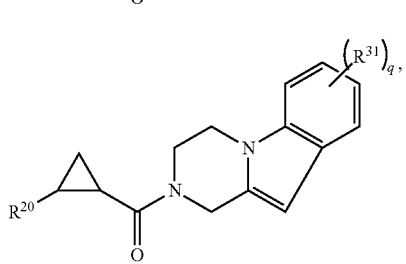

-continued formula XIII
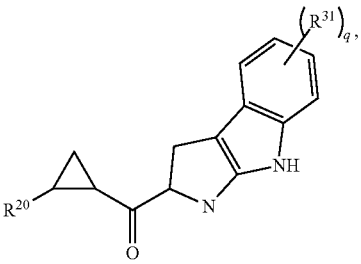

formula XIV
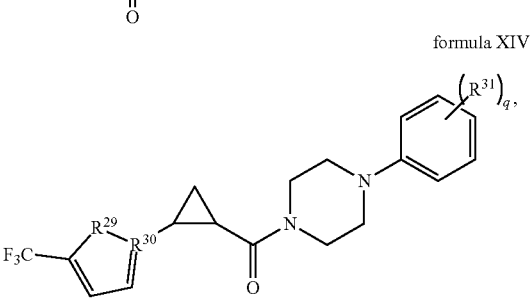

formula XV, XVI
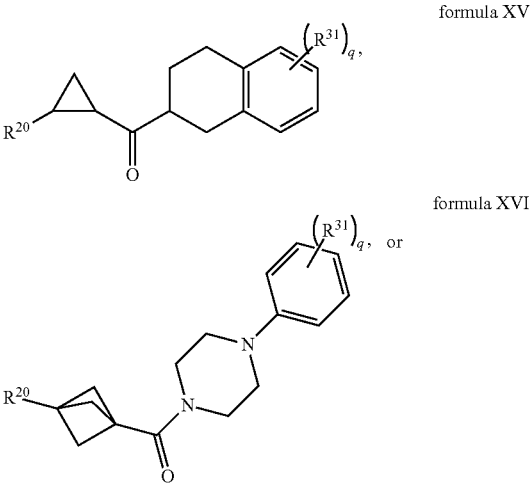

formula XVII
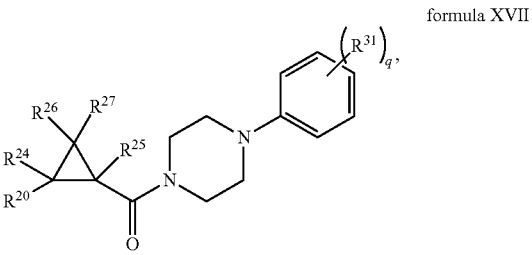

wherein $R^{20}$ is phenyl substituted with $C_1$-$C_3$ perfluoroalkyl, halo, or pentafluorosulfanyl; $R^{24}$-$R^{27}$ independently are hydrogen, deuterium, or halo; $R^{28}$ is O, N(CH$_3$), or CH$_2$; $R^{29}$ is N, O, or S; $R^{30}$ is CH or N; each $R^{31}$ independently is $C_1$-$C_3$ alkyl, $C_1$-$C_3$ perfluoroalkyl, halo, pentafluorosulfanyl, —C(O)Oalkyl, or C(O)N(H)alkyl; and q is 1, 2, or 3.

In any or all embodiments, $R^{20}$ may be phenyl substituted with —CF$_3$, —SF$_5$, or —F. In some embodiments, $R^{20}$ is substituted at the C3 or C4 position. In any or all embodiments, each $R^{31}$ independently may be $C_1$-$C_3$ alkyl, $C_1$-$C_3$ perfluoroalkyl, or halo. In any or all embodiments, each $R^{31}$ independently may be methyl, trifluoromethyl, or chloro. In any of the foregoing embodiments, q may be 2, and the $R^{31}$ substituents are para to one another.

Illustrative compounds are shown in FIGS. 1A-1H and 2A-2L. With respect to FIG. 2A-2L, each R independently is $C_1$-$C_3$ perfluoroalkyl, halo, pentafluorosulfanyl, —C(O)Oalkyl, or C(O)N(H)alkyl.

Figure 4:
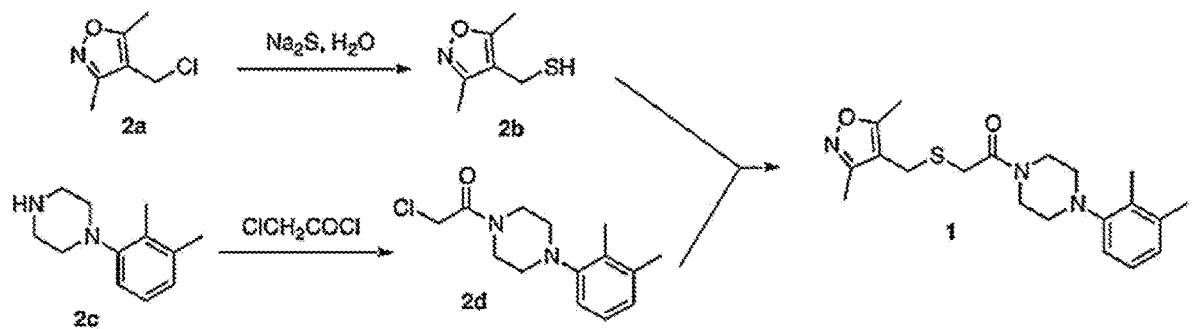
FIG. 4 is a reaction scheme showing the synthesis of 2-((isoxazol-4-ylmethyl)thio)-1-(4-phenylpiperazin-1-yl) ethanone 1.
Figure 5:
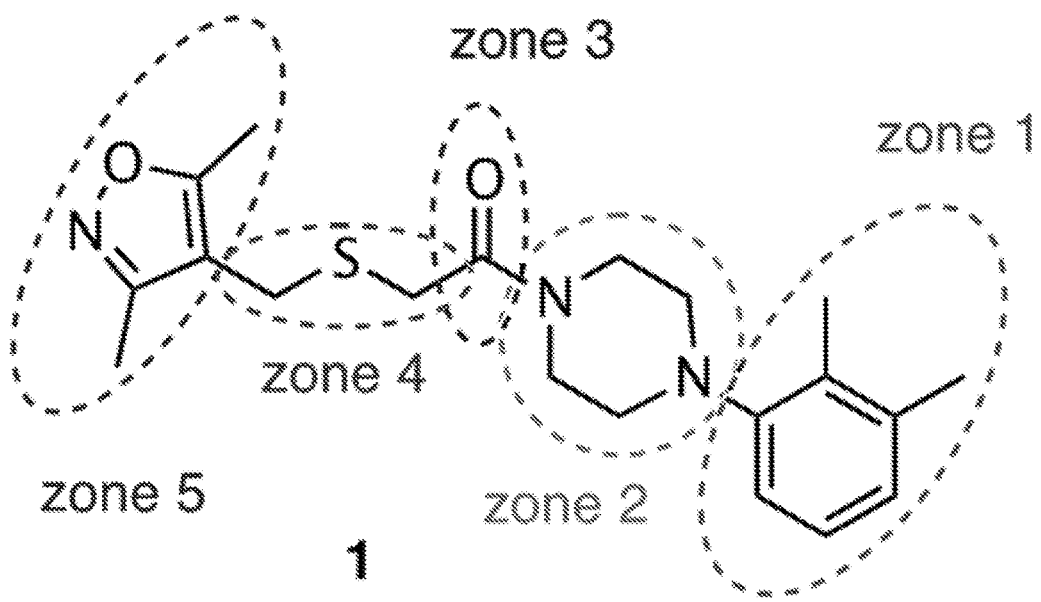
FIG. 5 is a chemical structure of 2-((isoxazol-4-ylmethyl) thio)-1-(4-phenylpiperazin-1-yl)ethanone showing zones of modification.

FIG. 4 shows a synthesis of a parent structure that is amenable to the modifications lined out in a zone model. Isoxazole 2a can be obtained from the chloromethylation of 3,5-dimethylisoxazole, or via the corresponding alcohol, and can be converted to thiol 2b. In situ alkylation of 2b with chloride 2d under the basic conditions of thiolate formation leads to 1. There are many methods known for pyridazine synthesis, and the preparation of 2c can follow one of these methods, for example starting with the aniline. Acylation of 2c with chloroacetyl chloride provides 2d. FIG. 5 shows zones of modification for compound 1. The building blocks for zones 1 and 4 have been selected to cover a large range of chemical diversity; in addition, they are commercially available and are therefore readily funneled into the segment-based synthesis plan. Zone 2 contains a few diamines that preserve the distance between zone 1 and zone 3, i.e. where the nitrogens are appropriately spaced, but this zone can also be contracted to a simple nitrogen linker in order to probe the need to maintain the overall distance and orientation between zone 1 and zone 4. Zone 3 contains another spacer functionality, but the amide carbonyl group might also be involved in specific interactions with the binding site on the protein. Therefore, the distance between the carboxyl function and the halide electrophile can be varied, and the carbonyl group can also be replaced by a sulfonyl function.

Figure 6:
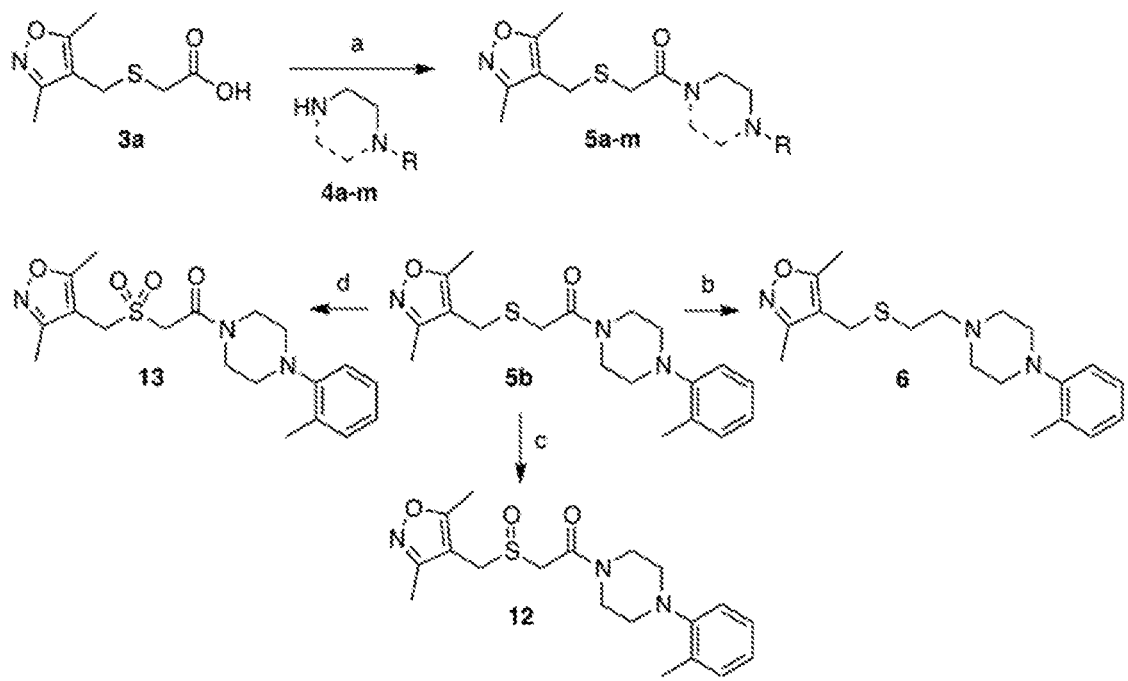
FIG. 6 is a reaction scheme showing synthesis of certain embodiments of the disclosed compounds. Reagents and conditions: (a) T3P (propylphosphonic anhydride), Et$_3$N (triethylamine), CH$_2$Cl$_2$, rt (room temperature), overnight, 52-98%; (b) LiAlH$_4$, dry THF (tetrahydrofuran), 0° C., 1 h, 42%; (c) NaIO$_4$, MeOH (methanol), H$_2$O, rt, 15 h, 68%; (d) m-CPBA (meta-chloroperoxybenzoic acid), CH$_2$Cl$_2$, rt, 15 h, 44%.

As described below, compounds 5a-h were synthesized directly from commercially available carboxylic acids 3a and N-arylated piperazines 4a-h under amide coupling conditions with T3P (Scheme 1 (FIG. 6) and Table 1) (Basavaprabhhu et al., *Synthesis* 2013, 45, 1569-1601). The diamine linker in zone 2 was examined in more detail through the synthesis of analogs 5i-5m. For these target molecules, the requisite diamines 4i-m were prepared by a Buchwald-Hartwig cross-coupling of mono Boc-protected diamines with bromoarenes (Cabello-Sanchez et al., *J. Org. Chem.* 2007, 72, 2030-2039; Larsen et al., *Tetrahedron* 2008, 64, 2938-2950). Reduction of amide 5b with lithium aluminum hydride led to diamine 6. For an initial set of zone 4 analogs, thioether 5b was also oxidized to sulfoxide 12 and sulfone 13 in good yields with sodium periodate and m-chloroperbenzoate, respectively (Scheme 1, FIG. 6).

Figure 7:
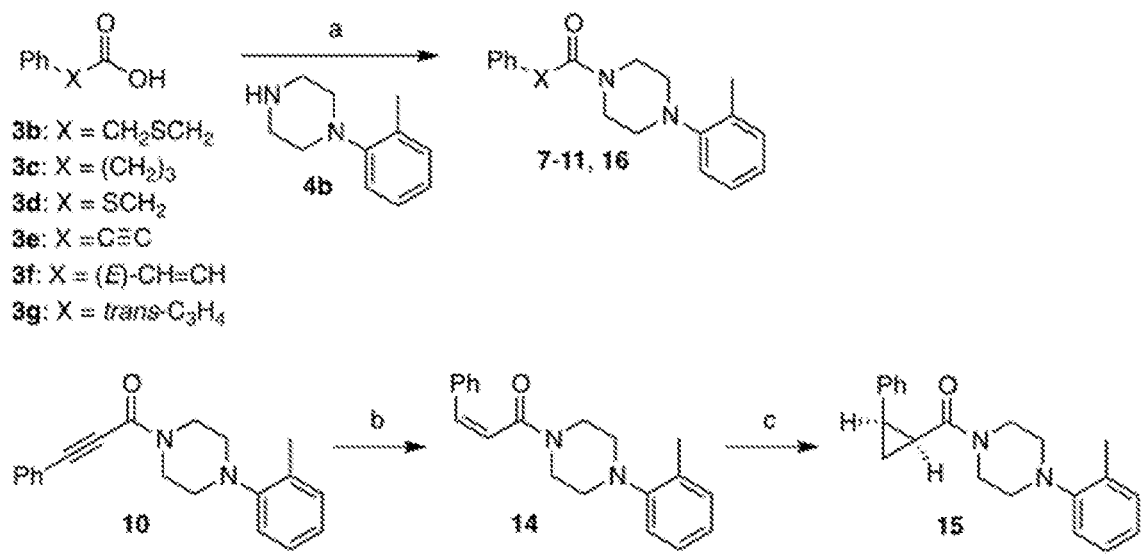
FIG. 7 is a reaction scheme showing synthesis of certain embodiments of the disclosed compounds. Reagents and conditions: (a) T3P, Et$_3$N, CH$_2$Cl$_2$, rt, overnight, 62-96%; (b) Lindlar's catalyst, quinoline, H$_2$, EtOAc (ethyl acetate), quant.; (c) CrCl$_2$, CH$_2$ICl, THF, reflux, overnight, 57%.

Additional zone 4 and zone 5 analogs with a phenyl group in place of the isoxazole ring were obtained from carboxylic acids 3b-3g (Scheme 2 (FIG. 7) and Table 1). Coupling to piperazine 4b provided amides 7-11 and 16 in high yields. Alkynyl amide 10 was further hydrogenated to cis-alkene 14 using a Lindlar catalyst. The cis-cyclopropane 15 was prepared by a Simmons-Smith cyclopropanation of cis-alkene 14 (Concellón et al., *Org. Lett.* 2007, 9, 2981-2984), whereas the trans-cyclopropane 16 was obtained by coupling of commercially available trans-2-phenylcyclopropanecarboxylic acid 3g with piperazine 4b.

Figure 8:
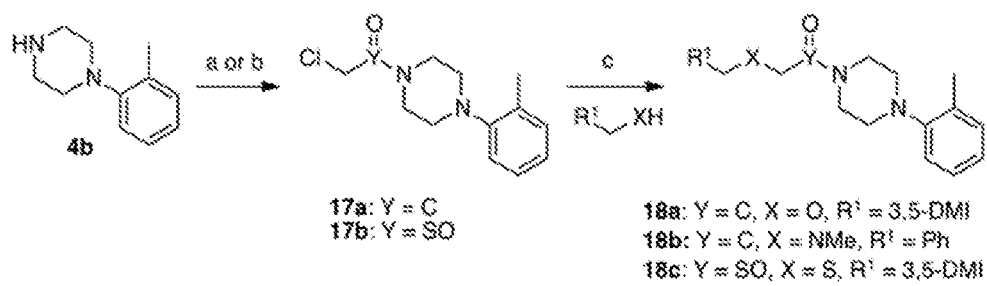
FIG. 8 is a reaction scheme showing synthesis of certain embodiments of the disclosed compounds. Reagents and conditions: (a) 2-chloroacetyl chloride, Et$_3$N, CH$_2$Cl$_2$, rt, overnight, 99%; (b) chloromethanesulfonyl chloride, Et$_3$N, CH$_2$Cl$_2$, rt, overnight, 85%; (c) NaH, THF, rt, 1-2 d, 4-99%; (d) DPPA (diphenyl phosphoryl azide), Et$_3$N, toluene, reflux, overnight, 17-65%.
Figure 8:
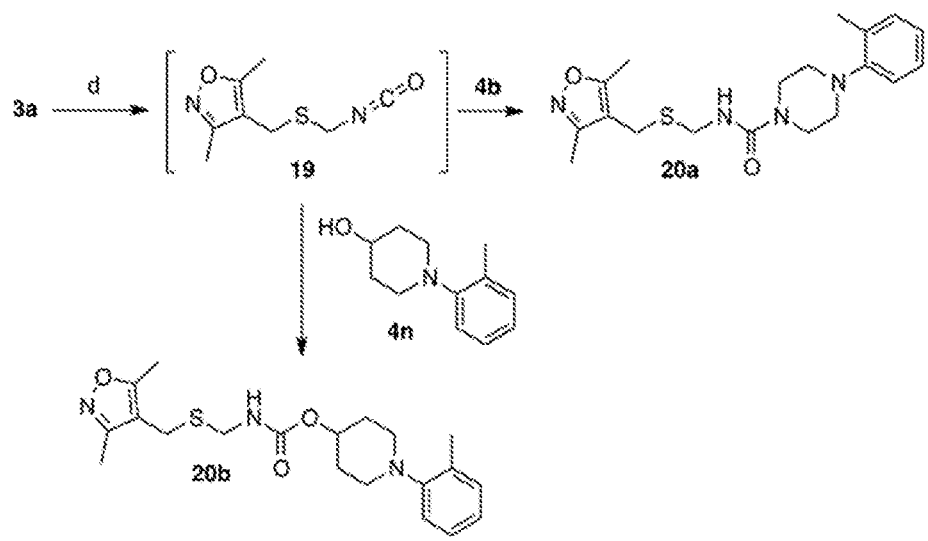

Further modifications in zones 3-4 were accomplished by acylation of piperazine 4b with either 2-chloroacetyl chloride or chloromethanesulfonyl chloride to form the corresponding amide 17a or sulfonamide 17b in good yields (Scheme 3 (FIG. 8) and Table 1). $S_N2$-reaction of 17a and 17b led to ether 18a, amine 18b, and thioether 18c. Starting with carboxylic acid 3a, urea 20a and carbamate 20b were obtained in moderate yields via a Curtius rearrangement and addition of the intermediate isocyanate 19 to amine 4b and alcohol 4n, respectively (Scheme 3, FIG. 8) (WO 2005/085275).

Figure 9:
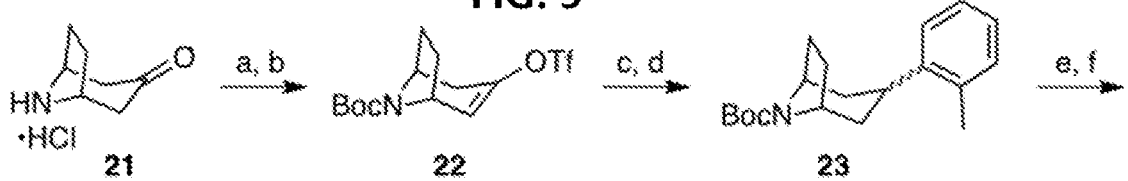
FIG. 9 is a reaction scheme showing synthesis of certain embodiments of the disclosed compounds. Reagents and conditions: (a) Boc$_2$O, DMAP, CH$_2$Cl$_2$, rt, overnight, 78%; (b) NaHMDS (sodium bis(trimethylsilyl)amide), PhNTf$_2$ (N-phenyl-bis(tifluoromethanesulfonamide), THF, −78° C. to rt, 4 h, 78%; (c) Pd(PPh$_3$)$_4$, LiCl, Na$_2$CO$_3$, (2-Me)PhB (OH)$_2$, DME (dimethoxyethane), H$_2$O, 60° C., 3 h, 78%; (d) H$_2$, Pd/C, EtOH (ethanol), rt, 14 h, 90%; (e) TFA (trifluoroacetic acid), CH$_2$Cl$_2$, rt, 16 h, quant.; (f) 2-chloroacetyl chloride, Et$_3$N, THF, rt, 22 h, 79%; (g) 25, NaH, THF, rt, 1 d, 30%.
Figure 9:
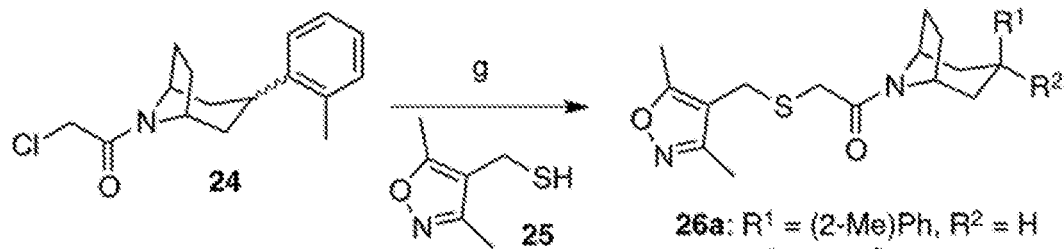

A bridged bicyclic ring was introduced to add a strong conformational constraint in zone 2 (Scheme 4 (FIG. 9) and Table 1). Boc-protection of nortropinone hydrochloride 21 followed by enolization with NaHMDS and trapping of the enolate with N-phenyltriflimide provided vinyl triflate 22 in good yield. A Suzuki coupling was used to install the o-tolyl group, and the styrene double bond was reduced with Pd/C to afford 23 as a mixture of diastereomers. Without separation, this mixture was deprotected and acylated with α-chloroacetyl chloride. Finally, the chloride was displaced using thiol 25 and sodium hydride to afford the thioether. Diastereomers 26a and 26b were separated by chromatography on $SiO_2$ to afford both analogs in modest yields.

TABLE 1

Structures of amine building blocks 4 and analogs 5, 7-11, and 16.

| Analog | Amine 4 | R | X |
|---|---|---|---|
| 5a | 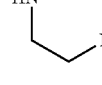 4a | Ph | — |
| 5b | 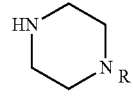 4b | (2-Me)Ph | — |
| 5c | 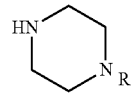 4c | (3-Me)Ph | — |
| 5d | 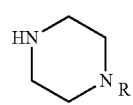 4d | (4-Me)Ph | — |
| 5e | 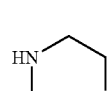 4e | (2-NC)Ph | — |
| 5f | 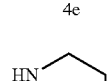 4f | (2-F)Ph | — |
| 5g | 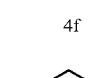 4g | 1-Naphthyl | — |

TABLE 1-continued

Structures of amine building blocks 4 and analogs 5, 7-11, and 16.

| Analog | Amine 4 | R | X |
|---|---|---|---|
| 5h | 4h | (2-MeO)Ph | — |
| 5i | 4i | (2-Me)Ph | — |
| 5j | 4j | (2-Me)Ph | — |
| 5k | 4k | (2-Me)Ph | — |
| 5l | 4l | Ph | — |
| 5m | 4m | (3-Me)Ph | — |
| 7 | 4b | (2-Me)Ph | $CH_2SCH_2$ |
| 8 | 4b | (2-Me)Ph | $(CH_2)_3$ |
| 9 | 4b | (2-Me)Ph | $SCH_2$ |
| 10 | 4b | (2-Me)Ph | C≡C |
| 11 | 4b | (2-Me)Ph | (E)-HC=CH |
| 16 | 4b | (2-Me)Ph | (E)-c-$C_3H_4$ |

Pharmaceutical Compositions and Method of Use

The agents disclosed herein may be administered to a subject for treating prostate cancer, particularly castration-resistant prostate cancer. In certain embodiments a subject is identified as having castration-resistant prostate cancer that may be responsive to the agents disclosed herein. For example, patients that are offered any form of androgen deprivation therapy or anti-androgen therapy, including treatment with abiraterone or MDV3100, for the management of prostate cancer would be candidates for treatment with the agents disclosed herein.

Administration of the agent may reduce the nuclear level of androgen receptor in castration-resistant prostate cancer (CRPC) cells relative to the untreated control CRPC cells. Reducing nuclear androgen receptor levels is expected to inhibit its activation. Reduction of androgen receptor activation can be determined via measuring androgen-responsive genes, such as prostate-specific antigen (PSA).

In certain embodiments, the agent may be co-administered with another therapeutic agent such as, for example, an immunostimulant, an anti-cancer agent, an antibiotic, or a combination thereof. In particular, the agents targeting AR nuclear localization could be used in combination with standard androgen deprivation therapy (ADT) or with abiratrone in the treatment of CRPC. In one embodiment, the agent is co-administered with MDV3100 (enzalutamide), which may produce synergistic results since MDV3100 targets the ligand binding domain whereas the agent targets other domain(s) of the androgen receptor.

The agents disclosed herein can be included in a pharmaceutical composition for administration to a subject. The pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

The pharmaceutical compositions may be in a dosage unit form such as an injectable fluid, an oral delivery fluid (e.g., a solution or suspension), a nasal delivery fluid (e.g., for delivery as an aerosol or vapor), a semisolid form (e.g., a topical cream), or a solid form such as powder, pill, tablet, or capsule forms.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The agents disclosed herein can be administered to subjects by a variety of mucosal administration modes, including by oral, rectal, intranasal, intrapulmonary, or transdermal delivery, or by topical delivery to other surfaces. Optionally, the agents can be administered by non-mucosal routes, including by intramuscular, subcutaneous, intravenous, intra-arterial, intra-articular, intraperitoneal, intrathecal, intracerebroventricular, or parenteral routes. In other alternative embodiments, the agents can be administered ex vivo by direct exposure to cells, tissues or organs originating from a subject.

To formulate the pharmaceutical compositions, the agents can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The agents can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The agents can be combined with the base or vehicle according to a variety of methods, and release of the agents can be by diffusion, disintegration of the vehicle, or associated formation of water channels. In some circumstances, the agent is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the agents can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the agents can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-caprolactone-CO-lactic acid), poly(epsilon.-caprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the agent can be delivered to a subject in a manner consistent with conventional methodologies associated with management of the disorder for which treatment or prevention is sought. In accordance with the disclosure herein, a prophylactically or therapeutically effective amount of the agent is administered to a subject in need of such treatment for a time and under conditions sufficient to prevent, inhibit, and/or ameliorate a selected disease or condition or one or more symptom(s) thereof.

The administration of the agent can be for either prophylactic or therapeutic purpose. When provided prophylactically, the agent is provided in advance of any symptom. The prophylactic administration of the agents serves to prevent or ameliorate any subsequent disease process. When provided therapeutically, the compound is provided at (or shortly after) the onset of a symptom of disease or infection.

For prophylactic and therapeutic purposes, the agent can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the agent can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the agents may simply inhibit or enhance one or more selected biological activities correlated with a disease or condition, as set forth herein, for either therapeutic or diagnostic purposes.

The actual dosage of the agents will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the agent for eliciting the desired activity or biological response in the subject. Dosage regimens can be adjusted to provide an optimum prophylactic or therapeutic response. A therapeutically effective amount is also one in which any toxic or detrimental side effects of the agent is outweighed in clinical terms by therapeutically beneficial effects. A non-limiting range for a therapeutically effective amount of an agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

Certain embodiments are described below in the following numbered clauses:
1. A compound, or a stereoisomer, pharmaceutically acceptable salt, or ester thereof, selected from:
(i) a compound according to formula III

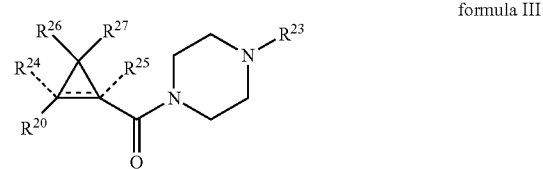

formula III where the bond represented by "-----" is a single or double bond; $R^{20}$ is (a) phenyl substituted with $C_1$-$C_3$ perfluoroalkyl, halo, or pentafluorosulfanyl, (b) thiophenyl substituted with $C_1$-$C_3$ alkyl, or (c) cycloalkyl substituted with $C_1$-$C_3$ perfluoroalkyl; $R^{23}$ is (a) phenyl mono- or di-substituted with substituents selected from halo, $C_1$-$C_3$ alkyl, $C_1$-$C_3$ perfluoroalkyl, pentafluorosulfanyl, cyano, —C(O)Oalkyl, or —C(O)N(H)alkyl (b) pyrimidinyl, (c) cycloalkyl, or (d) heterocycloalkyl; $R^{24}$ and $R^{25}$ are absent if the bond represented by "-----" is a double bond, or $R^{24}$ and $R^{25}$ independently are hydrogen, deuterium, $C_1$-$C_3$ perhaloalkyl, halo, or cyano, or $R^{24}$ and $R^{25}$ together form —CH$_2$—; and $R^{26}$ and $R^{27}$ independently are hydrogen, deuterium, or halo, wherein if $R^{24}$-$R^{27}$ are hydrogen, then $R^{20}$ is not halo-substituted phenyl; or (ii) a compound in Table A, where each R independently is $C_1$-$C_3$ perfluoroalkyl, halo, pentafluorosulfanyl, —C(O)Oalkyl, or C(O)N(H)alkyl, $R^{28}$ is O, N(CH$_3$), or CH$_2$, $R^{29}$ is N, O, or S, and $R^{30}$ is CH or N

TABLE A

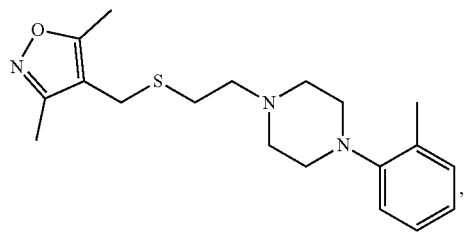 [SMILES: Cc1ccccc1N1CCN(CCSCc2c(C)noc2C)CC1]

,

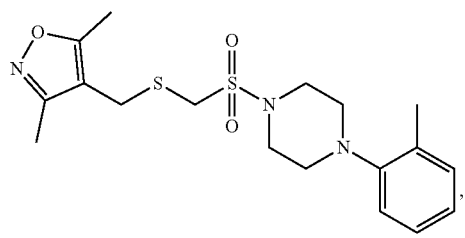 [SMILES: Cc1ccccc1N1CCN(S(=O)(=O)CSCc2c(C)noc2C)CC1]

,

TABLE A-continued
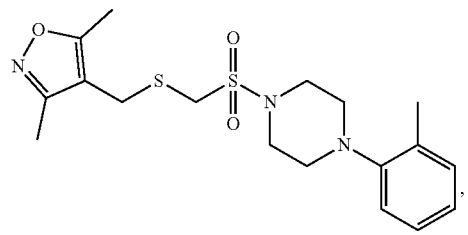 [SMILES: Cc1ccccc1N1CCN(S(=O)(=O)CSCc2c(C)noc2C)CC1],
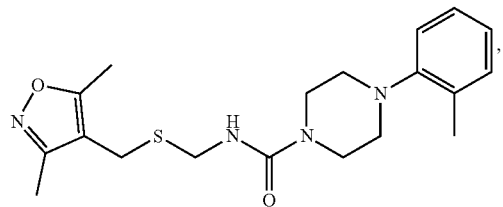 [SMILES: Cc1ccccc1N1CCN(C(=O)NCSCc2c(C)noc2C)CC1],
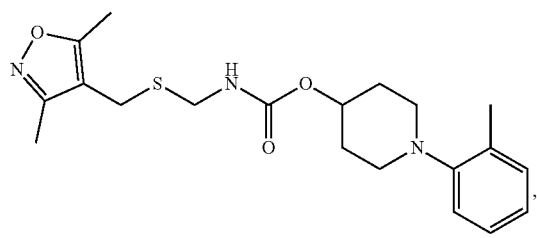 [SMILES: Cc1ccccc1N1CCC(OC(=O)NCSCc2c(C)noc2C)CC1],
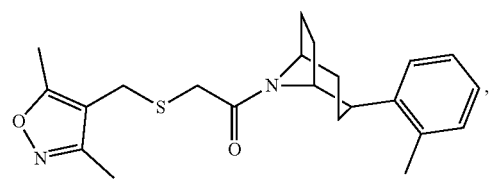 [SMILES: Cc1ccccc1C1CCC2CCC1N2C(=O)CSCc1c(C)noc1C],
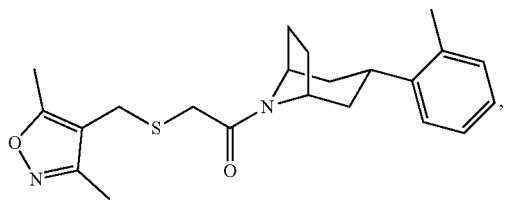 [SMILES: Cc1ccccc1C1CC2CCC(C1)N2C(=O)CSCc1c(C)noc1C],
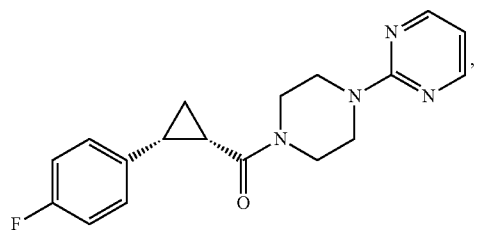 [SMILES: O=C([C@H]1C[C@H]1c1ccc(F)cc1)N1CCN(c2ncccn2)CC1],
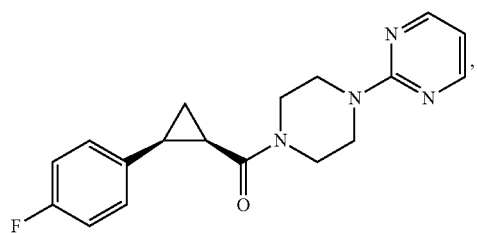 [SMILES: O=C([C@@H]1C[C@@H]1c1ccc(F)cc1)N1CCN(c2ncccn2)CC1], TABLE A-continued
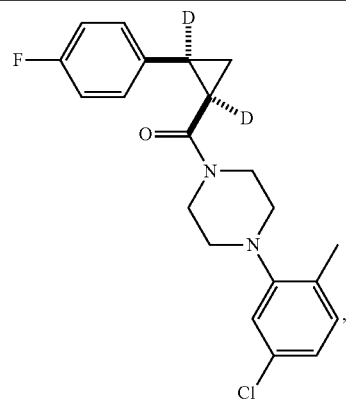
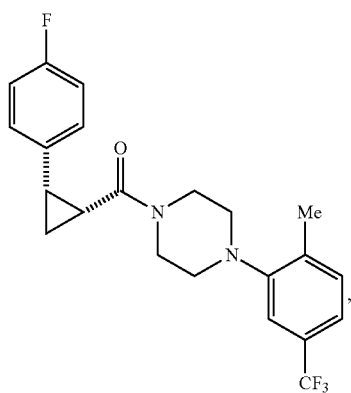
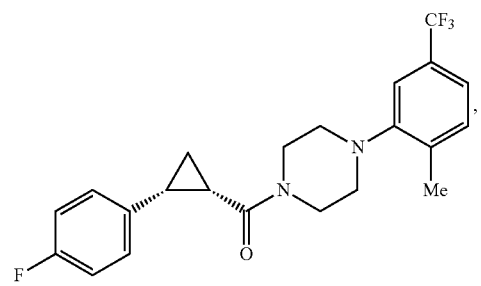 [SMILES: Cc1ccc(C(F)(F)F)cc1N1CCN(C(=O)[C@H]2C[C@H]2c2ccc(F)cc2)CC1]
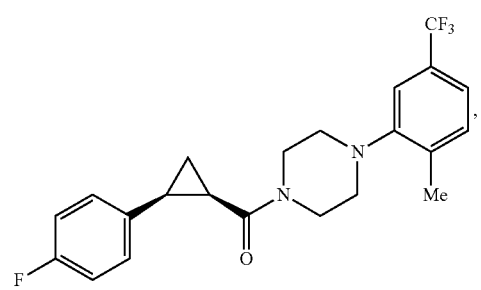 [SMILES: Cc1ccc(C(F)(F)F)cc1N1CCN(C(=O)[C@@H]2C[C@@H]2c2ccc(F)cc2)CC1]
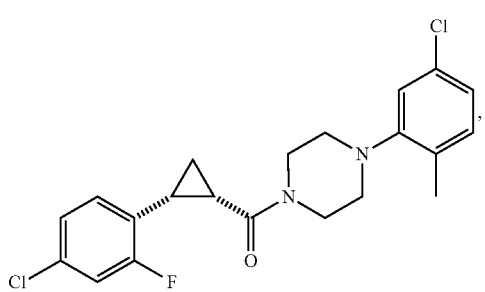

TABLE A-continued
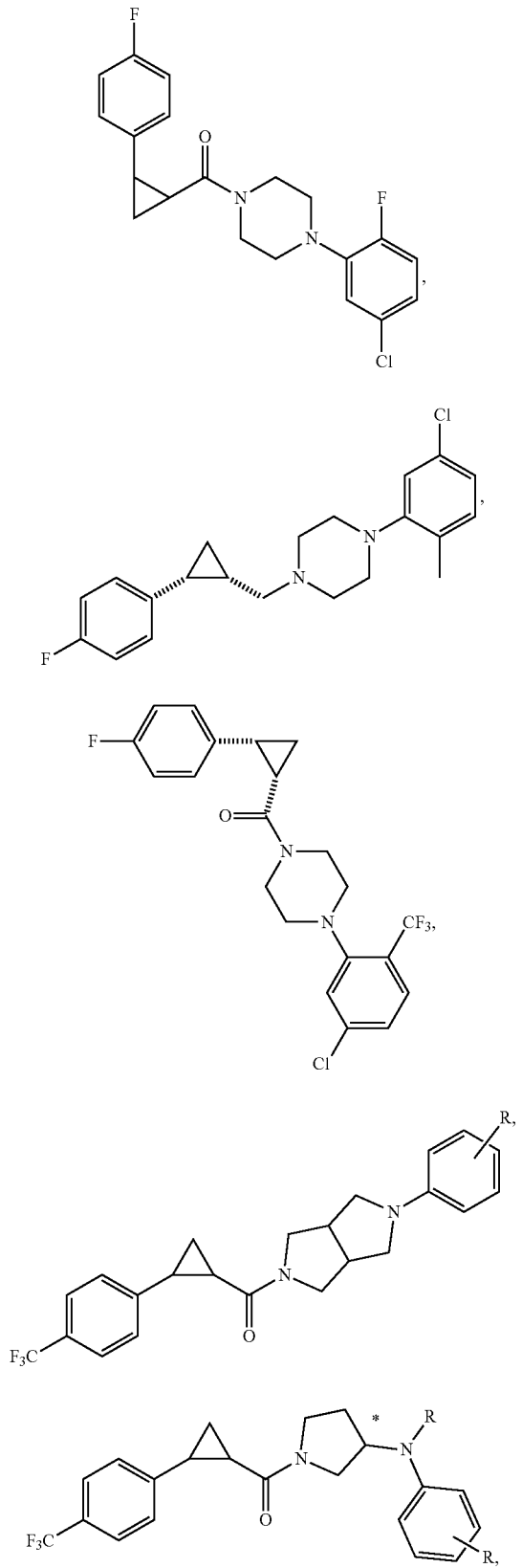

TABLE A-continued
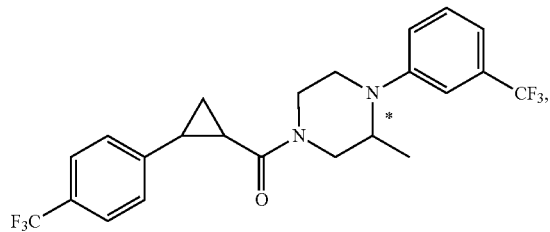 [SMILES: CC1CN(C(=O)C2CC2c2ccc(C(F)(F)F)cc2)CCN1c1cccc(C(F)(F)F)c1]
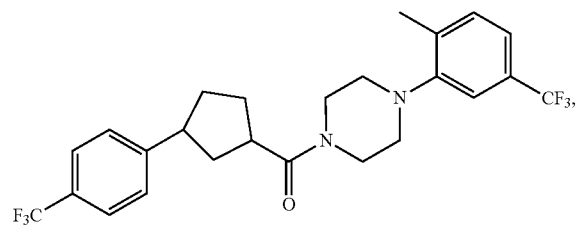 [SMILES: Cc1ccc(C(F)(F)F)cc1N1CCN(C(=O)C2CCC(c3ccc(C(F)(F)F)cc3)C2)CC1]
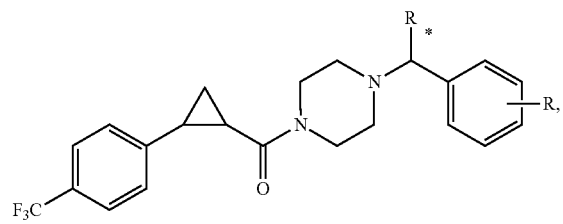
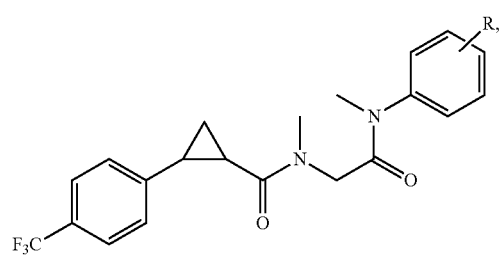
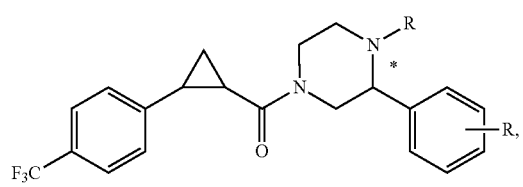
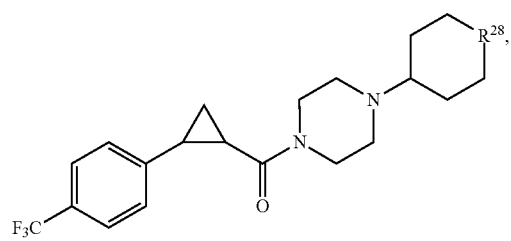

TABLE A-continued
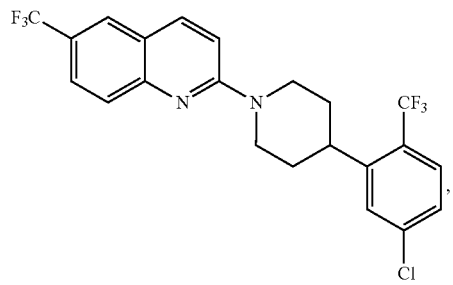 [SMILES: FC(F)(F)c1ccc2nc(N3CCC(c4cc(Cl)ccc4C(F)(F)F)CC3)ccc2c1]
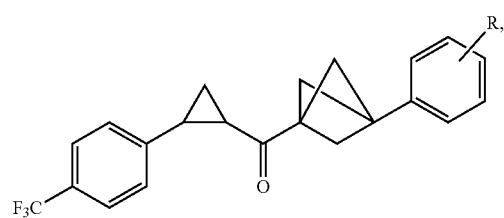
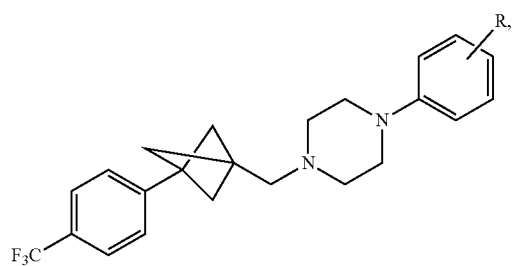
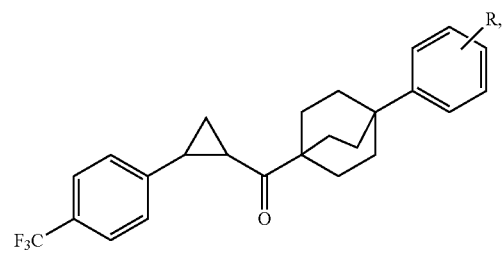
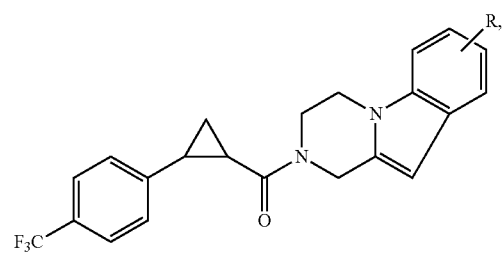
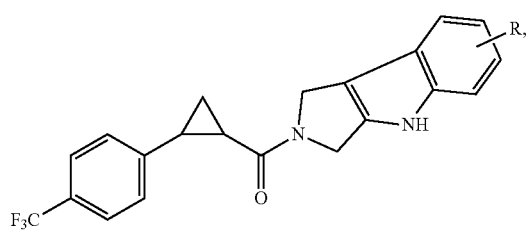

TABLE A-continued
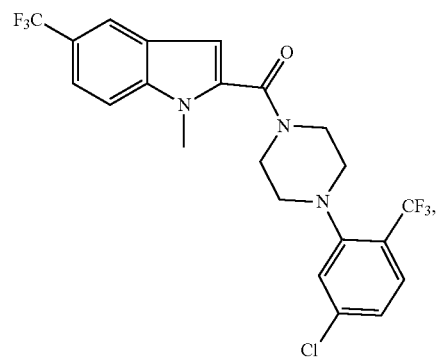 [SMILES: Cn1c(C(=O)N2CCN(c3cc(Cl)ccc3C(F)(F)F)CC2)cc2cc(C(F)(F)F)ccc21]
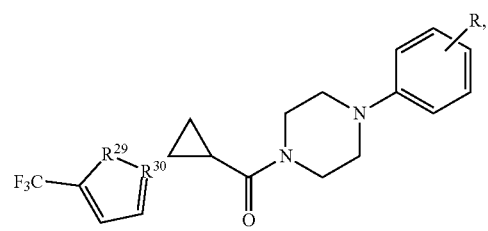
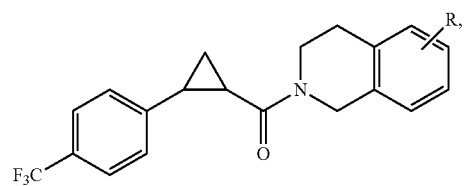
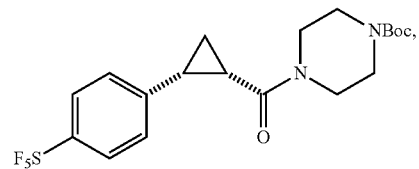
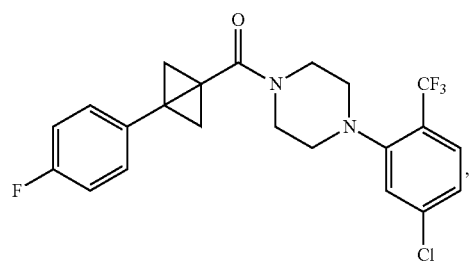 [SMILES: O=C(N1CCN(c2cc(Cl)ccc2C(F)(F)F)CC1)C12CC1(c1ccc(F)cc1)C2]
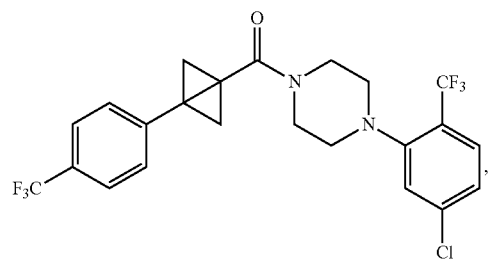

TABLE A-continued
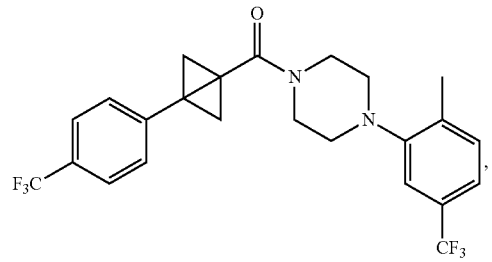 [SMILES: Cc1ccc(C(F)(F)F)cc1N1CCN(C(=O)C23CC2(c2ccc(C(F)(F)F)cc2)C3)CC1]
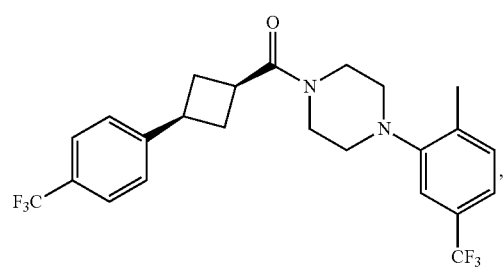 [SMILES: Cc1ccc(C(F)(F)F)cc1N1CCN(C(=O)[C@H]2C[C@@H](c3ccc(C(F)(F)F)cc3)C2)CC1]
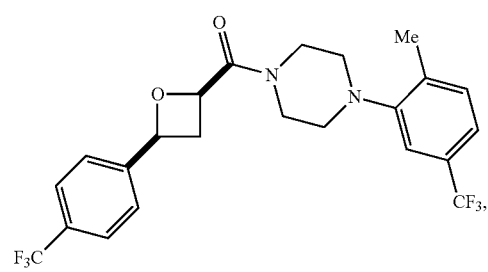
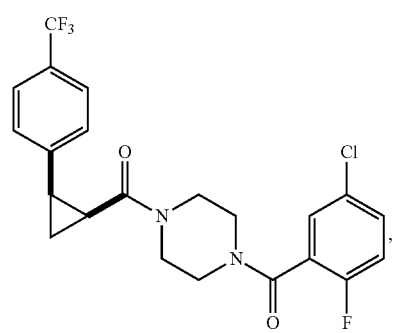
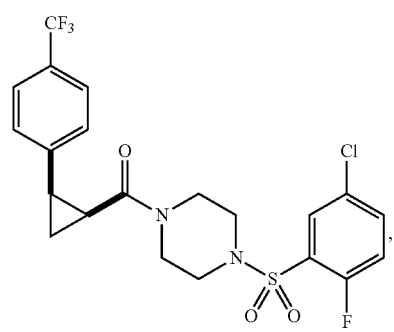

TABLE A-continued
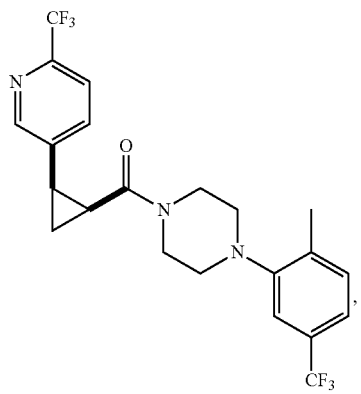
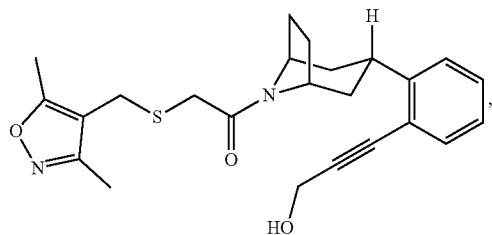 [SMILES: Cc1noc(C)c1CSCC(=O)N1C2CCC1CC(c1ccccc1C#CCO)C2]
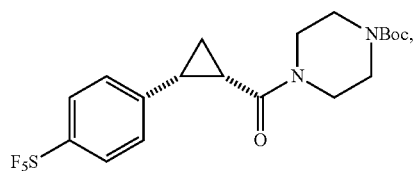
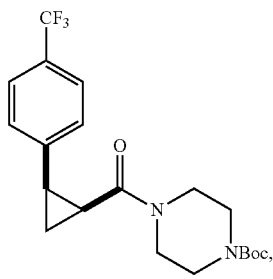
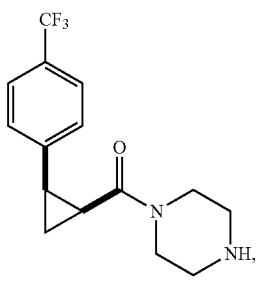
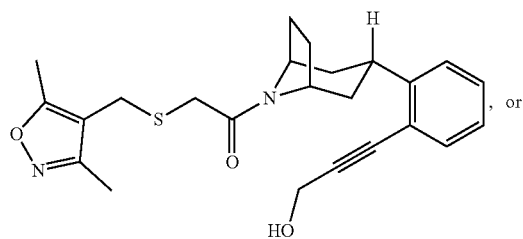 [SMILES: Cc1noc(C)c1CSCC(=O)N1C2CCC1CC(c1ccccc1C#CCO)C2]

TABLE A-continued

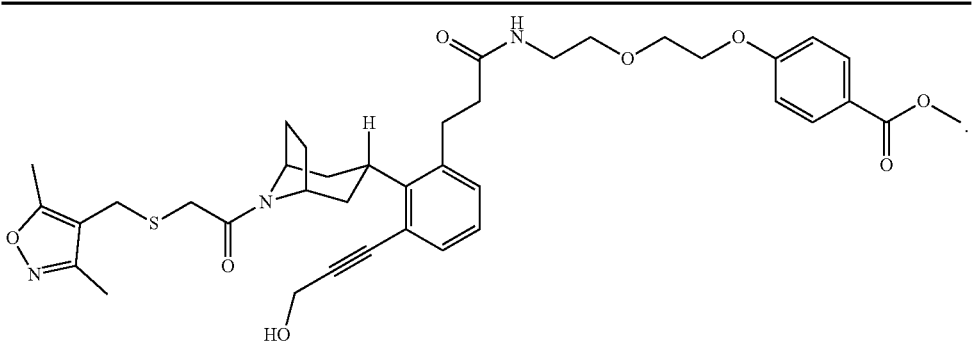

2. The compound of clause 1, wherein $R^{20}$ is: phenyl substituted with —$CF_3$, —$SF_5$, or —F; thiophenyl substituted with —$CH_3$; or cyclohexyl substituted with —$CF_3$.

3. The compound of clause 2, wherein $R^{20}$ is phenyl or cyclohexyl and is substituted at the C4 position.

4. The compound of any one of clauses 1-3, wherein $R^{23}$ is: phenyl substituted with —$CF_3$; phenyl disubstituted with two halo substituents, halo and —$CF_3$, halo and —$CH_3$, or halo and cyano; pyrimidinyl; cyclohexyl; or heterocyclohexyl.

5. The compound of clause 4, wherein $R^{23}$ is disubstituted phenyl and the two substituents are para to one another.

6. The compound of clause 1, wherein the compound is:

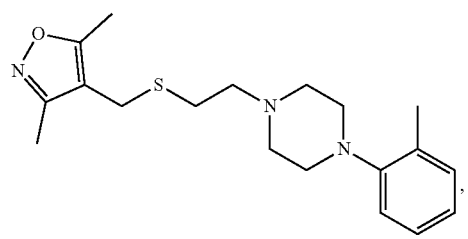

,

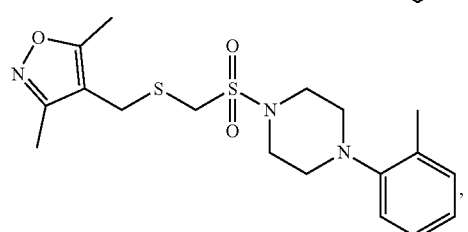

,

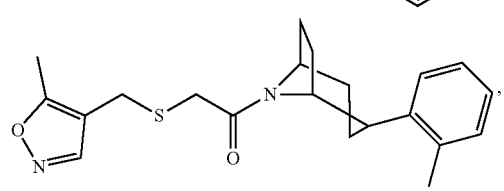

,

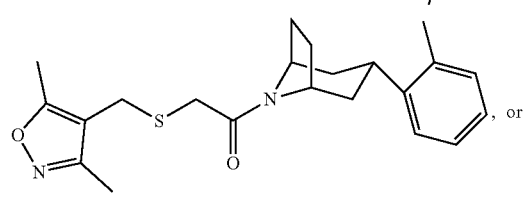

, or

7. The compound of clause 1, wherein the compound is:

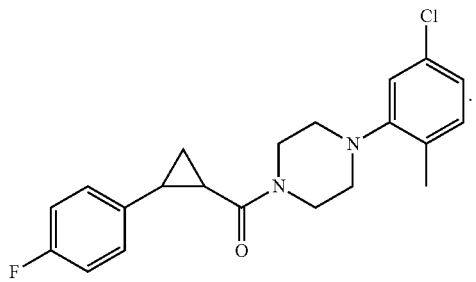

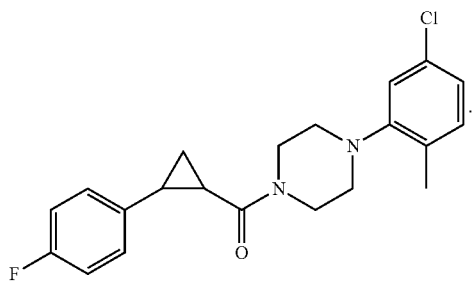 [SMILES: Cc1ccc(Cl)cc1N1CCN(C(=O)C2CC2c2ccc(F)cc2)CC1]

,

8. The compound of clause 1, wherein the compound is:

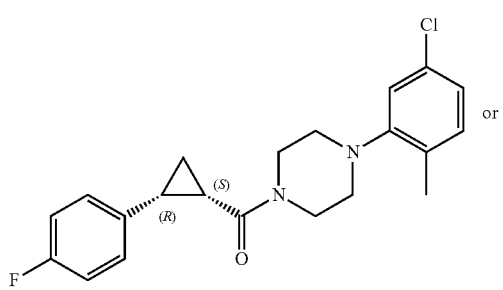

or

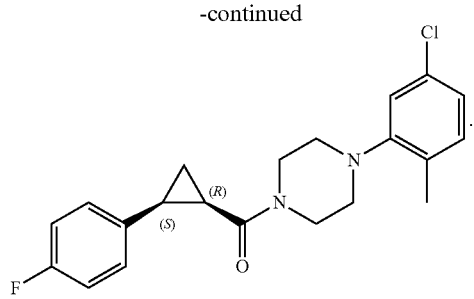
9. The compound of clause 1, wherein the compound is:
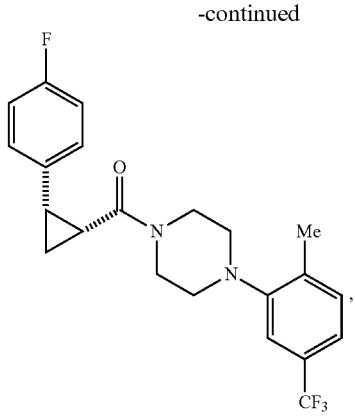
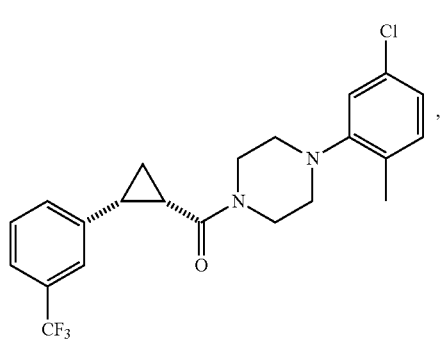
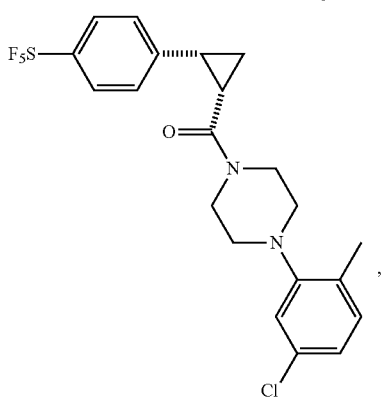
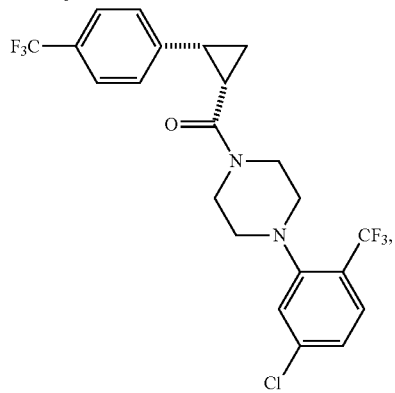
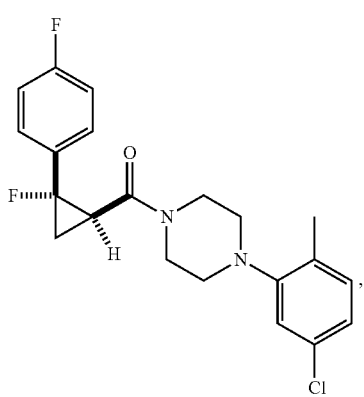
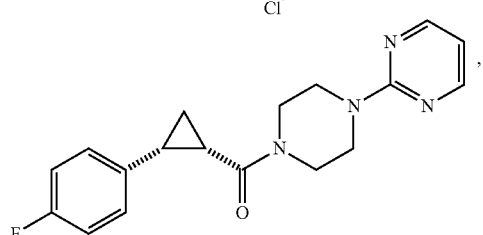
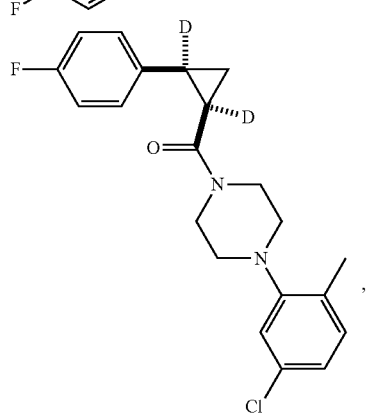
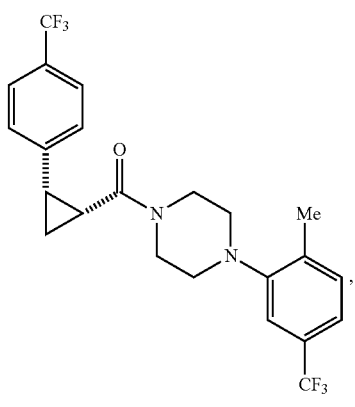

51
-continued
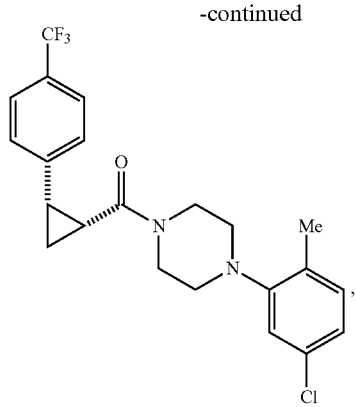
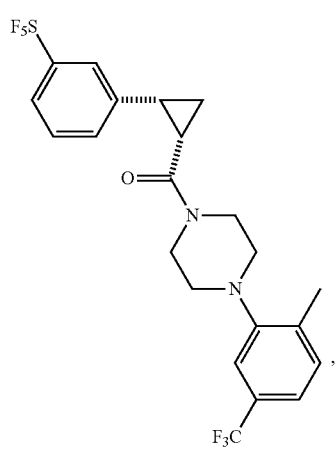
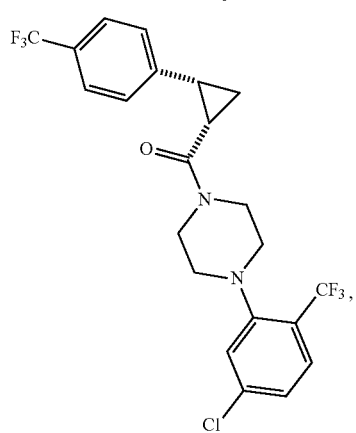
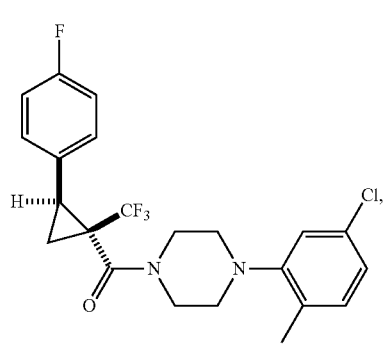
52
-continued
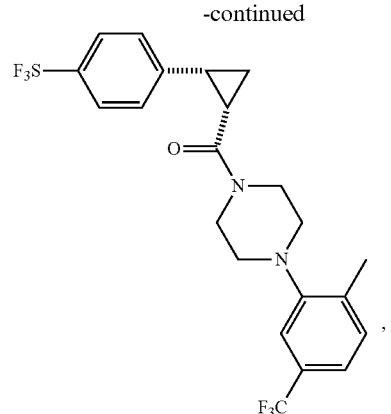
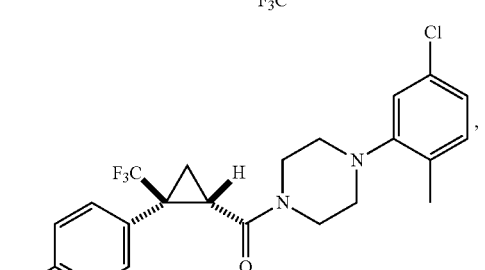
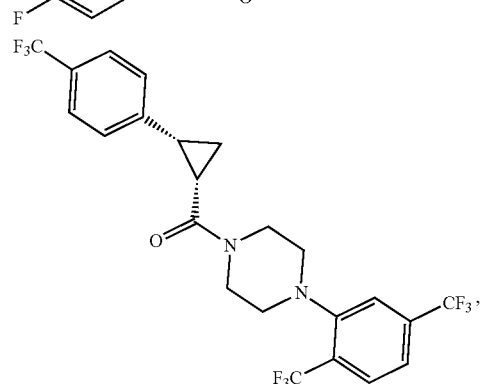
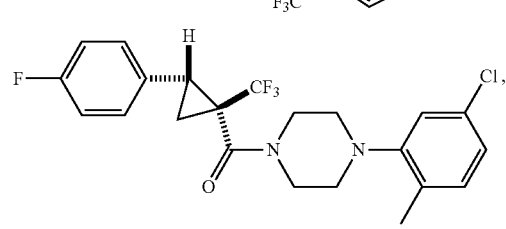
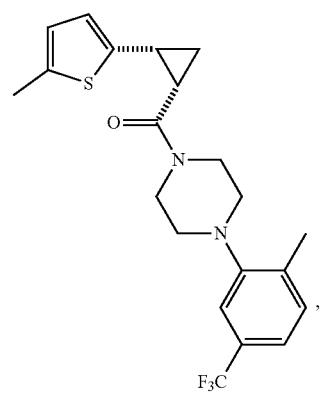

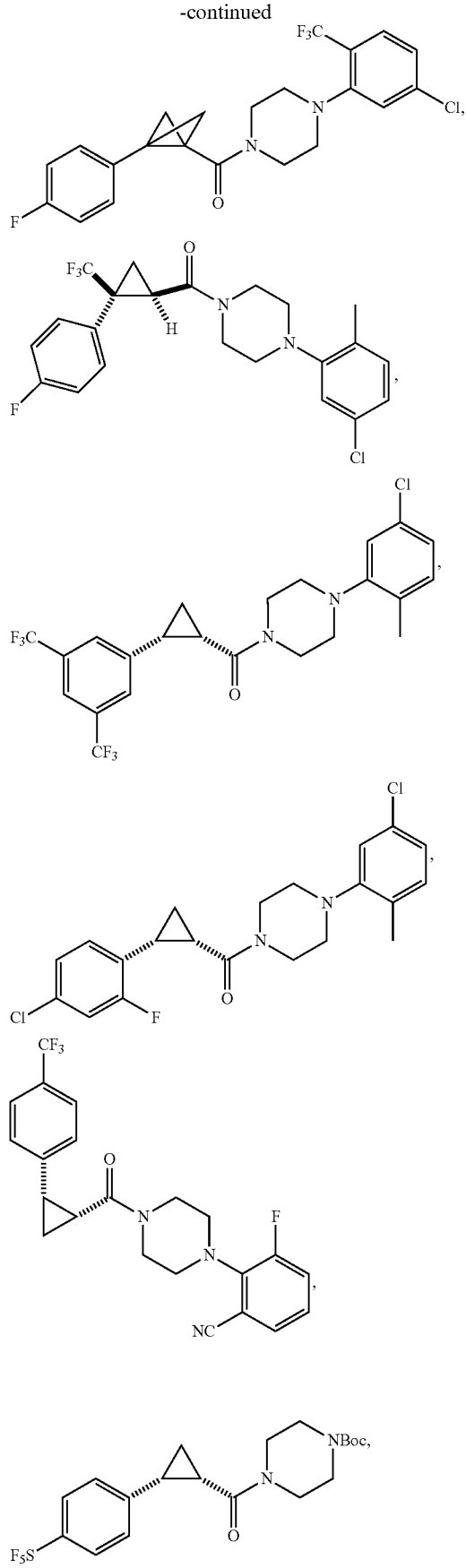
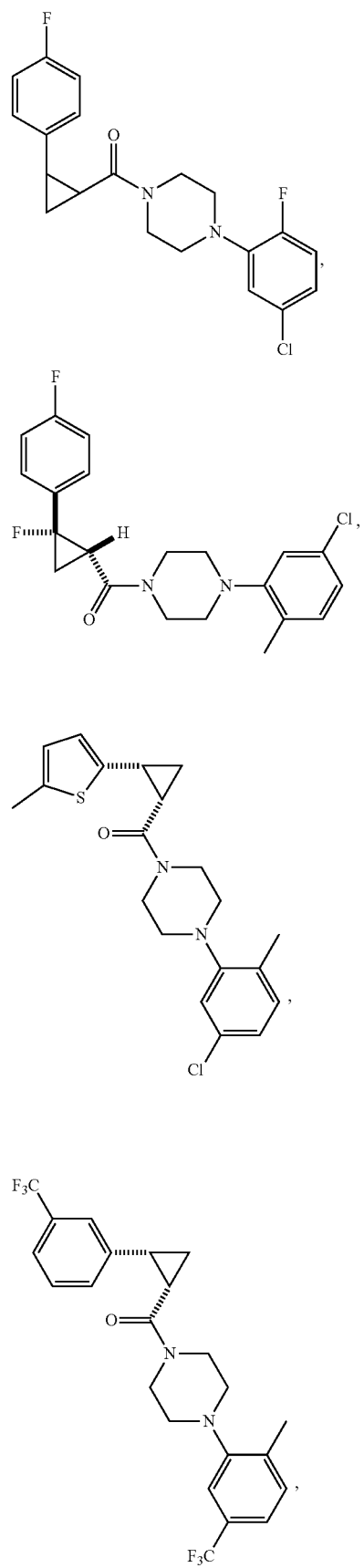

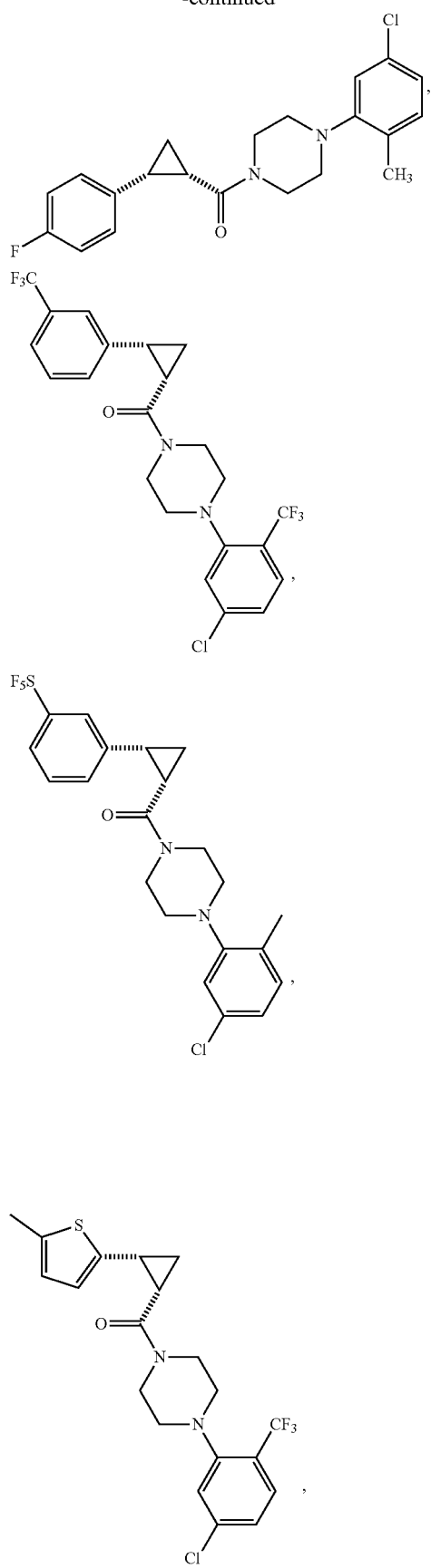
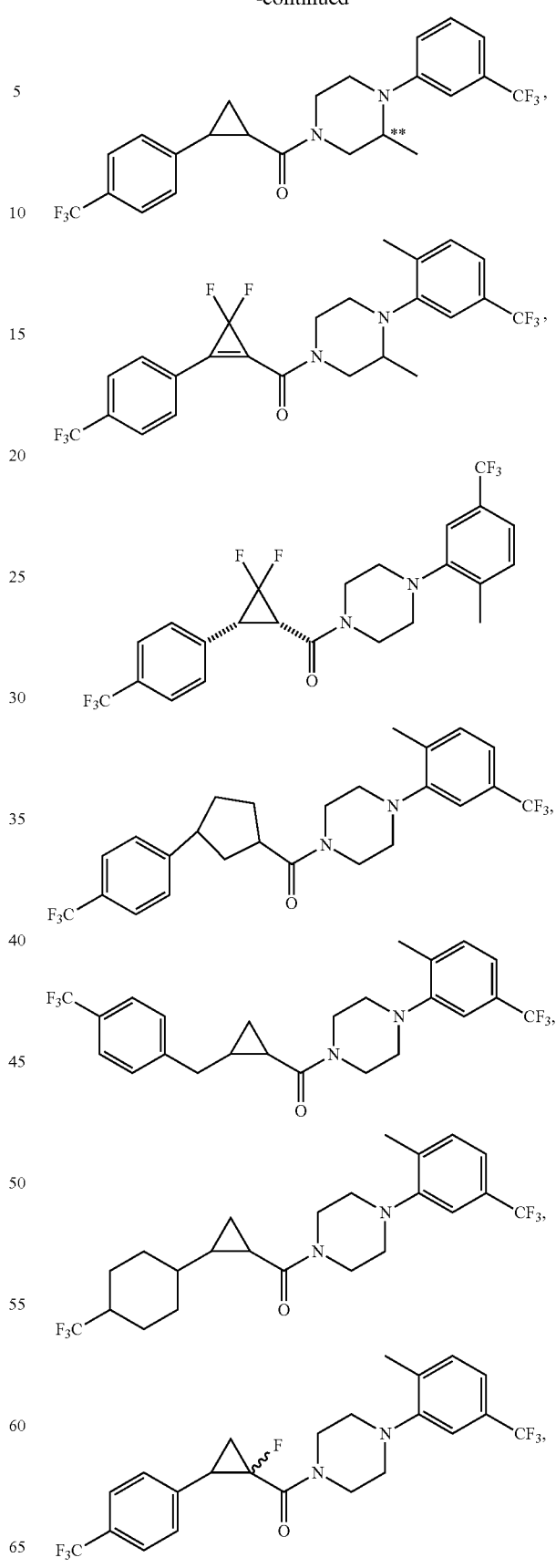

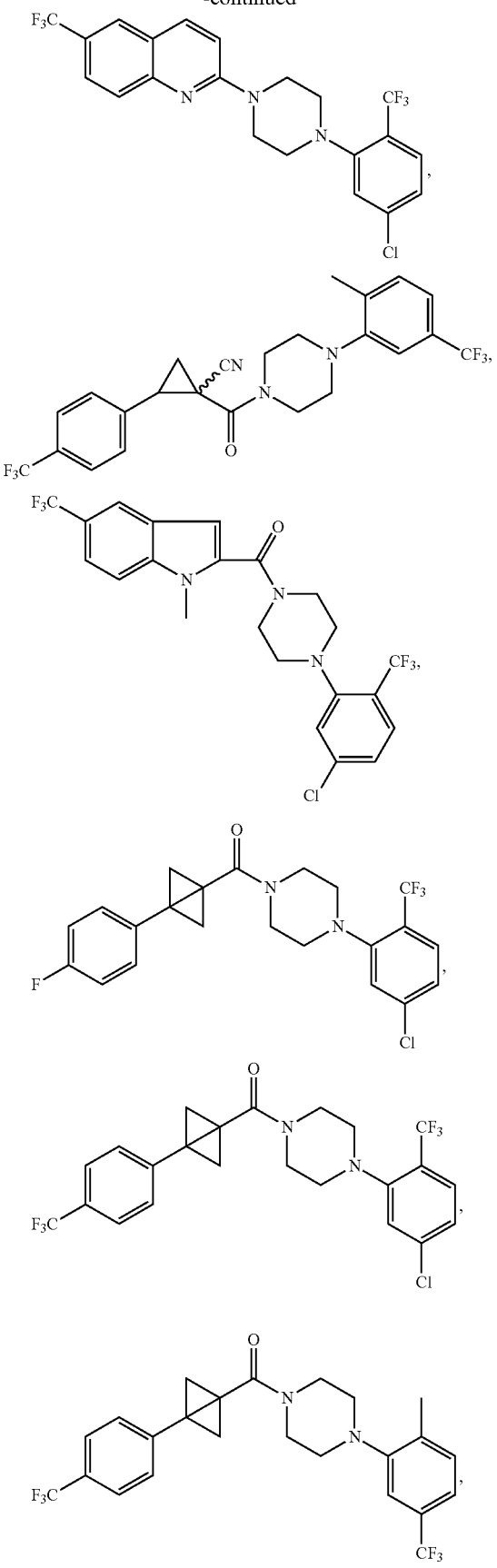
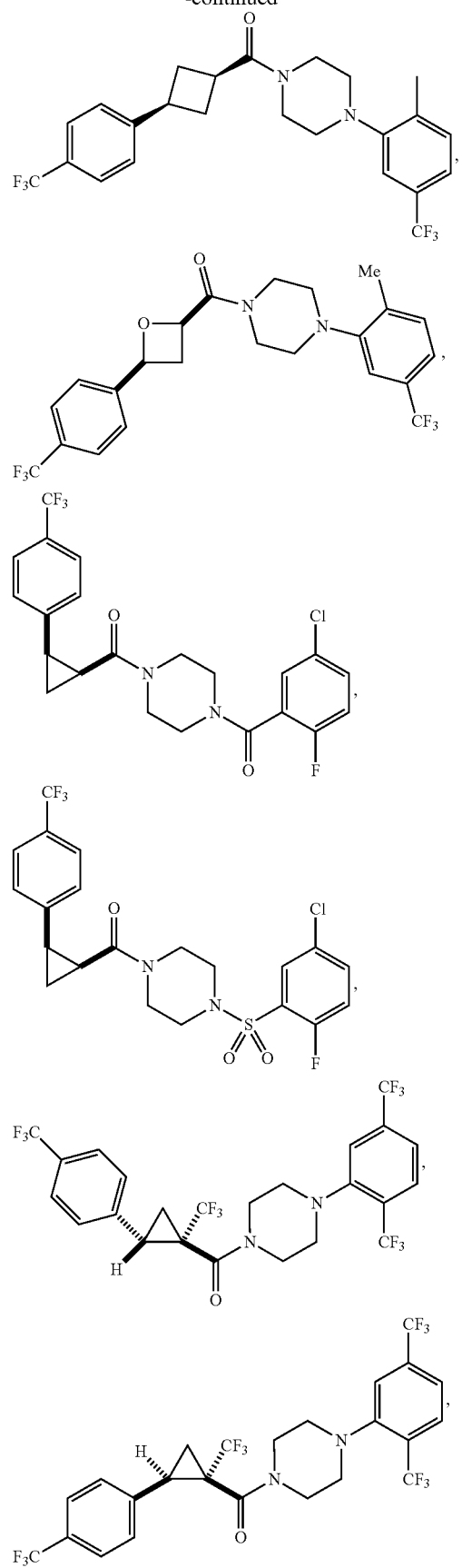

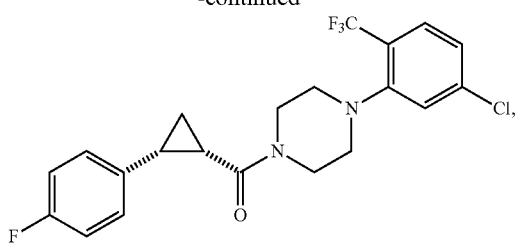
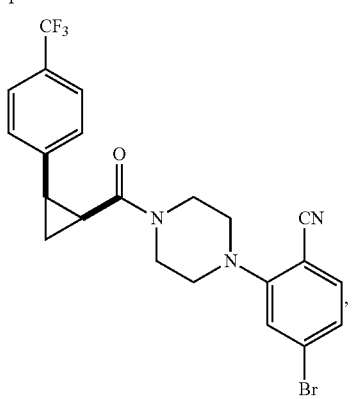
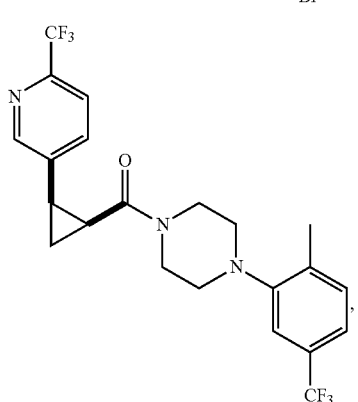
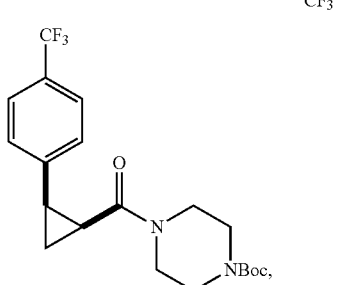
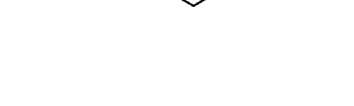
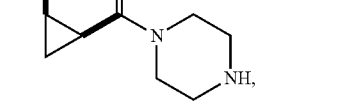
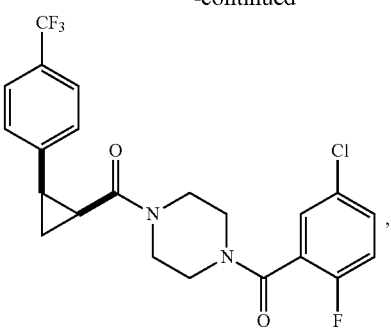
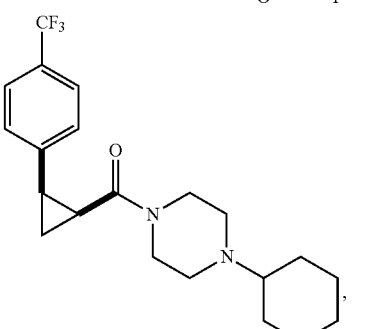
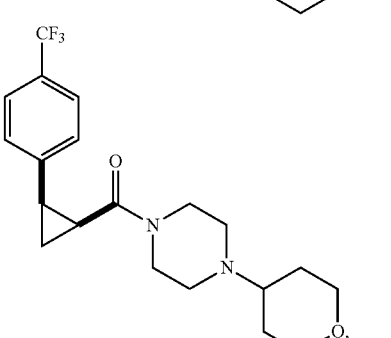
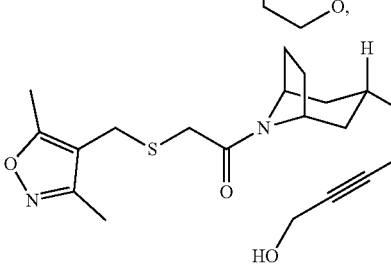
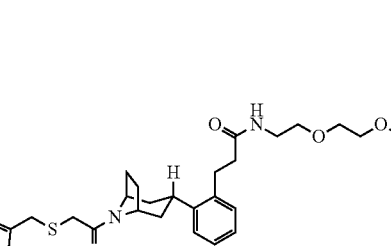
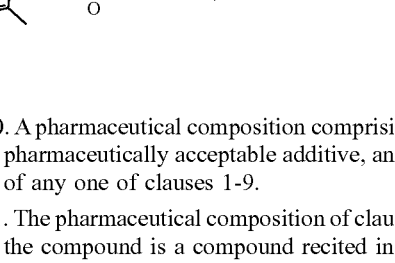
10. A pharmaceutical composition comprising at least one pharmaceutically acceptable additive, and a compound of any one of clauses 1-9.
11. The pharmaceutical composition of clause 10, wherein the compound is a compound recited in clause 6.

12. The pharmaceutical composition of clause 10, wherein the compound is:

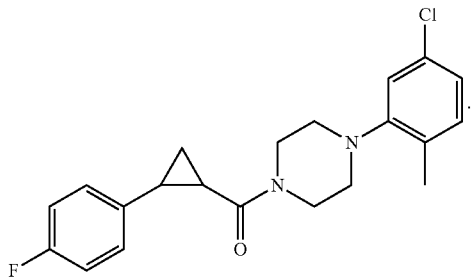 [SMILES: Cc1ccc(Cl)cc1N1CCN(C(=O)C2CC2c2ccc(F)cc2)CC1]

13. The pharmaceutical composition of clause 10, wherein the compound is:

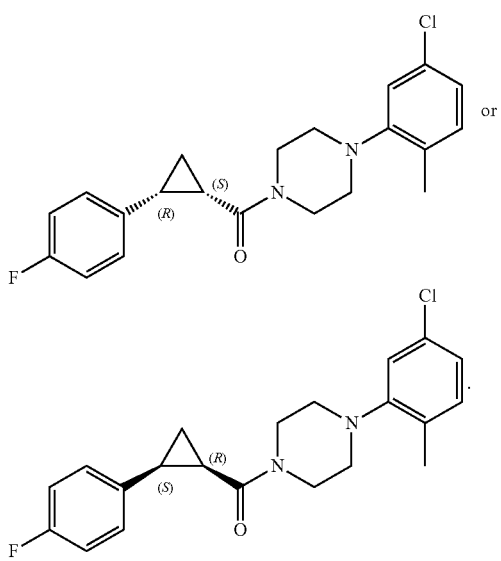

14. The pharmaceutical composition of clause 10, wherein the compound is a compound recited in clause 9.
15. A method for treating prostate cancer in a subject, comprising administering to the subject a therapeutically effective amount of a compound of any one of clauses 1-9.
16. The method of clause 15, wherein the prostate cancer is castration-resistant prostate cancer.
17. The method of clause 15 or clause 16, wherein the compound is orally administered.
18. The method of any one of clauses 15-17, wherein the method is used in combination with androgen deprivation therapy.
19. The method of any one of clauses 15-18, wherein the agent is co-administered with abiratrone.
20. The method of any one of clauses 15-18, wherein the agent is co-administered with enzalutamide.
21. The method of any one of clauses 15-20, wherein the method further comprises identifying a subject that is in need of treatment with the agent.
22. The method of any one of clauses 15-21, wherein the compound is a compound recited in clause 6.
23. The method of any one of clauses 15-21 wherein the compound is:

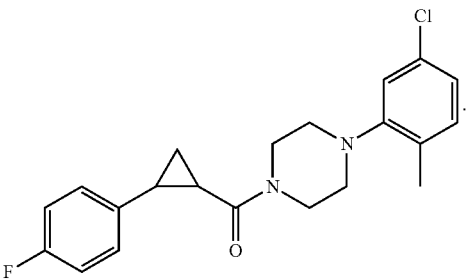 [SMILES: Cc1ccc(Cl)cc1N1CCN(C(=O)C2CC2c2ccc(F)cc2)CC1]

24. The method of any one of clauses 15-21, wherein the compound is:

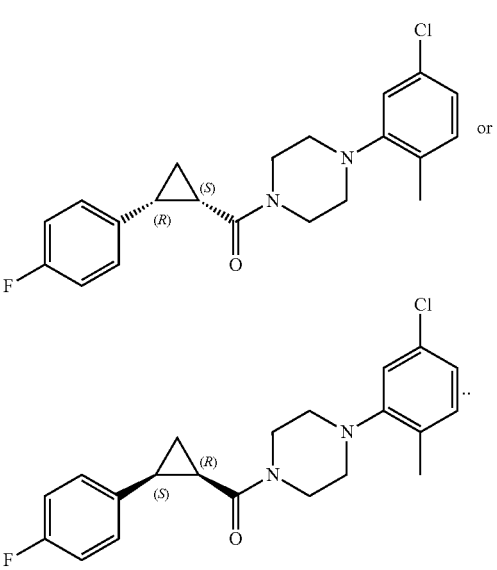

25. The method of any one of clauses 15-21, wherein the compound is a compound recited in clause 9.

EXAMPLES

1. Biological Materials and Methods

Materials

Phosphate buffered saline (PBS) solution was purchased from Fisher Scientific (MA, USA). Trypsin-EDTA solution, dimethyl sulfoxide (DMSO), Roswell Park Memorial Institute (RPMI) 1640 medium, ethanol (200 proof), puromycin powder, and G418 powder were purchased from Sigma-Aldrich (MO, USA). Fetal bovine Serum (FBS), penicillin-streptomycin solution were purchased from Invitrogen (NY, USA). Dual-Luciferase® Reporter Assay System was purchased from Promega (WI, USA). PSA6.1-luc plasmid was a gift from Dr. Marianne Sadar at the University of British Columbia (BC, CA) and pRL-TK *Renilla* luciferase reporter plasmid was purchased from Promega (WI, USA). The C4-2 castration-resistant prostate cancer cell line was kindly provided by Dr. Leland W. K. Chung (Cedars-Sinai Medical Center).

2. Chemistry
General

Moisture and air-sensitive reactions were performed under N$_2$ or Ar atmosphere and glassware used for these reactions was flamed dried and cooled under N$_2$ or Ar prior to use. THF and Et$_2$O were distilled from sodium/benzophenone ketyl. DMF and CH$_2$Cl$_2$ were distilled from CaH$_2$. 1,4-Dioxane was purchased from Acros (Sure/Seal bottle) and used as received. Et$_3$N was distilled from CaH$_2$ and stored over KOH. Toluene was purified by passage through an activated alumina filtration system. Melting points were determined using a Mel-Temp II instrument and are not corrected. Infrared spectra were determined using a Smiths Detection IdentifyIR FT-IR spectrometer. High-resolution mass spectra were obtained on a Micromass UK Limited, Q-TOF Ultima API, Thermo Scientific Exactive Orbitrap LC-MS. Automated column chromatography was done using an Isco Combiflash Rf. $^1$H and $^{13}$C NMR spectra were obtained on Bruker Advance 300 MHz, 400 MHz, or 500 MHz instruments. Chemical shifts (δ) were reported in parts per million with the residual solvent peak used as an internal standard, δ $^1$H/$^{13}$C (Solvent): 7.26/77.00 (CDCl$_3$); 2.05/29.84 (acetone-d6); 2.50/39.52 (DMSO-d6), 3.31/49.00 (CD$_3$OD); and are tabulated as follows: chemical shift, multiplicity (s=singlet, brs=broad singlet, d=doublet, brd=broad doublet, t=triplet, app t=apparent triplet, q=quartet, m=multiplet), number of protons, and coupling constant(s). $^{13}$C NMR spectra were obtained at 75 MHz, 100 MHz, or 125 MHz using a proton-decoupled pulse sequence and are tabulated by observed peak. CDCl$_3$ was filtered through dried basic alumina prior to use. Thin-layer chromatography was performed using pre-coated silica gel 60 F$_{254}$ plates (EMD, 250 μm thickness) and visualization was accomplished with a 254 nm UV light and by staining with a PMA solution (5 g of phosphomolybdic acid in 100 mL of 95% EtOH), Vaughn's reagent (4.8 g of (NH$_4$)$_6$Mo$_7$O$_{24}$·4H$_2$O and 0.2 g of Ce(SO$_4$)$_2$ in 100 mL of a 3.5 N H$_2$SO$_4$ solution) or a KMnO$_4$ solution (1.5 g of KMnO$_4$ and 1.5 g of K$_2$CO$_3$ in 100 mL of a 0.1% NaOH solution). Chromatography on SiO$_2$ (Silicycle, Silia-P Flash Silica Gel or SiliaFlash® P60, 40-63 μm) was used to purify crude reaction mixtures. Final products were >95% purity as analyzed by RP (reverse phase) HPLC (Alltech Prevail C-18, 100×4.6 mm, 1 mL/min, CH$_3$CN, H$_2$O and 0.1% TFA) with UV (210, 220 and 254 nm), ELS (nebulizer 45° C., evaporator 45° C., N$_2$ flow 1.25 SLM), and MS detection using a Thermo Scientific Exactive Orbitrap LC-MS (ESI positive). All other materials were obtained from commercial sources and used as received.

Example 1

Synthesis and Characterization

Synthesis of several of the compounds is described in detail below:

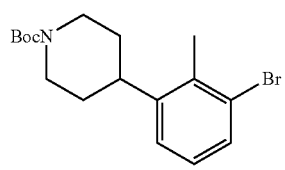 [SMILES: Cc1c(Br)cccc1C1CCN(C(=O)OC(C)(C)C)CC1]

tert-Butyl 4-(3-bromo-2-methylphenyl)piperazine-1-carboxylate (BRE454-64). A microwave vial under Ar was charged with tert-butyl 1-piperazinecarboxylate (154 mg, 0.825 mmol), NaO-t-Bu (0.0952 g, 0.990 mmol), (rac)-BINAP (0.0393 g, 0.0619 mmol, 7.5 mol %), Pd$_2$(dba)$_3$ (0.0192 g, 0.0206 mmol), and degassed toluene (2.1 mL). 2-Bromo-6-iodotoluene (121 μL, 0.825 mmol) was added, and the mixture was heated in sealed vial at 80° C. for 19 h, cooled to room temperature, diluted with CH$_2$Cl$_2$, filtered through Celite, and concentrated in vacuo. The mixture was purified by chromatography on SiO$_2$ (1:9, EtOAc/hexanes) to give the product (0.095 g, 0.27 mmol, 32%) as a yellow oil: $^1$H NMR (500 MHz, CDCl$_3$) δ 7.30 (d, J=8.0 Hz, 1H), 7.02 (t, J=8.0 Hz, 1H), 6.95 (d, J=7.5 Hz, 1H), 3.57 (m, 4H), 2.83 (t, J=4.5 Hz, 4H), 2.40 (s, 3H), 1.49 (s, 9H).

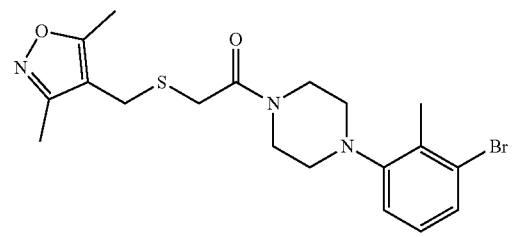 [SMILES: Cc1noc(C)c1CSCC(=O)N1CCN(c2cccc(Br)c2C)CC1]

1-(4-(3-Bromo-2-methylphenyl)piperazin-1-yl)-2-(((3,5-dimethylisoxazol-4-yl)methyl)thio) ethan-1-one (BRE454-75). A solution of BRE454-64 (0.0770 g, 0.22 mmol) in THF (0.3 mL) at 0° C. was treated with 4 M HCl in dioxane (1.3 mL) and stirred at 0° C. for 2 h. The yellow solid was collected by filtration, washed with Et$_2$O, dried under high vacuum and carried on to the next step without further purification.

To a solution of ([(3,5-dimethylisoxazol-4-yl)methyl]thio)acetic acid (0.0350 g, 0.174 mmol) in CH$_2$Cl$_2$ (1.7 mL) was added 4-(3-bromo-2-methylphenyl)piperazine hydrochloride and triethylamine (121 μL, 0.870 mmol). The mixture was cooled to 0° C., treated with T3P (50% solution in EtOAc, 184 μL, 0.261 mmol), warmed to room temperature, stirred for 20 h, diluted with CH$_2$Cl$_2$, and washed with sat. NH$_4$Cl, sat. NaHCO$_3$, and brine. The organic layer was dried (Na$_2$SO$_4$), filtered, and concentrated in vacuo. The crude material was purified by chromatography on SiO$_2$ (3:2, EtOAc/hexanes, base washed with 0.1% Et$_3$N prior to use) to give the product (0.0762 g, 0.174 mmol, quant. 100% pure by ELSD) as a colorless oil: IR (ATR) 2921, 2820, 1637, 1587, 1562, 1460, 1428, 1282, 1237, 1195, 1136, 1038, 994, 913, 780, 731, 714 cm$^{-1}$; $^1$H NMR (400 MHz, CDCl$_3$) δ 7.32 (dd, J=0.8, 7.6 Hz, 1H), 7.03 (t, J=8.0 Hz, 1H), 6.94 (dd, J=0.8, 8.0 Hz, 1H), 3.77 (br s, 2H), 3.63 (s, 2H), 3.63-3.57 (m, 2H), 3.23 (s, 2H), 2.90 (t, J=4.4 Hz, 2H), 2.88-2.83 (m, 2H), 2.43 (s, 3H), 2.40 (s, 3H), 2.31 (s, 3H); $^{13}$C-NMR (125 MHz, CDCl$_3$) δ 167.6, 166.8, 159.7, 152.2, 132.9, 128.1, 127.4, 126.6, 118.3, 109.7, 52.1, 51.8, 46.8, 42.2, 32.1, 23.8, 18.2, 11.1, 10.2; HRMS (ESI) m/z calcd for C$_{19}$H$_{25}$N$_3$O$_2$BrS ([M+H]$^+$) 438.0845, found 438.0831.

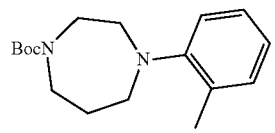 [SMILES: Cc1ccccc1N1CCCN(C(=O)OC(C)(C)C)CC1]

tert-Butyl 4-(o-tolyl)-1,4-diazepane-1-carboxylate (BRE454-66). A microwave vial under Ar was charged with 1-Boc-homopiperazine (223 mg, 1.10 mmol), NaO-t-Bu (0.116 g, 1.20 mmol), (rac)-BINAP (0.0478 g, 0.0752 mmol, 7.5% mol), Pd$_2$(dba)$_3$ (0.0233 g, 0.0251 mmol, 2.5% mol in Pd), and degassed toluene (2.8 mL). 2-Bromotoluene (0.175 g, 1.00 mmol) was added, and the mixture was heated in a sealed vial at 80° C. for 19 h, cooled to room temperature, diluted with CH$_2$Cl$_2$, filtered over Celite, and concentrated. The crude material was purified by chromatography on SiO$_2$ (1:9, EtOAc/hexanes) to give the product (0.139 g, 0.479 mmol, 48%) as a yellow oil: IR (ATR) 2973, 2828, 1689, 1598, 1491, 1457, 1411, 1364, 1233, 1215, 1156, 1122, 878, 761, 725 cm$^{-1}$; $^1$H NMR (500 MHz, CDCl$_3$, rt, rotamers) δ 7.16 (d, J=6.0 Hz, 1H), 7.12 (d, J=6.0 Hz, 1H), 7.04 (d, J=7.5 Hz, 1H), 6.95 (t, J=7.0 Hz, 1H), 3.62-3.52 (m, 4H), 3.12-3.04 (m, 4H), 2.31 (s, 3H), 2.00-1.88 (m, 2H), 1.49 (s, 9H); $^{13}$C-NMR (100 MHz, CDCl$_3$, rt, rotamers) δ 155.6, 155.5, 153.9, 153.8, 132.9, 130.9, 126.5, 123.1, 120.8 (2 C), 79.3, 56.2, 56.0, 55.5, 55.2, 48.4, 48.0, 46.2, 45.4, 29.0, 28.9, 28.5, 18.5; HRMS (ESI) m/z calcd for C$_{17}$H$_{27}$N$_2$O$_2$ ([M+H]$^+$) 291.2067, found 291.2062.

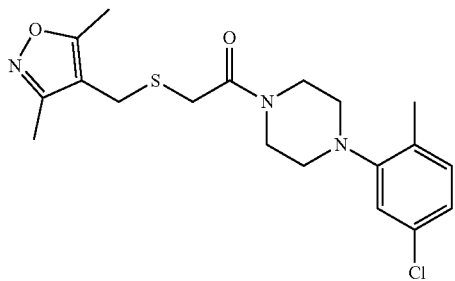 [SMILES: Cc1ccc(Cl)cc1N1CCN(C(=O)CSCc2c(C)noc2C)CC1]

1-(4-(5-Chloro-2-methylphenyl)piperazin-1-yl)-2-(((3,5-dimethylisoxazol-4-yl)methyl)thio) ethan-1-one (BRE454-58). To a solution of ([(3,5-dimethylisoxazol-4-yl)methyl]thio)acetic acid (0.0450 g, 0.224 mmol) in CH$_2$Cl$_2$ (2.2 mL) was added 1-(5-chloro-2-methylphenyl)piperazine (0.0565 g, 0.268 mmol) and triethylamine (93 μL, 0.671 mmol). The mixture was cooled to 0° C., treated with T3P (50% solution in EtOAc, 237 μL, 0.335 mmol), warmed to room temperature, stirred for 20 h, diluted with CH$_2$Cl$_2$, and washed with sat. NH$_4$Cl, sat. NaHCO$_3$, and brine. The organic layer was dried (Na$_2$SO$_4$), filtered, and concentrated in vacuo. The crude material was purified by chromatography on SiO$_2$ (1:1, EtOAc/hexanes, base washed with 0.1% Et$_3$N prior to use) to give the product (0.0881 g, 0.224 mmol, quant, 99.9% pure by ELSD) as a clear colorless oil: IR (ATR) 2921, 2818, 1635, 1592, 1489, 1438, 1270, 1224, 1195, 1148, 1039, 924, 910, 818, 728 cm$^{-1}$; $^1$H NMR (400 MHz, CDCl$_3$) δ 7.11 (d, J=8.0 Hz, 1H), 6.99 (dd, J=2.0, 8.0 Hz, 1H), 6.94 (d, J=2.4 Hz, 1H), 3.76 (t, J=4.8 Hz, 2H), 3.63 (s, 2H), 3.59 (t, J=4.8 Hz, 2H), 3.23 (s, 2H), 2.91 (t, J=4.8 Hz, 2H), 2.86 (t, J=4.8 Hz, 2H), 2.43 (s, 3H), 2.30 (s, 3H), 2.27 (s, 3H); $^{13}$C NMR (125 MHz, CDCl$_3$) δ 167.6, 166.8, 159.7, 151.7, 132.1, 131.8, 130.9, 123.7, 119.7, 109.7, 51.6, 51.5, 46.8, 42.2, 32.0, 23.7, 17.4, 11.1, 10.2; HRMS (ESI) calcd for C$_{19}$H$_{25}$N$_3$O$_2$ClS ([M+H]$^+$) 394.1351, found 394.1340.

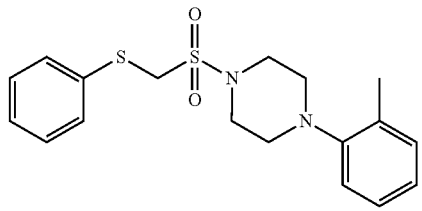 [SMILES: Cc1ccccc1N1CCN(S(=O)(=O)CSc2ccccc2)CC1]

1-(((Phenylthio)methyl)sulfonyl)-4-(o-tolyl)piperazine (BRE454-84). A solution of 1-(2-methylphenyl)piperazine (0.500 g, 2.75 mmol) and triethylamine (0.39 mL, 2.75 mmol) in CH$_2$Cl$_2$ (9.8 mL) at 0° C. was treated with chloromethanesulfonyl chloride (0.460 g, 3.03 mmol), gradually warmed to room temperature, and stirred for 14 h. The reaction mixture was quenched with sat. NH$_4$Cl (3 mL) and extracted with EtOAc (3×20 mL). The combined organic portion was washed with water (2×10 mL) and brine (10 mL), dried (Na$_2$SO$_4$), filtered, and concentrated. The crude solid was filtered through a plug of SiO$_2$ (pretreated with 0.1% Et$_3$N in 30% EtOAc/hexanes) and washed thoroughly with 30% EtOAc/hexanes to give the product as an orange solid (0.676 g, 2.34 mmol, 85%): $^1$H NMR (400 MHz, CDCl$_3$) δ 7.21-7.17 (m, 2H), 7.05-7.00 (m, 2H), 4.57 (s, 2H), 3.63 (t, J=4.8 Hz, 4H), 2.98 (t, J=5.2 Hz, 4H), 2.31 (s, 3H).

A solution of this product (0.0400 g, 0.139 mmol), thiophenol (0.0610 g, 0.554 mmol), and Cs$_2$CO$_3$ (0.0903 g, 0.277 mmol) in DMF (0.28 mL) was stirred at 80° C. for 2 d. The reaction mixture was diluted with brine (10 mL) and extracted with EtOAc (20 mL). The organic layer was separated, washed with brine (2×10 mL), dried (Na$_2$SO$_4$), and concentrated in vacuo. The crude material was purified by chromatography on SiO$_2$ (1:4, EtOAc/hexanes) the product as a clear colorless oil (0.0257 g, 0.0709 mmol, 51%): IR (ATR) 3054, 2918, 2823, 1598, 1581, 1493, 1440, 1342, 1324, 1262, 1225, 1153, 1112, 1070, 954, 765, 744, 725, 691 cm$^{-1}$; $^1$H NMR (500 MHz, CDCl$_3$) δ 7.59 (d, J=7.5 Hz, 2H), 7.39-7.30 (m, 3H), 7.21-7.14 (m, 2H), 7.02 (t, J=7.5 Hz, 1H), 6.98 (d, J=8.0 Hz, 1H), 4.33 (s, 2H), 3.51 (t, J=4.5 Hz, 4H), 2.92 (t, J=4.5 Hz, 4H), 2.28 (s, 3H); $^{13}$C NMR (100 MHz, CDCl$_3$) δ 150.7, 133.4, 132.7, 131.2, 131.1, 129.4, 128.1, 126.7, 123.9, 119.4, 54.2, 51.8, 46.8, 17.7; HRMS (+ESI) m/z calcd for C$_{18}$H$_{23}$N$_2$O$_2$S$_2$ ([M+H]$^+$) 363.1195, found 363.1190.

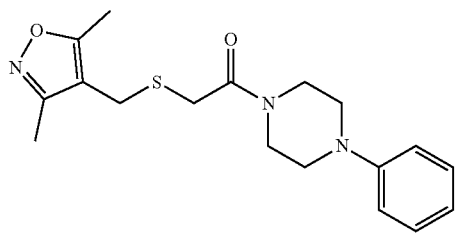 [SMILES: Cc1noc(C)c1CSCC(=O)N1CCN(c2ccccc2)CC1]

2-(((3,5-Dimethylisoxazol-4-yl)methyl)thio)-1-(4-phenylpiperazin-1-yl)ethanone (5a). To a solution of 2-(((3,5-dimethylisoxazol-4-yl)methyl)thio)acetic acid 3a (0.0200 g, 0.0994 mmol) in CH$_2$Cl$_2$ (1.25 mL) was added 1-phenylpiperazine 4a (0.0190 g, 0.119 mmol) and Et$_3$N (41 μL, 0.298 mmol). The reaction mixture was cooled to 0° C., treated with T3P (50 wt. % solution in EtOAc, 105 μL, 0.149 mmol), allowed to warm to room temperature, stirred for 2 d, diluted with CH$_2$Cl$_2$ and washed with satd. aqueous NH$_4$Cl, satd. aqueous NaHCO$_3$, brine, dried (Na$_2$SO$_4$), filtered, and concentrated in vacuo. The crude residue was purified by chromatography on SiO$_2$ (ISCO, 12 g column, liquid load in CH$_2$Cl$_2$, EtOAc/hexanes gradient (10-100%), product eluted at 60%) to give 5a (0.0330 g, 0.0955 mmol, 96%, 100% pure by ELSD) as a colorless solid: Mp 74-75° C.; IR (ATR) 2856, 2802, 1627, 1599, 1496, 1440, 1416, 1229, 1141, 1034, 909, 765, 698 cm$^{-1}$; $^1$H NMR (300 MHz, CDCl$_3$) δ 7.26-7.21 (m, 1H), 6.89-6.83 (m, 3H), 3.72 (app t, 2H, J=5.2 Hz), 3.56 (s, 2H), 3.56-3.54 (m, 2H), 3.18 (s, 2H), 3.15-3.10 (m, 2H), 2.34 (s, 3H), 2.23 (s, 3H); $^{13}$C NMR (75 MHz, CDCl$_3$) δ 166.5, 165.8, 158.6, 149.8, 128.2, 119.6, 115.6, 108.7, 48.5, 48.3, 45.3, 40.7, 31.0, 22.7, 10.0, 9.1; HRMS (ESI) m/z calcd for C$_{18}$H$_{24}$N$_3$O$_2$S ([M+H]$^+$) 346.1584, found: 346.1571.

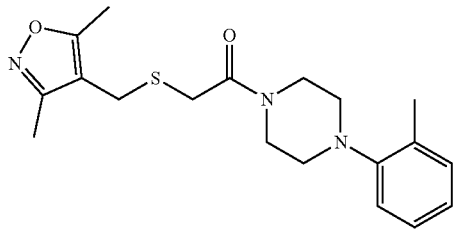 [SMILES: Cc1ccccc1N1CCN(C(=O)CSCc2c(C)noc2C)CC1]

2-(((3,5-Dimethylisoxazol-4-yl)methyl)thio)-1-(4-(o-tolyl)piperazin-1-yl)ethanone (5b). To a solution of 2-(((3,5-dimethylisoxazol-4-yl)methyl)thio)acetic acid (3a, 0.0200 g, 0.0994 mmol) in CH$_2$Cl$_2$ (1.25 mL) was added 1-(o-tolyl)piperazine 4b (0.0210 g, 0.119 mmol) and Et$_3$N (41 μL, 0.298 mmol). The reaction mixture was cooled to 0° C., treated with T3P (50 wt. % solution in EtOAc, 105 μL, 0.149 mmol), allowed to warm to room temperature, stirred for 2 d, diluted with CH$_2$Cl$_2$ and washed with satd. aqueous NH$_4$Cl, satd. aqueous NaHCO$_3$, brine, dried (Na$_2$SO$_4$), filtered, and concentrated in vacuo. The crude residue was purified by chromatography on SiO$_2$ (ISCO, 12 g column, liquid load in CH$_2$Cl$_2$, EtOAc/hexanes gradient (10-100%), product eluted at 40%) to give 5b (0.0348 g, 0.0968 mmol, 97%, 100% pure by ELSD) as a colorless solid: Mp 89-91° C.; IR (ATR) 2959, 2828, 1631, 1492, 1430, 1261, 1226, 1138, 1036, 979, 959, 776, 726 cm$^{-1}$; $^1$H NMR (300 MHz, CDCl$_3$) δ 7.18 (dd, 2H, J=9.0, 7.5 Hz), 7.01 (dd, 2H, J=14.1, 9.0 Hz), 3.76 (app t, 2H, J=4.9 Hz), 3.63 (s, 2H), 3.59 (app t, 2H, J=4.9 Hz), 3.24 (s, 2H), 2.93 (app t, 2H, J=4.9 Hz), 2.88 (app t, 2H, J=4.9 Hz), 2.43 (s, 3H), 2.32 (s, 3H), 2.30 (s, 3H); $^{13}$C NMR (75 MHz, CDCl$_3$) δ 166.5, 165.8, 158.7, 149.6, 131.7, 130.2, 125.7, 122.8, 118.1, 108.7, 50.8, 50.6, 46.0, 41.3, 31.1, 22.7, 16.7, 10.0, 9.1; HRMS (ESI) m/z calcd for C$_{19}$H$_{26}$N$_3$O$_2$S ([M+H]$^+$) 360.1740, found 360.1725.

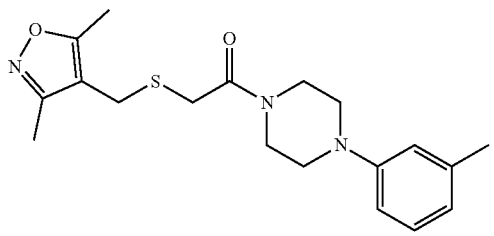 [SMILES: Cc1cccc(N2CCN(C(=O)CSCc3c(C)noc3C)CC2)c1]

2-(((3,5-Dimethylisoxazol-4-yl)methyl)thio)-1-(4-(m-tolyl)piperazin-1-yl)ethanone (5c). A solution of 2-(((3,5-dimethylisoxazol-4-yl)methyl)thio)acetic acid (3a, 0.0200 g, 0.0994 mmol) in CH$_2$Cl$_2$ (1.25 mL) was added 1-(m-tolyl)piperazine (4c, 21 μL, 0.119 mmol), Et$_3$N (41 μL, 0.298 mmol). The reaction mixture was cooled to 0° C., treated with T3P (50 wt. % solution in EtOAc, 105 μL, 0.149 mmol), allowed to warm to room temperature, stirred for 2 d, diluted with CH$_2$Cl$_2$ and washed with satd. aqueous NH$_4$Cl, satd. aqueous NaHCO$_3$, brine, dried (Na$_2$SO$_4$), filtered, and concentrated in vacuo. The crude residue was purified by chromatography on SiO$_2$ (ISCO, 12 g column, liquid load in CH$_2$Cl$_2$, EtOAc/hexanes gradient (10-100%), eluted at 60%) to give 5c (0.0343 g, 0.954 mmol, 96%, 99.5% pure by ELSD) as a yellow oil: IR (ATR) 2918, 2819, 1635, 1600, 1493, 1424, 1244, 1192, 1145, 995, 957, 775, 729, 694 cm$^{-1}$; $^1$H NMR (300 MHz, CDCl$_3$) δ 7.17 (app t, 1H, J=7.8 Hz), 6.75-6.72 (m, 3H), 3.76 (app t, 2H, J=5.2 Hz), 3.61 (s, 2H), 3.60-3.58 (m, 2H), 3.23 (s, 2H), 3.17 (ddd, 4H, J=5.5, 5.2, 5.0 Hz), 2.41 (s, 3H), 2.32 (s, 3H), 2.28 (s, 3H); $^{13}$C NMR (75 MHz, CDCl$_3$) δ 166.5, 165.8, 158.6, 149.8, 138.0, 128.1, 120.5, 116.5, 112.8, 108.7, 48.6, 48.5, 45.3, 40.8, 31.0, 22.7, 20.7, 10.0, 9.1; HRMS (ESI) m/z calcd for C$_{19}$H$_{26}$N$_3$O$_2$S ([M+H]$^+$) 360.1740, found: 360.1725.

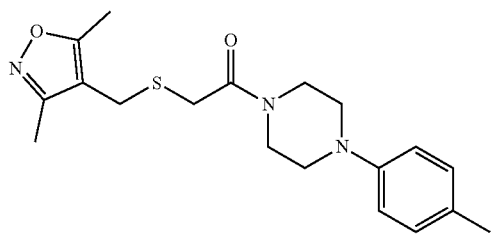 [SMILES: Cc1ccc(N2CCN(C(=O)CSCc3c(C)noc3C)CC2)cc1]

2-(((3,5-Dimethylisoxazol-4-yl)methyl)thio)-1-(4-(p-tolyl)piperazin-1-yl)ethanone (5d). A solution of 2-(((3,5-dimethylisoxazol-4-yl)methyl)thio)acetic acid (3a, 0.0200 g, 0.0994 mmol) in CH$_2$Cl$_2$ (1.25 mL) was added 1-(p-tolyl)piperazine (4d, 21 μL, 0.119 mmol), Et$_3$N (41 μL, 0.298 mmol). The reaction mixture was cooled to 0° C., treated with T3P (50 wt. % solution in EtOAc, 105 μL, 0.149 mmol), allowed to warm to room temperature, stirred for 2 d, diluted with CH$_2$Cl$_2$, washed with satd. aqueous NH$_4$Cl, satd. aqueous NaHCO$_3$, and brine, dried (Na$_2$SO$_4$), filtered, and concentrated in vacuo. The crude residue was purified by chromatography on SiO$_2$ (ISCO, 12 g column, liquid load in CH$_2$Cl$_2$, EtOAc/hexanes gradient ((10-100%), eluted at 60%) to give 5d (0.0266 g, 0.0740 mmol, 74%, 100% pure by ELSD) as a red solid: Mp 83-85° C.; IR (ATR) 2855, 2801, 1627, 1514, 1440, 1416, 1261, 1230, 1142, 1043, 960, 815, 724 cm$^{-1}$; $^1$H NMR (300 MHz, CDCl$_3$) δ 7.10 (d, 2H, J=8.1 Hz), 6.85 (d, 2H, J=8.1 Hz), 3.77 (app t, 2H, J=4.7 Hz), 3.61-3.58 (m, 4H), 3.23 (s, 2H), 3.13 (ddd, 4H, J=5.6, 5.5, 4.7 Hz), 2.41 (s, 3H), 2.28, (s, 6H); $^{13}$C NMR (75 MHz, CDCl$_3$) δ 167.5, 166.8, 159.7, 148.7, 130.3, 129.8, 117.0, 109.7, 50.1, 49.9, 46.4, 41.8, 32.1, 23.7, 20.4, 11.0, 10.1; HRMS (ESI) m/z calcd for C$_{19}$H$_{26}$N$_3$O$_2$S ([M+H]$^+$) 360.1740, found 360.1725.

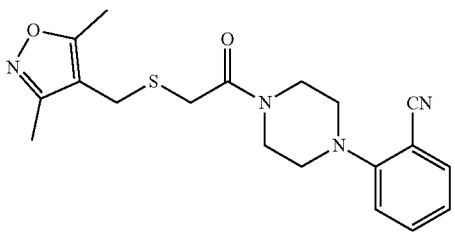 [SMILES: Cc1noc(C)c1CSCC(=O)N1CCN(c2ccccc2C#N)CC1]

2-(4-(2-(((3,5-Dimethylisoxazol-4-yl)methyl)thio)acetyl)piperazin-1-yl)benzonitrile (MK415-62; 5e). To a solution of ([(3,5-dimethylisoxazol-4-yl)methyl]thio)acetic acid (3a, 0.0280 g, 0.132 mmol) in CH$_2$Cl$_2$ (1.3 mL) was added 2-(piperazin-1-yl)benzonitrile (4e, 0.0253 g, 0.132 mmol) and Et$_3$N (56 µL, 0.400 mmol). The reaction mixture was cooled to 0° C., treated with T3P (50 wt. % solution in EtOAc, 140 µL, 0.200 mmol), allowed to warm to room temperature, stirred for 20 h, diluted with CH$_2$Cl$_2$, washed with satd. aqueous NH$_4$Cl, satd. aqueous NaHCO$_3$, and brine, dried (Na$_2$SO$_4$), filtered, and concentrated in vacuo. The crude residue was purified by chromatography on SiO$_2$ (95:5, CH$_2$Cl$_2$/MeOH) to give 5e (0.0390 g, 0.105 mmol, 80%, 99.9% pure by ELSD) as a yellow solid: Mp 142-143° C.; IR (neat) 2919, 2216, 1637, 1593, 1420, 1232 cm$^{-1}$; $^1$H NMR (400 MHz, CDCl$_3$) δ 7.61 (dd, 1H, J=7.6, 1.6 Hz), 7.51 (ddd, 1H, J=8.4, 7.6, 1.6 Hz), 7.09 (dt, 1H, J=7.6, 0.9 Hz), 7.02 (d, 1H, J=8.4 Hz), 3.82 (app t, 2H, J=4.8 Hz), 3.67 (app t, 2H, J=4.8 Hz), 3.62 (s, 2H), 3.24 (s, 2H), 3.24-3.21 (m, 2H) 3.15 (app t, 2H, J=5.4 Hz), 2.41 (s, 3H), 2.28 (s, 3H); $^{13}$C NMR (100 MHz, CDCl$_3$) δ 167.6, 166.7, 159.6, 154.9, 134.3, 133.9, 122.7, 118.9, 118.0, 109.7, 106.7, 51.9, 51.1, 46.6, 41.8, 32.1, 23.7, 11.0, 10.1; HRMS (ESI) m/z calcd for C$_{19}$H$_{23}$N$_4$O$_2$S ([M+H]$^+$) 371.1542, found 371.1536.

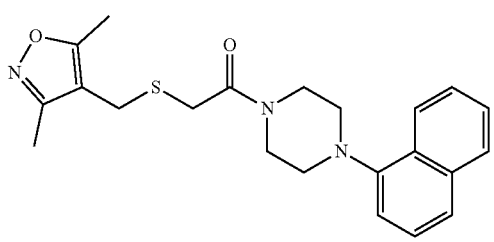 [SMILES: Cc1noc(C)c1CSCC(=O)N1CCN(c2cccc3ccccc23)CC1]

2-(((3,5-Dimethylisoxazol-4-yl)methyl)thio)-1-(4-(2-fluorophenyl)piperazin-1-yl)ethan-1-one (BRE454-54; 5f). To a solution of 2-(((3,5-dimethylisoxazol-4-yl)methyl)thio)acetic acid (3a, 0.0758 g, 0.377 mmol) in CH$_2$Cl$_2$ (3.8 mL) was added 1-(2-fluorophenyl)-piperazine (4f, 0.0814 g, 0.452 mmol) and Et$_3$N (262 µL, 1.88 mmol). The reaction mixture was cooled to 0° C., treated with T3P (50 wt. % solution in EtOAc, 399 µL, 0.565 mmol), allowed to warm to room temperature, stirred for 20 h, diluted with CH$_2$Cl$_2$, and washed with satd. aqueous NH$_4$Cl solution, satd. aqueous NaHCO$_3$ solution, and brine, dried (Na$_2$SO$_4$), filtered, and concentrated in vacuo. The crude residue was purified by chromatography on SiO$_2$ (3:2, EtOAc/hexanes, base washed with 0.1% Et$_3$N prior to use) to give 5f (0.134 g, 0.369 mmol, 98%, 100% pure by ELSD) as a light yellow oil: IR (ATR) 2918, 2827, 1636, 1613, 1500, 1439, 1237, 1195, 1147, 1031, 909, 811, 753, 725 cm$^{-1}$; $^1$H NMR (400 MHz, CDCl$_3$) δ 7.10-6.90 (m, 4H), 3.79 (app t, 2H, J=5.2 Hz), 3.63-3.59 (m, 4H), 3.23 (s, 2H), 3.10 (app t, 2H, J=4.8 Hz), 3.05 (app t, 2H, J=5.2 Hz), 2.28 (s, 3H), 2.42 (s, 3H); $^{13}$C NMR (125 MHz, CDCl$_3$) δ 167.5, 166.8, 159.7, 155.7 (d, J$_{C-F}$=245.0 Hz), 139.4 (d, J$_{C-F}$=8.8 Hz), 124.5 (d, J$_{C-F}$=3.8 Hz), 123.3 (d, J$_{C-F}$=8.8 Hz), 119.2 (d, J$_{C-F}$=2.5 Hz), 116.3 (d, J$_{C-F}$=20.0 Hz), 109.7, 50.7 (d, J$_{C-F}$=2.5 Hz), 50.3 (d, J$_{C-F}$=2.5 Hz), 46.6, 41.9, 32.1, 23.7, 11.1, 10.2; HRMS (ESI) m/z calcd for C$_{18}$H$_{23}$N$_3$O$_2$FS ([M+H]$^+$) 364.1490, found 364.1474.

2-(((3,5-Dimethylisoxazol-4-yl)methyl)thio)-1-(4-(naphthalen-1-yl)piperazin-1-yl)ethanone (5g). A Schlenk flask was charged under N$_2$ with piperazine (0.0500 g, 0.580 mmol), NaO-t-Bu (0.100 g, 1.06 mmol), (rac)-BINAP (0.0051 g, 0.0079 mmol), Pd$_2$(dba)$_3$ (0.0050 g, 0.0053 mmol), and degassed toluene (5 mL). After addition of 1-bromonaphthalene (75 µL, 0.530 mmol), the reaction mixture was heated at 110° C. for 24 h, cooled to room temperature, diluted with CH$_2$Cl$_2$, filtered through Celite, and concentrated in vacuo. The resulting 1-(naphthalen-1-yl)piperazine (4g) was used without further purification for the next reaction.

To a solution of (((3,5-dimethylisoxazol-4-yl)methyl)thio)acetic acid (3a, 0.0580 g, 0.272 mmol) in CH$_2$Cl$_2$ (4 mL) was added 1-(naphthalen-1-yl)piperazine 4g (0.0750 g, 0.353 mmol) and Et$_3$N (114 µL, 0.815 mmol). The reaction mixture was cooled to 0° C., treated with T3P (50 wt. % solution in EtOAc, 288 µL, 0.408 mmol), allowed to warm to room temperature, stirred for 20 h, diluted with CH$_2$Cl$_2$, and washed with satd. aqueous NH$_4$Cl, satd. aqueous NaHCO$_3$, and brine, dried (Na$_2$SO$_4$), filtered, and concentrated in vacuo. The crude residue was purified by chromatography on SiO$_2$ (95:5 CH$_2$Cl$_2$/MeOH) to give 5g (0.0700 g, 0.177 mmol, 65% 2 steps, 99.9% pure by ELSD) as a yellow oil: IR (neat) 2919, 1637, 1435, 1398, 1215, 1192 cm$^{-1}$; $^1$H NMR (500 MHz, CDCl$_3$) δ 8.21 (d, 1H, J=7.5 Hz), 7.85 (d, 1H, J=7.5 Hz), 7.61 (d, 1H, J=8.0 Hz), 7.54-7.49 (m, 2H), 7.42 (d, 1H, J=8.0 Hz), 7.08 (d, 1H, J=7.5 Hz), 3.73-3.66 (m, 4H), 3.64 (s, 2H), 3.28 (s, 2H), 3.27-2.85 (m, 4H), 2.45 (s, 3H), 2.32 (s, 3H); $^{13}$C NMR (125 MHz, CDCl$_3$) δ 167.6, 166.8, 159.7, 148.7, 134.7, 128.7, 128.5, 126.0, 125.7 (2 C), 124.2, 123.0, 115.0, 109.7, 52.9, 52.7, 47.0, 42.4, 32.1, 23.7, 11.1, 10.2; HRMS (ESI) m/z calcd for C$_{22}$H$_{26}$N$_3$O$_2$S ([M+H]$^+$) 396.1746, found 396.1740.

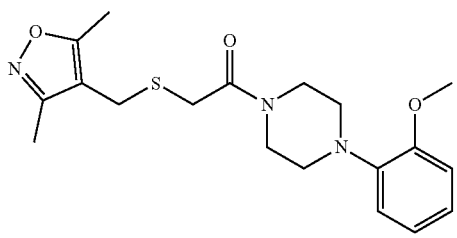 [SMILES: COc1ccccc1N1CCN(C(=O)CSCc2c(C)noc2C)CC1]

2-(((3,5-Dimethylisoxazol-4-yl)methyl)thio)-1-(4-(2-methoxyphenyl)piperazin-1-yl)ethanone (5h). To a solution of 2-(((3,5-dimethylisoxazol-4-yl)methyl)thio)acetic acid (3a, 0.0200 g, 0.0994 mmol) in CH$_2$Cl$_2$ (1.25 mL) was added 1-(o-methoxyphenyl)piperazine (4h, 0.0230 g, 0.119 mmol) and Et$_3$N (41 µL, 0.298 mmol). The reaction mixture was cooled to 0° C., treated with T3P (50 wt. % solution in EtOAc, 105 µL, 0.149 mmol), warmed to room temperature, stirred for 2 d, diluted with CH$_2$Cl$_2$ and washed with satd. aqueous NH$_4$Cl, satd. aqueous NaHCO$_3$, and brine, dried (Na$_2$SO$_4$), filtered, and concentrated in vacuo. The crude residue was purified by chromatography on SiO$_2$ (ISCO, 12 g column, liquid load in CH$_2$Cl$_2$, EtOAc/hexanes gradient (10-100%, eluted at 50-70%) to give 5h (0.0195 g, 0.0519 mmol, 52%, 100% pure by ELSD) as a colorless solid: Mp 91-93° C.; IR (ATR) 2997, 2926, 2812, 1626, 1500, 1447, 1243, 1223, 1143, 1023, 979, 751, 741, 726 cm$^{-1}$; $^1$H NMR (300 MHz, CDCl$_3$) δ 7.06-7.01 (m, 1H), 6.95-6.87 (m, 3H), 3.87 (s, 3H), 3.80 (app t, 2H, J=5.0 Hz), 3.64-3.62 (m, 4H), 3.23 (s, 2H), 3.07 (app t, 2H, J=5.0 Hz), 3.03 (app t, 2H, J=5.0 Hz), 2.41 (s, 3H), 2.28 (s, 3H); $^{13}$C NMR (75 MHz, CDCl$_3$) δ 167.4, 166.7, 159.8, 152.2, 140.4, 123.6, 121.0, 118.4, 111.3, 109.7, 55.4, 50.7, 50.5, 46.7, 42.0, 32.1, 23.7, 11.0, 10.1; HRMS (ESI) m/z calcd for C$_{19}$H$_{26}$N$_3$O$_2$$_3$S ([M+H]$^+$) 376.1689, found 376.1673.

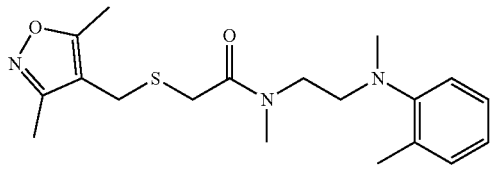 [SMILES: Cc1ccccc1N(C)CCN(C)C(=O)CSCc1c(C)noc1C]

2-(((3,5-Dimethylisoxazol-4-yl)methyl)thio)-N-methyl-N-(2-(methyl(o-tolyl)amino)ethyl) acetamide (5i). To a solution of 2-(((3,5-dimethylisoxazol-4-yl)methyl)thio)acetic acid (3a, 0.0608 g, 0.302 mmol) in CH$_2$Cl$_2$ (3.0 mL) was added N,N'-dimethyl-N-(o-tolyl)ethane-1,2-diamine (4i, 0.0500 g, 0.275 mmol) and Et$_3$N (115 µL, 0.825 mmol). The reaction mixture was cooled to 0° C., treated with T3P (50 wt. % solution in EtOAc, 292 µL, 0.412 mmol), warmed to room temperature, stirred for 20 h, diluted with CH$_2$Cl$_2$, and washed with satd. aqueous NH$_4$Cl solution, satd. aqueous NaHCO$_3$ solution, and brine, dried (Na$_2$SO$_4$), filtered, and concentrated in vacuo. The crude residue was purified by chromatography on SiO$_2$ (3:2, EtOAc/hexanes, base washed with 0.1% Et$_3$N prior to use) to give 5i (0.0752 g, 0.207 mmol, 75%, 99.6% pure by ELSD) as a light yellow oil: IR (ATR) 2932, 2795, 1640, 1598, 1493, 1451, 1421, 1393, 1196, 1108, 1047, 766, 738 cm$^{-1}$; $^1$H NMR (400 MHz, CDCl$_3$, room temperature, mixture of rotamers coalescing in DMSO-d$_6$ at 357 K) δ 7.20-7.12 (m, 2H), 7.07-6.95 (m, 2H), 3.59, 3.58 (2s, 2H), 3.54 (t, 1H, J=6.6 Hz), 3.39 (t, 1H, J=6.6 Hz), 3.16-3.08 (m, 3H), 2.97, 2.95 (2s, 4H), 2.71, 2.67 (2s, 3H), 2.38 (s, 3H), 2.30 (s, 2H), 2.27, 2.26 (3s, 4H); $^{13}$C NMR (125 MHz, CDCl$_3$, room temperature, mixture of rotamers coalescing in DMSO-d$_6$ at 357 K) δ 169.2, 168.8, 166.7 (2 C), 159.7, 151.7, 150.8, 133.8, 132.9, 131.4, 131.2, 126.7, 126.5, 124.0, 123.2, 120.2, 119.9, 109.8, 53.9, 53.2, 48.4, 46.6, 44.3, 42.3, 36.7, 33.8, 32.4, 31.6, 23.7, 23.4, 18.2, 18.0, 11.0 (2 C), 10.1; HRMS (ESI) m/z calcd for C$_{19}$H$_{28}$N$_3$O$_2$S ([M+H]$^+$) 362.1897, found 362.1890.

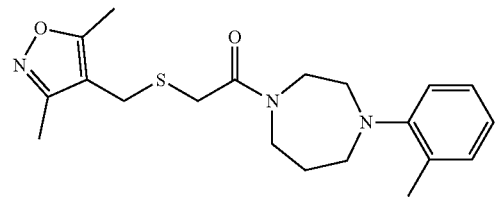 [SMILES: Cc1ccccc1N1CCCN(C(=O)CSCc2c(C)noc2C)CC1]

2-(((3,5-Dimethylisoxazol-4-yl)methyl)thio)-1-(4-(o-tolyl)-1,4-diazepan-1-yl)ethan-1-one (BRE454-76; 5j). A solution of tert-butyl 4-(o-tolyl)-1,4-diazepane-1-carboxylate (29a, 0.0750 g, 0.258 mmol) in THF (0.3 mL) was cooled to 0° C., treated with 4 M HCl in dioxane (1.6 mL) and stirred at 0° C. for 2 h. The reaction mixture was concentrated in vacuo and the yellow solid 4j was precipitated in Et$_2$O, filtered off from the solution, washed with Et$_2$O, dried under high vacuum, and used without further purification for the next step.

To a solution of 2-(((3,5-dimethylisoxazol-4-yl)methyl)thio)acetic acid (3a, 0.0460 g, 0.229 mmol) in CH$_2$Cl$_2$ (2.3 mL) was added 4-(o-tolyl)-1,4-diazepane hydrochloride (4j, 0.258 mmol) and Et$_3$N (159 µL, 1.14 mmol). The reaction mixture was cooled to 0° C., treated with T3P (50 wt. % solution in EtOAc, 242 µL, 0.343 mmol), warmed to room temperature, stirred for 20 h, diluted with CH$_2$Cl$_2$, and washed with satd. aqueous NH$_4$Cl solution, satd. aqueous NaHCO$_3$ solution, and brine, dried (Na$_2$SO$_4$), filtered, and concentrated in vacuo. The crude residue was purified by chromatography on SiO$_2$ (3:2, EtOAc/hexanes, base washed with 0.1% Et$_3$N) to give 5j (0.0854 g, 0.229 mmol, quant. 100% pure by ELSD) as a clear colorless oil: IR (ATR) 2945, 2825, 1634, 1598, 1491, 1447, 1423, 1215, 1194, 1136, 915, 762, 726 cm$^{-1}$; $^1$H NMR (400 MHz, CDCl$_3$, room temperature, mixture of rotamers) δ 7.20 (app d, 1H, J=7.6 Hz), 7.17 (app t, 1H, J=7.6 Hz), 7.05 (app d, 1H, J=7.6 Hz), 7.01 (app dt, 1H, J=7.2, 2.0 Hz), 3.82-3.78 (m, 2H), 3.71-3.65 (m, 4H), 3.24-3.20 (m, 3H), 3.15 (t, 1H, J=5.2 Hz), 3.12-3.07 (m, 2H), 2.46 (app s, 3H), 2.32 (2s, 6H), 2.04 (sept, 2H, J=6.0 Hz); $^{13}$C NMR (125 MHz, CDCl$_3$, room temperature, mixture of rotamers) δ 168.9, 168.8, 166.9, 166.8, 159.8 (2 C), 153.4, 153.3, 132.9 (2 C), 131.1 (2 C), 126.7, 126.6, 123.6, 123.4, 120.8, 120.7, 109.9, 56.4, 55.8, 55.5, 54.9, 50.1, 47.6, 47.2, 44.9, 32.2, 32.0, 29.5, 28.2, 23.7, 18.5 (2 C), 11.1, 10.2 (2 C); HRMS (ESI) m/z calcd for C$_{20}$H$_{28}$N$_3$O$_2$S ([M+H]$^+$) 374.1897, found 374.1883.

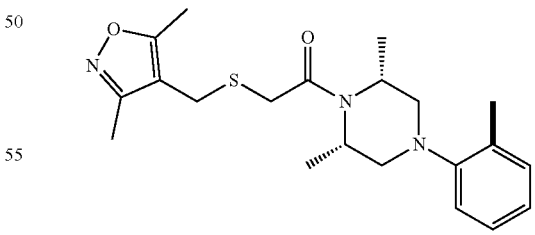

1-(2,6-Dimethyl-4-(o-tolyl)piperazin-1-yl)-2-(((3,5-dimethylisoxazol-4-yl)methyl)thio)ethanone (5k). A solution of (((3,5-dimethylisoxazol-4-yl)methyl)thio)acetic acid (3a, 0.0300 g, 0.142 mmol) in CH$_2$Cl$_2$ (2 mL) was treated with 3,5-dimethyl-1-(o-tolyl)piperazine (4k, 0.0350 g, 0.170 mmol) and Et$_3$N (59 µL, 0.425 mmol). The reaction mixture was cooled to 0° C., treated with T3P (50 wt. % solution in EtOAc, 150 µL, 0.212 mmol), warmed to room temperature, stirred for 20 h, diluted with CH$_2$Cl$_2$, and washed with satd. aqueous NH$_4$Cl, satd. aqueous NaHCO$_3$, and brine, dried (Na$_2$SO$_4$), filtered, and concentrated in vacuo. The crude residue was purified by chromatography on SiO$_2$ (95:5 CH$_2$Cl$_2$/MeOH) to give 5k (0.0450 g, 0.116 mmol, 82%, 99.8% pure by ELSD) as a light yellow oil: IR (neat) 2975, 1629, 1491, 1422, 1327, 1127 cm$^{-1}$; $^1$H NMR (500 MHz, CDCl$_3$) δ 7.22-7.19 (m, 2H), 7.06-7.02 (m, 2H), 4.68 (brs, 1H), 4.05 (brs, 1H), 3.73-3.70 (m, 1H), 3.66-3.61 (m, 1H), 3.30-3.19 (m, 2H), 2.98-2.96 (m, 2H), 2.94-2.89 (m, 1H), 2.81-2.78 (m, 1H), 2.44 (s, 3H), 2.41 (s, 3H), 2.31 (s, 3H), 1.55 (d, 3H, J=6.0 Hz), 1.48 (d, 3H, J=6.0 Hz); $^{13}$C NMR (125 MHz, CDCl$_3$) δ 168.2, 166.7, 151.2, 133.3, 131.2, 126.8, 124.1, 119.6, 109.8, 57.0, 56.8, 49.8, 45.8, 32.0, 23.6, 21.6, 20.3, 18.2, 11.0, 10.1; HRMS (ESI) m/z calcd for C$_{21}$H$_{30}$N$_3$O$_2$S ([M+H]$^+$) 388.2059, found 388.2053.

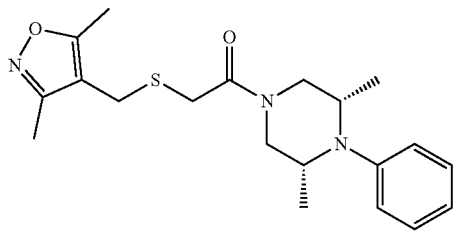 [SMILES: Cc1noc(C)c1CSCC(=O)N1C[C@@H](C)N(c2ccccc2)[C@@H](C)C1]

1-(3,5-Dimethyl-4-phenylpiperazin-1-yl)-2-(((3,5-dimethylisoxazol-4-yl)methyl)thio)ethan-1-one (5l). A solution of tert-butyl 3,5-dimethyl-4-phenylpiperazine-1-carboxylate (29b, 0.0330 g, 0.114 mmol) in THF (0.1 mL) at 0° C. was treated with 4 M HCl in dioxane (0.70 mL) and stirred at 0° C. for 1.5 h and at room temperature for 1.5 h. The yellow solid was filtered off, washed with Et$_2$O, dried under high vacuum and the resulting crude 4l was directly used for the next step.

To a solution of 2-(((3,5-dimethylisoxazol-4-yl)methyl)thio)acetic acid 3a (0.0229 g, 0.114 mmol) in CH$_2$Cl$_2$ (1.1 mL) was added 2,6-dimethyl-1-phenylpiperazine hydrochloride (4l, 0.0258 g, 0.114 mmol) and Et$_3$N (79 μL, 0.569 mmol). The reaction mixture was cooled to 0° C., treated with T3P (50 wt. % solution in EtOAc, 121 μL, 0.171 mmol), warmed to room temperature, stirred for 20 h, diluted with CH$_2$Cl$_2$, and washed with satd. aqueous NH$_4$Cl solution, satd. aqueous NaHCO$_3$ solution, and brine, dried (Na$_2$SO$_4$), filtered, and concentrated in vacuo. The crude residue was purified by chromatography on SiO$_2$ (1:1, acetone/hexanes, base washed with 0.1% Et$_3$N prior to use) to give 5l (0.0322 g, 0.0862 mmol, 76%, 100% pure by ELSD) as a colorless oil: IR (ATR) 2967, 2931, 1639, 1597, 1493, 1449, 1377, 1319, 1272, 1238, 1151, 1091, 886, 771, 731, 703 cm$^{-1}$; $^1$H NMR (400 MHz, CDCl$_3$) δ 7.31 (t, 2H, J=7.6 Hz), 7.18 (t, 1H, J=7.2 Hz), 7.10 (d, 2H, J=7.6 Hz), 4.42 (ddd, 1H, J=12.8, 4.0, 2.4 Hz), 3.70-3.60 (m, 3H), 3.29-3.18 (m, 2H), 3.10-2.93 (m, 3H), 2.67 (dd, 1H, J=13.2, 10.4 Hz), 2.43 (s, 3H), 2.30 (s, 3H), 0.77 (d, 3H, J=6.4 Hz), 0.76 (d, 3H, J=5.6 Hz); $^{13}$C NMR (100 MHz, CDCl$_3$) δ 167.1, 166.8, 159.7, 148.5, 128.9, 126.4, 125.6, 109.8, 56.0, 55.6, 53.4, 48.7, 31.9, 23.7, 18.2, 18.2, 11.1, 10.2; HRMS (ESI) m/z calcd for C$_{20}$H$_{28}$N$_3$O$_2$S ([M+H]$^+$) 374.1897, found 374.1887.

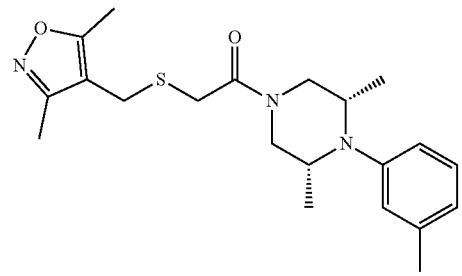 [SMILES: Cc1cccc(N2[C@H](C)CN(C(=O)CSCc3c(C)noc3C)C[C@@H]2C)c1]

1-(3,5-Dimethyl-4-(m-tolyl)piperazin-1-yl)-2-(((3,5-dimethylisoxazol-4-yl)methyl)thio)ethan-1-one (5m). A solution of tert-butyl 3,5-dimethyl-4-(m-tolyl)piperazine-1-carboxylate (29c, 0.0400 g, 0.131 mmol) in THF (0.1 mL) at 0° C. was treated with 4 M HCl in dioxane (0.80 mL), and stirred at 0° C. for 1.5 h and at room temperature for 1.5 h. A yellow precipitate formed and the solid was filtered off, washed with Et$_2$O, and dried under high vacuum and the resulting crude 4m was used directly for the next step.

To a solution of 2-(((3,5-dimethylisoxazol-4-yl)methyl)thio)acetic acid (3a, 0.0264 g, 0.131 mmol) in CH$_2$Cl$_2$ (1.3 mL) was added 2,6-dimethyl-1-(m-tolyl)piperazine hydrochloride (4m, 0.0316 g, 0.131 mmol) and Et$_3$N (91 μL, 0.656 mmol). The reaction mixture was cooled to 0° C., treated with T3P (50 wt. % solution in EtOAc, 139 μL, 0.197 mmol), warmed to room temperature, stirred for 20 h, diluted with CH$_2$Cl$_2$, washed with satd. aqueous NH$_4$Cl solution, satd. aqueous NaHCO$_3$ solution, and brine, dried (Na$_2$SO$_4$), filtered, and concentrated in vacuo. The crude residue was purified by chromatography on SiO$_2$ (3:2, EtOAc/hexanes, base washed with 0.1% Et$_3$N prior to use) to give 5m (0.0400 g, 0.103 mmol, 79%, 100% pure by ELSD) as a clear colorless oil: IR (ATR) 2966, 2929, 1637, 1602, 1451, 1376, 1319, 1271, 1194, 1149, 1108, 1088, 911, 889, 788, 730, 709 cm$^{-1}$; $^1$H NMR (400 MHz, CDCl$_3$) δ 7.18 (t, 1H, J=7.6 Hz), 6.97 (d, 1H, J=7.6 Hz), 6.90-6.88 (m, 2H), 4.41 (app d, 1H, J=12.8 Hz), 3.64 (brs, 3H), 3.27-3.19 (m, 2H), 3.15-2.91 (m, 3H), 2.67 (t, 1H, J=9.2 Hz), 2.43 (s, 3H), 2.32 (s, 3H), 2.30, (s, 3H), 0.77 (br app s, 6H); $^{13}$C NMR (100 MHz, CDCl$_3$) δ 167.1, 166.8, 159.7, 148.4, 138.7, 128.7, 127.1, 126.4, 123.4, 109.8, 56.0, 55.6, 53.4, 48.7, 32.0, 23.7, 21.4, 18.3, 18.2, 11.1, 10.2; HRMS (ESI) m/z calcd for C$_{21}$H$_{30}$N$_3$O$_2$S ([M+H]$^+$) 388.2053, found 388.2046.

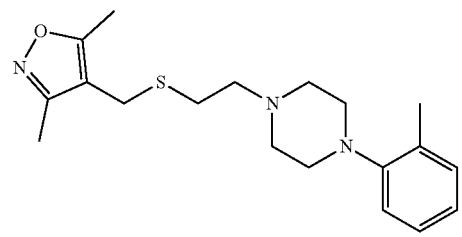 [SMILES: Cc1ccccc1N1CCN(CCSCc2c(C)noc2C)CC1]

3,5-Dimethyl-4-(((2-(4-(o-tolyl)piperazin-1-yl)ethyl)thio)methyl)isoxazole (6). A solution of 2-(((3,5-dimethylisoxazol-4-yl)methyl)thio)-1-(4-(o-tolyl)piperazin-1-yl)ethanone (5b, 0.0387 g, 0.108 mmol) in THF (1 mL) at 0° C. was treated with LiAlH$_4$ (1 M solution in Et$_2$O, 120 μL, 0.118 mmol), stirred at 0° C. for 1 h, and then quenched with Rochelle's salt (NaKC$_4$H$_4$O$_6$, satd. aqueous solution, 1 mL). The mixture was stirred for an additional 1 h at 0° C., diluted with EtOAc, extracted with EtOAc (2×15 mL), dried (Na$_2$SO$_4$), filtered, and concentrated in vacuo. The crude residue was purified by chromatography on SiO$_2$ (ISCO, 4 g column, liquid load in CH$_2$Cl$_2$, 0-20% MeOH/CH$_2$Cl$_2$, product eluted at 5% MeOH) to give a colorless oil. This oil was further purified by chromatography on SiO$_2$ (CH$_2$Cl$_2$ to 5:95, MeOH/CH$_2$Cl$_2$) on a pipette column to give 6 (0.0155 g, 0.0449 mmol, 42%, 100% pure by ELSD) as a colorless oil: IR (neat) 3393, 2925, 2814, 1637, 1599, 1493, 1448, 1424, 1372, 1227, 1195, 1130, 1041, 1006, 931, 763, 723 cm$^{-1}$; $^1$H NMR (300 MHz, CDCl$_3$) δ 7.16 (app t, 2H, J=7.4 Hz), 7.03-6.95 (m, 2H), 3.75 (t, 1H, J=5.7 Hz), 3.50 (s, 2H), 2.93 (app t, 4H, J=4.5 Hz), 2.63 (brs, 8H), 2.38 (s, 3H), 2.30 (s, 3H), 2.29 (s, 3H); $^{13}$C NMR (75 MHz, CDCl$_3$) δ 165.9, 159.6, 151.4, 132.6, 131.0, 126.6, 123.2, 119.0, 110.5, 77.2, 58.1, 53.6, 51.6, 29.1, 24.0, 23.5, 17.8, 11.1, 10.2; HRMS (ESI) m/z calcd for C$_{19}$H$_{28}$ON$_3$S ([M+H]$^+$) 346.1948, found 346.1946.

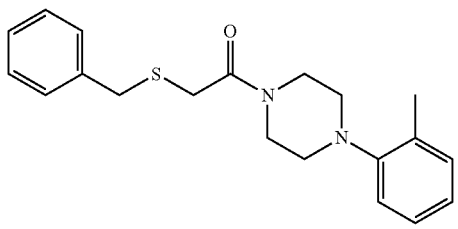 [SMILES: Cc1ccccc1N1CCN(C(=O)CSCc2ccccc2)CC1]

2-(Benzylthio)-1-(4-(o-tolyl)piperazin-1-yl)ethanone (7). A solution of 2-(benzylthio)acetic acid 3b (0.0440 g, 0.241 mmol) in CH$_2$Cl$_2$ (3.05 mL) was treated with 1-(o-tolyl)piperazine 4b (0.0521 g, 0.290 mmol) and Et$_3$N (101 µL, 0.724 mmol). The reaction mixture was cooled to 0° C., treated with T3P (50 wt. % solution in EtOAc, 256 µL, 0.362 mmol), warmed to room temperature and stirred for 2 d. The solution was diluted with CH$_2$Cl$_2$ and washed with satd. aqueous NH$_4$Cl, satd. aqueous NaHCO$_3$, and brine, dried (Na$_2$SO$_4$), filtered, and concentrated in vacuo. The crude residue was purified by chromatography on SiO$_2$ (ISCO, 12 g column, liquid load in CH$_2$Cl$_2$, EtOAc/hexanes gradient (10-100%)) to give 7 (0.0635 g, 0.187 mmol, 77%, 100% pure by ELSD) as a yellow oil: IR (ATR) 2917, 1815, 1634, 1598, 1492, 1437, 1223, 1150, 1031, 975, 761, 700 cm$^{-1}$; $^1$H NMR (300 MHz, CDCl$_3$) δ 7.45-7.23 (m, 7H), 7.06-7.01 (m, 2H), 3.89 (s, 2H), 3.79 (app t, 2H, J=4.9 Hz), 3.59 (app t, 2H, J=4.9 Hz), 3.30 (s, 2H), 2.95-2.90 (m, 4H), 2.37 (s, 3H); $^{13}$C NMR (75 MHz, CDCl$_3$) δ 167.7, 150.9, 137.7, 132.8, 131.2, 129.3, 128.5, 127.2, 126.7, 123.8, 119.3, 51.9, 51.7, 46.9, 42.4, 36.3, 32.4, 17.8; HRMS (ESI) m/z calcd for C$_{20}$H$_{25}$N$_2$OS ([M+H]$^+$) 341.1682, found: 341.1674.

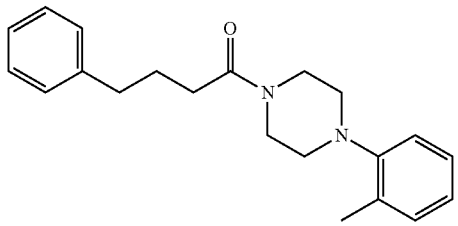 [SMILES: Cc1ccccc1N1CCN(C(=O)CCCc2ccccc2)CC1]

4-Phenyl-1-(4-(o-tolyl)piperazin-1-yl)butan-1-one (8). To a solution of phenyl butanoic acid (3c, 0.0500 g, 0.305 mmol) in CH$_2$Cl$_2$ (3.05 mL) was added 1-(o-tolyl)piperazine (4b, 0.0657 g, 0.365 mmol) and Et$_3$N (85 µL, 0.609 mmol). The reaction mixture was cooled to 0° C., treated with T3P (50 wt. % solution in EtOAc, 322 µL, 0.457 mmol), warmed to room temperature, stirred overnight, diluted with CH$_2$Cl$_2$ and washed with satd. aqueous NH$_4$Cl, satd. aqueous NaHCO$_3$, and brine, dried (Na$_2$SO$_4$), filtered, and concentrated in vacuo. The crude residue was purified by chromatography on SiO$_2$ (ISCO, 12 g column, liquid load in CH$_2$Cl$_2$, EtOAc/hexanes gradient (10-100%), eluted at 30%) to give 8 (0.0863 g, 0.268 mmol, 88%, 100% pure by ELSD) as a colorless oil: IR (ATR) 3024, 2917, 2813, 1641, 1492, 1432, 1223, 1150, 1025, 761, 722 cm$^{-1}$; $^1$H NMR (300 MHz, CDCl$_3$) δ 7.36-7.31 (m, 2H), 7.27-7.18 (m, 5H), 7.07-6.99 (m, 2H), 3.80 (app t, 2H, J=4.8 Hz), 3.55 (app t, 2H, J=4.8 Hz), 2.88 (app t, 4H, J=4.8 Hz), 2.75 (t, 2H, J=7.5 Hz), 2.41 (t, 2H, J=7.5 Hz), 2.36 (s, 3H), 2.06 (ddd, 2H, J=7.9, 7.7, 7.3 Hz); $^{13}$C NMR (75 MHz, CDCl$_3$) δ 171.2, 150.8, 141.6, 132.6, 131.0, 128.4, 128.3, 126.6, 125.8, 123.6, 119.0, 51.9, 51.6, 45.9, 41.9, 35.2, 32.3, 26.6, 17.7; HRMS (ESI) m/z calcd for C$_{21}$H$_{27}$N$_2$O ([M+H]$^+$) 323.2118, found: 323.2110.

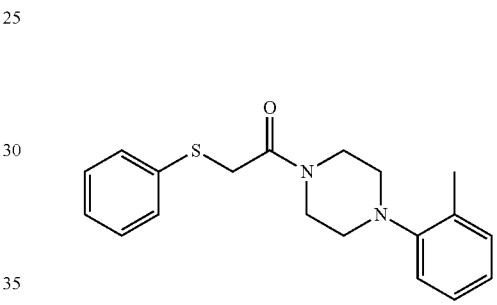

2-(Phenylthio)-1-(4-(o-tolyl)piperazin-1-yl)ethan-1-one (9). To a solution of 2-(phenylthio)acetic acid (3d, 0.0500 g, 0.297 mmol) in CH$_2$Cl$_2$ (3.0 mL) was added 1-(o-tolyl)piperazine (4b, 0.0642 g, 0.357 mmol) and Et$_3$N (83 µL, 0.594 mmol). The mixture was cooled to 0° C., treated with T3P (50 wt. % solution in EtOAc, 315 µL, 0.446 mmol), warmed to room temperature, stirred for 3 d, diluted with CH$_2$Cl$_2$ and washed with satd. aqueous NH$_4$Cl, satd. aqueous NaHCO$_3$, and brine. The organic layer was dried (Na$_2$SO$_4$), filtered, and concentrated in vacuo. The crude residue was purified by chromatography on SiO$_2$ (ISCO, 4 g column, liquid load in CH$_2$Cl$_2$, EtOAc/hexanes gradient (0-30%), eluted at 20-30%) to give 9 (0.0746 g, 0.229 mmol, 77%, 100% pure by ELSD) as a clear colorless oil: IR (ATR) 3057, 2947, 2911, 2856, 2815, 1639, 1598, 1492, 1482, 1382, 1275, 1223, 1203, 1149, 1115, 1032, 974, 950, 909, 762, 738, 723, 690 cm$^{-1}$; $^1$H NMR (400 MHz, CDCl$_3$) δ 7.48 (dd, 2H, J=7.6, 1.2 Hz), 7.34 (app t, 2H, J=7.6 Hz), 7.26-7.17 (m, 3H), 7.02 (app t, 1H, J=7.6 Hz), 6.98 (app d, 1H, J=7.6 Hz), 3.81 (s, 2H), 3.76 (app t, 2H, J=4.8 Hz), 3.63 (app t, 2H, J=4.8 Hz), 2.91 (app t, 2H, J=4.8 Hz), 2.86 (t, 2H, J=4.8 Hz), 2.33 (s, 3H); $^{13}$C NMR (100 MHz, CDCl$_3$) δ 167.1, 150.7, 134.9, 132.7, 131.2, 130.3, 129.1, 127.0, 126.7, 123.8, 119.2, 51.9, 51.6, 47.0, 42.5, 36.7, 17.8; HRMS (ESI) m/z calcd for C$_{19}$H$_{23}$N$_2$OS ([M+H]$^+$) 327.1526, found 327.1514.

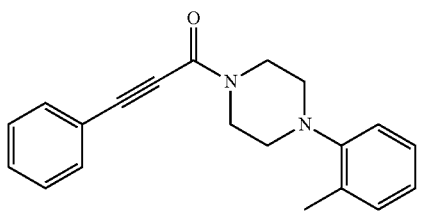 [SMILES: Cc1ccccc1N1CCN(C(=O)C#Cc2ccccc2)CC1]

3-Phenyl-1-(4-(o-tolyl)piperazin-1-yl)prop-2-yn-1-one (10). To a solution of phenyl propiolic acid (3e, 0.200 g, 1.37 mmol) in $CH_2Cl_2$ (12 mL) was added 1-(o-tolyl)piperazine (4b, 0.290 g, 1.64 mmol) and $Et_3N$ (570 μL, 4.11 mmol). The reaction mixture was cooled to 0° C., treated with T3P (50 wt. % solution in EtOAc, 1.45 mL, 2.05 mmol), warmed to room temperature, stirred for 3 d, diluted with $CH_2Cl_2$ (30 mL), and washed with satd. aqueous $NH_4Cl$ (5 mL), satd. aqueous $NaHCO_3$ (5 mL), and brine (5 mL), dried ($Na_2SO_4$), filtered, and concentrated in vacuo. The crude residue was purified by chromatography on $SiO_2$ (ISCO, 24 g column, liquid load in $CH_2Cl_2$, EtOAc/hexanes gradient (10-100%), product eluted at 40% EtOAc/hexanes) to give 10 (0.401 g, 1.32 mmol, 96%, >99.9% pure by ELSD) as a colorless solid: Mp 127-129° C.; IR (neat) 3037, 2907, 2857, 2206, 1616, 1491, 1424, 1279, 1226, 1207, 1035, 923, 758, 726, 686 $cm^{-1}$; $^1H$ NMR (300 MHz, $CDCl_3$) δ 7.59-7.56 (m, 2H), 7.43-7.34 (m, 3H), 7.22-7.16 (m, 2H), 7.05-6.99 (m, 2H), 3.99 (app t, 2H, J=5.0 Hz), 3.85 (app t, 2H, J=5.0 Hz), 2.99 (app t, 2H, J=5.0 Hz), 2.92 (app t, 2H, J=5.0 Hz), 2.35 (s, 3H); $^{13}C$ NMR (75 MHz, $CDCl_3$) δ 153.2, 150.8, 132.8, 132.4, 131.2, 130.1, 128.6, 126.8, 123.9, 120.5, 119.3, 90.9, 81.2, 52.2, 51.5, 47.7, 42.1, 17.8; HRMS (ESI) m/z calcd for $C_{20}H_{21}ON_2$ ([M+H]$^+$) 305.1648, found 305.1643.

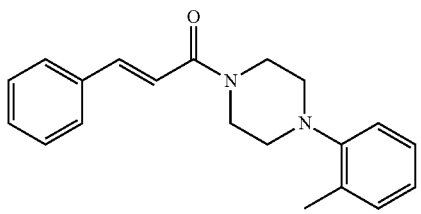 [SMILES: Cc1ccccc1N1CCN(C(=O)/C=C/c2ccccc2)CC1]

(E)-3-Phenyl-1-(4-(o-tolyl)piperazin-1-yl)prop-2-en-1-one (11). A solution of trans-cinnamic acid (3f, 0.0400 g, 0.270 mmol) in $CH_2Cl_2$ (2.5 mL) was treated with 1-(o-tolyl)piperazine (4b, 0.0570 g, 0.320 mmol), $Et_3N$ (113 μL, 0.810 mmol). The reaction mixture was cooled to 0° C., treated with T3P (50 wt. % solution in EtOAc, 290 μL, 0.405 mmol), warmed to room temperature, stirred for 3 d, diluted with $CH_2Cl_2$ (10 mL), and washed with satd. aqueous $NH_4Cl$ (2 mL), satd. aqueous $NaHCO_3$ (2 mL), and brine (2 mL), dried ($Na_2SO_4$), filtered, and concentrated in vacuo. The crude residue was purified by chromatography on $SiO_2$ (ISCO, 12 g column, liquid load in $CH_2Cl_2$, EtOAc/hexanes gradient (10-100%), product eluted at 35%, EtOAc/hexanes) to give 11 (0.0520 g, 0.168 mmol, 62%, >99% purity by ELSD) as a yellow solid: Mp 110-111° C.; IR (neat) 3045, 2920, 2840, 1643, 1595, 1423, 1327, 1225, 1152, 986, 765, 710, 682 $cm^{-1}$; $^1H$ NMR (400 MHz, $CDCl_3$) δ 7.72 (d, 1H, J=11.4 Hz), 7.55 (dd, 2H, J=6.8, 1.4 Hz), 7.41-7.36 (m, 3H), 7.20 (dd, 2H, J=14.6, 7.4 Hz), 7.02 (ddd, 2H, J=14.6, 7.4, 0.6 Hz), 6.95 (d, 1H, J=15.6 Hz), 3.90 (brs, 2H), 3.81 (brs, 2H), 2.96 (brs, 4H), 2.36 (s, 3H); $^{13}C$ NMR (75 MHz, $CDCl_3$) δ 165.5, 150.8, 142.8, 135.2, 132.7, 131.1, 129.6, 128.8, 127.7, 126.6, 123.7, 119.2, 117.1, 52.1, 51.6, 46.4, 42.6, 17.8; HRMS (ESI) m/z calcd for $C_{20}H_{23}ON_2$ ([M+H]$^+$) 307.1805, found 307.1796.

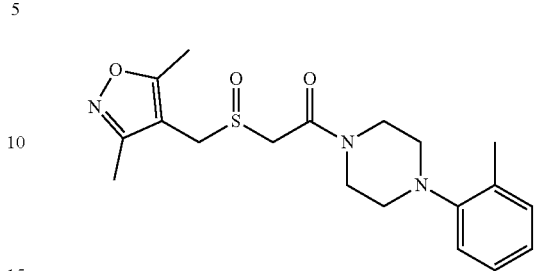

2-(((3,5-Dimethylisoxazol-4-yl)methyl)sulfinyl)-1-(4-(o-tolyl)piperazin-1-yl)ethan-1-one (12). To a solution of 2-(((3,5-dimethylisoxazol-4-yl)methyl)thio)-1-(4-(o-tolyl)piperazin-1-yl)ethanone (5b, 0.0500 g, 0.139 mmol) in MeOH (0.30 mL) at 0° C. was added dropwise a solution of sodium metaperiodate (0.0301 g, 0.139 mmol) in water (0.14 mL). The resulting heterogeneous mixture was allowed to warm to room temperature and stirred for 15 h. The reaction mixture was filtered through a plug of Celite (MeOH), concentrated, dissolved in $CH_2Cl_2$, dried ($MgSO_4$), filtered and concentrated in vacuo. The crude residue was purified by chromatography on $SiO_2$ (100% EtOAc) to give 12 (0.0356 g, 0.0948 mmol, 68%, 100% pure by ELSD) as a colorless foam: IR (ATR) 2917, 2818, 1631, 1599, 1493, 1441, 1384, 1275, 1224, 1195, 1151, 1053, 1028, 911, 764, 727 $cm^{-1}$; $^1H$ NMR (400 MHz, $CDCl_3$) δ 7.21-7.15 (m, 2H), 7.02 (app t, 1H, J=7.2 Hz), 6.97 (app d, 1H, J=8.0 Hz), 4.18 (d, 1H, J=14.0 Hz), 3.90-3.84 (m, 5H), 3.64 (app t, 2H, J=4.4 Hz), 2.95 (app t, 2H, J=4.4 Hz), 2.85 (brs, 2H), 2.45 (s, 3H), 2.32 (s, 3H), 2.31 (s, 3H); $^{13}C$ NMR (100 MHz, $CDCl_3$) δ 169.2, 162.9, 159.9, 150.4, 132.7, 131.2, 126.7, 124.0, 119.2, 104.5, 53.7, 52.0, 51.5, 47.0, 46.8, 42.5, 17.7, 11.6, 10.3; HRMS (ESI) m/z calcd for $C_{19}H_{26}N_3O_3S$ ([M+H]$^+$) 376.1689, found 376.1684.

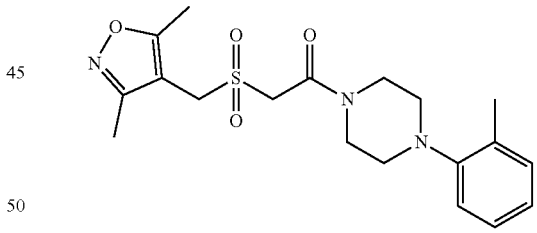

2-(((3,5-Dimethylisoxazol-4-yl)methyl)sulfonyl)-1-(4-(o-tolyl)piperazin-1-yl)ethan-1-one (13). A solution of 2-(((3,5-dimethylisoxazol-4-yl)methyl)thio)-1-(4-(o-tolyl)piperazin-1-yl)ethanone (5b, 0.0429 g, 0.117 mmol) in $CH_2Cl_2$ (0.65 mL) was treated with 3-chloroperoxybenzoic acid (70 wt. %, 0.0576 g, 0.234 mmol) in 2 portions. The reaction mixture was stirred at room temperature for 15 h, quenched with 10% aqueous sodium metabisulfite solution (2 mL), diluted with aqueous 1 M NaOH (10 mL) and extracted with $CH_2Cl_2$ (2×15 mL). The combined organic layers were washed with 1 M NaOH (10 mL), dried ($MgSO_4$), filtered, and concentrated in vacuo. The crude residue was purified by chromatography on $SiO_2$ (70-100% EtOAc/hexanes) to give 13 (0.0203 g, 0.0519 mmol, 44%, 100% pure by ELSD) as a colorless foam: IR (ATR) 2919, 2819, 1641, 1599, 1493, 1445, 1318, 1225, 1150, 1126, 1030, 911, 765, 728 cm$^{-1}$; $^1$H NMR (400 MHz, CDCl$_3$) δ 7.21-7.16 (m, 2H), 7.05-6.98 (m, 2H), 4.36 (s, 2H), 4.09 (s, 2H), 3.85 (app brs, 2H), 3.72 (brt, 2H, J=4.0 Hz), 3.00 (brt, 2H, J=4.0 Hz), 2.93 (brt, 2H, J=4.4 Hz), 2.50 (s, 3H), 2.35 (s, 3H), 2.33 (s, 3H); $^{13}$C NMR (100 MHz, CDCl$_3$) δ 170.1, 160.7, 160.3, 150.3, 132.7, 131.2, 126.7, 124.0, 119.2, 101.8, 54.9, 51.7, 51.4, 48.3, 47.8, 43.0, 17.8, 11.5, 10.2; HRMS (ESI) m/z calcd for C$_{19}$H$_{26}$N$_3$O$_4$S ([M+H]$^+$) 392.1639, found 392.1633.

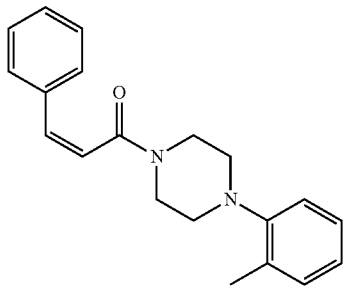 [SMILES: Cc1ccccc1N1CCN(C(=O)/C=C\c2ccccc2)CC1]

(Z)-3-Phenyl-1-(4-(o-tolyl)piperazin-1-yl)prop-2-en-1-one (14). To a solution of 3-phenyl-1-(4-(o-tolyl)piperazin-1-yl)prop-2-yn-1-one (10, 0.103 g, 0.337 mmol) in MeOH (2 mL) and EtOAc (1 mL) was added Lindlar's catalyst (5% Pd on CaCO$_3$, lead poisoned, 0.120 g) and quinoline (15 μL, 0.130 mmol). The reaction mixture was purged and backfilled with H$_2$ (balloon, 2×), allowed to stir for 45 min, filtered through SiO$_2$, and concentrated in vacuo. The crude residue was purified by chromatography on SiO$_2$ (ISCO, modified dry load in CH$_2$Cl$_2$, 0-90% EtOAc/hexanes gradient, product eluted at 25% EtOAc/hexanes) to give 14 (0.104 g, 0.339 mmol, quant., 99.6% purity by ELSD) as a yellow oil: IR (neat) 3022, 2914, 2815, 1513, 1597, 1493, 1434, 1364, 1223, 1149, 1115, 1034, 973, 913, 855, 762, 722, 698 cm$^{-1}$; $^1$H NMR (300 MHz, CDCl$_3$) δ 7.41-7.30 (m, 5H), 7.17-7.11 (m, 2H), 6.98 (t, 1H, J=7.1 Hz), 6.81 (d, 1H, J=7.8 Hz), 6.71 (d, 1H, J=12.6 Hz), 6.07 (d, 1H, J=12.6 Hz), 3.81 (app brt, 2H, J=4.8 Hz), 3.48 (app t, 2H, J=4.8 Hz), 2.81 (app t, 2H, J=4.8 Hz), 2.44 (app t, 2H, J=4.8 Hz), 2.25 (s, 3H); $^{13}$C NMR (75 MHz, CDCl$_3$) δ 167.6, 150.9, 135.6, 133.5, 132.7, 131.1, 128.7, 128.6, 128.5, 126.6, 123.7, 123.2, 119.1, 51.5, 51.3, 46.8, 41.7, 17.7; HRMS (ESI) m/z calcd for C$_{20}$H$_{23}$ON$_2$ ([M+H]$^+$) 307.1805, found 307.1800.

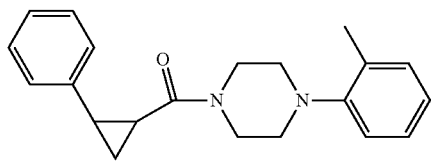 [SMILES: Cc1ccccc1N1CCN(C(=O)C2CC2c2ccccc2)CC1]

(2-Phenylcyclopropyl)(4-(o-tolyl)piperazin-1-yl)methanone (15). A solution of anhydrous CrCl$_2$ (0.0486 g, 0.392 mmol) in THF (0.6 mL) at room temperature under N$_2$ was treated with a solution of (Z)-3-phenyl-1-(4-(o-tolyl)piperazin-1-yl)prop-2-en-1-one (14, 0.0200 g, 0.0653 mmol) in THF (0.5 mL) and CH$_2$ICl (20 μL, 0.261 mmol). The reaction mixture was stirred for 18 h at reflux, quenched by addition of 1 M aqueous HCl (6 mL) and extracted with EtOAc. The combined organic layers were dried (Na$_2$SO$_4$), filtered, and concentrated in vacuo. The crude residue was purified by chromatography on SiO$_2$ (4:1, EtOAc/hexanes) to give 15 (0.0120 g, 0.0375 mmol, 57%, 100% pure by ELSD) as a brown oil: IR (neat) 2920, 1638, 1491, 1457, 1340, 1223, 1028 cm$^{-1}$; $^1$H NMR (400 MHz, CDCl$_3$) δ 7.30-7.27 (m, 2H), 7.22-7.11 (m, 5H), 6.98 (dt, 1H, J=7.2, 1.2 Hz), 6.72 (dd, 1H, J=7.9, 0.8 Hz), 3.93-3.90 (m, 1H), 3.77-3.73 (m, 1H), 3.60-3.53 (m, 1H), 3.30-3.22 (m, 1H), 2.75-2.72 (m, 2H), 2.50-2.41 (m, 1H), 2.26 (s, 3H), 2.24-2.16 (m, 1H), 2.10-2.00 (m, 1H), 1.87 (dd, 1H, J=12.4, 5.8 Hz), 1.40-1.33 (m, 1H), 0.92-0.80 (m, 1H); $^{13}$C NMR (100 MHz, CDCl$_3$) δ 167.2, 150.9, 137.6, 132.7, 131.0, 128.2, 127.4, 126.5, 126.4, 123.6, 119.2, 51.9, 51.6, 45.7, 42.3, 24.4, 24.1, 17.7, 10.6 □ HRMS (ESI) m/z calcd for C$_{21}$H$_{25}$ON$_2$ ([M+H]$^+$) 321.1967, found 321.1961.

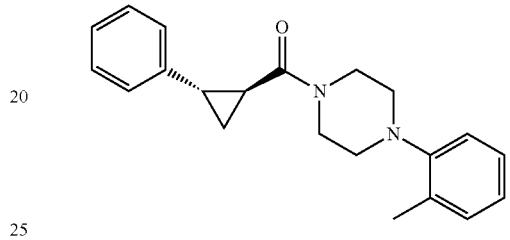

((1SR,2SR)-2-Phenylcyclopropyl)(4-(o-tolyl)piperazin-1-yl)methanone (16). To a solution of trans-2-phenylcyclopropanecarboxylic acid (3g, 0.0400 g, 0.247 mmol) in CH$_2$Cl$_2$ (2.5 mL) was treated with 1-(o-tolyl)piperazine (4b, 0.0540 g, 0.296 mmol), Et$_3$N (100 μL, 0.740 mmol). The reaction mixture was cooled to 0° C., treated with T3P (50 wt. % solution in EtOAc, 260 μL, 0.370 mmol, 1.5 equiv), warmed to room temperature, stirred for 3 d, diluted with EtOAc (10 mL), and washed with satd. aqueous NH$_4$Cl (2 mL), satd. aqueous NaHCO$_3$ (2 mL), and brine (2 mL), dried (Na$_2$SO$_4$), filtered, and concentrated in vacuo. The crude residue was purified by chromatography on SiO$_2$ (ISCO, 12 g column, liquid load in CH$_2$Cl$_2$, EtOAc/hexanes gradient (10-90%), product eluted at 20%) to give 16 (0.0676 g, 0.211 mmol, 86%, >99.9% pure by ELSD) as a yellow oil: IR (neat) 3026, 2912, 2814, 1631, 1600, 1493, 1440, 1381, 1223, 1150, 1033, 919, 910, 760, 723, 696 cm$^{-1}$; $^1$H NMR (300 MHz, CDCl$_3$) δ 7.32-7.26 (m, 2H), 7.23-7.12 (m, 5H), 7.01 (dd, 2H, J=11.1, 7.5 Hz), 3.79 (brs, 4H), 2.90 (brs, 4H), 2.52 (brpent, 1H, J=4.6 Hz), 2.33 (s, 3H), 2.02 (pent, 1H, J=4.6 Hz), 1.71 (pent, 1H, J=4.6 Hz), 1.34-1.26 (m, 2H); $^{13}$C NMR (100 MHz, CDCl$_3$) δ 170.6, 150.9, 141.0, 132.7, 131.2, 128.6, 126.7, 126.3, 126.1, 123.8, 119.2, 52.2, 51.7, 46.2, 25.6, 23.3, 17.9, 16.2; HRMS (ESI) m/z calcd for C$_{21}$H$_{25}$ON$_2$ ([M+H]$^+$) 321.1961, found 321.1957.

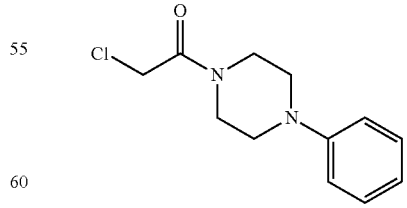

2-Chloro-1-(4-(o-tolyl)piperazin-1-yl)ethanone (17a) (Glennon et al., *J. Med. Chem.* 1986, 29, 2375-2380; Jorand-Lebrun et al., *J. Med. Chem.* 1997, 40, 3974-3978). To a solution of chloroacetyl chloride (0.698 g, 6.05 mmol) and potassium carbonate (1.14 g, 8.25 mmol) in THF (7.0 mL)

was added 1-(o-tolyl)piperazine (4b, 1.00 g, 5.50 mmol) in THF (12.6 mL) at 0° C. The reaction mixture was gradually warmed to room temperature, stirred for 16 h, diluted with water, and extracted with EtOAc (3×20 mL). The combined organic extracts were washed sequentially with satd. aqueous NaHCO$_3$, 0.1 M aqueous HCl, and brine, dried (Na$_2$SO$_4$), filtered and concentrated in vacuo. The crude solid was filtered through a plug of SiO$_2$ (3:7, EtOAc/hexanes v/v 1% Et$_3$N) and washed thoroughly with EtOAc/hexanes (3:7) to give 17a (1.37 g, 5.42 mmol, 99%) as an off white solid: $^1$H NMR (400 MHz, CDCl$_3$) δ 7.22-7.16 (m, 2H), 7.05-6.99 (m, 2H), 4.12 (s, 2H), 3.78 (app t, 2H, J=4.8 Hz), 3.67 (app t, 2H, J=4.8 Hz), 2.97 (app t, 2H, J=4.8 Hz), 2.91 (app t, 2H, J=4.8 Hz), 2.33 (s, 3H).

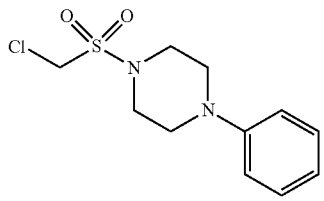 [SMILES: O=S(=O)(CCl)N1CCN(c2ccccc2)CC1]

1-((Chloromethyl)sulfonyl)-4-(o-tolyl)piperazine (17b) (Zhou et al., *J. Org. Lett.* 2008, 10, 2517-2520). To a solution of 1-(o-tolyl)piperazine (4b, 0.500 g, 2.75 mmol) in CH$_2$Cl$_2$ (9.8 mL) and Et$_3$N (0.390 mL, 2.75 mmol) at 0° C. was added chloromethanesulfonyl chloride (0.460 g, 3.03 mmol). The reaction mixture was stirred at 0° C., gradually warmed to room temperature quenched after 14 h with satd. aqueous NH$_4$Cl solution (3 mL), and extracted with EtOAc (3×20 mL). The combined organic extracts were washed water (2×10 mL) and brine (10 mL), dried (Na$_2$SO$_4$), filtered and concentrated in vacuo. The crude solid was filtered through a plug of SiO$_2$ (3:7, EtOAc/hexanes containing 1% Et$_3$N) and washed thoroughly with EtOAc/hexanes (3:7). The combined filtrates were concentrated in vacuo to give 17b (0.676 g, 2.34 mmol, 85%) as an orange solid: $^1$H NMR (300 MHz, CDCl$_3$) δ 7.19 (t, 2H, J=8.1 Hz), 7.03 (t, 2H, J=8.1 Hz), 4.56 (s, 2H), 3.63 (app t, 4H, J=5.0 Hz), 2.99 (app t, 4H, J=5.0 Hz), 2.32 (s, 3H); $^{13}$C NMR (75 MHz, CDCl$_3$) δ 150.6, 132.7, 131.2, 126.8, 124.1, 119.4, 54.5, 51.9, 47.1, 17.7.

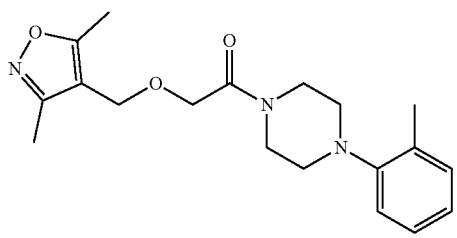

2-((3,5-Dimethylisoxazol-4-yl)methoxy)-1-(4-(o-tolyl)piperazin-1-yl)ethan-1-one (18a). A solution of (3,5-dimethylisoxazol-4-yl)methanol (27, 0.0302 g, 0.237 mmol) in THF (0.48 mL) was cooled to 0° C. and NaH (60% dispersion in mineral oil, 0.0190 g, 0.475 mmol) was added. The reaction mixture was stirred at 0° C. for 30 min, treated with 2-chloro-1-(4-(o-tolyl)piperazin-1-yl)ethanone (17a, 0.0600 g, 0.237 mmol), warmed to room temperature, stirred for 20 h, quenched with brine (1 mL), diluted with EtOAc (15 mL) and brine (5 mL), and extracted with EtOAc (2×15 mL). The combined organic layers were dried (Na$_2$SO$_4$) and concentrated in vacuo. The crude residue was purified by chromatography on SiO$_2$ (3:2, EtOAc/hexanes) to give 18a (0.0735 g, 0.214 mmol, 90%, 100% pure by ELSD) as a light yellow oil: IR (ATR) 2918, 2817, 1645, 1599, 1493, 1443, 1369, 1273, 1225, 1116, 1030, 977, 764, 725 cm$^{-1}$; $^1$H NMR (400 MHz, CDCl$_3$) δ 7.21-7.16 (m, 2H), 7.02 (dt, 1H, J=7.6, 1.2 Hz), 6.97 (app d, 1H, J=8.0 Hz), 4.41 (s, 2H), 4.17 (s, 2H), 3.77 (brs, 2H), 3.59 (app t, 2H, J=4.8 Hz), 2.89 (app t, 4H, J=3.6 Hz), 2.41 (s, 3H), 2.32 (s, 3H), 2.30 (s, 3H); $^{13}$C NMR (125 MHz, CDCl$_3$) δ 167.8, 167.5, 159.8, 150.7, 132.7, 131.2, 126.7, 123.9, 119.2, 110.5, 68.7, 61.7, 52.1, 51.7, 45.6, 42.3, 17.8, 11.1, 10.1; HRMS (ESI) m/z calcd for C$_{19}$H$_{26}$N$_3$O$_3$ ([M+H]$^+$) 344.1969, found 344.1960.

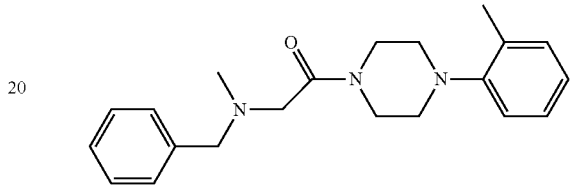

2-(Benzyl(methyl)amino)-1-(4-(o-tolyl)piperazin-1-yl)ethanone (18b). A solution of 2-chloro-1-(4-(o-tolyl)piperazin-1-yl)ethanone (17a, 0.0534 g, 0.211 mmol), in CH$_3$CN (4 mL) was treated with N-methylbenzylamine (23 μL, 0.176 mmol) and K$_2$CO$_3$ (0.730 g, 0.528 mmol). The reaction mixture was heated at reflux for 5 h, cooled to room temperature, filtered, and concentrated in vacuo. The crude residue was purified by chromatography on SiO$_2$ (2:3, EtOAc/hexanes) to give 18b (0.0590 g, 0.175 mmol, 99%, >95% pure by LCMS) as a light yellow oil: IR (neat) 2933, 2816, 1640, 1450, 1491, 1222 cm$^{-1}$; $^1$H NMR (500 MHz, CDCl$_3$) δ 7.39-7.33 (m, 4H), 7.31-7.27 (m, 1H), 7.23-7.19 (m, 2H), 7.04 (t, 1H, J=7.5 Hz), 7.01 (d, 1H, J=8.0 Hz), 3.77 (brs, 2H), 3.71-3.69 (m, 2H), 3.61 (s, 2H), 3.27 (s, 2H), 2.91-2.87 (m, 4H), 2.35 (s, 3H) 2.34 (s, 3H); $^{13}$C NMR (125 MHz, CDCl$_3$) δ 150.9, 138.1, 132.6, 131.1, 129.1, 128.2, 127.2, 126.6, 123.6, 119.1, 62.0, 60.3, 52.1, 51.7, 46.1, 42.4, 42.2, 17.8; HRMS (ESI) m/z calcd for C$_{21}$H$_{28}$N$_3$O ([M+H]$^+$) 338.2238, found 338.2211.

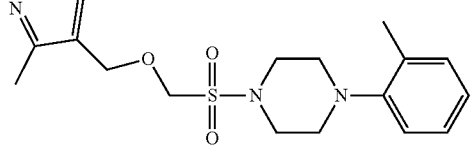

3,5-Dimethyl-4-(((((4-(o-tolyl)piperazin-1-yl)sulfonyl)methyl)thio)methyl)isoxazole (18c). A suspension of NaH (60% dispersion in mineral oil, 0.0200 g, 0.499 mmol) in THF (0.6 mL) was treated under an atmosphere of N$_2$ at 0° C. with a solution of (3,5-dimethylisoxazol-4-yl)methanethiol (25, 0.0536 g, 0.374 mmol) in THF (0.4 mL). The reaction mixture was stirred for 10 min, treated with 1-((chloromethyl)sulfonyl)-4-(o-tolyl)piperazine (17b, 0.0360 g, 0.125 mmol), stirred for 2 d at room temperature, quenched (water) and extracted (EtOAc). The combined organic layers were dried (Na$_2$SO$_4$), filtered, and concentrated in vacuo. The residue was purified by chromatography on SiO$_2$ (1:4, EtOAc/hexanes) to give crude 18c that was further purified by preparative TLC (2:3, Et$_2$O/hexanes) to give 18c (2.0 mg, 0.00506 mmol, 4%, 100% pure by ELSD) as a colorless oil: IR (neat) 2924, 1636, 1450, 1420, 1320, 1152 cm$^{-1}$; $^1$H NMR (400 MHz, CDCl$_3$) δ 7.20 (t, 2H, J=7.7 Hz), 7.06-7.00 (m, 2H), 3.87 (s, 2H), 3.76 (s, 2H), 3.58 (app t, 4H, J=4.8 Hz), 2.99 (app t, 4H, J=4.8 Hz), 2.44 (s, 3H), 2.32 (s, 3H), 2.31 (s, 3H); $^{13}$C NMR (100 MHz, CDCl$_3$) δ 167.5, 159.7, 150.6, 132.7, 131.2, 126.8, 124.0, 119.4, 108.7, 51.8, 48.6, 47.0, 24.1, 17.8, 11.1, 10.2; HRMS (ESI) m/z calcd for C$_{18}$H$_{26}$O$_3$N$_3$S$_2$ ([M+H]$^+$) 396.1416, found 396.1410.

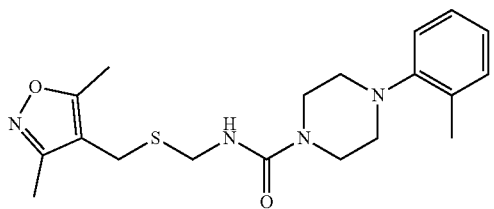 [SMILES: Cc1ccccc1N1CCN(C(=O)NCSCc2c(C)noc2C)CC1]

N-((((3,5-Dimethylisoxazol-4-yl)methyl)thio)methyl)-4-(o-tolyl)piperazine-1-carboxamide (20a). To a solution of 2-(((3,5-dimethylisoxazol-4-yl)methyl)thio)acetic acid (3a, 0.0500 g, 0.248 mmol) in toluene (4.0 mL) was added DPPA (57 μL, 0.261 mmol) and Et$_3$N (37 μL, 0.261 mmol). The reaction mixture was heated at 110° C. for 60 min, cooled and washed with satd. aqueous NaHCO$_3$, dried (MgSO$_4$), filtered and concentrated to give the isocyanate 19 as a pink oil that was used without further purification.

A solution of 1-(o-tolyl)piperazine (4b, 0.460 g, 0.261 mmol) and Et$_3$N (37 μL, 0.261 mmol) in CH$_2$Cl$_2$ (0.5 mL) was cooled to 0° C. and treated with a solution of the isocyanate 19 in CH$_2$Cl$_2$ (0.5 mL). The reaction mixture was stirred overnight at room temperature, then diluted with EtOAc and satd. aqueous NH$_4$Cl. The organic layer was washed with satd. aqueous NaHCO$_3$ and brine, dried (Na$_2$SO$_4$), filtered, and concentrated in vacuo. The residue was purified by chromatography on SiO$_2$ (ISCO, 4 g column, gradient hexanes to 1:1, EtOAc/hexanes, with an initial base wash of the column using hexanes containing 1% Et$_3$N) to give 20a (0.0606 g, 0.162 mmol, 65%, 98% pure by ELSD) as a clear oil that turns to a red oil upon standing: IR (CH$_2$Cl$_2$) 3336, 2941, 2891, 2850, 1629, 1523, 1491, 1495, 1420, 1254, 1223, 1193, 997, 907, 761, 731 cm$^{-1}$; $^1$H NMR (300 MHz, CDCl$_3$) δ 7.18 (dd, 2H, J=8.7, 7.5 Hz), 7.04-6.98 (m, 2H), 4.88 (brt, 1H, J=6.0 Hz), 4.44 (d, 2H, J=6.0 Hz), 3.67 (s, 2H), 3.50 (app t, 4H, J=5.0 Hz), 2.89 (app t, 4H, J=5.0 Hz), 2.39 (s, 3H), 2.32 (s, 3H), 2.29 (s, 3H); $^{13}$C NMR (75 MHz, CDCl$_3$) δ 166.0, 159.5, 156.9, 150.9, 132.7, 131.2, 126.7, 123.7, 119.1, 110.8, 51.6, 44.4, 43.9, 23.6, 17.8, 11.0, 10.2; HRMS (ESI) m/z calcd for C$_{19}$H$_{27}$N$_4$O$_2$S ([M+H]$^+$) 375.1849, found 375.1845.

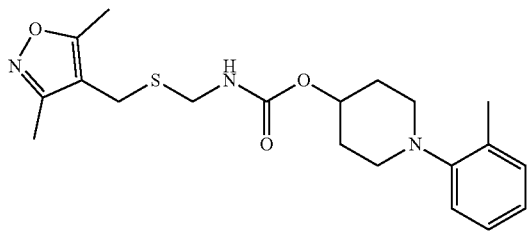 [SMILES: Cc1ccccc1N1CCC(OC(=O)NCSCc2c(C)noc2C)CC1]

1-(o-Tolyl)piperidin-4-yl((((3,5-dimethylisoxazol-4-yl)methyl)thio)methyl)-carbamate (20b). To a solution of 2-(((3,5-dimethylisoxazol-4-yl)methyl)thio)acetic acid (3a, 0.0500 g, 0.248 mmol) in toluene (4.0 mL) was added DPPA (0.06 mL, 0.261 mmol) and Et$_3$N (37 μL, 0.261 mmol). The reaction mixture was heated at 110° C. for 60 min, cooled to room temperature and treated with a solution of 1-(o-tolyl)piperidin-4-ol (4n, 0.0427 g, 0.224 mmol) in CH$_2$Cl$_2$ (0.5 mL). The reaction mixture was stirred overnight at 80° C., and diluted with EtOAc and satd. aqueous NH$_4$Cl. The organic layer was washed with satd. aqueous NaHCO$_3$ and brine, dried (Na$_2$SO$_4$), filtered, and concentrated in vacuo. The residue was purified by chromatography on SiO$_2$ (ISCO, 4 g column, gradient hexanes to 3:7, EtOAc/hexanes, with an initial base wash of the column with hexanes w/ 1% Et$_3$N) to give 20b (0.0168 g, 0.0431 mmol, 17%, 100% pure by ELSD) as a clear oil that eventually turned to a light yellow oil upon standing: IR (CH$_2$Cl$_2$) 3323, 2947, 2924, 2848, 2811, 1711, 1491, 1450, 1422, 1228, 1195, 1027, 762, 723 cm$^{-1}$; $^1$H NMR (400 MHz, DMSO-d6) δ 7.98 (t, 1H, J=6.4 Hz), 7.16-7.11 (m, 2H), 7.02 (d, 1H, J=7.2 Hz), 6.94 (dt, 1H, J=7.2, 1.2 Hz), 4.72-4.69 (m, 1H), 4.15 (d, 2H, J=6.4 Hz), 3.66 (s, 2H), 3.01-2.98 (m, 2H), 2.78-2.72 (m, 2H), 2.36 (s, 3H), 2.24 (s, 3H), 2.18 (s, 3H), 2.04-1.94 (m, 2H), 1.77-1.67 (m, 2H); $^{13}$C NMR (100 MHz, DMSO-d6) δ 165.7, 159.2, 155.5, 151.5, 131.8, 130.7, 126.5, 122.8, 118.9, 110.9, 69.9, 49.2, 42.9, 31.6, 21.9, 17.4, 10.5, 9.7; HRMS (ESI) m/z calcd for C$_{20}$H$_{28}$N$_3$O$_3$S ([M+H]$^+$) 390.1846, found 390.1846.

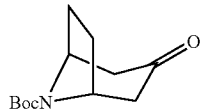

tert-Butyl 3-oxo-8-azabicyclo[3.2.1]octane-8-carboxylate (21a) (WO 2012/152854 A1). A solution of nortropinone-HCl (21, 2.00 g, 12.4 mmol) in a minimum amount of water (6.0 mL) was cooled to 0° C., treated dropwise with 1 M NaOH (14.8 mL, 14.8 mmol, 1.2 equiv), warmed to room temperature over 20 min, extracted with CH$_2$Cl$_2$ (3×40 mL), dried (MgSO$_4$), filtered, and concentrated in vacuo (water bath at 23° C.) to give nortropinone 21 as the free base (1.54 g, quant.). The colorless oil was used without further purification.

To a solution of nortropinone 21 (1.54 g, 12.3 mmol) in CH$_2$Cl$_2$ (50 mL) cooled to 0° C. was added Boc anhydride (4.26 mL, 18.6 mmol), DMAP (0.302 g, 2.47 mmol), and Et$_3$N (7.0 mL, 50.2 mmol). The reaction mixture was allowed to warm to room temperature and stirred overnight. After 19 h, the reaction mixture was concentrated in vacuo, and the residue was diluted with water, extracted with EtOAc (3×), washed with brine, dried (MgSO$_4$), filtered, and concentrated in vacuo to give a red sticky solid which was purified by chromatography on SiO$_2$ (CH$_2$Cl$_2$) to give 21a (2.18 g, 9.68 mmol, 78% over two steps) as a pale yellow oil that solidified to an off-white solid upon standing at room temperature: $^1$H NMR (300 MHz, DMSO-d6) δ 4.34-4.30 (m, 2H), 2.55 (dt, 2H, J=15.6, 4.2 Hz), 2.23 (d, 2H, J=15.6 Hz), 2.20 (app s, 1H), 2.03-1.94 (m, 2H), 1.60-1.52 (m, 2H), 1.44 (s, 9H); $^{13}$C NMR (75 MHz, DMSO-d6) δ 207.4, 152.6, 79.2, 52.7, 48.1, 28.0 (2 C).

tert-Butyl 3-(((trifluoromethyl)sulfonyl)oxy)-8-azabicyclo[3.2.1]oct-2-ene-8-carboxylate (22) (WO 2012/152854 A1). A solution of NaHMDS (0.895 g, 4.88 mmol) in THF (12 mL) was added dropwise (over 10 min) at −78° C. to a solution of tert-butyl 3-oxo-8-azabicyclo[3.2.1]octane-8-carboxylate (21a, 1.00 g, 4.44 mmol) in THF (12 mL). The reaction mixture was stirred at −78° C. for 2 h, treated dropwise (over 20 min) with a solution of PhN(Tf)$_2$ (1.90 g, 5.33 mmol) in THF (12 mL), stirred for an additional 30 min at −78° C. and then allowed to warm to room temperature and stirred for 2 h. After addition of 10% aqueous Na$_2$CO$_3$ (50 mL), the solution was extracted with Et$_2$O (2×75 mL). The combined organic layers were washed with 10% aqueous Na$_2$CO$_3$ solution, dried (MgSO$_4$), and concentrated in vacuo. The crude residue was purified by chromatography on SiO$_2$ (1:19, EtOAc/hexanes with 1% Et$_3$N) to give 22 (1.24 g, 3.47 mmol, 78%) as a clear oil that solidified to a wax upon storage at −20° C.: $^1$H NMR (400 MHz, CDCl$_3$) δ 6.09 (brs, 1H), 4.54-4.38 (m, 2H), 3.07-3.02 (m, 1H), 2.30-2.20 (m, 1H), 2.11-1.99 (m, 3H), 2.00-1.97 (m, 2H), 1.79-1.70 (m, 1H), 1.45 (s, 9H).

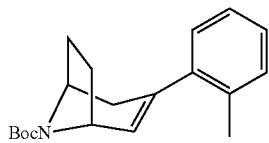 [SMILES: Cc1ccccc1C1=CC2CCC(C1)N2C(=O)OC(C)(C)C]

tert-Butyl 3-(o-tolyl)-8-azabicyclo[3.2.1]oct-2-ene-8-carboxylate (23a). A solution of Na$_2$CO$_3$ (0.330 g, 3.11 mmol), lithium chloride (0.0600 g, 1.41 mmol), tert-butyl 3-(((trifluoromethyl)sulfonyl)oxy)-8-azabicyclo[3.2.1]oct-2-ene-8-carboxylate (22, 0.460 g, 1.41 mmol) and o-tolylboronic acid (0.235 g, 1.70 mmol) in DME (11 mL) and H$_2$O (3 mL) was sparged with N$_2$ for 1 h, and treated with Pd(PPh$_3$)$_4$ (0.0376 g, 0.0325 mmol). The flask was evacuated and backfilled with nitrogen (3×) and the mixture was heated at 60° C. for 3 h. The mixture was allowed to cool to room temperature, diluted with brine, extracted with EtOAc (3×), dried (Na$_2$SO$_4$), and concentrated in vacuo. The resulting brown oil was dry loaded onto SiO$_2$ and purified by chromatography on SiO$_2$ (hexanes to 15:1, hexanes/EtOAc) to give 23a (0.330 g, 1.10 mmol, 78%) as a colorless solid: Mp 67.5-68.4° C.; IR (neat) 2975, 2934, 1685, 1420, 1364, 1329, 1169, 1094 cm$^{-1}$; $^1$H NMR (400 MHz, CDCl$_3$, mixture of rotamers) δ 7.20-7.12 (m, 3H), 7.02-7.00 (m, 1H), 5.94-5.86 (m, 1H), 4.50-4.30 (m, 2H), 3.11-2.91 (m, 1H), 2.27 (app s, 4H), 2.10-1.90 (m, 3H), 1.90-1.80 (m, 1H), 1.50 (s, 9H); $^{13}$C NMR (100 MHz, CDCl$_3$, 1:1 mixture of rotamers) δ 154.4, 141.6, 136.2, 135.5, 134.9, 131.3, 130.8, 130.7, 130.1, 129.3, 128.1, 126.9, 126.8, 125.6, 123.5, 120.0, 114.8, 79.3, 53.6, 52.9, 52.7, 52.0, 39.2, 38.4, 34.9, 34.3, 30.4, 29.6, 28.4, 19.5, 15.8; HRMS (ESI) m/z calcd for C$_{14}$H$_{17}$N ([M+H−C$_5$H$_9$O$_2$]$^+$) 200.1439, found 200.1435.

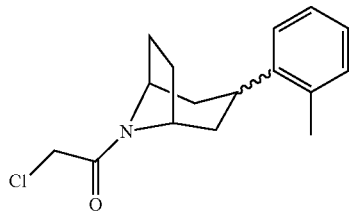 [SMILES: Cc1ccccc1C1CC2CCC(C1)N2C(=O)CCl]

2-Chloro-1-(3-(o-tolyl)-8-azabicyclo[3.2.1]octan-8-yl)ethan-1-one (24). A solution of tert-butyl 3-(o-tolyl)-8-azabicyclo[3.2.1]oct-2-ene-8-carboxylate (23a, 0.196 g, 0.655 mmol) in EtOH (5.0 mL) was treated with Pd/C (5%, 0.0480 g). The flask was evacuated and flushed with H$_2$ (balloon, 3×). The reaction mixture was stirred under H$_2$ (1 atm, balloon) overnight, filtered through Celite, rinsed with EtOH and concentrated in vacuo to give (23, 0.160 g, 0.531 mmol, 81%) as a yellow liquid that was used without further purification.

A solution of 23 (0.200 g, 0.664 mmol) in CH$_2$Cl$_2$ (5 mL) was treated at room temperature with TFA (0.30 mL, 3.98 mmol). After 16 h, the solution was concentrated in vacuo. The oily residue was extracted with CH$_2$Cl$_2$, washed with satd. aqueous NaHCO$_3$ and brine, dried (Na$_2$SO$_4$), filtered, and concentrated in vacuo to give 3-(o-tolyl)-8-azabicyclo[3.2.1]octane (23b, 0.133 g, 0.661 quant) as a light yellow oil that was used without further purification.

A solution of 23b (0.130 g, 0.646 mmol) and Et$_3$N (0.10 mL, 0.710 mmol) in THF (3 mL) was cooled to 0° C. and treated with chloroacetyl chloride (60 μL, 0.710 mmol) dropwise over 1 min. The reaction mixture was stirred at 0° C. for 1 h and then at room temperature for 20 h. The solution was filtered, concentrated in vacuo and the residue was dissolved in EtOAc, washed with water, dried (Na$_2$SO$_4$), filtered, and concentrated in vacuo. The crude residue was purified by chromatography on SiO$_2$ (1:1, hexanes/EtOAc) to give 24 (0.141 g, 0.508 mmol, 79%) as a brown oil. $^1$H NMR analysis indicated an approximately 4:3 ratio of endo/exo isomers: $^1$H NMR (400 MHz, CDCl$_3$) δ 7.22-7.09 (m, 6.8H), 4.85-4.80 (m, 1H), 4.80-4.74 (m, 0.7H), 4.38-4.30 (m, 1.7H), 4.14-4.04 (m, 3.6H), 3.49-3.39 (m, 1H), 2.99-2.88 (m, 0.7H), 2.58-2.49 (m, 1H), 2.38 (s, 3H), 2.32 (s, 2H), 2.22-1.70 (m, 11H), 1.55-1.48 (m, 1H); $^{13}$C NMR (100 MHz, CDCl$_3$) δ 163.4, 162.1, 141.8, 141.7, 135.9, 135.0, 130.4 (2 C), 126.5, 126.4, 126.2, 126.1 (2 C), 126.0, 55.7, 55.4, 52.6, 49.6, 41.5, 41.4, 39.5, 39.1, 37.9, 37.5, 32.8, 30.9, 30.3, 29.7, 28.9, 27.1, 19.4, 19.3; HRMS (ESI) m/z calcd for C$_{16}$H$_{21}$ClNO ([M+H]$^+$), 298.1312, found 298.1301.

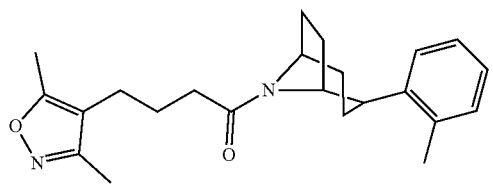

26a

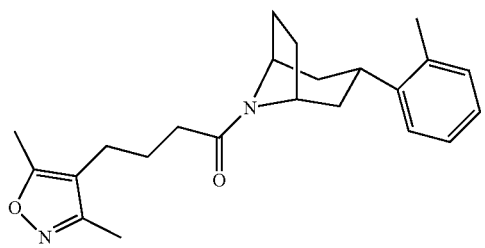

26b 2-(((3,5-Dimethylisoxazol-4-yl)methyl)thio)-1-(3-endo-(o-tolyl)-8-azabicyclo[3.2.1]octan-8-yl)ethanone (26a) and 2-(((3,5-dimethylisoxazol-4-yl)methyl)thio)-1-(3-exo-(o-tolyl)-8-azabicyclo[3.2.1]octan-8-yl)ethanone (26b). A solution of (3,5-dimethylisoxazol-4-yl)methanethiol (25, 0.0247 g, 0.172 mmol) in THF (0.4 mL) was added to a suspension of NaH (60% dispersion in mineral oil, 0.0115 g, 0. mmol) in THF (1.0 mL) at 0° C. The resultant slurry was stirred at 0° C. for 30 min and a solution of 2-chloro-1-(3-(o-tolyl)-8-azabicyclo[3.2.1]octan-8-yl)ethanone (24, 0.0400 g, 0.144 mmol) in THF (0.4 mL) was added. The reaction mixture was allowed to warm to room temperature, stirred for 24 h, quenched with brine (1 mL), diluted with EtOAc (15 mL) and brine (5 mL), and extracted with EtOAc (2×15 mL). The combined organic layers were dried (Na$_2$SO$_4$) and concentrated in vacuo. The crude residue was purified by chromatography on SiO$_2$ (3:7, EtOAc/hexanes) to give 26a (16.2 mg, 0.0421 mmol, 29%, 99.8% pure by ELSD) and 26b (16.6 mg, 0.0432 mmol, 30%, 100% pure by ELSD) as light yellow oils.

26a (dr 82:18 by $^1$HNMR): IR (neat) 2952, 2933, 1629, 1446, 1424, 1195 cm$^{-1}$; $^1$H NMR (400 MHz, CDCl$_3$) δ 7.17-7.11 (m, 4H), 4.81-4.80 (m, 1H), 4.25-4.24 (m, 1H), 3.72 (s, 2H), 3.46-3.40 (m, 1H), 3.19 (s, 2H), 2.44 (brs, 4H), 2.37 (s, 3H), 2.31 (s, 3H), 2.19-2.09 (m, 1H), 2.08-1.84 (m, 5H), 1.80-1.66 (m, 2H); $^{13}$C NMR (100 MHz, CDCl$_3$) δ 166.8, 164.8, 159.8, 141.9, 135.1, 130.5, 126.5, 126.2, 126.0, 109.9, 55.8, 52.2, 39.2, 37.6, 32.5, 30.4, 28.9, 27.3, 23.8, 19.3, 11.0, 10.1; HRMS (ESI) m/z calcd for C$_{22}$H$_{29}$O$_2$N$_2$S ([M+H]$^+$) 385.1950, found 385.1946.

26b (dr 92:8 by $^1$HNMR): IR (neat) 2952, 2934, 1629, 1489, 1446, 1193, 1163 cm$^{-1}$; $^1$H NMR (400 MHz, CDCl$_3$) δ 7.20-7.12 (m, 4H), 4.76 (t, 1H, J=7.6 Hz), 4.20 (t, 1H, J=7.6 Hz), 3.80 (d, 1H, J=14.0 Hz), 3.62 (d, 1H, J=14.0 Hz), 3.20 (d, 1H, J=12.8 Hz), 3.10 (d, 1H, J=13.6 Hz), 3.01-2.90 (m, 1H), 2.60-2.45 (m, 5H), 2.40 (s, 6H), 2.22-2.11 (m, 1H), 2.10-2.00 (m, 1H), 1.85-1.69 (m, 2H), 1.55-1.40 (m, 2H); $^{13}$C NMR (100 MHz, CDCl$_3$) δ 166.9, 166.3, 159.8, 142.0, 135.7, 130.4, 126.5, 126.2, 126.0, 109.9, 53.3, 49.3, 39.0, 38.0, 32.8, 31.9, 31.1, 29.9, 23.9, 19.5, 11.1, 10.2; HRMS (ESI) m/z calcd for C$_{22}$H$_{29}$O$_2$N$_2$S ([M+H]$^+$) 385.1950, found 385.1944.

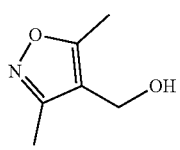

(3,5-Dimethylisoxazol-4-yl)methanol (27) (Natale et al., Synth. Commun. 1983, 13, 817-822.) To a solution of 3,5-dimethylisoxazole-4-carboxylic acid (1.60 g, 11.3 mmol) in THF (69 mL) at 0° C. was added dropwise a 2 M solution of LiAlH$_4$ in THF (5.6 mL, 11.2 mmol). The reaction mixture was allowed to warm to room temperature, stirred overnight, transferred to a 500-mL Erlenmeyer flask and treated with sodium sulfate decahydrate until the foaming subsided. Celite (2.3 g) was added and the slurry was filtered and washed with CH$_2$Cl$_2$ (75 mL). The filtrate was concentrated in vacuo to give 27 (1.14 g, 8.97 mmol, 79%) as a clear colorless oil: $^1$H NMR (400 MHz, CDCl$_3$) δ 4.46 (s, 2H), 2.38 (s, 3H), 2.29 (s, 3H).

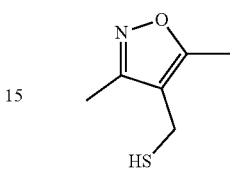

(3,5-Dimethylisoxazol-4-yl)methanethiol (25) (Moreno-Mañas et al., J. Heterocycl. Chem. 1992, 29, 1557-1560.) A solution of (3,5-dimethylisoxazol-4-yl)methanol (27, 0.500 g, 3.90 mmol) in toluene (13 mL) was treated with Lawesson's reagent (0.890 g, 2.15 mmol) at room temperature, heated to 80° C. and stirred for 1 d. The crude mixture was loaded directly onto SiO$_2$ and purified by chromatography on SiO$_2$ (4:1, hexanes/EtOAc) to give 25 (0.115 g, 0.803 mmol, 21%) as a light yellow oil: $^1$H NMR (300 MHz, CDCl$_3$) δ 3.49 (d, 2H, J=6.6 Hz), 2.36 (s, 3H), 2.30 (s, 3H), 1.64 (t, 1H, J=6.6 Hz); $^{13}$C NMR (75 MHz, CDCl$_3$) δ 165.2, 159.0, 113.3, 15.9, 10.9, 10.0.

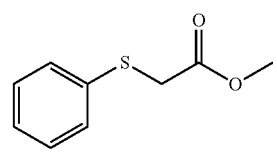

Methyl 2-(phenylthio)acetate (28) (Bahrami et al., J. Org. Chem. 2010, 75, 6208-6213.) A solution of thiophenol (0.10 mL, 0.977 mmol), and methyl bromoacetate (0.164 g, 1.07 mmol) in THF (13 mL) was treated with Et$_3$N (0.17 mL, 1.17 mmol), stirred at room temperature for 4 h, and diluted with Et$_2$O and satd. aqueous NaHCO$_3$. The aqueous layer was extracted with Et$_2$O (2×5 mL). The combined organic layers were dried (MgSO$_4$), filtered and concentrated in vacuo to give 28 (0.176 g, 0.966 mmol, 99%) as a clear oil: $^1$H NMR (300 MHz, CDCl$_3$) δ 7.42-7.38 (m, 2H), 7.33-7.20 (m, 3H), 3.71 (s, 3H), 3.65 (s, 2H); $^{13}$C NMR (75 MHz, CDCl$_3$) δ 170.1, 134.9, 129.9, 129.0, 127.0, 52.5, 36.5.

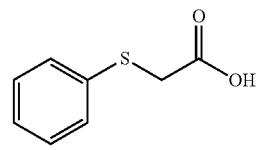 [SMILES: O=C(O)CSc1ccccc1]

2-(Phenylthio)acetic acid (3d) (Bahrami et al., J. Org. Chem. 2010, 75, 6208-6213; Miura et al., Org. Lett. 2001, 3, 2591-2594.) To a solution of methyl 2-(phenylthio)acetate (28, 0.176 g, 0.966 mmol) in MeOH (2 mL) was added 2 M LiOH (1 mL). The reaction mixture was stirred at room temperature for 1 h and TLC analysis (4:1, hexanes/EtOAc)

indicated that 28 had been consumed. The solution was concentrated in vacuo, diluted with water (3 mL) and acidified to pH 2 with 1 M HCl at 0° C. The aqueous layer was extracted with EtOAc (3×10 mL). The combined organic layers were dried (MgSO$_4$), filtered and concentrated in vacuo to give 3d (0.144 g, 0.857 mmol, 89%) as a colorless solid: $^1$H NMR (300 MHz, CDCl$_3$) δ 11.27 (brs, 1H), 7.43 (d, 2H, J=7.6 Hz), 7.36-7.24 (m, 3H), 3.69 (s, 2H); $^{13}$C NMR (75 MHz, CDCl$_3$) δ 175.9, 134.4, 130.1, 129.2, 127.2, 36.6.

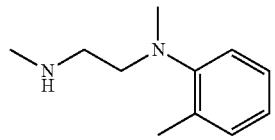

N,N'-Dimethyl-N-(o-tolyl)ethane-1,2-diamine (4i) (Gruseck et al., *Tet. Lett.* 1987, 28, 6027-6030). A microwave vial was flushed with argon and charged with the N,N'-dimethylethylene-diamine (0.180 g, 2.04 mmol), NaO-t-Bu (0.202 g, 2.04 mmol), (rac)-BINAP (0.0162 g, 0.0260 mmol), Pd$_2$(dba)$_3$ (0.0078 g, 0.0085 mmol), degassed toluene (10.2 mL), and 2-bromotoluene (0.297 g, 1.70 mmol). The reaction mixture was heated in the sealed vial under argon at 110° C. for 24 h, cooled to room temperature, diluted with CH$_2$Cl$_2$, filtered through Celite, and concentrated in vacuo. The residue was purified by chromatography on basic Al$_2$O$_3$ (95:5, CH$_2$Cl$_2$/MeOH) to give 4i (0.0508 g, 0.285 mmol, 17%) as a brown oil: $^1$H NMR (400 MHz, CDCl$_3$) δ 7.16 (t, 2H, J=7.6 Hz), 7.08 (d, 1H, J=7.6 Hz), 6.98 (d, 1H, J=7.2 Hz), 3.05 (t, 2H, J=6.4 Hz), 2.71 (t, 2H, J=6.4 Hz), 2.65 (s, 3H), 2.43 (s, 3H), 2.32 (s, 3H), 1.36 (brs, 1H); HRMS (ESI) m/z calcd for C$_{11}$H$_{19}$N$_2$ ([M+H]$^+$) 179.1543, found 179.1541.

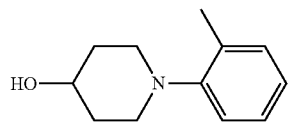

1-(o-Tolyl)piperidin-4-ol (4n) (Harris et al., *Org. Lett.* 2002, 4, 2885-2888.) An oven-dried microwave tube was charged with Pd$_2$(dba)$_3$ (0.0606 g, 0.0653 mmol), CyJohnphos (0.0292 g, 0.0816 mmol), and 4-piperidinol (0.330 g, 3.26 mmol). The microwave tube was evacuated and backfilled with argon. A 1 M solution of LiN(TMS)$_2$ (1.21 g, 7.17 mmol) in degassed THF (7.2 mL) was added via syringe along with 2-bromotoluene (0.600 g, 3.26 mmol). The reaction vessel was sealed and heated at 65° C. with stirring for 22 h. The reaction mixture was cooled to room temperature, quenched with 1 M HCl (10 mL), stirred at room temperature for 5 min, neutralized with a satd. aqueous NaHCO$_3$ solution, and diluted with EtOAc. The organic layer was dried (MgSO$_4$), filtered through Celite, and concentrated in vacuo. The crude residue was purified by chromatography on SiO$_2$ (ISCO, 12 g column, gradient hexanes to 3:7, EtOAc/hexanes) to give 4n (0.372 g, 1.94 mmol, 60%) as a brown oil: $^1$H NMR (300 MHz, CDCl$_3$) δ 7.17 (dd, 2H, J=9.3, 7.2 Hz), 7.04-6.96 (m, 2H), 3.87-3.81 (m, 1H), 3.15-3.08 (m, 2H), 2.74 (dt, 2H, J=9.6, 2.7 Hz), 2.32 (s, 3H), 2.06-2.00 (m, 2H), 1.80-1.69 (m, 3H); $^{13}$C NMR (75 MHz, CDCl$_3$) δ 151.9, 132.7, 130.9, 126.4, 123.0, 119.0, 68.0, 49.8, 35.2, 17.7; HRMS (ESI) m/z calcd for C$_{12}$H$_{18}$NO ([M+H]$^+$) 192.1383, found 192.1307.

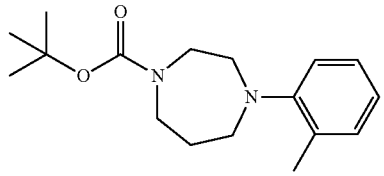 [SMILES: Cc1ccccc1N1CCCN(C(=O)OC(C)(C)C)CC1]

tert-Butyl 4-(o-tolyl)-1,4-diazepane-1-carboxylate (29a). A microwave vial was flushed with argon and charged with Boc-homopiperazine (0.223 g, 1.10 mmol), NaO-t-Bu (0.116 g, 1.20 mmol), (rac)-BINAP (0.0478 g, 0.0752 mmol, 7.5 mol %), Pd$_2$(dba)$_3$ (0.0233 g, 0.0251 mmol), degassed toluene (2.8 mL), and 2-bromotoluene (0.175 g, 1.00 mmol). The reaction mixture was heated in the sealed vial under argon at 80° C. for 19 h, cooled to room temperature, diluted with CH$_2$Cl$_2$, filtered through Celite, and concentrated in vacuo. The residue was purified by chromatography on SiO$_2$ (1:9, EtOAc/hexanes) to give 29a (0.139 g, 0.479 mmol, 48%) as a yellow oil: IR (ATR) 2973, 2828, 1689, 1598, 1491, 1457, 1411, 1364, 1233, 1215, 1156, 1122, 878, 761, 725 cm$^{-1}$; $^1$H NMR (500 MHz, CDCl$_3$, room temperature, mixture of rotamers) δ 7.16 (d, 1H, J=6.0 Hz), 7.12 (d, 1H, J=6.0 Hz), 7.04 (d, 1H, J=7.5 Hz), 6.95 (t, 1H, J=7.0 Hz), 3.61-3.56 (m, 4H), 3.11-3.04 (m, 4H), 2.31 (s, 3H), 1.96-1.91 (m, 2H), 1.49 (s, 9H); $^{13}$C NMR (100 MHz, CDCl$_3$, room temperature, mixture of rotamers) δ 155.6, 155.5, 153.9, 153.8, 132.9, 130.9, 126.5, 123.1, 120.8 (2 C), 79.3, 56.2, 56.0, 55.5, 55.2, 48.4, 48.0, 46.2, 45.4, 29.0, 28.9, 28.5, 18.5; HRMS (ESI) m/z calcd for C$_{17}$H$_{27}$N$_2$O$_2$ ([M+H]$^+$) 291.2067, found 291.2062.

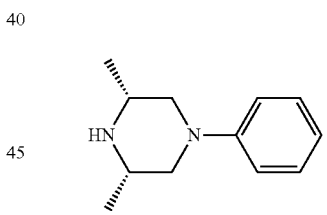

(3S,5R)-3,5-Dimethyl-1-(o-tolyl)piperazine (4k) (WO 2015/042297 A1). A Schlenk flask was flushed with N$_2$ and charged with cis-2,6-dimethylpiperazine (0.110 g, 0.963 mmol), NaO-t-Bu (0.170 g, 1.75 mmol), (rac)-BINAP (0.0084 g, 0.0130 mmol), Pd$_2$(dba)$_3$ (0.0083 g, 0.0087 mmol), degassed toluene (4 mL), and 2-bromotoluene (0.150 g, 0.880 mmol). The reaction mixture was heated under N$_2$ at 110° C. for 24 h, cooled to room temperature, diluted with CH$_2$Cl$_2$, filtered through Celite, and concentrated in vacuo. The crude residue was purified by chromatography on SiO$_2$ (1:19, MeOH/CH$_2$Cl$_2$) to give 4k (0.140 g, 0.685 mmol, 78%) as clear, yellow oil: $^1$H NMR (500 MHz, CDCl$_3$) δ 7.19-7.15 (m, 2H), 7.02-6.98 (m, 2H), 3.13-3.10 (m, 2H), 3.01 (app d, 2H, J=10.5 Hz), 2.35-2.31 (m, 5H), 1.12 (d, 6H, J=6.5 Hz).

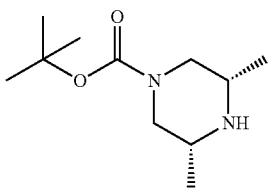

tert-Butyl (3R,5S)-3,5-dimethylpiperazine-1-carboxylate (30) (Jacobsen et al., *J. Med. Chem.* 1999, 42, 1123-1144.) To a solution of cis-2,6-dimethylpiperazine (0.500 g, 4.38 mmol) in CH$_2$Cl$_2$ (11 mL) at 0° C. was added dropwise a solution of Boc-anhydride (0.946 g, 4.33 mmol) in CH$_2$Cl$_2$ (2.6 mL). The reaction mixture was allowed to warm to room temperature, stirred overnight, diluted with CH$_2$Cl$_2$ and washed with satd. aqueous Na$_2$CO$_3$ solution. The aqueous layer was extracted with CH$_2$Cl$_2$. The combined organic layers were washed with brine, dried (MgSO$_4$), filtered, and concentrated in vacuo to give 30 (0.813 g, 3.79 mmol, 87%) as an off-white solid: $^1$H NMR (300 MHz, CDCl$_3$) δ 4.10-3.80 (m, 2H), 2.85-2.70 (m, 2H), 2.40-2.20 (m, 2H), 1.46 (s, 9H), 1.05 (d, 6H, J=6.3 Hz).

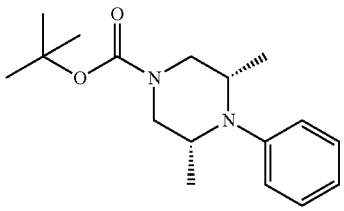 [SMILES: C[C@@H]1CN(C(=O)OC(C)(C)C)C[C@H](C)N1c1ccccc1]

tert-Butyl (3R,5S)-3,5-dimethyl-4-phenylpiperazine-1-carboxylate (29b). To a sealed tube under an argon atmosphere was added a solution of KHMDS (0.241 g, 1.15 mmol) in dry 1,4-dioxane (2.0 mL), a solution of tert-butyl 3,5-dimethylpiperazine-1-carboxylate (30, 0.246 g, 1.15 mmol) in dry 1,4-dioxane (0.9 mL) and bromobenzene (100 μL, 0.955 mmol). The reaction mixture was stirred at 100° C. for 18 h, cooled to room temperature, quenched with water (5 mL), diluted with Et$_2$O (15 mL) and the aqueous layer was extracted with Et$_2$O (2×15 mL). The combined organic layers were washed with brine, dried (Na$_2$SO$_4$), filtered, and concentrated in vacuo. The crude residue was purified by chromatography on SiO$_2$ (1:9, EtOAc/hexanes) to give 29b (0.0970 g, 0.334 mmol, 35%) as a colorless oil: $^1$H NMR (300 MHz, CDCl$_3$) δ 7.33-7.27 (m, 2H), 7.15-7.09 (m, 3H), 4.00-3.80 (m, 2H), 3.07-3.03 (m, 2H), 2.82 (brt, 2H, J=11.7 Hz), 1.50 (s, 9H), 0.77 (d, 6H, J=6.3 Hz).

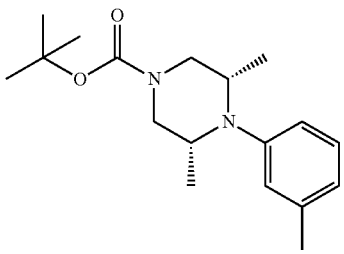 [SMILES: Cc1cccc(N2[C@H](C)CN(C(=O)OC(C)(C)C)C[C@@H]2C)c1]

tert-Butyl 3,5-dimethyl-4-(m-tolyl)piperazine-1-carboxylate (29c). A sealed tube under an argon atmosphere was treated with KHMDS (0.221 g, 1.05 mmol) in dry 1,4-dioxane (2.0 mL), a solution of tert-butyl 3,5-dimethylpiperazine-1-carboxylate (30, 0.226 g, 1.05 mmol) in dry 1,4-dioxane (0.7 mL) and bromotoluene (105 μL, 0.877 mmol). The reaction mixture was stirred at 100° C. for 18 h, cooled to room temperature, quenched with water (5 mL), diluted with Et$_2$O (15 mL) and the aqueous layer was extracted with Et$_2$O (2×15 mL). The combined organic layers were washed with brine, dried (Na$_2$SO$_4$), filtered, and concentrated in vacuo. The crude residue was purified by chromatography on SiO$_2$ (1:9, EtOAc/hexanes) to give 29c (0.0441 g, 0.145 mmol, 17%) as a colorless oil: $^1$H NMR (300 MHz, CDCl$_3$) δ 7.18 (t, 1H, J=7.5 Hz), 6.96-6.89 (m, 3H), 4.00-3.80 (m, 2H), 3.06-3.00 (m, 2H), 2.81 (brt, 2H, J=11.7 Hz), 2.32 (s, 3H), 1.50 (s, 9H), 0.77 (d, 6H, J=6.3 Hz).

Example 2

Synthesis and Characterization of (4-(5-Chloro-2-methylphenyl)piperazin-1-yl)((1RS,2SR)-2-(4-fluorophenyl)cyclopropyl)methanone (JJ-450)

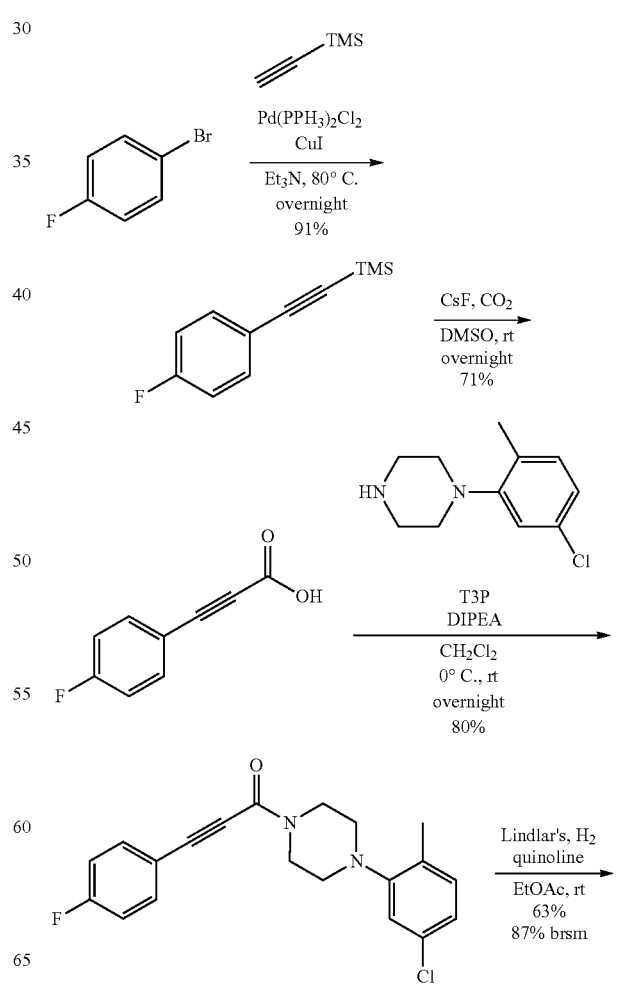

-continued

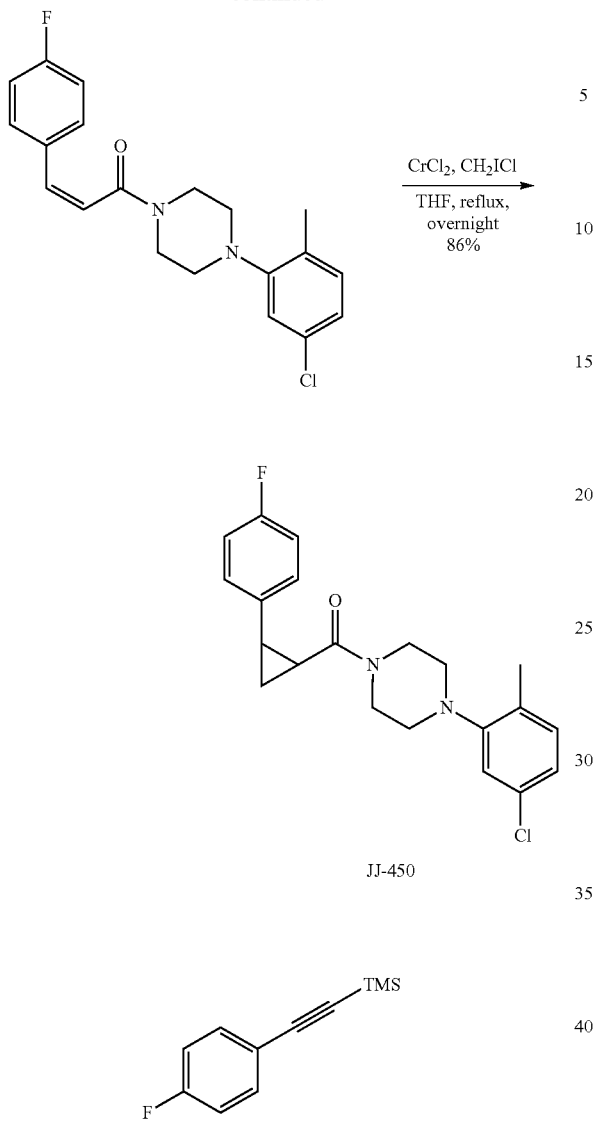

JJ-450

((4-Fluorophenyl)ethynyl)trimethylsilane (Everett et al., Org. Lett. 2013, 15, 2926-2929; Yonemoto-Kobayashi et al., Org. Biomol. Chem. 2013, 11, 3773-3775). A flame-dried flask under Ar was charged with Pd(PPh)$_2$Cl$_2$ (0.361 g, 0.514 mmol), CuI (0.0979 g, 0.514 mmol), and 4-fluorobromobenzene (5.66 mL, 51.4 mmol). Et$_3$N (110 mL) and (trimethylsilyl)acetylene (10.9 mL, 77.1 mmol) were added via syringe and the solution was sparged with Ar for 30 min. The reaction mixture was heated to 80° C. overnight and analysis by TLC (4:1, hexanes/EtOAc) indicated that 4-fluorobromobenzene had been consumed. The solution was cooled to room temperature and filtered through celite. The celite was washed (Et$_2$O) until the washes appeared colorless. The combined filtrates were concentrated in vacuo. The crude residue was purified by chromatography on SiO$_2$ (hexanes) to afford 4-fluorophenyl)ethynyl)trimethylsilane (9.03 g, 47.0 mmol, 91%) as a pale orange oil: $^1$H NMR (300 MHz, CDCl$_3$) δ 7.47-7.42 (m, 2H), 6.99 (t, 2H, J=8.7 Hz), 0.25 (s, 9H); $^{13}$C NMR (75 MHz, CDCl$_3$) δ 162.6 (d, J$_{C-F}$=248 Hz), 133.9 (d, J$_{C-F}$=8 Hz), 119.3 (d, J$_{C-F}$=4 Hz), 115.5 (d, J$_{C-F}$=22 Hz), 104.0, 93.8, −0.07.

3-(4-Fluorophenyl)propiolic acid (Yonemoto-Kobayashi et al., Org. Biomol. Chem. 2013, 11, 3773-3775). CsF (4.74 g, 31.2 mmol) was loaded into an oven-dried 250-mL round bottom flask in a glovebox. The flask was removed from the glovebox, attached to a CO$_2$ balloon, equipped with a magnetic stirrer and a septum, and filled with anhydrous DMSO (60 mL). Neat ((4-fluorophenyl)ethynyl)trimethylsilane (5.00 g, 26.0 mmol) was added dropwise. The reaction mixture was stirred under CO$_2$ at room temperature overnight, diluted with water (600 mL) and washed with CH$_2$Cl$_2$ (2×150 mL). The aqueous layer was acidified at 0° C. to pH 1 with 6 M HCl and then extracted with Et$_2$O (3×200 mL). The combined organic layers were dried (MgSO$_4$), filtered, and concentrated in vacuo to afford 3-(4-fluorophenyl)propiolic acid (3.02 g, 18.4 mmol, 71%) as an orange solid: $^1$H NMR (400 MHz, Acetone-d$_6$) δ 11.74 (brs, 1H), 7.71 (dd, 2H, J=8.6, 5.6 Hz), 7.26 (t, 2H, J=8.6 Hz); $^{13}$C NMR (100 MHz, Acetone-d$_6$) δ 164.8 (d, J$_{C-F}$=249 Hz), 154.7, 136.1 (d, J$_{C-F}$=9 Hz), 117.1 (d, J$_{C-F}$=23 Hz), 84.6, 81.8.

1-(4-(5-Chloro-2-methylphenyl)piperazin-1-yl)-3-(4-fluorophenyl)prop-2-yn-1-one. To a solution of 3-(4-fluorophenyl)propiolic acid (3.00 g, 18.3 mmol) in anhydrous CH$_2$Cl$_2$ (180 mL) at 0° C. was added 1-(5-chloro-2-methylphenyl)piperazine (4.62 g, 21.9 mmol), and Et$_3$N (6.35 mL, 45.7 mmol), followed by dropwise addition of T3P (50 wt. % solution in EtOAc, 19.4 mL, 27.4 mmol). The reaction mixture was stirred at 0° C. for 30 min, warmed to room temperature overnight, diluted with CH$_2$Cl$_2$ (200 mL), washed with 1 M HCl (150 mL), dried (MgSO$_4$), filtered, and concentrated in vacuo. The residue was purified by chromatography on SiO$_2$ (2:1, hexanes/EtOAc) to give 1-(4-(5-chloro-2-methylphenyl)piperazin-1-yl)-3-(4-fluorophenyl)prop-2-yn-1-one (5.22 g, 14.6 mmol, 80%) as an off white solid: Mp 138.7-140.4° C.; IR (neat) 2924, 2216, 1625, 1596, 1504, 1443, 1431, 1219, 1038, 837 cm$^{-1}$; $^1$H NMR (300 MHz, CDCl$_3$) δ 7.55 (dd, 2H, J=7.5, 5.4 Hz), 7.12-6.94 (m, 5H), 3.96 (app t, 2H, J=4.8 Hz), 3.82 (app t, 2H, J=4.8 Hz), 2.95 (app t, 2H, J=4.8 Hz), 2.87 (app t, 2H, J=4.8 Hz), 2.28 (s, 3H); $^{13}$C NMR (75 MHz, CDCl$_3$) δ 163.5 (d, J$_{C-F}$=251 Hz), 153.0, 151.7, 134.5 (d, J$_{C-F}$=9 Hz), 132.1, 131.8, 130.9, 123.7, 119.8, 116.4 (d, J$_{C-F}$=4 Hz), 116.0 (d, J$_{C-F}$=23 Hz), 89.9, 80.9, 51.9, 51.3, 47.4, 41.8, 17.3; HRMS (ESI) m/z calcd for C$_{20}$H$_{19}$ClFON$_2$ ([M+H]$^+$) 357.1164, found 357.1165.

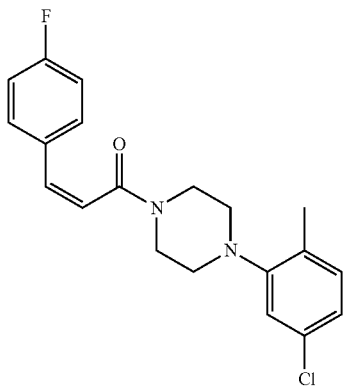 [SMILES: Cc1ccc(Cl)cc1N1CCN(C(=O)/C=C\c2ccc(F)cc2)CC1]

(Z)-1-(4-(5-Chloro-2-methylphenyl)piperazin-1-yl)-3-(4-fluorophenyl)prop-2-en-1-one. To a solution of 1-(4-(5-chloro-2-methylphenyl)piperazin-1-yl)-3-(4-fluorophenyl)prop-2-yn-1-one (5.00 g, 14.0 mmol) in dry EtOAc (140 mL) was added Lindlar's catalyst (5% Pd on CaCO$_3$, lead poisoned, 0.298 g, equivalent to 1 mol % Pd) and quinoline (0.83 mL, 7.01 mmol). The reaction vessel was placed under vacuum, backfilled with H$_2$ (balloon, 2×) and allowed to stir at room temperature for 6 h. Analysis by TLC (2:1, hexanes/EtOAc) indicated that 1-(4-(5-chloro-2-methylphenyl)piperazin-1-yl)-3-(4-fluorophenyl)prop-2-yn-1-one had been mostly consumed. The reaction mixture was filtered through Celite, washed with EtOAc, and concentrated under vacuum. The combined organic layers were washed with 1 M HCl, dried (MgSO$_4$), filtered, and concentrated in vacuo. The crude material was purified by chromatography on SiO$_2$ (1:1, hexanes/EtOAc) to afford (Z)-1-(4-(5-chloro-2-methylphenyl)piperazin-1-yl)-3-(4-fluorophenyl)prop-2-en-1-one (3.15 g, 8.78 mmol, 63%, 87% brsm) as a colorless solid: IR (neat) 2913, 2239, 1616, 1506, 1437, 1223, 837, 725 cm$^{-1}$; $^1$H NMR (400 MHz, CDCl$_3$) δ 7.41-7.36 (m, 2H), 7.08-7.02 (m, 3H), 6.96 (dd, 1H, J=8.1, 2.1 Hz), 6.80 (d, 1H, J=2.1 Hz), 6.66 (d, 1H J=12.5 Hz), 6.05 (d, 1H, J=12.5 Hz), 3.80 (m, 2H, J=5.0 Hz), 3.49 (t, 2H, J=5.0 Hz), 2.80 (t, 2H, J=5.0 Hz), 2.53 (t, 2H, J=5.0 Hz), 2.21 (s, 3H); $^{13}$C NMR (100 MHz, CDCl$_3$) δ 167.3, 162.7 (d, J$_{C-F}$=248 Hz), 151.7, 132.6, 132.0, 131.8, 131.5 (d, J$_{C-F}$=3 Hz), 132.1, 131.8, 130.9, 130.2 (d, J$_{C-F}$=8 Hz), 123.6, 122.7, 119.6, 115.6 (d, J$_{C-F}$=21 Hz), 51.4, 51.2, 46.5, 41.5, 17.3; HRMS (ESI) m/z calcd for C$_{20}$H$_{21}$ClFON$_2$ ([M+H]$^+$) 359.1321, found 359.1329.

(4-(5-Chloro-2-methylphenyl)piperazin-1-yl)((1RS,2SR)-2-(4-fluorophenyl)cyclopropyl)-methanone (JJ-450). THF (90 mL) was degassed by sparging with Ar for 60 min and treated at room temperature under Ar atmosphere with anhydrous CrCl$_2$ (6.43 g, 51.8 mmol) followed by (Z)-1-(4-(5-chloro-2-methylphenyl)piperazin-1-yl)-3-(4-fluorophenyl)prop-2-en-1-one (3.10 g, 8.64 mmol) and CH$_2$ICl (3.36 mL, 43.2 mmol). The reaction mixture was stirred for 20 h at 80° C., cooled to room temperature, quenched by the addition of 1.0 M aqueous HCl (300 mL) and extracted with EtOAc (3×300 mL). The combined organic layers were filtered through a plug of basic Al$_2$O$_3$, and concentrated in vacuo. The residue was purified by chromatography on SiO$_2$ (1:1, hexanes/EtOAc) to afford an oil that was further purified twice by chromatography on basic Al$_2$O$_3$ (1:1, hexanes/EtOAc) to give (4-(5-chloro-2-methylphenyl)piperazin-1-yl)((1RS,2SR)-2-(4-fluorophenyl)cyclopropyl)methanone (2.76 g, 7.41 mmol, 86%) as a clear oil that solidified after storage on high vacuum overnight: Mp 78.2-80.4° C. (hexanes); IR (CH$_2$Cl$_2$) 2936, 1637, 1592, 1510, 1487, 1435, 1223, 1033, 837, 815 cm$^{-1}$; $^1$H NMR (400 MHz, CDCl$_3$) δ 7.16-7.11 (m, 2H), 7.07 (dd, 1H, J=8.1, 0.5 Hz), 7.00-6.94 (m, 3H), 6.73 (d, 1H, J=2.1 Hz), 3.81-3.76 (m, 1H), 3.71-3.60 (m, 2H), 3.36 (ddd, 1H, J=12.4, 8.8, 3.1 Hz), 2.79-2.71 (m, 2H), 2.45 (td, 1H, J=8.8, 7.0 Hz), 2.35-2.29 (m, 1H), 2.26-2.16 (m, 5H), 1.83 (dt, 1H, J=7.0, 5.6 Hz), 1.35 (td, 1H, J=8.8, 5.6 Hz); $^{13}$C NMR (100 MHz, CDCl$_3$) δ 167.2, 161.7 (d, J$_{C-F}$=244 Hz), 151.9, 133.1 (d, J$_{C-F}$=3 Hz), 131.9 (d, J$_{C-F}$=14 Hz), 130.9, 129.1 (d, J$_{C-F}$=8 Hz), 123.6, 119.7, 115.0 (d, J$_{C-F}$=21 Hz), 51.8, 51.6, 45.6, 42.2, 23.8, 23.5, 17.3, 10.7; HRMS (ESI) m/z calcd for C$_{21}$H$_{23}$ClFON$_2$ ([M+H]$^+$) 373.1477, found 373.1478.

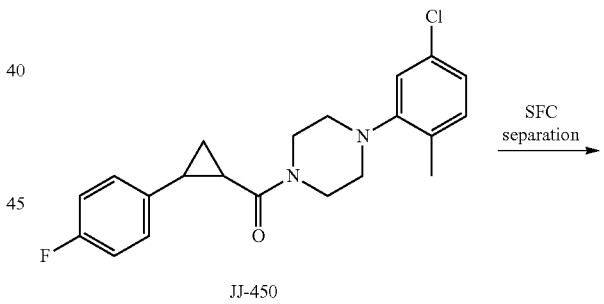

JJ-450

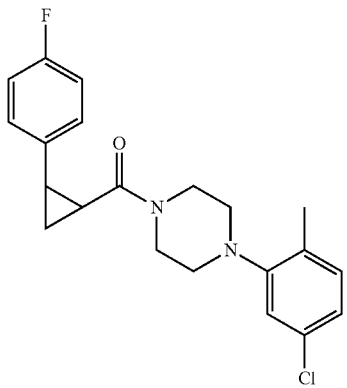

JJ-450

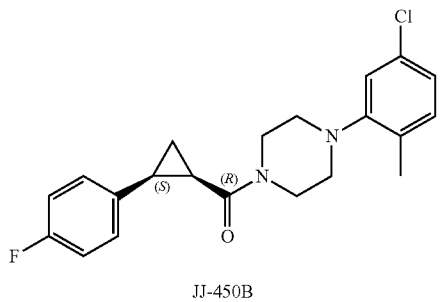

JJ-450B

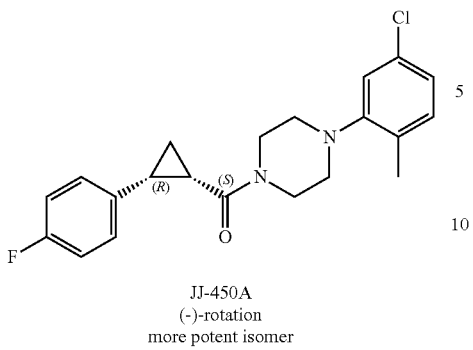

JJ-450A
(−)-rotation
more potent isomer

Racemic JJ-450 was separated on a SFC Chiralpak-IC semiprep (250×10 mm) column (20% MeOH, 6 mL/min, 220 nM, P=100) to afford (4-(5-chloro-2-methylphenyl)piperazin-1-yl)((1S,2R)-2-(4-fluorophenyl)cyclopropyl)methanone JJ-450A (retention time 13.1 min) as a colorless viscous oil (100% purity by ELSD): $[\alpha]^{20}_D$ −118.7 (c 0.39, CHCl$_3$); $^1$H NMR (300 MHz, CDCl$_3$) δ 7.17-7.10 (m, 2H), 7.07 (d, 1H, J=8.1 Hz), 7.02-6.94 (m, 3H), 6.72 (d, 1H J=2.1 Hz), 3.83-3.75 (m, 1H), 3.72-3.58 (m, 2H), 3.39-3.31 (m, 1H), 2.81-2.69 (m, 2H), 2.45 (td, 1H, J=8.7, 6.9 Hz), 2.36-2.25 (m, 1H), 2.25-2.15 (m, 5H), 1.83 (dt, 1H, J=6.9, 5.5 Hz), 1.35 (td, 1H, J=8.7, 5.5 Hz); HRMS (ESI) m/z calcd for C$_{21}$H$_{23}$ClFON$_2$ ([M+H]$^+$) 373.1477, found 373.1476. The enantiomeric excess was 100% ee (SFC Chiralpak-IC (250×4.6 mm); 20% MeOH, 220 nM, 2 mL/min; retention time: 9.8 min).

(4-(5-Chloro-2-methylphenyl)piperazin-1-yl)((1R,2S)-2-(4-fluorophenyl)cyclopropyl)-methanone JJ-450B (retention time 16.5 min) was obtained as a colorless viscous oil (100% purity by ELSD): $[\alpha]^{20}_D$ +117.4 (c 0.38, CHCl$_3$); $^1$H NMR (300 MHz, CDCl$_3$) δ 7.17-7.10 (m, 2H), 7.07 (d, 1H, J=8.1 Hz), 7.01-6.94 (m, 3H), 6.72 (d, 1H, J=2.1 Hz), 3.82-3.74 (m, 1H), 3.71-3.60 (m, 2H), 3.39-3.30 (m, 1H), 2.81-2.68 (m, 2H), 2.45 (td, 1H, J=8.6, 7.0 Hz), 2.35-2.26 (m, 1H), 2.25-2.15 (m, 5H), 1.83 (dt, 1H, J=7.0, 5.6 Hz), 1.35 (td, 1H, J=8.6, 5.6 Hz); HRMS (ESI) m/z calcd for C$_{21}$H$_{23}$ClFON$_2$ ([M+H]$^+$) 373.1477, found 373.1476. The enantiomeric excess was 100% ee (SFC Chiralpak-IC (250×4.6 mm); 20% MeOH, 220 nM, 2 mL/min; retention time: 12 min).

Example 3

Activity of Compounds in PSA Luciferase Assay

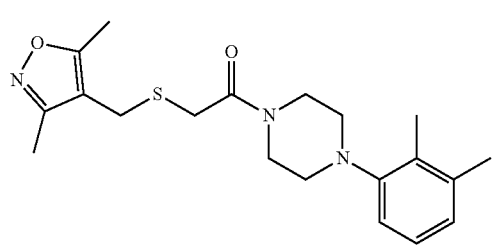

1

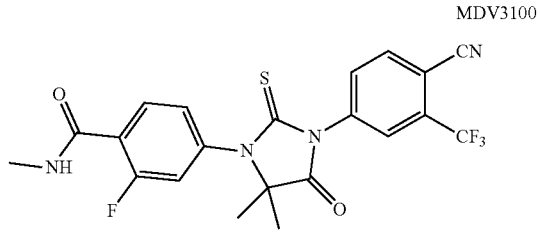

MDV3100

The biological activity of analogs 5-16, 18, 20, 26, JJ-450, and the resolved enantiomers JJ-450A and J-450B was determined and compared to HTS hit 1 (IC$_{50}$ 7.3 μM) and MDV3100 (IC$_{50}$ 1.1 M) using the Dual-Glo luciferase system (Promega, Wis., USA) in C4-2-PSA-rl cells, which were generated by transfection with PSA6.1-luc and pRL-TK followed by stable selection using G418 and puromycin. C4-2-PSA-rl stable cells were cultured in RPMI 1640 medium with 10% FBS, 1% penicillin-streptomycin, 1% L-glutamine, 10 mg/mL puromycin, and 50 mg/mL G418. C4-2-PSA-rl cells were seeded in 24-well plates such that they reached 75-80% cell monolayer density after 24 h. C4-2-PSA-rl cells were then treated for 24 h with 0, 0.2, 0.8, 3.2, 12.8, or 25 μM of each compound dissolved in DMSO (0.8% DMSO/well) in the presence of 1 nM synthetic androgen R1881, with each experimental condition in triplicate. The cells were also treated in parallel with 12.8 μM compound 1 and 12.8 μM MDV3100 as positive controls. Each compound was tested in at least two independent experiments. Luciferase activity was assayed using the Dual-Luciferase® Reporter Assay System (Promega) using LMax II Microplate Reader (Molecular Devices). The luciferase assay results were acquired using SoftMax Pro5.45 software (Molecular Devices) and analyzed using GraphPad Prism. PSA6.1-luc activity was normalized to the *Renilla* luciferase activity. Relative luciferase activity was calculated as the quotient of androgen-induced PSA-firefly/*Renilla* luciferase activity. Since PSA promoter activity correlates to AR transcriptional activity, inhibition of AR will result in decreased PSA-luciferase activity. IC$_{50}$ values were calculated using GraphPad Prism and data represent the mean and SD of 2-6 independent experiments (Table 2).

TABLE 2

In vitro activity of analogs in the PSA luciferase assay in C4-2-PSA-rl cells.

| Entry | Compound | IC$_{50}$ (μM) |
|---|---|---|
| 1 | 1 | 7.3 ± 2.5[c] |
| 2 | 5a | >25[a] |
| 3 | 5b | 14.5 ± 3.2[b] |
| 4 | 5c | >25[a] |
| 5 | 5d | >25[a] |
| 6 | 5e | 12.0 ± 1.6[b] |
| 7 | 5f | 12.6 ± 7.7[b] |
| 8 | 5g | 11.1 ± 5.3[b] |
| 9 | 5h | >25[a] |
| 10 | 5i | 18.4 ± 9.2[b] |
| 11 | 5j | 11.1 ± 3.3[a] |
| 12 | 5k | 3.1 ± 1.1[a] |
| 13 | 5l | 14.7 ± 4.4[a] |
| 14 | 5m | 16.6 ± 4.8[b] |
| 15 | 6 | 10.8 ± 5.7[b] |
| 16 | 7 | 13.7 ± 0.8[b] |
| 17 | 8 | 14.4 ± 3.7[b] |
| 18 | 9 | >25[a] |
| 19 | 10 | 20.3 ± 11.6[a] |
| 20 | 11 | >25[a] |

TABLE 2-continued

In vitro activity of analogs in the PSA luciferase assay in C4-2-PSA-rl cells.

| Entry | Compound | IC$_{50}$ (μM) |
|---|---|---|
| 21 | 12 | >25[b] |
| 22 | 13 | 16.1 ± 3.3[b] |
| 23 | 14 | 12.7 ± 0.8[a] |
| 24 | 15 | 2.9 ± 1.0[b] |
| 25 | 16 | >25[b] |
| 26 | 18a | >25[b] |
| 27 | 18b | >25[b] |
| 28 | 18c | 7.2 ± 2.7[c] |
| 29 | 20a | >25[a] |
| 30 | 20b | >25[c] |
| 31 | 26a | 7.7 ± 1.6[b] |
| 32 | 26b | 7.9 ± 2.8[a] |
| 33 | JJ-450 | 2.7 ± 1.1 |
| 34 | JJ-450A | 1.6 ± 0.1 |
| 35 | JJ-450B | 13.1 ± 1.8 |
| 36 | MDV3100 | 1.1 ± 0.5[e] |

Assay repeats: [a]n = 2; [b]n = 3; [c]n = 4; [d]n = 5; [e]n = 6.

Modifications of the substituents on the benzene ring in zone 1 revealed that methyl groups in the 3- and 4-positions (5c, 5d) led to loss of activity, while the 2-methyl analog 5b (IC$_{50}$ 14.5 μM) retained about half of the activity of the 2,3-dimethylated 1 (Table 2). Removal of the 2-methyl group in 5a deleted activity. In agreement with this trend in zone 1, the bulky 1-naphthyl substituent (5g) recovered activity (IC$_{50}$ 11.1 μM). Analogs with electron-withdrawing substituents at the benzene 2-position (2-NC, 5e, and 2-F, 5f) also maintained or slightly increased activity (IC$_{50}$ 12-13 μM); however, the electron-donating 2-methoxy substituted 5h was not tolerated and resulted in a complete loss of activity, possibly due to an increase in the pKa of the aniline and/or an unfavorable increase in the π-electron density of the aromatic ring.

The piperazine core (zone 2) was queried through substitutions with flexible as well as constrained acyclic and cyclic diamines. The flexible N,N'-dimethylethylenediamine linker in 5i (IC$_{50}$ 18.4 μM) and the 7-membered diazepane 5j (IC$_{50}$ 11.1 μM) both conserved activity. The dimethylated piperazines 5l and 5m (IC$_{50}$ 15-17 μM) were both also almost as active as the initial hit. In contrast, the conformationally more highly constraint 2,6-dimethylpiperazine 5k was considerably more active with an IC$_{50}$ of 3.1 μM. Installment of an ethylene bridge and a carbon-linked (2-Me)Ph group decreased activity again, since both diastereomers of the bicyclo[3.2.1] ring systems 26a and 26b, showed an IC$_{50}$ of 8 μM.

Reduction of amide 5b to amine 6 resulted in a 1.3-fold increase in activity to an IC$_{50}$ of 10.8 M. Sulfonamide 18c (IC$_{50}$ 7.2 μM) was twice as active as the initial hit 1, but urea 20a and carbamate 20b were inactive.

The replacement of the thioether linkage in zone 2 with an ether group abolished activity in 18a. Substituting the thioether with the N-methylated amine in 18b also abolished activity. In contrast, in an analogous system with a phenyl group in place of the isoxazole, both thioether 7 as well as the all-carbon chain containing 8 showed constant activity (IC$_{50}$-14 μM).

In order to verify that the biological effect in the thioether series was not a result of S-oxidation in the cellular assay, common products of thioether oxidation, i.e. sulfoxide 12 and sulfone 13, were tested. While sulfone 13 retained some activity (IC$_{50}$ 16.1 μM), sulfoxide 12 was inactive. Shortening the three-atom chain to afford the two-atom thioether-linked 9 also abolished activity. The rigidified alkyne 10 and the corresponding (E)-alkene 11 and its cyclopropane isostere 16 were also found to be essentially inactive. In contrast, the (Z)-alkene 14 surprisingly showed an IC$_{50}$ of 12.7 μM, and the corresponding cis-fused cyclopropane isostere 15 was even more potent than analog 1, showing an IC$_{50}$ of 2.9 μM (Table 2).

In summary, zone 1 modifications showed that the ortho-substituent on the phenyl ring was important for activity. In zone 2, the sterically encumbered 2,6-dimethylpiperazine proved superior to flexible, unsubstituted, and bridged analogs. In zone 3, a carbonyl group was not required, and a sulfonamide and even the reduced amine were well tolerated. In zone 4, thioether oxidation reduces activity, and only the cis-cyclopropane successfully and significantly improves the IC$_{50}$. Limited substitutions were performed in zone 5, but in general analogs with a phenyl group were equipotent with their 3,5-dimethylisoxazole congeners (see, for example, 7 vs 5b). Compounds 5k, 15, and JJ-450 (particularly JJ-450A) were found to be significantly more potent than 1. Compounds 15 and JJ-450 are of particular interest due to the isosteric replacement of the thioether linker with the metabolically more stable cyclopropane.

Compounds 559, 562, 475, 476, 484, and 458 are all also active in the PSA luciferase assay at sub-micromolar EC50s (450-900 nM), and they are inactive against androgen receptor (AR) negative cell lines in cell proliferation assays.

Additional compounds are shown below:

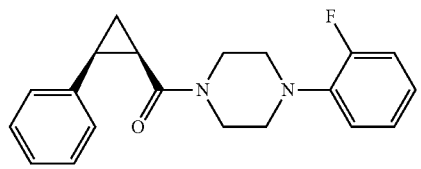

UPCMLD35AJKJ056582
Short #582
Sample weight: 0.88 mg
Chemical Formula: C$_{20}$H$_{21}$FN$_2$O
Exact Mass: 324.16

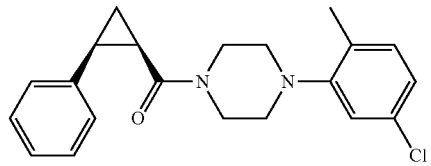

UPCMLD35AJKJ056583
Short #583
Sample weight: 0.55 mg
Chemical Formula: C$_{21}$H$_{23}$ClN$_2$O
Exact Mass: 354.15

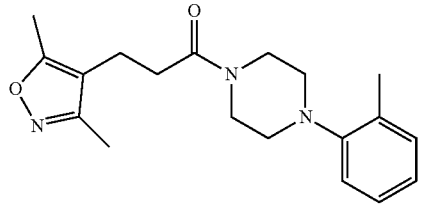

UPCMLD35AJKJ056588
Short #588
Sample weight: 0.70 mg
Chemical Formula: C$_{19}$H$_{25}$N$_3$O$_2$
Exact Mass: 327.19

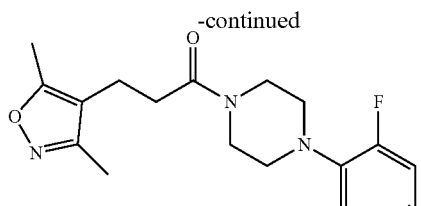

UPCMLD35AJKJ056589
Short #589
Sample weight: 0.54 mg
Chemical Formula: $C_{18}H_{22}FN_3O_2$
Exact Mass: 331.17

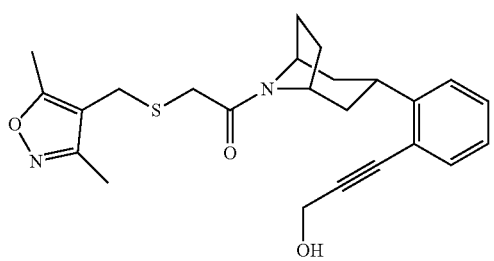

UPCMLD35AJKJ056571
Short #571
Sample weight: 0.54 mg
Chemical Formula: $C_{24}H_{28}N_2O_3S$
Exact Mass: 424.18

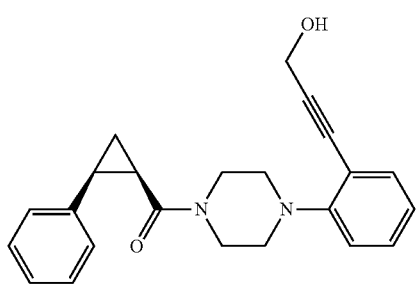

JKJ584-25
Short #: 425
Batch #: 1
Sample weight: 0.56 mg
Chemical Formula: $C_{23}H_{24}N_2O_2$
Exact Mass: 360.18

Figure 10A:
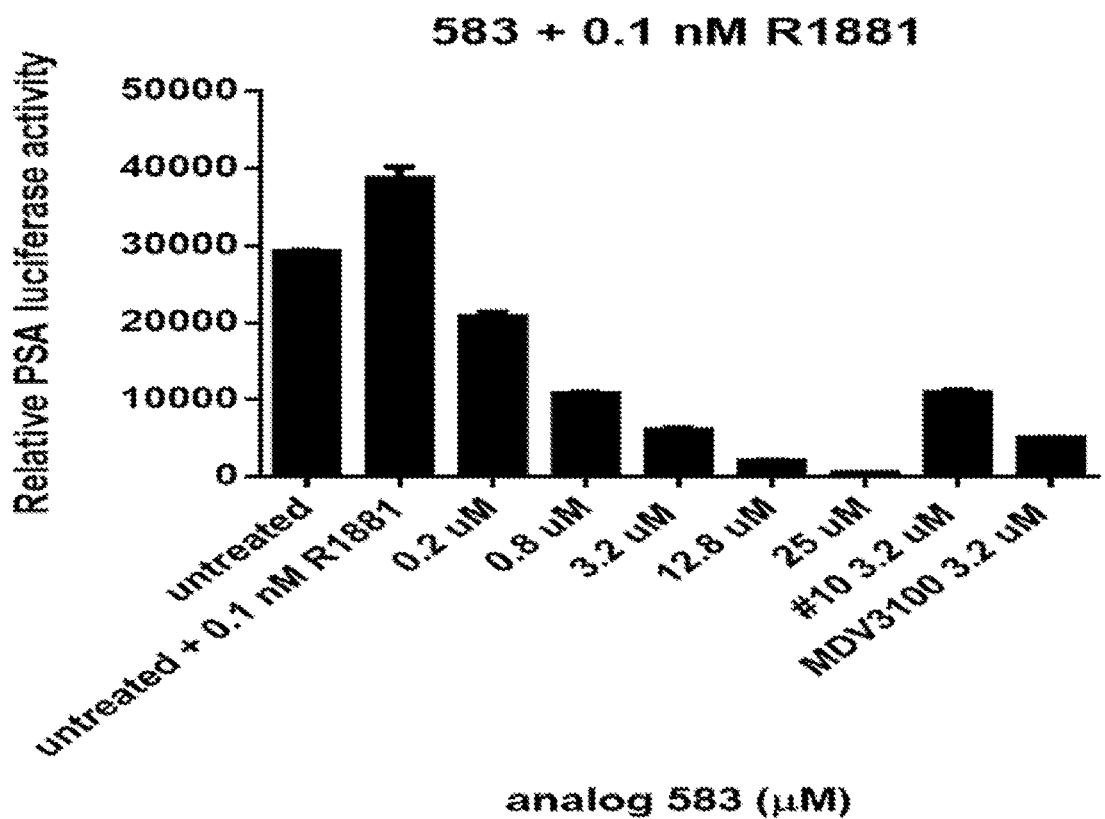
FIG. 10A is a graph showing the effect of compound #583 at indicated concentrations on PSA-driven luciferase activity in C4-2 cells.
Figure 10B:
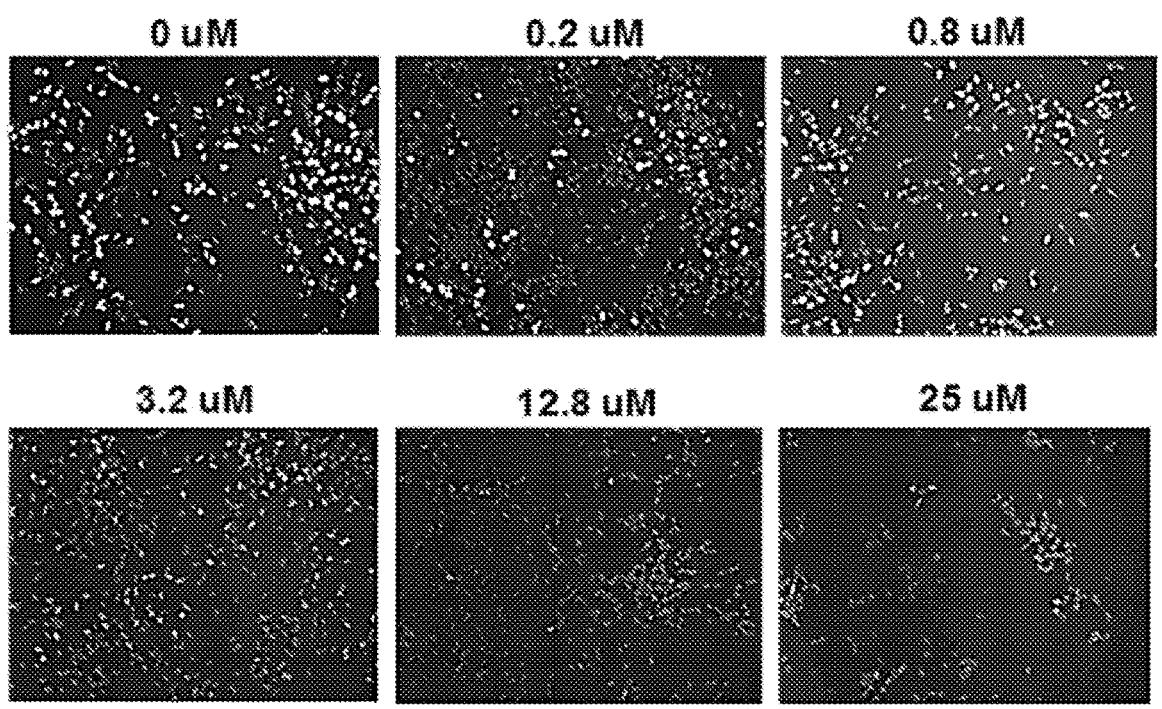
FIG. 10B shows the effect of compound #583 at indicated concentrations on C4-2 cell proliferation in BrdU assay.
Figure 10C:
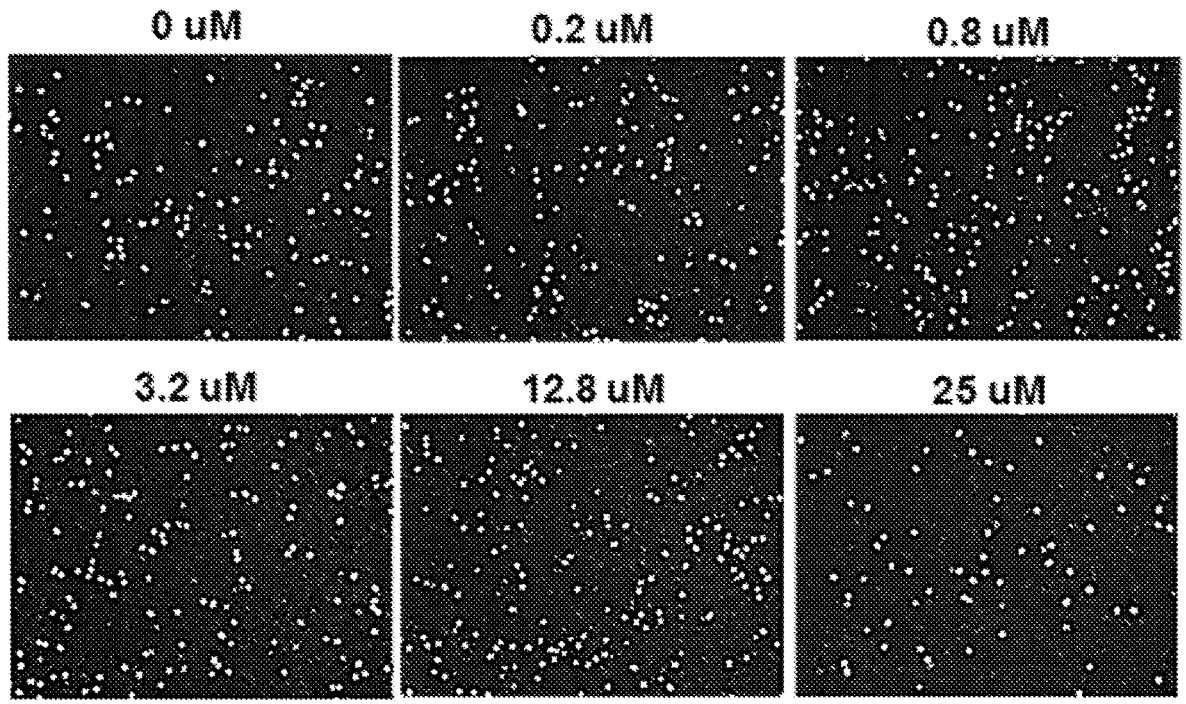
FIG. 10C shows the effect of analog #583 at indicated concentrations on PC3 cell proliferation in BrdU assay.

Compound #583 is very potent, with an $IC_{50}>1$ uM in inhibiting AR-dependent PSA promoter activity (FIG. 10A). As expected, #583 inhibited proliferation of AR-positive C4-2 (FIG. 10B), but not AR-negative PC3 (FIG. 10C), prostate cancer cells. Also, #583 does not contain a sulfur atom in the structure and should therefore be more resistant to oxidative metabolic degradation than the sulfur-containing compounds.

Figure 11:
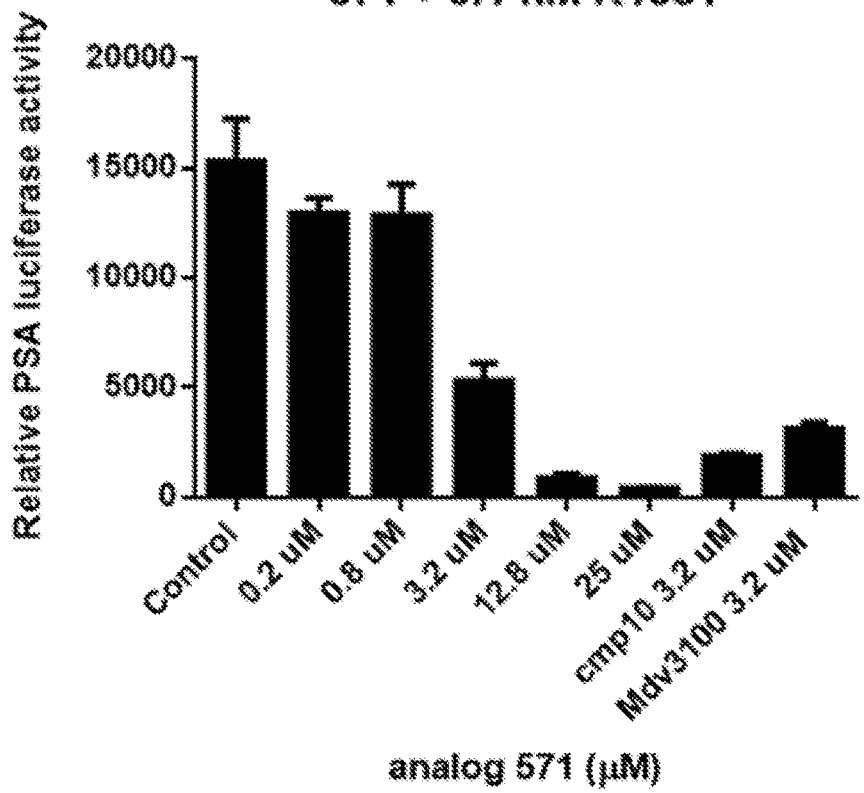
FIG. 11 is a graph showing the effect of compound #571 at indicated concentrations on PSA-driven luciferase activity in C4-2 cells.

Compounds #571 and #425 were developed for conjugation to agarose matrix. #571 is quite active, with an IC50 of ~3 uM in the inhibition of AR activation of PSA promoter in a luciferase assay (FIG. 11).

Example 4

Inhibition of Xenograft Tumor Growth by JJ-450

Figure 12:
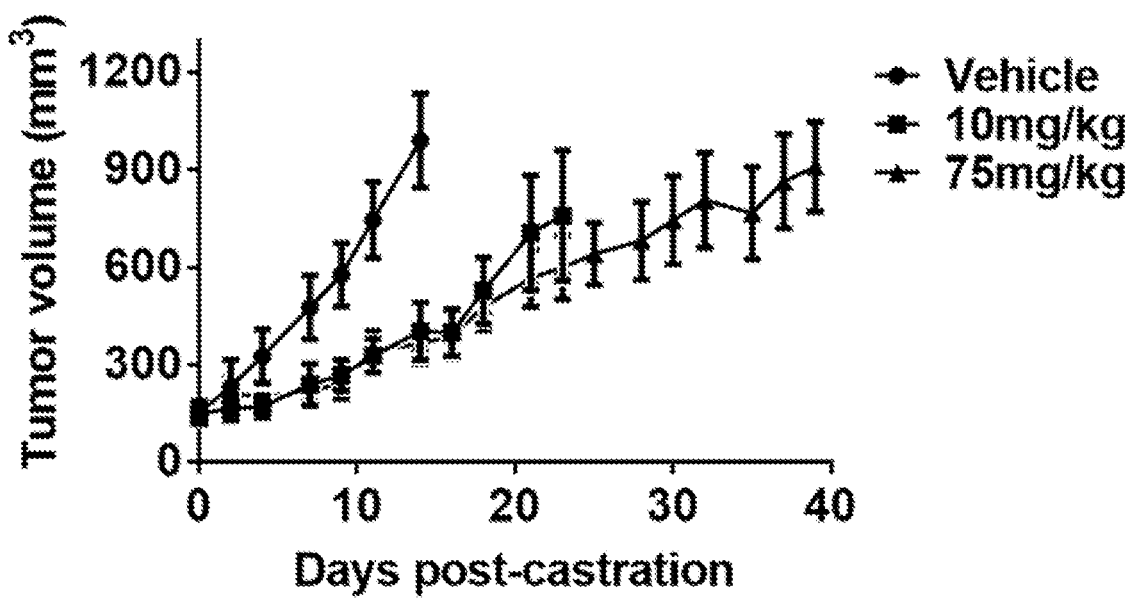
FIG. 12 is a graph showing the effect of compound JJ-450 at indicated concentrations on 22Rv1 xenograft tumor volume. JJ-450 was injected i.p. daily.

22Rv1 xenograft tumors were established in SCID mice by subcutaneous injection of $2 \times 10^6$ cells in Matrigel. Once the tumors reached ~150 μL in volume, the mice were castrated and randomized into 3 groups for daily IP injection of vehicle (n=11), 10 mg/kg (n=11) and 75 mg/kg (n=11) groups. Injection of JJ-450 was initiated at time of castration. Tumor volumes were measured 3 times every week. As shown in FIG. 12, compound JJ-450 significantly inhibited tumor growth. Error bars, SEM.

Figure 13:
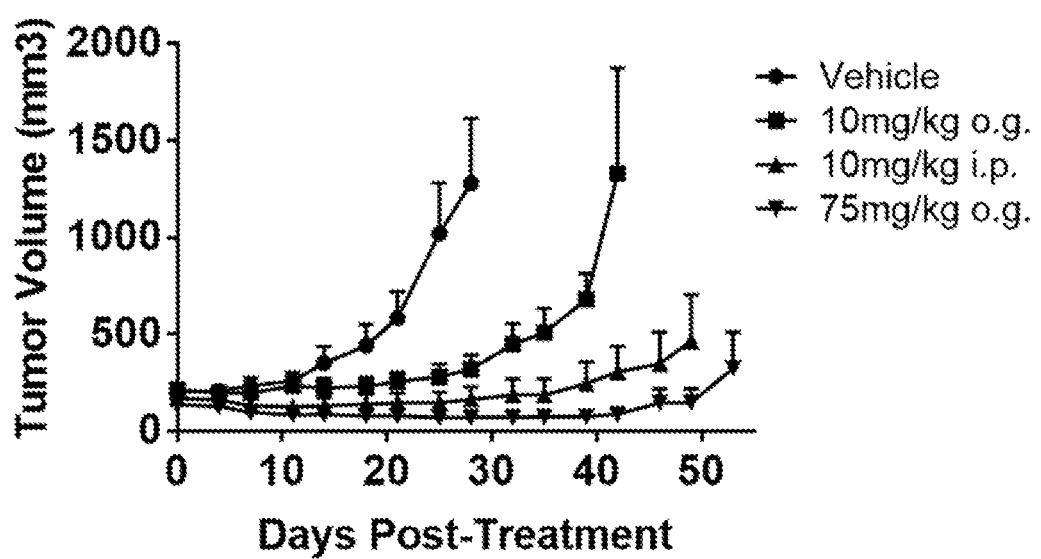
FIG. 13 is a graph showing the effect of compound JJ-450 at indicated concentrations and administration route on LNCaP xenograft tumor volume. JJ-450 was administered 6 times, from Monday to Saturday, every week

LNCaP xenograft tumors were established in SCID mice by subcutaneous injection of $2 \times 10^6$ cells in Matrigel. Once the tumors reached ~200 ul in volume, the mice were castrated and randomized into 4 groups: oral gavage of vehicle (n=6), oral gavage at 10 mg/kg (n=6), IP injection at 10 mg/kg (n=8), and oral gavage at 75 mg/kg (n=7) groups. Administration of JJ-450 was started 2 weeks after castration. Tumor volumes were measured twice every week. As shown in FIG. 13, compound JJ-450 significantly inhibited tumor growth. Error bars, SEM.

Example 5

Synthesis and Characterization of Additional Analogs

General:

All glassware was flame-dried or dried in an oven at 120° C. for more than two hours prior to use. All air- and moisture-sensitive reactions were performed under $N_2$ or Ar atmosphere. Reactions carried out at 0° C. or −78° C. employed an ice bath or an acetone/dry ice bath. Tetrahydrofuran and diethyl ether were either distilled over sodium/benzophenone ketyl, $CH_2Cl_2$ and toluene were distilled from $CaH_2$. All other materials were obtained from commercial sources and used as received. Infrared spectra were determined neat on a Smiths Detection Identify IR FT-IR spectrometer. $^1H$ and $^{13}C$ NMR spectra were obtained on a Bruker Advance 300 MHz, 400 MHz or 500 MHz NMR in $CDCl_3$ unless otherwise specified. Chemical shifts (δ) were reported in parts per million, with the residual solvent peak used as an internal standard δ $^1H/^{13}C$ (Solvent); 7.26/77.00 ($CDCl_3$), 2.50/39.50 (DMSO-d6); they are tabulated as follows: chemical shift, multiplicity (s=singlet, brs=broad singlet, d=doublet, brd=broad doublet, t=triplet, brt=broad triplet, q=quartet, m=multiplet), number of protons, and coupling constant(s). $^{13}C$ NMR spectra were obtained at 75 MHz, 100 MHz or 125 MHz unless otherwise specified using a proton-decoupled pulse sequence and are tabulated by observed peak. $^{19}F$ spectra were obtained at 471 MHz or 376 MHz unless otherwise specified using a proton-decoupled pulse sequence and are tabulated by observed peak. Reactions were monitored by thin-layer chromatography analysis using pre-coated silica gel 60 F254 plates (EMD, 250 m thickness), and visualization was accomplished with a 254 nm UV light. Flash chromatography was performed using $SiO_2$ (Silicycle, Silia-P Flash Silica Gel, 40-63 μm).

Figure 14:
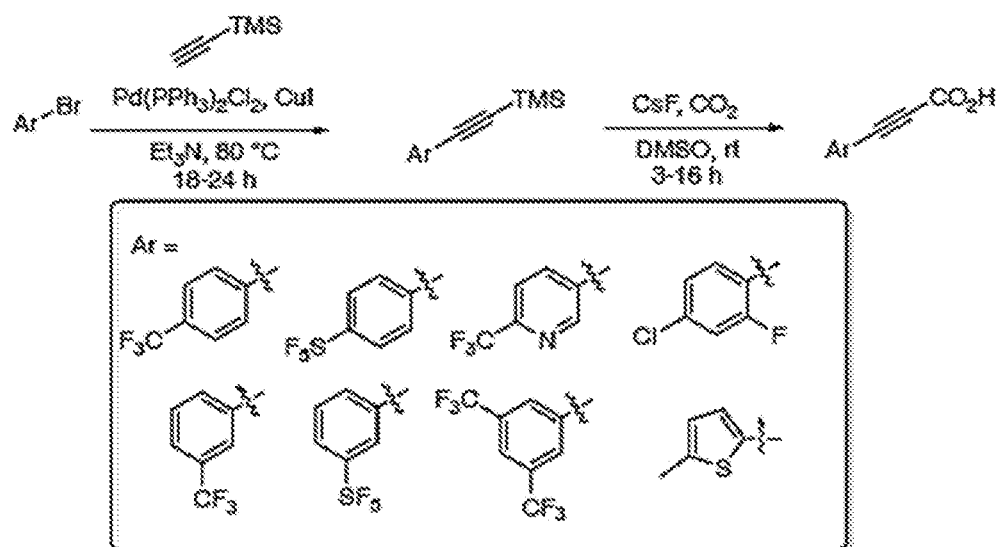
FIGS. 14-35 are reaction schemes showing synthesis of certain embodiments of the disclosed compounds.
Figure 15:
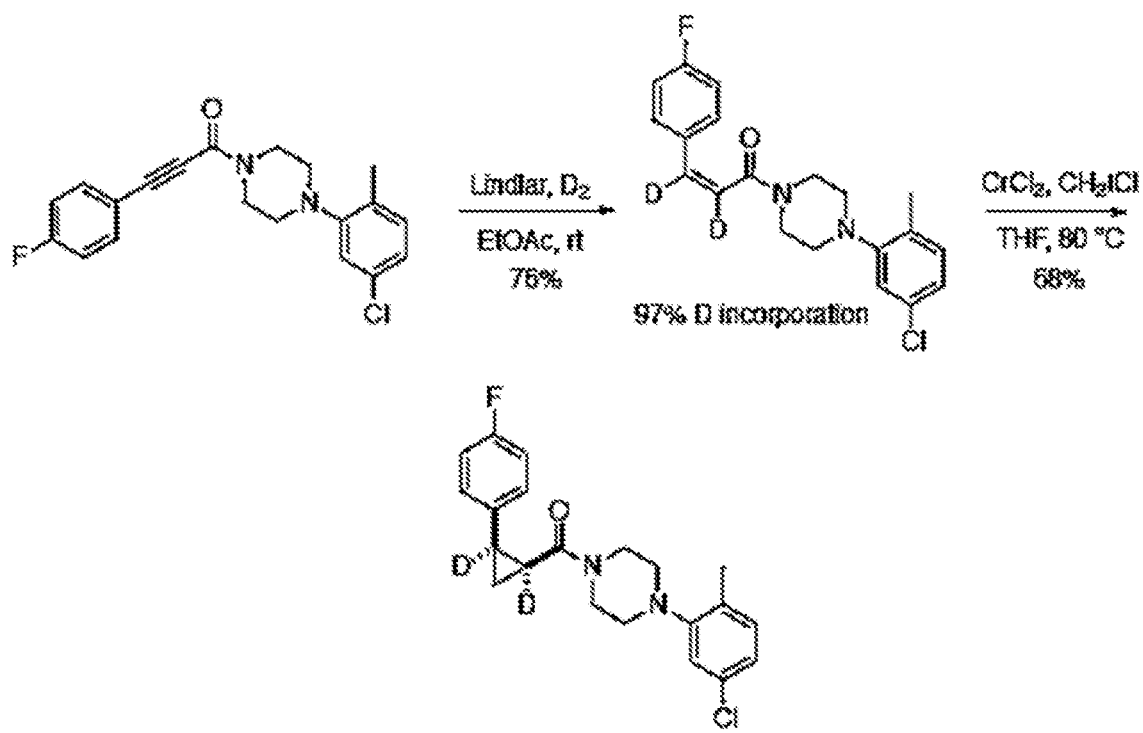
Figure 16:
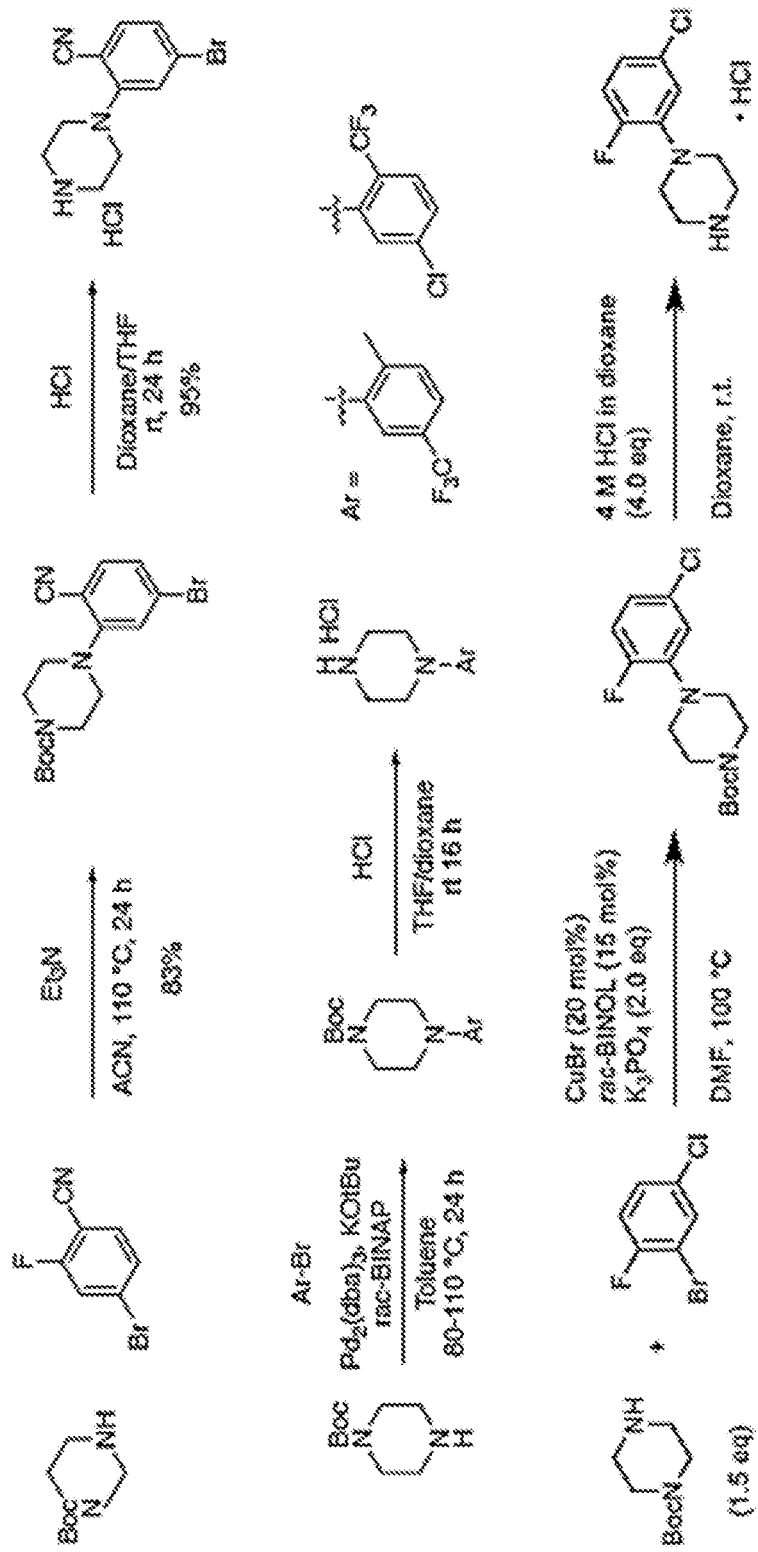
Figure 17:
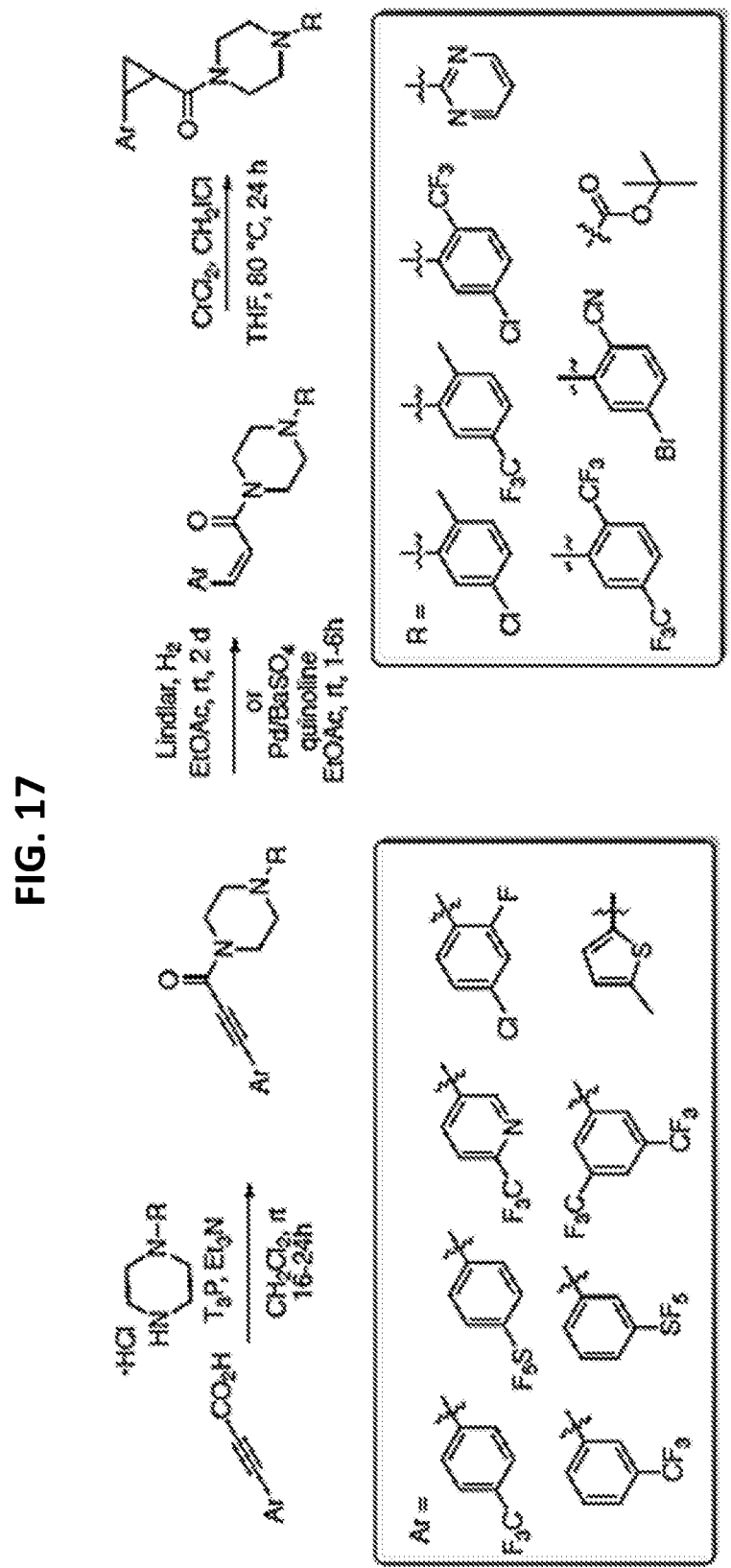
Figure 18:
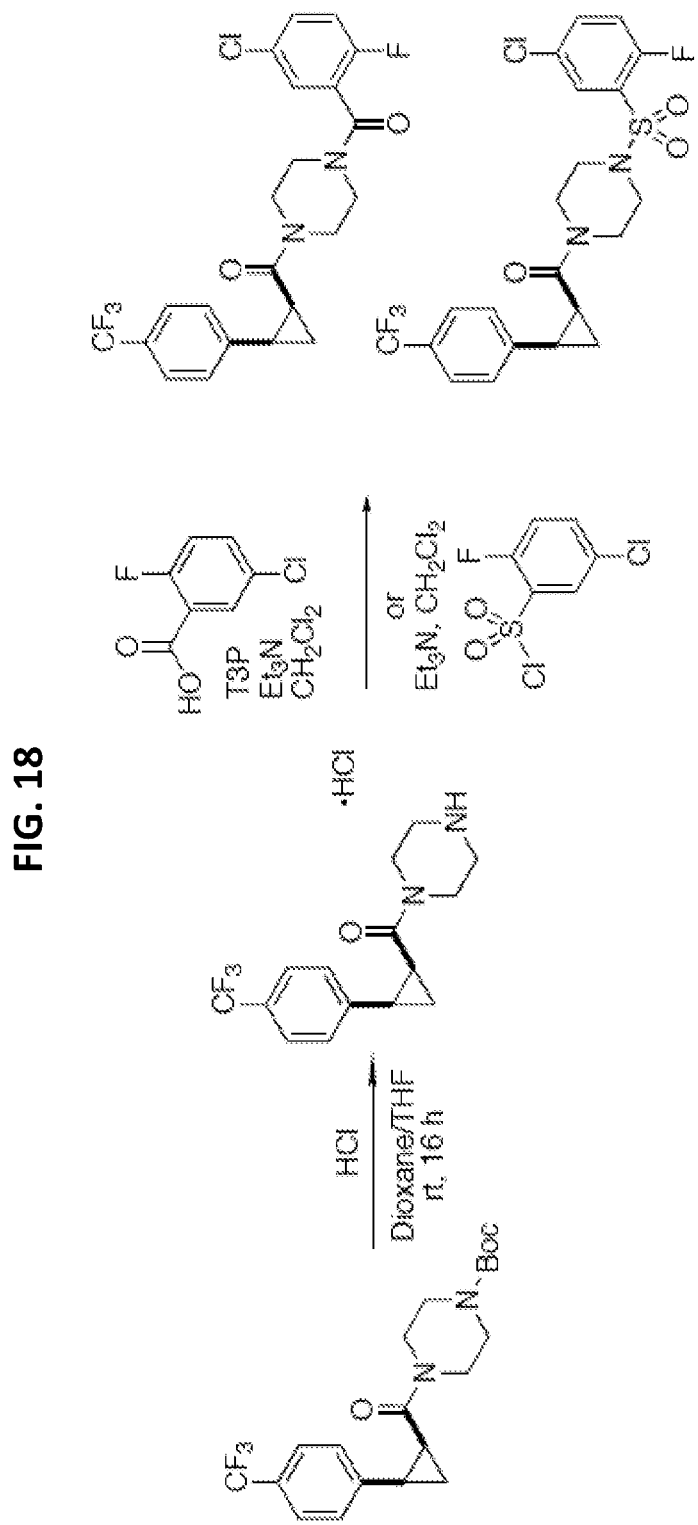

FIGS. 14-35 provide exemplary reaction schemes for several of the analogs described in detail below. FIG. 14 is a general reaction scheme for propiolic acid precursor compounds. FIG. 15 is a reaction scheme for (4-(5-chloro-2-methylphenyl)piperazin-1-yl)((1RS,2SR)-2-(4-fluorophenyl)-cyclopropyl-1,2-d2)-methanone. FIG. 16 shows three general reaction schemes for several precursor compounds including aryl and piperazinyl moieties. FIG. 17 is a general reaction scheme for several analogs comprising cyclopropyl and piperazinyl moieties. FIG. 18 is a reaction scheme for (4-(5-chloro-2-fluorobenzoyl)piperazin-1-yl)((1S,2R)-2-(4-(trifluoromethyl)phenyl)cyclopropyl)-methanone and (4-((5-chloro-2-fluorophenyl)-sulfonyl)piperazin-1-yl)((1S,2R)-2-(4-(trifluoromethyl)phenyl)-cyclopropyl)methanone.

Figure 19:
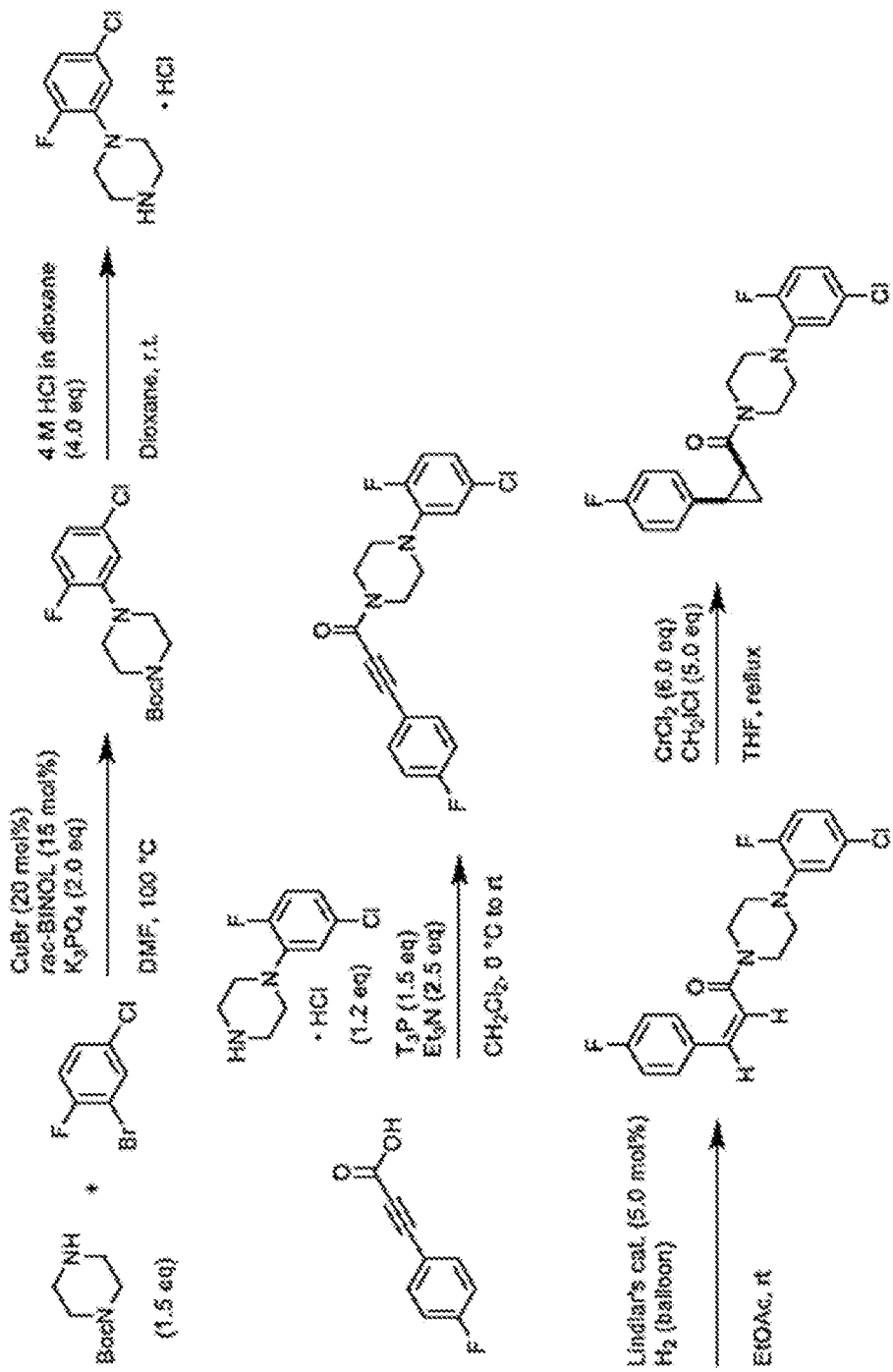
Figure 20:
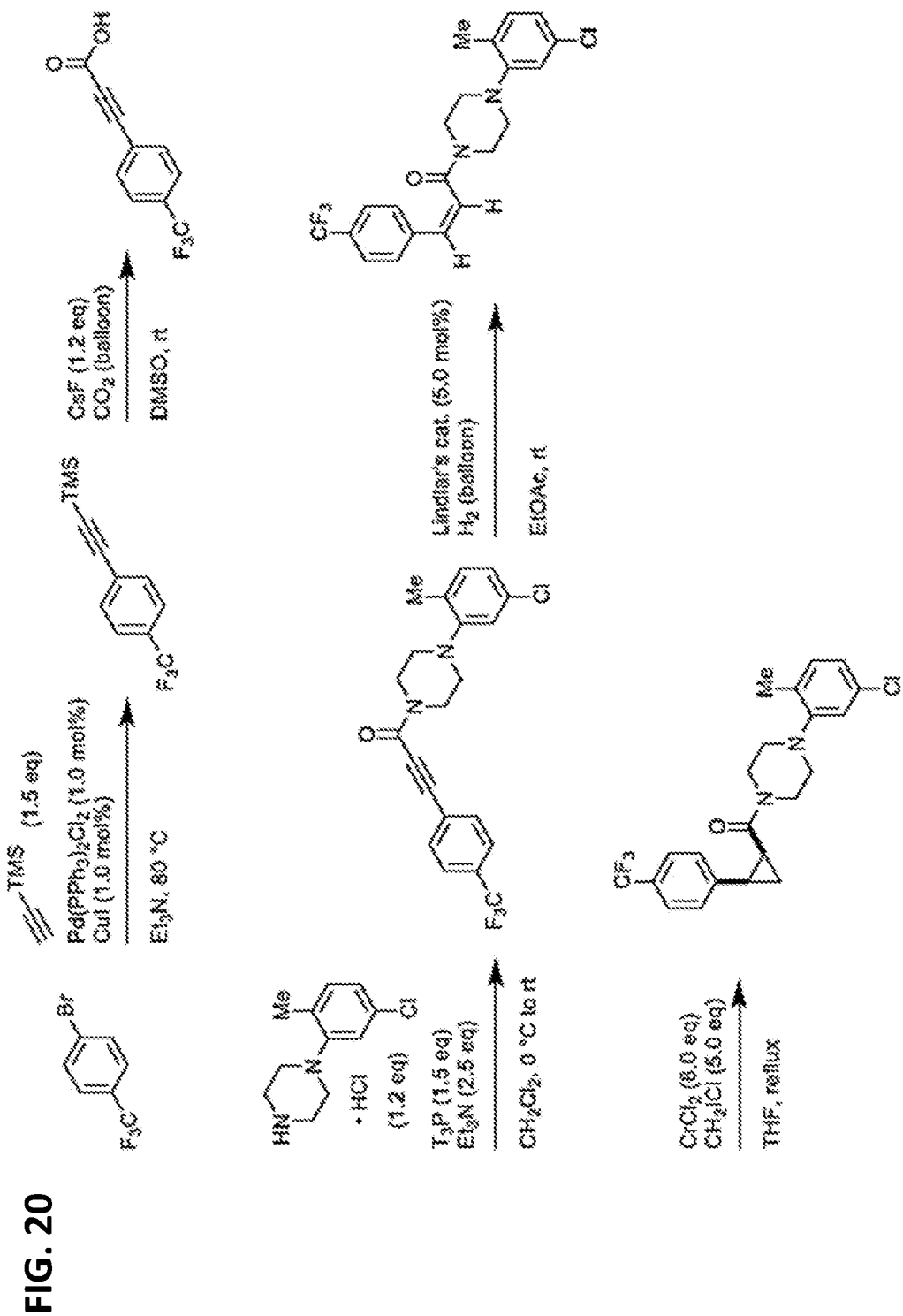
Figure 21:
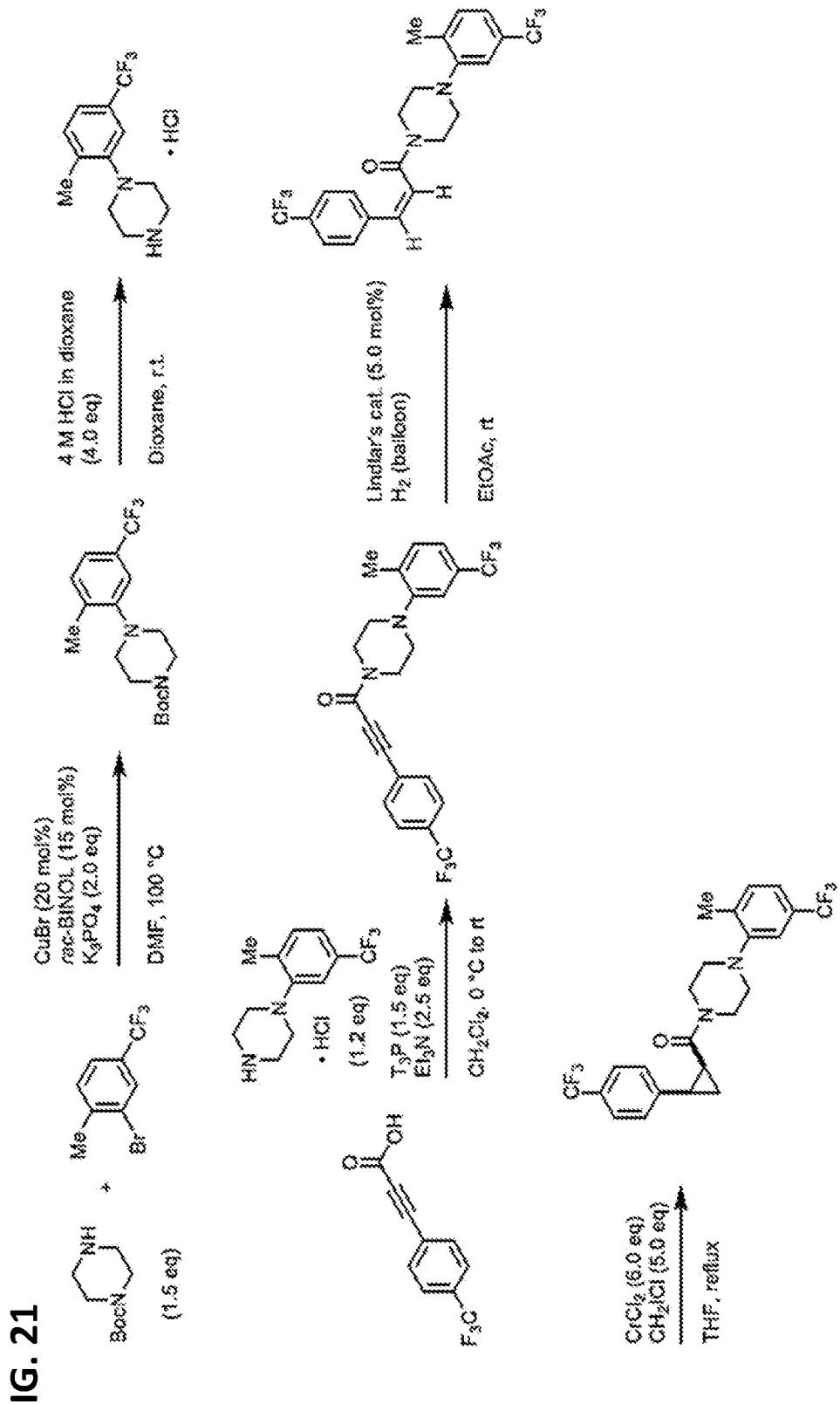
Figure 22:
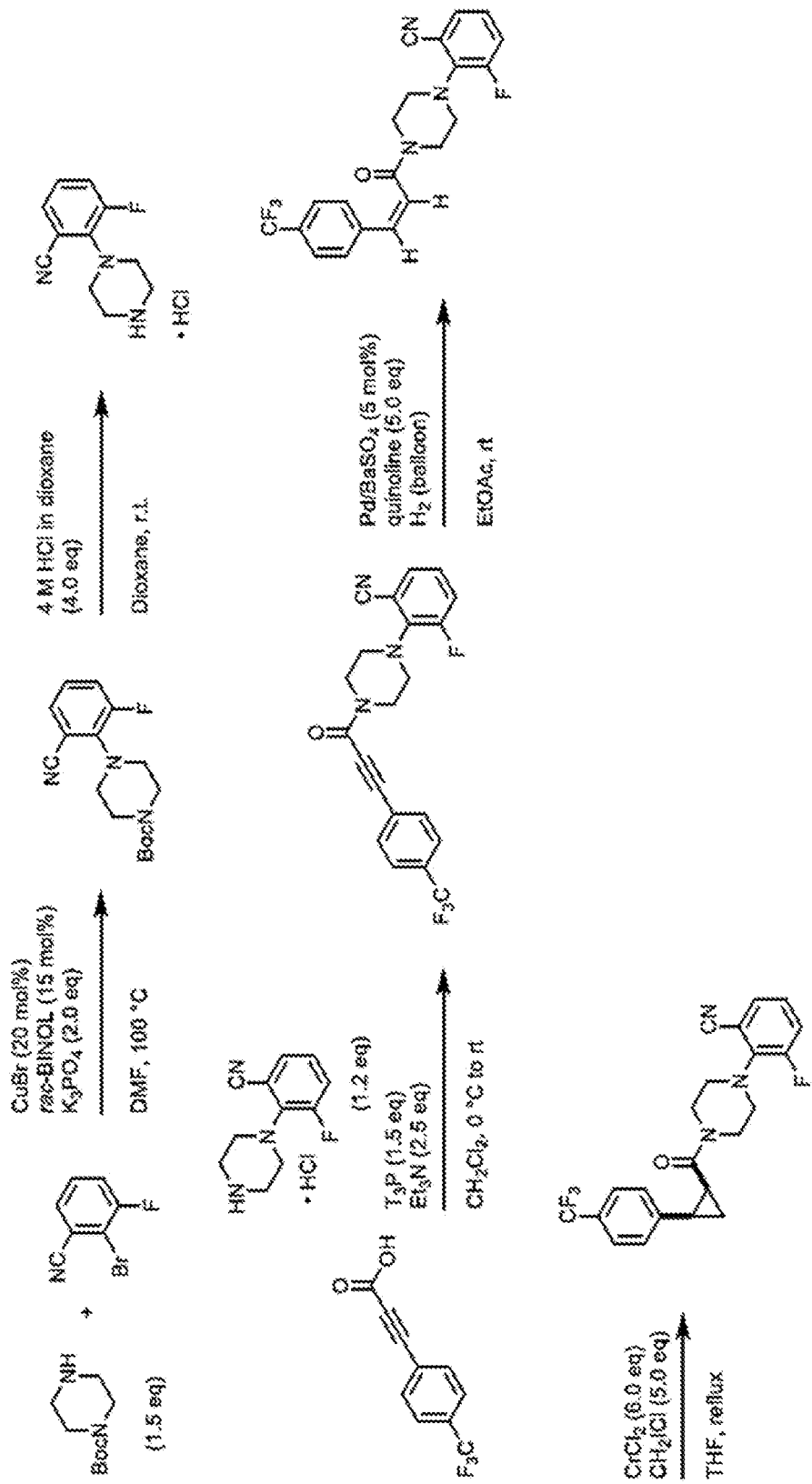
Figure 23:
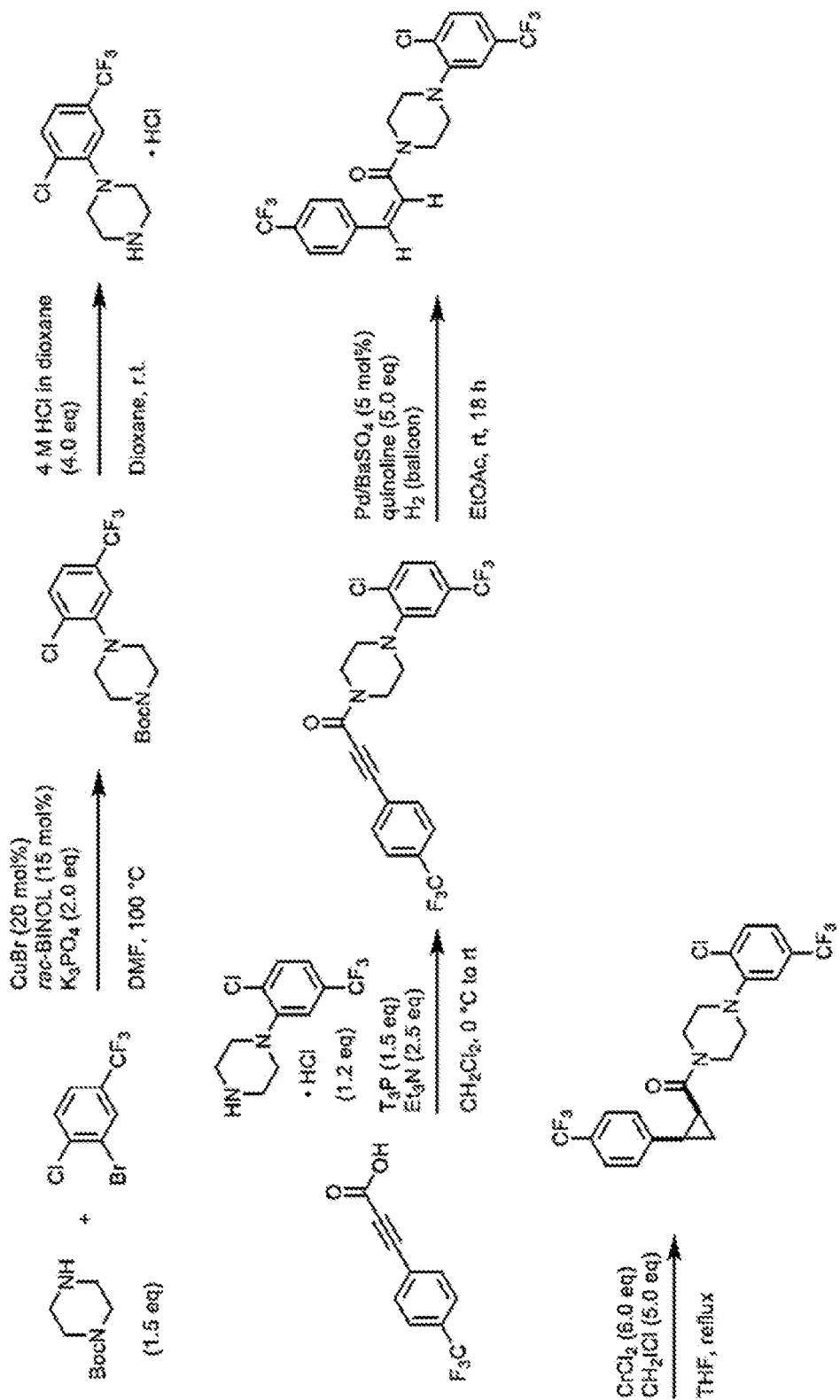
Figure 24:
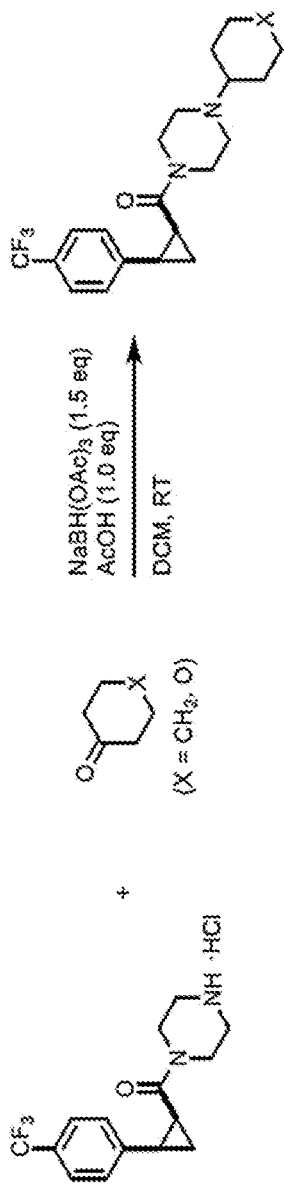
Figure 25:
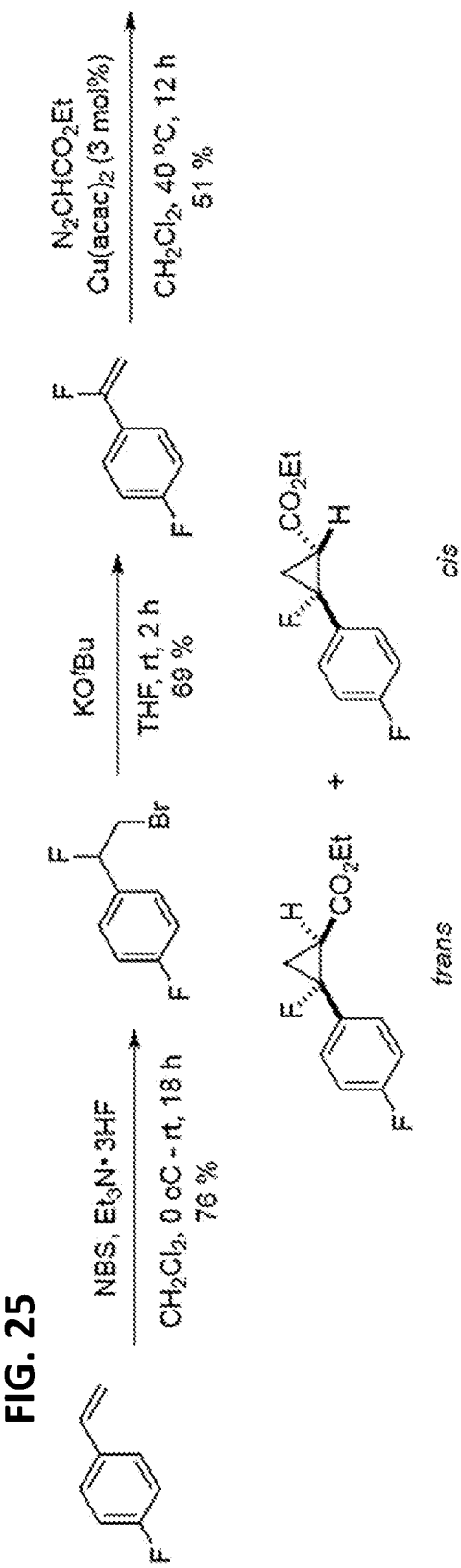
Figure 26:
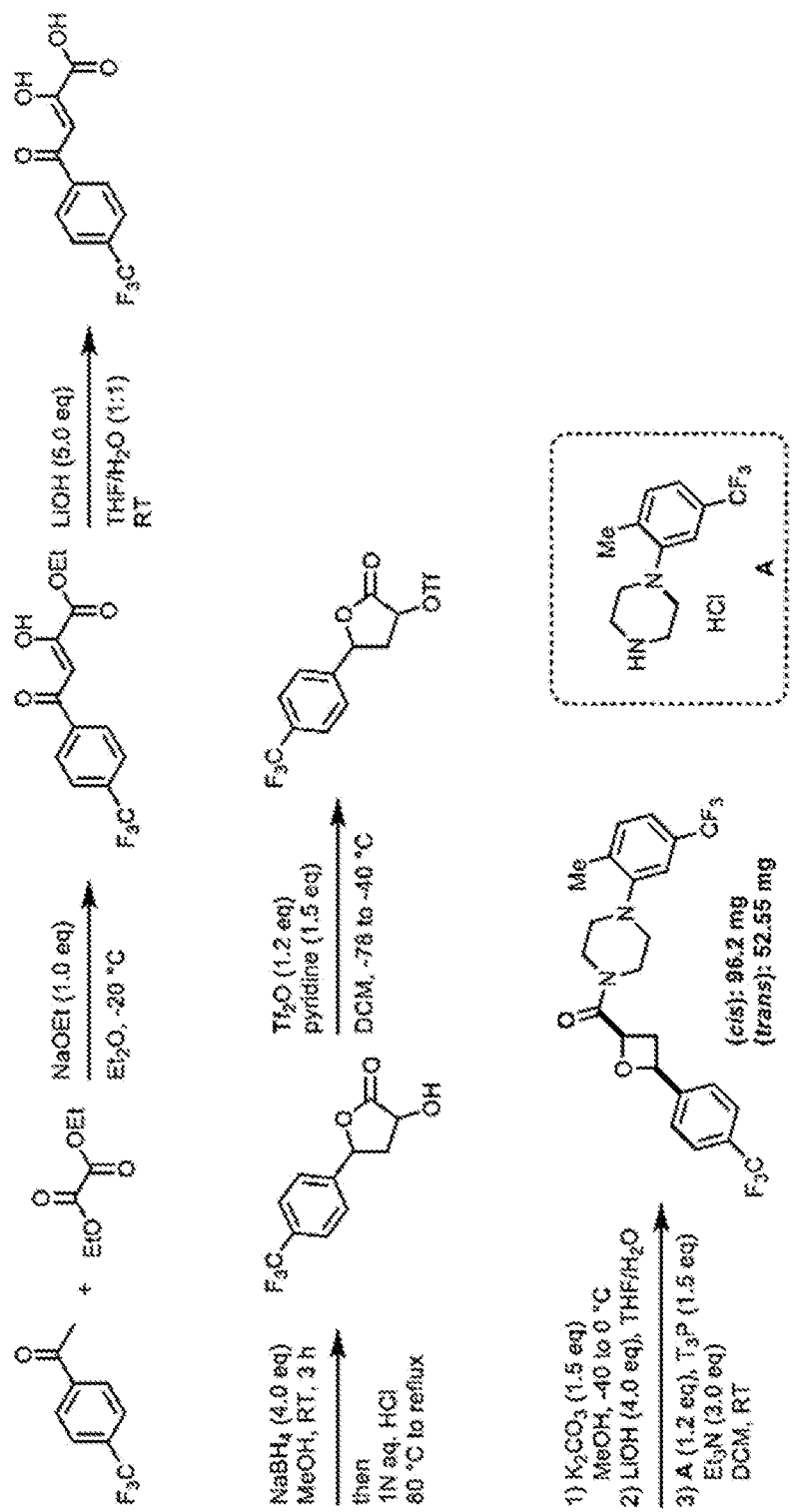
Figure 27:
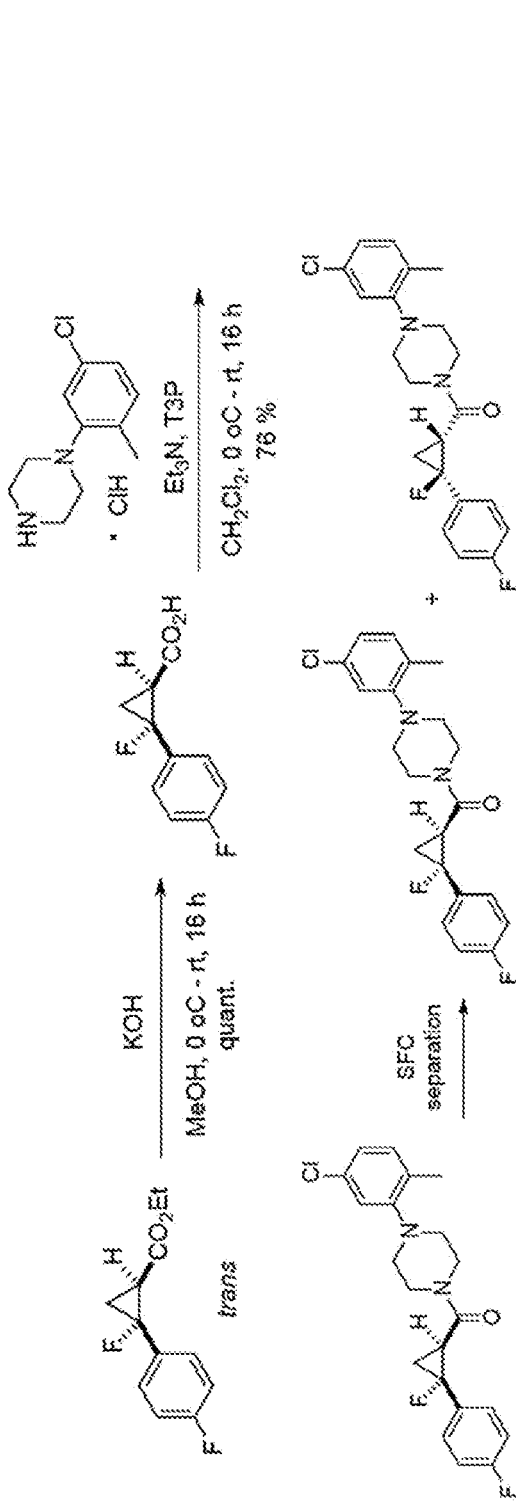
Figure 28:
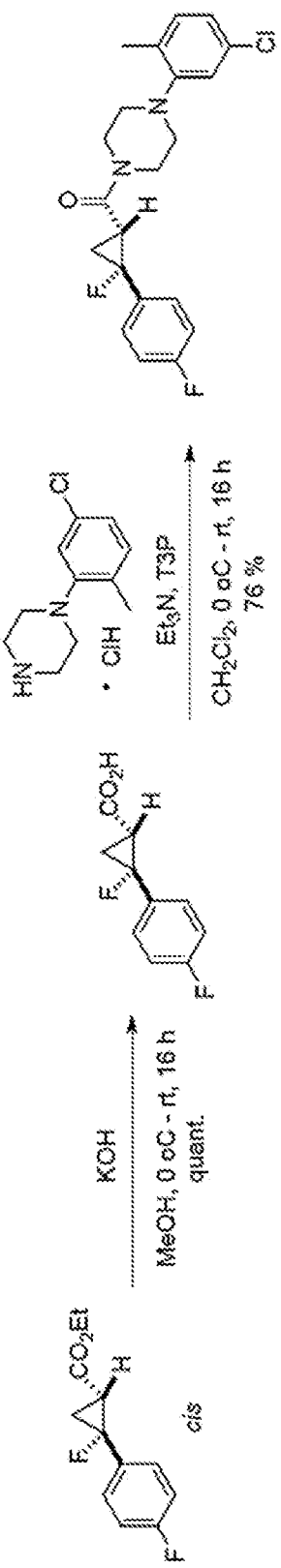
Figure 29:
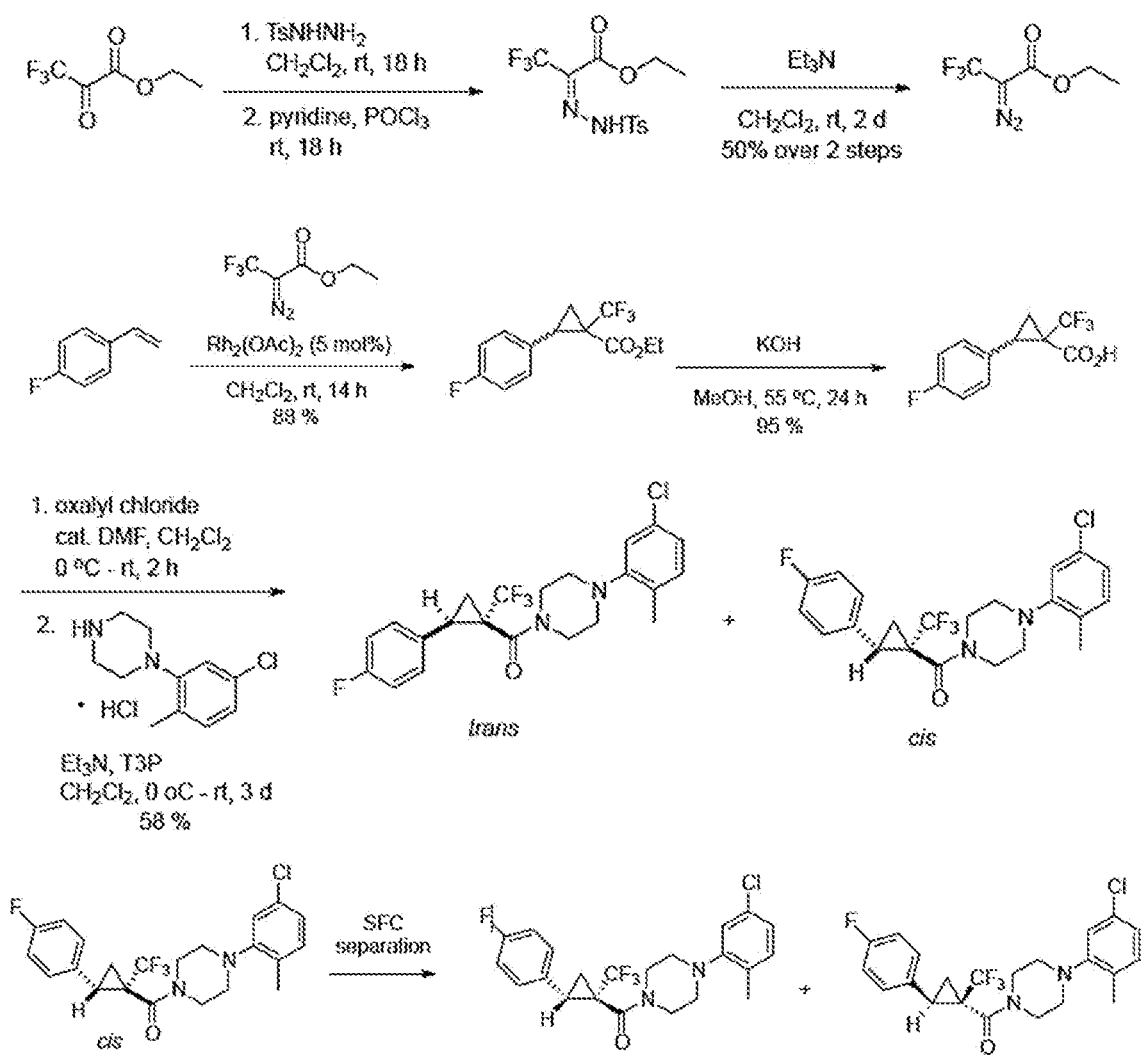
Figure 30:
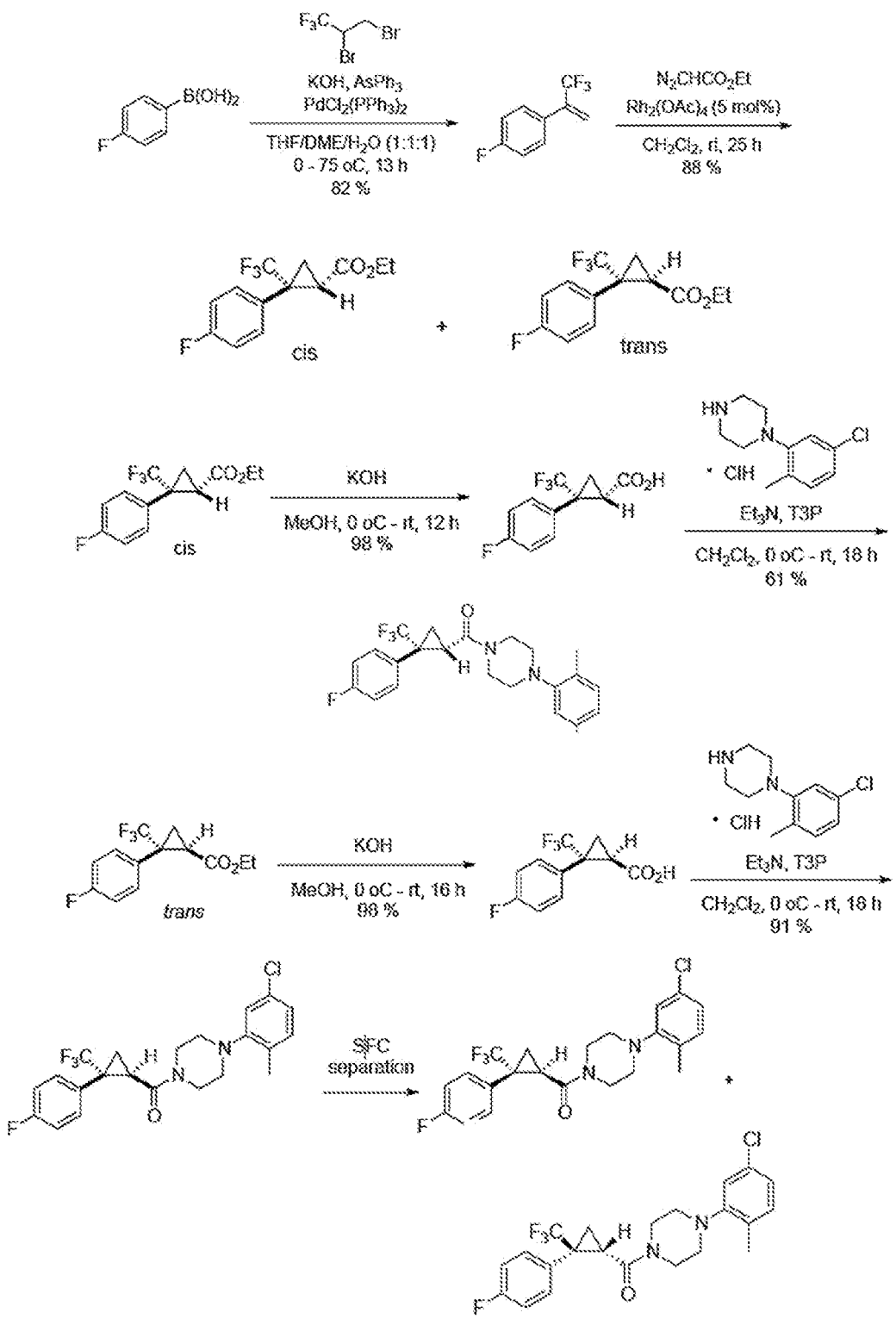
Figure 31:
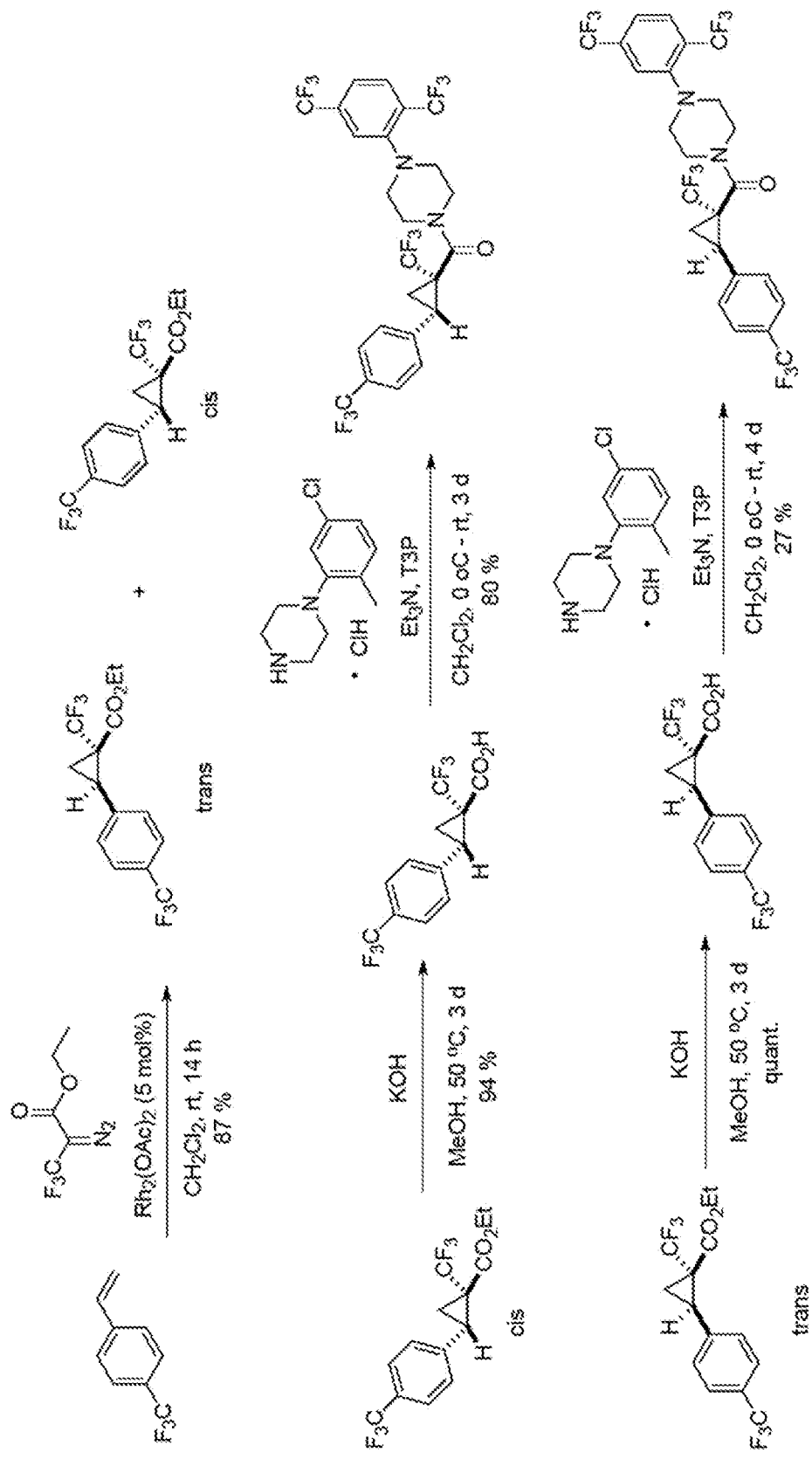
Figure 32:
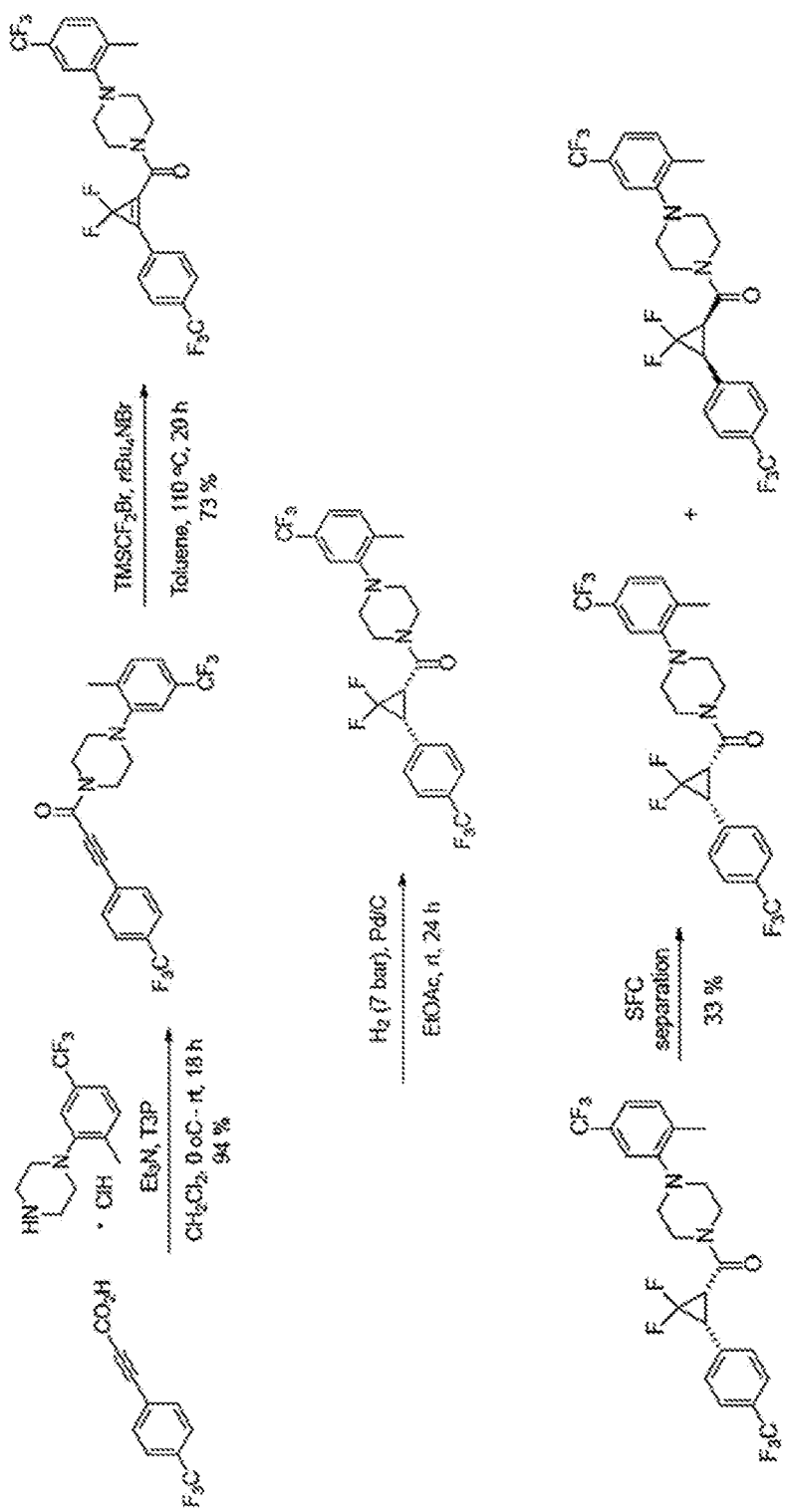
Figure 33:
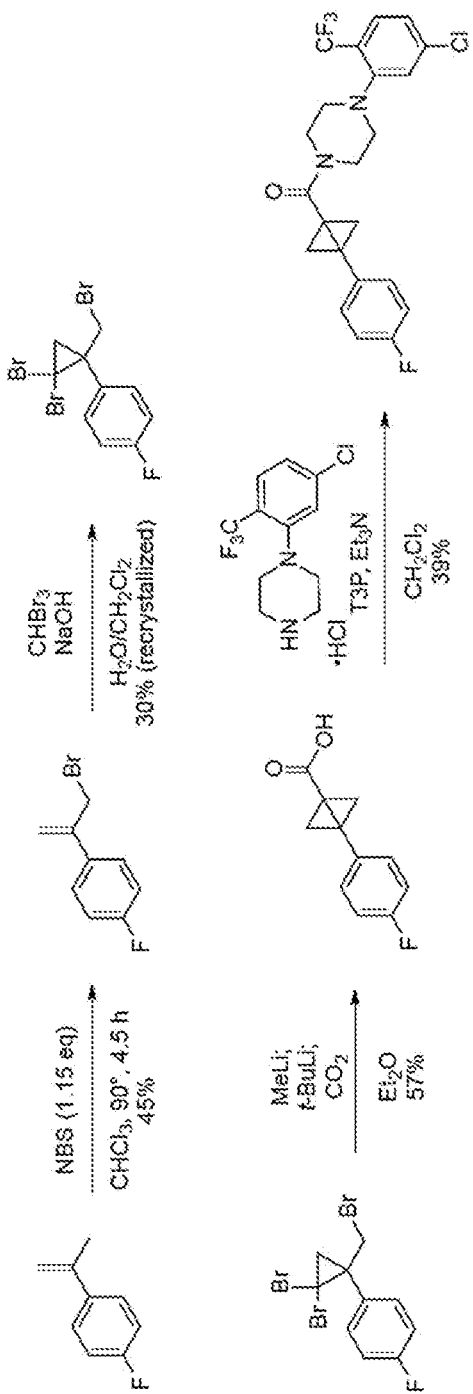
Figure 34:
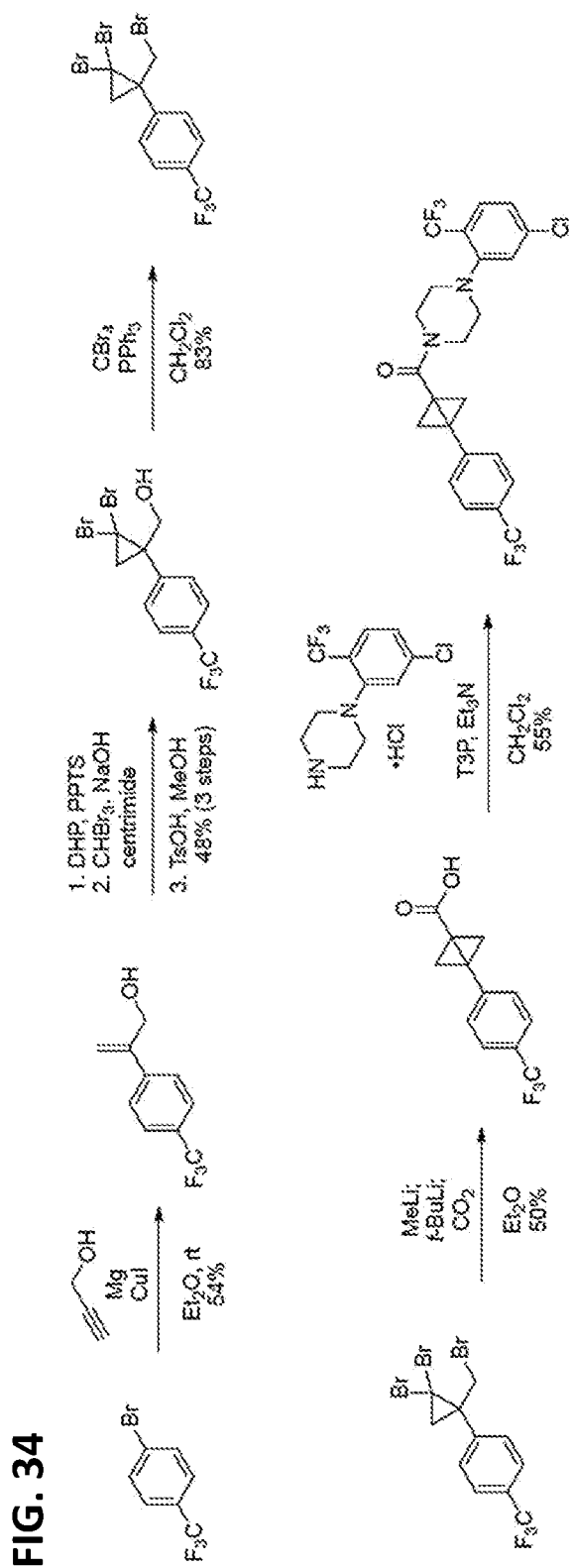
Figure 35:
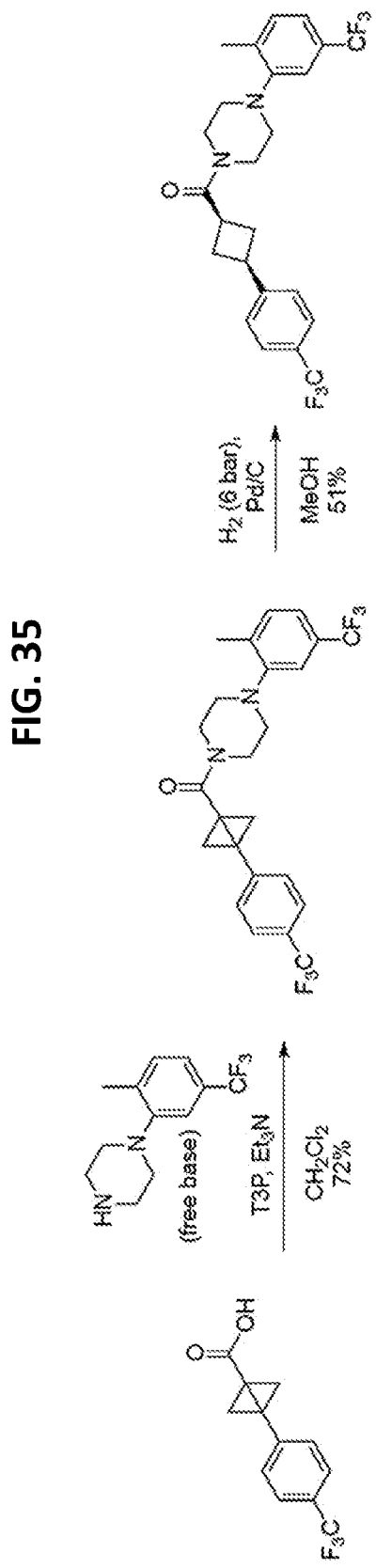

FIG. 19 is a reaction scheme for (4-(5-chloro-2-fluorophenyl)piperazin-1-yl)(2-(4-fluorophenyl)cyclopropyl)-methanone. FIG. 20 is a reaction scheme for (4-(5-chloro-2-methylphenyl)piperazin-1-yl)(2-(4-(trifluoromethyl)phenyl)-cyclopropyl)methanone. FIG. 21 is a reaction scheme for (4-(2-methyl-5-(trifluoromethyl)phenyl)piperazin-1-yl)(2-(4-(trifluoromethyl)phenyl)cyclopropyl)-methanone. FIG. 22 is a reaction scheme for 3-fluoro-2-(4-(2-(4-(trifluoromethyl)phenyl)cyclopropane-1-carbonyl)piperazin-1-yl)benzonitrile. FIG. 23 is a reaction scheme for (4-(2-chloro-5-(trifluoromethyl)phenyl)piperazin-1-yl)(2-(4-(trifluoromethyl)phenyl)-cyclopropyl)methanone. FIG. 24 is a reaction scheme for (4-cyclohexyl-piperazin-1-yl)(2-(4-(trifluoromethyl)phenyl)cyclopropyl)methanone and (4-(Tetrahydro-2H-pyran-4-yl)piperazin-1-yl)(2-(4-(trifluoromethyl)phenyl)cyclopropyl)methanone. FIG. 26 is a reaction scheme for (4-(2-methyl-5-(trifluoromethyl)phenyl)piperazin-1-yl)(4-(4-(trifluoromethyl)phenyl)oxetan-2-yl)methanone. FIG. 27 is a reaction scheme for trans-(4-(5-chloro-2-methylphenyl)piperazin-1-yl)((1SR,2RS)-2-fluoro-2-(4-fluorophenyl)-cyclopropyl)methanone. FIG. 28 is a reaction scheme for cis-(4-(5-chloro-2-methylphenyl)piperazin-1-yl)((1SR,2RS)-2-fluoro-2-(4-fluorophenyl)cyclopropyl)-methanone. FIG. 29 is a reaction scheme for cis- and trans-(4-(5-chloro-2-methylphenyl)piperazin-1-yl)(2-(4-fluorophenyl)-1-(trifluoromethyl)-cyclopropyl)methanone. FIG. 30 is a reaction scheme for trans-(4-(5-chloro-2-methylphenyl)piperazin-1-yl)((1RS,2RS)-2-(4-fluorophenyl)-2-(trifluoromethyl)cyclopropyl)-methanone. FIG. 31 is a reaction scheme for trans-(4-(2,5-bis(trifluoromethyl)phenyl)-piperazin-1-yl)(1-(trifluoromethyl)-2-(4-(trifluoromethyl)-phenyl)cyclopropyl)methanone. FIG. 32 is a reaction scheme for cis-((1SR,3RS)-2,2-difluoro-3-(4-(trifluoromethyl)phenyl)cyclopropyl)(4-(2-methyl-5-(trifluoromethyl)-phenyl)piperazin-1-yl)methanone. FIG. 33 is a reaction scheme for (4-(5-chloro-2-(trifluoromethyl)-phenyl)piperazin-1-yl)(3-(4-fluorophenyl)bicyclo[1.1.0]butan-1-yl)methanone. FIG. 34 is a reaction scheme for (4-(5-chloro-2-(trifluoromethyl)phenyl)piperazin-1-yl)(3-(4-(trifluoromethyl)phenyl)bicyclo[1.1.0]butan-1-yl)methanone. FIG. 35 is a reaction scheme for (4-(2-methyl-5-(trifluoromethyl)-phenyl)piperazin-1-yl)(3-(4-(trifluoromethyl)phenyl)cyclobutyl)-methanone.

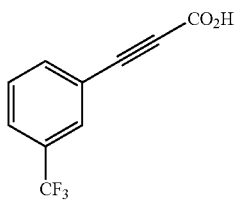 [SMILES: O=C(O)C#Cc1cccc(C(F)(F)F)c1]

3-(3-(Trifluoromethyl)phenyl)propiolic acid (Yonemoto-Kobayashi et al., *Org. & Biomolec. Chem.* 2013, 11:3773-3775; Solomon et al., *JACS* 1963, 85:3492-3496; Austin et al., *J. Org. Chem.* 1981, 46:2280-2286. A solution of Pd(PPh$_3$)$_2$Cl$_2$ (0.0134 g, 0.0436 mmol), CuI (0.00829 g, 0.0436 mmol), and 3-bromobenzo-triflouride (0.62 mL, 4.36 mol) in Et$_3$N (8.7 mL) was sparged with Ar for 15 min and treated with (trimethylsilyl)acetylene (0.93 mL, 6.53 mmol) and sparged for an additional 2 min. The resulting mixture was heated to 80° C. overnight, cooled to rt, filtered through Celite, washed (Et$_2$O) until the washes appeared colorless and the filtrate was concentrated under reduced pressure. The crude residue was purified by chromatography on SiO$_2$ (hexanes) to give the trimethyl((3-(trifluoromethyl)phenyl)ethynyl)silane (1.03 g, 4.24 mmol, 97%) as a pale yellow oil.

A solution of CsF (0.775 g, 5.10 mmol) in dry DMSO (6.5 mL) under an atmosphere of CO$_2$ (balloon) at rt was treated with a solution of trimethyl((3-(trifluoromethyl)phenyl)ethynyl)silane (1.03 g, 4.25 mmol) dropwise and the reaction was stirred under CO$_2$ at rt overnight. The reaction mixture was diluted with H$_2$O (80 mL) and extracted with CH$_2$Cl$_2$ (2×25 mL). The aqueous layer was acidified (>pH 1) with 6 M aqueous HCl at 0° C. and extracted with Et$_2$O (3×25 mL). The combined organic layers were dried (MgSO$_4$), concentrated under reduced pressure, and dried under high vacuum to give 3-(3-(trifluoromethyl)phenyl) propiolic acid (0.774 g, 3.62 mmol, 85%) as an pale tan orange waxy solid: $^1$H NMR (400 MHz, Acetone-d$_6$) δ 11.85 (bs, 1H), 7.95-7.87 (m, 3H), 7.36 (t, J=7.4 Hz, 1H); $^{13}$C NMR (100 MHz, Acetone-d$_6$) δ 154.3, 137.1, 131.7 (q, J$_{CF}$=33.0 Hz), 130.0 (q, J$_{CF}$=3.8 Hz), 128.1 (q, J$_{CF}$=3.4 Hz), 124.5 (q, J$_{CF}$=272.0 Hz), 121.7, 83.6, 82.9.

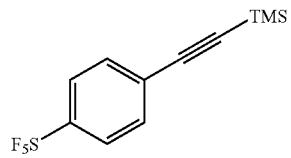

Trimethyl((4-(pentafluoro-λ6-sulfaneyl)phenyl)ethynyl) silane. A solution of Pd(PPh$_3$)$_2$Cl$_2$ (0.0365 g, 0.0519 mmol), CuI (0.0100 g, 0.0519 mmol), and (4-bromophenyl)pentafluoro-λ6-sulfane (1.50 g, 5.19 mmol) in Et$_3$N (11 mL) was sparged with Ar for 10 min, treated with (trimethylsilyl)acetylene (1.10 mL, 7.79 mmol), sparged with Ar for 5 min, heated to 80° C. for 22 h, cooled to rt, filtered through Celite, washed (Et$_2$O) until the washes appeared colorless, and the combined filtrates were concentrated under reduced pressure. The crude residue was purified by chromatography on SiO$_2$ (hexanes) to give trimethyl((4-(pentafluoro-λ6-sulfaneyl)phenyl)ethynyl)silane (1.32 g, 4.40 mmol, 85%) as a pale yellow oil: IR (CH$_2$Cl$_2$) 2963, 2165, 1599, 1493, 1401, 1251, 1095, 826, 802, 759 cm$^{-1}$; $^1$H NMR (400 MHz, CDCl$_3$) δ 7.68 (dt, J=9.0, 2.0 Hz, 2H), 7.52 (d, J=9.0 Hz, 2H), 0.28 (s, 9H); $^{13}$C NMR (100 MHz, CDCl$_3$) δ 153.2 (quint, J$_{CF}$=18.0 Hz), 126.9, 125.9 (quint, J$_{CF}$=5.0 Hz), 102.7, 98.0, –0.3; $^{19}$F NMR (376 MHz, CDCl$_3$) δ 84.0 (quint, J=150.2 Hz, 1 F), 62.6 (d, J=150.2 Hz, 4 F); HRMS (ESI) m/z calcd for C$_{11}$H$_{13}$F$_5$SiS ([M]$^+$) 300.0427, found 300.0400.

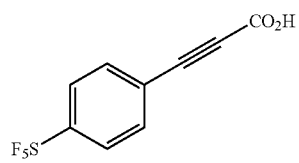

3-(4-(Pentafluoro-λ6-sulfaneyl)phenyl)propiolic acid. A solution of CsF (0.801 g, 5.27 mmol) in dry DMSO (3 mL) under CO$_2$ (balloon) at rt was treated with a solution of trimethyl((4-(pentafluoro-λ6-sulfaneyl)phenyl)ethynyl)silane (1.32 g, 4.40 mmol) in DMSO (5.8 mL) dropwise and the reaction was stirred under CO$_2$ at rt overnight, diluted with H$_2$O (90 mL) and extracted with CH$_2$Cl$_2$ (2×50 mL). The aqueous layer was acidified (>pH 1) with 6 M aqueous HCl at 0° C. and extracted with Et₂O (3×50 mL). The combined organic layers were washed with H₂O (50 mL), dried (MgSO₄), concentrated under reduced pressure, and dried under high vacuum to give 3-(4-(pentafluoro-λ6-sulfaneyl)phenyl)propiolic acid (0.338 g, 1.24 mmol, 28%) as brown solid. Mp 156.5-159.6° C.; IR (CHCl₃) 2979, 2876, 2577, 2235, 1677, 1416, 1298, 1217, 886, 829, 751 cm⁻¹; ¹H NMR (400 MHz, CDCl₃) δ 10.00 (bs, 1H), 7.82 (dt, J=9.0, 2.0 Hz, 2H), 7.73 (d, J=9.0 Hz, 2H); ¹³C NMR (100 MHz, CDCl₃) δ 157.7, 155.2 (quint, $J_{CF}$=19.0 Hz), 133.3, 126.5 (quint, $J_{CF}$=4.0 Hz), 122.7, 85.9, 81.7; ¹⁹F NMR (376 MHz, CDCl₃) δ 82.6 (quint, J=150.5 Hz, 1 F), 62.3 (d, J=150.3 Hz, 4 F); HRMS (ESI) m/z calcd for C₉H₄O₂F₅S ([M−H]⁻) 270.9858, found 270.9858.

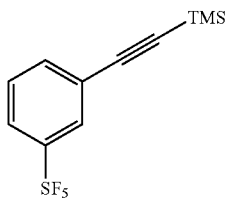

Trimethyl((3-(pentafluoro-λ6-sulfaneyl)phenyl)ethynyl)silane. A solution of Pd(PPh₃)₂Cl₂ (0.0365 g, 0.0519 mmol), CuI (0.0100 g, 0.0519 mmol), and (3-bromophenyl)pentafluoro-λ6-sulfane (1.50 g, 5.19 mmol) in Et₃N (11 mL) was sparged with Ar for 10 min, treated with (trimethylsilyl)acetylene (1.10 mL, 7.79 mmol), sparged with Ar for 5 min heated to 80° C. for 22 h, cooled to rt, filtered through Celite, washed (Et₂O) until the washes appeared colorless. The combined filtrates were concentrated under reduced pressure. The crude residue was purified by chromatography on SiO₂ (hexanes) to give trimethyl((3-(pentafluoro-λ6-sulfaneyl)phenyl)ethynyl)silane (1.29 g, 4.29 mmol, 83%) as a yellow oil: IR (CH₂Cl₂) 2963, 2902, 2168, 1601, 1479, 1421, 1251, 1109, 831, 803, 789, 759, 683 cm⁻¹; ¹H NMR (400 MHz, CDCl₃) δ 7.87 (t, J=2.0 Hz, 1H), 7.68 (ddd, J=8.0, 2.0, 0.8 Hz, 1H), 7.58 (d, J=8.0 Hz, 1H), 7.38 (t, J=8.0 Hz, 1H), 0.29 (s, 9H); ¹³C NMR (100 MHz, CDCl₃) δ 153.7 (quint, $J_{CF}$=17.8 Hz), 134.8, 129.5 (quint, $J_{CF}$=4.6 Hz), 128.6, 125.8 (quint, $J_{CF}$=4.8 Hz), 124.4, 102.8, 96.7, −0.3; ¹⁹F NMR (376 MHz, CDCl₃) δ 83.6 (quint, J=150.4 Hz, 1 F), 62.5 (d, J=150.3 Hz, 4 F); HRMS (ESI) m/z calcd for C₁₁H₁₃F₅SiS ([M]⁺) 300.0427, found 300.0405.

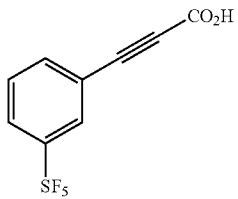

3-(3-(Pentafluoro-λ6-sulfaneyl)phenyl)propiolic acid. A solution of CsF (0.783 g, 5.15 mmol) in dry DMSO (3 mL) under CO₂ (balloon) at rt was treated a solution of trimethyl((3-(pentafluoro-λ6-sulfaneyl)phenyl)ethynyl)silane (1.29 g, 4.30 mmol) in DMSO (5.6 mL) dropwise and the reaction was stirred under CO₂ at rt overnight. The reaction mixture was diluted with H₂O (90 mL) and extracted with CH₂Cl₂ (2×50 mL). The aqueous layer was acidified (>pH 1) with 6M aqueous HCl at 0° C. and then extracted with Et₂O (3×50 mL). The combined organic layers were washed with H₂O (50 mL), dried (MgSO₄), concentrated under reduced pressure, and further dried under high vacuum to give 3-(3-(pentafluoro-λ6-sulfaneyl)phenyl)propiolic acid (0.935 g, 3.43 mmol, 80%) as tan solid: Mp 121.1-124.4° C.; IR (CHCl₃) 2831, 2218, 1688, 1479, 1426, 1214, 831, 791, 768, 680 cm⁻¹; ¹H NMR (400 MHz, CDCl₃) δ 10.92 (s, 1H), 8.01 (t, J=2.0 Hz, 1H), 7.87 (ddd, J=8.0, 2.0, 0.9 Hz, 1H), 7.75 (d, J=8.0 Hz, 1H), 7.54 (t, J=8.0 Hz, 1H); ¹³C NMR (100 MHz, CDCl₃) δ 158.1, 153.8 (quint, $J_{CF}$=19.0 Hz), 135.9, 130.7 (quint, $J_{CF}$=5.0 Hz), 129.3, 128.4 (quint, $J_{CF}$=4.0 Hz), 120.2, 86.2, 81.0; ¹⁹F NMR (376 MHz, CDCl₃) δ 82.5 (quint, J=150.4 Hz, 1 F), 62.5 (d, J=150.4 Hz, 4 F); HRMS (ESI) m/z calcd for C₉H₄O₂F₅S ([M−H]⁻) 270.9858, found 270.9856.

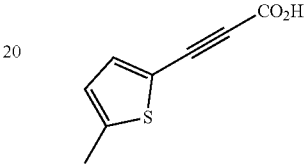

3-(5-Methylthiophen-2-yl)propiolic acid (He et al., Chem. Sci. 2013, 4:3478-3483; Paegle et al., Euro. J. Org. Chem. 2015; 2015:4389-4399; Kub et al., Macromolecules 2010, 34:2124-2129). A solution of Pd(PPh₃)₂Cl₂ (0.0269 g, 0.0877 mmol), CuI (0.0167 g, 0.0877 mmol), and 2-bromo-5-methyl thiophene (1.00 mL, 8.77 mmol) in Et₃N (17.5 mL) sparged with Ar for 15 min and treated with (trimethylsilyl)acetylene (1.9 mL, 13.2 mmol) and the mixture was further sparged for 2 min, heated to 80° C. overnight, cooled to rt, filtered through Celite, washed (Et₂O) until the washes appeared colorless and the filtrate was concentrated under reduced pressure. The crude residue was purified by chromatography on SiO₂ (hexanes) to give the trimethyl((5-methylthiophen-2-yl)ethynyl)silane 1.06 g, 5.47 mmol, 62%) as a pale yellow oil.

To a solution of CsF (0.994 g, 6.54 mmol) in dry DMSO (8 mL) under an atmosphere of CO₂ (balloon) at rt was added a solution of trimethyl((5-methylthiophen-2-yl)ethynyl)silane (1.06 g, 5.45 mmol) dropwise and the reaction was stirred under CO₂ at rt overnight. The reaction mixture was diluted with H₂O (100 mL) and extracted with CH₂Cl₂ (2×25 mL). The aqueous layer was acidified (>pH 1) with 6 M aqueous HCl at 0° C. and extracted with Et₂O (3×25 mL). The combined organic layers were washed with brine (50 mL), dried (MgSO₄), filtered, and concentrated under reduced pressure to give the product (0.571 g, 3.44 mmol, 63%) as a brown solid: ¹H NMR (300 MHz, CDCl₃) δ 10.14 (bs, 1H), 7.36 (d, J=3.3 Hz, 1H), 6.73 (dd, J=3.3 Hz, 1H), 2.52 (s, 3H).

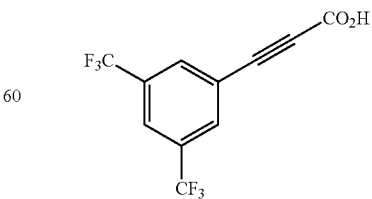

3-(3,5-Bis(trifluoromethyl)phenyl)propiolic acid. A solution of Pd(PPh₃)₂Cl₂ (0.239 g, 0.341 mmol), CuI (0.0650 g, 0.341 mmol), and 1-bromo-3,5-bis(trifluoromethyl)benzene (2.00 g, 6.83 mmol) in Et₃N (13 mL) was sparged with Ar for 10 min and treated with (trimethylsilyl)acetylene (1.42 mL, 10.2 mmol) and the solution was sparged with Ar for 2 min. The resulting mixture was heated to 80° C. for 22 h, cooled to rt, and filtered through Celite, which was washed with Et₂O until the washes appeared colorless. The filtrate was concentrated under reduced pressure and the crude residue was purified by chromatography on SiO₂ (hexanes) to give the desired product (1.79 g, 5.78 mmol) as a light yellow solid.

A solution of CsF (1.05 g, 6.92 mmol) in DMSO (4.6 mL) under CO₂ at rt was treated with a solution of ((3,5-bis (trifluoromethyl)phenyl)ethynyl)trimethylsilane (1.79 g, 5.77 mmol) in DMSO (7 mL) dropwise and the reaction was stirred under CO₂ at rt overnight. The reaction mixture was diluted with H₂O (90 mL) and extracted with CH₂Cl₂ (2×50 mL). The aqueous layer was acidified (>pH 1) with 6 M aqueous HCl at 0° C. and then extracted with Et₂O (3×100 mL). The combined organic layers were washed with H₂O (50 mL), dried (MgSO₄). The solvent was concentrated under reduced pressure and further dried under high vacuum to give 3-(3,5-bis(trifluoromethyl)phenyl)propiolic acid (0.859 g, 3.04 mmol, 45% (2 steps)) as brown solid: Mp 124.5-128.2° C.; IR (CH₂Cl₂) 2915, 2226, 1688, 1377, 1278, 1131, 972, 903, 683 cm⁻¹; ¹H NMR (400 MHz, CDCl₃) δ 11.25 (s, 1H), 8.06 (s, 2H), 7.98 (s, 1H); ¹³C NMR (100 MHz, CDCl₃) δ 157.7, 132.9 (q, $J_{CF}$=3.4 Hz), 132.6 (q, $J_{CF}$=34.4 Hz), 124.5 (q, $J_{CF}$=3.5 Hz), 122.5 (q, $J_{CF}$=273.2 Hz), 121.5, 84.5, 82.0; ¹⁹F NMR (376 MHz, CDCl₃) δ −63.3 (s, 6 F); HRMS (ESI) m/z calcd for C₁₁H₃F₆O₂ ([M−H]⁻) 281.0043, found 281.0039

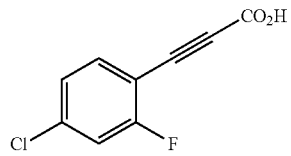 [SMILES: O=C(O)C#Cc1ccc(Cl)cc1F]

3-(4-Chloro-2-fluorophenyl)propiolic acid. A solution of Pd(PPh₃)₂Cl₂ (0.197 g, 0.281 mmol), CuI (0.0535 g, 0.281 mmol), and 4-chloro-2-fluoro-1-iodobenzene (1.80 g, 7.02 mmol) in Et₃N (14 mL) was sparged with Ar for 10 min followed by addition of (trimethylsilyl)acetylene (1.46 mL, 10.5 mmol) and the solution was further sparged with Ar for 2 min. The resulting mixture was heated to 80° C. for 22 h. After cooling the reaction to rt, the solution was filtered through Celite, which was washed with Et₂O until the washes appeared colorless. The filtrate was concentrated under reduced pressure. The crude residue was purified by chromatography on SiO₂ (hexanes) to give ((4-chloro-2-fluorophenyl)ethynyl)trimethylsilane (1.42 g, 6.26 mmol) as a yellow oil.

A solution of CsF (1.14 g, 7.51 mmol) in DMSO (5 mL) under CO₂ at rt was treated with a solution of ((4-chloro-2-fluorophenyl)ethynyl)trimethylsilane (1.42 g, 6.26 mmol) in DMSO (7 mL) dropwise and the reaction was stirred under CO₂ at rt overnight. The reaction mixture was diluted with H₂O (90 mL) and extracted with CH₂Cl₂ (2×50 mL). The aqueous layer was acidified (>pH 1) with 6 M aqueous HCl at 0° C. and then extracted with Et₂O (3×100 mL). The combined organic layers were washed with H₂O (50 mL), dried (MgSO₄), concentrated under reduced pressure, and dried under high vacuum to give 3-(4-chloro-2-fluorophenyl)propiolic acid (0.828 g, 4.17 mmol, 60% (2 steps)) as tan solid: Mp 174.1-176.4° C.; IR (CH₂Cl₂) 2972, 2233, 1720, 1603, 1486, 1387, 1298, 1189, 1072, 883, 827 cm⁻¹; ¹H NMR (400 MHz, CDCl₃) δ 9.09 (s, 1H), 7.53 (t, J=7.4 Hz, 1H), 7.20 (d, J=8.2 Hz, 2H); ¹³C NMR (100 MHz, CDCl₃) δ 163.6 (d, $J_{CF}$=259.9 Hz), 156.9, 138.7 (d, $J_{CF}$=10.0 Hz), 135.2 (d, $J_{CF}$=0.9 Hz), 125.1 (d, $J_{CF}$=3.7 Hz), 117.0 (d, $J_{CF}$=23.6 Hz), 106.8 (d, $J_{CF}$=15.5 Hz), 85.1, 81.1; ¹⁹F NMR (376 MHz, CDCl₃) δ −104.3 (s, 1 F); HRMS (ESI) m/z calcd for C₉H₃ClFO₂ ([M−H]⁻) 196.9811, found 196.9831.

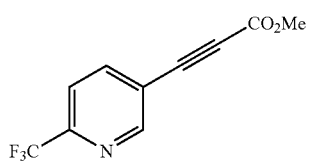 [SMILES: COC(=O)C#Cc1ccc(C(F)(F)F)nc1]

Methyl 3-(6-(trifluoromethyl)pyridin-3-yl)propiolate. To two flasks each containing a solution of Pd(PPh₃)₂Cl₂ (0.0466 g, 0.0664 mmol), CuI (0.0126 g, 0.0664 mmol), and 5-bromo-2-trifluoromethyl pyridine (1.50 g, 6.64 mmol) in Et₃N (13 mL) sparged with Ar for 10 min followed by addition of (trimethylsilyl)acetylene (1.4 mL, 9.96 mmol) and sparged with Ar for 2 min. The resulting mixtures were heated to 80° C. overnight where by TLC (hexanes/EtOAc, 4:1) the SM had been consumed. After cooling the reaction to rt, the reactions were combined, the solution was filtered through Celite, which was washed with Et₂O (100 mL) until the washes appeared colorless. The filtrate was concentrated under reduced pressure. The crude residue was purified by chromatography on SiO₂ (hexanes/EtOAc, 9:1) to give 2-(trifluoromethyl)-5-((trimethylsilyl)ethynyl)pyridine (3.37 g, 13.9 mmol) as orange/brown waxy solid that was taken on to the carboxylation.

A solution of CsF (2.52 g, 16.6 mmol) in DMSO (20 mL) under CO₂ at rt was treated with a solution of 2-(trifluoromethyl)-5-((trimethylsilyl)ethynyl)pyridine (3.37 g, 13.9 mmol) in DMSO (7 mL) dropwise and the reaction was stirred under CO₂ (balloon) at rt for 5 h, treated with MeI (0.95 mL, 15.2 mmol) was added and the solution was stirred for 1 h at rt. The reaction mixture was diluted with H₂O (200 mL), brine (100 mL) and extracted with Et₂O (3×150 mL). The combined organic layers were washed with H₂O (100 mL), dried (MgSO₄), and concentrated under reduced pressure. The crude product was purified by chromatography on SiO₂ (hexanes/EtOAc, 4:1) to give methyl 3-(6-(trifluoromethyl)pyridin-3-yl)propiolate (1.87 g, 8.17 mmol, 59% (2 steps)) as tan solid: Mp 98.2-99.7° C.; IR (neat) 2962, 2233, 1712, 1433, 1337, 1242, 1127, 1085, 864, 745 cm⁻¹; ¹H NMR (400 MHz, CDCl₃) δ 8.87 (s, 1H), 8.04 (ddd, J=8.0, 1.2, 0.6 Hz, 1H), 7.71 (d, J=8.0 Hz, 1H), 3.86 (s, 3H); ¹³C NMR (100 MHz, CDCl₃) δ 153.4, 153.1, 148.6 (q, $J_{CF}$=35.5 Hz), 141.2, 121.0 (q, $J_{CF}$=274.4 Hz), 120.1 (q, $J_{CF}$=2.8 Hz), 120.0, 84.7, 80.7, 53.2; ¹⁹F NMR (376 MHz, CDCl₃) δ −68.3 (s, 3 F); HRMS (ESI) m/z calcd for C₁₀H₇F₃NO₂ ([M+H]⁺) 230.0423, found 230.0422.

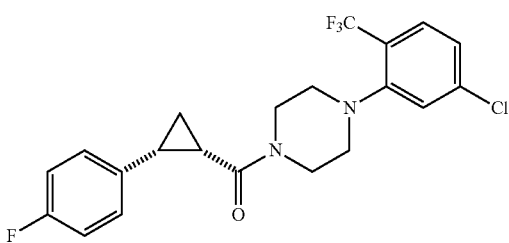

(4-(5-Chloro-2-(trifluoromethyl)phenyl)piperazin-1-yl)((1S,2R)-2-(4-fluorophenyl)cyclopropyl)-methanone. A solution of 3-(4-fluorophenyl)propiolic acid (0.0800 g, 0.487 mmol) and 1-(5-chloro-2-(trifluoromethyl)phenyl)piperazinehydrochloride (0.142 g, 0.536 mmol) in CH$_2$Cl$_2$ (4.9 mL) at 0° C. was treated Et$_3$N (0.27 mL, 1.95 mmol). The cooled solution was treated with T3P (50% solution in EtOAc) (0.52 mL, 0.73 mmol) dropwise and the reaction was stirred at 0° C. for 30 min, warmed to rt overnight, diluted with CH$_2$Cl$_2$ (30 mL), washed with H$_2$O (20 mL), satd. aqueous NaHCO$_3$ (20 mL), dried (MgSO$_4$), filtered, and concentrated under reduced pressure. The crude material was purified by automated chromatography on SiO$_2$ (4 g column, liquid load CH$_2$Cl$_2$, 100% hexanes to 30% EtOAc/hexanes), to give 1-(4-(5-chloro-2-(trifluoromethyl)phenyl)piperazin-1-yl)-3-(4-fluorophenyl)prop-2-yn-1-one (0.140 g, 0.341 mmol) as a colorless solid.

A solution of 1-(4-(5-chloro-2-(trifluoromethyl)phenyl)piperazin-1-yl)-3-(4-fluorophenyl)prop-2-yn-1-one (0.140 g, 0.341 mmol) in EtOAc (3.4 mL) was treated with Lindlar's catalyst (5% Pd on CaCO$_3$, lead poisoned, 0.0363 g, equivalent to 5 mol % Pd). The reaction was placed under a balloon of H$_2$ (3 vacuum/backfill cycles) and stirred at rt for 2 d. TLC (hexanes/EtOAc, 2:1) indicated that the SM had been mostly consumed. The reaction was filtered through Celite (eluting with EtOAc (10 mL)) and the combined filtrates were concentrated under reduced pressure. The crude residue was purified by automated chromatography on SiO$_2$ (4 g column, 100% hexanes to 40% EtOAc/hexanes, product eluted at 20% EtOAc/hexanes) to give (Z)-1-(4-(5-chloro-2-(trifluoromethyl)phenyl)piperazin-1-yl)-3-(4-fluorophenyl)prop-2-en-1-one (0.0510 g, 0.124 mmol) as a colorless solid.

A solution of CrCl$_2$ (0.0911 g, 0.741 mmol) and (Z)-1-(4-(5-chloro-2-(trifluoromethyl)phenyl)-piperazin-1-yl)-3-(4-fluorophenyl)prop-2-en-1-one (0.0510 g, 0.124 mmol) in dry degassed THF (1.2 mL) was sparged with Ar for 5 min and treated with CH$_2$ICl (0.071 mL, 0.618 mmol) at rt, stirred for 2 d at 80° C., cooled to rt, diluted with EtOAc (50 mL) and washed with 1 M aqueous HCl (3×20 mL). The organic layer was dried (MgSO$_4$), filtered and concentrated under reduced pressure. The crude residue was purified by automated chromatography on SiO$_2$ (4 g column, liquid load CH$_2$Cl$_2$, 100% hexanes to 30% EtOAc/hexanes, product eluted at 20% EtOAc/hexanes), filtered through basic Al$_2$O$_3$ (CH$_2$Cl$_2$/EtOAc, 1:1) and concentrated under reduced pressure. The resulting oil was recrystallized from a mixture of hexanes/cyclohexane (1:1), the crystals were washed with hexanes and dried under high vacuum to give (4-(5-chloro-2-(trifluoromethyl)phenyl)piperazin-1-yl)((1S,2R)-2-(4-fluorophenyl)cyclopropyl)-methanone. (0.0238 g, 0.0558 mmol, 11% (3 steps) (100% purity by ELSD)) as a colorless solid: Mp 101.0-103.2° C.; IR (CH$_2$Cl$_2$) 2917, 1639, 1513, 1418, 1308, 1225, 1126, 1085, 1031, 838 cm$^{-1}$; $^1$H NMR (400 MHz, CDCl$_3$) δ 7.45 (dd, J=8.4, 0.6 Hz, 1H), 7.25-7.22 (m, 1H), 7.16-7.11 (m, 2H), 7.00 (d, J=1.8 Hz, 1H), 6.99-6.93 (m, 2H), 3.92-3.86 (m, 1H), 3.79-3.73 (m, 1H), 3.67 (ddd, J=12.6, 8.6, 3.2 Hz, 1H), 3.37 (ddd, J=12.6, 9.0, 3.2 Hz, 1H), 3.01-2.95 (m, 2H), 2.49-2.39 (m, 2H), 2.31-2.25 (m, 1H), 2.19 (ddd, J=9.0, 8.6, 5.8 Hz, 1H), 1.83 (dt, J=6.8, 5.8 Hz, 1H), 1.36 (td, J=8.6, 5.6 Hz, 1H); $^{13}$C NMR (100 MHz, CDCl$_3$) δ 167.2, 161.6 (d, J$_{CF}$=245.1 Hz), 149.1, 132.5, 131.1, 130.1 (q, J$_{CF}$=32.7 Hz), 129.1, 129.0, 123.6 (q, J$_{CF}$=272.2 Hz), 120.8 (q, J$_{CF}$=3.8 Hz), 117.2 (q, J$_{CF}$=3.8 Hz), 115.0 (d, J$_{CF}$=21.3 Hz), 51.3, 51.0, 45.3, 41.9, 23.9, 23.5 10.7; $^{19}$F NMR (376 MHz, CDCl$_3$) δ −62.6 (s, 3 F), −116.4 (s, 1 F); HRMS (ESI) m/z calcd for C$_{21}$H$_2$OClF$_4$N$_2$O ([M+H]$^+$) 427.1195, found 427.1192.

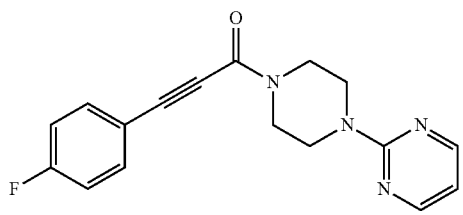 [SMILES: O=C(C#Cc1ccc(F)cc1)N1CCN(c2ncccn2)CC1]

3-(4-Fluorophenyl)-1-(4-(pyrimidin-2-yl)piperazin-1-yl)prop-2-yn-1-one. A solution of 3-(4-fluorolphenyl)propionic acid (0.150 g, 0.914 mmol) and 2-(1-piperazinyl)pyrimidine (0.188 g, 0.841 mmol) in CH$_2$Cl$_2$ (9.1 mL) at 0° C. was treated Et$_3$N (0.51 mL, 3.66 mmol). The cooled solution was treated with T3P (50% solution in EtOAc) (1.0 mL, 1.37 mmol) dropwise and the reaction was stirred at 0° C. for 30 min and allowed to warm to rt overnight. The reaction was diluted with CH$_2$Cl$_2$ (30 mL) and washed with H$_2$O (20 mL), dried (MgSO$_4$), filtered, and concentrated under reduced pressure. The crude material was purified by automated chromatography on SiO$_2$ (4 g column, gradient hexanes to EtOAc), to give 3-(4-fluorophenyl)-1-(4-(pyrimidin-2-yl)piperazin-1-yl)prop-2-yn-1-one (0.223 g, 0.719 mmol, 79%) as a colorless solid: Mp 168.4-170.8° C.; IR (CH$_2$Cl$_2$) 2859, 2217, 1618, 1585, 1506, 1435, 1355, 1261, 1227, 980, 838, 732 cm$^{-1}$; $^1$H NMR (400 MHz, CDCl$_3$) δ 8.34 (d, J=4.6 Hz, 2H), 7.56 (dd, J=8.8, 5.3 Hz, 2H), 7.08 (t, J=8.8 Hz, 2H), 6.56 (t, J=4.6 Hz, 1H), 3.95-3.93 (m, 2H), 3.88 (app dd, J=6.6, 3.4 Hz, 4H), 3.76 (app dd, J=6.6, 4.1 Hz, 2H); $^{13}$C NMR (100 MHz, CDCl$_3$) δ 163.6 (d, J=253.0 Hz), 161.4, 157.8, 153.1, 134.6 (d, J=8.7 Hz), 116.4 (d, J=3.6 Hz), 116.1 (d, J=22.1 Hz), 110.6, 90.0, 80.8, 46.8, 44.0, 43.3 41.5; $^{19}$F NMR (376 MHz, CDCl$_3$) δ −107.3 (s, 1 F); HRMS (ESI) m/z calcd for C$_{17}$H$_{16}$FN$_4$O ([M+H]$^+$) 311.1303, found 311.1301.

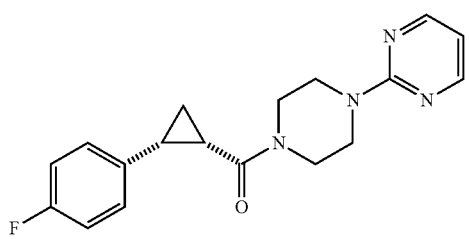

((1RS,2SR)-2-(4-Fluorophenyl)cyclopropyl)(4-(pyrimidin-2-yl)piperazin-1-yl)methanone. A solution of 3-(4-fluorophenyl)-1-(4-(pyrimidin-2-yl)piperazin-1-yl)prop-2-yn-1-one (0.200 g, 0.644 mmol) in EtOAc (6.4 mL) was treated with Lindlar's catalyst (5% Pd on CaCO$_3$, lead poisoned, 0.0685 g, equivalent to 5 mol % Pd). The reaction vessel was placed under vacuum and backfilled with H$_2$ (balloon, 4×) and stirred for 18 h at rt, filtered through Celite, washed (EtOAc), and the combined filtrates were concentrated under reduced pressure. The crude residue was purified by automated chromatography on SiO$_2$ (4 g column, hexanes to 60:40 hexanes:EtOAc) to give (Z)-3-(4-fluorophenyl)-1-(4-(pyrimidin-2-yl)piperazin-1-yl)prop-2-en-1-one (0.211 g, 0.676 mmol) as a colorless solid that was taken on to the cyclopropanation.

A solution of CrCl$_2$ (0.472 g, 3.84 mmol) and (Z)-3-(4-fluorophenyl)-1-(4-(pyrimidin-2-yl)piperazin-1-yl)prop-2-en-1-one (0.200 g, 0.640 mmol) in dry degassed THF (6.4 mL) (previously sparged with Ar for 15 min) was treated with CH$_2$ICl (0.37 mL, 3.20 mmol) and further sparged with Ar for 2 min. The reaction mixture was stirred for 20 h at 80° C., cooled to rt, diluted with EtOAc (10 mL), filtered through a plug of basic Al$_2$O$_3$(EtOAc), and concentrated under reduced pressure. The crude material was purified by automated chromatography on SiO$_2$ (4 g column, hexanes to 60% EtOAc:hexanes) to give ((1RS,2SR)-2-(4-fluorophenyl)cyclopropyl)(4-(pyrimidin-2-yl)piperazin-1-yl)methanone (0.128 g, 0.392 mmol, 61% (2 steps) (100% purity by ELSD)) as a colorless solid: Mp 141.9-145.3° C.; IR (CH$_2$Cl$_2$) 2922, 1636, 1583, 1510, 1432, 1359, 1224, 1027, 981, 837, 797 cm$^{-1}$; $^1$H NMR (400 MHz, CDCl$_3$) δ 8.28 (d, J=4.6 Hz, 2H), 7.12 (dd, J=8.7, 5.3 Hz, 2H), 6.92 (t, J=8.7 Hz, 2H), 6.50 (t, J=4.6 Hz, 1H), 4.00 (dt, J=13.3, 4.4 Hz, 1H), 3.93 (dt, J=13.0, 4.4 Hz, 1H), 3.76 (ddd, J=13.0, 5.1, 3.6 Hz, 1H), 3.66 (dt, J=13.0, 4.4 Hz, 1H), 3.53 (ddd, J=13.0, 8.8, 3.6 Hz, 1H), 3.26 (ddd, J=13.0, 8.8, 3.4 Hz, 1H), 3.13 (ddd, J=13.0, 8.8, 3.6 Hz, 1H), 3.00 (ddd, J=13.0, 8.8, 3.6 Hz, 1H), 2.49-2.43 (m, 1H), 2.18 (ddd, J=9.2, 8.4, 5.8 Hz, 1H), 1.83 (q, J=5.8 Hz, 1H), 1.34 (td, J=8.4, 5.8 Hz, 1H); $^{13}$C NMR (100 MHz, CDCl$_3$) δ 167.3, 161.7 (d, J$_{CF}$=244.9 Hz), 161.3, 157.7, 133.0, 129.0 (d, J$_{CF}$=8.0 Hz), 115.0 (d, J$_{CF}$=21.3 Hz), 110.3, 45.0, 43.8, 43.4, 41.6, 23.9, 23.5, 10.6; $^{19}$F NMR (470 MHz, CDCl$_3$) δ −116.4 (s, 1 F); HRMS (ESI) m/z calcd for C$_{18}$H$_{20}$FN$_4$O ([M+H]$^+$) 327.1616, found 327.1616.

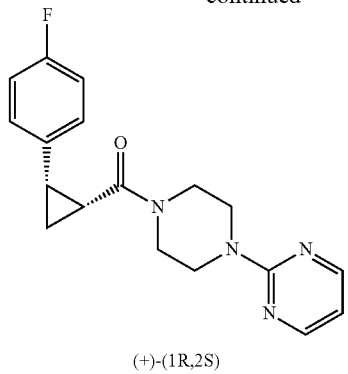

(+)-(1R,2S)

Racemic ((1RS,2SR)-2-(4-fluorophenyl)cyclopropyl)(4-(pyrimidin-2-yl)piperazin-1-yl)methanone was separated on a SFC Chiralpak-IC semiprep (250×10 mm) column (30% Methanol/CO$_2$, 7 mL/min, 100 bar, 90 μL injection, 20 mg/mL in MeOH) to give ((1S,2R)-2-(4-fluorophenyl)cyclopropyl)(4-(pyrimidin-2-yl)piperazin-1-yl)methanone (retention time 7.63 min) as a colorless solid (100% purity by ELSD): [α]$^{17}_D$ −207.0 (c 0.53, MeOH); $^1$H NMR (300 MHz, CDCl$_3$) δ 8.28 (d, J=4.6 Hz, 1H), 7.12 (dd, J=8.6, 5.3 Hz, 1H), 6.92 (t, J=8.6 Hz, 1H), 6.50 (t, J=4.6 Hz, 1H), 4.02-3.91 (m, 2H), 3.79-3.73 (m, 1H), 3.69-3.64 (m, 1H), 3.56-3.48 (m, 2H), 3.29-3.21 (m, 1H), 3.16-3.08 (m, 1H), 2.98 (ddd, J=12.6, 9.0, 3.7 Hz, 1H), 2.51-2.42 (m, 1H), 2.18 (ddd, J=9.0, 8.4, 6.0 Hz, 1H), 1.83 (q, J=5.6 Hz, 1H), 1.35 (td, J=8.4, 5.6 Hz, 1H). The enantiomeric excess was >99.9% ee (SFC Chiralpak-IC (250×10 mm); 30% Methanol:CO$_2$, 7 mL/min, p=100 bar, 220 nm; retention time: 8.0 min).

((1R,2S)-2-(4-Fluorophenyl)cyclopropyl)(4-(pyrimidin-2-yl)piperazin-1-yl)methanone (retention time 8.61 min) was obtained as a colorless solid (100% purity by ELSD): [α]$^{17}_D$ +213.2 (c 0.54, MeOH); $^1$H NMR (300 MHz, CDCl$_3$) δ 8.28 (d, J=4.6 Hz, 2H), 7.12 (dd, J=8.6, 5.3 Hz, 2H), 6.92 (t, J=8.6 Hz, 2H), 6.50 (t, J=4.6 Hz, 1H), 4.02-3.90 (m, 2H), 3.79-3.73 (m, 1H), 3.69-3.62 (m, 1H), 3.57-3.48 (m, 2H), 3.30-3.21 (m, 1H), 3.16-3.08 (m, 1H), 2.98 (ddd, J=13.0, 9.0, 3.5 Hz, 1H), 2.47 (td, J=9.0, 6.0 Hz, 1H), 2.18 (ddd, J=9.0, 8.4, 6.0 Hz, 1H), 1.83 (q, J=5.6 Hz, 1H), 1.35 (td, J=8.4, 5.6 Hz, 1 H). The enantiomeric excess was >99.9% ee (SFC Chiralpak-IC (250×10 mm); 30% Methanol:CO$_2$, 7 mL/min, p=100 bar, 220 nm; retention time: 9.0 min).

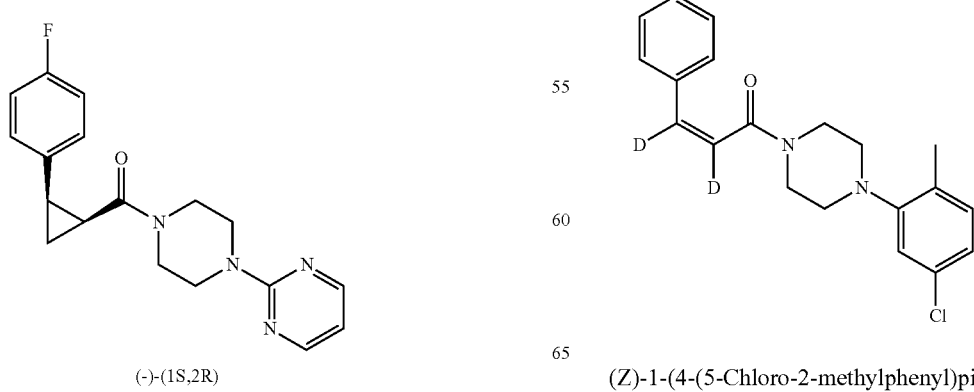

(-)-(1S,2R)

(Z)-1-(4-(5-Chloro-2-methylphenyl)piperazin-1-yl)-3-(4-fluorophenyl)prop-2-en-1-one-2,3-d2. A solution of 1-(4-(5- chloro-2-methylphenyl)piperazin-1-yl)-3-(4-fluorophenyl)prop-2-yn-1-one (0.150 g, 0.140 mmol) in anhydrous EtOAc (4.2 mL) was treated with Lindlar's catalyst (5% Pd on CaCO$_3$, lead poisoned, 0.0447 g, 0.0210 mmol, equivalent to 5 mol % Pd). The reaction was placed under a balloon of D$_2$ (3 vacuum/backfill cycles) and stirred vigorously at rt for 24 h, filtered through Celite, washed (EtOAc), and concentrated under reduced pressure. The crude residue was purified by automated chromatography on SiO$_2$ (4 g column, liquid load with CH$_2$Cl$_2$, hexanes to 30% EtOAc:hexanes, product eluted at 25% EtOAc:hexanes) to give (Z)-1-(4-(5-chloro-2-methylphenyl)piperazin-1-yl)-3-(4-fluorophenyl)prop-2-en-1-one-2,3-d2 (0.0919 g, 0.255 mmol, 61%, 97% deuterium incorporation) as a colorless solid: Mp 122.1-124.8° C.; IR (CH$_2$Cl$_2$) 2918, 2819, 1628, 1595, 1505, 1432, 1222, 1022, 852, 817, 735 cm$^{-1}$; $^1$H NMR (400 MHz, CDCl$_3$) δ 7.39 (dd, J=8.6, 5.4 Hz, 2H), 7.07-7.01 (m, 3H), 6.95 (dd, J=8.2, 2.0 Hz, 1H), 6.79 (d, J=2.0 Hz, 1H), 3.79 (bs, 2H), 3.48 (t, J=5.0 Hz, 2H), 2.80 (t, J=5.0 Hz, 2H), 2.52 (t, J=5.0 Hz, 2H), 2.20 (s, 3H); $^{13}$C NMR (100 MHz, CDCl$_3$) δ 167.2, 162.6 (d, J=249.3 Hz), 151.7, 132.1 (t, J$_{CD}$=23.6 Hz), 132.0, 131.7, 131.4 (d, J$_{CF}$=3.2 Hz), 130.8, 130.2 (d, J$_{CF}$=8.1 Hz), 123.6, 122.2 (t, J$_{CD}$=24.2 Hz), 119.5, 115.6 (d, J$_{CF}$=21.4 Hz), 51.4, 51.1, 46.5, 41.4 17.3; $^{19}$F NMR (376 MHz, CDCl$_3$) δ -112.0 (s, 1 F); HRMS (ESI) m/z calcd for C$_{20}$H$_{19}$D$_2$ClFN$_2$O ([M+H]$^+$) 361.1446, found 361.1446

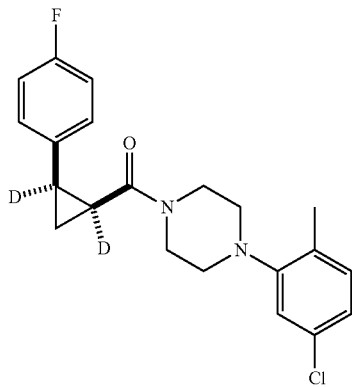 [SMILES: [2H][C@@]1(c2ccc(F)cc2)C[C@]1([2H])C(=O)N1CCN(c2cc(Cl)ccc2C)CC1]

(4-(5-Chloro-2-methylphenyl)piperazin-1-yl)((1RS,2SR)-2-(4-fluorophenyl)cyclopropyl-1,2-d2)methanone. A solution of CrCl$_2$ (0.225 g, 1.83 mmol) and (4-(5-chloro-2-methylphenyl)piperazin-1-yl)(2-(4-fluorophenyl)cyclopropyl-1,2-d2)methadone (0.110 g, 0.305 mmol) in dry degassed THF (3 mL) (previously sparged with Ar for 15 min) was treated with CH$_2$ICl (0.18 mL, 1.52 mmol) and sparged with Ar for 2 min. The reaction mixture was stirred for 24 h at 80° C., cooled to rt, diluted with EtOAc (50 mL), and washed with 1 M HCl (3×20 mL). The organic layer was dried (MgSO$_4$), filtered and concentrated under reduced pressure. The crude residue was purified by automated chromatography on SiO$_2$ (4 g column, liquid load CH$_2$Cl$_2$, hexanes to 40% EtOAc/hexanes) to give a yellow oil that was filtered through basic Al$_2$O$_3$ (1:1 CH$_2$Cl$_2$/EtOAc) concentrated under reduced pressure to a clear oil that was triturated in minimal cyclohexane to give a colorless solid that was dried under high vacuum to give (4-(5-chloro-2-methylphenyl)piperazin-1-yl)((1RS,2SR)-2-(4-fluorophenyl)cyclopropyl-1,2-d2)methanone (0.0799 g, 0.213 mmol, 70% (100% purity by ELSD)) as a colorless solid: Mp 100.2-102.7° C.; IR (CH$_2$Cl$_2$) 2917, 1632, 1512, 1431, 1221, 1032, 818, 729 cm$^{-1}$; $^1$H NMR (400 MHz, CDCl$_3$) δ 7.16-7.11 (m, 2H), 7.06 (d, J=8.2 Hz, 1H), 7.00-6.94 (m, 3H), 6.71 (d, J=2.0 Hz, 1H), 3.81-3.77 (m, 1H), 3.72-3.59 (m, 2H), 3.37-3.31 (m, 1H), 2.79-2.69 (m, 2H), 2.33-2.28 (m, 1H), 2.24-2.20 (m, 4H), 1.81 (d, J=5.4 Hz, 1H), 1.32 (d, J=5.4 Hz, 1H); $^{13}$C NMR (100 MHz, CDCl$_3$) δ 167.2, 161.5 (d, J$_{CF}$=244.7 Hz), 151.8, 133.0 (d, J$_{CF}$=3.1 Hz), 131.9, 131.7, 130.9, 129.0 (d, J$_{CF}$=7.7 Hz), 123.5, 119.6, 114.9 (d, J$_{CF}$=21.3 Hz), 51.7, 51.5, 45.5, 42.1, 23.4 (t, J$_{CD}$=25.4 Hz), 23.0 (t, J$_{CD}$=24.6 Hz) 17.3, 10.4; $^{19}$F NMR (376 MHz, CDCl$_3$) δ -116.3 (s, 1 F); HRMS (ESI) m/z calcd for C$_{21}$H$_{21}$D$_2$ClFN$_2$O ([M+H]$^+$) 375.1603, found 375.1602.

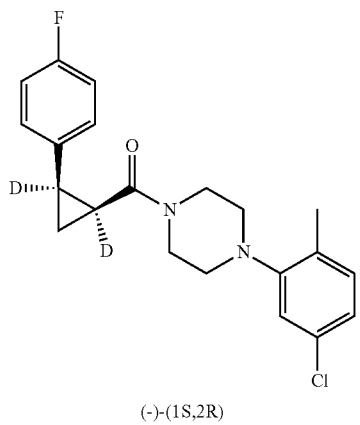

(-)-(1S,2R)

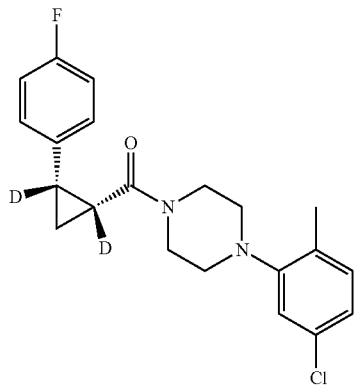

(+)-(1R,2S)

Racemic (4-(5-chloro-2-methylphenyl)piperazin-1-yl)((1RS,2SR)-2-(4-fluorophenyl)cyclopropyl-1,2-d2)methanone was separated on a SFC Chiralpak-IC semiprep (250× 10 mm) column (30% Methanol:CO$_2$, 7 mL/min, p=100 bar, 220 nm) injection volume 90 μL, 20 mg/mL) to give (4-(5-chloro-2-methylphenyl)piperazin-1-yl)((1S,2R)-2-(4-fluorophenyl)cyclopropyl-1,2-d2)methanone (retention time 7.58 min) as a colorless viscous oil (100% purity by ELSD): [α]$^{18}_D$ -152.0 (c 0.70, MeOH); $^1$H NMR (300 MHz, CDCl$_3$) δ 7.16-7.12 (m, 2H), 7.07 (d, J=8.1 Hz, 1H), 7.01-6.94 (m, 3H), 6.72 (d, J=1.8 Hz, 1H), 3.82-3.76 (m, 1H), 3.74-3.58 (m, 2H), 3.39-3.31 (m, 1H), 2.80-2.69 (m, 2H), 2.80-2.69

(m, 2H), 2.35-2.17 (m, 5H), 1.82 (d, J=5.4 Hz, 1H), 1.33 (d, J=5.4 Hz, 1H). The enantiomeric excess was >99.9% ee (SFC Chiralpak-IC (250×10 mm); 30% Methanol:CO$_2$, 7 mL/min, p=100 bar, 220 nm; retention time: 7.8 min).

(4-(5-Chloro-2-methylphenyl)piperazin-1-yl)((1R,2S)-2-(4-fluorophenyl)cyclopropyl-1,2-d2)methanone (retention time 9.28 min) was obtained as a colorless viscous oil (100% purity by ELSD): [α]$^{19}_D$+154.0 (c 0.66, MeOH); $^1$H NMR (300 MHz, CDCl$_3$) δ 7.17-7.10 (m, 2H), 7.07 (d, J=8.2 Hz, 1H), 7.02-6.94 (m, 3H), 6.72 (d, J=2.0 Hz, 1H), 3.83-3.74 (m, 1H), 3.73-3.58 (m, 2H), 3.39-3.31 (m, 1H), 2.80-2.69 (m, 2H), 2.36-2.18 (m, 5H), 1.82 (d, J=5.4 Hz, 1H), 1.33 (d, J=5.4 Hz, 1H). The enantiomeric excess was >99.9% ee (SFC Chiralpak-IC (250×10 mm); 30% Methanol:CO$_2$, 7 mL/min, p=100 bar, 220 nm; retention time: 9.6 min).

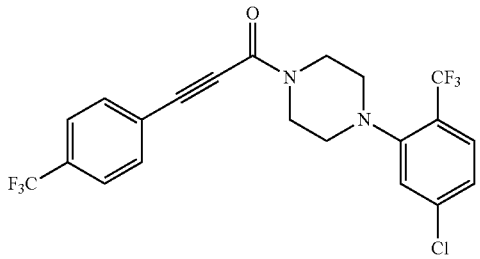 [SMILES: O=C(C#Cc1ccc(C(F)(F)F)cc1)N1CCN(c2cc(Cl)ccc2C(F)(F)F)CC1]

1-(4-(5-Chloro-2-(trifluoromethyl)phenyl)piperazin-1-yl)-3-(4-(trifluoromethyl)phenyl)prop-2-yn-1-one. A solution of 3-(4-(trifluoromethyl)phenyl)propiolic acid (0.100 g, 0.467 mmol) and 1-(5-chloro-2-(trifluoromethyl)phenyl)piperazinehydrochloride (0.155 g, 0.514 mmol) in CH$_2$Cl$_2$ (4.7 mL) cooled to 0° C. was treated with Et$_3$N (0.26 mL, 1.87 mmol). The cooled solution was treated with T3P (50 wt. % solution in EtOAc, 0.49 mL, 0.701 mmol) dropwise and the reaction was stirred at 0° C. for 30 min and allowed to warm to rt overnight, diluted with CH$_2$Cl$_2$ (30 mL) and washed with H$_2$O (20 mL), satd. aqueous NaHCO$_3$ (20 mL), dried (MgSO$_4$), filtered, and concentrated under reduced pressure. The crude material was purified by automated chromatography on SiO$_2$ (4 g column, liquid load CH$_2$Cl$_2$, hexanes to 30% EtOAc/hexanes), to give 1-(4-(5-chloro-2-(trifluoromethyl)phenyl)piperazin-1-yl)-3-(4-(trifluoromethyl)phenyl)prop-2-yn-1-one (0.161 g, 0.350 mmol, 75%) as a colorless solid: Mp 145.8-148.8° C.; IR (CH$_2$Cl$_2$) 2928, 2827, 2223, 1634, 1596, 1432, 1322, 1310, 1122, 1107, 1033, 844 cm$^{-1}$; $^1$H NMR (400 MHz, CDCl$_3$) δ 7.65 (app q, J=7.3 Hz, 4H), 7.58 (d, J=8.4 Hz, 1H), 7.28-7.24 (m, 2H), 3.96 (app t, J=5.0 Hz, 2H), 3.84 (app t, J=5.0 Hz, 2H), 3.00 (app t, J=5.0 Hz, 2H), 2.94 (app t, J=5.0 Hz, 2H); $^{13}$C NMR (100 MHz, CDCl$_3$) δ 152.5, 138.8, 132.5, 131.6 (q, J$_{CF}$=33.0 Hz), 128.5 (q, J$_{CF}$=5.4 Hz), 125.7 (q, J$_{CF}$=29.4 Hz), 125.7, 125.4 (q, J$_{CF}$=3.7 Hz), 124.7, 124.1, 123.5 (q, J$_{CF}$=270.8 Hz, 2C), 89.0, 82.7, 53.6, 52.7, 47.3, 41.8; $^{19}$F NMR (376 MHz, CDCl$_3$) δ −60.3 (s, 3F), −63.1 (s, 3F); HRMS (ESI) m/z calcd for C$_{21}$H$_{16}$ClF$_6$N$_2$O ([M+H]$^+$) 461.0850, found 461.0847.

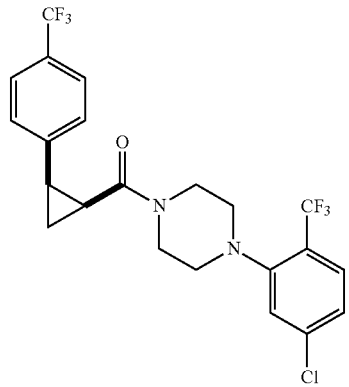

(4-(5-Chloro-2-(trifluoromethyl)phenyl)piperazin-1-yl)((1RS,2SR)-2-(4-(trifluoromethyl)phenyl)-cyclopropyl)methanone. A solution of 1-(4-(5-chloro-2-(trifluoromethyl)phenyl)piperazin-1-yl)-3-(4-(trifluoromethyl)phenyl)prop-2-yn-1-one (0.127 g, 0.276 mmol) in EtOAc (2.8 mL) was treated with quinoline (0.16 mL, 1.38 mmol) and 5% Pd/BaSO$_4$ (0.0059 g, equivalent to 1 mol % Pd). The reaction was placed under and atmosphere of H$_2$ (balloon) (3 vacuum/backfill cycles) and stirred at rt for 1.5 h, filtered through Celite, washed (EtOAc), and the combined filtrates were washed with 1 M aqueous HCl (10 mL), dried (MgSO$_4$), filtered, and concentrated under reduced pressure. The crude residue was purified by automated chromatography on SiO$_2$ (4 g column, liquid load CH$_2$Cl$_2$, hexanes to 30% EtOAc/hexanes; product eluted at 20% EtOAc) to give the product (0.114 g, 0.246 mmol) as a colorless solid.

To a flame dried 5 mL microwave vial containing anhydrous CrCl$_2$ (0.182 g, 0.148 mmol) was added a solution of (Z)-1-(4-(5-chloro-2-(trifluoromethyl)phenyl)piperazin-1-yl)-3-(4-(trifluoromethyl)-phenyl)prop-2-en-1-one (0.114 g, 0.246 mmol) in anhydrous THF (2.5 mL) and the mixture was sparged with Ar for 15 min and added CH$_2$ICl (0.14 mL, 1.23 mmol) at rt and under Ar atmosphere. The reaction mixture was stirred for 2 d at 80° C. The reaction was cooled to rt, combined, quenched by the addition of EtOAc (50 mL) and washed with 1 M aqueous HCl (3×20 mL). The organic layer was dried (MgSO$_4$), filtered and concentrated under reduced pressure. The crude material was purified by automated chromatography on SiO$_2$ (4 g column, liquid load CH$_2$Cl$_2$, 100% hexanes to 30% EtOAc/hexanes, product eluted at 20% EtOAc/hexanes) to give a clear oil that was filtered through basic Al$_2$O$_3$ (1:1 CH$_2$Cl$_2$/EtOAc) concentrated, and dried under high vacuum to give (4-(5-chloro-2-(trifluoromethyl)phenyl)piperazin-1-yl)((1RS,2SR)-2-(4-(trifluoromethyl)phenyl)cyclopropyl)methanone (0.0681 g, 0.143 mmol, 52% (2 steps) (100% purity by ELSD)) as a colorless solid: Mp 138.0-139.9° C.; IR (CH$_2$Cl$_2$) 3014, 2825, 1641, 1596, 1326, 1309, 1116, 1031, 844 cm$^{-1}$; $^1$H NMR (400 MHz, CDCl$_3$) δ 7.56 (d, J=8.2 Hz, 2H), 7.51 (d, J=8.5 Hz, 1H), 7.29 (d, J=8.2 Hz, 2H), 7.19 (dd, J=8.5, 1.4 Hz, 1H), 6.89 (d, J=1.4 Hz, 1H), 3.95 (bd, J=12.4 Hz, 1H), 3.73 (bd, J=12.4 Hz, 1H), 3.54 (bt, J=10.0 Hz, 1H), 3.21 (bt, J=10.0 Hz, 1H), 2.74 (bt, J=10.0 Hz, 2H), 2.50 (td, J=8.9, 7.1 Hz, 1H), 2.29-2.19 (m, 2H), 1.98 (bt, J=8.9 Hz, 1H), 1.92 (q, J=6.2 Hz, 1H), 1.43 (td, J=8.4, 5.6 Hz, 1H); $^{13}$C NMR (100 MHz, CDCl$_3$) δ 166.5, 152.7, 142.1, 138.9, 128.8 (q, J$_{CF}$=32.6 Hz), 128.4 (q, J$_{CF}$=5.8 Hz), 127.9, 125.7 (q, J$_{CF}$=30.2 Hz), 125.6, 125.0 (q, J$_{CF}$=3.7 Hz), 124.6 (q, J$_{CF}$=273.0 Hz), 124.4, 123.6 (q, J$_{CF}$=272.9 Hz), 53.7, 52.9, 45.5, 42.1, 24.7, 23.9, 11.2; $^{19}$F NMR (376 MHz, CDCl$_3$) δ

−60.4 (s, 3F), −62.2 (s, 3F); HRMS (ESI) m/z calcd for C$_{22}$H$_{20}$ClF$_6$N$_2$O ([M+H]$^+$) 477.1163, found 477.1160.

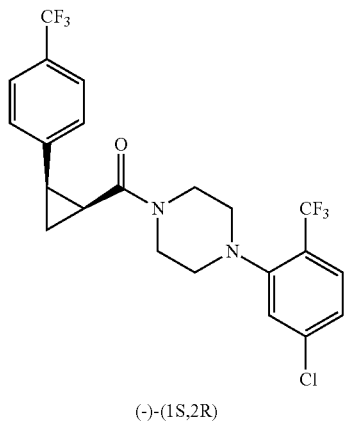

(−)-(1S,2R)

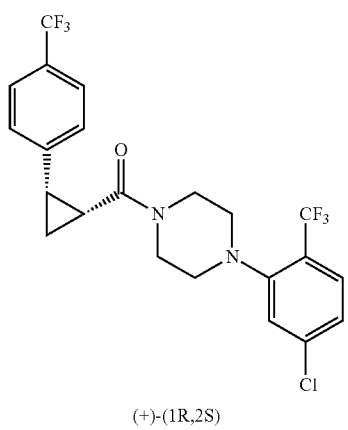

(+)-(1R,2S)

Racemic (4-(5-chloro-2-(trifluoromethyl)phenyl)piperazin-1-yl)((1RS,2SR)-2-(4-(trifluoromethyl)phenyl)-cyclopropyl)methanone was separated on a SFC Chiralpak-IC semiprep (250×10 mm) column (25% Methanol:CO$_2$, 7 mL/min, p=100 bar, 220 nm) injection volume 90 μL, 20 mg/mL) to give (4-(5-chloro-2-(trifluoromethyl)phenyl)piperazin-1-yl)((1S,2R)-2-(4-(trifluoromethyl)phenyl)cyclopropyl)methanone (retention time 3.57 min) as a colorless viscous oil (100% purity by ELSD): [α]$^{19}$$_D$ −106.6 (c 0.68, MeOH); $^1$H NMR (300 MHz, CDCl$_3$) δ 7.57 (d, J=8.1 Hz, 2H), 7.52 (d, J=8.4 Hz, 1H), 7.29 (d, J=8.1 Hz, 2H), 7.20 (d, J=8.4 Hz, 1H), 6.88 (d, J=0.9 Hz, 1H), 3.98-3.93 (m, 1H), 3.76-3.70 (m, 1H), 3.54 (ddd, J=12.3, 9.3, 3.0 Hz, 2H), 3.21 (ddd, J=12.3, 9.3, 3.0 Hz, 2H), 2.76-2.71 (m, 2H), 2.51 (td, J=9.3, 7.2 Hz, 1H), 2.30-2.18 (m, 2H), 2.00-1.89 (m, 2H), 1.44 (td, J=8.4, 5.7 Hz, 1H). The enantiomeric excess was >99.9% ee (SFC Chiralpak-IC (250×10 mm); 25% Methanol:CO$_2$, 7 mL/min, p=100 bar, 220 nm; retention time: 3.8 min).

(4-(5-Chloro-2-(trifluoromethyl)phenyl)piperazin-1-yl)((1R,2S)-2-(4-(trifluoromethyl)phenyl)-cyclopropyl)methanone (retention time 4.20 min) was obtained as a colorless viscous oil (100% purity by ELSD): [α]$^{19}$$_D$+111.1 (c 0.71, MeOH); $^1$H NMR (300 MHz, CDCl$_3$) δ 7.57 (d, J=8.1 Hz, 2H), 7.52 (d, J=8.4 Hz, 1H), 7.29 (d, J=8.1 Hz, 2H), 7.20 (d, J=8.4 Hz, 1H), 6.88 (s, 1H), 3.99-3.93 (m, 1H), 3.76-3.70 (m, 1H), 3.58-3.49 (m, 1H), 3.25-3.16 (m, 1H), 2.76-2.71 (m, 2H), 2.51 (q, J=9.6 Hz, 1H), 2.30-2.18 (m, 2H), 2.00-1.89 (m, 2H), 1.44 (td, J=8.4, 5.6 Hz, 1H). The enantiomeric excess was >99.9% ee (SFC Chiralpak-IC (250×10 mm); 25% Methanol:CO$_2$, 7 mL/min, p=100 bar, 220 nm; retention time: 4.1 min).

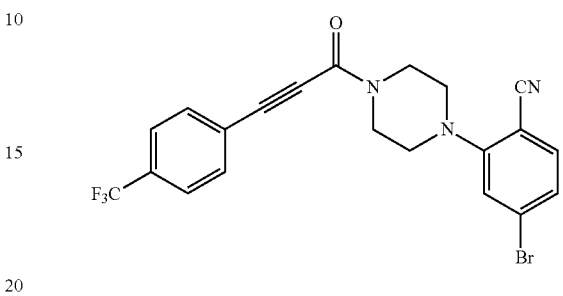

4-Bromo-2-(4-(3-(4-(trifluoromethyl)phenyl)propioloyl)piperazin-1-yl)benzonitrile. A solution of 3-(4-trifluoromethylphenyl)propiolic acid (0.400 g, 1.87 mmol) and 4-bromo-2-(piperazin-1-yl)benzonitrile hydrochloride (0.735 g, 2.43 mmol) in CH$_2$Cl$_2$ (19 mL) at 0° C. was treated Et$_3$N (1.0 mL, 7.47 mmol). The cooled solution was treated with T3P (50% solution in EtOAc) (2.0 mL, 2.80 mmol) dropwise and the reaction was stirred at 0° C. for 30 min, warmed to rt overnight, diluted with EtOAc (80 mL) and washed with H$_2$O (20 mL), satd. aqueous NaHCO$_3$ (20 mL), dried (MgSO$_4$), filtered, and concentrated under reduced pressure. The crude residue was purified by chromatography on SiO$_2$ (hexanes/EtOAc, 1:1), to give 4-bromo-2-(4-(3-(4-(trifluoromethyl)phenyl)propioloyl)piperazin-1-yl)benzonitrile (0.784 g, 1.70 mmol, 91%) as a pale yellow solid: Mp 176.3-179.1° C.; IR (CH$_2$Cl$_2$) 2824, 2222, 1626, 1583, 1432, 1324, 1163, 1129, 1107, 1035, 949, 928, 846, 816 cm$^{-1}$; $^1$H NMR (500 MHz, CDCl$_3$) δ 7.66 (dd, J=7.8 Hz, 4H), 7.45 (d, J=8.0 Hz, 1H), 7.22 (dd, J=8.0, 1.6 Hz, 1H), 7.15 (d, J=1.6 Hz, 1H), 4.05 (t, J=5.0 Hz, 2H), 3.91 (t, J=5.0 Hz, 2H), 3.31 (t, J=5.0 Hz, 2H), 3.22 (t, J=5.0 Hz, 2H); $^{13}$C NMR (125 MHz, CDCl$_3$) δ 155.6, 152.6, 135.1, 132.6, 131.8 (q, J$_{CF}$=32.8 Hz), 128.8, 125.9, 125.5 (q, J$_{CF}$=3.8 Hz), 124.0, 123.5 (q, J$_{CF}$=272.5 Hz), 122.7, 117.4, 105.1, 89.3, 82.5, 52.0, 50.7, 47.0, 41.5; $^{19}$F NMR (470 MHz, CDCl$_3$) δ −63.1 (s, 3F); HRMS (ESI) m/z calcd for C$_{21}$H$_{16}$BrF$_3$N$_3$O ([M+H]$^+$) 462.0423, found 462.0423.

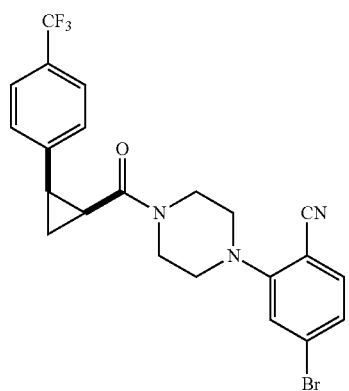

4-Bromo-2-(4-((1RS,2SR)-2-(4-(trifluoromethyl)phenyl)cyclopropane-1-carbonyl)piperazin-1-yl)benzonitrile. A solution of 4-bromo-2-(4-(3-(4-(trifluoromethyl)phenyl)propioloyl)piperazin-1-yl)benzonitrile (0.750 g, 1.62 mmol) in EtOAc (16 mL) was treated with Lindlar's catalyst (5% Pd on CaCO$_3$, lead poisoned, 0.691 g, equivalent to 20 mol % Pd). The reaction was placed under a balloon of H$_2$ (3 vacuum/backfill cycles) and stirred at rt for 3 d, filtered through Celite, washed (EtOAc), and the combined filtrates were concentrated under reduced pressure. The crude residue was purified by chromatography on SiO$_2$ (hexanes/EtOAc, 1:4) to give (Z)-4-bromo-2-(4-(3-(4-(trifluoromethyl)phenyl)acryloyl)piperazin-1-yl)benzonitrile (0.318 g, 0.685 mmol) as a tan foam.

A solution of CrCl$_2$ (0.477 g, 0.899 mmol) and (Z)-4-bromo-2-(4-(3-(4-(trifluoromethyl)phenyl)-acryloyl)piperazin-1-yl)benzonitrile (0.300 g, 0.646 mmol) in dry degassed THF (6.5 mL) was sparged with Ar for 5 min and treated with CH$_2$ICl (0.37 mL, 3.23 mmol) at rt, stirred for 2 d at 80° C., cooled to rt, diluted with EtOAc (150 mL) and washed with 1 M aqueous HCl (3×50 mL). The organic layer was dried (MgSO$_4$), filtered and concentrated under reduced pressure. The crude residue was purified by chromatography on SiO$_2$ (hexanes/EtOAc, 1:9) to give a colorless oil that was filtered through basic Al$_2$O$_3$(EtOAc) concentrated and further dried under high vacuum to give 4-bromo-2-(4-((1RS,2SR)-2-(4-(trifluoromethyl)phenyl)cyclopropane-1-carbonyl)piperazin-1-yl)benzonitrile (0.148 g, 0.309 mmol, 20% (2 steps) (100% purity by ELSD)) as a colorless oil: IR (CH$_2$Cl$_2$) 2833, 2222, 1642, 1583, 1484, 1436, 1326, 1228, 1116, 1069, 844 cm$^{-1}$; $^1$H NMR (400 MHz, CDCl$_3$) δ 7.52 (d, J=8.5 Hz, 2H), 7.38 (d, J=8.0 Hz, 1H), 7.27 (d, J=8.5 Hz, 2H), 7.17 (dd, J=8.0, 1.5 Hz, 1H), 6.90 (d, J=1.5 Hz, 1H), 3.93 (dt, J=13.0, 3.5 Hz, 1H), 3.78 (dt, J=13.0, 3.5 Hz, 1H), 3.67 (ddd, J=13.0, 9.0, 3.0 Hz, 1H), 3.35 (ddd, J=13.0, 9.0, 3.0 Hz, 1H), 3.18-3.15 (m, 1H), 3.08-3.06 (m, 1H), 2.55-2.45 (m, 2H), 2.29-2.24 (m, 2H), 1.92 (q, J=6.0 Hz, 1H), 1.43 (td, J=8.0, 6.0 Hz, 1H); $^{13}$C NMR (125 MHz, CDCl$_3$) δ 166.8, 155.7, 141.8, 135.0, 128.8, 128.8 (q, J$_{CF}$=32.6 Hz), 127.9, 125.7, 125.1 (q, J$_{CF}$=3.6 Hz), 124.1 (q, J$_{CF}$=271.8 Hz), 122.4, 117.5, 105.0, 52.1, 50.8, 45.2, 41.7, 24.5, 24.1, 11.2; $^{19}$F NMR (376 MHz, CDCl$_3$) δ −62.3 (s, 3F); HRMS (ESI) m/z calcd for C$_{22}$H$_{20}$BrF$_3$N$_3$O ([M+H]$^+$) 478.0736, found 478.0734.

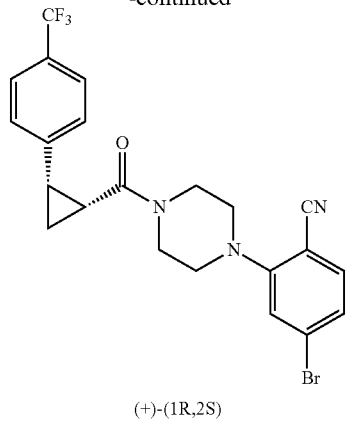

(+)-(1R,2S)

Racemic 4-bromo-2-(4-((1RS,2SR)-2-(4-(trifluoromethyl)phenyl)cyclopropane-1-carbonyl)piperazin-1-yl)benzonitrile was separated on a SFC Chiralpak-IC semiprep (250×10 mm) column (25% Methanol/CO$_2$, 7 mL/min, 220 nm, p=100 bar, 20 mg/mL in MeOH) to give 4-bromo-2-(4-((1S,2R)-2-(4-(trifluoromethyl)-phenyl)cyclopropane-1-carbonyl)piperazin-1-yl)benzonitrile (retention time 10.5 min) as a colorless solid (100% purity by ELSD): [α]$^{19}$$_D$ −144.1 (c 1.31, MeOH); $^1$H NMR (300 MHz, CDCl$_3$) δ 7.52 (d, J=8.1 Hz, 2H), 7.39 (d, J=8.1 Hz, 1H), 7.27 (d, J=8.1 Hz, 2H), 7.17 (dd, J=8.1, 1.5 Hz, 1H), 6.90 (d, J=1.5 Hz, 1H), 3.95-3.89 (m, 1H), 3.76-3.67 (m, 2H), 3.38-3.33 (m, 1H), 3.16-3.04 (m, 2H), 2.56-2.45 (m, 2H), 2.27 (td, J=8.7, 6.0 Hz, 2H), 1.92 (q, J=6.0 Hz, 1H), 1.44 (td, J=8.4, 5.5 Hz, 1H). The enantiomeric excess was >99.9% ee (SFC Chiralpak-IC (250×10 mm); 25% MeOH, 7 mL/min, 220 nm, p=100 bar; retention time: 10.8 min).

4-Bromo-2-(4-((1R,2S)-2-(4-(trifluoromethyl)phenyl)cyclopropane-1-carbonyl)piperazin-1-yl)benzonitrile (retention time 11.6 min) was obtained as a colorless solid (100% purity by ELSD): [α]$^{19}$$_D$ +135.8 (c 1.43, MeOH); $^1$H NMR (300 MHz, CDCl$_3$) δ 7.52 (d, J=8.1 Hz, 2H), 7.39 (d, J=8.1 Hz, 1H), 7.29 (s, 2H), 7.17 (dd, J=8.1, 1.5 Hz, 1H), 6.90 (d, J=1.5 Hz, 1H), 3.93-3.90 (m, 1H), 3.78-3.67 (m, 2H), 3.38-3.33 (m, 1H), 3.17-3.04 (m, 2H), 2.56-2.43 (m, 2H), 2.27 (td, J=8.7, 6.0 Hz, 2H), 1.92 (q, J=6.0 Hz, 1H), 1.44 (td, J=8.4, 5.6 Hz, 1H). The enantiomeric excess was >99.9% ee (SFC Chiralpak-IC (250×10 mm); 25% MeOH, 7 mL/min, 220 nm, p=100 bar; retention time: 11.8 min).

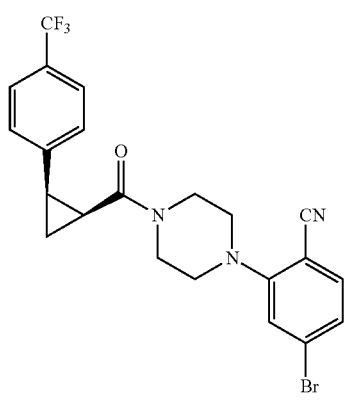

(−)-(1S,2R)

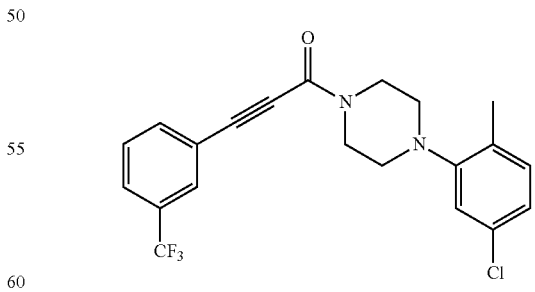

1-(4-(5-Chloro-2-methylphenyl)piperazin-1-yl)-3-(3-(trifluoromethyl)phenyl)prop-2-yn-1-one. A solution of 3-(3-(trifluoromethyl)phenyl)propionic acid (0.0750 g, 0.350 mmol) and 1-(5-chloro-2-methylphenyl)piperazine hydrochloride (0.104 g, 0.420 mmol) in CH$_2$Cl$_2$ (3.5 mL) cooled to 0° C. was treated with Et$_3$N (0.15 mL, 1.05 mmol). The cooled solution was treated with T3P (50 wt. % solution in EtOAc 0.37 mL, 0.525 mmol) dropwise and the reaction was stirred at 0° C. for 30 min, warmed to rt overnight, diluted with CH$_2$Cl$_2$ (30 mL), washed with 1 M aqueous HCl (20 mL), dried (MgSO$_4$), filtered, and concentrated under reduced pressure. The crude material was purified by automated chromatography on SiO$_2$ (4 g column, liquid load CH$_2$Cl$_2$, hexanes to 40% EtOAc/hexanes), to give 1-(4-(5-chloro-2-methylphenyl)piperazin-1-yl)-3-(3-(trifluoromethyl)phenyl)prop-2-yn-1-one (0.106 g, 0.261 mmol, 75%) as a colorless solid: Mp 130.3-132.8° C.; IR (CH$_2$Cl$_2$) 2820, 2218, 2161, 1631, 1489, 1435, 1201, 1128, 1041, 805, 695 cm$^{-1}$; $^1$H NMR (400 MHz, CDCl$_3$) δ 7.81 (s, 1H), 7.74 (d, J=7.8 Hz, 1H), 7.68 (d, J=7.8 Hz, 1H), 7.52 (t, J=7.8 Hz, 1H), 7.12 (d, J=8.1 Hz, 1H), 7.00 (dd, J=8.1, 2.1 Hz, 1H), 6.96 (d, J=2.1 Hz, 1H), 3.98 (app t, J=5.0 Hz, 2H), 3.84 (app t, J=5.0 Hz, 2H), 2.98 (app t, J=5.0 Hz, 2H), 2.90 (app t, J=5.0 Hz, 2H), 2.29 (s, 3H); $^{13}$C NMR (100 MHz, CDCl$_3$) δ 152.6, 151.6, 135.4, 132.1, 131.8, 131.2 (q, J$_{CF}$=33.0 Hz), 130.9, 129.17, 129.0 (q, J$_{CF}$=4.1 Hz), 126.6 (q, J$_{CF}$=3.6 Hz), 123.8, 123.5 (q, J$_{CF}$=272.5 Hz), 121.4, 119.8, 88.9, 82.1, 51.9, 51.3, 47.4, 41.9; HRMS (ESI) m/z calcd for C$_{21}$H$_{19}$ClF$_3$N$_2$O ([M+H]$^+$) 407.1133, found 407.1130.

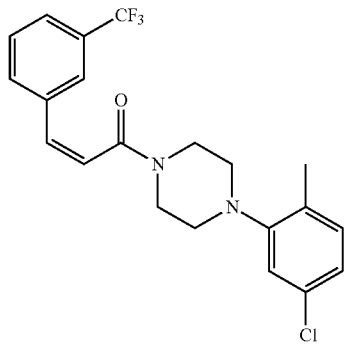 [SMILES: Cc1ccc(Cl)cc1N1CCN(C(=O)/C=C\c2cccc(C(F)(F)F)c2)CC1]

(Z)-1-(4-(5-Chloro-2-methylphenyl)piperazin-1-yl)-3-(3-(trifluoromethyl)phenyl)prop-2-en-1-one. To a solution of 1-(4-(5-chloro-2-methylphenyl)piperazin-1-yl)-3-(3-(trifluoromethyl)phenyl)prop-2-yn-1-one (0.100 g, 0.246 mmol) in EtOAc (2.5 mL) was added Lindlar's catalyst (5% Pd on CaCO$_3$, lead poisoned, 0.0105 g, equivalent to 2 mol % Pd) and quinoline (0.015 mL, 0.123 mmol). The reaction vessel was placed under vacuum and backfilled with H$_2$ (balloon, 4×) stirred for 3.5 h at rt, filtered through Celite, washed (EtOAc), and the combined filtrates were washed with 1 M aqueous HCl, dried (Na$_2$SO$_4$), filtered, and concentrated under reduced pressure. The crude residue was purified by automated chromatography on SiO$_2$ (4 g column, liquid load CH$_2$Cl$_2$, 10% EtOAc/hexanes to 40% EtOAc/hexanes) to give (Z)-1-(4-(5-chloro-2-methylphenyl)piperazin-1-yl)-3-(3-(trifluoromethyl)phenyl)prop-2-en-1-one (0.0932 g, 0.228 mmol, 93%) as a clear colorless solid: Mp 130.3-132.8° C.; IR (CH$_2$Cl$_2$) 2918, 1619, 1489, 1440, 1327, 1161, 1096, 1074, 805, 737, 696 cm$^{-1}$; $^1$H NMR (400 MHz, CDCl$_3$) δ 7.66 (s, 1H), 7.59 (t, J=7.6 Hz, 2H), 7.49 (t, J=7.6 Hz, 1H), 7.06 (d, J=8.1 Hz, 1H), 6.96 (dd, J=8.1, 2.1 Hz, 1H), 6.77 (d, J=2.1 Hz, 1H), 6.73 (d, J=12.5 Hz, 1H), 6.19 (d, J=12.5 Hz, 1H), 3.80 (app t, J=5.0 Hz, 2H), 3.48 (app t, J=5.0 Hz, 2H), 2.80 (app t, J=5.0 Hz, 2H), 2.49 (app t, J=5.0 Hz, 2H), 2.20 (s, 3H); $^{13}$C NMR (100 MHz, CDCl$_3$) δ 166.7, 151.7, 136.1, 132.0 (2C), 131.8, 131.6, 131.4 (q, J$_{CF}$=30.4 Hz), 130.9, 129.2, 125.2 (q, J$_{CF}$=4.0 Hz), 125.0 (q, J$_{CF}$=3.8 Hz), 124.9, 123.8 (q, J$_{CF}$=272.3 Hz), 123.7, 119.7, 51.4, 51.1, 46.6, 41.5, 17.3; HRMS (ESI) m/z calcd for C$_{21}$H$_{21}$ClF$_3$N$_2$O ([M+H]$^+$) 409.1289, found 409.1289.

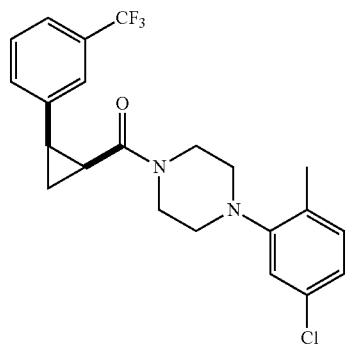

(4-(5-Chloro-2-methylphenyl)piperazin-1-yl)((1RS,2SR)-2-(3-(trifluoromethyl)phenyl)cyclopropyl)-methanone. A solution of CrCl$_2$ (0.105 g, 0.851 mmol) and (Z)-1-(4-(5-chloro-2-methylphenyl)piperazin-1-yl)-3-(3-(trifluoromethyl)phenyl)prop-2-en-1-one (0.0580 g, 0.142 mmol) in dry degassed THF (1.4 mL)(previously sparged with Ar for 15 min) was treated with CH$_2$ICl (82 uL, 0.709 mmol) and the mixture was sparged with Ar for 2 min, stirred for 20 h at 80° C., cooled to rt, diluted with Et$_2$O (50 mL) and washed with 1 M HCl (3×20 mL). The organic layer was dried (MgSO$_4$), filtered and concentrated under reduced pressure. The crude material was purified by automated chromatography on SiO$_2$ (4 g column, liquid load CH$_2$Cl$_2$, 100% hexanes to 40% EtOAc/hexanes) to give a clear oil that filtered through basic Al$_2$O$_3$(CH$_2$Cl$_2$/EtOAc, 1:1), recrystallized from hot cyclohexane the mother liquor was decanted and the crystals were washed with hexanes (2×1 mL) and dried under high vacuum to give (4-(5-chloro-2-methylphenyl)-piperazin-1-yl)((1RS,2SR)-2-(3-(trifluoromethyl)phenyl)cyclopropyl)methanone (0.0356 g, 0.0842 mmol, 59% (100% purity by ELSD)) as colorless needles: Mp 115.6-117.4° C.; IR (CH$_2$Cl$_2$) 2914, 2820, 1639, 1593, 1490, 1437, 1225, 1161, 1123, 1074, 806 cm$^{-1}$; $^1$H NMR (400 MHz, CDCl$_3$) δ 7.49-7.48 (m, 2H), 7.40 (t, J=8.0 Hz, 1H), 7.32 (d, J=8.0 Hz, 1H), 7.06 (d, J=8.0 Hz, 1H), 6.95 (dd, J=8.0, 2.1 Hz, 1H), 6.67 (d, J=2.1 Hz, 1H), 3.86 (dt, J=13.0, 2.9 Hz, 1H), 3.74 (dt, J=13.0, 3.2 Hz, 1H), 3.62-3.56 (m, 1H), 3.26 (ddd, J=12.4, 9.0, 3.2 Hz, 1H), 2.79-2.70 (m, 2H), 2.53 (td, J=9.0, 6.9 Hz, 1H), 2.26 (ddd, J=9.0, 8.4, 5.9 Hz, 1H), 2.20 (s, 3H), 2.10 (ddd, J=11.2, 9.0, 2.4 Hz, 1H), 1.91 (app q, J=5.8 Hz, 1H), 1.41 (td, J=8.4, 5.8 Hz, 1H); $^{13}$C NMR (100 MHz, CDCl$_3$) δ 166.7, 151.7, 138.7, 131.9, 131.8, 130.9, 130.5, 130.5 (d, J$_{CF}$=32.2 Hz) 128.7, 125.1 (d, J$_{CF}$=4.0 Hz), 124.2 (d, J$_{CF}$=272.2 Hz), 123.6, 123.3 (d, J$_{CF}$=3.7 Hz), 119.6, 51.7, 51.6, 45.5, 42.2, 24.1, 23.9, 17.3, 10.8; $^{19}$F NMR (376 MHz, CDCl$_3$) δ −62.4 (s, 3F); HRMS (ESI) m/z calcd for C$_{22}$H$_{23}$ClF$_3$N$_2$O ([M+H]$^+$) 423.1446, found 423.1443.

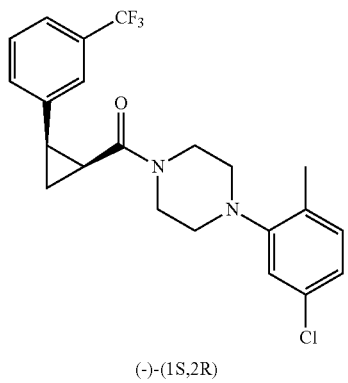

(−)-(1S,2R)

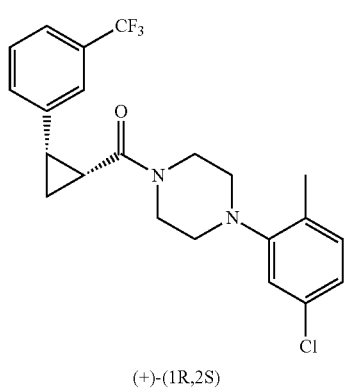

(+)-(1R,2S)

Racemic (4-(5-chloro-2-methylphenyl)piperazin-1-yl)((1RS,2SR)-2-(3-(trifluoromethyl)phenyl)-cyclopropyl)methanone was separated on a SFC Chiralpak-IC semiprep (250×10 mm) column (30% Methanol:CO₂, 7 mL/min, p=100 bar, 220 nm) injection volume 90 μL, 20 mg/mL) to give (4-(5-chloro-2-methylphenyl)piperazin-1-yl)((1S,2R)-2-(3-(trifluoromethyl)phenyl)cyclopropyl)methanone (retention time 4.82 min) as a colorless viscous oil (100% purity by ELSD): [α]$^{19}_D$ −133.5 (c 0.70, MeOH); ¹H NMR (300 MHz, CDCl₃) δ 7.48 (bs, 2H), 7.41 (t, J=8.0 Hz, 1H), 7.33 (d, J=7.4 Hz, 1H), 7.06 (d, J=8.1 Hz, 1H), 6.95 (dd, J=8.1, 2.0 Hz, 1H), 6.67 (d, J=2.0 Hz, 1H), 3.89-3.82 (m, 1H), 3.78-3.71 (m, 1H), 3.63-3.55 (m, 1H), 3.31-3.23 (m, 1H), 2.79-2.69 (m, 2H), 2.53 (td, J=8.4, 7.2 Hz, 1H), 2.30-2.07 (m, 6H), 1.92 (q, J=5.4 Hz, 1H), 1.41 (td, J=8.4, 5.4 Hz, 1H). The enantiomeric excess was >99.9% ee (SFC Chiralpak-IC (250×10 mm); 30% Methanol:CO₂, 7 mL/min, p=100 bar, 220 nm; retention time: 5.0 min).

(4-(5-Chloro-2-methylphenyl)piperazin-1-yl)((1R,2S)-2-(3-(trifluoromethyl)phenyl)cyclopropyl)methanone (retention time 5.57 min) was obtained as a colorless viscous oil (100% purity by ELSD): [α]$^{19}_D$ +133.1 (c 0.65, MeOH); ¹H NMR (300 MHz, CDCl₃) δ 7.48 (bs, 2H), 7.41 (t, J=8.0 Hz, 1H), 7.33 (d, J=8.0 Hz, 1H), 7.06 (d, J=8.0 Hz, 1H), 6.95 (dd, J=8.0, 2.0 Hz, 1H), 6.67 (d, J=2.0 Hz, 1H), 3.90-3.82 (m, 1H), 3.78-3.70 (m, 1H), 3.64-3.55 (m, 1H), 3.31-3.23 (m, 1H), 2.80-2.69 (m, 2H), 2.53 (td, J=8.4, 6.8 Hz, 1H), 2.30-2.07 (m, 6H), 1.92 (q, J=5.4 Hz, 1H), 1.41 (td, J=8.4, 5.4 Hz, 1H). The enantiomeric excess was >99.9% ee (SFC Chiralpak-IC (250×10 mm); 30% Methanol:CO₂, 7 mL/min, p=100 bar, 220 nm; retention time: 5.7 min).

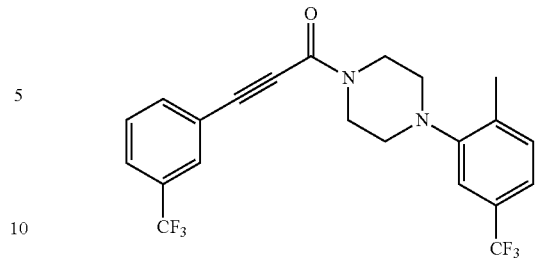

1-(4-(2-Methyl-5-(trifluoromethyl)phenyl)piperazin-1-yl)-3-(3-(trifluoromethyl)phenyl)prop-2-yn-1-one. A solution of 3-(3-(trifluoromethyl)phenyl)propionic acid (0.0763 g, 0.356 mmol) and 1-(2-methyl-5-(trifluoromethyl)phenyl)piperazine hydrochloride (0.100 g, 0.356 mmol) in CH₂Cl₂ (3.6 mL) cooled to 0° C. was treated with Et₃N (0.20 mL, 1.42 mmol). The cooled solution was treated with T3P (50 wt. % solution in EtOAc, 0.38 mL, 0.534 mmol) dropwise and the reaction was stirred at 0° C. for 30 min, warmed to rt overnight, diluted with CH₂Cl₂ (30 mL), washed with 1 M aqueous HCl (20 mL), dried (MgSO₄), filtered, and concentrated under reduced pressure. The crude residue was purified by automated chromatography on SiO₂ (4 g column, liquid load CH₂Cl₂, 100% hexanes to 40% EtOAc/hexanes), to give 1-(4-(2-methyl-5-(trifluoromethyl)phenyl)piperazin-1-yl)-3-(3-(trifluoromethyl)phenyl)prop-2-yn-1-one (0.0819 g, 0.186 mmol, 52%) as a pink solid: Mp 121.8-125.2° C.; IR (CH₂Cl₂) 2924, 2217, 1633, 1436, 1333, 1310, 1166, 1076, 1042, 695 cm⁻¹; ¹H NMR (400 MHz, CDCl₃) δ 7.81 (s, 1H), 7.74 (d, J=7.8 Hz, 1H), 7.67 (d, J=7.8 Hz, 1H), 7.52 (t, J=7.8 Hz, 1H), 7.30 (d, J=8.1 Hz, 1H), 7.26 (d, J=8.1 Hz, 1H), 7.22 (s, 1H), 4.00 (app t, J=5.0 Hz, 2H), 3.86 (app t, J=4.8 Hz, 2H), 3.03 (app t, J=5.0 Hz, 2H), 2.93 (app t, J=5.0 Hz, 2H), 2.39 (s, 3H); ¹³C NMR (100 MHz, CDCl₃) δ 152.6, 150.9, 136.8, 135.4, 135.4, 131.5, 131.2 (q, J$_{CF}$=33.0 Hz), 129.2 (s), 129.0 (q, J$_{CF}$=32.2 Hz), 129.0 (q, J$_{CF}$=3.9 Hz), 126.6 (q, J$_{CF}$=3.7 Hz), 124.0 (q, J$_{CF}$=272.0 Hz), 123.4 (q, J$_{CF}$=272.3 Hz), 121.3, 120.5 (q, J$_{CF}$=3.8 Hz), 88.9, 82.0, 51.8, 51.3, 47.4, 41.9, 17.9; ¹⁹F NMR (376 MHz, CDCl₃) δ −62.3 (s, 3F), −63.0 (s, 3F); HRMS (ESI) m/z calcd for C₂₂H₁₉F₆N₂O ([M+H]⁺) 441.1396, found 441.1391.

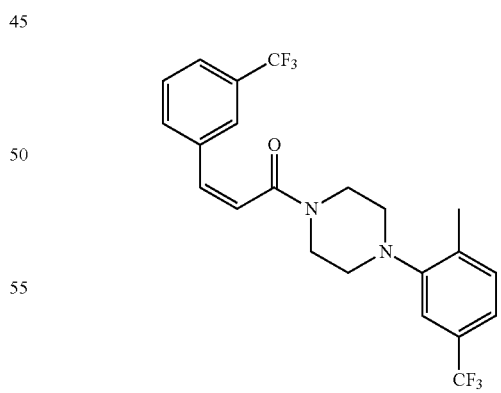

(Z)-1-(4-(2-Methyl-5-(trifluoromethyl)phenyl)piperazin-1-yl)-3-(3-(trifluoromethyl)phenyl)prop-2-en-1-one. A solution of 1-(4-(2-methyl-5-(trifluoromethyl)phenyl)piperazin-1-yl)-3-(3-(trifluoromethyl)-phenyl)prop-2-yn-1-one (0.0800 g, 0.182 mmol) in EtOAc (1.8 mL) was treated with Lindlar's catalyst (5% Pd on CaCO₃, lead poisoned, 0.0193 g, equivalent to 5 mol % Pd). The reaction was placed under a balloon of H₂ (3 vacuum/backfill cycles) and stirred at rt for 2 d, filtered through Celite, washed (EtOAc), and concentrated under reduced pressure. The crude residue was purified by automated chromatography on SiO₂ (4 g column, liquid load CH₂Cl₂, 100% hexanes to 40% EtOAc/hexanes, product eluted at 10% EtOAc/hexanes) to give the (Z)-1-(4-(2-methyl-5-(trifluoromethyl)phenyl)piperazin-1-yl)-3-(3-(trifluoromethyl)phenyl)prop-2-en-1-one (0.0572 g, 0.129 mmol, 71%) as clear/tan viscous oil: IR (CH₂Cl₂) 2922, 1621, 1443, 1418, 1329, 1309, 1163, 1076, 1044, 823 cm⁻¹; ¹H NMR (400 MHz, CDCl₃) δ 7.68 (s, 1H), 7.59 (t, J=7.7 Hz, 2H), 7.49 (t, J=7.7 Hz, 1H), 7.27-7.22 (m, 2H), 7.01 (s, 1H), 6.74 (d, J=12.5 Hz, 1H), 6.20 (d, J=12.5 Hz, 1H), 3.82 (bt, J=4.1 Hz, 2H), 3.50 (app t, J=5.0 Hz, 2H), 2.82 (app t, J=5.0 Hz, 2H), 2.47 (app t, J=5.0 Hz, 2H), 2.30 (s, 3H); ¹³C NMR (100 MHz, CDCl₃) δ 166.7, 151.0, 136.8, 136.2, 132.0, 131.6, 131.4, 131.2 (q, $J_{CF}$=32.1 Hz), 129.2, 129.0 (q, $J_{CF}$=32.3 Hz), 125.2 (q, $J_{CF}$=3.7 Hz), 125.0 (q, $J_{CF}$=3.8 Hz), 124.9, 124.1 (q, $J_{CF}$=271.9 Hz), 123.8 (q, $J_{CF}$=272.5 Hz), 120.4 (q, $J_{CF}$=3.9 Hz), 116.0 (q, $J_{CF}$=3.7 Hz), 51.3, 51.1, 46.6, 41.5, 17.8; ¹⁹F NMR (376 MHz, CDCl₃) δ −62.4 (s, 3F), −62.7 (s, 3F); HRMS (ESI) m/z calcd for C₂₂H₂₁F₆N₂O ([M+H]⁺) 443.1553, found 443.1551.

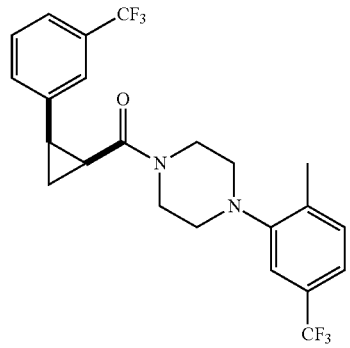

(4-(2-Methyl-5-(trifluoromethyl)phenyl)piperazin-1-yl)((1RS,2SR)-2-(3-(trifluoromethyl)phenyl)-cyclopropyl)methanone. A solution of CrCl₂ (0.0955 g, 0.777 mmol) and (Z)-1-(4-(2-methyl-5-(trifluoromethyl)phenyl)piperazin-1-yl)-3-(3-(trifluoromethyl)phenyl)prop-2-en-1-one (0.0573 g, 0.130 mmol) in dry degassed THF (1.3 mL) was sparged with Ar for 5 min and treated with CH₂ICl (75 uL, 0.648 mmol) at rt and under Ar atmosphere, heated for 20 h at 80° C., cooled to rt, diluted with Et₂O (50 mL), and washed with 1 M aqueous HCl (3×20 mL). The organic layer was dried (MgSO₄), filtered and concentrated under reduced pressure. The crude material was purified by automated chromatography on SiO₂ (4 g column, liquid load CH₂Cl₂, 100% hexanes to 40% EtOAc/hexanes) to give a clear oil that was filtered through basic Al₂O₃(CH₂Cl₂/EtOAc, 1:1), recrystallized from CH₂Cl₂/hexanes (ca. 1:5) the mother liquor was decanted and the clear colorless cubes were washed with hexanes (2×1 mL) and dried under high vacuum to give (4-(2-methyl-5-(trifluoromethyl)phenyl)piperazin-1-yl)((1RS,2SR)-2-(3-(trifluoromethyl)phenyl)cyclopropyl)methanone (0.0115 g, 0.0252 mmol, 20% (100% purity by ELSD)) as a colorless solid: Mp 113.4-116.8° C.; IR (CH₂Cl₂) 2914, 2824, 1641, 1418, 1328, 1309, 1163, 1121, 1073 cm⁻¹; ¹H NMR (400 MHz, CDCl₃) δ 7.47 (bd, J=7.1 Hz, 2H), 7.41 (t, J=7.8 Hz, 1H), 7.33 (d, J=7.8 Hz, 1H), 7.24 (s, 2H), 6.92 (s, 1H), 3.94 (d, J=12.2 Hz, 1H), 3.79 (d, J=12.2 Hz, 1H), 3.58 (ddd, J=12.2, 9.2, 3.0 Hz, 1H), 3.24 (ddd, J=12.2, 9.2, 2.6 Hz, 1H), 2.77 (td, J=12.2, 3.7 Hz, 2H), 2.53 (td, J=9.2, 7.0 Hz, 1H), 2.29 (s, 3H), 2.28-2.18 (m, 2H), 2.11-2.05 (m, 1H), 1.92 (q, J=6.0 Hz, 1H), 1.42 (td, J=8.5, 6.0 Hz, 1H); ¹³C NMR (100 MHz, CDCl₃) δ 166.7, 151.1, 138.8, 136.9, 131.4, 130.6 (q, $J_{CF}$=31.2 Hz), 130.5, 129.1 (q, $J_{CF}$=32.1 Hz), 128.7, 125.1 (q, $J_{CF}$=3.7 Hz), 124.2 (q, $J_{CF}$=272.3 Hz, 2C), 123.2 (q, $J_{CF}$=3.8 Hz), 120.4 (q, $J_{CF}$=3.8 Hz), 116.1 (q, $J_{CF}$=3.7 Hz), 51.7 (2C), 45.6, 42.2, 24.2, 24.0, 17.8, 10.9; ¹⁹F NMR (376 MHz, CDCl₃) δ −62.4 (s, 3H), −62.6 (s, 3H); HRMS (ESI) m/z calcd for C₂₂H₂₃F₆N₂O ([M+H]⁺) 457.1709, found 457.1704.

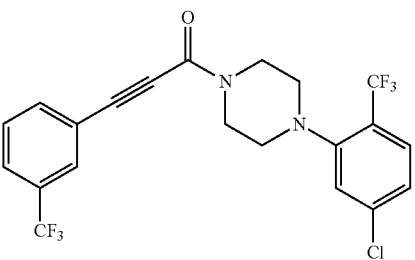 [SMILES: O=C(C#Cc1cccc(C(F)(F)F)c1)N1CCN(c2cc(Cl)ccc2C(F)(F)F)CC1]

1-(4-(5-Chloro-2-(trifluoromethyl)phenyl)piperazin-1-yl)-3-(3-(trifluoromethyl)phenyl)prop-2-yn-1-one. A solution of 3-(3-(trifluoromethyl)phenyl)propiolic acid (0.100 g, 0.467 mmol) and 1-(5-chloro-2-(trifluoromethyl)phenyl)piperazinehydrochloride (0.155 g, 0.514 mmol) in CH₂Cl₂ (4.7 mL) cooled to 0° C. was treated with Et₃N (0.26 mL, 1.87 mmol). The cooled solution was treated with T3P (50 wt. % solution in EtOAc, 0.49 mL, 0.701 mmol) dropwise and the reaction was stirred at 0° C. for 30 min, warmed to rt overnight, diluted with CH₂Cl₂ (30 mL) and washed with H₂O (20 mL), satd. aqueous NaHCO₃ (20 mL), dried (MgSO₄), filtered, and concentrated under reduced pressure. The crude residue was purified by automated chromatography on SiO₂ (4 g column, liquid load CH₂Cl₂, 100% hexanes to 30% EtOAc/hexanes), to give the crude product that was contaminated with the piperazine starting material (ca 10%). The product was dissolved in hot absolute EtOH then stored overnight in the freezer (−20° C.) to facilitate crystallization. The supernatant was removed and the crystals were washed with hexanes and then dried under high vacuum overnight to give 1-(4-(5-chloro-2-(trifluoromethyl)phenyl)piperazin-1-yl)-3-(3-(trifluoromethyl)phenyl)prop-2-yn-1-one (0.168 g, 0.365 mmol, 78%) as a colorless solid: Mp 87.6-91.2° C.; IR (CH₂Cl₂) 2921, 2827, 2222, 1633, 1596, 1436, 1332, 1309, 1121, 1034, 695 cm⁻¹; ¹H NMR (400 MHz, CDCl₃) δ 7.78 (s, 1H), 7.71 (d, J=7.8 Hz, 1H), 7.65 (d, J=8.5 Hz, 1H), 7.56 (d, J=8.5 Hz, 1H), 7.50 (t, J=7.8 Hz, 1H), 7.26-7.22 (m, 2H), 3.95 (app t, J=5.0 Hz, 2H), 3.81 (app t, J=5.0 Hz, 2H), 2.99 (app t, J=5.0 Hz, 2H), 2.92 (app t, J=5.0 Hz, 2H); ¹³C NMR (100 MHz, CDCl₃) δ 152.6, 138.8, 135.4, 131.2 (q, $J_{CF}$=33.0 Hz), 129.2, 129.0 (q, $J_{CF}$=3.7 Hz), 128.6 (q, $J_{CF}$=5.4 Hz), 126.6 (q, $J_{CF}$=3.7 Hz), 125.8 (q, $J_{CF}$=29.5 Hz), 125.7, 124.7, 123.5 (q, $J_{CF}$=273.0 Hz), 123.2 (q, $J_{CF}$=272.5 Hz), 121.3, 88.9, 82.0, 53.6, 52.7, 47.4, 41.8; ¹⁹F NMR (376 MHz, CDCl₃) δ −60.3 (s, 3F), −63.0 (s, 3F); HRMS (ESI) m/z calcd for C₂₁H₁₆ClF₆N₂O ([M+H]⁺) 461.0850, found 461.0849.

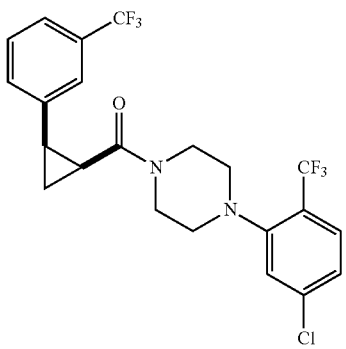

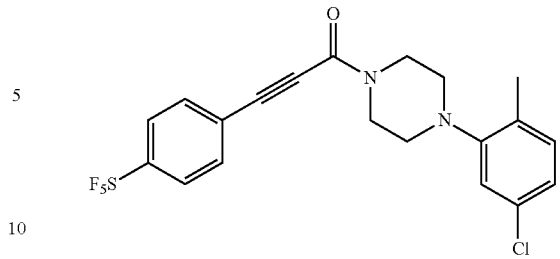

(4-(5-Chloro-2-(trifluoromethyl)phenyl)piperazin-1-yl) (2-(3-(trifluoromethyl)phenyl)cyclopropyl)-methanone. A solution of 1-(4-(5-chloro-2-(trifluoromethyl)phenyl)piperazin-1-yl)-3-(3-(trifluoromethyl)-phenyl)prop-2-yn-1-one (0.0684 g, 0.148 mmol) in EtOAc (1.5 mL) was treated with Lindlar's catalyst (5% Pd on CaCO$_3$, lead poisoned, 0.0158 g, equivalent to 5 mol % Pd). The reaction was placed under a balloon of H$_2$ (3 vacuum/backfill cycles) and stirred at rt for 3 d, filtered through Celite, washed (EtOAc), and the combined filtrates were concentrated under reduced pressure. The crude residue was purified by automated chromatography on SiO$_2$ (4 g column, liquid load CH$_2$Cl$_2$, 100% hexanes to 40% EtOAc:hexanes) to give (Z)-1-(4-(5-chloro-2-(trifluoromethyl)phenyl)piperazin-1-yl)-3-(3-(trifluoromethyl)phenyl)prop-2-en-1-one (0.0512 g, 0.111 mmol) as a colorless solid.

A solution of CrCl$_2$ (0.816 g, 0.940 mmol) and (Z)-1-(4-(5-chloro-2-(trifluoromethyl)phenyl)-piperazin-1-yl)-3-(3-(trifluoromethyl)phenyl)prop-2-en-1-one (0.0512 g, 0.111 mmol) in dry degassed THF (1.6 mL) was sparged with Ar for 5 min and treated with CH$_2$ICl (0.064 mL, 0.553 mmol) at rt, heated for 2 d at 80° C., cooled to rt, diluted with EtOAc (50 mL), and washed with 1 M aqueous HCl (3×20 mL). The organic layer was dried (MgSO$_4$), filtered and concentrated under reduced pressure. The crude residue was purified by automated chromatography on SiO$_2$ (4 g column, liquid load CH$_2$Cl$_2$, hexanes to 30% EtOAc/hexanes, product eluted at 20% EtOAc/hexanes) to give a clear oil that was filtered through basic Al$_2$O$_3$ (eluting with 1:1 CH$_2$Cl$_2$/EtOAc), concentrated, and dried under high vacuum to give (4-(5-chloro-2-(trifluoromethyl)phenyl)piperazin-1-yl)(2-(3-(trifluoromethyl)phenyl)cyclopropyl)methanone (0.0409 g, 0.0858 mmol, 59% (2 steps) (100% purity by ELSD)) as a clear colorless oil: IR (CH$_2$Cl$_2$) 2918, 1641, 1596, 1437, 1327, 1120, 1032, 809, 702 cm$^{-1}$; $^1$H NMR (400 MHz, CDCl$_3$) δ 7.54-7.50 (m, 3H), 7.44 (t, J=8.0 Hz, 1H), 7.34 (d, J=8.0 Hz, 1H), 7.20 (dd, J=8.5, 1.4 Hz, 1H), 6.87 (d, J=1.6 Hz, 1H), 4.02 (d, J=13.0 Hz, 1H), 3.80 (d, J=13.0 Hz, 1H), 3.51 (ddd, J=12.8, 9.8, 3.0 Hz, 1H), 3.13 (ddd, J=12.5, 9.8, 2.7 Hz, 1H), 2.73 (td, J=7.7, 3.6 Hz, 2H), 2.52 (td, J=9.0, 7.0 Hz, 1H), 2.25 (ddd, J=9.0, 8.4, 6.0 Hz, 1H), 2.21-2.15 (m, 1H), 1.97-1.90 (m, 2H), 1.42 (td, J=8.4, 6.0 Hz, 1H); $^{13}$C NMR (100 MHz, CDCl$_3$) δ 166.6, 152.7, 138.9, 138.7, 130.6 (q, J$_{CF}$=32.1 Hz), 130.5, 128.7, 128.3 (q, J$_{CF}$=5.4 Hz), 125.8 (q, J$_{CF}$=29.4 Hz), 125.6, 125.1 (q, J$_{CF}$=3.8 Hz), 124.6, 124.2 (q, J$_{CF}$=272.4 Hz), 123.5 (q, J$_{CF}$=272.9 Hz), 123.2 (q, J$_{CF}$=3.7 Hz), 53.5, 53.0, 45.5, 42.1, 24.3, 23.9, 10.9; $^{19}$F NMR (376 MHz, CDCl$_3$) δ −60.4 (s, 3F), −62.4 (s, 3F); HRMS (ESI) m/z calcd for C$_{22}$H$_{20}$ClF$_6$N$_2$O ([M+H]$^+$) 477.1163, found 477.1166.

1-(4-(5-Chloro-2-methylphenyl)piperazin-1-yl)-3-(4-(pentafluoro-λ6-sulfaneyl)phenyl)prop-2-yn-1-one. A solution of 3-(4-(pentafluoro-λ6-sulfaneyl)phenyl)propiolic acid (0.100 g, 0.367 mmol) and 1-(1-(5-chloro-2-methylphenyl) piperazine hydrochloride (0.0999 g, 0.404 mmol) in CH$_2$Cl$_2$ (3.7 mL) cooled to 0° C. was treated with Et$_3$N (0.20 mL, 1.47 mmol). The cooled solution was treated with T3P (50 wt. % solution in EtOAc, 0.39 mL, 0.551 mmol) dropwise and the reaction was stirred at 0° C. for 30 min, warmed to rt overnight, diluted with EtOAc (30 mL), washed with H$_2$O (20 mL), satd. aqueous NaHCO$_3$ (20 mL), dried (MgSO$_4$), filtered, and concentrated under reduced pressure. The crude residue was purified by automated chromatography on SiO$_2$ (4 g column, liquid load CH$_2$Cl$_2$, 100% hexanes to 30% EtOAc/hexanes), to give 1-(4-(5-chloro-2-methylphenyl)piperazin-1-yl)-3-(4-(pentafluoro-λ6-sulfaneyl)phenyl)prop-2-yn-1-one (0.127 g, 0.272 mmol, 74%) as a pale yellow foam: IR (CHCl$_3$) 2981, 2222, 1627, 1490, 1432, 1275, 832, 792, 727 cm$^{-1}$; $^1$H NMR (400 MHz, CDCl$_3$) δ 7.76 (d, J=8.8 Hz, 2H), 7.64 (d, J=8.8 Hz, 2H), 7.11 (d, J=8.1 Hz, 1H), 6.99 (dd, J=8.1, 2.1 Hz, 1H), 6.95 (d, J=2.1 Hz, 1H), 3.96 (app t, J=5.0 Hz, 2H), 3.84 (app t, J=5.0 Hz, 2H), 2.97 (app t, J=5.0 Hz, 2H), 2.89 (app t, J=5.0 Hz, 2H), 2.29 (s, 3H); $^{13}$C NMR (100 MHz, CDCl$_3$) δ 154.4 (quint, J$_{CF}$=18.3 Hz), 152.4, 151.6, 132.4, 132.1, 131.9, 131.0, 126.2 (quint, J$_{CF}$=4.6 Hz), 124.1, 123.8, 119.8, 88.2, 83.2, 51.9, 51.3, 47.4, 42.0, 17.3; $^{19}$F NMR (376 MHz, CDCl$_3$) δ 83.0 (quint, J=150.3 Hz, 1F), 62.4 (d, J=150.3 Hz, 4F); HRMS (ESI) m/z calcd for C$_{20}$H$_{19}$ClF$_5$N$_2$OS ([M+H]$^+$) 465.0821, found 465.0819.

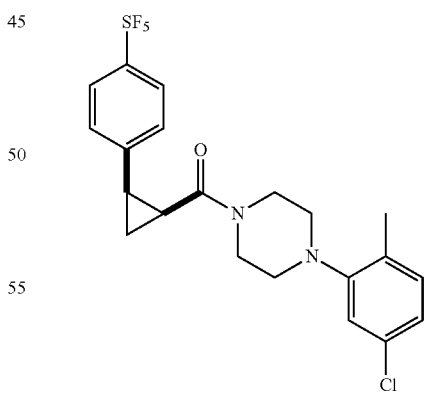

(4-(5-Chloro-2-methylphenyl)piperazin-1-yl)((1RS, 2SR)-2-(4-(pentafluoro-λ6-sulfaneyl)phenyl)-cyclopropyl) methanone. A solution of 1-(4-(5-chloro-2-methylphenyl) piperazin-1-yl)-3-(4-(pentafluoro-λ6-sulfaneyl)phenyl) prop-2-yn-1-one (0.0850 g, 0.183 mmol) in EtOAc (1.8 mL) was treated with Lindlar's catalyst (5% Pd on CaCO$_3$, lead poisoned, 0.0195 g, equivalent to 5 mol % Pd). The reaction was placed under a balloon of H₂ (3 vacuum/backfill cycles) and stirred at rt for 2 d, filtered through Celite, washed (EtOAc), and the combined filtrates were concentrated under reduced pressure. The crude residue was purified by automated chromatography on SiO₂ (4 g column, liquid load CH₂Cl₂, 100% hexanes to 40% EtOAc/hexanes, product eluted at 35% EtOAc/hexanes) to give (Z)-1-(4-(5-chloro-2-methylphenyl)-piperazin-1-yl)-3-(4-(pentafluoro-λ6-sulfaneyl)phenyl)prop-2-en-1-one (0.0811 g, 0.174 mmol) as a colorless solid.

A solution of CrCl₂ (0.126 g, 1.03 mmol) and (Z)-1-(4-(5-chloro-2-methylphenyl)piperazin-1-yl)-3-(4-(pentafluoro-λ6-sulfaneyl)phenyl)prop-2-en-1-one (0.0800 g, 0.171 mmol) in dry degassed THF (1.7 mL) was sparged with Ar for 5 min and added CH₂ICl (0.10 mL, 0.857 mmol) at rt, heated for 2 d at 80° C., cooled to rt, diluted with EtOAc (50 mL) and washed with 1 M aqueous HCl (3×20 mL). The organic layer was dried (MgSO₄), filtered and concentrated under reduced pressure. The crude residue was purified by automated chromatography on SiO₂ (4 g column, liquid load CH₂Cl₂, 100% hexanes to 30% EtOAc/hexanes, product eluted at 30% EtOAc/hexanes) to give a clear oil that was filtered through basic Al₂O₃(CH₂Cl₂/EtOAc, 1:1), concentrated under reduced pressure, and dried under high vacuum to give (4-(5-chloro-2-methylphenyl)piperazin-1-yl)((1RS,2SR)-2-(4-(pentafluoro-λ6-sulfaneyl)phenyl)cyclopropyl)-methanone (0.0451 g, 0.0938 mmol, 52% (2 steps) (100% purity by ELSD)) as a colorless solid: Mp 169.8-172.0° C.; IR (CH₂Cl₂) 2919, 1639, 1490, 1466, 1438, 1225, 1035, 835, 750 cm⁻¹; ¹H NMR (400 MHz, CDCl₃) δ 7.66 (d, J=8.6 Hz, 2H), 7.25 (d, J=8.6 Hz, 2H), 7.06 (dd, J=8.1, 0.4 Hz, 1H), 6.95 (dd, J=8.1, 2.1 Hz, 1H), 6.69 (d, J=2.1 Hz, 1H), 3.82 (bd, J=14.0 Hz, 1H), 3.70-3.58 (m, 2H), 3.33 (ddd, J=12.4, 8.9, 3.0 Hz, 1H), 2.75 (tdd, J=14.0, 7.7, 3.4 Hz, 2H), 2.50 (td, J=8.9, 7.0 Hz, 1H), 2.32-2.23 (m, 2H), 2.20 (s, 3H), 2.10 (ddd, J=11.1, 8.2, 3.0 Hz, 1H), 1.91 (q, J=6.3 Hz, 1H), 1.44 (td, J=8.4, 5.6 Hz, 1H); ¹³C NMR (100 MHz, CDCl₃) δ 166.5, 152.1 (quint, $J_{CF}$=17.3 Hz), 151.6, 141.9, 131.9 (2C), 130.9, 127.7, 125.7 (quint, $J_{CF}$=4.6 Hz), 123.7, 119.5, 51.9, 51.5, 45.5, 42.2, 24.6, 23.7, 17.3, 11.3; ¹⁹F NMR (376 MHz, CDCl₃) δ 84.8 (quint, J=150.4 Hz, 1F), 63.2 (d, J=150.4 Hz, 4F); HRMS (ESI) m/z calcd for C₂₁H₂₃ClF₅N₂OS ([M+H]⁺) 481.1134, found 481.1134.

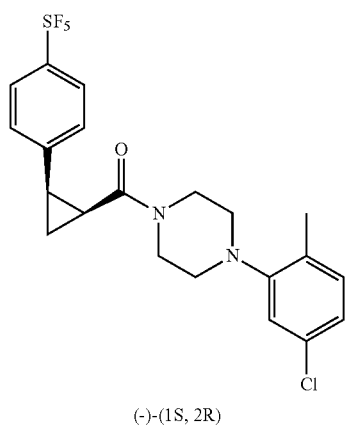

(-)-(1S, 2R)

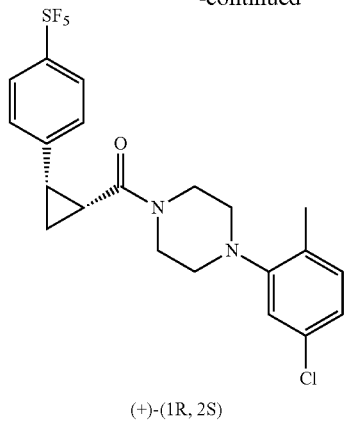

(+)-(1R, 2S)

Racemic (4-(5-chloro-2-methylphenyl)piperazin-1-yl)((1RS,2SR)-2-(4-(pentafluoro-λ6-sulfaneyl)phenyl)-cyclopropyl)methanone was separated on a SFC Chiralpak-IC semiprep (250×10 mm) column (30% Methanol:CO₂, 7 mL/min, p=100 bar, 220 nm) injection volume 90 µL, 20 mg/mL) to give (4-(5-chloro-2-methylphenyl)piperazin-1-yl)((1S,2R)-2-(4-(pentafluoro-λ6-sulfaneyl)phenyl)cyclopropyl)methanone (retention time 5.14 min) as a colorless viscous oil (100% purity by ELSD): $[\alpha]^{17}_D$ −134.2 (c 0.60, MeOH); ¹H NMR (300 MHz, CDCl₃) δ 7.66 (d, J=8.7 Hz, 2H), 7.26 (overlap, 2H), 7.06 (d, J=8.1 Hz, 1H), 6.96 (dd, J=8.1, 1.8 Hz, 1H), 6.70 (d, J=1.8 Hz, 1H), 3.87-3.79 (m, 1H), 3.73-3.58 (m, 3H), 3.38-3.31 (m, 1H), 2.81-2.70 (m, 2H), 2.50 (q, J=8.7 Hz, 1H), 2.33-2.24 (m, 2H), 2.20 (s, 3H), 2.16-2.08 (m, 1H), 1.91 (q, J=5.7 Hz, 1H), 1.44 (td, J=8.1, 5.7 Hz, 1H). The enantiomeric excess was >99.9% ee (SFC Chiralpak-IC (250×10 mm); 30% Methanol:CO₂, 7 mL/min, p=100 bar, 220 nm; retention time: 5.1 min).

(4-(5-Chloro-2-methylphenyl)piperazin-1-yl)((1S,2R)-2-(4-(pentafluoro-λ6-sulfaneyl)phenyl)cyclopropyl)-methanone (retention time 6.57 min) was obtained as a colorless viscous oil (100% purity by ELSD): $[\alpha]^{17}_D$+136.3 (c 0.59, MeOH); ¹H NMR (300 MHz, CDCl₃) δ 7.66 (d, J=8.7 Hz, 2H), 7.26-7.24 (overlap, 2H), 7.06 (d, J=8.4 Hz, 1H), 6.96 (dd, J=8.4, 1.8 Hz, 1H), 6.70 (d, J=1.8 Hz, 1H), 3.85-3.78 (m, 1H), 3.67-3.61 (m, 2H), 3.39-3.30 (m, 1H), 2.81-2.70 (m, 2H), 2.50 (q, J=8.7 Hz, 1H), 2.33-2.24 (m, 2H), 2.20 (s, 3H), 2.16-2.10 (m, 1H), 1.91 (q, J=5.7 Hz, 1H), 1.44 (td, J=8.4, 5.7 Hz, 2H). The enantiomeric excess was >99.9% ee (SFC Chiralpak-IC (250×10 mm); 30% Methanol:CO₂, 7 mL/min, p=100 bar, 220 nm; retention time: 6.5 min).

1-(4-(2-Methyl-5-(trifluoromethyl)phenyl)piperazin-1-yl)-3-(4-(pentafluoro-λ6-sulfaneyl)phenyl)prop-2-yn-1-one. A solution of 3-(4-(pentafluoro-λ6-sulfaneyl)phenyl)propiolic acid (0.100 g, 0.367 mmol) and 1-(2-methyl-5-(trifluoromethyl)phenyl)piperazine hydrochloride (0.113 g, 0.404 mmol) in CH$_2$Cl$_2$ (3.7 mL) cooled to 0° C. was treated with Et$_3$N (0.20 mL, 1.47 mmol). The cooled solution was treated with T3P (50 wt. % solution in EtOAc, 0.39 mL, 0.551 mmol) dropwise and the reaction was stirred at 0° C. for 30 min, warmed to rt overnight, diluted with EtOAc (30 mL), washed with H$_2$O (20 mL), satd. aqueous NaHCO$_3$ (20 mL), dried (MgSO$_4$), filtered, and concentrated under reduced pressure. The crude residue was purified by automated chromatography on SiO$_2$ (4 g column, liquid load CH$_2$Cl$_2$, 100% hexanes to 40% EtOAc/hexanes), to give 1-(4-(2-methyl-5-(trifluoromethyl)phenyl)piperazin-1-yl)-3-(4-(pentafluoro-λ6-sulfaneyl)phenyl)prop-2-yn-1-one (0.139 g, 0.278 mmol, 76%) as a tan foam: IR (CH$_2$Cl$_2$) 2920, 2222, 1632, 1418, 1340, 1310, 1279, 1122, 839, 793 cm$^{-1}$; H NMR (400 MHz, CDCl$_3$) δ 7.75 (d, J=8.8 Hz, 2H), 7.63 (d, J=8.8 Hz, 2H), 7.31-7.25 (m, 2H), 7.21 (s, 1H), 3.98 (t, J=5.0 Hz, 2H), 3.85 (app t, J=5.0 Hz, 2H), 3.02 (app t, J=5.0 Hz, 2H), 2.92 (app t, J=5.0 Hz, 2H), 2.38 (s, 3H); $^{13}$C NMR (100 MHz, CDCl$_3$) δ 154.3 (quint, J$_{CF}$=18.1 Hz), 152.4, 150.9, 136.8, 132.4, 131.5, 129.0 (q, J$_{CF}$=32.1 Hz), 126.2 (quint, J$_{CF}$=4.6 Hz), 124.1 (q, J$_{CF}$=272.1 Hz), 124.0, 120.5 (q, J$_{CF}$=3.8 Hz), 116.0 (q, J$_{CF}$=3.6 Hz), 88.2, 83.1, 51.8, 51.3, 47.4, 41.9, 17.8; $^{19}$F NMR (376 MHz, CDCl$_3$) δ 83.0 (quint, J=150.4 Hz, 1F), 62.4 (d, J=150.2 Hz, 4F), −62.3 (s, 3F); HRMS (ESI) m/z calcd for C$_{21}$H$_{19}$F$_8$N$_2$OS ([M+H]$^+$) 499.1085, found 499.1086.

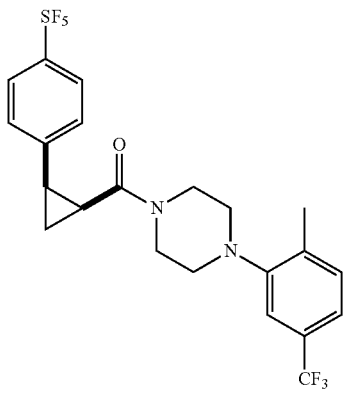

(4-(2-Methyl-5-(trifluoromethyl)phenyl)piperazin-1-yl) ((1RS,2SR)-2-(4-(pentafluoro-λ6-sulfaneyl)-phenyl)cyclopropyl)methanone (JKJ741.040). A solution of 1-(4-(2-methyl-5-(trifluoromethyl)phenyl)-piperazin-1-yl)-3-(4-(pentafluorosulfanyl)phenyl)prop-2-yn-1-one (0.100 g, 0.201 mmol) in EtOAc (2 mL) was treated with Lindlar's catalyst (5% Pd on CaCO$_3$, lead poisoned, 0.0214 g, equivalent to 5 mol % Pd). The reaction was placed under a balloon of H$_2$ (3 vacuum/backfill cycles) and stirred at rt for 2 d, filtered through Celite, washed (EtOAc), and the combined filtrates were concentrated under reduced pressure. The crude residue was purified by automated chromatography on SiO$_2$ (4 g column, 100% hexanes to 40% EtOAc/hexanes, product eluted at 30% EtOAc/hexanes) to give (Z)-1-(4-(2-methyl-5-(trifluoromethyl)-phenyl)piperazin-1-yl)-3-(4-(pentafluoro-λ6-sulfaneyl)phenyl)prop-2-en-1-one (0.0765 g, 0.153 mmol, 76% (92% brsm) as a colorless foam.

To a flame dried 5 mL microwave vial containing anhydrous CrCl$_2$ (0.111 g, 0.899 mmol) was treated with solution of (Z)-1-(4-(2-methyl-5-(trifluoromethyl)phenyl)piperazin-1-yl)-3-(4-(pentafluoro-λ6-sulfaneyl)phenyl)prop-2-en-1-one (0.0750 g, 0.150 mmol) in anhydrous THF (1.5 mL) and the mixture was sparged with Ar for 15 min and added CH$_2$ICl (0.087 mL, 0.749 mmol) at rt and under Ar atmosphere. The reaction mixture was stirred for 2 d at 80° C. The reaction was cooled to rt, quenched by the addition of EtOAc (50 mL) and washed with 1 M aqueous HCl (3×20 mL). The organic layer was dried (MgSO$_4$), filtered and concentrated under reduced pressure. The crude material was purified by automated chromatography on SiO$_2$ (4 g column, liquid load CH$_2$Cl$_2$, hexanes to 30% EtOAc/hexanes, product eluted at 30% EtOAc/hexanes) to give the product as a clear oil. The product was filtered through basic Al$_2$O$_3$ (eluting with 1:1 CH$_2$Cl$_2$/EtOAc) concentrated to a colorless solid. The solid was recrystallized from hot cyclohexane (2×). The supernatant was removed and the crystals were washed with rt cyclohexane (rt, 2×1 mL) and hexanes (2×1 mL) and dried under high vacuum to give the product (0.0176 g, 0.0342 mmol, 18% (2 steps) (100% purity by ELSD)) as a colorless solid: Mp 122.1-125.8° C.; IR (CH$_2$Cl$_2$) 2919, 1638, 1417, 1338, 1308, 1120, 824, 749 cm$^{-1}$; $^1$H NMR (400 MHz, CDCl$_3$) δ 7.65 (d, J=8.8 Hz, 2H), 7.26-7.24 (m, 5H), 6.96 (s, 1H), 3.85 (bd, J=13.0 Hz, 1H), 3.72-3.60 (m, 2H), 3.38-3.32 (m, 1H), 2.86-2.75 (m, 2H), 2.51 (td, J=8.9, 7.0 Hz, 1H), 2.32-2.26 (m, 5H), 2.14 (ddd, J=11.0, 8.6, 2.6 Hz, 1H), 1.92 (q, J=6.2 Hz, 1H), 1.45 (td, J=8.4, 5.6 Hz, 1H); $^{13}$C NMR (100 MHz, CDCl$_3$) δ 166.5, 152.2 (quint, J$_{CF}$=17.4 Hz), 150.9, 141.8, 136.7, 131.4, 129.1 (q, J$_{CF}$=32.1 Hz), 127.7, 125.7, 125.7 (quint, J$_{CF}$=4.6 Hz), 124.0 (q, J$_{CF}$=271.9 Hz), 120.4 (q, J$_{CF}$=3.9 Hz), 115.7 (q, J$_{CF}$=3.8 Hz), 51.9, 51.4, 45.5, 42.2, 24.6, 23.7, 17.9, 11.3; $^{19}$F NMR (376 MHz, CDCl$_3$) δ 84.6 (quint, J=149.9 Hz, 1F), 63.0 (d, J=149.8 Hz, 4F), −62.4 (s, 3F); HRMS (ESI) m/z calcd for C$_{22}$H$_{23}$F$_8$N$_2$OS ([M+H]$^+$) 515.1398, found 515.1378.

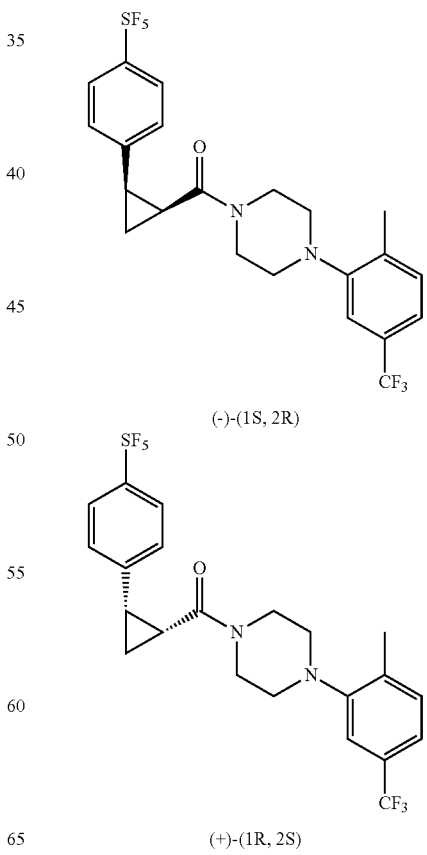

Racemic (4-(2-methyl-5-(trifluoromethyl)phenyl)piperazin-1-yl)((1RS,2SR)-2-(4-(pentafluoro-λ6-sulfaneyl)phenyl)cyclopropyl)methanone was separated on a SFC Chiralpak-IC semiprep (250×10 mm) column (30% Methanol:CO$_2$, 7 mL/min, p=100 bar, 220 nm) injection volume (90 μL, 20 mg/mL) to give (4-(2-methyl-5-(trifluoromethyl)phenyl)piperazine-1-yl)((1S,2R)-2-(4-(pentafluoro-λ6-sulfaneyl)phenyl)-cyclopropyl)methanone (retention time 3.40 min) as a colorless viscous oil (100% purity by ELSD): $[\alpha]^{17}_D$ –119.1 (c 0.79, MeOH); $^1$H NMR (300 MHz, CDCl$_3$) δ 7.66 (d, J=8.7 Hz, 2H), 7.25 (d, J=8.7 Hz, 3H), 6.97 (s, 1H), 3.89-3.80 (m, 1H), 3.72-3.60 (m, 2H), 3.40-3.31 (m, 1H), 2.86-2.74 (m, 2H), 2.50 (q, J=8.4 Hz, 1H), 2.33-2.25 (m, 5H), 2.18-2.12 (m, 1H), 1.92 (q, J=6.0 Hz, 1H), 1.44 (td, J=8.4, 6.0 Hz, 1H). The enantiomeric excess was >99.9% ee (SFC Chiralpak-IC (250×10 mm); 30% Methanol:CO$_2$, 7 mL/min, p=100 bar, 220 nm; retention time: 3.3 min).

(4-(2-Methyl-5-(trifluoromethyl)phenyl)piperazine-1-yl)((1R,2S)-2-(4-(pentafluoro-λ6-sulfaneyl)-phenyl)cyclopropyl)methanone (retention time 3.65 min) was obtained as a colorless viscous oil (100% purity by ELSD): $[\alpha]^{17}_D$+117.0 (c 0.87, MeOH); $^1$H NMR (300 MHz, CDCl$_3$) δ 7.66 (d, J=8.7 Hz, 2H), 7.26 (d, J=8.7 Hz, 3H), 6.97 (s, 1H), 3.88-3.82 (m, 2H), 3.69-3.63 (m, 3H), 3.40-3.31 (m, 2H), 2.89-2.70 (m, 3H), 2.50 (q, J=8.4 Hz, 2H), 2.34-2.25 (m, 5H), 2.20-2.12 (m, 1H), 1.92 (q, J=6.0 Hz, 1H), 1.44 (td, J=8.4, 6.0 Hz, 1H). The enantiomeric excess was >99.9% ee (SFC Chiralpak-IC (250×10 mm); 30% Methanol:CO$_2$, 7 mL/min, p=100 bar, 220 nm; retention time: 3.7 min).

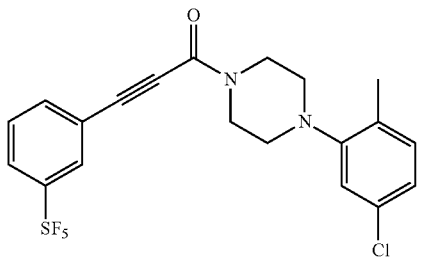

1-(4-(5-Chloro-2-methylphenyl)piperazin-1-yl)-3-(3-(pentafluoro-λ6-sulfaneyl)phenyl)prop-2-yn-1-one. A solution of 3-(3-(pentafluoro-λ6-sulfaneyl)phenyl)propiolic acid (0.100 g, 0.367 mmol) and 1-(1-(5-chloro-2-methylphenyl)piperazine hydrochloride (0.0999 g, 0.404 mmol) in CH$_2$Cl$_2$ (3.7 mL) cooled to 0° C. was treated with Et$_3$N (0.20 mL, 1.47 mmol). The cooled solution was treated with T3P (50 wt. % solution in EtOAc, 0.39 mL, 0.551 mmol) dropwise and the reaction was stirred at 0° C. for 30 min and allowed to warm to rt overnight. The reaction was diluted with EtOAc (30 mL) and washed with H$_2$O (20 mL), satd. aqueous NaHCO$_3$ (20 mL), dried (MgSO$_4$), filtered, and concentrated under reduced pressure. The crude residue was purified by automated chromatography on SiO$_2$ (4 g column, liquid load CH$_2$Cl$_2$, 100% hexanes to 30% EtOAc/hexanes), to give 1-(4-(5-chloro-2-methylphenyl)piperazin-1-yl)-3-(3-(pentafluoro-λ6-sulfaneyl)phenyl)prop-2-yn-1-one (0.113 g, 0.244 mmol, 66%) as a pale yellow solid: Mp 127.9-133.0° C.; IR (CHCl$_3$) 2921, 2219, 1627, 1432, 1288, 1223, 1041, 838, 797, 728 cm$^{-1}$; $^1$H NMR (400 MHz, CDCl$_3$) δ 7.94 (t, J=2.0 Hz, 1H), 7.80 (ddd, J=8.4, 2.0, 0.8 Hz, 1H), 7.69 (d, J=7.7 Hz, 1H), 7.49 (t, J=8.1 Hz, 1H), 7.11 (d, J=8.1 Hz, 1H), 6.99 (dd, J=8.1, 2.1 Hz, 1H), 6.96 (d, J=2.1 Hz, 1H), 3.97 (app t, J=5.0 Hz, 2H), 3.84 (app t, J=5.0 Hz, 2H), 2.98 (app t, J=5.0 Hz, 2H), 2.89 (app t, J=5.0 Hz, 2H), 2.29 (s, 3H); $^{13}$C NMR (100 MHz, CDCl$_3$) δ 153.8 (quint, J$_{CF}$=18.5 Hz), 152.4, 151.6, 135.1, 132.1, 131.9, 131.0, 129.7 (quint, J$_{CF}$=7.1 Hz), 129.0, 127.3 (quint, J$_{CF}$=4.5 Hz), 123.8, 121.6, 119.8, 88.4, 82.3, 51.9, 51.3, 47.4, 42.0, 17.3; $^{19}$F NMR (376 MHz, CDCl$_3$) δ 82.9 (quint, J=150.6 Hz, 1F), 62.6 (d, J=150.5 Hz, 4F); HRMS (ESI) m/z calcd for C$_{20}$H$_{19}$ClF$_5$N$_2$OS ([M+H]$^+$) 465.0821, found 465.0821.

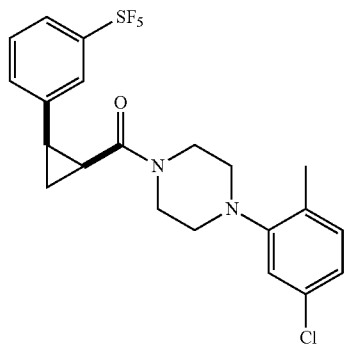

(4-(5-Chloro-2-methylphenyl)piperazine-1-yl)((1RS, 2SR)-2-(3-(pentafluoro-λ6-sulfaneyl)phenyl)cyclopropyl)methanone. A solution of 1-(4-(5-chloro-2-methylphenyl)piperazine-1-yl)-3-(4-(pentafluorosulfanyl)phenyl)prop-2-yn-1-one (0.0930 g, 0.200 mmol) in EtOAc (2 mL) was treated with Lindlar's catalyst (5% Pd on CaCO$_3$, lead poisoned, 0.0213 g, equivalent to 5 mol % Pd). The reaction was placed under a balloon of H$_2$ (3 vacuum/backfill cycles) and stirred at rt for 3 d, filtered through Celite, washed (EtOAc) and the combined filtrates were concentrated under reduced pressure. The crude residue was purified by automated chromatography on SiO$_2$ (4 g column, liquid load CH$_2$Cl$_2$, 100% hexanes to 30% EtOAc/hexanes, product eluted at 20% EtOAc/hexanes) to give (Z)-1-(4-(5-chloro-2-methylphenyl)-piperazine-1-yl)-3-(3-(pentafluoro-λ6-sulfaneyl)phenyl)prop-2-en-1-one (0.0470 g, 0.101 mmol) as a colorless solid.

To a flame dried 5 mL microwave vial containing CrCl$_2$ (0.0742 g, 0.604 mmol) was added a solution of (Z)-1-(4-(5-chloro-2-methylphenyl)piperazine-1-yl)-3-(3-(pentafluoro-λ6-sulfaneyl)phenyl)prop-2-en-1-one (0.0470 g, 0.101 mmol) in dry degassed THF (1 mL) and the mixture was sparged with Ar for 15 min and added CH$_2$Icl (0.058 mL, 0.503 mmol) at rt, heated for 2 d at 80° C. The reaction was cooled to rt, diluted with EtOAc (50 mL) and washed with 1 M aqueous HCl (3×20 mL). The organic layer was dried (MgSO$_4$), filtered and concentrated under reduced pressure. The crude residue was purified by automated chromatography on SiO$_2$ (4 g column, liquid load CH$_2$Cl$_2$, 100% hexanes to 30% EtOAc/hexanes, product eluted at 20% EtOAc/hexanes) to give the product as a clear oil. The product was filtered through basic Al$_2$O$_3$(CH$_2$Cl$_2$/EtOAc, 1:1) concentrated and dried under high vacuum to give (4-(5-chloro-2-methylphenyl)piperazine-1-yl)((1RS,2SR)-2-(3-(pentafluoro-λ6-sulfaneyl)phenyl)cyclopropyl)methanone (0.0182 g, 0.0378 mmol, 19% (2 steps) (100% purity by ELSD)) as a colorless solid: Mp 112.9-116.1° C.; IR (CH$_2$Cl$_2$) 2854, 1640, 1490, 1439, 1225, 1036, 841 cm$^{-1}$; $^1$H NMR (400 MHz, CDCl$_3$) δ 7.62-7.59 (m, 2H), 7.38 (t, J=8.1 Hz, 1H), 7.29 (d, J=7.8 Hz, 1H), 7.06 (d, J=8.5 Hz, 1H), 6.95 (dd, J=8.1, 2.1 Hz, 1H), 6.70 (d, J=2.1 Hz, 1H), 3.84 (bd, J=12.8 Hz, 1H), 3.76-3.71 (m, 1H), 3.61 (ddd, J=12.8, 8.9, 3.2 Hz, 1H), 3.29 (ddd, J=12.8, 9.0, 3.1 Hz, 1H), 2.80-2.71 (m, 2H), 2.53 (td, J=8.9, 6.9 Hz, 1H), 2.31-2.23 (m, 2H), 2.20 (s, 3H), 2.15-2.09 (m, 1H), 1.91 (q, J=6.2 Hz, 1H), 1.43 (td, J=8.4, 5.6 Hz, 1H); $^{13}$C NMR (100 MHz, CDCl$_3$) δ 166.6, 153.9 (quint, J$_{CF}$=16.8 Hz), 151.8, 139.0, 132.0, 131.8, 131.0, 130.2, 128.6, 125.9 (quint, J$_{CF}$=4.5 Hz), 124.0 (quint, J$_{CF}$=4.6 Hz), 123.7, 119.7, 51.8, 51.6, 45.6, 42.2, 24.1, 24.0, 17.3, 11.0; $^{19}$F NMR (376 MHz, CDCl$_3$) δ 84.7 (quint, J=150.1 Hz, 1F), 62.9 (d, J=149.9 Hz, 4F); HRMS (ESI) m/z calcd for C$_{21}$H$_{23}$ClF$_5$N$_2$OS ([M+H]$^+$) 481.1134, found 481.1133.

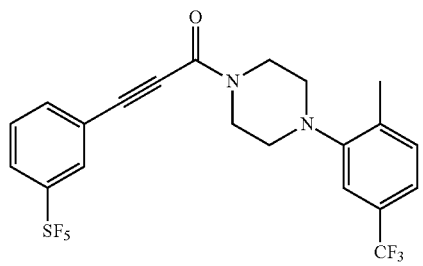

1-(4-(2-Methyl-5-(trifluoromethyl)phenyl)piperazine-1-yl)-3-(3-(pentafluoro-λ6-sulfaneyl)phenyl)-prop-2-yn-1-one. A solution of 3-(3-(pentafluoro-λ6-sulfaneyl)phenyl) propiolic acid (0.100 g, 0.367 mmol) and 1-(2-methyl-5-(trifluoromethyl)phenyl)piperazine hydrochloride (0.113 g, 0.404 mmol) in CH$_2$Cl$_2$ (3.7 mL) cooled to 0° C. was treated with Et$_3$N (0.20 mL, 1.47 mmol). The cooled solution was treated with T3P (50 wt. % solution in EtOAc, 0.39 mL, 0.551 mmol) dropwise and the reaction was stirred at 0° C. for 30 min, warmed to rt overnight, diluted with EtOAc (30 mL), washed with H$_2$O (20 mL), satd. aqueous NaHCO$_3$ (20 mL), dried (MgSO$_4$), filtered, and concentrated under reduced pressure. The crude residue was purified by automated chromatography on SiO$_2$ (4 g column, liquid load CH$_2$Cl$_2$, 100% hexanes to 40% EtOAc/hexanes), to give 1-(4-(2-methyl-5-(trifluoromethyl)phenyl)piperazine-1-yl)-3-(3-(pentafluoro-λ6-sulfaneyl)phenyl)prop-2-yn-1-one (0.150 g, 0.300 mmol, 82%) as a tan foam: IR (CH$_2$Cl$_2$) 2919, 2825, 2219, 1629, 1418, 1309, 1152, 1119, 840, 797, 730 cm$^{-1}$; $^1$H NMR (400 MHz, CDCl$_3$) δ 7.94 (t, J=1.8 Hz, 1H), 7.81 (dt, J=8.2, 1.1 Hz, 1H), 7.70 (d, J=7.8 Hz, 1H), 7.50 (t, J=8.2 Hz, 1H), 7.29 (q, J=7.8 Hz, 2H), 7.22 (s, 1H), 4.00 (app t, J=5.0 Hz, 2H), 3.87 (app t, J=5.0 Hz, 2H), 3.04 (app t, J=5.0 Hz, 2H), 2.94 (app t, J=5.0 Hz, 2H), 2.39 (s, 3H); $^{13}$C NMR (100 MHz, CDCl$_3$) δ 153.8 (quint, J$_{CF}$=18.2 Hz), 152.5, 150.9, 136.8, 135.1, 131.6, 129.7 (quint, J$_{CF}$=4.7 Hz), 129.1 (q, J$_{CF}$=32.3 Hz), 129.1, 127.4 (quint, J$_{CF}$=4.7 Hz), 124.1 (q, J$_{CF}$=271.8 Hz), 121.5, 120.6 (q, J$_{CF}$=3.9 Hz), 116.1 (q, J$_{CF}$=3.6 Hz), 88.4, 82.3, 51.9, 51.3, 47.4, 42.0, 17.9; $^{19}$F NMR (376 MHz, CDCl$_3$) δ 82.9 (quint, J=150.6 Hz, 1F), 62.6 (d, J=150.4 Hz, 4F), −62.3 (s, 3F); HRMS (ESI) m/z calcd for C$_{21}$H$_{19}$F$_8$N$_2$OS ([M+H]$^+$) 499.1085, found 499.1086.

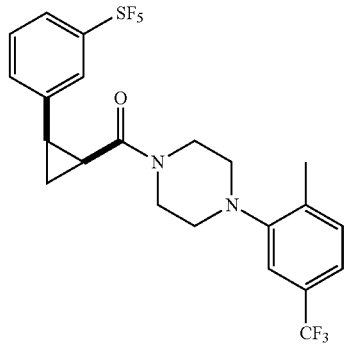

(4-(2-Methyl-5-(trifluoromethyl)phenyl)piperazine-1-yl) ((1RS,2SR)-2-(3-(pentafluoro-λ6-sulfaneyl)phenyl)cyclopropyl)methanone. A solution of 1-(4-(2-methyl-5-(trifluoromethyl)phenyl)-piperazine-1-yl)-3-(3-(pentafluoro-λ6-sulfaneyl)phenyl)prop-2-yn-1-one (0.100 g, 0.201 mmol) in EtOAc (2 mL) was treated with Lindlar's catalyst (5% Pd on CaCO$_3$, lead poisoned, 0.0214 g, equivalent to 5 mol % Pd). The reaction was placed under a balloon of H$_2$ (3 vacuum/ backfill cycles) and stirred at rt for 2 d, filtered through Celite, washed (EtOAc), and the combined filtrates were concentrated under reduced pressure. The crude residue was purified by automated chromatography on SiO$_2$ (4 g column, liquid load CH$_2$Cl$_2$, hexanes to 40% EtOAc/hexanes, product eluted at 30% EtOAc/hexanes) to give (Z)-1-(4-(2-methyl-5-(trifluoromethyl)phenyl)piperazine-1-yl)-3-(3-(pentafluoro-λ6-sulfaneyl)phenyl)prop-2-en-1-one (0.0938 g, 0.187 mmol) as a colorless foam.

A solution of CrCl$_2$ (0.138 g, 1.12 mmol) and (Z)-1-(4-(2-methyl-5-(trifluoromethyl)phenyl)-piperazine-1-yl)-3-(3-(pentafluoro-λ6-sulfaneyl)phenyl)prop-2-en-1-one (0.0938 g, 0.187 mmol) in dry degassed THF (1.9 mL) (degassed by sparging with Ar for 15 min) was treated with CH$_2$ICl (0.11 mL, 0.937 mmol) at rt, heated for 2 d at 80° C., cooled to rt, diluted with EtOAc (50 mL), and washed with 1 M aqueous HCl (3×20 mL). The organic layer was dried (MgSO$_4$), filtered and concentrated under reduced pressure. The crude residue was purified by automated chromatography on SiO$_2$ (4 g column, liquid load CH$_2$Cl$_2$, 100% hexanes to 40% EtOAc/hexanes, product eluted at 30% EtOAc/hexanes), filtered through basic Al$_2$O$_3$ (CH$_2$Cl$_2$/ EtOAc, 1:1), concentrated under reduced pressure, and dried under high vacuum to give (4-(2-methyl-5-(trifluoromethyl) phenyl)piperazine-1-yl)((1RS,2SR)-2-(3-(pentafluoro-λ6-sulfaneyl)-phenyl)cyclopropyl)methanone (0.0641 g, 0.125 mmol, 62% (2 steps) (100% purity by ELSD)) as a pale yellow oil: IR (CH$_2$Cl$_2$) 2917, 1638, 1438, 1417, 1337, 1307, 1120, 835, 758 cm$^{-1}$; $^1$H NMR (400 MHz, CDCl$_3$) δ 7.62-7.58 (m, 2H), 7.38 (t, J=7.8 Hz, 1H), 7.30 (d, J=7.8 Hz, 1H), 7.24-7.21 (m, 2H), 6.96 (s, 1H), 3.93 (d, J=13.0 Hz, 1H), 3.79 (dt, J=13.0, 3.8 Hz, 1H), 3.60 (ddd, J=12.6, 9.2, 3.1 Hz, 1H), 3.25 (ddd, J=12.6, 9.2, 3.0 Hz, 1H), 2.79 (ddt, J=20.7, 11.9, 3.8 Hz, 2H), 2.53 (td, J=8.9, 6.9 Hz, 1H), 2.31-2.20 (m, 5H), 2.16-2.10 (m, 1H), 1.92 (q, J=6.2 Hz, 1H), 1.43 (td, J=8.4, 5.6 Hz, 1H); $^{13}$C NMR (100 MHz, CDCl$_3$) δ 166.5, 153.9 (quint, J$_{CF}$=16.9 Hz), 151.0, 139.0, 136.8, 131.3, 130.3, 129.0 (q, J$_{CF}$=33.1 Hz), 128.5, 125.7 (quint, J$_{CF}$=4.6 Hz), 124.2 (q, J$_{CF}$=272.0 Hz), 123.9 (quint, J$_{CF}$=4.6 Hz), 120.3 (q, J$_{CF}$=3.9 Hz), 115.9 (q, J$_{CF}$=3.6 Hz), 51.7, 51.6, 45.5, 42.2, 24.0 (2C), 24.0, 17.8, 10.9; $^{19}$F NMR (376 MHz, CDCl$_3$) δ 84.5 (quint, J=150.0 Hz, 1F), 62.7 (d, J=149.8 Hz, 4F), −62.4 (s, 3F); HRMS (ESI) m/z calcd for $C_{22}H_{23}F_8N_2OS$ ([M+H]$^+$) 515.1398, found 515.1380.

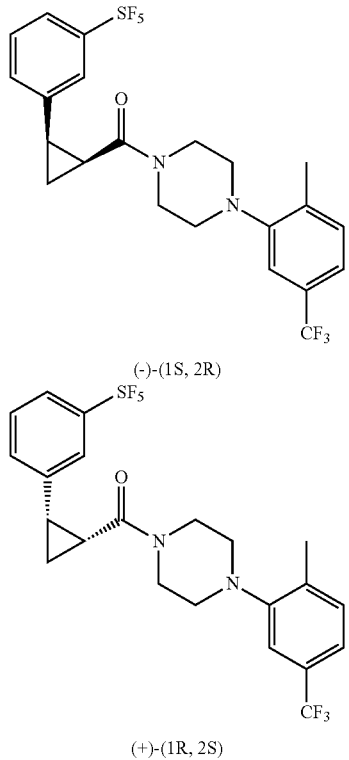

Racemic (4-(2-methyl-5-(trifluoromethyl)phenyl)-106-iperazine-1-yl)((1RS,2SR)-2-(3-(pentafluoro-λ6-sulfaneyl)phenyl)cyclopropyl)methanone was separated on a SFC Chiralpak-IC semiprep (250×10 mm) column (30% Methanol:CO$_2$, 7 mL/min, p=100 bar, 220 nm) injection volume 90 μL, 20 mg/mL) to give (4-(2-methyl-5-(trifluoromethyl)phenyl)piperazin-1-yl)((1S,2R)-2-(3-(pentafluoro-λ6-sulfaneyl)phenyl)-cyclopropyl)methanone (retention time 3.25 min) as a colorless viscous oil (100% purity by ELSD): [α]$^{18}_D$ −104.7 (c 0.84, MeOH); $^1$H NMR (300 MHz, CDCl$_3$) δ 7.62-7.58 (m, 2H), 7.38 (t, J=7.7 Hz, 1H), 7.31-7.24 (m, 3H), 6.96 (s, 1H), 3.94-3.89 (m, 1H), 3.81-3.75 (m, 1H), 3.65-3.56 (m, 1H), 3.31-3.22 (m, 1H), 2.84-2.74 (m, 2H), 2.53 (td, J=9.3, 6.9 Hz, 1H), 2.32-2.21 (m, 5H), 2.19-2.11 (m, 1H), 1.93 (q, J=5.7 Hz, 1H), 1.43 (td, J=8.4, 5.7 Hz, 1H). The enantiomeric excess was >99.9% ee (SFC Chiralpak-IC (250×10 mm); 30% Methanol:CO$_2$, 7 mL/min, p=100 bar, 220 nm; retention time: 3.3 min).

(4-(2-Methyl-5-(trifluoromethyl)phenyl)piperazin-1-yl)((1R,2S)-2-(3-(pentafluoro-λ6-sulfaneyl)phenyl)-cyclopropyl)methanone (retention time 3.60 min) was obtained as a colorless viscous oil (100% purity by ELSD): [α]$^{18}_D$ +103.4 (c 0.87, MeOH); $^1$H NMR (300 MHz, CDCl$_3$) δ 8.54-7.81 (m, 2H), 7.62-7.59 (m, 2H), 7.38 (t, J=7.8 Hz, 1H), 7.31-7.24 (m, 3H), 6.96 (s, 1H), 3.94-3.88 (m, 1H), 3.81-3.75 (m, 1H), 3.65-3.56 (m, 1H), 3.31-3.22 (m, 1H), 2.84-2.74 (m, 2H), 2.53 (td, J=9.0, 7.2 Hz, 1H), 2.32-2.22 (m, 5H), 2.18-2.11 (m, 1H), 1.93 (q, J=5.7 Hz, 1H), 1.43 (td, J=8.4, 5.7 Hz, 1H). The enantiomeric excess was >99.9% ee (SFC Chiralpak-IC (250×10 mm); 30% Methanol:CO$_2$, 7 mL/min, p=100 bar, 220 nm; retention time: 3.6 min).

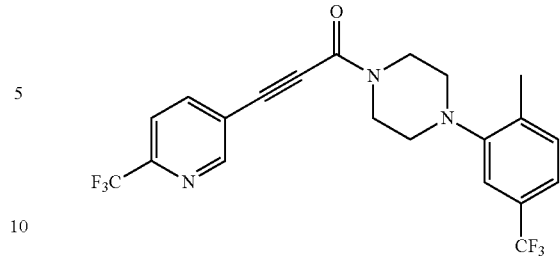

1-(4-(2-Methyl-5-(trifluoromethyl)phenyl)piperazin-1-yl)-3-(6-(trifluoromethyl)pyridin-3-yl)prop-2-yn-1-one. A solution of methyl 3-(5-chloropyridin-2-yl)propionate (0.500 g, 2.18 mmol) in THF (4 mL) was treated with 2 M NaOH (1.2 mL, 2.40 mmol) and the mixture was stirred at rt for 3 h, acidified with 1 M aqueous HCl, and extracted with EtOAc (3×20 mL). The combined organic layers were dried (MgSO$_4$), filtered and concentrated under reduced pressure to give the product (0.422 g, 1.96 mmol) as a colorless solid. This solid was taken on to the coupling reaction with no further purification.

A solution of 3-(6-(trifluoromethyl)pyridin-3-yl)propionic acid (0.422 g, 1.96 mmol) and 1-(2-methyl-5-(trifluoromethyl)phenyl)piperazine hydrochloride (0.661 g, 2.35 mmol) in CH$_2$Cl$_2$ (19 mL) cooled to 0° C. was treated Et$_3$N (0.83 mL, 5.88 mmol). The cooled solution was treated with T3P (50% solution in EtOAc) (2.1 mL, 2.94 mmol) dropwise and the reaction was stirred at 0° C. for 30 min, warmed to rt overnight, diluted with EtOAc (50 mL), washed with H$_2$O (20 mL), satd. aqueous NaHCO$_3$ (20 mL), dried (MgSO$_4$), filtered, and concentrated under reduced pressure. The crude material was purified by chromatography on SiO$_2$ (4 g column, 1:1 hexanes:EtOAc), to give the product (0.781 g, 1.77 mmol, 81% (2 steps)) as a pale yellow solid: Mp 110.7-113.5° C.; IR (CH$_2$Cl$_2$) 3652, 2981, 2890, 1635, 1382, 1337, 1240, 1150, 1087, 956 cm$^{-1}$; $^1$H NMR (400 MHz, CDCl$_3$) δ 8.85 (dd, J=1.6, 0.6 Hz, 1H), 8.04 (ddd, J=8.2, 1.6, 0.6 Hz, 1H), 7.72 (dd, J=8.2, 0.6 Hz, 1H), 7.32-7.26 (m, 2H), 7.21 (s, 1H), 3.99 (t, J=5.0 Hz, 2H), 3.87 (t, J=5.0 Hz, 2H), 3.04 (t, J=5.0 Hz, 2H), 2.95 (t, J=5.0 Hz, 2H), 2.39 (s, 3H); $^{13}$C NMR (100 MHz, CDCl$_3$) δ 152.5, 152.0, 150.8, 148.2 (q, J$_{CF}$=35.3 Hz), 140.7, 136.8, 131.6, 129.1 (q, J$_{CF}$=32.3 Hz), 124.1 (q, J$_{CF}$=272.1 Hz), 121.0 (q, J$_{CF}$=274.4 Hz), 120.7, 120.6 (q, J$_{CF}$=3.9 Hz), 120.0 (q, J$_{CF}$=2.8 Hz), 116.1 (q, J$_{CF}$=3.6 Hz), 85.6, 51.8, 51.3, 47.4, 42.0, 17.9; $^{19}$F NMR (376 MHz, CDCl$_3$) δ −62.3 (s, 3F). −68.2 (s, 3F); HRMS (ESI) m/z calcd for $C_{21}H_{18}F_6N_3O$ ([M+H]$^+$) 442.1349, found 442.1345.

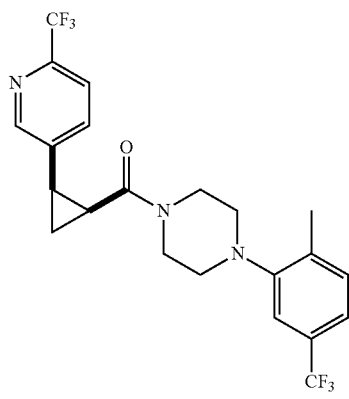

(4-(2-Methyl-5-(trifluoromethyl)phenyl)piperazin-1-yl)((1RS,2SR)-2-(6-(trifluoromethyl)pyridin-3-yl)cyclopropyl)methanone. A solution of 1-(4-(2-methyl-5-(trifluoromethyl)phenyl)piperazin-1-yl)-3-(6-(trifluoromethyl)pyridin-3-yl)prop-2-yn-1-one (0.720 g, 1.63 mmol) in EtOAc (16 mL) at rt was treated with quinoline (1.0 mL, 8.16 mmol) and 5% Pd/BaSO$_4$ (0.0347 g, 0.0163 mmol, equivalent to 1 mol % Pd) and the reaction was stirred under an atmosphere of H$_2$ (3×backfill cycles) for 4 h. Analysis by TLC (hexanes/EtOAc, 1:1) indicated that the starting material had been mostly consumed. The reaction was filtered (eluting with EtOAc), and the filtrate was washed with 1 M aqueous HCl (3×30 mL), dried (Na$_2$SO$_4$), filtered and concentrated under reduced pressure. The crude residue was purified by chromatography on SiO$_2$ (hexanes/EtOAc, 1:1 to EtOAc) to give (Z)-1-(4-(2-methyl-5-(trifluoromethyl)-phenyl)piperazin-1-yl)-3-(6-(trifluoromethyl)pyridin-3-yl)prop-2-en-1-one (0.640 g, 1.44 mmol) as a yellow/orange oil.

A solution of CrCl$_2$ (1.06 g, 8.66 mmol) and (Z)-1-(4-(2-methyl-5-(trifluoromethyl)phenyl)-piperazin-1-yl)-3-(6-(trifluoromethyl)pyridin-3-yl)prop-2-en-1-one (0.640 g, 1.44 mmol) in dry degassed THF (14 mL) was sparged with Ar for 5 min and treated with CH$_2$ICl (0.83 mL, 7.22 mmol) at rt and under Ar atmosphere. The reaction mixture was stirred for 2 d at 80° C., cooled to rt, diluted with EtOAc (50 mL), and washed with 1 M aqueous HCl (3×20 mL). The organic layer was dried (MgSO$_4$), filtered and concentrated under reduced pressure. The crude material was purified by chromatography on SiO$_2$ (4:1, EtOAc:hexanes). filtered through basic Al$_2$O$_3$ (eluting with EtOAc) concentrated under reduced pressure, and dried under high vacuum to give (4-(2-methyl-5-(trifluoromethyl)phenyl)piperazin-1-yl)((1RS,2SR)-2-(6-(trifluoromethyl)pyridin-3-yl)cyclopropyl)methanone (0.280 g, 0.612 mmol, 37% (2 steps) (100% purity by ELSD)) as an orange oil: IR (CH$_2$Cl$_2$) 2981, 1640, 1418, 1339, 1309, 1166, 1126, 1035, 828 cm$^{-1}$; $^1$H NMR (400 MHz, CDCl$_3$) δ 8.64 (s, 1H), 7.60 (t, J=2.0 Hz, 2H), 7.24 (t, J=2.0 Hz, 2H), 7.02 (s, 1H), 3.78-3.65 (m, 3H), 3.53-3.46 (m, 1H), 2.92-2.87 (m, 1H), 2.80-2.75 (m, 1H), 2.59-2.53 (m, 1H), 2.47-2.35 (m, 4H), 2.30 (s, 3H), 1.95 (q, J=5.6 Hz, 1H), 1.49 (td, J=8.4, 5.6 Hz, 1H); $^{13}$C NMR (100 MHz, CDCl$_3$) δ 166.4, 150.8, 150.5, 146.3 (q, J$_{CF}$=34.8 Hz), 136.9, 136.7, 135.5, 131.4, 129.1 (q, J$_{CF}$=32.2 Hz), 124.1 (q, J$_{CF}$=272.1 Hz), 121.6 (q, J$_{CF}$=273.7 Hz), 120.4 (q, J$_{CF}$=3.9 Hz), 119.8 (q, J$_{CF}$=2.6 Hz), 115.9 (q, J$_{CF}$=3.7 Hz), 52.0, 51.5, 45.6, 42.3, 23.7, 21.5, 17.9, 11.0; $^{19}$F NMR (376 MHz, CDCl$_3$) δ −62.4 (s, 3F), −67.8 (s, 3F); HRMS (ESI) m/z calcd for C$_{22}$H$_{22}$F$_6$N$_3$O ([M+H]$^+$) 458.1662, found 458.1660.

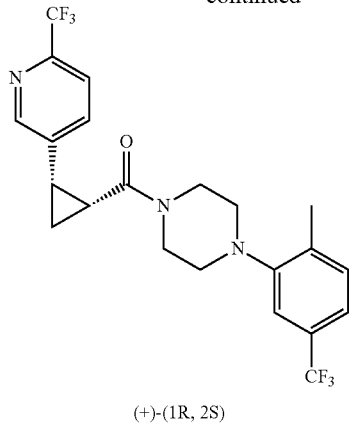

(+)-(1R, 2S)

Racemic (4-(2-methyl-5-(trifluoromethyl)phenyl)piperazin-1-yl)((1RS,2SR)-2-(6-(trifluoromethyl)pyridin-3-yl)cyclopropyl)methanone was separated on a SFC Chiralpak-IC semiprep (250×10 mm) column (15% Methanol/CO$_2$, 7 mL/min, 220 nm, p=100 bar, 20 mg/mL in MeOH) to give (4-(2-methyl-5-(trifluoromethyl)phenyl)piperazin-1-yl)((1S,2R)-2-(6-(trifluoromethyl)pyridin-3-yl)cyclopropyl)methanone (retention time 7.65 min) as a colorless solid (100% purity by ELSD): [α]$^{19}_D$ −134.8 (c 0.90, MeOH); $^1$H NMR (300 MHz, CDCl$_3$) δ 8.64 (s, 1H), 7.60 (s, 2H), 7.26 (s, 4H), 7.04 (s, 1H), 3.75-3.64 (m, 3H), 3.55-3.47 (m, 1H), 2.94-2.87 (m, 1H), 2.82-2.74 (m, 1H), 2.56 (q, J=8.4 Hz, 1H), 2.49-2.34 (m, 3H), 2.31 (s, 3H), 1.96 (q, J=5.8 Hz, 1H), 1.50 (td, J=8.4, 5.8 Hz, 1H). The enantiomeric excess was >99.9% ee (SFC Chiralpak-IC (250×10 mm); 15% Methanol:CO$_2$, 7 mL/min, p=100 bar, 220 nm; retention time: 7.8 min).

(4-(2-Methyl-5-(trifluoromethyl)phenyl)piperazin-1-yl)((1R,2S)-2-(6-(trifluoromethyl)pyridin-3-yl)-cyclopropyl)methanone (retention time 8.38 min) was obtained as a colorless solid (100% purity by ELSD): [α]$^{19}_D$+128.2 (c 1.08, MeOH); $^1$H NMR (300 MHz, CDCl$_3$) δ 8.64 (s, 1H), 7.60 (s, 2H), 7.26 (s, 2H), 7.04 (s, 1H), 3.77-3.63 (m, 3H), 3.55-3.47 (m, 1H), 2.93-2.87 (m, 1H), 2.81-2.75 (m, 1H), 2.61-2.52 (m, 1H), 2.50-2.35 (m, 3H), 2.31 (s, 3H), 1.96 (q, J=5.8 Hz, 1H), 1.50 (td, J=8.4, 5.8 Hz, 1H). The enantiomeric excess was >99.9% ee (SFC Chiralpak-IC (250×10 mm); 15% Methanol:CO$_2$, 7 mL/min, p=100 bar, 220 nm; retention time: 8.4 min).

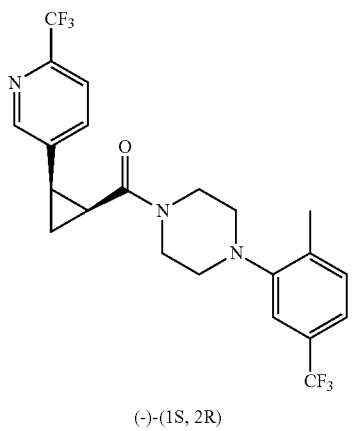

(−)-(1S, 2R)

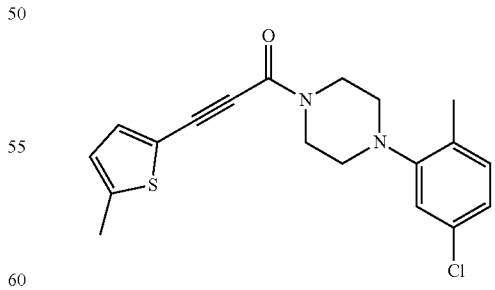

1-(4-(5-Chloro-2-methylphenyl)piperazin-1-yl)-3-(5-methylthiophen-2-yl)prop-2-yn-1-one. A solution of 3-(5-methylthiophen-2-yl)propiolic acid (0.0750 g, 0.451 mmol) and 1-(5-chloro-2-methylphenyl)-piperazine hydrochloride (0.134 g, 0.542 mmol) in CH$_2$Cl$_2$ (4.5 mL) cooled to 0° C. was treated with Et$_3$N (0.19 mL, 1.35 mmol). The cooled solution was treated with T3P (50 wt. % solution in EtOAc, 0.48 mL, 0.677 mmol) dropwise and the reaction was stirred at 0° C. for 30 min, warmed to rt overnight, diluted with CH$_2$Cl$_2$ (30 mL), washed with 1 M aqueous HCl (20 mL), dried (MgSO$_4$), filtered, and concentrated under reduced pressure. The crude residue was purified by automated chromatography on SiO$_2$ (4 g column, liquid load CH$_2$Cl$_2$, hexanes to 40% EtOAc/hexanes), to give 1-(4-(5-chloro-2-methylphenyl)piperazin-1-yl)-3-(5-methylthiophen-2-yl)prop-2-yn-1-one (0.0620 g, 0.173 mmol, 38%) as a colorless solid: Mp 114.4-116.0° C.; IR (CH$_2$Cl$_2$) 2919, 2197, 1643, 1593, 1489, 1426, 1224, 1025, 806 cm$^{-1}$; $^1$H NMR (400 MHz, CDCl$_3$) δ 7.24 (d, J=3.6 Hz, 1H), 7.10 (d, J=8.1 Hz, 1H), 6.98 (dd, J=8.1, 1.9 Hz, 1H), 6.94 (d, J=1.9 Hz, 1H), 6.69 (dd, J=3.6, 0.8 Hz, 1H), 3.91 (app t, J=5.0 Hz, 2H), 3.81 (app t, J=5.0 Hz, 2H), 2.94 (app t, J=5.0 Hz, 2H), 2.86 (app t, J=5.0 Hz, 2H), 2.49 (s, 3H), 2.28 (s, 3H); $^{13}$C NMR (100 MHz, CDCl$_3$) δ 153.1, 151.7, 145.5, 135.7, 132.0, 131.8, 130.9, 125.8, 123.6, 119.7, 117.4, 85.4, 84.5, 51.8, 51.3, 47.2, 41.8, 17.4, 15.5; HRMS (ESI) m/z calcd for C$_{19}$H$_{20}$ClN$_2$OS ([M+H]$^+$) 359.0979, found 359.0978.

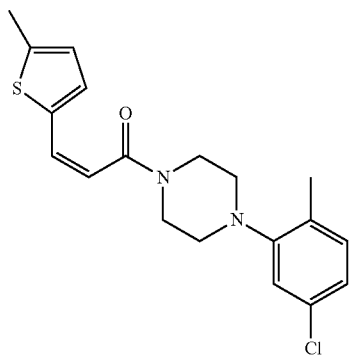 [SMILES: Cc1ccc(/C=C\C(=O)N2CCN(c3cc(Cl)ccc3C)CC2)s1]

(Z)-1-(4-(5-Chloro-2-methylphenyl)piperazin-1-yl)-3-(5-methylthiophen-2-yl)prop-2-en-1-one. A solution of 1-(4-(5-chloro-2-methylphenyl)piperazin-1-yl)-3-(5-methylthiophen-2-yl)prop-2-yn-1-one (0.0620 g, 0.173 mmol) in EtOAc (1.7 mL) was treated with Lindlar's catalyst (5% Pd on CaCO$_3$, lead poisoned, 0.00735 g, equivalent to 2 mol % Pd) and quinoline (10 μL, 0.172 mmol). The reaction was placed under a balloon of H$_2$ (4 vacuum/backfill cycles) and stirred at rt for 6 h, filtered through Celite, washed (EtOAc), and the combined filtrates were washed with 1 M aqueous HCl, dried (Na$_2$SO$_4$), filtered, and concentrated under reduced pressure. The crude residue was purified by automated chromatography on SiO$_2$ (4 g column, liquid load CH$_2$Cl$_2$, 10% EtOAc/hexanes to 40% EtOAc/hexanes) to give (Z)-1-(4-(5-chloro-2-methylphenyl)piperazin-1-yl)-3-(5-methylthiophen-2-yl)prop-2-en-1-one (0.0263 g, 0.0729 mmol, 42% (100% purity by ELSD)) as a colorless solid: Mp 113.2-116.4° C.; IR (CH$_2$Cl$_2$) 2917, 2818, 1643, 1593, 1489, 1435, 1226, 1039, 805 cm$^{-1}$; $^1$H NMR (400 MHz, CDCl$_3$) δ 7.09 (dd, J=8.1, 0.8 Hz, 1H), 6.98-6.95 (m, 2H), 6.90 (d, J=2.1 Hz, 1H), 6.75 (d, J=12.4 Hz, 1H), 6.67 (dq, J=3.5, 1.1 Hz, 1H), 5.88 (d, J=12.4 Hz, 1H), 3.87 (app t, J=5.0 Hz, 2H), 3.67 (app t, J=5.0 Hz, 2H), 2.90 (app t, J=5.0 Hz, 2H), 2.78 (app t, J=5.0 Hz, 2H), 2.48 (d, J=0.8 Hz, 3H), 2.26 (s, 3H); $^{13}$C NMR (100 MHz, CDCl$_3$) δ 166.9, 151.9, 143.7, 135.9, 132.0, 131.7, 131.2, 130.9, 128.6, 125.2, 123.6, 119.7, 117.2, 51.7, 51.3, 46.6, 41.7, 17.4, 15.5; HRMS (ESI) m/z calcd for C$_{19}$H$_{22}$ClN$_2$OS ([M+H]$^+$) 361.1136, found 361.1135.

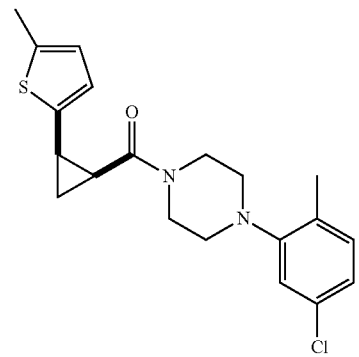

(4-(5-Chloro-2-methylphenyl)piperazin-1-yl)((1RS,2SR)-2-(5-methylthiophen-2-yl)cyclopropyl)-methanone. A solution of CrCl$_2$ (0.0511 g, 0.416 mmol) and (Z)-1-(4-(5-chloro-2-methylphenyl)piperazin-1-yl)-3-(5-methylthiophen-2-yl)prop-2-en-1-one (0.0250 g, 0.0693 mmol) in dry degassed THF (0.7 mL) was sparged with Ar for 5 min and treated with CH$_2$ICl (40 uL, 0.346 mmol) at rt, heated for 20 h at 80° C., cooled to rt, combined, diluted with Et$_2$O (50 mL), and washed with 1 M aqueous HCl (3×20 mL). The organic layer was dried (MgSO$_4$), filtered and concentrated under reduced pressure. The crude residue was purified by automated chromatography on SiO$_2$ (4 g column, liquid load CH$_2$Cl$_2$, hexanes to 40% EtOAc/hexanes) to give the product as a yellow oil. The product was filtered through basic Al$_2$O$_3$ (eluting with 1:1 CH$_2$Cl$_2$/EtOAc) concentrated under reduced pressure and dried under high vacuum to give (4-(5-chloro-2-methylphenyl)piperazin-1-yl)((1RS,2SR)-2-(5-methylthiophen-2-yl)cyclopropyl)methanone (0.0154 g, 0.0411 mmol, 59% (100% purity by ELSD)) as a pale yellow oil: IR (CH$_2$Cl$_2$) 2918, 1643, 1593, 1490, 1462, 1436, 1226, 1029, 802 cm$^{-1}$; $^1$H NMR (400 MHz, CDCl$_3$) δ 7.08 (dd, J=8.1, 0.4 Hz, 1H), 6.97 (dd, J=8.1, 2.1 Hz, 1H), 6.79 (d, J=2.1 Hz, 1H), 6.57-6.55 (m, 2H), 3.96 (d, J=13.0 Hz, 1H), 3.85 (dt, J=13.0, 3.5 Hz, 1H), 3.63 (ddd, J=13.0, 8.9, 3.5 Hz, 1H), 3.34 (ddd, J=13.0, 9.0, 3.2 Hz, 1H), 2.79 (ddt, J=19.3, 11.2, 4.1 Hz, 2H), 2.52 (td, J=8.9, 6.8 Hz, 1H), 2.45-2.36 (m, 5H), 2.24 (s, 3H), 2.16 (ddd, J=8.9, 8.2, 6.3 Hz, 1H), 1.77 (td, J=6.3, 5.6 Hz, 1H), 1.38 (ddd, J=8.9, 8.2, 5.6 Hz, 1H). $^{13}$C NMR (100 MHz, CDCl$_3$) δ 167.2, 152.1, 138.2, 137.5, 131.9, 131.7, 131.1, 125.0, 124.1, 123.5, 119.7, 51.8, 51.7, 45.7, 42.4, 24.1, 19.3, 17.3, 15.3, 12.2; HRMS (ESI) m/z calcd for C$_{19}$H$_{24}$ClN$_2$OS ([M+H]$^+$) 375.1292, found 375.1292.

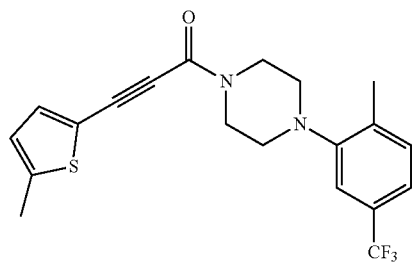 [SMILES: Cc1ccc(C#CC(=O)N2CCN(c3cc(C(F)(F)F)ccc3C)CC2)s1]

1-(4-(2-Methyl-5-(trifluoromethyl)phenyl)piperazin-1-yl)-3-(5-methylthiophen-2-yl)prop-2-yn-1-one. A solution of 3-(5-methylthiophen-2-yl)propiolic acid (0.0592 g, 0.356 mmol) and 1-(2-methyl-5-(trifluoromethyl)phenyl)piperazine hydrochloride (0.100 g, 0.356 mmol) in CH$_2$Cl$_2$ (3.6 mL) cooled to 0° C. was treated with Et$_3$N (0.20 mL, 1.42 mmol). The cooled solution was treated with T3P (50 wt. % solution in EtOAc, 0.38 mL, 0.534 mmol) dropwise and the reaction was stirred at 0° C. for 30 min, warmed to rt overnight, diluted with CH$_2$Cl$_2$ (30 mL), washed with 1 M aqueous HCl (20 mL), dried (MgSO$_4$), filtered, and concentrated under reduced pressure. The crude material was purified by automated chromatography on SiO$_2$ (4 g column, liquid load CH$_2$Cl$_2$, hexanes to 40% EtOAc/hexanes), to give 1-(4-(2-methyl-5-(trifluoromethyl)phenyl)piperazin-1-yl)-3-(5-methylthiophen-2-yl)prop-2-yn-1-one (0.0685, 0.175 mmol, 49% (100% purity by ELSD)) as a yellow solid. Mp 145.7-149.3° C.; IR (CH$_2$Cl$_2$) 2919, 2199, 1635, 1420, 1340, 1309, 1120, 1029, 955, 732 cm$^{-1}$; $^1$H NMR (400 MHz, CDCl$_3$) δ 7.31-7.24 (m, 3H), 7.21 (s, 1H), 6.69 (dd, J=3.6, 0.8 Hz, 1H), 3.94 (app t, J=5.0 Hz, 2H), 3.83 (app t, J=5.0 Hz, 2H), 3.01 (app t, J=5.0 Hz, 2H), 2.91 (app t, J=5.0 Hz, 2H), 2.49 (d, J=0.8 Hz, 3H), 2.38 (s, 3H); $^{13}$C NMR (100 MHz, CDCl$_3$) δ 153.2, 151.0, 145.5, 136.8, 135.7, 131.5, 129.0 (q, $J_{CF}$=32.2 Hz), 125.9, 124.1 (q, $J_{CF}$=272.1 Hz), 120.4 (q, $J_{CF}$=3.8 Hz), 117.4, 116.0 (q, $J_{CF}$=3.6 Hz), 85.4, 84.5, 51.8, 51.3, 47.3, 41.8, 17.9, 15.5; $^{19}$F NMR (376 MHz, CDCl$_3$) δ −62.2 (s, 3F); HRMS (ESI) m/z calcd for C$_{20}$H$_{20}$F$_3$N$_2$OS ([M+H]$^+$) 393.1243, found 393.1241.

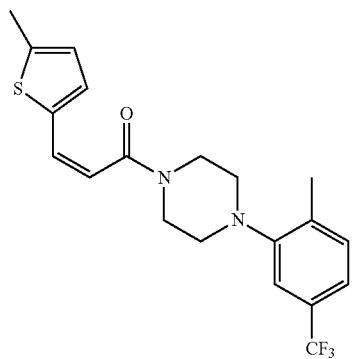 [SMILES: Cc1ccc(/C=C\C(=O)N2CCN(c3cc(C(F)(F)F)ccc3C)CC2)s1]

(Z)-1-(4-(5-Chloro-2-methylphenyl)piperazin-1-yl)-3-(3-(trifluoromethyl)phenyl)prop-2-en-1-one. A solution of 1-(4-(2-methyl-5-(trifluoromethyl)phenyl)piperazin-1-yl)-3-(5-methylthiophen-2-yl)prop-2-yn-1-one (0.0650 g, 0.166 mmol) in EtOAc (1.7 mL) was treated with Lindlar's catalyst (5% Pd on CaCO$_3$, lead poisoned, 0.0176 g, equivalent to 5 mol % Pd). The reaction was placed under a balloon of H$_2$ (3 vacuum/backfill cycles) and stirred at rt for 3 d, filtered through Celite, washed (EtOAc), and the combined filtrates were concentrated under reduced pressure. The crude residue was purified by automated chromatography on SiO$_2$ (4 g column, liquid load CH$_2$Cl$_2$, hexanes to 40% EtOAc/hexanes, product eluted at 20% EtOAc/hexanes) to give (Z)-1-(4-(5-chloro-2-methylphenyl)piperazin-1-yl)-3-(3-(trifluoromethyl)-phenyl)prop-2-en-1-one (0.0443 g, 0.112 mmol, 68%) as a colorless solid: Mp 125.8-128.1° C.; IR (CH$_2$Cl$_2$) 2919, 2857, 1635, 1435, 1339, 1308, 1118, 1040, 806 cm$^{-1}$; $^1$H NMR (400 MHz, CDCl$_3$) δ 7.28 (d, J=8.0 Hz, 1H), 7.25 (dd, J=8.0, 1.3 Hz, 1H), 7.15 (s, 1H), 6.96 (d, J=3.5 Hz, 1H), 6.76 (d, J=12.4 Hz, 1H), 6.67 (dq, J=3.5, 1.0 Hz, 1H), 5.89 (d, J=12.4 Hz, 1H), 3.89 (app t, J=4.8 Hz, 2H), 3.69 (app t, J=4.8 Hz, 2H), 2.94 (app t, J=4.8 Hz, 2H), 2.82 (app t, J=4.8 Hz, 2H), 2.47 (d, J=1.0 Hz, 3H), 2.36 (s, 3H); $^{13}$C NMR (100 MHz, CDCl$_3$) δ 166.9, 151.2, 143.7, 136.8, 135.9, 131.5, 131.2, 128.9 (q, $J_{CF}$=32.2 Hz), 128.7, 125.2, 124.1 (q, $J_{CF}$=272.1 Hz), 120.3 (q, $J_{CF}$=3.7 Hz), 117.2, 115.9 (q, $J_{CF}$=3.7 Hz), 51.6, 51.3, 46.6, 41.7, 17.9, 15.4; $^{19}$F NMR (376 MHz, CDCl$_3$) δ −62.2 (s, 3F); HRMS (ESI) m/z calcd for C$_{20}$H$_{22}$F$_3$N$_2$OS ([M+H]$^+$) 395.1399, found 393.1399.

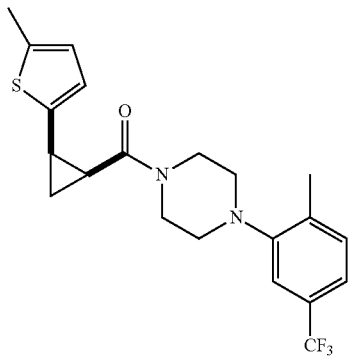

(4-(2-Methyl-5-(trifluoromethyl)phenyl)piperazin-1-yl)((1RS,2SR)-2-(5-methylthiophen-2-yl)cyclopropyl)methanone. A solution of CrCl$_2$ (0.105 g, 0.851 mmol) and (Z)-1-(4-(5-chloro-2-methylphenyl)piperazin-1-yl)-3-(3-(trifluoromethyl)phenyl)prop-2-en-1-one (0.0420 g, 0.142 mmol) in dry degassed THF (1.1 mL) was sparged with Ar for 5 min and treated with CH$_2$ICl (62 uL, 0.532 mmol) at rt, heated for 22 h at 80° C., cooled to rt, diluted with Et$_2$O (50 mL), and washed with 1 M aqueous HCl (3×20 mL). The organic layer was dried (MgSO$_4$), filtered and concentrated under reduced pressure. The crude residue was purified by automated chromatography on SiO$_2$ (4 g column, liquid load CH$_2$Cl$_2$, 100% hexanes to 40% EtOAc/hexanes) to give a clear oil that was filtered through basic Al$_2$O$_3$ (eluting with 1:1 CH$_2$Cl$_2$/EtOAc), concentrated under reduced pressure, and dried under high vacuum to give (4-(2-methyl-5-(trifluoromethyl)phenyl)piperazin-1-yl)((1RS,2SR)-2-(5-methylthiophen-2-yl)cyclopropyl)methanone (0.0187 g, 0.0458 mmol, 43% (100% purity by ELSD)) as pale yellow viscous oil: IR (CH$_2$Cl$_2$) 2921, 2822, 1639, 1464, 1434, 1417, 1337, 1306, 1116, 1079, 1031, 801 cm$^{-1}$; $^1$H NMR (400 MHz, CDCl$_3$) δ 7.26 (d, J=8.4 Hz, 1H), 7.24 (dd, J=8.4, 1.4 Hz, 1H), 7.04 (s, 1H), 6.58 (t, J=4.7 Hz, 1H), 6.55 (dt, J=3.5, 1.0 Hz, 1H), 4.00 (bd, J=13.0 Hz, 1H), 3.88 (dt, J=13.0, 3.5 Hz, 1H), 3.64 (ddd, J=12.4, 9.0, 3.2 Hz, 1H), 3.34 (ddd, J=13.0, 9.2, 2.9 Hz, 1H), 2.82 (ddt, J=19.4, 11.6, 3.7 Hz, 2H), 2.53 (td, J=8.6, 6.6 Hz, 1H), 2.48-2.40 (m, 1H), 2.38 (d, J=1.0 Hz, 3H), 2.34 (s, 3H), 2.17 (td, J=8.6, 6.6 Hz, 1H), 1.77 (q, J=6.0 Hz, 1H), 1.38 (td, J=8.6, 5.3 Hz, 1H); $^{13}$C NMR (100 MHz, CDCl$_3$) δ 167.2, 151.4, 138.3, 137.6, 136.9, 131.4, 128.9 (q, $J_{CF}$=32.0 Hz), 124.9, 124.3 (q, $J_{CF}$=272.1 Hz), 124.2, 120.3 (q, $J_{CF}$=4.0 Hz), 116.0 (q, $J_{CF}$=3.7 Hz), 51.8, 51.7, 45.7, 42.3, 24.1, 19.4, 17.9, 15.1, 12.3; $^{19}$F NMR (376 MHz, CDCl$_3$) δ −62.2 (s, 3F); HRMS (ESI) m/z calcd for C$_{21}$H$_{24}$F$_3$N$_2$OS ([M+H]$^+$) 409.1556, found 409.1555.

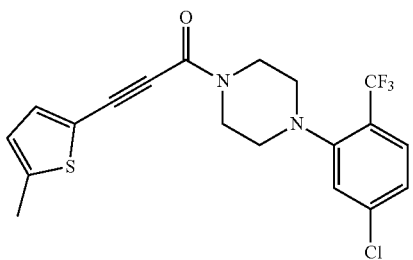 [SMILES: Cc1ccc(C#CC(=O)N2CCN(c3cc(Cl)ccc3C(F)(F)F)CC2)s1]

1-(4-(5-Chloro-2-(trifluoromethyl)phenyl)piperazin-1-yl)-3-(5-methylthiophen-2-yl)prop-2-yn-1-one. A solution of 3-(5-methylthiophen-2-yl)propiolic acid (0.0770 g, 0.463 mmol) and 1-(5-chloro-2-(trifluoromethyl)phenyl)piperazine hydrochloride (0.153 g, 0.510 mmol) in $CH_2Cl_2$ (4.6 mL) cooled to 0° C. was treated with $Et_3N$ (0.26 mL, 1.85 mmol). The cooled solution was treated with T3P (50 wt. % solution in EtOAc, 0.49 mL, 0.695 mmol) dropwise and the reaction was stirred at 0° C. for 30 min, warmed to rt overnight, diluted with $CH_2Cl_2$ (30 mL), washed with $H_2O$ (20 mL), satd. aqueous $NaHCO_3$ (20 mL), dried ($MgSO_4$), filtered, and concentrated under reduced pressure. The crude material was purified by automated chromatography on $SiO_2$ (4 g column, liquid load $CH_2Cl_2$, hexanes to 40% EtOAc/hexanes), to give 1-(4-(5-chloro-2-(trifluoromethyl)phenyl)piperazin-1-yl)-3-(5-methylthiophen-2-yl)prop-2-yn-1-one (0.135 g, 0.326 mmol, 70%) as a light orange waxy solid: IR ($CH_2Cl_2$) 2918, 2200, 1629, 1596, 1425, 1309, 1224, 1144, 1120, 1027, 809 cm$^{-1}$; $^1$H NMR (400 MHz, $CDCl_3$) δ 7.58 (d, J=8.4 Hz, 1H), 7.27-7.23 (m, 3H), 6.69 (dd, J=3.6, 0.8 Hz, 1H), 3.91 (app t, J=4.9 Hz, 2H), 3.81 (app t, J=5.0 Hz, 2H), 2.98 (app t, J=5.0 Hz, 2H), 2.91 (app t, J=5.0 Hz, 2H), 2.49 (d, J=0.8 Hz, 3H); $^{13}$C NMR (100 MHz, $CDCl_3$) δ 153.2, 152.7, 152.6, 145.5, 138.8, 135.7, 128.5 (q, $J_{CF}$=5.4 Hz), 125.9, 125.8 (q, $J_{CF}$=29.3 Hz), 125.6, 124.7, 123.6 (q, $J_{CF}$=273.0 Hz), 117.4, 85.4, 84.5, 53.6, 52.8, 47.3, 41.7, 15.5; $^{19}$F NMR (376 MHz, $CDCl_3$) δ −60.3 (s, 3F); HRMS (ESI) m/z calcd for $C_{19}H_{17}ClF_3N_2OS$ ([M+H]$^+$) 413.0697, found 413.0693.

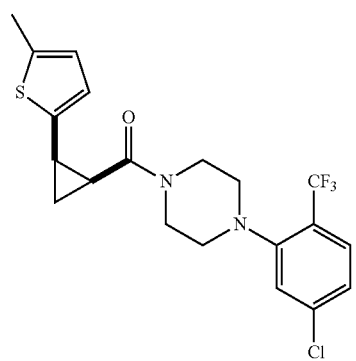

(4-(5-Chloro-2-(trifluoromethyl)phenyl)piperazin-1-yl) ((1RS,2SR)-2-(5-methylthiophen-2-yl)cyclopropyl)methanone. A solution of 1-(4-(5-chloro-2-(trifluoromethyl)phenyl)piperazin-1-yl)-3-(5-methylthiophen-2-yl)prop-2-yn-1-one (0.112 g, 0.271 mmol) in EtOAc (2.7 mL) was treated with Lindlar's catalyst (5% Pd on $CaCO_3$, lead poisoned, 0.0289 g, equivalent to 5 mol % Pd). The reaction was placed under a balloon of $H_2$ (3 vacuum/backfill cycles) and stirred at rt for 3 d, filtered through Celite, washed (EtOAc), and the combined filtrates were concentrated under reduced pressure. The crude residue was purified by automated chromatography on $SiO_2$ (4 g column, liquid load $CH_2Cl_2$, hexanes to 40% EtOAc/hexanes, product eluted at 20% EtOAc/hexanes) to give (Z)-1-(4-(5-chloro-2-(trifluoromethyl)-phenyl)piperazin-1-yl)-3-(5-methylthiophen-2-yl) prop-2-en-1-one (0.0655 g, 0.158 mmol) as a colorless foam.

A solution of $CrCl_2$ (0.116 g, 0.947 mmol) and (Z)-1-(4-(5-chloro-2-(trifluoromethyl)phenyl-piperazin-1-yl)-3-(5-methylthiophen-2-yl)prop-2-en-1-one (0.0655 g, 0.158 mmol) in dry degassed THF (1.6 mL) was sparged with Ar for 5 min and treated with $CH_2ICl$ (0.091 mL, 0.789 mmol) at rt, heated for 2 days at 80° C., cooled to rt, diluted with EtOAc (50 mL), and washed with 1 M aqueous HCl (3×20 mL). The organic layer was dried ($MgSO_4$), filtered and concentrated under reduced pressure. The crude residue was purified by automated chromatography on $SiO_2$ (4 g column, liquid load $CH_2Cl_2$, 100% hexanes to 30% EtOAc/hexanes, product eluted at 20% EtOAc/hexanes), filtered through basic $Al_2O_3$ ($CH_2Cl_2$/EtOAc, 1:1), and concentrated under reduced pressure. The resulting oil was crystalized from cyclohexane (~0.5 mL at rt), the crystals were washed with hexanes and dried under high vacuum to give (4-(5-chloro-2-(trifluoromethyl)phenyl)piperazin-1-yl)((1RS,2SR)-2-(5-methylthiophen-2-yl)cyclopropyl)methanone (0.0313 g, 0.0730 mmol, 27% (2 steps) (100% purity by ELSD)) as a colorless solid: Mp 84.5-86.8° C.; IR ($CH_2Cl_2$) 3007, 2920, 1642, 1595, 1464, 1435, 1405, 1308, 1144, 1120, 1031, 825, 803 cm$^{-1}$; $^1$H NMR (400 MHz, $CDCl_3$) δ 7.54 (d, J=8.5 Hz, 1H), 7.21 (dd, J=8.5, 1.5 Hz, 1H), 7.03 (d, J=1.5 Hz, 1H), 6.61 (dd, J=3.4, 1.0 Hz, 1H), 6.59 (d, J=3.4 Hz, 1H), 4.08 (d, J=13.0 Hz, 1H), 3.87 (d, J=13.0 Hz, 1H), 3.57 (ddd, J=13.0, 9.4, 3.0 Hz, 1H), 3.23 (ddd, J=13.0, 9.6, 3.0 Hz, 1H), 2.78 (tt, J=9.6, 4.7 Hz, 2H), 2.52 (td, J=8.8, 6.8 Hz, 1H), 2.46-2.40 (m, 4H), 2.31-2.25 (m, 1H), 2.16 (ddd, J=8.8, 8.2, 6.0 Hz, 1H), 1.77 (q, J=6.0 Hz, 1H), 1.39 (td, J=8.6, 6.0 Hz, 1H); $^{13}$C NMR (100 MHz, $CDCl_3$) δ 167.1, 153.2, 138.6, 138.5, 137.4, 128.4 (q, $J_{CF}$=5.4 Hz), 126.0 (q, $J_{CF}$=28.2 Hz), 125.5, 125.1, 124.8, 124.0, 123.6 (q, $J_{CF}$=273.0 Hz), 53.6, 53.2, 45.7, 42.4, 24.4, 19.4, 15.3, 12.4; $^{19}$F NMR (376 MHz, $CDCl_3$) δ −60.4 (s, 3F); HRMS (ESI) m/z calcd for $C_{20}H_{21}ClF_3N_2OS$ ([M+H]$^+$) 429.1010, found 429.1006.

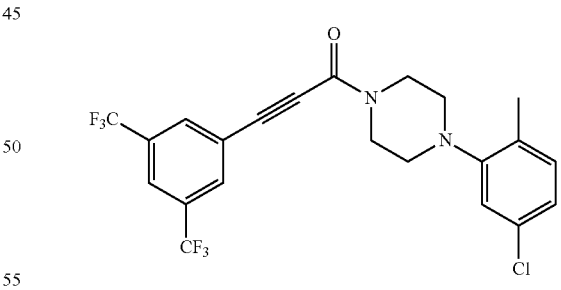

3-(3,5-Bis(trifluoromethyl)phenyl)-1-(4-(5-chloro-2-methylphenyl)piperazin-1-yl)prop-2-yn-1-one. A solution of 3-(3,5-bis(trifluoromethyl)phenyl)propiolic acid (0.250 g, 0.886 mmol) and 1-(5-chloro-2-methylphenyl)piperazine hydrochloride (0.263 g, 1.06 mmol) in $CH_2Cl_2$ (9.0 mL) cooled to 0° C. was treated $Et_3N$ (0.5 mL, 3.54 mmol). The cooled solution was treated with T3P (50% solution in EtOAc) (1.0 mL, 1.33 mmol) dropwise and the reaction was stirred at 0° C. for 30 min and allowed to warm to rt overnight. The reaction was diluted with EtOAc (40 mL) and washed with $H_2O$ (20 mL), satd. aqueous $NaHCO_3$ (20 mL), dried (MgSO$_4$), filtered, and concentrated under reduced pressure. The crude material was purified by automated chromatography on SiO$_2$ (4 g column, gradient hexanes to EtOAc), to give the product (0.280 g, 0.590 mmol, 67%) as a pale yellow solid: Mp 129.7-132.4° C.; IR (CH$_2$Cl$_2$) 2927, 2221, 1638, 1432, 1381, 1279, 1180, 1137, 1044, 900, 684 cm$^{-1}$; $^1$H NMR (400 MHz, CDCl$_3$) δ 8.00 (s, 2H), 7.92 (s, 1H), 7.13 (dd, J=8.4, 0.4 Hz, 1H), 7.01 (dd, J=8.4, 2.0 Hz, 1H), 6.96 (d, J=2.0 Hz, 1H), 3.97 (t, J=5.0 Hz, 2H), 3.85 (t, J=5.0 Hz, 2H), 3.00 (t, J=5.0 Hz, 2H), 2.91 (t, J=5.0 Hz, 2H), 2.30 (s, 3H); $^{13}$C NMR (100 MHz, CDCl$_3$) δ 152.0, 151.6, 132.3 (q, J=34.1 Hz), 132.2, 131.9, 131.0, 123.9, 123.5 (q, J=3.6 Hz), 122.8, 122.6 (q, J=273.1 Hz), 119.8, 87.0, 83.5, 51.9, 51.3, 47.5, 42.1, 17.4; $^{19}$F NMR (376 MHz, CDCl$_3$) δ −63.2 (s, 6F); HRMS (ESI) m/z calcd for C$_{22}$H$_{18}$ClF$_6$N$_2$O ([M+H]$^+$) 475.1006, found 475.1004.

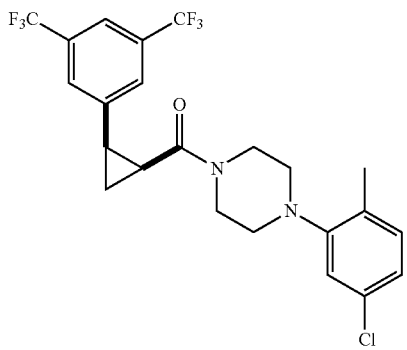

((1RS,2SR)-2-(3,5-Bis(trifluoromethyl)phenyl)cyclopropyl)(4-(5-chloro-2-methylphenyl)piperazin-1-yl)methanone. A solution of 3-(3,5-bis(trifluoromethyl)phenyl)-1-(4-(5-chloro-2-methylphenyl)piperazin-1-yl)prop-2-yn-1-one (0.280 g, 0.590 mmol) in EtOAc (6 mL) was treated with Lindlar's catalyst (5% Pd on CaCO$_3$, lead poisoned, 0.0628 g, equivalent to 5 mol % Pd). The reaction was placed under a balloon of H$_2$ (3 vacuum/backfill cycles) and stirred at rt for 3 d, filtered through Celite, washed (EtOAc), and the combined filtrates were concentrated under reduced pressure. The crude residue was purified by automated chromatography on SiO$_2$ (4 g column, liquid load CH$_2$Cl$_2$, hexanes to 40% EtOAc/hexanes, pdt eluted at 30% EtOAc/hexanes) to give (Z)-3-(3,5-bis(trifluoromethyl)phenyl)-1-(4-(5-chloro-2-methylphenyl)piperazin-1-yl)prop-2-en-1-one (0.0710 g, 0.149 mmol) as a pale yellow oil.

A solution of CrCl$_2$ (0.110 g, 0.893 mmol) and (Z)-3-(3,5-bis(trifluoromethyl)phenyl)-1-(4-(5-chloro-2-methylphenyl)piperazin-1-yl)prop-2-en-1-one (0.0710 g, 0.149 mmol) in dry degassed THF (1.5 mL) was sparged with Ar for 5 min and treated with CH$_2$ICl (0.086 mL, 0.744 mmol) at rt, further sparged for 2 min, heated for 20 h at 80° C., cooled to rt, diluted with EtOAc (50 mL), and washed with 1 M aqueous HCl (3×20 mL). The organic layer was dried (MgSO$_4$), filtered and concentrated under reduced pressure. The crude residue was purified by automated chromatography on SiO$_2$ (4 g column, liquid load CH$_2$Cl$_2$, 100% hexanes to 40% EtOAc:hexanes), filtered through basic Al$_2$O$_3$ (CH$_2$Cl$_2$/EtOAc, 1:1), recrystallized from cyclohexane, and dried under high vacuum to give ((1RS,2SR)-2-(3,5-bis(trifluoromethyl)phenyl)cyclopropyl)(4-(5-chloro-2-methylphenyl)piperazin-1-yl)methanone (0.0560 g, 0.114 mmol, 19% (2 steps) (100% purity by ELSD)) as a pale yellow oil: IR (CH$_2$Cl$_2$) 2820, 1641, 1466, 1277, 1167, 1132, 1036, 899, 682 cm$^{-1}$; $^1$H NMR (400 MHz, CDCl$_3$) δ 7.73 (s, 1H), 7.65 (s, 2H), 7.07 (dd, J=8.4, 0.6 Hz, 1H), 6.97 (dd, J=8.4, 2.0 Hz, 1H), 6.73 (d, J=2.0 Hz, 1H), 3.81-3.64 (m, 3 H), 3.35 (ddd, J=12.5, 8.8, 3.1 Hz, 1H), 2.86 (dt, J=11.4, 4.1 Hz, 1H), 2.76 (dt, J=11.9, 4.0 Hz, 1H), 2.59 (td, J=8.4, 6.8 Hz, 1H), 2.38-2.27 (m, 3H), 2.21 (s, 3H), 1.96 (dt, J=6.8, 5.6 Hz, 1H), 1.47 (td, J=8.4, 5.6 Hz, 1H); $^{13}$C NMR (100 MHz, CDCl$_3$) δ 166.4, 151.6, 140.4, 132.0, 131.8, 131.4 (q, J$_{CF}$=33.1 Hz), 130.9, 128.3 (q, J$_{CF}$=1.1 Hz), 123.7, 123.3 (q, J$_{CF}$=272.7 Hz), 120.4 (q, J$_{CF}$=3.8 Hz), 119.6, 51.8, 51.6, 45.6, 42.3, 23.8, 23.4, 17.3, 11.3; $^{19}$F NMR (376 MHz, CDCl$_3$) δ −62.7 (s, 6F); HRMS (ESI) m/z calcd for C$_{23}$H$_{22}$ClF$_6$N$_2$O ([M+H]$^+$) 491.1319, found 491.1312.

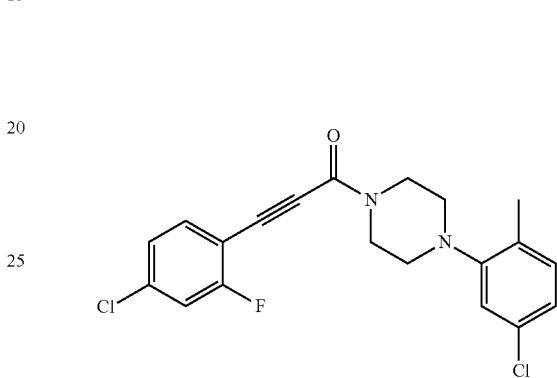

3-(4-Chloro-2-fluorophenyl)-1-(4-(5-chloro-2-methylphenyl)piperazin-1-yl)prop-2-yn-1-one. A solution of 3-(4-chloro-2-fluorophenyl)propiolic acid (0.190 g, 0.957 mmol) and 1-(5-chloro-2-methylphenyl)-piperazine hydrochloride (0.284 g, 1.15 mmol) in CH$_2$Cl$_2$ (9.6 mL) cooled to 0° C. was treated with Et$_3$N (0.53 mL, 3.83 mmol). The cooled solution was treated with T3P (50% solution in EtOAc) (1.0 mL, 1.44 mmol) dropwise and the reaction was stirred at 0° C. for 30 min, warmed to rt overnight, diluted with EtOAc (40 mL) and washed with H$_2$O (20 mL), satd. aqueous NaHCO$_3$ (20 mL), dried (MgSO$_4$), filtered, and concentrated under reduced pressure. The crude residue was purified by automated chromatography on SiO$_2$ (4 g column, liquid load CH$_2$Cl$_2$, gradient 100% hexanes to 100% EtOAc) to give 3-(4-chloro-2-fluorophenyl)-1-(4-(5-chloro-2-methylphenyl)piperazin-1-yl)prop-2-yn-1-one (0.302 g, 0.772 mmol, 81%) as a pale yellow solid: Mp 135.1-137.3° C.; IR (CH$_2$Cl$_2$) 2917, 2820, 2219, 1632, 1489, 1431, 1291, 1224, 1039, 898, 819 cm$^{-1}$; $^1$H NMR (400 MHz, CDCl$_3$) δ 7.50 (dd, J=8.8, 8.0 Hz, 1H), 7.17 (t, J=2.0 Hz, 1H), 7.15 (q, J=2.0 Hz, 1H), 7.11 (d, J=8.4 Hz, 1H), 6.98 (dd, J=8.0, 2.0 Hz, 1H), 6.94 (d, J=2.4 Hz, 1H), 3.97 (t, J=5.0 Hz, 2H), 3.83 (t, J=5.0 Hz, 2H), 2.96 (t, J=5.0 Hz, 2H), 2.88 (t, J=5.0 Hz, 2H), 2.28 (s, 3H); $^{13}$C NMR (100 MHz, CDCl$_3$) δ 163.0 (d, J$_{CF}$=257.4 Hz), 152.5, 151.6, 137.4 (d, J$_{CF}$=10.1 Hz), 134.7 (d, J$_{CF}$=1.4 Hz), 131.9 (d, J$_{CF}$=25.0 Hz), 130.9, 125.0 (d, J$_{CF}$=3.7 Hz), 123.7, 119.8, 116.8, 116.6, 107.9 (d, J$_{CF}$=15.9 Hz), 86.6 (d, J$_{CF}$=3.6 Hz), 83.0, 51.8, 51.2, 47.3, 41.9, 17.4; $^{19}$F NMR (376 MHz, CDCl$_3$) δ −105.8 (s, 1F); HRMS (ESI) m/z calcd for C$_{20}$H$_{18}$Cl$_2$FN$_2$O ([M+H]$^+$) 391.0775, found 391.0781.

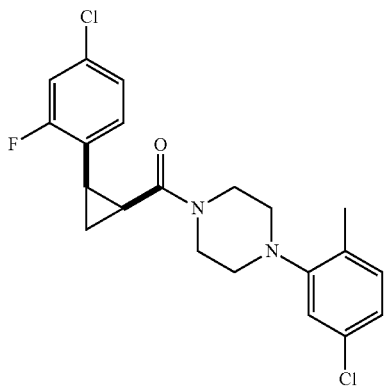

((1RS,2SR)-2-(4-Chloro-2-fluorophenyl)cyclopropyl)(4-(5-chloro-2-methylphenyl)piperazin-1-yl)methanone A solution of 3-(4-chloro-2-fluorophenyl)-1-(4-(5-chloro-2-methylphenyl)piperazin-1-yl)prop-2-yn-1-one (0.300 g, 0.767 mmol) in EtOAc (7.8 mL) was treated with Lindlar's catalyst (5% Pd on CaCO$_3$, lead poisoned, 0.0816 g, equivalent to 5 mol % Pd). The reaction was placed under a balloon of H$_2$ (3 vacuum/backfill cycles) and stirred at rt for 3 d, filtered through Celite, washed (EtOAc), and the combined filtrates were concentrated under reduced pressure. The crude residue was purified by automated chromatography on SiO$_2$ (4 g column, liquid load CH$_2$Cl$_2$, 100% hexanes to 40% EtOAc/hexanes, pdt eluted at 30% EtOAc/hexanes) to give (Z)-3-(4-chloro-2-fluorophenyl)-1-(4-(5-chloro-2-methylphenyl)piperazin-1-yl)prop-2-en-1-one (0.138 g, 0.351 mmol, 46%) as a pale yellow oil.

A solution of CrCl$_2$ (0.259 g, 2.11 mmol) and (Z)-3-(4-chloro-2-fluorophenyl)-1-(4-(5-chloro-2-methylphenyl)piperazin-1-yl)prop-2-en-1-one (0.138 g, 0.351 mmol) in dry degassed THF (3.5 mL) was sparged with Ar for 5 min and treated with CH$_2$ICl (0.20 mL, 1.75 mmol) at rt, further sparged for 5 min, heated for 20 h at 80° C., cooled to rt, diluted with EtOAc (50 mL) and washed with 1 M aqueous HCl (3×20 mL). The organic layer was dried (MgSO$_4$), filtered, and concentrated under reduced pressure. The crude residue was purified by automated chromatography on SiO$_2$ (4 g column, liquid load CH$_2$Cl$_2$, 100% hexanes to 40% EtOAc/hexanes), filtered through basic Al$_2$O$_3$ (1:1 CH$_2$Cl$_2$/EtOAc) and dried under high vacuum to give ((1RS,2SR)-2-(4-chloro-2-fluorophenyl)cyclopropyl)(4-(5-chloro-2-methylphenyl)piperazin-1-yl)methanone (0.0930 g, 0.228 mmol, 65% (100% purity by ELSD)) as a colorless solid: Mp 100.2-103.0° C.; IR (CH$_2$Cl$_2$) 2950, 2819, 1638, 1490, 1435, 1225, 1034, 899, 818, 731 cm$^{-1}$; $^1$H NMR (400 MHz, CDCl$_3$) δ 7.09-7.03 (m, 4H), 6.97 (dd, J=8.0, 2.0 Hz, 1H), 6.81 (d, J=2.0 Hz, 1H), 3.81-3.66 (m, 3H), 3.38 (ddd, J=12.4, 8.0, 3.4 Hz, 1H), 2.91-2.86 (m, 1H), 2.77-2.72 (m, 1H), 2.58 (qd, J=8.4, 0.8 Hz, 1H), 2.50 (ddd, J=11.2, 8.0, 2.8 Hz, 1H), 2.40 (ddd, J=11.2, 8.0, 2.8 Hz, 1H), 2.29 (ddd, J=9.2, 8.0, 5.6 Hz, 1H), 2.23 (s, 3H), 1.90 (dt, J=6.8, 5.6 Hz, 1H), 1.34 (td, J=8.4, 5.6 Hz, 1H); $^{13}$C NMR (100 MHz, CDCl$_3$) δ 167.0, 161.9 (d, J$_{CF}$=247.9 Hz), 151.9, 132.8 (d, J$_{CF}$=10.5 Hz), 132.0, 131.8, 130.9, 129.8 (d, J$_{CF}$=4.5 Hz), 124.2 (d, J$_{CF}$=3.4 Hz), 123.5, 123.1 (d, J$_{CF}$=14.3 Hz), 119.6, 115.4 (d, J$_{CF}$=25.3 Hz), 51.8, 51.6, 45.6, 42.2, 22.2, 17.4, 17.4, 9.3; $^{19}$F NMR (376 MHz, CDCl$_3$) δ −116.4 (s, 1F); HRMS (ESI) m/z calcd for C$_{21}$H$_{22}$Cl$_2$FN$_2$O ([M+H]$^+$) 407.1088, found 407.1089.

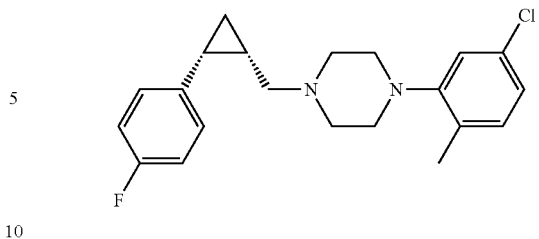

1-(5-Chloro-2-methylphenyl)-4-(((1S,2R)-2-(4-fluorophenyl)cyclopropyl)methyl)piperazine (JKJ741.047) A solution of (4-(5-chloro-2-methylphenyl)piperazin-1-yl)((1S,2R)-2-(4-fluorophenyl)-cyclopropyl)methanone (0.0372 g, 0.0998 mmol) in THF (0.4 mL) was treated with BH$_3$·DMS (1M solution in THF, 0.4 mL, 0.400 mmol) under Ar and the reaction was heated at reflux for overnight. The reaction was cooled to 0° C. and quenched by the addition of 1M NaOH and stirred for 20 min at 0° C. until all of the bubbling subsided. The reaction was extracted with EtOAc (3×20 mL), and the combined organic layers were dried (Na$_2$SO$_4$), filtered and concentrated in vacuo. The crude material was stirred in 1M HCl overnight at rt. The resulting solution was made basic with 1M NaOH and extracted with EtOAc (3×10 mL). The combined organic layers were dried (Na$_2$SO$_4$), filtered and concentrated in vacuo. The crude residue was purified by automated chromatography on SiO$_2$ (4 g column, hexanes to EtOAc; pdt eluted at 30% EtOAc/hexanes) to afford the product (0.0157 g, 0.0437 mmol, 44%) as a pale yellow oil: IR (CH$_2$Cl$_2$) 2927, 2819, 1591, 1510, 1489, 1224, 1095, 835 cm$^{-1}$; $^1$H NMR (600 MHz, acetone-d6) δ 7.32-7.29 (m, 2H), 7.14 (d, J=8.0 Hz, 1H), 7.06-7.02 (m, 2H), 6.98 (d, J=2.1 Hz, 1H), 6.95 (dd, J=8.0, 2.2 Hz, 1H), 2.85 (bs, 4H), 2.46 (bs, 4H), 2.26 (dd, J=12.7, 6.2 Hz, 1H), 2.20 (q, J=8.0 Hz, 4H), 1.93 (dd, J=12.7, 7.1 Hz, 1H), 1.35-1.29 (m, 2H), 1.09 (td, J=8.4, 5.4 Hz, 1H), 0.84 (q, J=5.4 Hz, 1H); $^{13}$C NMR (150 MHz, CDCl$_3$) δ 162.1 (d, J=242.0 Hz), 154.0, 135.9 (d, J=3.1 Hz), 132.9, 132.1, 131.8, 131.6 (d, J=8.0 Hz), 123.4, 119.9, 115.3 (d, J=21.1 Hz), 58.3, 54.2, 52.4, 20.4, 17.6, 17.1 10.1; $^{19}$F NMR (376 MHz, CDCl$_3$) δ −119.1 (s, 1F); HRMS (ESI) m/z calcd for C$_{21}$H$_{25}$ClFN$_2$ ([M+H]$^+$) 359.1685, found 359.1682. [α]$^{19}$$_D$+30.7 (c 0.48, MeOH).

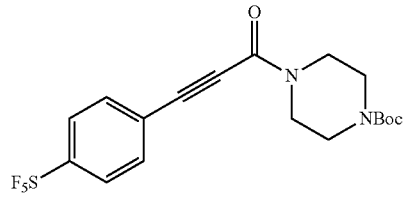

tert-Butyl 4-(3-(4-(pentafluoro-λ6-sulfaneyl)phenyl)propioloyl)piperazine-1-carboxylate (JKJ759.024). A solution of 3-(4-(pentafluoro-L-sulfanyl)phenyl)propiolic acid (0.400 g, 1.47 mmol) and N-boc-piperazine (0.328 g, 1.76 mmol) in CH$_2$Cl$_2$ (15 mL) at 0° C. was treated Et$_3$N (0.62 mL, 4.41 mmol). The cooled solution was treated with T3P (50% solution in EtOAc) (1.6 mL, 2.20 mmol) dropwise and the reaction was stirred at 0° C. for 30 min and allowed to warm to rt overnight. The reaction was diluted with EtOAc (50 mL) and washed with water (20 mL), satd. aqueous NaHCO$_3$ (20 mL), dried (MgSO$_4$), filtered, and concentrated in vacuo. The crude material was purified by chromatography on SiO$_2$ (1:1 hexanes/EtOAc), to give tert-butyl 4-(3-

(4-(pentafluoro-λ6-sulfaneyl)phenyl)propioloyl)piperazine-1-carboxylate (0.457 g, 1.04 mmol, 71%) as a tan solid: Mp 192.4-195.0° C.; IR (CH$_2$Cl$_2$) 2981, 1697, 1635, 1419, 1255, 1239, 1167, 841 cm$^{-1}$; $^1$H NMR (400 MHz, CDCl$_3$) δ 7 7.76 (dt, J=9.0, 2.0 Hz, 2H), 7.63 (d, J=9.0 Hz, 2H), 3.79-3.76 (m, 2H), 3.67 (t, J=4.8 Hz, 2H), 3.54-3.51 (m, 2H), 3.46 (t, J=4.8 Hz, 2H); $^{13}$C NMR (100 MHz, CDCl$_3$) δ 154.4 (quint, J=40.0 Hz), 152.4, 132.5, 126.3 (t, J=4.7 Hz), 123.9, 99.9, 88.4, 83.0, 80.6, 46.9, 43.3, 41.5, 28.3; $^{19}$F NMR (376 MHz, CDCl$_3$) δ 83.0 (t, J=150.5 Hz, 1F), 62.4 (d, J=150.2 Hz, 4F); HRMS (ESI) m/z calcd for C$_{18}$H$_{22}$F$_5$N$_2$O$_2$S ([M+H]$^+$) 441.1266, found 441.1264.

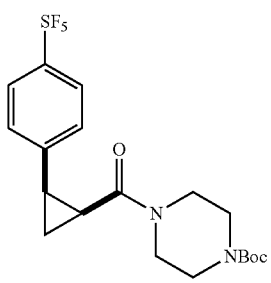

tert-Butyl 4-((1RS,2SR)-2-(4-(pentafluoro-λ6-sulfaneyl)phenyl)cyclopropane-1-carbonyl)piperazine-1-carboxylate (JKJ759.031/035). A solution of tert-butyl 4-(3-(4-(pentafluorosulfanyl)phenyl)propioloyl)-piperazine-1-carboxylate (0.420 g, 0.954 mmol) in EtOAc (10 mL) at rt was treated with quinoline (0.56 mL, 4.77 mmol) and 5% Pd/BaSO$_4$ (0.0203 g, 0.0096 mmol, 1 mol % based on Pd) and the reaction was stirred under an atmosphere of H$_2$ (3×backfill cycles) for 4 h. Analysis by TLC (1:1 H:EA) indicated that the starting material had been mostly consumed. The reaction was filtered (eluting with EtOAc), and the filtrate was washed with 1M HCl (3×25 mL), dried (Na$_2$SO$_4$), filtered and concentrated in vacuo. The crude residue was purified by chromatography on SiO$_2$ (1:1 hexanes/EtOAc to EtOAc) to afford the product (0.408 g, 0.922 mmol) as a colorless solid. This solid was carried on to the cyclopropanation 759.035.

A solution of CrCl$_2$ (0.667 g, 5.43 mmol) and (Z)-tert-butyl 4-(3-(4-(pentafluorosulfanyl)phenyl)-acryloyl)piperazine-1-carboxylate (0.400 g, 0.904 mmol) in anhydrous THF (9 mL) and the mixture was sparged with Ar for 15 min and added CH$_2$ICl (0.52 mL, 4.52 mmol) at rt and under Ar atmosphere. The reaction mixture was stirred for 24 h at 80° C., cooled to rt, diluted with EtOAc (80 mL) and washed with 1M aqueous HCl (3×20 mL). The organic layer was dried (MgSO$_4$), filtered and concentrated in vacuo. The crude material was purified by chromatography on SiO$_2$ (EtOAc) to afford a the product as a clear oil. The product was filtered through basic Al$_2$O$_3$ (eluting with EtOAc) concentrated to afford the product (0.0920 g, 0.202 mmol, 21% (2 steps)) as a colorless solid: Mp 125.3-128.5° C.; IR (neat) 2980, 1679, 1635, 1429, 1364, 1239, 1171, 1030, 829 cm$^{-1}$; $^1$H NMR (400 MHz, CDCl$_3$) δ 7.62 (d, J=8.6 Hz, 2H), 7.22 (d, J=8.6 Hz, 2H), 3.55-3.48 (m, 4H), 3.40-3.35 (m, 1H), 3.26-3.20 (m, 1H), 2.85-2.75 (m, 2H), 2.48 (q, J=8.8 Hz, 1H), 2.24 (td, J=8.8, 6.0 Hz, 1H), 1.89 (q, J=6.0 Hz, 1H), 1.46-1.38 (m, 10H); $^{13}$C NMR (100 MHz, CDCl$_3$) δ 166.7, 154.4, 152.1 (quint, J$_{CF}$=17.3 Hz), 141.6, 127.8, 125.6 (quint, J$_{CF}$=4.6 Hz), 80.3, 45.0, 43.2, 41.6, 28.3, 24.3, 23.7 11.2; $^{19}$F NMR (376 MHz, CDCl$_3$) δ 84.9 (quint, J=150.2 Hz, 1F), 63.1 (d, J=150.0 Hz, 4F); HRMS (ESI) m/z calcd for C$_{19}$H$_{25}$F$_5$N$_2$O$_3$SNa ([M+Na]$^+$) 479.1398, found 479.1395.

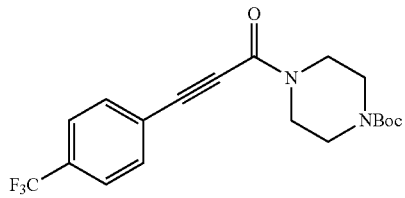

tert-Butyl 4-(3-(4-(trifluoromethyl)phenyl)propioloyl)piperazine-1-carboxylate (JKJ759.025). A solution of 3-(4-trifluoromethylphenyl)propiolic acid (0.500 g, 2.33 mmol) and N-Boc-pipreazine (0.522 g, 2.80 mmol) in CH$_2$Cl$_2$ (23 mL) at 0° C. was treated Et$_3$N (1.0 mL, 7.00 mmol). The cooled solution was treated with T3P (50% solution in EtOAc) (2.5 mL, 3.50 mmol) dropwise and the reaction was stirred at 0° C. for 30 min and allowed to warm to rt overnight. The reaction was diluted with EtOAc (100 mL) and washed with water (20 mL), satd. aqueous NaHCO$_3$ (20 mL), dried (MgSO$_4$), filtered, and concentrated in vacuo. The crude material was purified by chromatography on SiO$_2$ (1:1 hexanes/EtOAc), to give the product (0.841 g, 2.20 mmol, 94%) as a colorless solid: Mp 174.2-175.9° C.; IR (CH$_2$Cl$_2$) 2981, 2230, 1678, 1622, 1425, 1321, 1162, 1123, 1064, 837 cm$^{-1}$; $^1$H NMR (400 MHz, CDCl$_3$) δ 7.65 (d, J=8.8 Hz, 2H), 7.63 (d, J=8.8 Hz, 2H), 3.80-3.77 (m, 2H), 3.66 (t, J=5.0 Hz, 2H), 3.54-3.51 (m, 2H), 3.46 (t, J=5.0 Hz, 2H), 1.47 (s, 9H); $^{13}$C NMR (100 MHz, CDCl$_3$) δ 154.4, 152.6, 132.6, 131.8 (q, J$_{CF}$=32.8 Hz), 125.5 (q, J$_{CF}$=3.9 Hz), 124.0, 123.6 (q, J$_{CF}$=272.7 Hz), 89.2, 82.5, 80.5, 46.8, 41.5, 28.3; $^{19}$F NMR (376 MHz, CDCl$_3$) δ −63.1 (s, 3F); HRMS (ESI) m/z calcd for C$_{19}$H$_{21}$F$_3$N$_2$O$_3$ ([M+H]$^+$) 383.1577, found 383.1576.

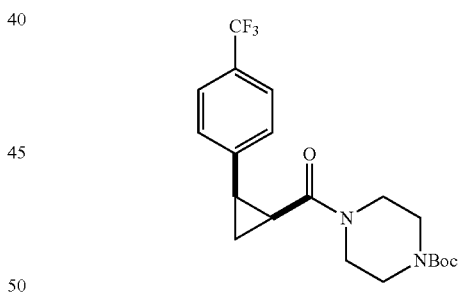

tert-Butyl 4-((1RS,2SR)-2-(4-(trifluoromethyl)phenyl)cyclopropane-1-carbonyl)piperazine-1-carboxylate (JKJ759.043). A solution of tert-butyl 4-(3-(4-(trifluoromethyl)phenyl)propioloyl)piperazine-1-carboxylate (0.840 g, 2.20 mmol) in EtOAc (22 mL) at rt was treated with quinoline (1.3 mL, 11.0 mmol) and 5% Pd/BaSO$_4$ (0.0468 g, 0.0220 mmol, 1 mol % based on Pd) and the reaction was stirred under an atmosphere of H$_2$ (3×backfill cycles) for 2 h. Analysis by TLC (1:1 H:EA) indicated that the starting material had been mostly consumed. The reaction was filtered (eluting with EtOAc), and the filtrate was washed with 1M HCl (3×25 mL), dried (Na$_2$SO$_4$), filtered and concentrated in vacuo. The crude residue was purified by chromatography on SiO2 (1:1 hexanes/EtOAc to EtOAc) to afford the product (0.718 g, 1.87 mmol, 85%) as a colorless solid.

A solution of CrCl$_2$ (1.38 g, 11.2 mmol) and tert-butyl (Z)-4-(3-(4-(trifluoromethyl)phenyl)-acryloyl)piperazine-1-carboxylate (0.718 g, 1.87 mmol) in dry degassed THF (19 mL) (previously sparged with Ar for 15 min) and treated with CH$_2$ICl (1.08 mL, 9.34 mmol) and sparged with Ar for 2 min. The reaction mixture was stirred for 24 h at 80° C. under an atmosphere of Ar, cooled to rt, diluted with EtOAc (80 mL), and washed with 1 M aqueous HCl (3×20 mL). The organic layer was dried (MgSO$_4$), filtered and concentrated in vacuo. The crude material was purified by chromatography on SiO$_2$ (EtOAc) to afford the product as a colorless oil. The product was filtered through basic Al$_2$O$_3$ (eluting with EtOAc) concentrated to give tert-butyl 4-((1RS,2SR)-2-(4-(trifluoromethyl)phenyl)cyclopropane-1-carbonyl)piperazine-1-carboxylate (0.194 g, 0.487 mmol, 26%) as a colorless solid: Mp 108.6-111.9° C.; IR (CH$_2$Cl$_2$) 2978, 1693, 1641, 1417, 1324, 1236, 1162, 1116, 1069, 1017, 997, 844 cm$^{-1}$; $^1$H NMR (400 MHz, CDCl$_3$) δ 7.50 (d, J=8.4 Hz, 2H), 7.24 (d, J=8.4 Hz, 2H), 3.59-3.54 (m, 1H), 3.51-3.36 (m, 4H), 3.23-3.16 (m, 1H), 2.82-2.76 (m, 1H), 2.71-2.66 (m, 1H), 2.50 (q, J=8.8 Hz, 1H), 2.23 (td, J=8.8, 6.0 Hz, 1H), 1.90 (q, J=6.0 Hz, 1H), 1.46-1.37 (m, 10H); $^{13}$C NMR (100 MHz, CDCl$_3$) δ 166.9, 154.4, 141.6, 128.7 (q, J=32.4 Hz), 127.9, 125.0 (q, J=3.9 Hz), 124.1 (q, J=272.0 Hz), 80.3, 45.0, 41.6, 28.3, 24.3, 24.0, 11.0; $^{19}$F NMR (376 MHz, CDCl$_3$) δ -62.4 (s, 3F); HRMS (ESI) m/z calcd for C$_{20}$H$_{26}$F$_3$N$_2$O$_3$ ([M+H]$^+$) 399.1890, found 399.1888.

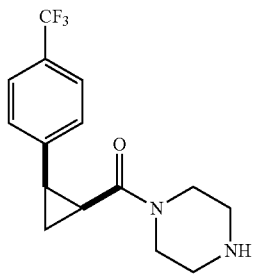

Piperazin-1-yl((1S,2R)-2-(4-(trifluoromethyl)phenyl)cyclopropyl)methanone (JKJ759.045). A solution of tert-butyl 4-(2-(4-(trifluoromethyl)phenyl)cyclopropanecarbonyl)piperazine-1-carboxylate 759.043 (0.169 g, 0.424 mmol) in THF (0.4 mL) was treated with 4M HCl in dioxane (0.5 mL, 2.12 mmol) was added and the reaction was stirred at rt for overnight. The soln was diluted with hexanes (20 mL) and the resulting precipitate was filtered and washed with additional hexanes and Et$_2$O. The product was dried under high vacuum to afford the product (0.141 g, 0.421 mmol, 99%) as a colorless solid.

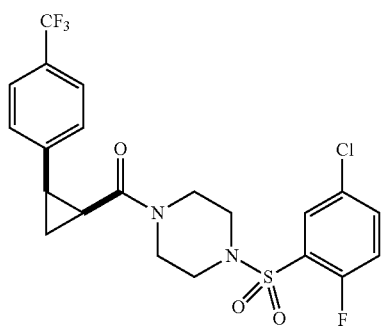

(4-((5-Chloro-2-fluorophenyl)sulfonyl)piperazin-1-yl)((1S,2R)-2-(4-(trifluoromethyl)phenyl)-cyclopropyl)methanone (JKJ759.047). A solution of piperazin-1-yl((1RS,2SR)-2-(4-(trifluoromethyl)-phenyl)cyclopropyl)methanone hydrochloride (0.0610 g, 0.182 mmol) and 5-chloro-2-fluorobenzene-1-sulfonyl chloride (0.0500 g, 0.219 mmol) in CH$_2$Cl$_2$ (2.0 mL) at 0° C. was treated with Et$_3$N (1.0 mL, 7.00 mmol), stirred at 0° C. for 30 min, warmed to rt overnight, and concentrated under reduced pressure. The crude material was purified by chromatography on SiO$_2$ (EtOAc), to give the product (0.0834 g, 0.170 mmol, 93% (100% purity by ELSD)) as a colorless solid: Mp 139.7-142.3° C.; IR (CH$_2$Cl$_2$) 3095, 2859, 1642, 1469 1324, 1163, 1113, 1069, 939, 844, 736 cm$^{-1}$; $^1$H NMR (400 MHz, CDCl$_3$) δ 7.73 (dd, J=5.6, 2.6 Hz, 1H), 7.53 (ddd, J=8.8, 4.0, 2.6 Hz, 1H), 7.39 (d, J=8.4 Hz, 2H), 7.18 (d, J=8.4 Hz, 2H), 7.13 (t, J=8.8 Hz, 1H), 3.86 (bd, J=13.2 Hz, 1H), 3.72 (bd, J=13.2 Hz, 1H), 3.51 (ddd, J=13.2, 9.2, 2.8 Hz, 1H), 3.38 (bd, J=13.2 Hz, 1H), 3.26-3.14 (m, 2H), 2.49 (q, J=8.8 Hz, 1H), 2.35-2.27 (bq, J=11.6 Hz, 2H), 2.19 (ddd, J=9.2, 8.8, 6.0 Hz, 1H), 1.86 (q, J=6.0 Hz, 1H), 1.39 (td, J=8.8, 5.6 Hz, 1H); $^{13}$C NMR (100 MHz, CDCl$_3$) δ 166.6, 157.1 (d, J=255.5 Hz), 141.4, 135.1 (d, J=8.6 Hz), 130.5, 130.0 (d, J=3.6 Hz), 128.5 (q, J=32.5 Hz), 127.7, 126.3 (d, J=16.4 Hz), 124.8 (q, J=3.8 Hz), 124.1 (q, J=271.6 Hz), 118.7 (d, J=23.8 Hz), 46.0, 45.4, 44.9, 41.3, 24.3, 23.9, 10.9; $^{19}$F NMR (376 MHz, CDCl$_3$) δ -62.2 (s, 3F), -111.2 (s, 1F); HRMS (ESI) m/z calcd for C$_{21}$H$_{20}$F$_4$N$_2$O$_3$SCl ([M+H]$^+$) 491.0814, found 491.0812.

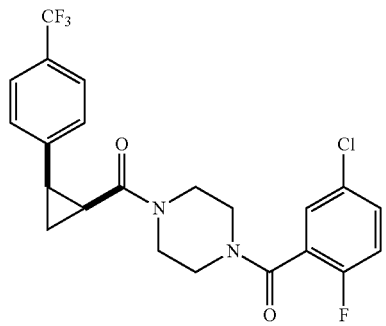

(4-(5-Chloro-2-fluorobenzoyl)piperazin-1-yl)((1S,2R)-2-(4-(trifluoromethyl)phenyl)cyclopropyl)-methanone (JKJ759.046). A solution of piperazin-1-yl((1RS,2SR)-2-(4-(trifluoromethyl)phenyl)-cyclopropyl)methanone hydrochloride (0.0800 g, 0.239 mmol) and 5-chloro-2-fluorobenzoic acid (0.0501 g, 0.287 mmol) in CH$_2$Cl$_2$ (2.5 mL) cooled to 0° C. was treated with Et$_3$N (0.13 mL, 0.956 mmol). The cooled solution was treated with T3P (50% solution in EtOAc) (0.25 mL, 0.358 mmol) dropwise and the reaction was stirred at 0° C. for 30 min, warmed to rt overnight, diluted with EtOAc (50 mL), and washed with water (20 mL), satd. Aqueous NaHCO$_3$ (20 mL), dried (MgSO$_4$), filtered, and concentrated under reduced pressure. The crude residue was purified by chromatography on SiO$_2$ (EtOAc), to give (4-(5-chloro-2-fluorobenzoyl)piperazin-1-yl)((1S,2R)-2-(4-(trifluoromethyl)phenyl)cyclopropyl)methanone (0.0982 g, 0.216 mmol, 90% (100% purity by ELSD) as a colorless solid: Mp 143.2-145.9° C.; IR (CH$_2$Cl$_2$) 3010, 2865, 1635, 1432, 1324, 1113, 1068, 1009, 844, 734 cm$^{-1}$; $^1$H NMR (400 MHz, CDCl$_3$, 50° C. rotomers) δ 7.50 (d, J=8.0 Hz, 2H), 7.36-7.24 (m, 4H), 7.01 (t, J=8.8 Hz, 1H), 3.90 (bs, 1H), 3.60 (bs, 3H), 3.21 (bs, 2H), 2.98 (bs, 1H), 2.79 (bs, 1H), 2.51 (bs, 1H), 2.23 (bs, 1H), 1.91 (q, J=6.0 Hz, 1H), 1.40 (td, J=8.4, 5.6 Hz, 1H); $^{13}$C NMR (100 MHz, CDCl$_3$, 20° C.) δ 167.0, 163.8, 156.4 (d, J=248.1 Hz), 141.5, 131.6 (d, J=8.1 Hz), 130.2, 129.2, 128.8 (q, J=32.7 Hz), 127.9, 125.1 (q, J=3.7 Hz), 124.2 (q, J=271.8 Hz), 117.3 (d, J=23.6 Hz), 46.7, 44.8, 42.3, 41.9, 24.2, 24.1, 11.0; $^{19}$F NMR (376 MHz, CDCl$_3$) δ −62.4 (s, 3F), −117.7 (s, 1F); HRMS (ESI) m/z calcd for C$_{22}$H$_{20}$F$_4$N$_2$O$_2$Cl ([M+H]$^+$) 455.1144, found 455.1143.

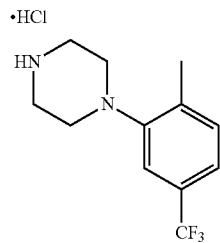 [SMILES: Cl ; Cc1ccc(C(F)(F)F)cc1N1CCNCC1]

1-(2-Methyl-5-(trifluoromethyl)phenyl)piperazine hydrochloride. A solution of Boc-piperazine (2.14 g, 11.5 mmol), KOtBu (2.35 g, 20.9 mmol), (racemic)-BINAP (0.671 g, 1.05 mmol), Pd$_2$(dba)$_3$ (0.194 g, 0.209 mmol) in dry toluene (105 mL) was sparged with Ar for 20 min, treated with 2-bromo-1-methyl-4-(trifluoromethyl)benzene (2.50 g, 10.5 mmol), and the mixture was heated under Ar at 100° C. overnight, cooled to rt, diluted with Et$_2$O (125 mL), filtered through Celite, washed (Et$_2$O), and the combined filtrates were concentrated under reduced pressure. The crude residue was purified by chromatography on SiO$_2$ (hexanes/EtOAc, 9:1) to give tert-butyl 4-(2-methyl-5-(trifluoromethyl)phenyl)piperazine-1-carboxylate (2.49 g, 7.23 mmol) as an orange oil.

A solution of tert-butyl 4-(2-methyl-5-(trifluoromethyl)phenyl)piperazine-1-carboxylate (2.49 g, 7.23 mmol) in THF (3.5 mL) was cooled to 0° C. and treated with 4M HCl in dioxane (9.0 mL, 36.2 mmol) was added and the reaction was stirred at 0° C. for 30 min and then rt for 4 h. The solution was concentrated under reduced pressure and the tan solid was precipitated in ether, filtered off from the solution, washed with Et$_2$O, dried under vacuum to give the crude product. The crude material was recrystallized from EtOH/hexanes (1:1) to give the product (1.71 g, 6.10 mmol, 58% (2 steps)) as colorless needles. Mp 296° C. (decomp); IR (CH$_2$Cl$_2$) 2939, 2799, 2498, 1610, 1418, 1338, 1307, 1153, 1076, 950, 827 cm$^{-1}$; $^1$H NMR (400 MHz, DMSO-d$_6$) δ 9.44 (bs, 2H), 7.42 (d, J=7.9 Hz, 1H), 7.35 (dd, J=7.9, 1.0 Hz, 1H), 7.25 (d, J=1.0 Hz, 1H), 3.22 (dd, J=6.2, 3.6 Hz, 4H), 3.12 (dd, J=6.2, 3.6 Hz, 4H), 2.33 (s, 3H); $^{13}$C NMR (100 MHz, DMSO-d$_6$) δ 150.8, 137.2, 131.9, 127.5 (q, J$_{CF}$=31.6 Hz), 124.2 (q, J$_{CF}$=272.1 Hz), 120.1 (q, J$_{CF}$=3.9 Hz), 115.3 (q, J$_{CF}$=3.8 Hz), 47.9, 43.1, 17.7; $^{19}$F NMR (376 MHz, CDCl$_3$) δ −60.7 (s, 3F); HRMS (ESI) m/z calcd for C$_{12}$H$_{16}$F$_3$N$_2$ ([M+H]$^+$) 245.1260, found 245.1261.

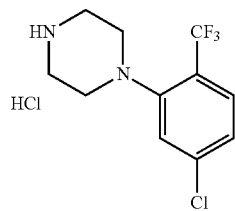 [SMILES: Cl ; FC(F)(F)c1ccc(Cl)cc1N1CCNCC1]

1-(5-Chloro-2-(trifluoromethyl)phenyl)piperazine hydrochloride. Two flasks each containing a solution Boc-piperazine (1.58 g, 8.48 mmol), KOtBu (1.73 g, 15.4 mmol), (racemic)-BINAP (0.480 g, 0.771 mmol), Pd$_2$dba$_3$ (0.142 g, 0.154 mmol) in toluene (8 mL) was sparged with argon for 15 min and treated with 2-bromo-4-chloro-1-(trifluoromethyl)benzene (2.00 g, 7.71 mmol), heated under N$_2$ at 80° C. for 24 h, cooled to rt, combined, diluted with Et$_2$O (100 mL) and added Celite and filtered through Celite, washed (Et$_2$O), and the combined organic layers were concentrated in vacuo. The crude residue was purified by chromatography on SiO$_2$ (hexanes/EtOAc, 9:1) to give 4-(5-chloro-2-(trifluoromethyl)phenyl)piperazine-1-carboxylate (3.12 g, 8.55 mmol) as an orange oil.

A solution of tert-butyl 4-(5-chloro-2-(trifluoromethyl)phenyl)piperazine-1-carboxylate (3.12 g, 8.55 mmol) in THF (8 mL) was treated with 4M HCl in dioxane (10.7 mL, 42.8 mmol), stirred at rt overnight, diluted with hexanes (100 mL), and the resulting precipitate was filtered and washed with additional hexanes and Et$_2$O. The crude material was recrystallized at rt (EtOH/hexanes), crystals were collected by vacuum filtration, washed (hexanes) and dried under high vacuum to give 1-(5-chloro-2-(trifluoromethyl)phenyl)-piperazine hydrochloride (1.88 g, 6.24 mmol, 41% (2 steps)) as tan solid: Mp 272° C. (decomp); IR (neat) 2947, 2726, 2480, 1599, 1576, 1307, 1118, 1037, 946, 819 cm$^{-1}$; $^1$H NMR (400 MHz, DMSO-d$_6$) δ 9.58 (s, 2H), 7.72 (d, J=8.8 Hz, 1H), 7.57 (d, J=1.6 Hz, 1H), 7.46 (dd, J=8.8, 1.6 Hz, 1H), 3.13 (bs, 8H); $^{13}$C NMR (100 MHz, DMSO-d$_6$) δ 152.2, 138.3, 129.0 (q, J=5.4 Hz), 125.9, 124.7, 124.2 (q, J=29.7 Hz), 123.7 (q, J=273.0 Hz), 49.6, 43.1; $^{19}$F NMR (376 MHz, CDCl$_3$) δ −59.0 (s, 3F); HRMS (ESI) m/z calcd for C$_{11}$H$_{13}$N$_2$ClF$_3$ ([M+H]$^+$) 265.0714, found 265.0712.

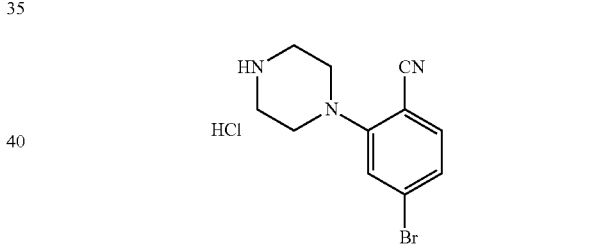

4-Bromo-2-(piperazin-1-yl)benzonitrile hydrochloride. A suspension of 4-bromo-2-fluorobenzonitrile (2.00 g, 10.0 mmol), 1-boc-piperazine (1.86 g, 10.0 mmol), and Et$_3$N (1.4 mL, 10.0 mmol) in anhydrous MeCN (5.0 mL) was heated to 110° C. for 21 h, cooled to rt, and concentrated under reduced pressure. The crude residue was purified by chromatography on SiO$_2$ (hexanes/EtOAc, 9:1) to give tert-butyl 4-(5-bromo-2-cyanophenyl)piperazine-1-carboxylate (3.03 g, 8.27 mmol) as a yellow oil.

A solution of tert-butyl 4-(5-bromo-2-cyanophenyl)piperazine-1-carboxylate (3.03 g, 8.27 mmol) in THF (4 mL) was cooled to 0° C. and treated with 4M HCl in dioxane (10.3 mL, 41.4 mmol), stirred at 0° C. for 30 min, rt for 16 h, diluted with hexanes (200 mL), and the resulting precipitate was collected by vacuum filtration, washed with hexanes, ether, and dried under high vacuum to give 4-bromo-2-(piperazin-1-yl)benzonitrile hydrochloride (3.82 g, 13.6 mmol, 79% (2 steps)) as a colorless solid: Mp 288° C. (decomp); IR (neat) 2901, 2748, 1459, 1129, 1581, 1411, 1241, 1118, 949, 874 cm$^{-1}$; $^1$H NMR (400 MHz, MeOD-d4) δ 7.59 (d, J=8.0 Hz, 1H), 7.44 (d, J=1.6 Hz, 1H), 7.37 (dd, J=8.0, 1.6 Hz, 1H), 3.49 (td, J=4.0, 1.2 Hz, 4H), 3.44 (td, J=4.0, 1.2 Hz, 4H); $^{13}$C NMR (100 MHz, MeOD-d4) δ 156.5, 136.4, 129.9, 127.8, 124.2, 118.2, 106.7, 49.6, 44.9; HRMS (ESI) m/z calcd for $C_{11}H_{13}N_3Br$ ([M+H]$^+$) 266.0287, found 266.0286.

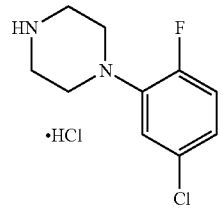 [SMILES: Fc1ccc(Cl)cc1N1CCNCC1 ; Cl]

1-(5-Chloro-2-fluorophenyl)piperazine hydrochloride. Under N$_2$ atmosphere, CuBr (0.471 g, 3.22 mmol), 1,1'-bi-2-naphthol (0.692 g, 2.41 mmol) and DMF (8.04 mL) was added to the flame-dried flask. The mixture was stirred for 10 minutes before the addition of 1-Boc-piperazine (4.49 g, 24.1 mmol), K$_3$PO$_4$ (7.04 g, 32.2 mmol) and 2-bromo-4-chloro-1-fluorobenzene (2.00 mL, 16.1 mmol). The reaction mixture was stirred at 120° C. for 22.0 h. After cooling to room temperature, the mixture was diluted with EtOAc (50 mL) and filtered through Celite pad. The filtrate was sequentially washed with saturated aqueous NH$_4$Cl (50 mL) and brine (50 mL×3). The resulting organic phase was dried (MgSO$_4$), filtered and concentrated in vacuo. The crude product was filtered through a short column of SiO$_2$ (EtOAc/hexanes, 1:15) to yield a mixture of tert-butyl 4-(5-chloro-2-fluorophenyl)piperazine-1-carboxylate (1.50 g) as a light yellow oil. This mixture was used without further purification.

To a solution of the above product (1.50 g) in 1,4-dioxane (11.7 mL), HCl (4 M in 1,4-dioxane, 4.76 mL) was added at 0° C. The mixture was stirred at RT for 14 h. The thick suspension was diluted with hexanes (50 mL) and the resulting solid was collected by filtration, washed with hexanes and Et$_2$O, and dried to give the desired compound as a light yellow solid (0.408 g, 10% over 2 steps). Mp: 173-174° C.; IR (neat): 3013, 2956, 2838, 2528, 2484, 2391, 1516, 1478, 1456, 1393, 1269, 1123, 1042, 1019 cm 1; $^1$H-NMR (500 MHz; DMSO-d6): δ 9.29 (s, 2H), 7.23 (ddd, J=12.5, 8.7, 0.8 Hz, 1H), 7.13 (dd, J=7.7, 2.5 Hz, 1H), 7.08-7.05 (m, 1H), 3.30-3.25 (brd, 4H), 3.25-3.18 (brd, 4H); $^{13}$C-NMR (125 MHz; DMSO-d6): δ 153.5 (d, J=244.6 Hz), 139.8 (d, J=9.9 Hz), 128.6 (d, J=2.9 Hz), 122.4 (d, J=8.3 Hz), 119.4 (d, J=3.1 Hz), 117.6 (d, J=22.6 Hz), 46.6 (d, J=3.7 Hz), 42.6; $^{19}$F-NMR (471 MHz; DMSO-d6): δ −124.65 (ddd, J=11.4, 7.0, 3.8 Hz, 1F); HRMS (ESI): m/z calculated for $C_{10}H_{13}ClF$ ([M+H]$^+$) 215.0746, found 215.0747

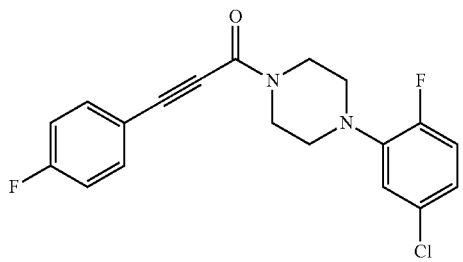 [SMILES: O=C(C#Cc1ccc(F)cc1)N1CCN(c2cc(Cl)ccc2F)CC1]

1-(4-(5-Chloro-2-fluorophenyl)piperazin-1-yl)-3-(4-fluorophenyl)prop-2-yn-1-one. To a solution of 3-(4-fluorophenyl)propiolic acid (0.200 g, 1.22 mmol) in CH$_2$Cl$_2$ (6.09 mL) at 0° C. was added 1-(5-chloro-2-fluorophenyl)piperazine hydrochloride (0.367 g, 1.46 mmol), and Et$_3$N (0.432 mL, 3.05 mmol). T$_3$P (1.29 mL, 1.83 mmol) was added dropwise and the reaction was stirred at 0° C. for 30 min and allowed to warm to room temperature for 33 h. The reaction was diluted with CH$_2$Cl$_2$ (30 mL) and sequentially washed with 1 M HCl (30 mL×2) and saturated aqueous NaHCO$_3$ (30 mL×2). The resulting organic phase was dried (MgSO$_4$), filtered and concentrated in vacuo. The crude material was purified by chromatography on SiO$_2$ (hexanes/EtOAc, 1:1) to give 1-(4-(5-chloro-2-fluorophenyl)piperazin-1-yl)-3-(4-fluorophenyl)prop-2-yn-1-one (0.296 g, 0.821 mmol, 67%) as a light yellow crystal. Mp: 139-140° C.; IR (neat): 2217, 1629, 1601, 1506, 1498, 1432, 1286, 1244, 1227, 1205, 1156, 1039 cm$^{-1}$; $^1$H-NMR (400 MHz; CDCl$_3$): δ 7.58-7.54 (m, 2H), 7.11-7.05 (m, 2H), 7.01-6.89 (m, 3H), 3.99 (t, J=5.1 Hz, 2H), 3.86 (t, J=5.1 Hz, 2H), 3.15 (t, J=5.1 Hz, 2H), 3.09 (t, J=5.1 Hz, 2H); $^{13}$C-NMR (100 MHz; CDCl$_3$): δ 163.5 (d, J=252.8 Hz), 154.0 (d, J=245.8 Hz), 140.3 (d, J=9.9 Hz), 134.6 (d, J=8.8 Hz), 129.5 (d, J=3.3 Hz), 122.8 (d, J=8.1 Hz), 119.6 (d, J=2.9 Hz), 117.2 (d, J=22.4 Hz), 116.4 (d, J=3.7 Hz), 116.1 (d, J=22.4 Hz), 90.1, 80.7, 50.7 (d, J=3.2 Hz), 50.0 (d, J=3.4 Hz), 46.9, 41.4; $^{19}$F-NMR (376 MHz; CDCl$_3$): δ −107.24 (tt, J=8.1, 5.5 Hz, 1F), −125.19 (ddd, J=11.4, 7.3, 4.6 Hz, 1F); HRMS (ESI): m/z calculated for $C_{19}H_{16}ClON_2F_2$ ([M+H]$^+$) 361.0914, found 361.0912.

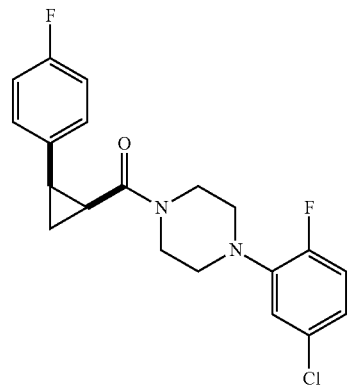

(4-(5-chloro-2-fluorophenyl)piperazin-1-yl)(2-(4-fluorophenyl)cyclopropyl)methanone. To a solution of 1-(4-(5-chloro-2-fluorophenyl)piperazin-1-yl)-3-(4-fluorophenyl)prop-2-yn-1-one (0.275 g, 0.763 mmol) in EtOAc (7.63 mL, 0.1 M) was added Lindlar's catalyst (5% Pd on CaCO$_3$, lead poisoned, 0.0812 g, 5.0 mol %). The reaction vessel was placed under vacuum and backfilled with H$_2$ (balloon, 2×) and allowed to stir for 14 h. The reaction mixture was then filtered through celite, washed with EtOAc and concentrated in vacuo. The crude residue was purified by chromatography on SiO$_2$ (hexanes/EtOAc, 1:1) to afford (Z)-1-(4-(5-chloro-2-fluorophenyl)piperazin-1-yl)-3-(4-fluorophenyl)prop-2-en-1-one (0.107 g, 39%) as a light yellow oil. $^1$H-NMR (300 MHz; CDCl$_3$): δ 7.38 (dd, J=8.6, 5.4 Hz, 2H), 7.03 (t, J=8.6 Hz, 2H), 6.95-6.91 (m, 2H), 6.78 (dd, J=7.7, 1.9 Hz, 1H), 6.68 (d, J=12.5 Hz, 1H), 6.05 (d, J=12.5 Hz, 1H), 3.83 (t, J=5.1 Hz, 2H), 3.51 (t, J=5.1 Hz, 2H), 3.02 (t, J=5.1 Hz, 2H), 2.71 (t, J=5.1 Hz, 2H).

To a solution of anhydrous CrCl$_2$ (0.169 g, 1.37 mmol) in THF (2.29 mL) that was degassed by sparging with Ar for 30 min followed by the addition of (Z)-1-(4-(5-chloro-2-fluorophenyl)piperazin-1-yl)-3-(4-fluorophenyl)prop-2-en- 1-one (83.0 mg, 0.229 mmol) and CH$_2$ICl (0.132 mL, 1.14 mmol) at RT and under Ar atmosphere. The reaction mixture was stirred at 80° C. After stirring for 14 h, the mixture was cooled to RT and quenched by the addition of 1.0 M aqueous HCl (10 mL) and extracted with EtOAc (3×20 mL). The combined organic layer was concentrated, then the residue was diluted in EtOAc (3 mL) and the solution was filtered through a plug of basic alumina, and concentrated. The crude material was purified by chromatography on SiO$_2$ (EtOAc/hexanes, 1:1) to afford (4-(5-chloro-2-fluorophenyl) piperazin-1-yl)(2-(4-fluorophenyl)cyclopropyl)methanone as a white crystal (67 mg, 78%): Mp: 108-109° C.; IR (neat): 1638, 1606, 1512, 1498, 1436, 1230, 1209, 1032 cm$^{-1}$; $^1$H-NMR (400 MHz; CDCl$_3$): δ 7.12 (dd, J=8.5, 5.5 Hz, 2H), 6.97-6.88 (m, 4H), 6.72 (dd, J=7.3, 1.9 Hz, 1H), 3.79 (d, J=12.8 Hz, 1H), 3.69 (t, J=17.1 Hz, 2H), 3.39 (t, J=9.5 Hz, 1H), 2.99 (t, J=13.9 Hz, 2H), 2.52-2.42 (m, 2H), 2.40-2.34 (m, 1H), 2.20-2.15 (m, 1H), 1.84-1.80 (m, 1H), 1.37-1.32 (m, 1H). $^{13}$C-NMR (125 MHz; CDCl$_3$): δ 167.2, 161.6 (d, J=245.2 Hz), 154.1 (d, J=246.1 Hz), 140.4 (d, J=9.9 Hz), 133.0 (d, J=2.8 Hz), 129.4 (d, J=3.3 Hz), 129.0 (d, J=7.5 Hz), 122.4 (d, J=8.1 Hz), 119.3 (d, J=2.8 Hz), 117.1 (d, J=22.7 Hz), 115.0 (d, J=21.2 Hz), 50.6, 50.1, 45.1, 41.7, 23.7, 23.5, 10.6. HRMS (ESI): m/z calculated for C$_{20}$H$_{20}$N$_2$OClF$_2$ ([M+H]$^+$) 377.1227, found 377.1221.

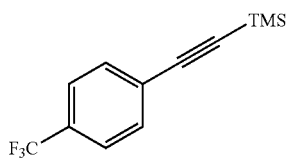

Trimethyl((4-(trifluoromethyl)phenyl)ethynyl)silane. A flame-dried flask under Ar was added with Pd(PPh)$_2$Cl$_2$ (0.496 g, 0.707 mmol), CuI (0.137 g, 0.707 mmol), and 4-bromobenzotrifluoride (10.0 mL, 70.7 mmol). The flask was purged with Ar before triethylamine (141 mL) and (trimethylsilyl)acetylene (15.0 mL, 106 mmol) were added via syringe and the solution was sparged with Ar for 10 min. The resulting mixture was heated to 80° C. for 22.5 h. After cooling the reaction to RT, the solution was filtered through celite, which was washed with EtOAc until the washes appeared colorless. The filtrate was concentrated in vacuo. The crude product was purified by chromatography on SiO$_2$ (hexanes) to afford trimethyl((4-(trifluoromethyl)phenyl) ethynyl)silane (17.1 g, >99%) as a light yellow oil: $^1$H-NMR (400 MHz; CDCl$_3$): δ 7.55 (s, 4H), 0.26 (s, 9H). The spectra obtained are in agreement with previously reported data (Rahaim et al., J. Org. Chem. 2008, 73:2912-2915).

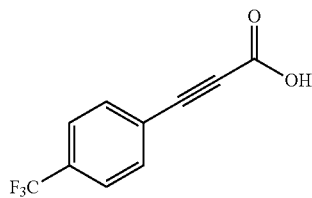 [SMILES: O=C(O)C#Cc1ccc(C(F)(F)F)cc1]

3-(4-(Trifluoromethyl)phenyl)propionic acid. A dried and CO$_2$ (balloon) infused flask, equipped with a magnetic stirrer and a septum, was charged with CsF (13.0 g, 84.7 mmol). A solution of ((4-trifluoro-phenyl)ethynyl)trimethylsilane (17.1 g, 70.6 mmol) in dry DMSO (141 mL) was added dropwise to a reaction mixture by using equal-dropping funnel and the reaction was stirred under CO$_2$ at room temperature for 21 h. After that, the reaction mixture was quenched with water (300 mL) at 0° C. Then the mixture was washed with CH$_2$Cl$_2$ (300 mL×2) and the resulting water phase was acidified with 1 M aqueous HCl (300 mL). Then the solution was extracted with Et$_2$O (500 mL×3), dried (Na$_2$SO$_4$), filtered and concentrated in vacuo. The resulting solid was collected during washing it with hexanes. The collecting solid was dried under reduced pressure to yield 3-(4-(trifluoromethyl)phenyl)propionic acid (14.8 g, 98%) as a light brown solid: $^1$H-NMR (400 MHz; DMSO-d$_6$): δ 14.27-13.92 (brs, 1H), 7.88-7.83 (m, 4H). The spectra obtained are in agreement with previously reported data (Cheng et al., Green Chem. 2015, 17:1675-1682).

1-(4-(5-Chloro-2-methylphenyl)piperazin-1-yl)-3-(4-(trifluoromethyl)phenyl)prop-2-yn-1-one. To a solution of 3-(4-trifluorophenyl)propionic acid (0.20 g, 0.934 mmol) in CH$_2$Cl$_2$ (9.34 mL) at 0° C. was added 1-(5-chloro-2-methylphenyl)piperazine (0.276 g, 1.12 mmol), and Et$_3$N (0.530 mL, 3.74 mmol). T$_3$P (0.991 mL, 1.40 mmol) was added dropwise and the reaction was stirred at 0° C. for 30 min and allowed to warm to room temperature for 18.5 h. The reaction was quenched with saturated aqueous NH$_4$Cl solution (20 mL) and extracted with CH$_2$Cl$_2$ (40 mL×3). The combined organic phase was dried (MgSO$_4$), filtered and concentrated in vacuo. The crude material was purified by chromatography on SiO$_2$ (EtOAc/hexanes, 1:4) to afford 1-(4-(5-chloro-2-methylphenyl)piperazin-1-yl)-3-(4-(trifluoromethyl)phenyl)prop-2-yn-1-one (0.222 g, 58%) as a light yellow crystal. Mp: 104-106° C.; IR (neat): 1633, 1593, 1490, 1431, 1322, 1126 cm$^{-1}$; $^1$H-NMR (400 MHz; CDCl$_3$): δ 7.67 (d, J=8.5 Hz, 2H), 7.64 (d, J=8.5 Hz, 2H), 7.12 (dd, J=8.1, 0.4 Hz, 1H), 7.00 (dd, J=8.1, 2.1 Hz, 1H), 6.96 (d, J=2.1 Hz, 1H), 3.97 (t, J=5.0 Hz, 2H), 3.85 (t, J=5.0 Hz, 2H), 2.98 (t, J=5.0 Hz, 2H), 2.90 (t, J=5.0 Hz, 2H), 2.29 (s, 3H). $^{13}$C-NMR (100 MHz; CDCl$_3$): δ 152.6, 151.6, 132.6, 132.1, 131.7 (q, J=32.9 Hz), 131.0, 125.5 (q, J=3.7 Hz), 124.2, 123.9, 123.6 (q, J=273.7 Hz), 119.8, 89.0, 82.73, 51.9, 51.3, 47.4, 42.0, 17.4. $^{19}$F-NMR (376 MHz; CDCl$_3$): δ −63.07 (s, 3F). HRMS (ESI): m/z calculated for C$_{21}$H$_{19}$N$_2$OClF$_3$ ([M+H]$^+$) 407.1133, found 407.1132.

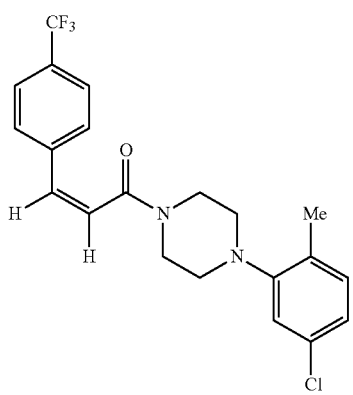 [SMILES: Cc1ccc(Cl)cc1N1CCN(C(=O)/C=C\c2ccc(C(F)(F)F)cc2)CC1]

(Z)-1-(4-(5-Chloro-2-methylphenyl)piperazin-1-yl)-3-(4-(trifluoromethyl)phenyl)prop-2-en-1-one. To a solution of 1-(4-(5-chloro-2-methylphenyl)piperazin-1-yl)-3-(4-(trifluoromethyl)phenyl)prop-2-yn-1-one (0.186 g, 0.457 mmol) in EtOAc (4.60 mL, 0.1 M) was added Lindlar's catalyst (5% Pd on CaCO$_3$, lead poisoned, 0.0487 g, 5.0 mol %). The reaction vessel was placed under vacuum and backfilled with H$_2$ (balloon, 2×) and allowed to stir for 18 h. The reaction mixture was then filtered through celite, washed with EtOAc and concentrated in vacuo. The crude product was purified by chromatography on SiO$_2$ (hexanes/EtOAc, 1:1) to afford (Z)-1-(4-(5-chloro-2-methylphenyl)piperazin-1-yl)-3-(4-(trifluoromethyl)phenyl)prop-2-en-1-one (0.184 g, 98%) as a white crystal. Mp: 109-111° C.; IR (neat): 1621, 1594, 1490, 1440, 1325, 1124 cm$^{-1}$; $^1$H-NMR (400 MHz; CDCl$_3$): δ 7.62 (d, J=8.2 Hz, 2H), 7.52 (d, J=8.2 Hz, 2H), 7.07 (d, J=8.1 Hz, 1H), 6.96 (dd, J=8.1, 2.1 Hz, 1H), 6.78 (d, J=2.1 Hz, 1H), 6.74 (d, J=12.6 Hz, 1H), 6.21 (d, J=12.6 Hz, 1H), 3.81 (t, J=5.0 Hz, 2H), 3.49 (t, J=5.0 Hz, 2H), 2.80 (t, J=5.0 Hz, 2H), 2.51 (t, J=5.0 Hz, 2H), 2.21 (s, 3H). $^{13}$C-NMR (100 MHz; CDCl$_3$): δ 166.8, 151.6, 138.9, 132.3, 132.1, 131.9, 131.0, 130.5 (q, J=32.2 Hz), 128.7, 125.6 (q, J=3.9 Hz), 125.3, 123.9 (q, J=270.5 Hz), 123.8, 119.7, 51.5, 51.3, 46.6, 41.6, 17.3. $^{19}$F-NMR (376 MHz; CDCl$_3$): δ −62.66 (s, 3F). HRMS (ESI): m/z calculated for C$_{21}$H$_{19}$N$_2$OClF$_3$ ([M+H]$^+$) 407.1133, found 407.1132.

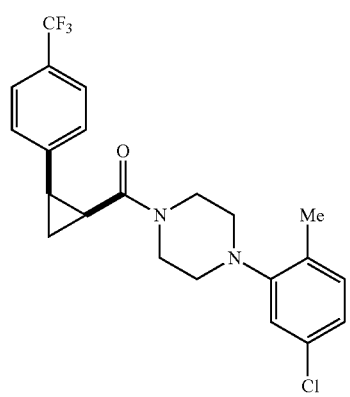

(4-(5-Chloro-2-methylphenyl)piperazin-1-yl)(2-(4-(trifluoromethyl)phenyl)cyclopropyl)methanone. To a solution of anhydrous CrCl$_2$ (0.273 g, 2.16 mmol) in THF (162 mL) that was degassed by sparging with Ar for 30 min followed by the addition of (Z)-1-(4-(5-chloro-2-methylphenyl)piperazin-1-yl)-3-(4-trifluorophenyl)prop-2-en-1-one (0.147 g, 0.360 mmol) and CH$_2$ICl (0.134 mL, 1.80 mmol) at room temperature and under Ar atmosphere. The reaction mixture was stirred at 80° C. After stirring for 17.5 h, the reactions were was cooled to room temperature, combined, quenched by the addition of 1.0 M aqueous HCl (10 mL) and extracted with EtOAc (3×20 mL). The organic layers were combined, dried (Na$_2$SO$_4$), filtered through a plug of basic alumina and concentrated in vacuo. The crude material was purified by chromatography on SiO$_2$ (EtOAc/hexanes, 1:1) to afford (4-(5-chloro-2-methylphenyl)piperazin-1-yl)(2-(4-(trifluoromethyl)phenyl)cyclopropyl)methanone (127 mg) as a white solid. Then the product was recrystallized with cyclohexane to afford the target product as a white crystal (89 mg, 59%): Mp: 109-110° C.; IR (neat): 1638, 1619, 1593, 1437, 1324, 1116, 1069 cm$^{-1}$; $^1$H-NMR (400 MHz; CDCl$_3$): δ 7.54 (d, J=8.1 Hz, 2H), 7.28 (d, J=8.1 Hz, 2H), 7.06 (d, J=8.1 Hz, 1H), 6.95 (dd, J=8.1, 2.1 Hz, 1H), 6.67 (d, J=2.1 Hz, 1H), 3.82-3.78 (m, 1H), 3.70-3.58 (m, 2H), 3.37-3.31 (m, 1H), 2.79-2.69 (m, 2H), 2.51 (q, J=8.0 Hz, 1H), 2.30-2.23 (m, 2H), 2.19 (s, 3H), 2.13-2.08 (m, 1H), 1.91 (q, J=6.2 Hz, 1H), 1.45-1.40 (m, 1H). $^{13}$C-NMR (100 MHz; CDCl$_3$): δ 166.7, 151.7, 141.9, 141.9, 131.9, 131.8, 130.9, 128.7 (q, J=32.5 Hz), 127.9, 125.0 (q, J=3.8 Hz), 124.2 (q, J=270.0 Hz), 123.7, 119.6, 51.8, 51.5, 45.5, 42.2, 24.5, 24.0, 17.3, 11.1. $^{19}$F-NMR (376 MHz; CDCl$_3$): δ −62.31 (s, 1F). HRMS (ESI): m/z calculated for C$_{22}$H$_{23}$N$_2$OClF$_3$ ([M+H]$^+$) 423.1446, found 423.1443.

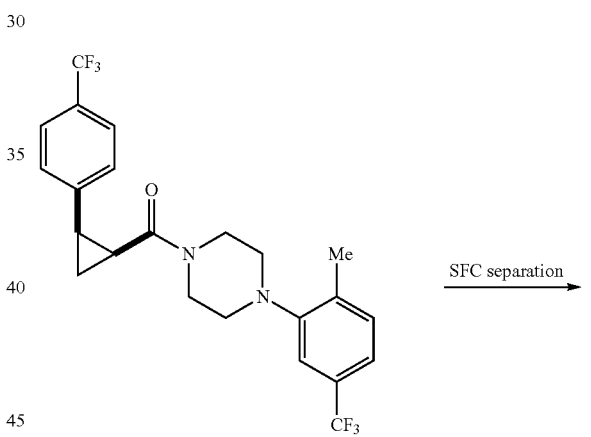

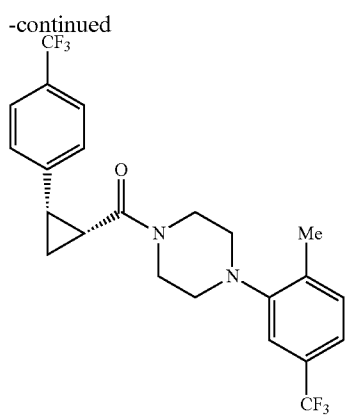

Racemic (2-(4-fluorophenyl)cyclopropyl)(4-(2-methyl-5-(trifluoromethyl)phenyl)piperazin-1-yl)methanone was separated on a SFC Chiralpak-IC semiprep (250×10 mm) column (30% MeOH, 7 mL/min, 220 nM, P=100) to afford (4-(2-methyl-5-(trifluoromethyl)phenyl)piperazin-1-yl)((1S,2R)-2-(4-(trifluoromethyl)-phenyl)cyclopropyl)methanone (retention time; 5.12 min) as a colorless oil (>99.9% purity by ELSD): $[\alpha]^{18}{}_D$ −150.5 (c 0.51, MeOH); HRMS (ESI): m/z calculated for $C_{22}H_{23}N_2OClF_3$ ([M+H]$^+$) 423.1446, found 423.1449. The enantiomeric excess was >99.9% ee (SFC Chiralpak-IC semiprep; 30% MeOH, 220 nM, 7 mL/min; retention time: 5.12 min). $^1$H-NMR (400 MHz; CDCl$_3$): δ 7.54 (d, J=8.1 Hz, 2H), 7.28 (d, J=8.1 Hz, 2H), 7.06 (d, J=8.1 Hz, 1H), 6.95 (dd, J=8.1, 2.1 Hz, 1H), 6.67 (d, J=2.1 Hz, 1H), 3.82-3.78 (m, 1H), 3.70-3.58 (m, 2H), 3.37-3.31 (m, 1H), 2.79-2.69 (m, 2H), 2.51 (q, J=8.0 Hz, 1H), 2.30-2.23 (m, 2H), 2.19 (s, 3H), 2.13-2.08 (m, 1H), 1.91 (q, J=6.2 Hz, 1H), 1.45-1.40 (m, 1H).

(4-(2-Methyl-5-(trifluoromethyl)phenyl)piperazin-1-yl)((1R,2S)-2-(4-(trifluoromethyl)phenyl)-cyclopropyl)methanone (retention time; 6.43 min) as a colorless oil (>99.9% purity by ELSD): $[\alpha]^{18}{}_D$ +148.4 (c 0.51, MeOH); HRMS (ESI): m/z calculated for $C_{22}H_{23}N_2OClF_3$ ([M+H]$^+$) 423.1446, found 423.1444. The enantiomeric excess was >99.9% ee (SFC Chiralpak-IC semiprep; 30% MeOH, 220 nM, 7 mL/min; retention time: 6.43 min). $^1$H-NMR (400 MHz; CDCl$_3$): δ 7.54 (d, J=8.1 Hz, 2H), 7.28 (d, J=8.1 Hz, 2H), 7.06 (d, J=8.1 Hz, 1H), 6.95 (dd, J=8.1, 2.1 Hz, 1H), 6.67 (d, J=2.1 Hz, 1H), 3.82-3.78 (m, 1H), 3.70-3.58 (m, 2H), 3.37-3.31 (m, 1H), 2.79-2.69 (m, 2H), 2.51 (q, J=8.0 Hz, 1H), 2.30-2.23 (m, 2H), 2.19 (s, 3H), 2.13-2.08 (m, 1H), 1.91 (q, J=6.2 Hz, 1H), 1.45-1.40 (m, 1H).

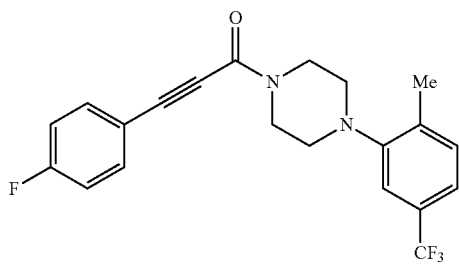 [SMILES: Cc1ccc(C(F)(F)F)cc1N1CCN(C(=O)C#Cc2ccc(F)cc2)CC1]

3-(4-Fluorophenyl)-1-(4-(2-methyl-5-(trifluoromethyl)phenyl)piperazin-1-yl)prop-2-yn-1-one. To a solution of 3-(4-fluorophenyl)propionic acid (0.100 g, 0.609 mmol) in CH$_2$Cl$_2$ (6.09 mL) at 0° C. was added 1-(5-trifluoromethyl-2-methylphenyl)piperazine (0.205 g, 0.731 mmol), and Et$_3$N (0.259 mL, 1.83 mmol). T$_3$P (0.646 mL, 0.914 mmol) was added dropwise and the reaction was stirred at 0° C. for 30 min and allowed to warm to room temperature for 20.5 h. The reaction was diluted with CH$_2$Cl$_2$ (40 mL) and washed with 1 M HCl (50 mL). The aqueous phase was extracted with CH$_2$Cl$_2$ (30×2) and combined organic phase was dried (MgSO$_4$), filtered and concentrated in vacuo. The crude material was purified by chromatography on SiO$_2$ (EtOAc/hexanes, 1:4) to afford 3-(4-fluorophenyl)-1-(4-(2-methyl-5-(trifluoromethyl)phenyl)piperazin-1-yl)prop-2-yn-1-one (219 mg, 92%) as a white crystal: Mp: 176-177° C.; IR (neat): 2220, 1630, 1600, 1507, 1419, 1310, 1226, 1120 cm$^{-1}$; $^1$H-NMR (400 MHz; CDCl$_3$): δ 7.56 (dd, J=8.8, 5.3 Hz, 2H), 7.31 (d, J=8.1 Hz, 1H), 7.28 (d, J=8.1 Hz, 1H), 7.22 (s, 1H), 7.08 (t, J=8.8 Hz, 2H), 4.00 (t, J=5.0 Hz, 2H), 3.87 (t, J=5.0 Hz, 2H), 3.03 (t, J=4.9 Hz, 2H), 2.94 (t, J=5.0 Hz, 2H), 2.40 (s, 3H). $^{13}$C-NMR (100 MHz; CDCl$_3$): δ 163.6 (d, J=252.4 Hz), 153.1, 151.0, 136.8, 134.6, 134.5, 131.6, 129.1 (q, J=32.2 Hz), 124.1 (q, J=270.4 Hz), 120.5 (q, J=3.8 Hz,), 116.4 (d, J=3.7 Hz), 116.1 (q, J=3.7 Hz), 116.0 (d, J=22.0 Hz), 90.0, 80.8, 80.8, 77.3, 77.0, 76.7, 51.9, 51.4, 47.4, 41.9, 18.0. $^{19}$F-NMR (376 MHz; CDCl$_3$): δ −62.29 (s, 3F), −107.28--107.35 (m, 1F). HRMS (ESI): m/z calculated for $C_{21}H_{19}N_2OF_4$ ([M+H]$^+$) 391.1428, found 391.1402.

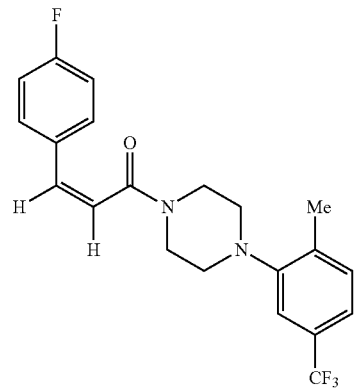 [SMILES: Cc1ccc(C(F)(F)F)cc1N1CCN(C(=O)/C=C\c2ccc(F)cc2)CC1]

(Z)-3-(4-Fluorophenyl)-1-(4-(2-methyl-5-(trifluoromethyl)phenyl)piperazin-1-yl)prop-2-en-1-one. To a solution of 3-(4-fluorophenyl)-1-(4-(2-methyl-5-(trifluoromethyl)phenyl)piperazin-1-yl)prop-2-yn-1-one (0.193 g, 0.494 mmol) in EtOAc (4.90 mL, 0.1 M) was added Lindlar's catalyst (5% Pd on CaCO$_3$, lead poisoned, 0.0526 g, 5.0 mol %). The reaction vessel was placed under vacuum and backfilled with H$_2$ (balloon, 2×) and allowed to stir for 18 h. The reaction mixture was then filtered through celite, washed with EtOAc and concentrated in vacuo. The crude residue was purified by chromatography on SiO$_2$ (hexanes/EtOAc, 1:1) to afford (Z)-3-(4-fluorophenyl)-1-(4-(2-methyl-5-(trifluoromethyl)phenyl)piperazin-1-yl)prop-2-en-1-one (0.107 g, 55%) as a light yellow oil: Mp: 176-177° C.; IR (neat): 2917, 1640, 1617, 1602, 1508, 1439, 1417, 1338, 1309, 1225, 1162, 1119 cm$^{-1}$; $^1$H-NMR (400 MHz; CDCl$_3$): δ 7.42 (dd, J=8.7, 5.3 Hz, 2H), 7.30-7.25 (m, 2H), 7.10-7.06 (m, 3H), 6.71 (d, J=12.5 Hz, 1H), 6.09 (d, J=12.5 Hz, 1H), 3.85 (t, J=5.0 Hz, 2H), 3.54 (t, J=5.0 Hz, 2H), 2.87 (t, J=5.0 Hz, 2H), 2.58 (t, J=5.0 Hz, 2H), 2.34 (s, 3H); $^{13}$C-NMR (100 MHz; CDCl$_3$): δ 167.3, 162.7 (d, J=249.4 Hz), 151.0, 136.8, 132.7, 131.6 (d, J=3.6 Hz), 131.5, 130.3 (d, J=8.1 Hz), 129.0 (q, J=32.2 Hz), 124.1 (q, J=270.4 Hz), 122.7, 122.7, 120.4 (q, J=3.9 Hz), 115.9 (q, J=3.7 Hz), 115.7, 115.6, 51.4, 51.3, 46.6, 41.5, 17.9: $^{19}$F-NMR (376 MHz; CDCl$_3$): δ −62.36 (s, 3F), −112.02-−112.09 (m, 1F): HRMS (ESI): m/z calculated for C$_{21}$H$_{21}$N$_2$OF$_4$ ([M+H]$^+$) 393.1585, found 393.1585.

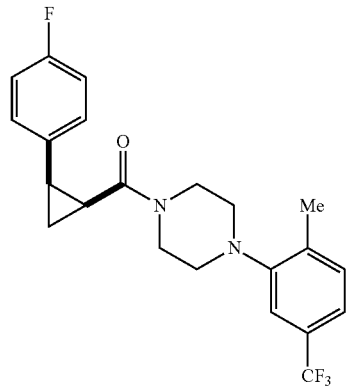 [SMILES: Cc1ccc(C(F)(F)F)cc1N1CCN(C(=O)[C@H]2C[C@H]2c2ccc(F)cc2)CC1]

(2-(4-Fluorophenyl)cyclopropyl)(4-(2-methyl-5-(trifluoromethyl)phenyl)piperazin-1-yl)methanone. To a solution of anhydrous CrCl$_2$ (0.172 g, 1.36 mmol) in THF (2.27 mL) that was degassed by sparging with Ar for 10 min followed by the addition of (Z)-3-(4-fluorophenyl)-1-(4-(2-methyl-5-(trifluoromethyl)phenyl)-piperazin-1-yl)prop-2-en-1-one (0.0889 g, 0.227 mmol) and CH$_2$ICl (0.0842 mL, 1.13 mmol) at room temperature and under Ar atmosphere. The reaction mixture was stirred at 80° C. After stirring for 13 h, the reactions were was cooled to room temperature, combined, quenched by the addition of 1.0 M aqueous HCl (10 mL) and extracted with EtOAc (30 mL). The organic layer was sequentially washed with 1 M aqueous HCl (30 mL) and saturated aqueous sodium thiosulfate (30 mL). Then the organic phase was dried (Na$_2$SO$_4$), filtered and concentrated in vacuo. The residue was diluted in minimum amount of 3:2 mixed solvent of EtOAc and hexanes, and the solution was filtered through a plug of basic alumina, and concentrated in vacuo. The crude material was purified by chromatography on SiO$_2$ (EtOAc/hexanes, 3:2) to afford (2-(4-fluorophenyl) cyclopropyl)(4-(2-methyl-5-(trifluoromethyl)phenyl)piperazin-1-yl)methanone (0.0878 g, 95%) as a brown oil: IR (neat): 2918, 1637, 1513, 1417, 1337, 1307, 1223, 1161, 1118 cm$^{-1}$; $^1$H-NMR (500 MHz; CDCl$_3$): δ 7.27 (t, J=1.6 Hz, 2H), 7.17 (dd, J=8.7, 5.3 Hz, 2H), 7.02-6.98 (m, 3H), 3.90-3.85 (m, 1H), 3.78-3.74 (m, 1H), 3.70-3.65 (m, 1H), 3.40-3.35 (m, 1H), 2.86-2.77 (m, 2H), 2.51-2.46 (m, 1H), 2.33-2.20 (m, 6H), 1.86 (q, J=6.2 Hz, 1H), 1.38 (td, J=8.5, 5.5 Hz, 1H): $^{13}$C-NMR (125 MHz; CDCl$_3$): δ 167.2, 161.6 (d, J=245.2 Hz), 151.1, 136.8, 133.0 (d, J=2.7 Hz), 131.4, 129.0 (d, J=7.9 Hz), 129.0 (q, J=25.5 Hz), 124.1 (q, J=272.0 Hz), 120.3 (q, J=3.7 Hz), 115.9 (q, J=3.7 Hz), 115.0, 114.8, 51.7, 51.6, 45.5, 42.2, 23.9, 23.4, 17.8, 10.6. $^{19}$F-NMR (471 MHz; CDCl$_3$): δ −62.36 (s, 1F), −116.30-−116.41 (m, 1F); HRMS (ESI): m/z calculated for C$_{22}$H$_{23}$N$_2$OF$_4$ ([M+H]$^+$) 407.1741, found 407.1732.

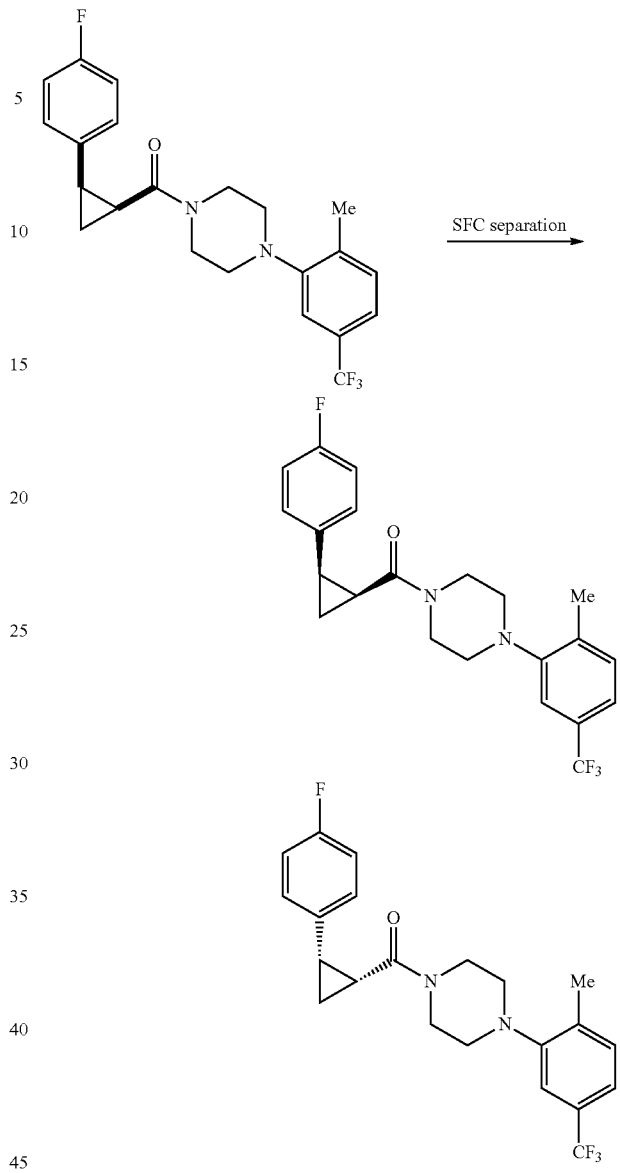

Racemic (2-(4-fluorophenyl)cyclopropyl)(4-(2-methyl-5-(trifluoromethyl)phenyl)piperazin-1-yl)methanone was separated on a SFC Chiralpak-IC semiprep (250×10 mm) column (30% MeOH, 7 mL/min, 220 nM, P=100) to afford ((1S,2R)-2-(4-fluorophenyl)cyclopropyl)(4-(2-methyl-5-(trifluoromethyl)phenyl)piperazin-1-yl)methanone (retention time; 4.40 min) as a colorless oil (>99.9% purity by ELSD): [α]$^{18}$$_D$ −145.6 (c 0.86, MeOH); HRMS (ESI): m/z calculated for C$_{22}$H$_{23}$N$_2$OF$_4$ ([M+H]$^+$) 407.1741, found 407.1741. The enantiomeric excess was >99.9% ee (SFC Chiralpak-IC semiprep; 30% MeOH, 220 nM, 7 mL/min; retention time: 4.40 min). $^1$H-NMR (500 MHz; CDCl$_3$): δ 7.27 (t, J=1.6 Hz, 2H), 7.17 (dd, J=8.7, 5.3 Hz, 2H), 7.02-6.98 (m, 3H), 3.90-3.85 (m, 1H), 3.78-3.74 (m, 1H), 3.70-3.65 (m, 1H), 3.40-3.35 (m, 1H), 2.86-2.77 (m, 2H), 2.51-2.46 (m, 1H), 2.33-2.20 (m, 6H), 1.86 (q, J=6.2 Hz, 1H), 1.38 (td, J=8.5, 5.5 Hz, 1H).

((1R,2S)-2-(4-Fluorophenyl)cyclopropyl)(4-(2-methyl-5-(trifluoromethyl)phenyl)piperazin-1-yl)methanone (retention time; 4.74 min) as a colorless oil (>99.9% purity by ELSD): [α]¹⁸$_D$+139.8 (c 1.14, MeOH); HRMS (ESI): m/z calculated for $C_{22}H_{23}N_2OF_4$ ([M+H]⁺) 407.1741, found 407.1741. The enantiomeric excess was >99.9% ee (SFC Chiralpak-IC semiprep; 30% MeOH, 220 nM, 7 mL/min; retention time: 4.74 min). ¹H-NMR (500 MHz; CDCl₃): δ 7.27 (t, J=1.6 Hz, 2H), 7.17 (dd, J=8.7, 5.3 Hz, 2H), 7.02-6.98 (m, 3H), 3.90-3.85 (m, 1H), 3.78-3.74 (m, 1H), 3.70-3.65 (m, 1H), 3.40-3.35 (m, 1H), 2.86-2.77 (m, 2H), 2.51-2.46 (m, 1H), 2.33-2.20 (m, 6H), 1.86 (q, J=6.2 Hz, 1H), 1.38 (td, J=8.5, 5.5 Hz, 1H).

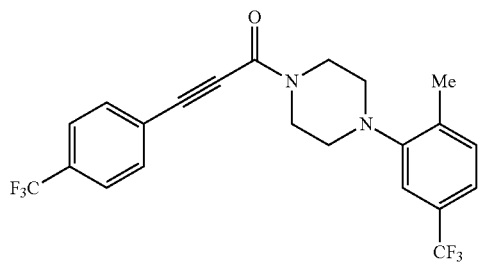

1-(4-(2-Methyl-5-(trifluoromethyl)phenyl)piperazin-1-yl)-3-(4-(trifluoromethyl)phenyl)prop-2-yn-1-one. To a solution of 3-(4-trifluorophenyl)propionic acid (0.100 g, 0.467 mmol) in CH₂Cl₂ (6.09 mL) at 0° C. was added 1-(5-trifluoromethyl-2-methylphenyl)piperazine (0.157 g, 0.560 mmol), and Et₃N (0.199 mL, 1.40 mmol). T₃P (0.495 mL, 0.700 mmol) was added dropwise and the reaction was stirred at 0° C. for 30 min and allowed to warm to room temperature for 20.5 h. The reaction was diluted with CH₂Cl₂ (40 mL) and washed with 1 M HCl (50 mL). The aqueous phase was extracted with CH₂Cl₂ (30 mL×2) and combined organic phase was dried (MgSO₄), filtered and concentrated in vacuo. The crude material was purified by chromatography on SiO₂ (EtOAc/hexanes, 1:4) to afford 1-(4-(2-methyl-5-(trifluoromethyl)-phenyl)piperazin-1-yl)-3-(4-(trifluoromethyl)phenyl)prop-2-yn-1-one (188 mg, 91%) as a white crystal: Mp: 159-160° C.; IR (neat): 2224, 1631, 1458, 1431, 1418, 1339, 1321, 1310, 1279, 1165, 1119 cm⁻¹; ¹H-NMR (400 MHz; CDCl₃): δ 7.68 (d, J=8.5 Hz, 2H), 7.65 (d, J=8.5 Hz, 2H), 7.32 (d, J=8.3 Hz, 1H), 7.28 (dd, J=8.3, 1.2 Hz, 1H), 7.22 (s, 1H), 4.00 (t, J=5.0 Hz, 2H), 3.88 (t, J=5.0 Hz, 2H), 3.04 (t, J=5.0 Hz, 2H), 2.95 (t, J=5.0 Hz, 2H), 2.40 (s, 3H); ¹³C-NMR (100 MHz; CDCl₃): δ 152.6, 150.9, 136.8, 132.6, 131.8 (q, J=32.4 Hz), 131.6, 129.2 (q, J=32.2 Hz), 125.5 (q, J=3.7 Hz), 124.1 (q, J=270.5 Hz), 123.6 (q, J=271.1 Hz), 120.6 (q, J=3.8 Hz), 116.1 (q, J=3.7 Hz), 89.1, 82.7, 77.4 77.0, 76.7, 51.9, 51.4, 47.5, 42.0, 18.0; ¹⁹F-NMR (376 MHz; CDCl₃): δ -62.29 (s, 3F), -63.09 (s, 3F); HRMS (ESI): m/z calculated for $C_{22}H_{19}N_2OF_6$ ([M+H]⁺) 441.1396, found 441.1385.

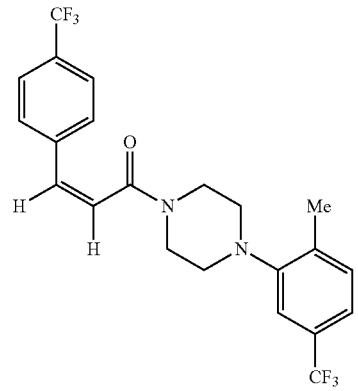 [SMILES: Cc1ccc(C(F)(F)F)cc1N1CCN(C(=O)/C=C\c2ccc(C(F)(F)F)cc2)CC1]

(Z)-1-(4-(2-Methyl-5-(trifluoromethyl)phenyl)piperazin-1-yl)-3-(4-(trifluoromethyl)phenyl)prop-2-en-1-one. To a solution of 1-(4-(2-methyl-5-(trifluoromethyl)phenyl)piperazin-1-yl)-3-(4-(trifluoromethyl)-phenyl)prop-2-yn-1-one (0.164 g, 0.372 mmol) in EtOAc (3.72 mL, 0.1 M) was added Lindlar's catalyst (5% Pd on CaCO₃, lead poisoned, 0.0396 g, 5.0 mol %). The reaction vessel was placed under vacuum and backfilled with H₂ (balloon, 2×) and allowed to stir for 18 h. The reaction mixture was then filtered through celite, washed with EtOAc and concentrated in vacuo. The crude residue was purified by chromatography on SiO₂ (hexanes/EtOAc, 1:1) to afford (Z)-1-(4-(2-methyl-5-(trifluoromethyl)phenyl)piperazin-1-yl)-3-(4-(trifluoromethyl)phenyl)prop-2-en-1-one (0.0998 g, 61%) as a light yellow oil: IR (neat): 2978, 1622, 1442, 1417, 1327, 1118 cm⁻¹; ¹H-NMR (400 MHz; CDCl₃): δ 7.40 (dd, J=8.7, 5.4 Hz, 2H), 7.28-7.23 (m, 2H), 7.05 (t, J=8.7 Hz, 3H), 6.68 (d, J=12.5 Hz, 1H), 6.07 (d, J=12.5 Hz, 1H), 3.83 (t, J=4.9 Hz, 2H), 3.52 (t, J=4.9 Hz, 2H), 2.85 (d, J=4.9 Hz, 2H), 2.57 (d, J=4.9 Hz, 2H), 2.32 (s, 3H); ¹³C-NMR (125 MHz; CDCl₃): δ 166.8, 150.9, 138.8, 136.8, 132.4, 131.5, 130.5 (q, J=32.7 Hz), 129.1 (q, J=29.3 Hz), 128.7, 125.6 (q, J=3.7 Hz), 125.3, 124.1 (q, J=216.1 Hz), 123.9 (q, J=216.4 Hz), 120.5 (q, J=3.9 Hz), 115.9 (q, J=3.6 Hz), 77.3, 77.0, 76.8, 51.4, 51.3, 46.6, 41.6, 17.9; ¹⁹F-NMR (376 MHz; CDCl₃): δ -62.41 (s, 3F), -62.79 (s, 3F); HRMS (ESI): m/z calculated for $C_{22}H_{21}N_2OF_6$ ([M+H]⁺) 443.1553, found 443.1551.

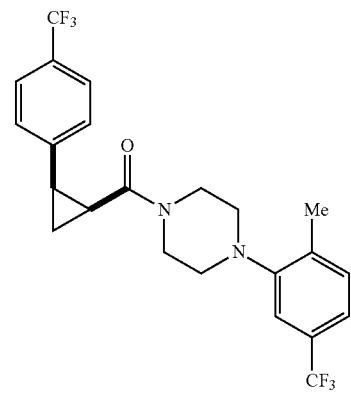 [SMILES: Cc1ccc(C(F)(F)F)cc1N1CCN(C(=O)[C@H]2C[C@H]2c2ccc(C(F)(F)F)cc2)CC1]

(4-(2-Methyl-5-(trifluoromethyl)phenyl)piperazin-1-yl)(2-(4-(trifluoromethyl)phenyl)cyclopropyl)-methanone. To a solution of anhydrous CrCl₂ (0.134 g, 1.06 mmol) in THF (1.80 mL) that was degassed by sparging with Ar for 10 min followed by the addition of (Z)-1-(4-(2-methyl-5-(trifluoromethyl)phenyl)-piperazin-1-yl)-3-(4-(trifluoromethyl)phenyl)prop-2-en-1-one (0.0782 g, 0.177 mmol) and CH₂ICl (0.0657 mL, 0.884 mmol) at room temperature and under Ar atmosphere. The reaction mixture was stirred at 80° C. After stirring for 16.5 h, the reactions were was cooled to room temperature, combined, quenched by the addition of 1.0 M aqueous HCl (10 mL) and extracted with EtOAc (30 mL). The organic layer was sequentially washed with 1 M aqueous HCl (30 mL×2) and saturated aqueous sodium thiosulfate (30 mL). Then the organic phase was dried (Na₂SO₄), filtered and concentrated in vacuo. The residue was diluted in EtOAc, and the solution was filtered through a plug of basic alumina, and concentrated in vacuo. The crude material was purified by chromatography on SiO₂ (EtOAc/hexanes, 3:2) to afford (4-(2-methyl-5-(trifluoromethyl)phenyl)piperazin-1-yl)(2-(4-(trifluoromethyl)phenyl)cyclopropyl)methanone (0.0878 g, 61%) as a white solid: Mp: 99-101° C.; IR (neat): 1639, 1619, 1438, 1418, 1325, 1308, 1162, 1114 cm⁻¹; ¹H-NMR (400 MHz; CDCl₃): δ 7.53 (d, J=8.1 Hz, 2H), 7.29 (d, J=8.1 Hz, 2H), 7.24 (d, J=1.6 Hz, 2H), 6.94 (s, 1H), 3.88-3.82 (m, 1H), 3.73-3.60 (m, 2H), 3.38-3.31 (m, 1H), 2.84-2.73 (m, 2H), 2.52 (q, J=7.9 Hz, 1H), 2.31-2.25 (m, 5H), 2.16-2.10 (m, 1H), 1.92 (q, J=6.3 Hz, 1H), 1.43 (td, J=8.4, 5.6 Hz, 1H); ¹³C-NMR (100 MHz; CDCl₃): δ 166.7, 151.0, 141.9, 141.9, 136.8, 131.4, 129.1 (q, J=31.9 Hz), 128.8 (q, J=32.1 Hz), 127.9, 125.0 (q, J=3.7 Hz), 124.2 (q, J=270.3 Hz), 124.1 (q, J=270.4 Hz), 120.4 (q, J=3.9 Hz), 115.8 (q, J=3.7 Hz), 77.4, 77.1, 76.7, 51.8, 51.6, 45.5, 42.2, 24.6, 24.0, 17.8, 11.1; ¹⁹F-NMR (376 MHz; CDCl₃): δ −62.46 (s, 3F), −62.52 (s, 3F); HRMS (ESI): m/z calculated for C₂₃H₂₃N₂OF₆ ([M+H]⁺) 457.1709, found 457.1709.

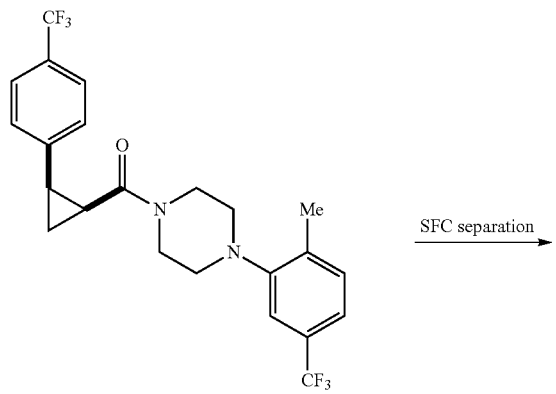

SFC separation

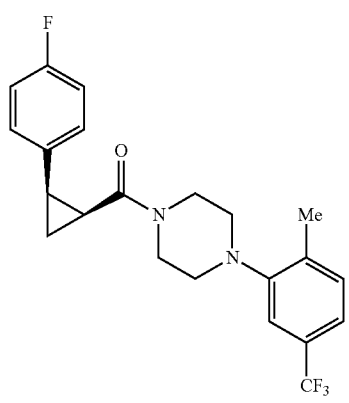

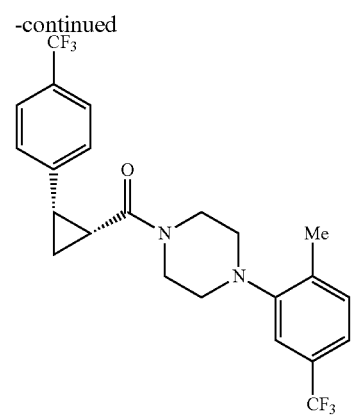

Racemic (4-(2-methyl-5-(trifluoromethyl)phenyl)piperazin-1-yl)(2-(4-(trifluoromethyl)phenyl)cyclopropyl)methanone was separated on a SFC Chiralpak-IC semiprep (250×10 mm) column (30% MeOH, 7 mL/min, 220 nM, P=100) to afford (4-(2-methyl-5-(trifluoromethyl)phenyl)piperazin-1-yl)((1S,2R)-2-(4-(trifluoromethyl)phenyl)cyclopropyl)methanone (retention time; 3.36 min) as a colorless oil (>99.9% purity by ELSD): [α]¹⁸_D −139.3 (c 0.77, MeOH); HRMS (ESI): m/z calculated for C₂₃H₂₃N₂OF₆ ([M+H]⁺) 457.1709, found 457.1709. The enantiomeric excess was >99.9% ee (SFC Chiralpak-IC semiprep; 30% MeOH, 220 nM, 7 mL/min; retention time: 3.36 min). ¹H-NMR (400 MHz; CDCl₃): δ 7.53 (d, J=8.1 Hz, 2H), 7.29 (d, J=8.1 Hz, 2H), 7.24 (d, J=1.6 Hz, 2H), 6.94 (s, 1H), 3.88-3.82 (m, 1H), 3.73-3.60 (m, 2H), 3.38-3.31 (m, 1H), 2.84-2.73 (m, 2H), 2.52 (q, J=7.9 Hz, 1H), 2.31-2.25 (m, 5H), 2.16-2.10 (m, 1H), 1.92 (q, J=6.3 Hz, 1H), 1.43 (td, J=8.4, 5.6 Hz, 1H).

(4-(2-Methyl-5-(trifluoromethyl)phenyl)piperazin-1-yl)((1R,2S)-2-(4-(trifluoromethyl)phenyl)cyclopropyl)-methanone (retention time; 3.74 min) as a colorless oil (>99.9% purity by ELSD): [α]¹⁸_D +135.7 (c 0.91, MeOH); HRMS (ESI): m/z calculated for C₂₃H₂₃N₂OF₆ ([M+H]⁺) 457.1709, found 457.1704. The enantiomeric excess was >99.9% ee (SFC Chiralpak-IC semiprep; 30% MeOH, 220 nM, 7 mL/min; retention time: 3.74 min). ¹H-NMR (400 MHz; CDCl₃): δ 7.53 (d, J=8.1 Hz, 2H), 7.29 (d, J=8.1 Hz, 2H), 7.24 (d, J=1.6 Hz, 2H), 6.94 (s, 1H), 3.88-3.82 (m, 1H), 3.73-3.60 (m, 2H), 3.38-3.31 (m, 1H), 2.84-2.73 (m, 2H), 2.52 (q, J=7.9 Hz, 1H), 2.31-2.25 (m, 5H), 2.16-2.10 (m, 1H), 1.92 (q, J=6.3 Hz, 1H), 1.43 (td, J=8.4, 5.6 Hz, 1H).

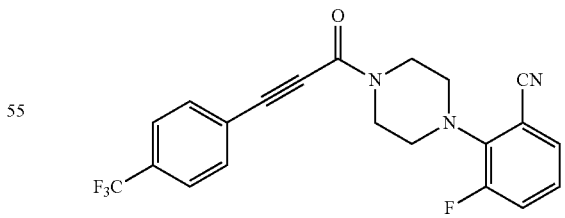

3-Fluoro-2-(4-(3-(4-(trifluoromethyl)phenyl)propioloyl)piperazin-1-yl)benzonitrile. Under N₂ atmosphere, CuBr (0.717 g, 4.90 mmol), 1,1'-bi-2-naphthol (1.05 g, 3.67 mmol) and DMF (12.3 mL) was added to the flame-dried flask. The mixture was stirred for 10 minutes before the addition of 1-Boc-piperazine (6.84 g, 36.7 mmol), K₃PO₄ (10.7 g, 49.0 mmol) and 2-bromo-3-fluorobenzonitrile (5.00 g, 24.5 mmol). The reaction mixture was stirred at 120° C. for 22.5 h. After cooling to room temperature, the mixture was diluted with dichloromethane and filtered through Celite pad. The filtrate was concentrated under reduced pressure. The residue was diluted with Et$_2$O (100 mL) and the solution was sequentially washed with saturated aqueous NH$_4$Cl (100 mL×2) and brine (100 mL×2), dried (Na$_2$SO$_4$), filtered and concentrated in vacuo. The crude product was filtered through a short column of SiO$_2$ (EtOAc/hexanes, 1:9) to remove the remained piperazine. And the obtained mixture (1.10 g) was used without further purification.

To a solution of the above mixture (1.10 g) in 1,4-dioxane (8.40 mL), HCl (4 M in 1,4-dioxane, 3.60 mL) was added at 0° C. The mixture was stirred at RT for 12 h. The thick suspension was diluted with hexanes (50 mL) and the resulting solid was collected by filtration, washed with hexanes and Et$_2$O and dried to give a yellow solid (0.3827 g). This product was used without further purification.

To a solution of 3-(4-(trifluoromethyl)phenyl)propiolic acid (0.200 g, 0.934 mmol) in dry CH$_2$Cl$_2$ (12.2 mL) at 0° C. was added the above solid (0.271 g), and Et$_3$N (0.398 mL, 2.80 mmol). T$_3$P (0.991 mL, 1.40 mmol) was added dropwise and the reaction was stirred at 0° C. for 30 min and allowed to warm to RT for 6.5 h. The reaction was diluted with CH$_2$Cl$_2$ (40 mL) and washed with 1 M HCl (50 mL). The aqueous phase was extracted with CH$_2$Cl$_2$ (30 mL×2) and combined organic phase was dried (MgSO$_4$), filtered, and concentrated in vacuo. The crude material was purified by chromatography on SiO$_2$ (EtOAc/hexanes, 1:2) to afford 3-fluoro-2-(4-(3-(4-(trifluoromethyl)phenyl)propioloyl)piperazin-1-yl)benzonitrile (260 mg, 3% over 3 steps) as a light yellow solid. Mp: 127-129° C.; IR (neat): 2224, 1629, 1464, 1432, 1321, 1281, 1127, 1067, 1032 cm$^{-1}$; $^1$H-NMR (500 MHz; CDCl$_3$): δ 7.68 (d, J=8.4 Hz, 2H), 7.65 (d, J=8.5 Hz, 2H), 7.41 (d, J=7.7 Hz, 1H), 7.29 (dd, J=8.4, 1.4 Hz, 1H), 7.28-7.26 (dd, J=8.5, 1.4 Hz, 1H), 4.01 (t, J=4.9 Hz, 2H), 3.89 (t, J=5.0 Hz, 2H), 3.39 (t, J=4.0 Hz, 2H), 3.32 (t, J=4.0 Hz, 2H). $^{13}$C-NMR (125 MHz; CDCl$_3$): δ 158.4 (d, J=250.3 Hz), 152.7, 141.7 (d, J=12.7 Hz), 132.6, 131.8 (d, J=32.8 Hz), 129.6 (d, J=3.4 Hz), 125.5 (d, J=3.8 Hz), 125.4 (d, J=8.4 Hz), 124.2 (d, J=1.4 Hz), 123.6 (q, J=108.4 Hz), 121.8, 121.6, 117.0 (d, J=4.5 Hz), 111.7 (d, J=6.3 Hz), 51.9 (d, J=4.4 Hz), 51.2 (d, J=4.6 Hz), 47.9, 42.4; $^{19}$F-NMR (470 MHz; CDCl$_3$): δ −63.08 (s, 3F), −119.85 (d, J=11.3 Hz, 1F); HRMS (ESI): m/z calculated for C$_{21}$H$_{16}$F$_4$N$_3$O ([M+H]$^+$) 402.1224, found 402.1223.

(5.98 mL, 0.1 M) was added Pd/BaSO$_4$ (5% Pd on CaCO$_3$, lead poisoned, 0.0636 g, 5.0 mol %). The reaction vessel was placed under vacuum and backfilled with H2 (balloon, 2×) and allowed to stir for 21 h. Then the reaction mixture was then filtered through celite, washed with EtOAc and concentrated in vacuo. The crude residue was purified by chromatography on SiO$_2$ (hexanes/EtOAc, 1:1) to afford 3-fluoro-2-(4-(2-(4-(trifluoromethyl)phenyl)cyclopropane-1-carbonyl)piperazin-1-yl)benzonitrile (0.213 g) as a light yellow oil. This product was used without further purification.

To a solution of anhydrous CrCl$_2$ (0.364 g, 2.87 mmol) in THF (4.78 mL) that was degassed by sparging with Ar for 30 min followed by the addition of the above product (0.193 g, 0.478 mmol) and CH$_2$ICl (0.178 mL, 2.39 mmol) at RT and under Ar atmosphere. The reaction mixture was stirred at 80° C. After stirring for 14.5 h, the reactions were was cooled to RT and added to EtOAc (30 mL). Then the mixture was sequentially washed with 1.0 M aqueous HCl (30 mL×3) and saturated aqueous sodium thiosulfate (30 mL×2). The resulting organic phase was dried (Na$_2$SO$_4$), filtered and concentrated in vacuo. The crude material was diluted with EtOAc (5 mL) and filtered through basic aluminum. This process was repeated two times to remove residual chromium. Then the mixture was purified by chromatography on SiO$_2$ (EtOAc/hexanes, 1:1) to afford 3-fluoro-2-(4-(2-(4-(trifluoromethyl)phenyl)cyclopropane-1-carbonyl)-piperazin-1-yl)benzonitrile as a brown viscous oil (21.4 mg, 10% over 2 steps): IR (neat): 2233, 1639, 1465, 1436, 1325, 1163, 1116, 1069, 1028 cm$^{-1}$; $^1$H-NMR (400 MHz; CDCl$_3$): δ 7.53 (d, J=8.1 Hz, 2H), 7.34 (ddd, J=7.7, 1.4, 0.8 Hz, 1H), 7.28 (d, J=8.3 Hz, 2H), 7.20 (ddd, J=12.0, 8.3, 1.4 Hz, 1H), 7.07 (td, J=8.1, 4.7 Hz, 1H), 3.97-3.92 (m, 1H), 3.80-3.75 (m, 1H), 3.66-3.60 (m, 1H), 3.33-3.27 (m, 1H), 3.11-3.04 (m, 2H), 2.72-2.67 (m, 1H), 2.54-2.45 (m, 2H), 2.27 (ddd, J=9.2, 8.4, 6.2 Hz, 1H), 1.92 (q, J=6.2 Hz, 1H), 1.43 (td, J=8.4, 5.6 Hz, 1H); $^{13}$C-NMR (125 MHz; CDCl$_3$): δ 166.7, 158.5 (d, J=251.5 Hz), 141.8 (d, J=1.8 Hz), 141.7 (d, J=9.4 Hz), 129.4 (d, J=3.2 Hz), 128.7 (q, J=32.3 Hz), 127.8, 125.2 (q, J=7.1 Hz), 125.1 (q, J=3.7 Hz), 124.2 (q, J=270.1 Hz), 121.7, 121.5, 116.9 (d, J=4.5 Hz), 111.8 (d, J=6.4 Hz), 51.9 (d, J=4.2 Hz), 51.3 (d, J=5.0 Hz), 46.0, 42.6, 24.5, 24.0, 11.1; $^{19}$F-NMR (376 MHz; CDCl$_3$): δ-62.47 (s, 3F), −119.74 (d, J=11.3 Hz, 1F). HRMS (ESI): m/z calculated for C$_{22}$H$_{20}$O N$_3$F$_4$ ([M+H]$^+$) 418.1537, found 418.1537.

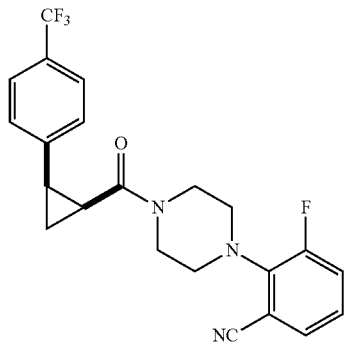 [SMILES: N#Cc1cccc(F)c1N1CCN(C(=O)[C@H]2C[C@H]2c2ccc(C(F)(F)F)cc2)CC1]

3-Fluoro-2-(4-(2-(4-(trifluoromethyl)phenyl)cyclopropane-1-carbonyl)piperazin-1-yl)benzonitrile. To a solution of 3-fluoro-2-(4-(3-(4-(trifluoromethyl)phenyl)propioloyl) piperazin-1-yl)benzonitrile (0.240 g, 0.598 mmol) in EtOAc

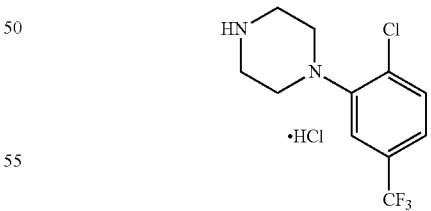

1-(2-Chloro-5-(trifluoromethyl)phenyl)piperazine hydrochloride. Under N$_2$ atmosphere, CuBr (0.565 g, 3.86 mmol), 1,1'-bi-2-naphthol (0.830 g, 2.89 mmol) and DMF (9.65 mL) was added to the flame-dried flask. The mixture was stirred for 10 minutes before the addition of 1-Boc-piperazine (5.39 g, 28.9 mmol), K$_3$PO$_4$ (8.44 g, 38.6 mmol) and 2-bromo-1-chloro-4-(trifluoromethyl)benzene (3.00 mL, 19.3 mmol). The reaction mixture was stirred at RT for 24 h. Then the mixture was stirred at 100° C. for 22 h. After cooling to room temperature, the mixture was diluted with EtOAc (20 mL) and filtered through Celite pad. The filtrate was concentrated under reduced pressure. Then the residue was sequentially washed with sat. NH₄Cl aq. (150 mL×2) and brine (150 mL×2). The resulting organic layer was dried (Na₂SO₄), filtered and concentrated under reduced pressure. The crude product was filtered through a short column of SiO₂ (EtOAc/hexanes, 1:9) to remove unreacted piperazines. And the obtained mixture (2.96 g) was used without further purification.

To a solution of the above product (2.96 g) in 1,4-dioxane (19.9 mL), HCl (4 M in 1,4-dioxane, 8.11 mL) was added at 0° C. The mixture was stirred at RT for 14 h. The thick suspension was diluted with hexanes (50 mL) and the resulting solid was collected by filtration, washed with hexanes and Et₂O, and dried to give 1-(2-chloro-5-(trifluoromethyl)phenyl)piperazine hydrochloride as a light yellow solid (0.408 g, 11% yield over 2 steps). Mp: 270° C. (decomposition); IR (neat): 2937, 2816, 2725, 2495, 1423, 1305, 1178, 1156, 1114, 1084, 1044 cm⁻¹; ¹H-NMR (400 MHz; DMSO-d6): δ 9.49 (s, 1H), 9.41 (s, 1H), 7.70 (d, J=8.0 Hz, 1H), 7.46 (d, J=8.8 Hz, 1H), 7.45 (s, 1H), 3.24 (brs, 4H); ¹³C-NMR (125 MHz; DMSO-d6): δ 148.6, 131.8, 131.5, 128.8 (q, J=32.2 Hz), 123.7 (q, J=272.5 Hz), 121.1 (q, J=3.9 Hz), 117.6 (q, J=3.6 Hz), 47.4, 42.9; ¹⁹F-NMR (376 MHz; DMSO-d6): δ −60.94 (d, J=2.8 Hz, 1F); HRMS (ESI): m/z calculated for C₁₁H₁₃F₃N₂Cl ([M+H]⁺) 265.0714, found 265.0710.

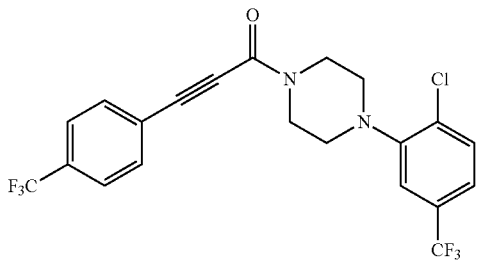

1-(4-(2-Chloro-5-(trifluoromethyl)phenyl)piperazin-1-yl)-3-(4-(trifluoromethyl)phenyl)prop-2-yn-1-one. To a solution of 3-(4-(trifluoromethyl)phenyl)propiolic acid (0.300 g, 1.40 mmol) in CH₂Cl₂ (14.0 mL) at 0° C. was added 1-(2-chloro-5-(trifluoromethyl)phenyl)piperazine hydrochloride (0.506 g, 1.68 mmol), and Et₃N (0.597 mL, 4.20 mmol). T₃P (1.49 mL, 2.10 mmol) was added dropwise and the reaction was stirred at 0° C. for 30 min and allowed to warm to RT for 23.5 h. Then the reaction was diluted with CH₂Cl₂ (30 mL) and washed with 1 M HCl (30 mL). The aqueous phase was extracted with CH₂Cl₂ (30 mL×3) and combined organic phase was dried (Na₂SO₄), filtered and concentrated in vacuo. The crude material was purified by chromatography on SiO₂ (EtOAc/hexanes, 1:3) to afford 1-(4-(2-chloro-5-(trifluoromethyl)-phenyl)piperazin-1-yl)-3-(4-(trifluoromethyl)phenyl)prop-2-yn-1-one (641 mg, 99%) as a yellow solid: Mp: 124-125° C.; IR (neat): 2225, 1631, 1419, 1321, 1310, 1276, 1167, 1122, 1107, 1086, 1068, 1035, 1017 cm⁻¹; ¹H-NMR (500 MHz; CDCl₃): δ 7.68 (d, J=8.4 Hz, 2H), 7.65 (d, J=8.4 Hz, 2H), 7.51 (d, J=8.3 Hz, 1H), 7.28 (d, J=8.3 Hz, 1H), 7.24 (d, J=1.5 Hz, 1H), 4.03 (t, J=4.9 Hz, 2H), 3.91 (t, J=4.9 Hz, 2H), 3.18 (t, J=4.9 Hz, 2H), 3.11 (t, J=4.9 Hz, 2H); ¹³C-NMR (125 MHz; CDCl₃): δ 152.6, 149.0, 132.7, 132.6, 131.8 (q, J=32.9 Hz), 131.3, 130.2 (q, J=32.9 Hz), 125.5 (q, J=3.7 Hz), 124.1, 123.6 (q, J=271.0 Hz), 121.0 (q, J=3.8 Hz), 117.5 (q, J=3.6 Hz), 89.1, 82. 7, 51.4, 50.7, 47.2, 41.7; ¹⁹F-NMR (471 MHz; CDCl₃): δ-62.58 (s, 1F), −63.10 (s, 1F); HRMS (ESI): m/z calculated for C₂₀H₁₄ON₃ClF₆ ([M+H]⁺) 461.0724, found 461.0639.

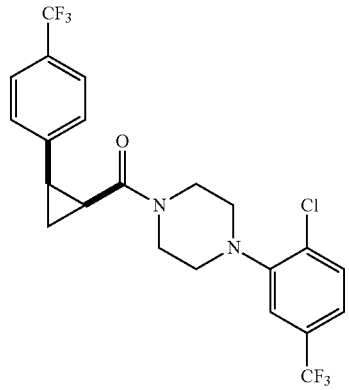 [SMILES: O=C([C@H]1C[C@H]1c1ccc(C(F)(F)F)cc1)N1CCN(c2cc(C(F)(F)F)ccc2Cl)CC1]

(4-(2-Chloro-5-(trifluoromethyl)phenyl)piperazin-1-yl)(2-(4-(trifluoromethyl)phenyl)cyclopropyl)-methanone. Under Ar atmosphere, a solution of 1-(4-(2-chloro-5-(trifluoromethyl)phenyl)piperazin-1-yl)-3-(4-(trifluoromethyl)phenyl)prop-2-yn-1-one (0.610 g, 1.32 mmol) in EtOAc (13.2 mL) was treated with quinoline (0.806 mL, 6.62 mmol) and 5% Pd/BaSO₄ (0.0282 g, 5 mol % based on Pd). The reaction was placed under a balloon of H₂ (3 vacuum/backfill cycles) and stirred at RT for 4 h. The reaction was filtered through Celite (eluting with EtOAc (100 mL) and the filtrates were washed with 1M aqueous HCl (100 mL). The organic phase was concentrated in vacuo to afford a crude product as a brown solid. The crude product was purified by chromatography on SiO₂ (EtOAc/hexanes, 1:2) to give the corresponding alkene (0.530 g, 86%) as a white crystal. ¹H-NMR (400 MHz; CDCl₃): δ 7.61 (d, J=8.2 Hz, 2H), 7.52 (d, J=8.2 Hz, 2H), 7.46 (dd, J=8.4, 0.7 Hz, 1H), 7.24 (dd, J=8.4, 0.7 Hz, 1H), 7.06 (d, J=1.8 Hz, 1H), 6.76 (d, J=12.6 Hz, 1H), 6.21 (d, J=12.6 Hz, 1H), 3.86 (t, J=4.8 Hz, 2H), 3.54 (t, J=5.0 Hz, 2H), 3.00 (t, J=5.0 Hz, 2H), 2.66 (t, J=4.9 Hz, 2H). ¹⁹F-NMR (376 MHz; CDCl₃): δ −62.69 (s, 1F), −62.79 (s, 1F).

To a solution of anhydrous CrCl₂ (0.134 g, 1.06 mmol) in THF (1.80 mL) that was degassed by sparging with Ar for 10 min followed by the addition of (Z)-1-(4-(2-chloro-5-(trifluoromethyl)phenyl)-piperazin-1-yl)-3-(4-(trifluoromethyl)phenyl)prop-2-en-1-one (0.469 g, 1.01 mmol) and CH₂ICl (0.376 mL, 5.06 mmol) at RT and under Ar atmosphere. The reaction mixture was stirred at 80° C. After stirring for 21 h, the reaction was cooled to RT and then diluted with EtOAc (50 mL). The organic layer was sequentially washed with 1 M aqueous HCl (50 mL×3) and sat. aqueous sodium thiosulfate (50 mL×2). Then the organic phase was dried (Na₂SO₄), filtered and concentrated in vacuo. The residue was diluted in minimum amount of EtOAc and the solution was filtered through a plug of basic alumina two times. The resulting crude material was purified by chromatography on SiO₂ (EtOAc/hexanes, 1:2) to afford (4-(2-chloro-5-(trifluoromethyl)phenyl)piperazin-1-yl)(2-(4-(trifluoromethyl)phenyl)cyclopropyl)methanone (0.332 g, 69%) as a white solid: Mp: 122-123° C.; IR (neat): 1641, 1619, 1437, 1418, 1326, 1308, 1166, 1117, 1085, 1070, 1031 cm⁻¹; ¹H-NMR (500 MHz; CDCl₃): δ 7.55 (d, J=8.2 Hz, 2H), 7.46 (dd, J=8.3, 0.6 Hz, 1H), 7.31 (d, J=8.2 Hz, 2H), 7.25 (dd, J=8.3, 1.7 Hz, 1H), 6.98 (d, J=1.7 Hz, 1H), 3.94 (d, J=13.0 Hz, 1H), 3.77 (d, J=13.0 Hz, 1H), 3.67 (td, J=10.7, 2.8 Hz, 1H), 3.37 (ddd, J=12.5, 9.2, 2.8 Hz, 1H), 3.00 (t, J=12.5 Hz, 2H), 2.54 (q, J=8.0 Hz, 1H), 2.38 (t, J=8.8 Hz, 1H), 2.30 (ddd, J=9.3, 8.4, 6.2 Hz, 1H), 2.16 (t, J=8.8 Hz, 1H), 1.94 (q, J=6.2 Hz, 1H), 1.46 (td, J=8.4, 5.6 Hz, 1H); $^{13}$C-NMR (125 MHz; CDCl$_3$): δ 166.7, 149.0, 141.9, 132.5 (d, J=1.2 Hz), 131.1, 130.2 (q, J=32.7 Hz), 128.8 (q, J=32.5 Hz), 127.8, 125.0 (q, J=3.7 Hz), 124.1 (q, J=270.5 Hz), 123.5 (q, J=270.8 Hz), 120.8 (q, J=3.8 Hz), 117.2 (q, J=3.7 Hz), 51.4, 50.8, 45.2, 41.9, 24.6, 24.0, 11.2; $^{19}$F-NMR (471 MHz; CDCl$_3$): δ −62.53 (s, 1F), −62.76 (s, 1F); HRMS (ESI): m/z calculated for C$_{22}$H$_{20}$F$_6$N$_2$ClO ([M+H]$^+$) 477.1163, found 477.1152.

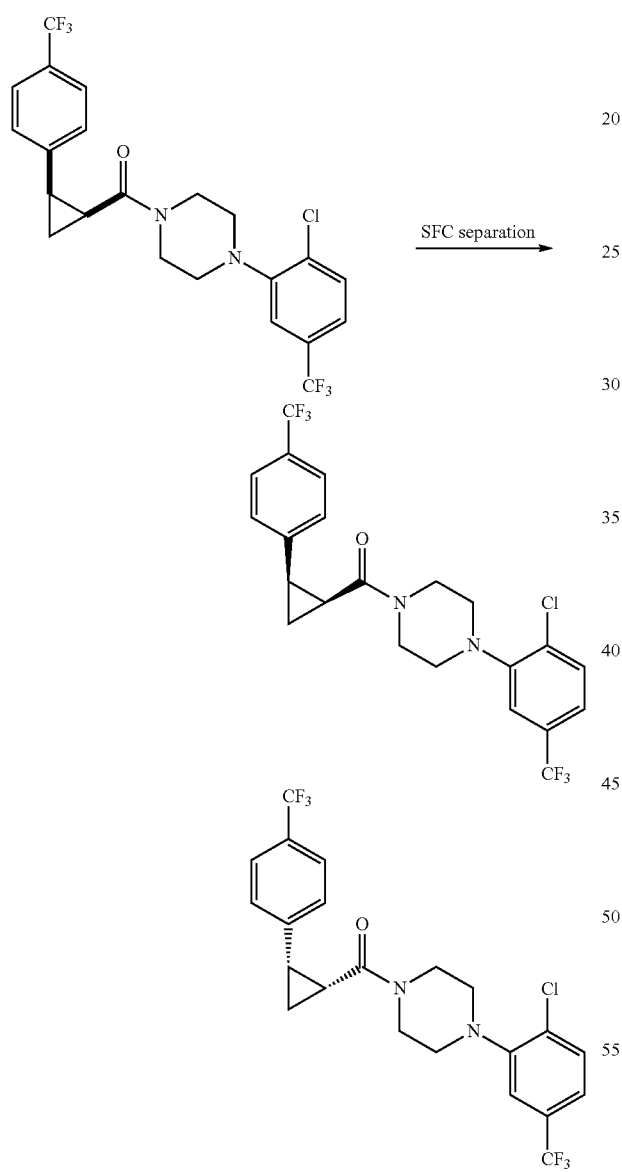

Racemic (4-(2-chloro-5-(trifluoromethyl)phenyl)piperazin-1-yl)(2-(4-(trifluoromethyl)phenyl)cyclopropyl)-methanone was separated on a SFC Chiralpak-IC semiprep (250×10 mm) column (15% MeOH, 7 mL/min, 220 nM, P=100) to afford (4-(2-chloro-5-(trifluoromethyl)phenyl)piperazin-1-yl)((1S,2R)-2-(4-(trifluoromethyl)phenyl)cy- clopropyl)methanone (retention time; 5.70 min) as a white solid (>99.9% purity by ELSD): [α]$^{18}_D$ −127.0 (c=0.29, MeOH); HRMS (ESI): m/z calculated for C$_{22}$H$_{20}$F$_6$ON$_2$Cl ([M+H]$^+$) 477.1163, found 477.1164. The enantiomeric excess was >99.9% ee (SFC Chiralpak-IC semiprep; 15% MeOH, 220 nM, 7 mL/min; retention time: 5.70 min). $^1$H-NMR (500 MHz; CDCl$_3$): δ 7.55 (d, J=8.2 Hz, 2H), 7.46 (dd, J=8.3, 0.6 Hz, 1H), 7.31 (d, J=8.2 Hz, 2H), 7.25 (dd, J=8.3, 1.7 Hz, 1H), 6.98 (d, J=1.7 Hz, 1H), 3.94 (d, J=13.0 Hz, 1H), 3.77 (d, J=13.0 Hz, 1H), 3.67 (td, J=10.7, 2.8 Hz, 1H), 3.37 (ddd, J=12.5, 9.2, 2.8 Hz, 1H), 3.00 (t, J=12.5 Hz, 2H), 2.54 (q, J=8.0 Hz, 1H), 2.38 (t, J=8.8 Hz, 1H), 2.30 (ddd, J=9.3, 8.4, 6.2 Hz, 1H), 2.16 (t, J=8.8 Hz, 1H), 1.94 (q, J=6.2 Hz, 1H), 1.46 (td, J=8.4, 5.6 Hz, 1H).

(4-(2,5-bis(trifluoromethyl)phenyl)piperazin-1-yl)((1R,2S)-2-(4-(trifluoromethyl)phenyl)-cyclopropyl)methanone; (retention time; 6.40 min) as a white solid (>99.9% purity by ELSD): [α]$^{18}_D$ +130.0 (c=0.23, MeOH); HRMS (ESI): m/z calculated for C$_{22}$H$_{20}$F$_6$ON$_2$Cl ([M+H]$^+$) 477.1163, found 477.1160. The enantiomeric excess was >99.9% ee (SFC Chiralpak-IC semiprep; 15% MeOH, 220 nM, 7 mL/min; retention time: 6.40 min). $^1$H-NMR (500 MHz; CDCl$_3$): δ 7.55 (d, J=8.2 Hz, 2H), 7.46 (dd, J=8.3, 0.6 Hz, 1H), 7.31 (d, J=8.2 Hz, 2H), 7.25 (dd, J=8.3, 1.7 Hz, 1H), 6.98 (d, J=1.7 Hz, 1H), 3.94 (d, J=13.0 Hz, 1H), 3.77 (d, J=13.0 Hz, 1H), 3.67 (td, J=10.7, 2.8 Hz, 1H), 3.37 (ddd, J=12.5, 9.2, 2.8 Hz, 1H), 3.00 (t, J=12.5 Hz, 2H), 2.54 (q, J=8.0 Hz, 1H), 2.38 (t, J=8.8 Hz, 1H), 2.30 (ddd, J=9.3, 8.4, 6.2 Hz, 1H), 2.16 (t, J=8.8 Hz, 1H), 1.94 (q, J=6.2 Hz, 1H), 1.46 (td, J=8.4, 5.6 Hz, 1H).

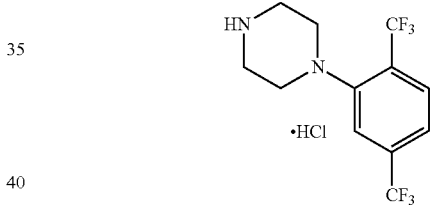

1-(2,5-Bis(trifluoromethyl)phenyl)piperazine hydrochloride. Under N$_2$ atmosphere, CuBr (0.511 g, 3.49 mmol), 1,1'-bi-2-naphthol (0.751 g, 2.62 mmol) and DMF (8.73 mL) was added to the flame-dried flask. The mixture was stirred for 10 minutes before the addition of 1-Boc-piperazine (4.88 g, 26.2 mol), K$_3$PO$_4$ (7.64 g, 34.9 mmol) and the 2,5-bis(trifluoromethyl)bromobenzene (3.00 mL, 17.5 mmol). The mixture was stirred at 100° C. for 26.5 h. After cooling to room temperature, the mixture was diluted with EtOAc (20 mL) and filtered through celite pad. The filtrate was concentrated under reduced pressure. Then the residue was sequentially washed with sat. NH$_4$Cl aq. (150 mL×2) and brine (150 mL×2). The resulting organic layer was dried (Na$_2$SO$_4$), filtered and concentrated under reduced pressure. The crude product was filtered through a short column of SiO$_2$ (EtOAc/hexanes 1:9) to remove unreacted piperazines. And the obtained mixture (2.76 g) was used without further purification.

To a solution of the above product (2.76 g) in 1,4-dioxane (17.0 mL), HCl (4 M in 1,4-dioxane, 6.93 mL) was added at 0° C. The mixture was stirred at RT for 16 h. The thick suspension was diluted with hexanes (50 mL) and the resulting solid was collected by filtration, washed with hexanes and dried to give 1-(2,5-bis(trifluoromethyl)phenyl)piperazine hydrochloride as a white fluffy solid (0.811 g, 16% over 2 steps): Mp: 268° C.; IR (neat): 2722, 2478, 1569, 1424, 1311, 1180, 1117, 1081, 1038 cm$^{-1}$; $^1$H-NMR (500 MHz; DMSO-d6): δ 9.47-9.29 (brs, 2H), 7.82 (s, 1H), 7.78 (d, J=8.2 Hz, 1H), 3.18 (s, 4H); $^{13}$C-NMR (125 MHz; DMSO-d6): δ 152.1, 134.3 (q, J=32.5 Hz), 129.6 (q, J=28.7 Hz), 129.3 (q, J=5.1 Hz), 123.6 (q, J=274.0 Hz), 123.1 (d, J=3.6 Hz), 121.8 (d, J=3.4 Hz), 50.0, 43.6; $^{19}$F-NMR (471 MHz; DMSO-d6): δ -59.66 (s, 3F), -61.67 (s, 3F); HRMS (ESI): m/z calculated for $C_{12}H_{13}F_6N_2$ ([M+H]$^+$) 299.0977, found 299.0971.

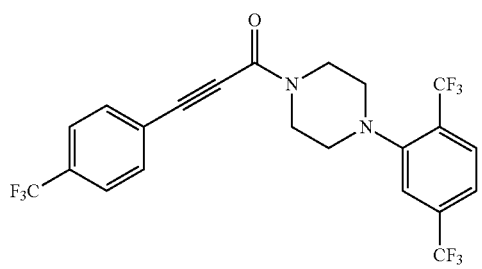 [SMILES: O=C(C#Cc1ccc(C(F)(F)F)cc1)N1CCN(c2cc(C(F)(F)F)ccc2C(F)(F)F)CC1]

1-(4-(2,5-Bis(trifluoromethyl)phenyl)piperazin-1-yl)-3-(4-(trifluoromethyl)phenyl)prop-2-yn-1-one. To a solution of 3-(4-(trifluoromethyl)phenyl)propiolic acid (0.300 g, 1.40 mmol) in CH$_2$Cl$_2$ (14.0 mL) at 0° C. was added 1-(2,5-bis(trifluoromethyl)phenyl)piperazine hydrochloride (0.563 g, 1.68 mmol), and Et$_3$N (0.597 mL, 4.20 mmol). T$_3$P (1.49 mL, 2.10 mmol) was added dropwise and the reaction was stirred at 0° C. for 30 min and allowed to warm to RT for 23.5 h. The reaction was diluted with CH$_2$Cl$_2$ (30 mL) and washed with 1 M HCl (30 mL). The aqueous phase was extracted with CH$_2$Cl$_2$ (30 mL×3) and combined organic phase was dried (Na$_2$SO$_4$), filtered and concentrated in vacuo. The crude material was purified by chromatography on SiO$_2$ (EtOAc/hexanes, 1:3) to afford 1-(4-(2,5-bis(trifluoromethyl)phenyl)piperazin-1-yl)-3-(4-(trifluoromethyl) phenyl)prop-2-yn-1-one (155 mg, 50%) as a light yellow oil: IR (neat): 1632, 1424, 1311, 1285, 1274, 1172, 1121, 1107, 1034 cm$^{-1}$; $^1$H-NMR (500 MHz; CDCl$_3$): δ 7.80 (d, J=8.1 Hz, 1H), 7.67 (d, J=8.4 Hz, 2H), 7.64 (d, J=8.4 Hz, 2H), 7.56 (s, 1H), 7.55 (d, J=8.1 Hz, 1H), 3.99 (t, J=4.9 Hz, 2H), 3.87 (t, J=4.9 Hz, 2H), 3.06 (t, J=4.9 Hz, 2H), 2.99 (t, J=4.9 Hz, 2H); $^{13}$C-NMR (125 MHz; CDCl$_3$): δ 152.6, 152.1, 135.2 (q, J=33.3 Hz), 132.6, 131.8 (q, J=32.9 Hz), 130.7 (q, J=29.6 Hz), 128.4 (q, J=5.4 Hz), 125.5 (q, J=3.7 Hz), 124.1 (d, J=1.8 Hz), 123.6 (q, J=270.8 Hz), 123.2 (q, J=272.0 Hz), 123.1 (q, J=271.0 Hz), 122.4 (q, J=3.6 Hz), 121.1 (q, J=3.5 Hz), 89.1, 82.7, 53.6, 52.8, 47.4, 41.9. $^{19}$F-NMR (471 MHz; CDCl$_3$): δ-60.91 (s, 3F), -63.12 (s, 3F), -63.23 (s, 3F); HRMS (ESI): m/z calculated for $C_{22}H_{16}F_9ON_2$ ([M+H]$^+$) 495.1113, found 495.0934

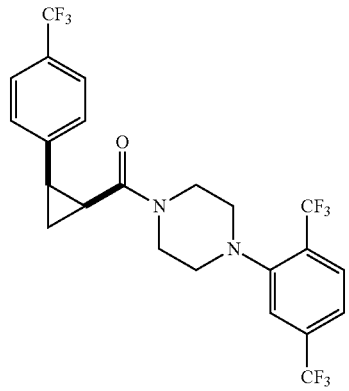 [SMILES: O=C([C@H]1C[C@H]1c1ccc(C(F)(F)F)cc1)N1CCN(c2cc(C(F)(F)F)ccc2C(F)(F)F)CC1]

(4-(2,5-bis(trifluoromethyl)phenyl)piperazin-1-yl)(2-(4-(trifluoromethyl)phenyl)cyclopropyl)-methanone. Under Ar atmosphere, a solution of 1-(4-(2,5-bis(trifluoromethyl)phenyl)piperazin-1-yl)-3-(4-(trifluoromethyl)phenyl)prop-2-yn-1-one (0.657 g, 1.33 mmol) in EtOAc (13.3 mL) was treated with quinoline (0.810 mL, 6.65 mmol) and 5% Pd/BaSO$_4$ (0.0283 g, 10 mol % based on Pd). The reaction was placed under a balloon of H$_2$ (3 vacuum/backfill cycles) and stirred at RT for 6 h. The reaction was filtered through Celite (eluting with EtOAc (100 mL) and the filtrates were washed with 1M aqueous HCl (100 mL×2). The organic phase was dried (Na$_2$SO$_4$), filtered and concentrated in vacuo. The crude product was purified by chromatography on SiO$_2$ (EtOAc/hexanes, 2:3) to give (Z)-1-(4-(2,5-bis(trifluoromethyl)phenyl)-piperazin-1-yl)-3-(4-(trifluoromethyl)phenyl)prop-2-en-1-one (0.655 g, 99%) as a light yellow oil. $^1$H-NMR (400 MHz; CDCl$_3$): δ 7.75 (d, J=8.2 Hz, 1H), 7.64 (d, J=8.4 Hz, 2H), 7.53 (d, J=8.4 Hz, 2H), 7.50 (d, J=8.2 Hz, 1H), 7.33 (s, 1H), 6.75 (d, J=12.5 Hz, 1H), 6.21 (d, J=12.5 Hz, 1H), 3.82 (t, J=4.9 Hz, 2H), 3.51 (t, J=4.9 Hz, 2H), 2.87 (t, J=4.9 Hz, 2H), 2.51 (t, J=4.9 Hz, 2H). $^{19}$F-NMR (376 MHz; CDCl$_3$): δ-60.96 (s, 3F), -62.82 (s, 3F), -63.35 (s, 3F).

To a solution of anhydrous CrCl$_2$ (0.850 g, 6.71 mmol) in THF (11.2 mL) that was degassed by sparging with Ar for 10 min followed by the addition of (Z)-1-(4-(2,5-bis(trifluoromethyl)phenyl)piperazin-1-yl)-3-(4-(trifluoromethyl)phenyl)prop-2-en-1-one (0.555 g, 1.12 mmol) and CH$_2$ICl (0.416 mL, 5.59 mmol) at RT and under Ar atmosphere. The reaction mixture was stirred at 80° C. After stirring for 22.5 h, the reaction was cooled to RT and then diluted with EtOAc (80 mL). The solution was sequentially washed with 1 M aqueous HCl (80 mL×3) and sat. aqueous sodium thiosulfate (100 mL×2). Then the organic phase was dried (Na$_2$SO$_4$), filtered and concentrated in vacuo. The residue was diluted with minimum amount of EtOAc, and the solution was filtered through a plug of basic alumina. This process was repeated two times. Then the resulting crude material was purified by chromatography on SiO$_2$ (EtOAc/hexanes, 2:1) to afford (4-(2,5-bis(trifluoromethyl)phenyl)piperazin-1-yl)(2-(4-(trifluoromethyl)-phenyl)cyclopropyl)methanone (0.472 g, 83%) as a white solid: Mp: 111-112° C.; IR (neat): 1644, 1425, 1327, 1314, 1123, 1032 cm$^{-1}$; $^1$H-NMR (500 MHz; CDCl$_3$): δ 7.72 (d, J=8.2 Hz, 1H), 7.54 (d, J=8.2 Hz, 2H), 7.47 (d, J=8.2 Hz, 1H), 7.29 (d, J=8.2 Hz, 2H), 7.18 (s, 1H), 3.96 (d, J=12.0 Hz, 1H), 3.75 (d, J=12.6 Hz, 1H), 3.56 (t, J=9.9 Hz, 1H), 3.23 (t, J=9.9 Hz, 1H), 2.78 (t, J=15.3 Hz, 2H), 2.51 (q, J=7.9 Hz, 1H), 2.29-2.23 (m, 2H), 2.05 (t, J=9.0 Hz, 1H), 1.92 (q, J=6.2 Hz, 1H), 1.43 (td, J=8.4, 5.6 Hz, 1H); $^{13}$C-NMR (125 MHz; CDCl$_3$): δ 166.6, 152.2, 142.0, 135.1 (q, J=33.0 Hz), 128.8 (q, J=32.6 Hz), 128.1 (q, J=5.4 Hz), 127.9, 124.9 (q, J=3.7 Hz), 124.1 (q, J=269.9 Hz), 123.1 (q, J=270.9 Hz), 123.0 (q, J=271.1 Hz), 122.0 (q, J=3.6 Hz), 120.7 (q, J=3.4 Hz), 53.7, 52.9, 45.4, 42.1, 24.6, 23.9, 11.1. $^{19}$F-NMR (471 MHz; CDCl$_3$): δ-60.98 (s, 3F), −62.58 (s, 3F), −63.48 (s, 3F); HRMS (ESI): m/z calculated for C$_{23}$H$_{20}$F$_9$ON$_2$ ([M+H]$^+$) 511.1426, found 511.1426.

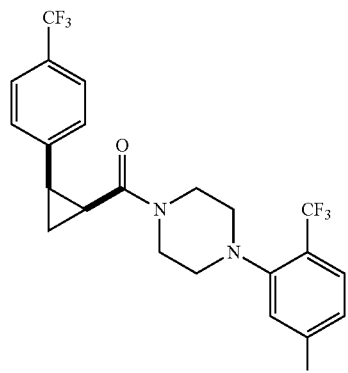

SFC separation →

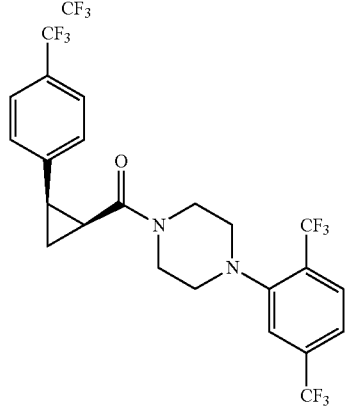

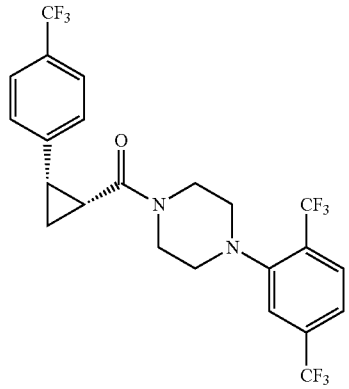

Racemic (4-(2,5-bis(trifluoromethyl)phenyl)piperazin-1-yl)(2-(4-(trifluoromethyl)phenyl)cyclopropyl)-methanone was separated on a SFC Chiralpak-IC semiprep (250×10 mm) column (5% MeOH, 7 mL/min, 220 nM, P=100) to afford (4-(2,5-bis(trifluoromethyl)phenyl)piperazin-1-yl) ((1S,2R)-2-(4-(trifluoromethyl)-phenyl)cyclopropyl)methanone (retention time; 7.60 min) as a colorless oil (>99.9% purity by ELSD): [α]$^{19}$$_D$ −109.7 (c=0.25, MeOH); HRMS (ESI): m/z calculated for C$_{23}$H$_{20}$F$_9$ON$_2$ ([M+H]$^+$) 511.1426, found 511.1423. The enantiomeric excess was >99.9% ee (SFC Chiralpak-IC semiprep; 5% MeOH, 220 nM, 7 mL/min; retention time: 7.60 min). $^1$H-NMR (500 MHz; CDCl$_3$): δ 7.72 (d, J=8.2 Hz, 1H), 7.54 (d, J=8.2 Hz, 2H), 7.47 (d, J=8.2 Hz, 1H), 7.29 (d, J=8.2 Hz, 2H), 7.18 (s, 1H), 3.96 (d, J=12.0 Hz, 1H), 3.75 (d, J=12.6 Hz, 1H), 3.56 (t, J=9.9 Hz, 1H), 3.23 (t, J=9.9 Hz, 1H), 2.78 (t, J=15.3 Hz, 2H), 2.51 (q, J=7.9 Hz, 1H), 2.29-2.23 (m, 2H), 2.05 (t, J=9.0 Hz, 1H), 1.92 (q, J=6.2 Hz, 1H), 1.43 (td, J=8.4, 5.6 Hz, 1H).

(4-(2,5-bis(trifluoromethyl)phenyl)piperazin-1-yl)((1R,2S)-2-(4-(trifluoromethyl)phenyl)-cyclopropyl)methanone; (retention time; 9.20 min) as a colorless oil (>99.9% purity by ELSD): [α]$^{18}$$_D$ +108.8 (c=0.22, MeOH); HRMS (ESI): m/z calculated for C$_{23}$H$_{23}$F$_6$O$_2$N$_2$ ([M+H]$^+$) 511.1426, found 511.1425. The enantiomeric excess was >99.9% ee (SFC Chiralpak-IC semiprep; 5% MeOH, 220 nM, 7 mL/min; retention time: 9.20 min). $^1$H-NMR (500 MHz; CDCl$_3$): δ 7.72 (d, J=8.2 Hz, 1H), 7.54 (d, J=8.2 Hz, 2H), 7.47 (d, J=8.2 Hz, 1H), 7.29 (d, J=8.2 Hz, 2H), 7.18 (s, 1H), 3.96 (d, J=12.0 Hz, 1H), 3.75 (d, J=12.6 Hz, 1H), 3.56 (t, J=9.9 Hz, 1H), 3.23 (t, J=9.9 Hz, 1H), 2.78 (t, J=15.3 Hz, 2H), 2.51 (q, J=7.9 Hz, 1H), 2.29-2.23 (m, 2H), 2.05 (t, J=9.0 Hz, 1H), 1.92 (q, J=6.2 Hz, 1H), 1.43 (td, J=8.4, 5.6 Hz, 1H).

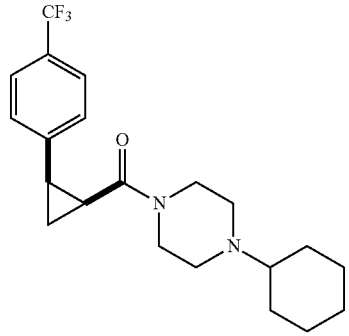 [SMILES: O=C([C@H]1C[C@H]1c1ccc(C(F)(F)F)cc1)N1CCN(C2CCCCC2)CC1]

(4-Cyclohexylpiperazin-1-yl)(2-(4-(trifluoromethyl)phenyl)cyclopropyl)methanone. To a solution of piperazin-1-yl (2-(4-(trifluoromethyl)phenyl)cyclopropyl)methanone hydrochloride (0.09 g, 0.269 mmol) and cyclohexanone (0.0279 mL, 0.269 mmol) in dichloromethane (1.00 mL) was added NaBH(OAc)$_3$ (0.256 g, 1.21 mmol) and acetic acid (0.0154 mL, 0.269 mmol). The mixture was stirred for 45 h at room temperature. Then the mixture was quenched with 1N aqueous NaOH (40 mL) and extracted with EtOAc (40 mL×3). The combined organic phase was dried (Na$_2$SO$_4$), filtered and concentrated in vacuo. The crude product was purified by chromatography on SiO$_2$ (MeOH/CH$_2$Cl$_2$, 1:9) to yield (4-cyclohexylpiperazin-1-yl)(2-(4-(trifluoromethyl)phenyl)cyclopropyl)methanone (0.0883 g, 86%) as a light yellow solid: Mp: 99-101° C.; IR (neat): 2933, 1634, 1618, 1468, 1439, 1325, 1161, 1116, 1070, 1017 cm$^{-1}$; $^1$H-NMR (500 MHz; CDCl$_3$): δ 7.49 (d, J=8.2 Hz, 2H), 7.24 (d, J=8.2 Hz, 2H), 3.78 (d, J=12.8 Hz, 1H), 3.58 (d, J=12.8 Hz, 1H), 3.38 (ddd, J=12.5, 9.4, 3.0 Hz, 1H), 3.06 (ddd, J=12.5, 9.4, 3.0 Hz, 1H), 2.47-2.41 (m, 3H), 2.22 (td, J=8.8, 6.3 Hz, 1H), 2.09 (tt, J=11.4, 3.1 Hz, 1H), 1.87-1.82 (m, 2H), 1.73 (d, J=12.8 Hz, 2H), 1.61-1.57 (m, 4H), 1.39 (td, J=8.4, 5.6 Hz, 1H), 1.19-1.10 (m, 2H), 1.06-0.94 (m, 3H); $^{13}$C-NMR (125 MHz; CDCl$_3$): δ 166.3, 142.2, 128.5 (q, J=32.4 Hz), 127.8, 124.9 (q, J=3.9 Hz), 124.2 (q, J=270.0 Hz), 63.5, 49.2, 48.4, 45.6, 42.3, 28.6, 28.5, 26.2, 25.8, 24.8, 23.8, 11.2; $^{19}$F-NMR (471 MHz; CDCl$_3$): δ-62.43 (s, 3F); HRMS (ESI): m/z calculated for C$_{23}$H$_{20}$F$_9$ON$_2$ ([M+H]$^+$) 381.2154, found 381.2147.

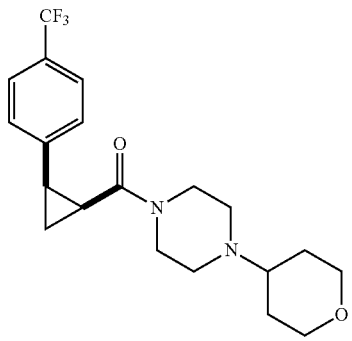

(4-(Tetrahydro-2H-pyran-4-yl)piperazin-1-yl)(2-(4-(trifluoromethyl)phenyl)cyclopropyl)methanone To a solution of piperazin-1-yl(2-(4-(trifluoromethyl)phenyl)cyclopropyl)methanone hydrochloride (0.09 g, 0.269 mmol) and tetrahydro-4H-pyran-4-one (0.0269 mL, 0.269 mmol) in dichloromethane (1.00 mL) was added NaBH(OAc)$_3$ (0.205 g, 0.269 mmol) and acetic acid (0.0154 mL, 0.269 mmol). The mixture was stirred for 13 h at room temperature. Then the mixture was quenched with 1N aqueous NaOH (30 mL) and extracted with CH$_2$Cl$_2$ (30 mL×3). The combined organic phase was dried (Na$_2$SO$_4$), filtered and concentrated in vacuo. The crude product was purified by chromatography on SiO$_2$ (MeOH:CH$_2$Cl$_2$=1:9) to give (4-(tetrahydro-2H-pyran-4-yl)piperazin-1-yl)(2-(4-(trifluoromethyl)phenyl)cyclopropyl)methanone (0.0845 g, 82%) as a light yellow solid: Mp: 84-86° C.; IR (neat): 2949, 2845, 1637, 1619, 1468, 1439, 1325, 1161, 1115, 1069 cm$^{-1}$; $^1$H-NMR (500 MHz; CDCl$_3$): δ 7.49 (d, J=8.2 Hz, 2H), 7.24 (d, J=8.2 Hz, 2H), 3.95 (dd, J=11.5, 3.4 Hz, 2H), 3.83 (d, J=13.1 Hz, 1H), 3.61 (d, J=12.9 Hz, 1H), 3.37 (ddd, J=12.7, 9.5, 3.1 Hz, 1H), 3.28 (tt, J=11.8, 2.8 Hz, 2H), 3.04 (ddd, J=12.7, 9.5, 3.1 Hz, 1H), 2.47-2.43 (m, 3H), 2.28-2.19 (m, 2H), 1.87-1.78 (m, 2H), 1.51-1.30 (m, 6H). $^{13}$C-NMR (125 MHz; CDCl$_3$): δ 166.3, 142.2, 128.5 (q, J=32.4 Hz), 127.7, 125.0 (q, J=3.9 Hz), 124.2 (q, J=270.4 Hz), 67.4, 67.3, 60.8, 49.0, 48.6, 45.4, 42.1, 29.1, 28.9, 24.9, 23.8, 11.3; $^{19}$F-NMR (471 MHz; CDCl$_3$): δ −62.37 (s, 3F); HRMS (ESI): m/z calculated for C$_{20}$H$_{26}$F$_3$O$_2$N$_2$ ([M+H]$^+$) 383.1946, found 383.1938.

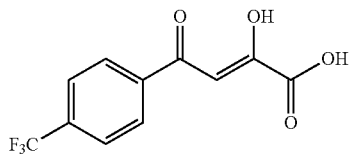 [SMILES: O=C(O)/C(O)=C/C(=O)c1ccc(C(F)(F)F)cc1]

2-Hydroxy-4-oxo-4-(4-(trifluoromethyl)phenyl)but-2-enoic acid. To a heterogeneous solution of Na (0.121 g, 5.26 mmol) in Et$_2$O (2.56 mL) was added dropwise dry EtOH (0.307 mL) at 0° C. The mixture was stirred for 20 min at that temperature. Then a mixture of dimethyl oxalate (0.583 mL, 5.26 mmol) and 4'-(trifluoromethyl)acetophenone (1.00 g, 5.26 mmol) in dry Et$_2$O (0.850 mL) was added carefully in small portions at −20° C. and stirred for 19.5 h at that temperature. The mixture was then poured into 1N HCl and extracted with ethyl acetate (50 mL×3). The combined organic layers were dried (Na$_2$SO$_4$), filtered and concentrated under vacuum. The resulting crude product was used without further purification.

To a 250-mL round-bottom flask was added the above product (1.51 g) in THF (6.55 mL), followed by LiOH monohydrate (1.10 g, 26.2 mmol) in water (6.55 mL) in one portion. Saponification was terminated when the starting material was consumed completely by TLC analysis (petroleum ether/EtOAc, 1:1). The mixture was concentrated under vacuum to remove the THF and then was extracted with CH$_2$Cl$_2$ (100 mL×3). The aqueous layer was acidified with 1N HCl (100 mL) and extracted with EtOAc (100 mL×3). The combined organic layer was dried (Na$_2$SO$_4$), filtered and concentrated in vacuo to yield 2-hydroxy-4-oxo-4-(4-(trifluoromethyl)phenyl)but-2-enoic acid (0.311 g, 23% over 2 steps) as a white solid. $^1$H-NMR (300 MHz; CDCl$_3$): δ 8.12 (d, J=8.2 Hz, 2H), 7.79 (d, J=8.2 Hz, 2H), 7.20 (s, 1H). The spectra obtained are in agreement with previously reported data (Zeng et al., Bioorg. Med. Chem. 2008, 16:7777-7787).

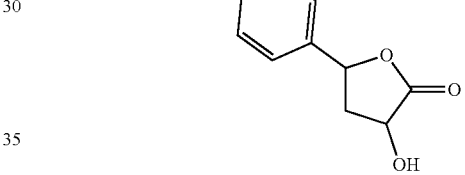

3-Hydroxy-5-(4-(trifluoromethyl)phenyl)dihydrofuran-2(3H)-one. To a 100-mL round-bottom flask containing a stirrer, 2-hydroxy-4-oxo-4-(4-(trifluoromethyl)phenyl)but-2-enoic acid (1.03 g, 3.96 mmol) in 13.2 mL MeOH was added, followed by NaBH$_4$ (0.611 g, 15.8 mmol) in small portions at room temperature. The mixture was stirred for 3 h. 1 mL water was added to decompose residual NaBH$_4$ and the mixture was concentrated under vacuum to remove the solvent. Then the mixture was acidified to pH 1.0-2.0 by adding 1N HCl (10 mL) and refluxed for 17.5 h. Then the mixture was extracted with EtOAc (50 mL×3) and the combined organic layer was dried (Na$_2$SO$_4$), filtered and concentrated in vacuo. The crude mixture was purified by chromatography on SiO$_2$ (CH$_2$Cl$_2$/MeOH, 20:1) to afford 3-Hydroxy-5-(4-(trifluoromethyl)-phenyl)dihydrofuran-2(3H)-one (0.456 g, 47%, dr=1:2) as a white solid: IR (neat): 3421, 1772, 1322, 1166, 1110, 1067, 1016 cm$^{-1}$; (Major diastereomer) $^1$H-NMR (500 MHz; CDCl$_3$): δ 7.68 (d, J=8.1 Hz, 2H), 7.50 (d, J=8.1 Hz, 2H), 5.43 (dd, J=10.9, 5.4 Hz, 1H), 4.73 (t, J=9.6 Hz, 1 H), 3.06 (ddd, J=12.9, 7.9, 5.2 Hz, 1H), 3.01 (d, J=0.4 Hz, 1H), 2.21 (q, J=11.8 Hz, 1H); $^{13}$C-NMR (125 MHz; CDCl$_3$): δ 176.9, 141.8, 131.1 (q, J=32.7 Hz), 126.0, 125.9 (q, J=4.0 Hz), 123.8 (q, J=272.4 Hz), 77.9, 68.8, 39.5; $^{19}$F-NMR (471 MHz; CDCl$_3$): δ-62.74 (s, 3F).

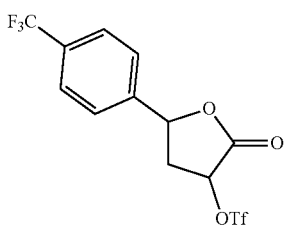 [SMILES: O=C1OC(c2ccc(C(F)(F)F)cc2)CC1OS(=O)(=O)C(F)(F)F]

2-Oxo-5-(4-(trifluoromethyl)phenyl)tetrahydrofuran-3-yl trifluoromethanesulfonate. To a solution of 3-hydroxy-5-(4-(trifluoromethyl)phenyl)dihydrofuran-2(3H)-one (0.140 g, 0.569 mmol) and pyridine (0.0696 mL, 0.853 mmol) in dry CH$_2$Cl$_2$ (2.84 mL) was added trifluoromethanesulfonic anhydride (0.116 mL) at 0° C. The mixture was stirred for 1.5 h at that temperature. Then the mixture was diluted with CH$_2$Cl$_2$ (15 mL) and quenched with 1N aqueous HCl (15 mL). The aqueous layer was extracted with CH$_2$Cl$_2$ (15 mL×3) and a combined organic layer was dried (Na$_2$SO$_4$), filtered and concentrated in vacuo. The crude mixture was purified by chromatography on SiO$_2$ (hexanes/EtOAc, 3:1) to yield 2-oxo-5-(4-(trifluoromethyl)phenyl)tetrahydrofuran-3-yl trifluoromethanesulfonate (0.586 g, 89%, dr=2:1) as a light yellow solid. (Major-diastereomer)$^1$H-NMR (400 MHz; CDCl$_3$): δ 7.72 (d, J=8.3 Hz, 3H), 7.50 (d, J=8.2 Hz, 2H), 5.61 (dd, J=10.6, 8.4 Hz, 1H), 5.52 (d, J=10.6, 5.5 Hz, 1H), 3.29 (ddd, J=13.0, 8.4, 5.5 Hz, 1H), 2.52 (dt, J=13.0, 10.7 Hz, 1H).

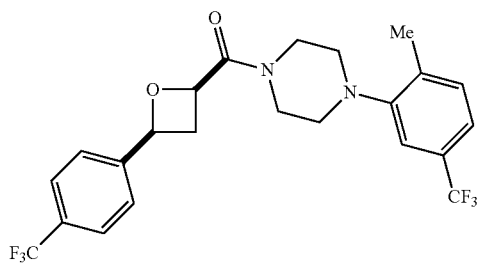 [SMILES: Cc1ccc(C(F)(F)F)cc1N1CCN(C(=O)[C@H]2C[C@@H](c3ccc(C(F)(F)F)cc3)O2)CC1]

(4-(2-Methyl-5-(trifluoromethyl)phenyl)piperazin-1-yl)(4-(4-(trifluoromethyl)phenyl)oxetan-2-yl)methanone. To a solution of 2-oxo-5-(4-(trifluoromethyl)phenyl)tetrahydrofuran-3-yl trifluoromethane-sulfonate (0.0680 g, 0.180 mmol) in dry MeOH (0.899 mL) was added potassium carbonate (0.0301 g, 0.216 mmol). The mixture was stirred for 1 h at 0° C. Then the mixture was quenched with water, extracted with EtOAc, dried (Na$_2$SO$_4$), filtered and concentrated in vacuo. The crude product was filtered through a short column of SiO$_2$ (hexanes/EtOAc, 3:1) to yield a mixture of methyl 4-(4-(trifluoromethyl)-phenyl)-oxetane-2-carboxylate as a light yellow oil. This product was used without further purification.

To a solution of the above product (97.0 mg) in THF/H$_2$O (1.85 mL/1.85 mL) was added LiOH (62.6 mg, 1.49 mmol) at room temperature. After stirring for 16 h, the mixture was diluted with H$_2$O (10 mL) and extracted with CH$_2$Cl$_2$ (15 mL×2). Then the aqueous layer was acidified with 1N HCl (20 mL) and extracted with EtOAc (30 mL×3). The combined organic phase was dried (Na$_2$SO$_4$), filtered and concentrated in vacuo. The crude product was used without further purification.

To a solution of the above crude product (0.095 g) in CH$_2$Cl$_2$ (3.86 mL) at 0° C. was added 1-(2-methyl-5-(trifluoromethyl)phenyl)piperazine hydrochloride (0.130 g, 0.463 mmol) and Et$_3$N (0.164 mL, 1.16 mmol). T$_3$P (0.409 mL, 0.579 mmol) was added dropwise and the reaction was stirred at 0° C. for 30 min and allowed to warm to RT for 12.5 h. The reaction was diluted with CH$_2$Cl$_2$ (20 mL) and washed with 1 M HCl (20 mL). The aqueous phase was extracted with CH$_2$Cl$_2$ (30 mL×3) and combined organic phase was dried (Na$_2$SO$_4$), filtered and concentrated in vacuo. The crude material was purified by chromatography on SiO$_2$ (EtOAc/hexanes, 2:3) to afford (4-(2-methyl-5-(trifluoromethyl)phenyl)piperazin-1-yl)(4-(4-(trifluoromethyl)phenyl)oxetan-2-yl)methanone (cis-diastereomer (light yellow oil): 96.2 mg, trans-diastereomer (white solid): 52.55 mg). (cis-isomer) IR (neat): 2913, 1652, 1445, 1419, 1325, 1310, 1163, 1120, 1067 cm$^{-1}$; $^1$H-NMR (500 MHz; CDCl$_3$): δ 7.64 (d, J=8.2 Hz, 2H), 7.55 (d, J=8.2 Hz, 2H), 7.30 (d, J=8.0 Hz, 1H), 7.26 (d, J=8.0 Hz, 1H), 7.19 (s, 1H), 5.73 (t, J=7.7 Hz, 2H), 5.43 (t, J=7.7 Hz, 2H), 3.91-3.87 (m, 1H), 3.79-3.72 (m, 2H), 3.61-3.57 (m, 1H), 3.21-3.09 (m, 2H), 2.99-2.91 (m, 4H), 2.37 (s, 3H); $^{13}$C-NMR (125 MHz; CDCl$_3$): δ 168.87, 151.09, 145.93, 136.79, 131.53, 130.35 (q, J=32.4 Hz), 129.05 (q, J=32.1 Hz), 126.08, 125.52 (q, J=3.8 Hz), 124.22 (d, J=272.3 Hz), 124.0 (d, J=270.5 Hz), 120.37 (q, J=3.8 Hz), 115.99 (q, J=3.6 Hz), 78.66, 74.22, 51.89, 51.63, 45.40, 42.39, 32.58, 17.92; $^{19}$F-NMR (471 MHz; CDCl$_3$): δ-62.28 (s, 3F), −62.59 (s, 3F); HRMS (ESI): m/z calculated for C$_{23}$H$_{23}$F$_6$O$_2$N$_2$ ([M+H]$^+$) 473.1658, found 473.1649; (trans-isomer) IR (neat): 2918, 1651, 1444, 1418, 1324, 1309, 1163, 1119, 1067 cm$^{-1}$; $^1$H-NMR (500 MHz; CDCl$_3$): δ 7.67 (d, J=8.2 Hz, 2H), 7.56 (d, J=8.2 Hz, 2H), 7.30 (d, J=8.2 Hz, 1H), 7.26 (d, J=8.2 Hz, 1H), 7.21 (s, 1H), 5.80 (t, J=7.4 Hz, 1H), 5.39 (dd, J=8.8, 5.9 Hz, 1H), 3.95-3.92 (m, 1H), 3.79-3.76 (m, 1H), 3.72 (ddd, J=13.0, 6.4, 3.0 Hz, 1H), 3.59-3.53 (m, 2H), 3.01-2.91 (m, 4H), 2.77 (ddd, J=11.5, 8.8, 6.5 Hz, 1H), 2.38 (s, 3H); $^{13}$C-NMR (125 MHz; CDCl$_3$): δ 169.2, 151.1, 146.6, 136.8 (d, J=1.3 Hz), 131.5, 130.2 (q, J=32.4 Hz), 129.1 (q, J=32.2 Hz), 125.6 (q, J=3.8 Hz), 125.4, 124.1 (q, J=272.3 Hz), 124.0 (q, J=270.5 Hz), 120.4 (q, J=3.8 Hz), 116.1 (q, J=3.7 Hz), 79.6, 75.4, 51.8, 51.6, 45.5, 42.4, 32.3, 18.0; $^{19}$F-NMR (471 MHz; CDCl$_3$): δ-62.27 (s, 3F), −62.53 (s, 3F); HRMS (ESI): m/z calculated for C$_{23}$H$_{23}$F$_6$O$_2$N$_2$ ([M+H]$^+$) 473.1658, found 473.1656.

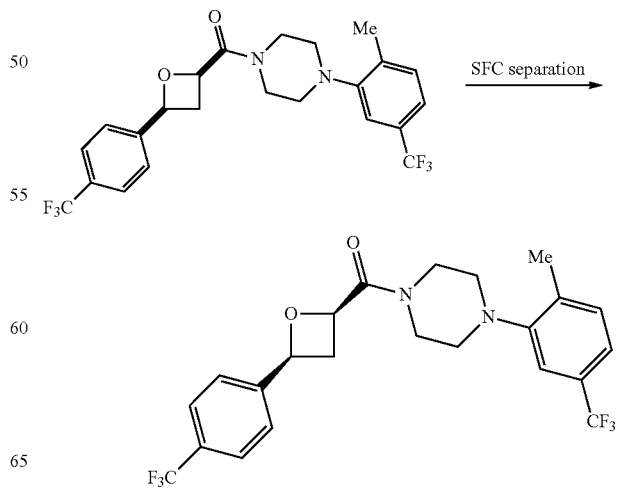

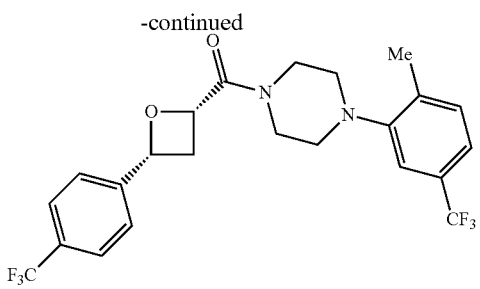

Racemic (4-(2-methyl-5-(trifluoromethyl)phenyl)piperazin-1-yl)(4-(4-(trifluoromethyl)phenyl)-oxetan-2-yl) methanone was separated on a SFC Chiralpak-IC semiprep (250×10 mm) column (9% MeOH, 5 mL/min, 220 nM, P=100) to afford (+)-enantiomer (retention time; 12.60 min) as a colorless oil (>99.9% purity by ELSD): $[\alpha]^{20}_D$+55.5 (MeOH); HRMS (ESI): m/z calculated for $C_{23}H_{23}F_6O_2N_2$ ([M+H]$^+$) 473.1658, found 473.1656. The enantiomeric excess was >99.9% ee (SFC Chiralpak-IC semiprep; 9% MeOH, 220 nM, 5 mL/min; retention time: 12.60 min). $^1$H-NMR (500 MHz; CDCl$_3$): δ 7.64 (d, J=8.2 Hz, 2H), 7.55 (d, J=8.2 Hz, 2H), 7.30 (d, J=8.0 Hz, 1H), 7.26 (d, J=8.0 Hz, 1H), 7.19 (s, 1H), 5.73 (t, J=7.7 Hz, 2H), 5.43 (t, J=7.7 Hz, 2H), 3.91-3.87 (m, 1H), 3.79-3.72 (m, 2H), 3.61-3.57 (m, 1H), 3.21-3.09 (m, 2H), 2.99-2.91 (m, 4H), 2.37 (s, 3H).

(−)-enantiomer; (retention time; 13.80 min) as a colorless oil (>99.9% purity by ELSD): $[\alpha]^{20}_D$ −70.8 (MeOH); HRMS (ESI): m/z calculated for $C_{23}H_{23}F_6O_2N_2$ ([M+H]$^+$) 473.1658, found 473.1657. The enantiomeric excess was >99.9% ee (SFC Chiralpak-IC semiprep; 9% MeOH, 220 nM, 5 mL/min; retention time: 13.80 min). $^1$H-NMR (500 MHz; CDCl$_3$): δ 7.64 (d, J=8.2 Hz, 2H), 7.55 (d, J=8.2 Hz, 2H), 7.30 (d, J=8.0 Hz, 1H), 7.26 (d, J=8.0 Hz, 1H), 7.19 (s, 1H), 5.73 (t, J=7.7 Hz, 2H), 5.43 (t, J=7.7 Hz, 2H), 3.91-3.87 (m, 1H), 3.79-3.72 (m, 2H), 3.61-3.57 (m, 1H), 3.21-3.09 (m, 2H), 2.99-2.91 (m, 4H), 2.37 (s, 3H).

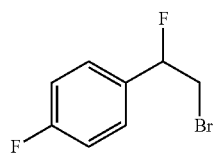

1-(2-Bromo-1-fluoroethyl)-4-fluorobenzene (Schlossera et al., Tetrahedron 2004, 7731-7742; Rosen et al., J. Med. Chem. 2004, 47:5860-5871). To a stirred solution of 4-fluorostyrene (2.00 g, 1.95 mL, 15.9 mmol) in distilled CH$_2$Cl$_2$ (16 mL) was added triethylamine trihydrofluoride (3.96 mL, 23.8 mmol) and NBS (3.43 g, 19.1 mmol) at 0° C. After 15 min, the ice bath was removed and the mixture was stirred at room temperature for 18 h. The reaction mixture was poured into ice water (200 mL) and made slightly basic with NH$_4$OH. The mixture was extracted with CH$_2$Cl$_2$ (4×40 mL). The combined organic layers were washed with 0.1 M HCl (2×40 mL), 5% NaHCO$_3$ (2×40 mL), dried over anhydrous MgSO$_4$ and concentrated under reduced pressure. The crude product was purified via flash column chromatography on SiO$_2$ (1:20 EtOAc/hexanes) to afford 1-(2-bromo-1-fluoroethyl)-4-fluorobenzene (2.67 g, 12.1 mmol, 76%) as a colorless oil: $^1$H-NMR (500 MHz, CDCl$_3$) δ 7.35 (dd, J=8.3, 5.3 Hz, 2H), 7.10 (t, J=8.6 Hz, 2H), 5.61 (ddd, J=46.4, 7.5, 4.5 Hz, 1H), 3.68 (ddd, J=15.0, 11.3, 7.6 Hz, 1H), 3.59 (ddd, J=24.2, 11.3, 4.4 Hz, 1H).

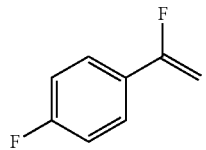

1-Fluoro-4-(1-fluorovinyl)benzene (Schlossera et al., Tetrahedron 2004, 7731-7742). To a flame-dried 25-mL round-bottom flask containing 1-(2-Bromo-1-fluoroethyl)-4-fluorobenzene (2.66 g, 12.0 mmol) was added potassium tert-butoxide (1.49 g, 13.2 mmol) dissolved in distilled THF (6 mL). The mixture was stirred at room temperature for 2 h and filtered. The red-color filtrate was purified via distillation to give 1-fluoro-4-(1-fluorovinyl)benzene (1.16 g, 8.27 mmol, 69%) as a colorless oil (bp 144-146° C.): $^1$H NMR (500 MHz, CDCl$_3$) δ 7.54 (dd, J=8.7, 5.3 Hz, 2H), 7.07 (t, J=8.4 Hz, 2H), 4.96 (dd, J=49.6, 3.6 Hz, 2H), 4.83 (dd, J=17.9, 3.6 Hz, 2H).

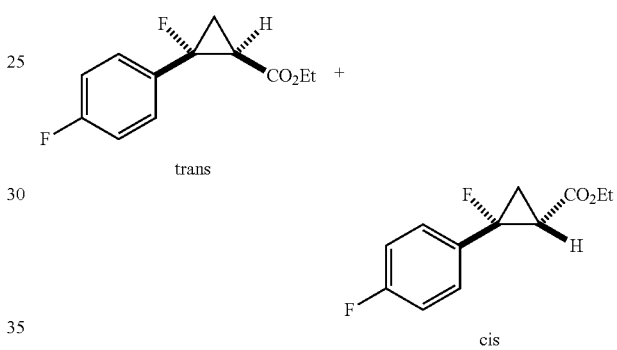

cis- and trans-Ethyl 2-fluoro-2-(4-fluorophenyl)cyclopropane-1-carboxylate (Rosen et al., J. Med. Chem. 2004, 47:5860-5871). In a flame-dried 3-neck round-bottom flask equipped with a stir bar, reflux condenser, septum, and stopper, Cu(acac)$_2$ (64.9 mg, 0.248 mmol, 3 mol %) was dissolved in distilled CH$_2$Cl$_2$ (11 mL). The solution was stirred for several minutes. A few drops of phenylhydrazine were added and the stirring continued. 1-fluoro-4-(1-fluorovinyl)benzene (1.16 g, 8.27 mmol) was added and the mixture was heated to reflux. A solution of ethyl diazoacetate (1.48 mL, 12.4 mmol) dissolved in distilled CH$_2$Cl$_2$ (22 mL) was added via syringe pump over 8 h. The solution was then refluxed for an additional 4 hr, after which it was cooled and diluted with CH$_2$Cl$_2$ (150 mL). The solution was washed with saturated NaHCO$_3$ solution and distilled water (300 mL). The organic layer was dried over anhydrous MgSO$_4$, filtered, and concentrated under reduced pressure. NMR analysis of the crude product revealed a conversion of 65%. Purification of the crude product with flash column chromatography on SiO$_2$ (1:1 CH$_2$Cl$_2$/hexanes) afforded a mixture of 1:1 cis/trans diastereomers as a yellow oil. The diastereomers were then separated by flash column chromatography on SiO$_2$ (1:2 CH$_2$Cl$_2$/hexanes) to give cis- and trans-ethyl 2-fluoro-2-(4-fluorophenyl)cyclopropane-1-carboxylate respectively as colorless oil: cis-(474 mg, 2.10 mmol, 25%); $^1$H NMR (500 MHz, CDCl$_3$) δ 7.32 (dd, J=8.1, 5.2 Hz, 2H), 7.08 (t, J=8.4 Hz, 2H), 4.29-4.19 (m, 2H), 2.28 (dt, J=20.1, 7.4 Hz, 1H), 2.15 (ddd, J=9.5, 7.7, 2.7 Hz, 1H), 1.59 (ddd, J=10.5, 9.5, 7.1 Hz, 1H), 1.30 (t, J=7.1 Hz, 3H); $^{13}$C NMR (75 MHz, CDCl$_3$) δ 167.9 (d, $J_{C-F}$=2 Hz), 162.9

(dd, $J_{C-F}$=248, 2 Hz), 133.4 (dd, $J_{C-F}$=22, 3 Hz), 127.3 (dd, $J_{C-F}$=8, 6 Hz), 115.8 (d, $J_{C-F}$=22 Hz), 80.7 (d, $J_{C-F}$=228 Hz), 61.4, 28.8 (d, $J_{C-F}$=12 Hz), 18.8 (d, $J_{C-F}$=13 Hz), 14.4; $^{19}$F NMR (CDCl$_3$, 470 MHz) δ −113.2 (s, 1F), −184.9 (s, 1F).

trans-(481 mg, 2.13 mmol, 26%); $^1$H NMR (CDCl$_3$, 500 MHz) δ 7.48-7.44 (m, 2H), 7.06 (t, J=8.4 Hz, 2H), 3.98-3.90 (m, 2H), 2.56 (ddd, J=17.8, 10.3, 7.6 Hz, 1H), 1.95 (dt, J=12.2, 7.3 Hz, 1H), 1.82 (ddd, J=19.2, 10.3, 7.1 Hz, 1H), 1.04 (t, J=7.1 Hz, 3H); $^{13}$C NMR (CDCl$_3$, 125 MHz) δ 169.0 (d, $J_{C-F}$=2 Hz), 163.3 (dd, $J_{C-F}$=249, 3 Hz), 130.6 (dd, $J_{C-F}$=8, 4 Hz), 129.3 (dd, $J_{C-F}$=21, 3 Hz), 115.5 (dd, $J_{C-F}$=22, 2 Hz), 82.6 (d, $J_{C-F}$=221 Hz), 60.98, 27.9 (d, $J_{C-F}$=17 Hz), 16.8 (d, $J_{C-F}$=11 Hz), 14.14; $^{19}$F NMR (CDCl$_3$, 470 MHz) δ −111.8 (s, 1F), −152.6 (s, 1F).

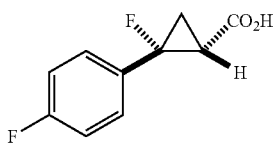

cis-2-Fluoro-2-(4-fluorophenyl)cyclopropane-1-carboxylic acid.[2] To a solution of cis-ethyl 2-fluoro-2-(4-fluorophenyl)cyclopropane-1-carboxylate (0.200 g, 0.884 mmol) in methanol (1.8 mL) was added KOH (0.500 g, 8.84 mmol) dissolved in methanol (4.4 ml) at 0° C. The reaction mixture was warm to room temperature and stirred for 16 h. The mixture was poured into water and extracted with CH$_2$Cl$_2$ (25 mL). The organic layer was discarded and the aqueous layer was acidified with 6 M HCl and extracted with CH$_2$Cl$_2$ (2×25 mL). The combined organic layers were dried over anhydrous Na$_2$SO$_4$ and concentrated under reduced pressure to afford cis-2-fluoro-2-(4-fluorophenyl)cyclopropane-1-carboxylic acid (0.171 g, 0.864 mmol, 98%) as a white solid: $^1$H NMR (CDCl$_3$, 500 MHz) δ 7.36-7.32 (m, 2H), 7.12-7.07 (m, 2H), 2.32 (dt, J=20.1, 7.5 Hz, 1H), 2.18 (ddd, J=9.5, 7.5, 2.2 Hz, 1H), 1.70 (ddd, J=10.7, 9.4, 7.2 Hz, 1H); $^{13}$C NMR (CDCl$_3$, 125 MHz) δ 173.0, 163.0 (dd, $J_{C-F}$=248, 2 Hz), 132.8 (dd, $J_{C-F}$=22, 3 Hz), 127.5 (dd, $J_{C-F}$=9, 6 Hz), 115.9 (d, $J_{C-F}$=22 Hz), 81.3 (d, $J_{C-F}$=229 Hz), 28.3 (d, $J_{C-F}$=12 Hz), 19.3 (d, $J_{C-F}$=12 Hz).

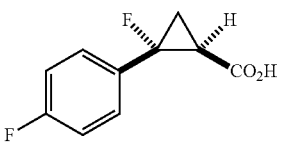

trans-2-Fluoro-2-(4-fluorophenyl)cyclopropane-1-carboxylic acid (Rosen et al., *J. Med. Chem.* 2004, 47:5860-5871). To a solution of trans-ethyl 2-fluoro-2-(4-fluorophenyl)cyclopropane-1-carboxylate (0.200 g, 0.884 mmol) in methanol (1.8 mL) was added KOH (0.500 g, 8.84 mmol) dissolved in methanol (4.4 ml) at 0° C. The reaction mixture was warm to room temperature and stirred for 16 h. The mixture was poured into water and extracted with CH$_2$Cl$_2$ (25 mL). The organic layer was discarded and the aqueous layer was acidified with 6 M HCl and extracted with CH$_2$Cl$_2$ (2×25 mL). The combined organic layers were dried over anhydrous Na$_2$SO$_4$ and concentrated under reduced pressure to afford trans-2-fluoro-2-(4-fluorophenyl)cyclopropane-1-carboxylic acid (0.175 g, 0.884 mmol, quant.) as a white solid: $^1$H NMR (CDCl$_3$, 500 MHz) δ 7.45-7.41 (m, 2H), 7.05 (t, J=8.6 Hz, 2H), 2.52 (ddd, J=17.4, 10.0, 7.5 Hz, 1H), 1.94-1.83 (m, 2H); $^{13}$C NMR (CDCl$_3$, 100 MHz) δ 174.3, 163.4 (dd, $J_{C-F}$=249, 3 Hz), 130.6 (dd, $J_{C-F}$=9, 4 Hz), 128.6 (dd, $J_{C-F}$=21, 3 Hz), 115.5 (d, $J_{C-F}$=22 Hz), 83.1 (d, $J_{C-F}$=222 Hz), 27.5 (d, $J_{C-F}$=17 Hz), 17.5 (d, $J_{C-F}$=10 Hz).

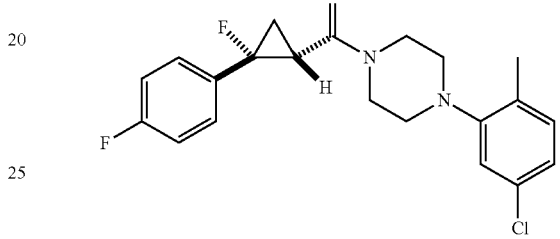

cis-(4-(5-Chloro-2-methylphenyl)piperazin-1-yl)((1SR,2RS)-2-fluoro-2-(4-fluorophenyl)cyclopropyl)-methanone. To a solution of cis-2-fluoro-2-(4-fluorophenyl)cyclopropane-1-carboxylic acid (0.0500 g, 0.252 mmol) in distilled CH$_2$Cl$_2$ (2.5 mL) at 0° C. was added 1-(5-chloro-2-methylphenyl)piperazine hydrochloride (0.0750 g, 0.303 mmol) and triethylamine (0.11 mL, 0.757 mmol). The cooled solution was then treated with T3P (50 wt. % solution in EtOAc, 0.27 mL, 0.378 mmol) dropwise. The reaction mixture was stirred at 0° C. for 30 min and allowed to warm to room temperature and stirred for 16 h. The reaction was diluted with CH$_2$Cl$_2$ (30 mL) and washed with 1 M HCl (20 mL), saturated NaHCO$_3$ (20 mL), dried over anhydrous MgSO$_4$, filtered and concentrated in vacuo. The crude brown oil residue was purified via flash column chromatography on SiO$_2$ (2:3 EtOAc/hexanes) to afford cis-(4-(5-chloro-2-methylphenyl)-piperazin-1-yl)((1SR,2RS)-2-fluoro-2-(4-fluorophenyl)cyclopropyl)methanone (79.1 mg, 0.200 mmol, 79%) as a white solid: Mp 110.2-110.8° C. (hexanes); IR (CDCl$_3$) 2918, 2819, 1646, 1593, 1516, 1430, 1223, 831, 809, 730 cm$^{-1}$; $^1$H NMR (CDCl$_3$, 500 MHz) δ 7.26 (m, 2H), 7.10 (t, J=7.8 Hz, 3H), 6.98 (dd, J=8.1, 1.9 Hz, 1H), 6.93 (d, J=1.8 Hz, 1H), 4.04-4.01 (m, 1H), 3.67-3.57 (m, 3H), 2.92-2.79 (m, 4H), 2.39 (dt, J=20.7, 7.6 Hz, 1H), 2.25 (s, 3H), 2.19 (ddd, J=9.8, 7.9, 4.6 Hz, 1H), 1.63-1.58 (m, 2H); $^{13}$C NMR (CDCl$_3$, 150 MHz) δ 164.7, 162.6 (d, $J_{C-F}$=248 Hz), 152.0, 133.9 (d, $J_{C-F}$=22 Hz), 132.2 (d, $J_{C-F}$=24 Hz), 132.0, 131.1, 125.6-125.5 (m), 123.8 (d, $J_{C-F}$=25 Hz), 119.9 (d, $J_{C-F}$=22 Hz), 116.2-115.9 (m), 79.9 (d, $J_{C-F}$=222 Hz), 52.1, 51.7, 46.2, 43.0, 30.5 (d, $J_{C-F}$=14 Hz), 17.7 (d, $J_{C-F}$=12 Hz), 17.6; $^{19}$F NMR (CDCl$_3$, 470 MHz) δ −113.88 (s, 1F), −188.55 (s, 1F); HRMS (ESI) m/z calcd for C$_{21}$H$_{22}$ClF$_2$N$_2$O ([M+H]$^+$) 391.1383, found 391.1386.

189

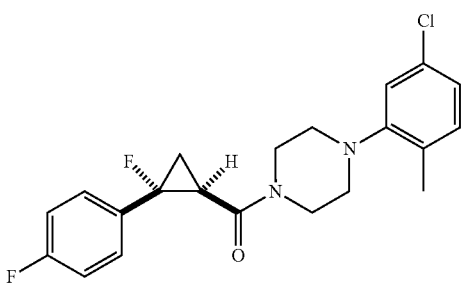

trans-(4-(5-Chloro-2-methylphenyl)piperazin-1-yl)((1SR,2RS)-2-fluoro-2-(4-fluorophenyl)-cyclopropyl)methanone. To a solution of trans-2-fluoro-2-(4-fluorophenyl)cyclopropane-1-carboxylic acid (0.0500 g, 0.252 mmol) in distilled CH$_2$Cl$_2$ (2.5 mL) at 0° C. was added 1-(5-chloro-2-methylphenyl)-piperazine hydrochloride (0.0750 g, 0.303 mmol) and triethylamine (0.11 mL, 0.757 mmol). The cooled solution was then treated with T3P (50 wt. % solution in EtOAc, 0.27 mL, 0.378 mmol) dropwise. The reaction mixture was stirred at 0° C. for 30 min and allowed to warm to room temperature and stirred for 16 h. The reaction was diluted with CH$_2$Cl$_2$ (30 mL) and washed with 1 M HCl (20 mL), saturated NaHCO$_3$ (20 mL), dried over anhydrous MgSO4, filtered and concentrated in vacuo. The crude brown oil residue was purified via flash column chromatography on SiO2 (2:3 EtOAc/hexanes) to afford trans-(4-(5-Chloro-2-methylphenyl)piperazin-1-yl)((1SR,2RS)-2-fluoro-2-(4-fluorophenyl)cyclopropyl)methanone (76.0 mg, 0.195 mmol, 77%) as a colorless oil: IR (CDCl$_3$) 2922, 2855, 1641, 1593, 1517, 1432, 1225, 1193, 812, 735. $^1$H NMR (CDCl$_3$, 500 MHz) δ 7.34-7.30 (m, 2H), 7.10-7.06 (m, 3H), 6.97 (dd, J=8.1, 2.1 Hz, 1H), 6.74 (d, J=2.1 Hz, 1H), 3.78-3.75 (m, 1H), 3.66 (t, J=5.0 Hz, 2H), 3.40 (ddd, J=12.4, 8.6, 3.3 Hz, 1H), 2.85-2.81 (m, 1H), 2.77-2.73 (m, 1H), 2.68 (ddd, J=18.8, 10.9, 7.9 Hz, 1H), 2.38 (ddd, J=11.5, 8.3, 3.0 Hz, 1H), 2.30 (dt, 1H, J=11.4, 5.7 Hz), 2.22 (s, 3H), 2.11 (dt, J=12.3, 7.6 Hz, 1H), 1.84 (ddd, J=20.6, 10.8, 7.4 Hz, 1 h); $^{13}$C NMR (CDCl$_3$, 100 MHz) δ 165.3, 162.8 (d, J$_{C-F}$=248 Hz), 151.8, 132.1 (d, J$_{C-F}$=21 Hz), 131.1, 130.6 (dd, J$_{C-F}$=21, 3 Hz), 127.6 (d, J$_{C-F}$=7 Hz), 127.5, 123.9, 119.8, 115.5 (d, J$_{C-F}$=22 Hz), 81.5 (d, J$_{C-F}$=222 Hz), 51.9, 51.6, 46.1, 42.5, 29.6 (d, J$_{C-F}$=13 Hz), 17.5, 16.5 (d, J$_{C-F}$=10 Hz); $^{19}$F NMR (CDCl$_3$, 470 MHz) δ −113.19 (s, 1F), −164.01 (s, 1F); HRMS (ESI) m/z calcd for C$_{21}$H$_{22}$ClF$_2$N$_2$O ([M+H]$^+$) 391.1383, found 391.1384.

190

-continued

Racemic trans-(4-(5-Chloro-2-methylphenyl)piperazin-1-yl)((1SR,2RS)-2-fluoro-2-(4-fluorophenyl)-cyclopropyl)methanone was separated on a SFC Chiralpak-IC semiprep (250×10 mm) column (30% MeOH, 7 mL/min, 220 nM, P=100) to afford (−)-(4-(5-Chloro-2-methylphenyl)piperazin-1-yl)(-2-fluoro-2-(4-fluorophenyl)cyclopropyl)methanone (retention time 4.76 min) as a colorless oil (100% purity by ESLD): [α]$^{20}_D$ −141.9 (c 0.84, MeOH); $^1$H NMR (CDCl$_3$, 500 MHz) δ 7.35-7.31 (m, 2H), 7.10-7.06 (m, 3H), 6.97 (dd, J=8.1, 2.1 Hz, 1H), 6.75 (d, J=2.1 Hz, 1H), 3.78-3.74 (m, 1H), 3.69-3.64 (m, 2H), 3.43-3.38 (m, 1H), 2.85-2.81 (m, 1H), 2.77-2.73 (m, 1H), 2.68 (ddd, J=18.8, 10.9, 7.9 Hz, 1H), 2.41-2.37 (m, 1H), 2.31 (td, J=11.0, 5.4 Hz, 1H), 2.22 (s, 3H), 2.11 (dt, J=12.3, 7.6 Hz, 1H), 1.84 (ddd, J=20.5, 10.8, 7.4 Hz, 1H); HRMS (ESI) m/z calcd for C$_{21}$H$_{22}$ClF$_2$N$_2$O ([M+H]$^+$) 391.1383, found 391.1379. The enantiomeric excess was >99% ee (SFC Chiralpak-IC (250×10 mm); 30% MeOH, 220 nm, 7 mL/min; retention time: 4.77 min).

(+)-(4-(5-Chloro-2-methylphenyl)piperazin-1-yl)(-2-fluoro-2-(4-fluorophenyl)cyclopropyl)-methanone (retention time 5.60 min) was obtained as a colorless oil (100% purity by ESLD): [α]$^{20}_D$+145.1 (c 0.86, MeOH); $^1$H NMR (CDCl$_3$, 500 MHz) δ 7.34-7.31 (m, 2H), 7.10-7.06 (m, 3H), 6.97 (dd, J=8.1, 2.1 Hz, 1H), 6.75 (d, J=2.0 Hz, 1H), 3.79-3.74 (m, 1H), 3.69-3.65 (m, 2H), 3.43-3.38 (m, 1H), 2.85-2.81 (m, 1H), 2.77-2.73 (m, 1H), 2.68 (ddd, J=18.9, 10.9, 8.0 Hz, 1H), 2.39 (ddd, J=11.2, 8.8, 2.6 Hz, 1H), 2.31 (dt, J=11.3, 5.8 Hz, 1H), 2.22 (s, 3H), 2.11 (dt, J=12.3, 7.6 Hz, 1H), 1.84 (ddd, J=20.5, 10.8, 7.4 Hz, 1H); HRMS (ESI) m/z calcd for C$_{21}$H$_{22}$ClF$_2$N$_2$O ([M+H]$^+$) 391.1383, found 391.1374. The enantiomeric excess was >99% ee (SFC Chiralpak-IC (250×10 mm); 30% MeOH, 220 nm, 7 mL/min; retention time: 5.60 min).

Ethyl 2-diazo-3,3,3-trifluoropropanoate (Bartrum et al., *Chem. Eur. J.* 2011, 17:9586-9589; Shi et al., *J. Org. Chem.* 1990, 55:3383-3386). To a stirred solution of p-toluenesulfonyl hydrazide (11.5 g, 60.5 mmol) in distilled $CH_2Cl_2$ (65 mL) was added ethyl trifluoropyruvate (7.79 mL, 57.6 mmol). The reaction was stirred at room temperature for 18 h. Phosphorus oxychloride (7.05 mL, 74.9 mmol) was added dropwise followed by pyridine (6.11 mL, 74.9 mmol) (Note: when pyridine was added dropwise the reaction mixture warmed up to a self-sustaining gentle reflux). The reaction mixture was stirred at room temperature for another 18 h. The mixture was washed with water and the organic layer was separated. The aqueous layer was extracted with $CH_2Cl_2$ (3×100 mL). The combined organic layers were washed with brine, dried over anhydrous $MgSO_4$, filtered and concentrated in vacuo to give ethyl 3,3,3-trifluoro-2-(2-tosylhydrazineylidene)propanoate as a yellow liquid which solidified to a white solid upon standing. The crude product was used in the next step without further purification.

To a solution of ethyl 3,3,3-trifluoro-2-(2-tosylhydrazineylidene)propanoate (18.3 g, 54.1 mmol) in anhydrous $CH_2Cl_2$ (433 mL) was added triethylamine (15.2 mL, 0.108 mol) dropwise. The reaction mixture was stirred at room temperature for 2 days. The solution was carefully concentrated in vacuo and the crude product was purified via distillation. The distillate was washed with 1 M HCl (20 mL×2) to remove the excess triethylamine. The organic layers collected were dried over anhydrous $MgSO_4$, filtered and carefully concentrated in vacuo to afford ethyl 2-diazo-3,3,3-trifluoropropanoate (4.89 g, 26.9 mmol, 50% over 2 steps) as a yellow oil: Bp lit: 60-62° C. (100 mmHg)[4]; $^1$H NMR ($CDCl_3$, 500 MHz) δ 4.32 (q, J=7.1 Hz, 2H), 1.32 (t, J=7.1 Hz, 3H); $^{13}$C NMR ($CDCl_3$, 125 MHz) δ 161.0, 122.8 (q, $J_{C-F}$=269 Hz), 62.3, 14.4 (C=N signal not observed).

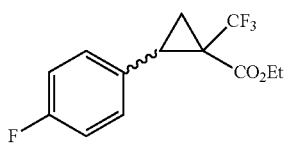

cis- and trans-Ethyl 2-(4-fluorophenyl)-1-(trifluoromethyl)cyclopropane-1-carboxylate. To a flame-dried flask containing 4-fluorostyrene (3.3 mL, 27.5 mmol) and $Rh_2(OAc)_4$ (0.121 g, 0.275 mmol, 5 mol %) in distilled $CH_2Cl_2$ (25 mL) was added ethyl 2-diazo-3,3,3-trifluoropropanoate (1.00 g, 5.49 mmol) in distilled $CH_2Cl_2$ (20 mL) via a syringe pump over 16 h at room temperature. After consumption of the diazo compound by TLC, the mixture was passed through a pad of silica gel to remove the rhodium catalyst and washed with $CH_2Cl_2$. The solvent was removed in vacuo. The crude product was purified by column chromatography (1:2 $CH_2Cl_2$/hexanes) to give an inseparable mixture of cis- and trans-ethyl 2-(4-fluorophenyl)-1-(trifluoromethyl)cyclopropane-1-carboxylate (cis/trans ratio 1:1.6) as an yellow oil (Note: The mixture also contained side product from the dimerization of the diazo compound): cis- (597 mg, 2.16 mmol, 34% calcd yield); $^1$H NMR ($CDCl_3$, 500 MHz) δ 7.26 (m, 2H), 7.00 (t, J=8.7 Hz, 2H), 4.33-4.25 (m, 2H), 3.04 (t, J=8.9 Hz, 1H), 1.95 (ddq, J=9.5, 5.4, 1.8 Hz, 1H), 1.88 (dd, J=8.2, 5.3 Hz, 1H), 1.34 (t, J=7.1 Hz, 3H); $^{19}$F NMR ($CDCl_3$, 470 MHz) δ −61.1 (s, 3F), −114.5 (s, 1F).

trans- (955 mg, 3.46 mmol, 54% calcd yield); $^1$H NMR ($CDCl_3$, 500 MHz) δ 7.22 (dd, J=8.2, 5.4 Hz, 2H), 6.98 (t, J=8.7 Hz, 2H), 3.96-3.87 (m, 2H), 2.90 (t, J=9.0 Hz, 1H), 2.14-2.11 (m, 1H), 1.78 (dd, J=9.7, 5.7 Hz, 1H), 0.94 (t, J=7.1 Hz, 3H); $^{19}$F NMR ($CDCl_3$, 470 MHz) δ −66.8 (s, 3F), −114.5 (s, 1F).

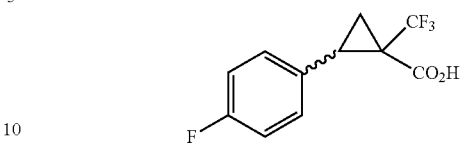

cis- and trans-2-(4-Fluorophenyl)-1-(trifluoromethyl)cyclopropane-1-carboxylic acid. To a solution of to KOH (1.02 g, 18.1 mmol) in methanol (9 ml) was added cis- and trans-ethyl 2-(4-fluorophenyl)-1-(trifluoromethyl)cyclopropane-1-carboxylate (0.500 g, 1.81 mmol) dissolved in methanol (3.8 mL). The reaction mixture was heated to 55° C. and stirred at this temperature for 24 h. The mixture was cooled to room temperature and poured into water and extracted with $CH_2Cl_2$ (25 mL). The organic layer was discarded and the aqueous layer acidified with 6 M HCl and extracted with $CH_2Cl_2$ (2×25 mL). The combined organic layers were dried over anhydrous $Na_2SO_4$ and concentrated under reduced pressure to give a mixture of cis- and trans-2-(4-Fluorophenyl)-1-(trifluoromethyl)cyclopropane-1-carboxylic acid as a pale yellow solid (cis/trans ratio 1:1.16) which was used in the next step without purification: cis- (168 mg, 0.677 mmol, 37% calcd yield); $^1$H NMR ($CDCl_3$, 500 MHz) δ 7.29-7.26 (m, 2H), 7.02 (t, J=8.6 Hz, 2H), 3.16 (t, J=9.0 Hz, 1H), 2.04-1.97 (m, 2H); $^{19}$F NMR ($CDCl_3$, 471 MHz) δ −61.5 (s, 3F), −114.0 (s, 1F).

trans- (262 mg, 1.06 mmol, 58% calcd yield); $^1$H NMR ($CDCl_3$, 500 MHz) δ 7.18 (dd, J=8.4, 5.4 Hz, 2H), 6.97 (t, J=8.6 Hz, 2H), 2.99 (t, J=9.0 Hz, 1H), 2.09 (t, J=6.5 Hz, 1H), 1.84 (dd, J=9.7, 5.8 Hz, 1H); $^{19}$F NMR ($CDCl_3$, 470 MHz) δ −66.9 (s, 3F), −114.1 (s, 1F).

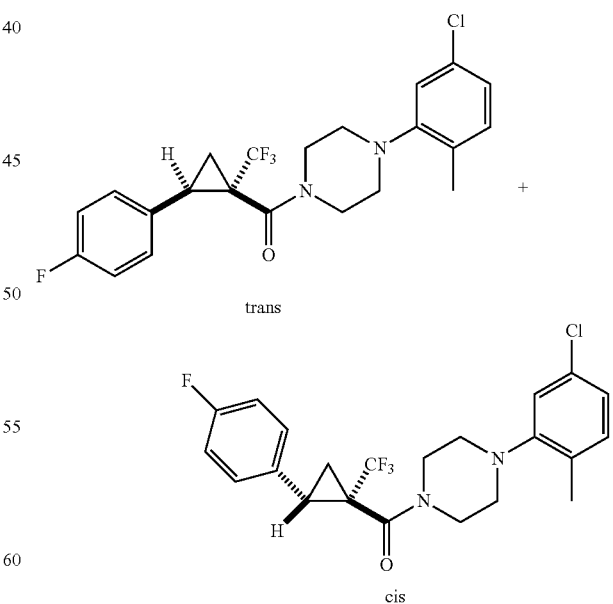

cis- and trans-(4-(5-Chloro-2-methylphenyl)piperazin-1-yl)(2-(4-fluorophenyl)-1-(trifluoromethyl)-cyclopropyl)methanone. To a suspension of cis- and trans-2-(4-Fluorophenyl)-1-(trifluoromethyl)-cyclopropane-1-carboxylic acid (0.250 g, 1.01 mmol) in distilled CH₂Cl₂ (10 mL) cooled to 0° C. was added oxalyl chloride (0.18 mL, 2.01 mmol) followed by a catalytic amount of DMF and the reaction was gradually warmed to room temperature and stirred for another 2 h. The reaction was concentrated in vacuo (water bath 25° C.) to afford the yellow crude acid chloride. The crude residue formed above was dissolved in distilled CH₂Cl₂ (10 mL) cooled to 0° C. and added with 1-(5-chloro-2-methylphenyl)piperazine hydrochloride (0.349 g, 1.41 mmol) and Et₃N (0.50 mL, 3.60 mmol) and the reaction was allowed to warm to room temperature and stirred for 20 h. LCMS and NMR analysis showed presence of starting material carboxylic acid (possibly due to hydrolysis of the acyl chloride). The reaction mixture was cooled to 0° C. and T3P (50 wt. % in EtOAc, 0.85 mL, 1.21 mmol) was added to couple the remaining of the carboxylic acid to the piperazine. The mixture was stirred at room temperature for 3 days until no starting material was seen in LCMS. The reaction was diluted with CH₂Cl₂ (30 mL) and washed with saturated NaHCO₃ (20 mL), dried over anhydrous MgSO₄, filtered and concentrated in vacuo. The crude oil residue was dissolved purified via flash column chromatography on SiO₂ (1:2 Et₂O/hexanes) to afford the cis- and trans-(4-(5-Chloro-2-methylphenyl)piperazin-1-yl)(2-(4-fluorophenyl)-1-(trifluoromethyl)cyclopropyl)methanone respectively as yellow oil: cis- (107 mg, 0.244 mmol, 24%); IR (CDCl₃) 2926, 1647, 1515, 1438, 1226, 1153, 1125, 842, 738 cm⁻¹; ¹H NMR (CDCl₃, 500 MHz) δ 7.32 (dd, J=8.5, 5.4 Hz, 2H), 7.12 (d, J=8.1 Hz, 1H), 7.05-7.00 (m, 3H), 6.96 (d, J=2.1 Hz, 1H), 3.88 (br s, 4H), 2.94 (br s, 4H), 2.79 (t, J=8.7 Hz, 1H), 2.30 (s, 3H), 1.98 (dd, J=7.9, 6.2 Hz, 1H), 1.73-1.69 (m, 1H); ¹³C NMR (CDCl₃, 151 MHz) δ 164.6, 162.3 (d, J=246 Hz), 151.8, 132.3, 132.1, 131.1, 130.7 (d, $J_{C-F}$=8 Hz), 129.3 (d, $J_{C-F}$=3 Hz), 124.7 (q, $J_{C-F}$=276 Hz), 124.0, 120.0, 115.5 (d, $J_{C-F}$=21 Hz), 51.8, 47.1, 43.4, 34.8 (q, $J_{C-F}$=32 Hz), 27.6, 17.6, 14.8; ¹⁹F NMR (CDCl₃, 470 MHz) δ −60.7 (s, 3F), −114.8 (s, 1F); HRMS (ESI) m/z calcd for C₂₂H₂₂ClF₄N₂O ([M+H]⁺) 441.1351, found 441.1352.

trans- (151 mg, 0.342 mmol, 34%); IR (CDCl₃) 2925, 2860, 1643, 1516, 1437, 1226, 1149, 1132, 845, 812, 733 cm⁻¹; ¹H NMR (CDCl₃, 500 MHz) δ 7.12-7.04 (m, 5H), 6.95 (dd, J=8.1, 2.1 Hz, 1H), 6.65 (d, J=1.7 Hz, 1H), 3.77 (s, 1H), 3.49-3.47 (m, 2H), 3.03 (s, 1H), 2.80 (dd, J=9.8, 7.5 Hz, 1H), 2.74-2.71 (m, 1H), 2.53-2.42 (m, 2H), 2.16 (s, 3H), 1.87 (t, J=7.0 Hz, 1H), 1.79 (dd, J=9.8, 6.6 Hz, 1H), 1.51 (s, 1H); ¹³C NMR (CDCl₃, 101 MHz) δ 162.6 (d, $J_{C-F}$=248 Hz), 161.7, 151.7, 132.1, 132.0, 131.1, 130.9 (d, $J_{C-F}$=3 Hz), 128.8 (d, $J_{C-F}$=8 Hz), 124.6 (q, $J_{C-F}$=272 Hz), 123.9, 119.8, 116.0 (d, $J_{C-F}$=22 Hz), 51.3, 50.9, 46.8, 43.2, 36.8 (q, $J_{C-F}$=33 Hz), 27.3, 17.4, 15.5; ¹⁹F NMR (CDCl₃, 470 MHz) δ −66.3 (s, 3F), −114.0 (s, 1F); HRMS (ESI) m/z calcd for C₂₂H₂₂ClF₄N₂O ([M+H]⁺) 441.1351, found 441.1349.

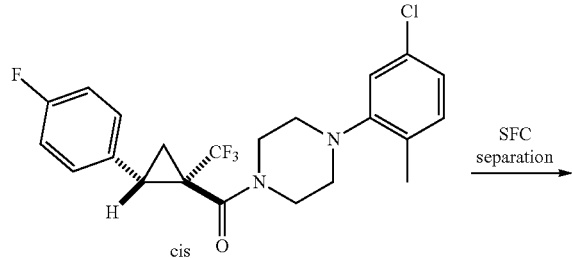

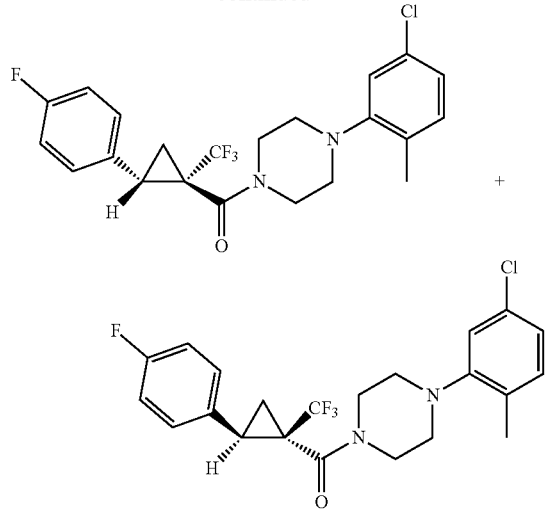

Racemic cis-(4-(5-chloro-2-methylphenyl)piperazin-1-yl)((1SR,2SR)-2-(4-fluorophenyl)-1-(trifluoromethyl)cyclopropyl)methanone was separated on a SFC Chiralpak-IC semiprep (250×10 mm) column (10% MeOH, 6 mL/min, 220 nM, P=100) to afford (−)-(4-(5-chloro-2-methylphenyl)piperazin-1-yl)(-2-(4-fluorophenyl)-1-(trifluoromethyl)cyclopropyl)methanone (retention time 14.46 min) as a colorless oil which foamed up upon drying (100% purity by ESLD): $[\alpha]^{20}_D$ −57.3 (c 0.44, MeOH); ¹H NMR (CDCl₃, 500 MHz) δ 7.32 (dd, J=8.5, 5.4 Hz, 2H), 7.13 (d, J=8.1 Hz, 1H), 7.05-7.00 (m, 3H), 6.96 (d, J=2.1 Hz, 1H), 3.89-3.88 (m, 4H), 2.94 (s, 4H), 2.79 (t, J=8.7 Hz, 1H), 2.30 (s, 3H), 1.98 (dd, J=7.9, 6.2 Hz, 1H), 1.71 (ddq, J=9.5, 6.0, 1.8 Hz, 1H). HRMS (ESI) m/z calcd for C₂₂H₂₂ClF₄N₂O ([M+H]⁺) 441.1348, found 441.1351. The enantiomeric excess was >99% ee (SFC Chiralpak-IC (250×10 mm); 10% MeOH, 220 nm, 6 mL/min; retention time: 14.55 min).

(+)-(4-(5-chloro-2-methylphenyl)piperazin-1-yl)(-2-(4-fluorophenyl)-1-(trifluoromethyl)-cyclopropyl)methanone (retention time 16.17 min) was obtained as a colorless oil which foamed up upon drying (100% purity by ESLD): $[\alpha]^{20}_D$+58.4 (c 0.42, MeOH); ¹H NMR (CDCl₃, 500 MHz) δ 7.32 (dd, J=8.5, 5.3 Hz, 2H), 7.13 (d, J=8.1 Hz, 1H), 7.05-7.00 (m, 3H), 6.96 (d, J=2.1 Hz, 1H), 3.89-3.88 (m, 4H), 2.94 (s, 4H), 2.79 (t, J=8.7 Hz, 1H), 2.30 (s, 3H), 1.98 (dd, J=7.9, 6.2 Hz, 1H), 1.71 (ddq, J=9.6, 6.0, 1.9 Hz, 1H); HRMS (ESI) m/z calcd for C₂₂H₂₂ClF₄N₂O ([M+H]⁺) 441.1348, found 441.1351. The enantiomeric excess was >99% ee (SFC Chiralpak-IC (250×10 mm); 10% MeOH, 220 nm, 6 mL/min; retention time: 16.31 min).

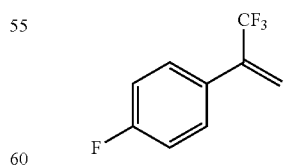

1-fluoro-4-(3,3,3-trifluoroprop-1-en-2-yl)benzene (Miura et al., Chem. Lett. 2008, 37:1006-1007; Kobayashi et al., J. Fluorine Chem. 2009, 130:591-594). To a solution of 1,2-dibromo-3,3,3-trifluoropropane (6.35 mL, 52.0 mmol) in THF/DME/H2O (1:1:1, 105 mL), 4-fluorophenylboronic acid (5.00 g, 34.7 mmol), PdCl₂(PPh₃)₂ (0.973 g, 1.39 mmol), AsPh₃ (1.64 g, 5.20 mmol), and KOH (11.7 g, 0.208 mol) were added under an inert atmosphere. The reaction mixture was stirred in an ice bath for 10 min, and gradually warmed up to room temperature and then heated at 75° C. for 13 h. After completion of reaction, water (200 mL) was added, then the mixture was extracted with diethyl ether (2×200 mL). The combined organic layers were washed with brine (300 mL) and dried over anhydrous MgSO₄. The solvent was carefully removed in vacuo. The crude material was purified via vacuum distillation to give 1-fluoro-4-(3,3,3-trifluoroprop-1-en-2-yl)benzene (5.25 g, 82%) as a colorless oil: Bp 53° C. @ 20 mmHg; ¹H NMR (CDCl₃, 500 MHz) δ 7.43 (dd, J=8.6, 5.5 Hz, 2H), 7.10-7.05 (m, 2H), 5.95 (d, J=1.2 Hz, 1H), 5.73 (q, J=1.6 Hz, 1H); ¹³C NMR (CDCl₃, 125 MHz) δ 163.4 (d, $J_{C-F}$=249 Hz), 138.3 (q, $J_{C-F}$=30 Hz), 129.9 (d, $J_{C-F}$=4 Hz), 129.5 (d, $J_{C-F}$=8 Hz), 123.4 (q, $J_{C-F}$=274 Hz), 120.6 (q, $J_{C-F}$=6 Hz), 115.7 (d, $J_{C-F}$=22 Hz); ¹⁹F NMR (CDCl₃, 471 MHz) δ −65.1 (s, 3F), −112.5 (s, 1F).

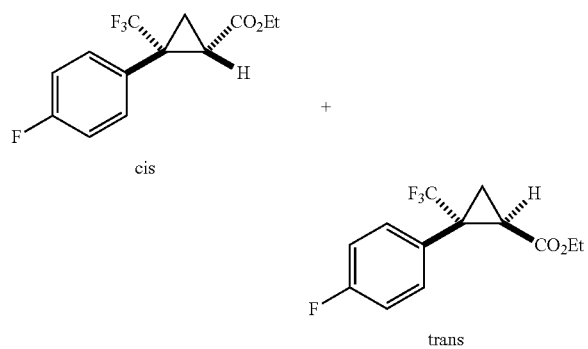

cis- and trans-Ethyl-2-(4-fluorophenyl)-2-(trifluoromethyl)cyclopropane-1-carboxylate. To a flame-dried round-bottom flask was added Rh₂ (OAc)₄ (128 mg, 0.290 mmol, 5 mol %) and 1-fluoro-4-(3,3,3-trifluoroprop-1-en-2-yl)benzene (1.20 g, 5.81 mmol) in distilled CH₂Cl₂ (5 mL). A solution of ethyl diazoacetate (1.04 mL, 8.71 mmol) in CH₂Cl₂ (18 mL) was added via syringe pump over 16 h at room temperature. After addition of the diazo compound, TLC analysis showed that there was still presence of the alkene. Another 2 mol % of the Rh₂ (OAc)₄ catalyst was added and 0.5 equiv of diazo compound dissolved in CH₂Cl₂ (10 mL) was added dropwise over 9 h. The mixture was filtered through a silica gel plug and washed with CH₂Cl₂. The solution was concentrated under reduced pressure and the crude mixture was purified via flash column chromatography on SiO₂ (1:2 CH₂Cl₂/hexanes) to afford cis- and trans-ethyl-2-(4-fluorophenyl)-2-(trifluoromethyl)cyclopropane-1-carboxylate respectively as yellow oils: cis- (554 mg, 2.01 mmol, 35%); ¹H NMR (CDCl₃, 500 MHz) δ 7.47 (dd, J=8.6, 5.3 Hz, 2H), 7.08-7.02 (m, 2H), 4.32-4.18 (m, 2H), 2.23 (t, J=8.1 Hz, 1H), 2.04 (dd, J=7.2, 5.9 Hz, 1H), 1.46 (ddq, J=8.9, 5.7, 1.7 Hz, 1H), 1.31 (t, J=7.1 Hz, 3H); ¹³C NMR (CDCl₃, 125 MHz) δ 168.0, 163.0 (d, $J_{C-F}$=248 Hz), 132.8 (d, $J_{C-F}$=9 Hz), 131.8 (d, $J_{C-F}$=3 Hz), 125.2 (q, $J_{C-F}$=276 Hz), 115.7 (d, $J_{C-F}$=22 Hz), 61.7, 35.0 (q, $J_{C-F}$=34 Hz), 27.5, 14.5 (q, $J_{C-F}$=2 Hz), 14.2; ¹⁹F NMR (CDCl₃, 471 MHz) δ −65.6 (s, 3F), −112.4 (s, 1F).

trans- (662 mg, 2.40 mmol, 41%); ¹H NMR (CDCl₃, 500 MHz) δ 7.34 (dd, J=8.6, 5.3 Hz, 2H), 7.05-7.00 (m, 2H), 4.01-3.91 (m, 2H), 2.48 (dd, J=8.8, 6.3 Hz, 1H), 1.83 (tq, J=5.8, 1.8 Hz, 1H), 1.72 (dd, J=8.8, 5.5 Hz, 1H), 1.07 (t, J=7.1 Hz, 3H); ¹³C NMR (CDCl₃, 100 MHz) δ 168.7, 163.0 (d, $J_{C-F}$=248 Hz), 133.0 (d, $J_{C-F}$=9 Hz), 127.4 (d, $J_{C-F}$=3 Hz), 125.0 (q, $J_{C-F}$=274 Hz), 115.6 (d, $J_{C-F}$=22 Hz), 61.3, 35.2 (q, $J_{C-F}$=34 Hz), 23.8 (q, $J_{C-F}$=2 Hz), 14.7 (q, $J_{C-F}$=2 Hz), 14.1; ¹⁹F NMR (CDCl₃, 471 MHz) δ −70.7 (s, 3F), −112.4 (s, 1F). A fraction containing a mixture of both diastereomers was also obtained (192 mg, 0.694 mmol, 12%).

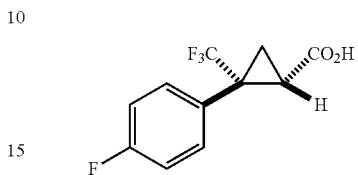

cis-2-(4-fluorophenyl)-2-(trifluoromethyl)cyclopropane-1-carboxylic acid. To a solution of KOH (0.463 g, 8.25 mmol) in methanol (3.6 ml) was added cis-ethyl-2-(4-fluorophenyl)-2-(trifluoromethyl)-cyclopropane-1-carboxylate (0.228 g, 0.825 mmol) dissolved in methanol (1.5 mL) at 0° C. The reaction mixture was gradually warm to room temperature and stirred for 12 h. The mixture was poured into water and extracted with CH₂Cl₂ (25 mL). The organic layer was discarded and the aqueous layer acidified with 6 M HCl and extracted with CH₂Cl₂ (2×25 mL). The combined organic layers were dried over anhydrous Na₂SO₄ and concentrated under reduced pressure to give the cis-2-(4-fluorophenyl)-2-(trifluoromethyl)-cyclopropane-1-carboxylic acid (0.202 g, 0.812 mmol, 98%) as a white solid: ¹H NMR (CDCl₃, 500 MHz) δ 7.47 (dd, J=8.6, 5.2 Hz, 2H), 7.09-7.02 (m, 2H), 2.28 (t, J=8.0 Hz, 1H), 2.09 (dd, J=7.3, 5.9 Hz, 1H), 1.57-1.53 (m, 1H); ¹⁹F NMR (CDCl₃, 471 MHz) δ −65.3 (s, 3F), −112.1 (s, 1F).

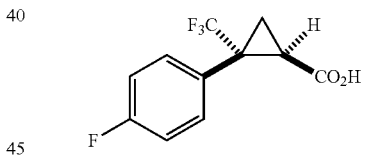

trans-2-(4-fluorophenyl)-2-(trifluoromethyl)cyclopropane-1-carboxylic acid. To a solution of KOH (0.406 g, 7.24 mmol) in methanol (3.6 ml) was added trans-ethyl-2-(4-fluorophenyl)-2-(trifluoromethyl)-cyclopropane-1-carboxylate (0.200 g, 0.724 mmol) dissolved in methanol (1.5 mL) at 0° C. The reaction mixture was gradually warm to room temperature and stirred for 12 h. The mixture was poured into water and extracted with CH₂Cl₂ (25 mL). The organic layer was discarded and the aqueous layer acidified with 6 M HCl and extracted with CH₂Cl₂ (2×25 mL). The combined organic layers were dried over anhydrous Na₂SO₄ and concentrated under reduced pressure to give the trans-2-(4-fluorophenyl)-2-(trifluoromethyl)-cyclopropane-1-carboxylic acid (0.181 g, 0.731 mmol, 98%) as a white solid: ¹H NMR (CDCl₃, 500 MHz) δ 7.32 (dd, J=8.3, 5.4 Hz, 2H), 7.02 (t, J=8.6 Hz, 2H), 2.49-2.45 (m, 1H), 1.77 (dq, J=8.3, 2.9 Hz, 2H); ¹⁹F NMR (CDCl₃, 471 MHz) δ −70.9 (s, 3F), −112.1 (s, 1F).

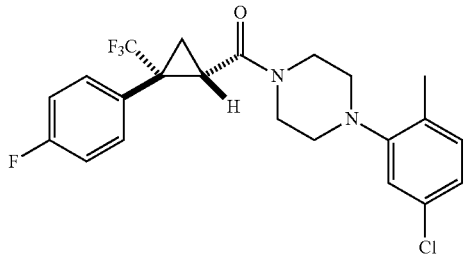

cis-(4-(5-Chloro-2-methylphenyl)piperazin-1-yl)((1SR,2RS)-2-(4-fluorophenyl)-2-(trifluoromethyl)-cyclopropyl)methanone. A solution of cis-2-(4-fluorophenyl)-2-(trifluoromethyl)cyclopropane-1-carboxylic acid (0.100 g, 0.403 mmol) and 1-(5-chloro-2-methylphenyl)piperazine hydrochloride (0.120 g, 0.484 mmol) in distilled $CH_2Cl_2$ (4 mL) was cooled to 0° C. and then added with triethylamine (0.168 mL, 1.21 mmol). The cooled solution was then treated with T3P (50 wt. % solution in EtOAc), 0.43 mL, 0.604 mmol) dropwise. The reaction mixture was stirred at 0° C. for 30 min and allowed to warm to room temperature and stirred for 18 h. After completion of the reaction by TLC analysis, the reaction was diluted with $CH_2Cl_2$ (30 mL) and washed with 1 M HCl (30 mL), saturated $NaHCO_3$ solution (20 mL), dried over anhydrous $MgSO_4$, filtered and concentrated in vacuo. The brown crude oil residue was purified via automated flash column chromatography on $SiO_2$ (100 hexanes—40% EtOAc/hexanes gradient) to afford cis-(4-(5-chloro-2-methylphenyl)piperazin-1-yl)((1SR,2RS)-2-(4-fluorophenyl)-2-(trifluoromethyl)-cyclopropyl)methanone (108 mg, 0.245 mmol, 61%) as a colorless oil which foamed up upon drying: IR (CDCl$_3$) 2917, 2825, 1651, 1593, 1513, 1435, 1227, 1159, 1137, 835, 727 cm$^{-1}$; $^1$H NMR (CDCl$_3$, 500 MHz) δ 7.47 (dd, J=8.7, 5.2 Hz, 2H), 7.14-7.06 (m, 3H), 7.00 (dd, J=8.1, 2.1 Hz, 1H), 6.97 (d, J=2.1 Hz, 1H), 3.99-3.87 (m, 3H), 3.81-3.76 (m, 1H), 3.01 (t, J=5.0 Hz, 2H), 2.94-2.86 (m, 2H), 2.31 (s, 3H), 2.22-2.17 (m, 2H), 1.60-1.56 (m, 1H); $^{13}$C NMR (CDCl$_3$, 125 MHz) δ 164.9, 162.9 (d, $J_{C-F}$=249 Hz), 152.0, 132.3, 132.0, 131.8 (d, $J_{C-F}$=8 Hz), 131.1, 125.6 (q, $J_{C-F}$=276 Hz), 123.9, 119.9, 116.0 (d, $J_{C-F}$=22 Hz), 51.7, 51.6, 46.3, 42.9, 35.1 (q, $J_{C-F}$=34 Hz), 28.1, 17.60, 14.55; $^{19}$F NMR (CDCl$_3$, 471 MHz) δ −64.7 (s, 3F), −112.2 (s, 1F); HRMS (ESI) m/z calcd for $C_{22}H_{22}ClF_4N_2O$ ([M+H]$^+$) 441.1351, found 441.1350.

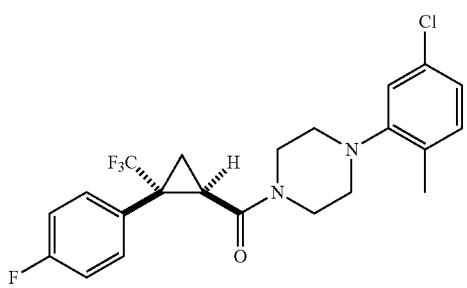

trans-(4-(5-chloro-2-methylphenyl)piperazin-1-yl)((1RS,2RS)-2-(4-fluorophenyl)-2-(trifluoromethyl)-cyclopropyl)methanone. A solution of trans-2-(4-fluorophenyl)-2-(trifluoromethyl)cyclopropane-1-carboxylic acid (0.100 g, 0.403 mmol) and 1-(5-chloro-2-methylphenyl)piperazine hydrochloride (0.120 g, 0.484 mmol) in distilled $CH_2Cl_2$ (4 mL) was cooled to 0° C. and then added with triethylamine (0.168 mL, 1.21 mmol). The cooled solution was then treated with T3P (50 wt. % solution in EtOAc), 0.43 mL, 0.604 mmol) dropwise. The reaction mixture was stirred at 0° C. for 30 min and allowed to warm to room temperature and stirred for 18 h. After completion of the reaction by TLC analysis, the reaction was diluted with $CH_2Cl_2$ (30 mL) and washed with 1 M HCl (30 mL), saturated $NaHCO_3$ solution (20 mL), dried over anhydrous $MgSO_4$, filtered and concentrated in vacuo. The brown crude oil residue was purified via automated flash column chromatography on $SiO_2$ (100 hexanes—40% EtOAc/hexanes gradient) to afford trans-(4-(5-chloro-2-methylphenyl)piperazin-1-yl)((1SR,2RS)-2-(4-fluorophenyl)-2-(trifluoromethyl)-cyclopropyl)methanone (162 mg, 0.367 mmol, 91%) as a colorless oil which foamed up upon drying: IR (CDCl$_3$) 2894, 2820, 1652, 1593, 1514, 1436, 1296, 1226, 1160, 1143, 830, 735; $^1$H NMR (CDCl$_3$, 500 MHz) δ 7.31 (dd, J=8.6, 5.3 Hz, 2H), 7.13 (d, J=8.1 Hz, 1H), 7.06-7.00 (m, 3H), 6.96 (d, J=2.0 Hz, 1H), 3.99-3.86 (m, 2H), 3.70-3.56 (m, 2H), 3.07-2.99 (m, 2H), 2.86-2.75 (m, 2H), 2.59 (dd, J=8.8, 6.2 Hz, 1H), 2.30 (s, 3H), 2.12-2.09 (m, 1H), 1.70 (dd, J=8.8, 5.3 Hz, 1H); $^{13}$C NMR (CDCl$_3$, 101 MHz) δ 165.3, 162.9 (d, $J_{C-F}$=248 Hz), 151.8, 132.8 (d, $J_{C-F}$=8 Hz), 132.3, 132.1, 131.1, 127.1 (d, $J_{C-F}$=3 Hz), 125.4 (q, $J_{C-F}$=274 Hz), 124.0, 119.8, 115.8 (d, $J_{C-F}$=22 Hz), 52.1, 51.7, 46.2, 42.8, 34.9 (q, $J_{C-F}$=33 Hz), 22.8, 17.6, 13.9. $^{19}$F NMR (CDCl$_3$, 471 MHz) δ −69.6 (s, 3F), −112.4 (s, 1F); HRMS (ESI) m/z calcd for $C_{22}H_{22}ClF_4N_2O$ ([M+H]$^+$) 441.1351, found 441.1351.

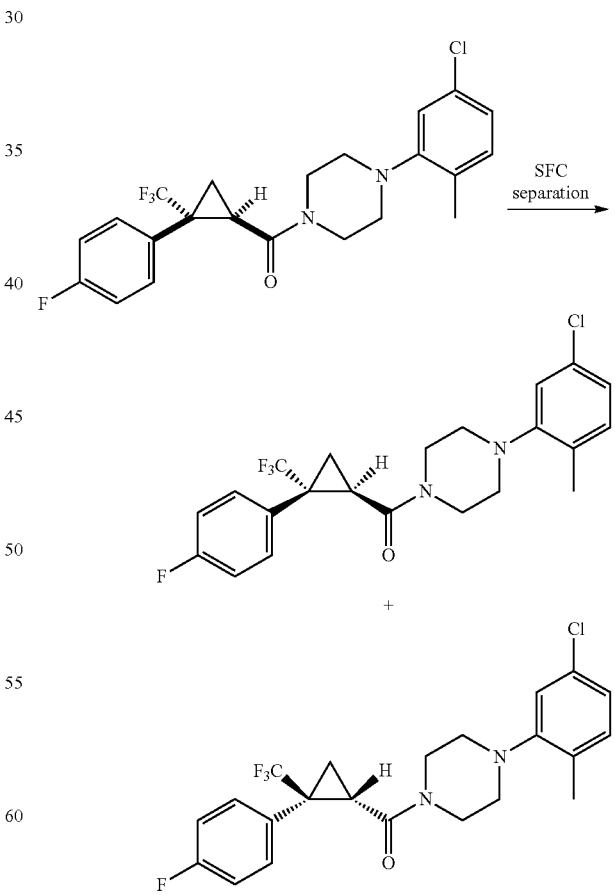

Racemic trans-(4-(5-chloro-2-methylphenyl)piperazin-1-yl)((1SR,2RS)-2-(4-fluorophenyl)-2-(trifluoromethyl)cyclopropyl)methanone was separated on a SFC Chiralpak-IC semiprep (250×10 mm) column (13% MeOH, 7 mL/min, 220 nM, P=100) to afford (−)-(4-(5-chloro-2-methylphenyl)piperazin-1-yl)(2-(4-fluorophenyl)-2-(trifluoromethyl)cyclopropyl)methanone (retention time 6.01 min) as a colorless oil which foamed up upon drying (100% purity by ESLD): $[\alpha]^{20}_D$ −179.6 (c 0.69, MeOH); $^1$H NMR (CDCl$_3$, 400 MHz) δ 7.31 (dd, J=8.6, 5.3 Hz, 2H), 7.13 (d, J=7.6 Hz, 1H), 7.07-7.00 (m, 3H), 6.96 (d, J=2.1 Hz, 1H), 3.99-3.85 (m, 2H), 3.71-3.54 (m, 2H), 3.08-2.98 (m, 2H), 2.86-2.74 (m, 2H), 2.59 (dd, J=8.8, 6.1 Hz, 1H), 2.30 (s, 3H), 2.13-2.08 (m, 1H), 1.70 (dd, J=8.8, 5.3 Hz, 1H); HRMS (ESI) m/z calcd for C$_{22}$H$_{22}$ClF$_4$N$_2$O ([M+H]$^+$) 441.1344, found 441.1351. The enantiomeric excess was >99% ee (SFC Chiralpak-IC (250×10 mm); 10% MeOH, 220 nm, 7 mL/min; retention time: 6.01 min).

(+)-(4-(5-chloro-2-methylphenyl)piperazin-1-yl)(2-(4-fluorophenyl)-2-(trifluoromethyl)-cyclopropyl)methanone (retention time 7.16 min) was obtained as a colorless oil which foamed up upon drying (100% purity by ESLD): $[\alpha]^{20}_D$ −177.9 (c 0.67, MeOH); $^1$H NMR (CDCl$_3$, 400 MHz) δ 7.31 (dd, J=8.6, 5.3 Hz, 2H), 7.13 (d, J=8.1 Hz, 1H), 7.07-7.00 (m, 3H), 6.96 (d, J=2.1 Hz, 1H), 3.99-3.85 (m, 2H), 3.71-3.54 (m, 2H), 3.07-3.00 (m, 2H), 2.87-2.74 (m, 2H), 2.59 (dd, J=8.9, 6.1 Hz, 1H), 2.30 (s, 3H), 2.12-2.08 (m, 1H), 1.70 (dd, J=8.8, 5.3 Hz, 1H); HRMS (ESI) m/z calcd for C$_{22}$H$_{22}$ClF$_4$N$_2$O ([M+H]$^+$) 441.1340, found 441.1351. The enantiomeric excess was >99% ee (SFC Chiralpak-IC (250×10 mm); 13% MeOH, 220 nm, 7 mL/min; retention time: 7.12 min).

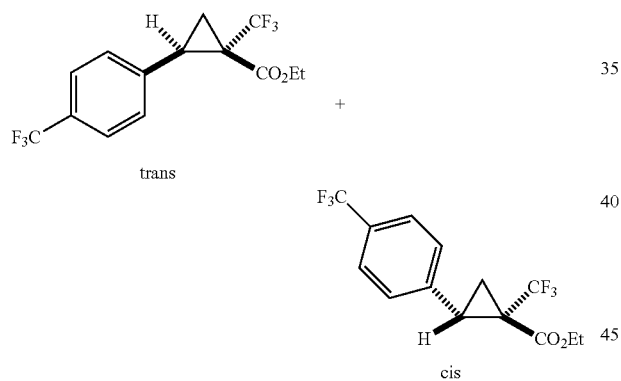

trans cis cis- and trans-Ethyl-1-(trifluoromethyl)-2-(4-(trifluoromethyl)phenyl)cyclopropane-1-carboxylate. To a flame-dried round-bottom flask was added rhodium acetate (64.2 mg, 0.145 mmol) and 4-(trifluoromethyl)styrene in distilled CH$_2$Cl$_2$ (3 mL). A solution of ethyl 2-diazo-3,3,3-trifluoropropanoate (0.793 g, 4.36 mmol) in distilled CH$_2$Cl$_2$ (10 mL) was added via a syringe pump over 18 h. The mixture was stirred for another 2 hour and then filtered through a silica gel plug and washed with CH$_2$Cl$_2$. The solution was concentrated under reduced pressure and the crude residue was purified via flash column chromatography on SiO$_2$ (1:2 CH$_2$Cl$_2$/hexanes) to afford cis- and trans-ethyl-1-(trifluoromethyl)-2-(4-(trifluoromethyl)phenyl)cyclopropane-1-carboxylate respectively as pale yellow oil: cis- (224 mg, 0.686 mmol, 24%); $^1$H NMR (CDCl$_3$, 500 MHz) δ 7.58 (d, J=8.2 Hz, 2H), 7.42 (d, J=8.1 Hz, 2H), 4.35-4.27 (m, 2H), 3.11 (t, J=8.9 Hz, 1H), 1.99 (ddq, J=9.5, 5.5, 1.8 Hz, 1H), 1.94 (dd, J=8.3, 5.4 Hz, 1H), 1.35 (t, J=7.1 Hz, 3H); $^{19}$F NMR (CDCl$_3$, 470 MHz) δ −61.1 (s, 3F), −62.6 (s, 3F).

trans- (435 mg, 1.33 mmol, 46%); $^1$H NMR (CDCl$_3$, 500 MHz) δ 7.56 (d, J=8.1 Hz, 2H), 7.37 (d, J=8.6 Hz, 2H), 3.91 (q, J=7.1 Hz, 2H), 2.97 (t, J=8.9 Hz, 1H), 2.18 (ddq, J=8.0, 6.0, 2.0 Hz, 1H), 1.84 (dd, J=9.7, 5.8 Hz, 1H), 0.91 (t, J=7.1 Hz, 3H); $^{19}$F NMR (CDCl$_3$, 470 MHz) δ −62.6 (s, 3F), −67.0 (s, 3F). A fraction containing a mixture of both diastereomers was also obtained (157 mg, 0.481 mmol, 17%).

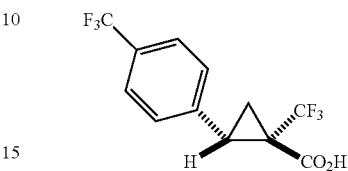

cis-1-(trifluoromethyl)-2-(4-(trifluoromethyl)phenyl)cyclopropane-1-carboxylic acid. A solution of cis-ethyl-1-(trifluoromethyl)-2-(4-(trifluoromethyl)phenyl)cyclopropane-1-carboxylate (0.220 g, 0.674 mmol) in methanol (1.4 mL) was added to KOH (0.378 g, 6.74 mmol) in methanol (3.4 ml). The reaction mixture was heated to 55° C. and stirred for 3 d. The mixture was cooled to room temperature and poured into water and extracted with CH$_2$Cl$_2$ (15 mL). The organic layer was discarded and the aqueous layer acidified with 6 M HCl and extracted with CH$_2$Cl$_2$ (2×15 mL). The combined organic layers were dried over anhydrous Na$_2$SO$_4$ and concentrated under reduced pressure to give cis-1-(trifluoromethyl)-2-(4-(trifluoromethyl)phenyl)cyclopropane-1-carboxylic acid (0.190 g, 0.636 mmol, 94%) as a white solid: $^1$H NMR (CDCl$_3$, 500 MHz) δ 7.60 (d, J=8.2 Hz, 2H), 7.44 (d, J=8.2 Hz, 2H), 3.24 (t, J=9.1 Hz, 1H), 2.10-2.04 (m, 2H); $^{13}$C NMR (CDCl$_3$, 125 MHz) δ 173.7, 137.1, 130.4 (q, $J_{C-F}$=33 Hz), 130.0, 125.6 (q, $J_{C-F}$=4 Hz), 124.1 (q, $J_{C-F}$=272 Hz), 123.6 (q, $J_{C-F}$=275 Hz), 32.9 (q, $J_{C-F}$=34 Hz), 32.6, 17.0; $^{19}$F NMR (CDCl$_3$, 470 MHz) δ −61.6 (s, 3F), −62.7 (s, 3F).

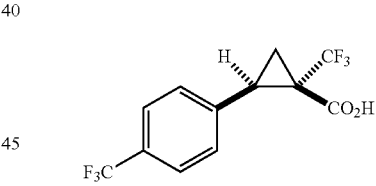

trans-1-(trifluoromethyl)-2-(4-(trifluoromethyl)phenyl)cyclopropane-1-carboxylic acid. A solution of trans-ethyl-1-(trifluoromethyl)-2-(4-(trifluoromethyl)phenyl)cyclopropane-1-carboxylate (0.200 g, 0.613 mmol) in methanol (1.3 mL) was added to KOH (0.344 g, 6.13 mmol) in methanol (3 mL). The reaction mixture was heated to 55° C. and stirred for 3 d. The mixture was cooled to room temperature and poured into water and extracted with CH$_2$Cl$_2$ (15 mL). The organic layer was discarded and the aqueous layer acidified with 6 M HCl and extracted with CH$_2$Cl$_2$ (2×15 mL). The combined organic layers were dried over anhydrous Na$_2$SO$_4$ and concentrated under reduced pressure to give trans-1-(trifluoromethyl)-2-(4-(trifluoromethyl)phenyl)cyclopropane-1-carboxylic acid (187 mg, 0.627 mmol, quant.) as a white solid: $^1$H NMR (CDCl$_3$, 500 MHz) δ 7.54 (d, J=8.2 Hz, 2H), 7.33 (d, J=8.2 Hz, 2H), 3.04 (t, J=9.1 Hz, 1H), 2.16-2.13 (m, 1H), 1.89 (dd, J=9.7, 5.9 Hz, 1H); $^{13}$C NMR (CDCl$_3$, 125 MHz) δ 170.7, 137.1 (d, $J_{C-F}$=1 Hz), 130.3 (q, $J_{C-F}$=33 Hz), 129.6, 125.4 (q, $J_{C-F}$=4 Hz), 124.1 (q, $J_{C-F}$=272 Hz), 123.9 (q, $J_{C-F}$=274 Hz), 34.3 (q, $J_{C-F}$=34 Hz), 30.1 (d, $J_{C-F}$=1 Hz), 16.2; $^{19}$F NMR (CDCl$_3$, 470 MHz) δ −62.7 (s, 3F), −67.1 (s, 3F).

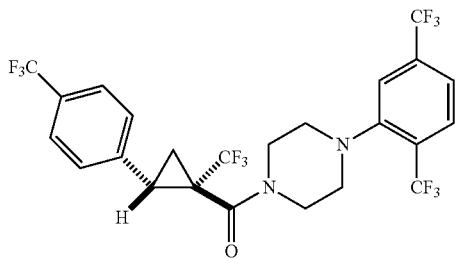 [SMILES: O=C(N1CCN(c2cc(C(F)(F)F)ccc2C(F)(F)F)CC1)[C@]1(C(F)(F)F)C[C@H]1c1ccc(C(F)(F)F)cc1]

cis-(4-(2,5-bis(trifluoromethyl)phenyl)piperazin-1-yl)(1-(trifluoromethyl)-2-(4-(trifluoromethyl)phenyl)cyclopropyl)methanone. A solution of cis-1-(trifluoromethyl)-2-(4-(trifluoromethyl)phenyl)cyclopropane-1-carboxylic acid (50.0 mg, 0.168 mmol) and 1-(2,5-trifluoromethylphenyl)piperazine hydrochloride (73 mg, 0.218 mmol) in distilled CH$_2$Cl$_2$ (0.85 mL) was cooled to 0° C. and then added with triethylamine (0.12 mL, 0.838 mmol). The cooled solution was then treated with T3P (50 wt. % solution in EtOAc, 0.14 mL, 0.201 mmol) dropwise. The reaction mixture was stirred at 0° C. for 30 min and allowed to warm to room temperature and stirred for 3 d. After completion of the reaction by TLC and LCMS analysis, the reaction mixture was diluted with CH$_2$Cl$_2$ (10 mL) and washed with 1 M HCl (10 mL), saturated NaHCO$_3$ (10 mL), dried over anhydrous MgSO$_4$, filtered and concentrated in vacuo. The crude residue was purified via automated flash column chromatography on SiO$_2$ (1:3 EtOAc/hexanes) to afford cis-(4-(2,5-bis(trifluoromethyl)phenyl)piperazin-1-yl)(1-(trifluoromethyl)-2-(4-(trifluoromethyl)phenyl)cyclopropyl)methanone as a white solid (77.6 mg, 0.134 mmol, 80%): Mp 128.4-131.7° C.; IR (CDCl$_3$) 2925, 2833, 1648, 1425, 1326, 1313, 1122, 1085, 846, 736; $^1$H NMR (CDCl$_3$, 500 MHz) δ 7.81 (d, J=8.1 Hz, 1H), 7.60 (d, J=8.2 Hz, 2H), 7.56 (d, J=8.3 Hz, 2H), 7.48 (d, J=8.1 Hz, 2H), 3.91-3.87 (m, 4H), 3.02 (t, J=4.6 Hz, 4H), 2.88 (t, J=8.6 Hz, 1H), 2.07 (t, J=7.1 Hz, 1H), 1.75 (t, J=7.8 Hz, 1H); $^{13}$C NMR (CDCl$_3$, 126 MHz) δ 164.2, 152.2, 137.8, 135.3 (q, $J_{C-F}$=33 Hz), 130.9 (q, $J_{C-F}$=29 Hz), 130.1 (t, $J_{C-F}$=33 Hz), 129.5, 128.5 (q, $J_{C-F}$=5 Hz), 125.5 (q, $J_{C-F}$=4 Hz), 124.5 (q, $J_{C-F}$=281 Hz), 124.2 (q, $J_{C-F}$=272 Hz), 123.4 (q, $J_{C-F}$=274 Hz), 123.2 (q, $J_{C-F}$=273 Hz), 122.6 (q, $J_{C-F}$=4 Hz), 121.2 (q, $J_{C-F}$=4 Hz), 53.3, 53.2, 46.9, 43.1, 35.1 (q, $J_{C-F}$=33 Hz), 27.9, 14.8 (d, $J_{C-F}$=2 Hz); $^{19}$F NMR (CDCl$_3$, 470 MHz) δ −60.9 (d, 6F), −62.6 (s, 3F), −63.2 (s, 3F); HRMS (ESI) m/z calcd for C$_{24}$H$_{19}$F$_{12}$N$_2$O ([M+H]$^+$) 579.1300, found 579.1298.

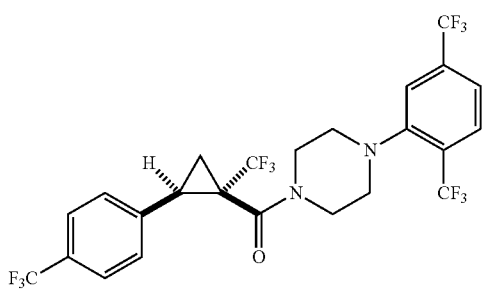

trans-(4-(2,5-bis(trifluoromethyl)phenyl)piperazin-1-yl)(1-(trifluoromethyl)-2-(4-(trifluoromethyl)-phenyl)cyclopropyl)methanone. A solution of trans-1-(trifluoromethyl)-2-(4-(trifluoromethyl)phenyl)-cyclopropane-1-carboxylic acid (0.100 g, 0.335 mmol) and 1-(2,5-trifluoromethylphenyl)piperazine hydrochloride (0.146 g, 0.436 mmol) in distilled CH$_2$Cl$_2$ (1.7 mL) was cooled to 0° C. and then added with triethylamine (0.24 mL, 1.68 mmol). The cooled solution was then treated with T3P (50 wt. % solution in EtOAc, 0.28 mL, 0.402 mmol) dropwise. The reaction mixture was stirred at 0° C. for 30 min and allowed to warm to room temperature and stirred for 4 d. After completion of the reaction by TLC and LCMS analysis, the reaction mixture was diluted with CH$_2$Cl$_2$ (15 mL) and washed with 1 M HCl (15 mL), saturated NaHCO$_3$ (15 mL), dried over anhydrous MgSO$_4$, filtered and concentrated in vacuo. The crude residue was purified via automated flash column chromatography on SiO$_2$ (1:3 EtOAc/hexanes) to afford trans-(4-(2,5-bis(trifluoromethyl)phenyl)piperazin-1-yl)(1-(trifluoromethyl)-2-(4-(trifluoromethyl)phenyl)-cyclopropyl)methanone as colorless oil (51.5 mg, 0.0890 mmol, 27%): IR (CDCl$_3$) 2925, 2833, 1643, 1510, 1424, 1310, 1115, 1070, 908, 851, 732 cm$^{-1}$; $^1$H NMR (CDCl$_3$, 500 MHz) δ 7.71 (d, J=8.2 Hz, 1H), 7.63 (d, J=8.2 Hz, 2H), 7.48 (d, J=8.2 Hz, 1H), 7.27 (d, J=8.0 Hz, 2H), 7.14 (s, 1H), 4.06-4.01 (m, 1H), 3.44-3.29 (m, 2H), 3.19-3.15 (m, 1H), 2.86 (dd, J=9.7, 7.5 Hz, 1H), 2.82-2.80 (m, 1H), 2.56-2.43 (m, 2H), 1.98 (t, J=7.0 Hz, 1H), 1.86 (dd, J=9.7, 6.7 Hz, 1H), 1.20 (s, 1H); $^{13}$C NMR (CDCl$_3$, 125 MHz) δ 161.4, 152.0, 139.6, 135.3 (q, $J_{C-F}$=33 Hz), 130.7 (q, $J_{C-F}$=29 Hz), 130.4 (q, $J_{C-F}$=33 Hz), 128.4 (q, $J_{C-F}$=5 Hz), 127.7, 125.8 (q, $J_{C-F}$=4 Hz), 124.5 (q, $J_{C-F}$=271 Hz), 123.9 (q, $J_{C-F}$=272 Hz), 123.2 (q, $J_{C-F}$=274 Hz), 123.1 (q, $J_{C-F}$=273 Hz), 122.4 (q, $J_{C-F}$=4 Hz), 120.6 (q, $J_{C-F}$=3 Hz), 52.7, 52.4, 46.7, 43.1, 37.4 (q, $J_{C-F}$=33 Hz), 27.5, 15.7; $^{19}$F NMR (CDCl$_3$, 470 MHz) δ −61.1 (s, 3F), −62.8 (s, 3F), −63.5 (s, 3F), −66.2 (s, 3 F); HRMS (ESI) m/z calcd for C$_{24}$H$_{19}$F$_{12}$N$_2$O ([M+H]$^+$) 579.1300, found 579.1299.

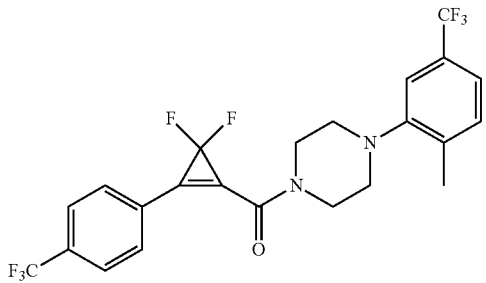 [SMILES: Cc1ccc(C(F)(F)F)cc1N1CCN(C(=O)C2=C(c3ccc(C(F)(F)F)cc3)C2(F)F)CC1]

(3,3-Difluoro-2-(4-(trifluoromethyl)phenyl)cycloprop-1-en-1-yl)(4-(2-methyl-5-(trifluoromethyl)-phenyl)piperazin-1-yl)methanone. Under an inert atmosphere, 1-(4-(2-methyl-5-(trifluoromethyl)-phenyl)piperazin-1-yl)-3-(4-(trifluoromethyl)phenyl)prop-2-yn-1-one (0.400 g, 0.908 mmol), TMSCF$_2$Br (0.28 mL, 1.82 mmol), nBu$_4$NBr (14.6 mg, 0.0454 mmol), and toluene (3.6 mL) were added into an oven-dried pressure tube at room temperature. After being heated at 110° C. for 20 h, The reaction mixture was cooled to room temperature and poured into saturated NaHCO$_3$ solution (15 mL) and extracted with EtOAc (2×20 mL). The combined organic layers were dried over anhydrous Na$_2$SO$_4$, filtered, and concentrated under reduced pressure. The crude product was subjected to flash column chromatography on SiO$_2$ (1:9 EtOAc/hexanes). The fractions collected contained ~10% of impurities. The product was resubjected to flash column chromatography on SiO$_2$ (1:2 CH$_2$Cl$_2$/hexanes) to afford (3,3-difluoro-2-(4-(trifluoromethyl)phenyl)cycloprop-1-en-1-yl)(4-(2-methyl-5-(trifluoromethyl)phenyl)piperazin-1-yl)methanone (0.325 g, 0.663 mmol, 73%) as a pale yellow oil that foamed up upon drying under vacuum: IR (CDCl$_3$) 2925, 2825, 1776, 1643, 1442, 1303, 1120, 1061, 1031, 909, 850, 730 cm$^{-1}$; $^1$H NMR (CDCl$_3$, 500 MHz) δ 8.13 (d, J=8.0 Hz, 2H), 7.79 (d, J=8.1 Hz, 2H), 7.31 (q, J=8.7 Hz, 2H), 7.22 (s, 1H), 3.94 (t, J=4.7 Hz, 2H), 3.88 (t, J=5.0 Hz, 2H), 3.04 (dt, J=25.5, 5.0 Hz, 4H), 2.41 (s, 3H); $^{13}$C NMR (CDCl$_3$, 125 MHz) δ 155.1, 150.9, 137.0, 135.5 (t, J=10 Hz), 134.4 (q, J=33 Hz), 132.6, 131.8, 129.4 (q, J=32 Hz), 126.3 (q, J=3.6 Hz), 126.0, 124.3 (q, J=272 Hz), 123.6 (q, J=273 Hz), 120.9 (q, J=3.9 Hz), 119.7 (t, J=13 Hz), 116.3 (q, J=3.6 Hz), 98.8 (t, J=278 Hz), 52.2, 51.5, 46.9, 42.6, 18.1; $^{19}$F NMR (CDCl$_3$, 470 MHz) δ −62.3 (s, 3F), −63.2 (s, 3F), −102.3 (s, 2F); HRMS (ESI) m/z calcd for C$_{23}$H$_{19}$ON$_2$F$_8$ ([M+H]$^+$) 491.1364, found 491.1363.

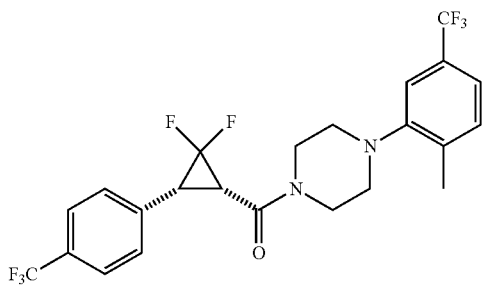 [SMILES: Cc1ccc(C(F)(F)F)cc1N1CCN(C(=O)[C@@H]2[C@H](c3ccc(C(F)(F)F)cc3)C2(F)F)CC1]

cis-((1SR,3RS)-2,2-difluoro-3-(4-(trifluoromethyl)phenyl)cyclopropyl)(4-(2-methyl-5-(trifluoromethyl)phenyl)piperazin-1-yl)methanone. A solution of (3,3-difluoro-2-(4-(trifluoromethyl)-phenyl)cycloprop-1-en-1-yl)(4-(2-methyl-5-(trifluoromethyl)phenyl)piperazin-1-yl)methanone (260 mg, 0.530 mmol) in EtOAc (4.6 mL) was added Pd/C (10% Pd on carbon, 56.4 mg, 10.0 mol %). The reaction vessel was placed in the parr hydrogenator (7 bar) and stirred for 24 h at room temperature. The mixture was filtered through celite and concentrated in vacuo. The crude oil was then passed through a plug of silica gel to remove baseline impurities. The crude residue (270 mg) contained a mixture of the desired cis-product and ring-opening side products which was inseparable by normal phase column chromatography.

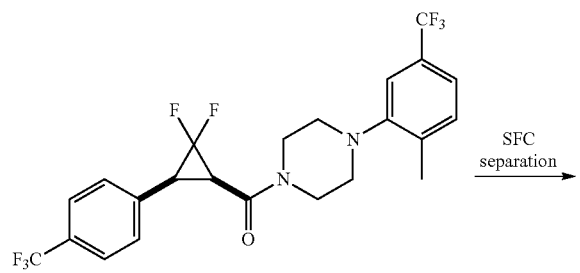

SFC separation

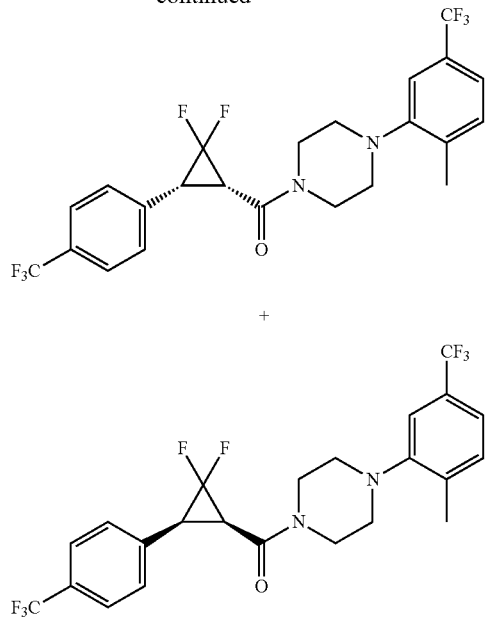

The crude racemic cis-((1SR,3RS)-2,2-difluoro-3-(4-(trifluoromethyl)phenyl)cyclopropyl)(4-(2-methyl-5-(trifluoromethyl)phenyl)piperazin-1-yl)methanone was purified and separated on a SFC Chiralpak-IC semiprep (250×10 mm) column (15% iPrOH, 6 mL/min, 220 nM, P=100) to afford the (−)-enantiomer (45.1 mg, 0.0916 mmol, 17%) and (+)-enantiomer (41.3 mg, 0.0839 mmol, 16%) respectively as a white solid: Mp 123.5-127.8° C.; IR (CDCl$_3$) 2917, 2820, 1648, 1416, 1323, 1308, 1115, 1070, 986, 856, 731 cm$^{-1}$.

(−)-2,2-difluoro-3-(4-(trifluoromethyl)phenyl)cyclopropyl)(4-(2-methyl-5-(trifluoromethyl)-phenyl)piperazin-1-yl)methanone (retention time 7.52 min) was obtained as a white solid (99.5% purity by ESLD): [α]$^{20}_D$ −32.1 (c 1.03, iPrOH); $^1$H NMR (CDCl$_3$, 500 MHz) δ 7.60 (d, J=8.3 Hz, 2H), 7.44 (d, J=8.1 Hz, 2H), 7.28-7.24 (m, 4H), 7.02 (s, 1H), 3.80-3.77 (m, 1H), 3.66-3.53 (m, 3H), 3.13 (td, J=12.6, 2.0 Hz, 1H), 2.90 (td, J=12.5, 2.4 Hz, 1H), 2.83 (dtd, J=11.5, 5.8, 3.4 Hz, 2H), 2.61 (ddd, J=11.2, 8.0, 3.0 Hz, 1H), 2.39-2.33 (m, 1H), 2.31 (s, 3H); $^{19}$F NMR (CDCl$_3$, 470 MHz) δ −62.4 (s, 3F), −62.8 (s, 3F), −118.9 (d, J$_{F-F}$=161 Hz, 1F), −147.2 (d, J$_{F-F}$=161 Hz, 1F); HRMS (ESI) m/z calcd for C$_{23}$H$_{21}$ON$_2$F$_8$ ([M+H]$^+$) 493.1521, found 493.1522. The enantiomeric excess was >99% ee (SFC Chiralpak-IC (250× 10 mm); 15% iPrOH, 220 nm, 6 mL/min; retention time: 7.54 min).

(+)-2,2-difluoro-3-(4-(trifluoromethyl)phenyl)cyclopropyl)(4-(2-methyl-5-(trifluoromethyl)-phenyl)piperazin-1-yl)methanone (retention time 9.64 min) was obtained as a white solid (99.5% purity by ESLD): [α]$^{20}_D$+33.5 (c 0.60, iPrOH); $^1$H NMR (CDCl$_3$, 500 MHz) δ 7.60 (d, J=8.2 Hz, 2H), 7.44 (d, J=8.1 Hz, 2H), 7.28-7.24 (m, 5H), 7.02 (s, 1H), 3.81-3.76 (m, 1H), 3.66-3.52 (m, 3H), 3.13 (td, J=12.6, 2.2 Hz, 1H), 2.90 (td, J=12.5, 2.6 Hz, 1H), 2.83 (dtd, J=11.5, 5.8, 3.3 Hz, 2H), 2.61 (ddd, J=11.4, 7.9, 3.0 Hz, 1H), 2.39-2.33 (m, 1H), 2.31 (s, 3H); $^{13}$C NMR (CDCl$_3$, 126 MHz) δ 160.94 (s, 1C), 150.94 (s, 1C), 136.92 (s, 1C), 134.96 (s, 1C), 131.67 (s, 1C), 130.13 (q, J=32.8 Hz, 1C), 129.53 (d, J=2.7 Hz, 1C), 129.30 (q, J=34.0 Hz, 1C), 125.39 (q, J=3.6 Hz, 1C), 124.22 (q, J=272.0 Hz, 1C), 124.06 (q, J=272.1 Hz, 1C), 120.72 (q, J=3.7 Hz, 1C), 116.01 (q, J=3.6 Hz, 1C), 110.99 (t, J=289.7 Hz, 1C), 51.70 (s, 1C), 51.49 (s, 1C), 46.17 (s, 1C), 42.12 (s, 1C), 31.35 (dd, J=12.9, 9.8 Hz, 1C), 30.28 (dd, J=10.4, 8.9 Hz, 1C), 18.00 (s, 1C). $^{19}$F NMR (CDCl$_3$, 470 MHz) δ −62.4 (s, 3F), −62.8 (s, 3F), −118.9 (d, J$_{F-F}$=161 Hz, 1F), −147.2 (d, J$_{F-F}$=161 Hz, 1F). HRMS (ESI) m/z calcd for C$_{23}$H$_{21}$ON$_2$F$_8$ ([M+H]$^+$) 493.1521, found 493.1522. The enantiomeric excess was >99% ee (SFC Chiralpak-IC (250×10 mm); 15% iPrOH, 220 nm, 6 mL/min; retention time: 9.66 min).

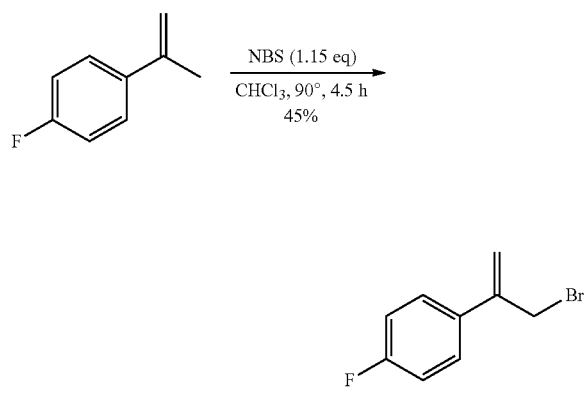

1-(3-Bromoprop-1-en-2-yl)-4-fluorobenzene. A solution of 4-fluoro-α-methylstyrene (4.78 g, 35.1 mmol) in CHCl$_3$ (7 mL) was treated with NBS (8.50 g, 47.7 mmol, 1.36 eq). The reaction was heated to reflux (~90° C.) for 6 h then it was cooled and filtered through Celite. The filter cake was then washed with hexane (50 mL) and the eluent was concentrated. The residue was purified by chromatography on SiO$_2$ (hexane) to afford the allylic bromide (3.38 g, 15.7 mmol, 45%) as a colorless oil: $^1$H NMR (400 MHz, CDCl$_3$) δ 7.48-7.43 (m, 2H), 7.13-7.01 (m, 2H), 5.50 (s, 1H), 5.48 (s, 1H), 4.36 (s, 2H); $^{19}$F NMR (376 MHz, CDCl$_3$) δ −113.7.

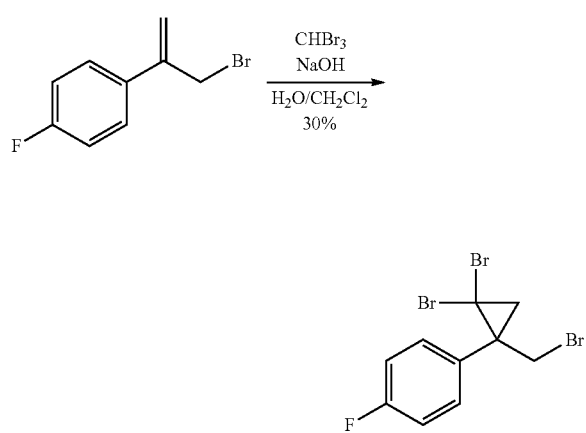

1-(2,2-Dibromo-1-(bromomethyl)cyclopropyl)-4-fluorobenzene. A solution of allylic bromide (3.17 g, 14.7 mmol) and cetyltrimethyl ammonium bromide (0.054 g, 0.15 mmol, 1 mol %) in CH$_2$Cl$_2$ (4 mL) was charged to a 100 mL 3-neck flask affixed with an N$_2$ inlet, mechanical stirrer, and septum. Bromoform (3.9 mL, 44 mmol, 3.0 eq) was added by syringe, and the solution was cooled to 0° C. Sodium hydroxide (7.07 g, 0.177 mol) was added as a solution in water (15 mL, ~50 g/100 mL) via syringe over 5 min. The ice bath was removed and the flask stirred for 26 h at 300 rpm over which period the color changed from clear to a dark, opaque brown. The reaction mixture was then partitioned between water (50 mL) and CH$_2$Cl$_2$ (50 mL). The layers were separated, and the aqueous phase was extracted with CH$_2$Cl$_2$ (50 mL). The combined extracts were washed with water (25 mL), 1:1 water/brine (25 mL), and then were dried (Na$_2$SO$_4$) and concentrated. The residue was purified by column chromatography on SiO$_2$ (10% EtOAc in hexane). Upon concentration of the product-containing fractions, a solid mass formed. This material was then recrystallized from ~1:1 EtOAc/hexanes (~15 mL), and the crystals were washed with cold hexanes (30 mL). After drying under vacuum, the tribromide (1.68 g, 4.35 mmol, 30%) was obtained as a colorless crystalline solid: Mp 101-103° C.; $^1$H NMR (300 MHz, CDCl$_3$) δ 7.38-7.30 (m, 2H), 7.08 (app t, 2H, J=3.3 Hz), 3.91 (dd, 2H, J=7.8 Hz, 1.2 Hz), 3.82 (d, 1H, J=7.8 Hz), 2.21 (dd, 1H, J=6.0 Hz, 0.9 Hz), 2.01 (d, 1H, J=6.3 Hz); $^{19}$F NMR (376 MHz, CDCl$_3$) δ −113.2.

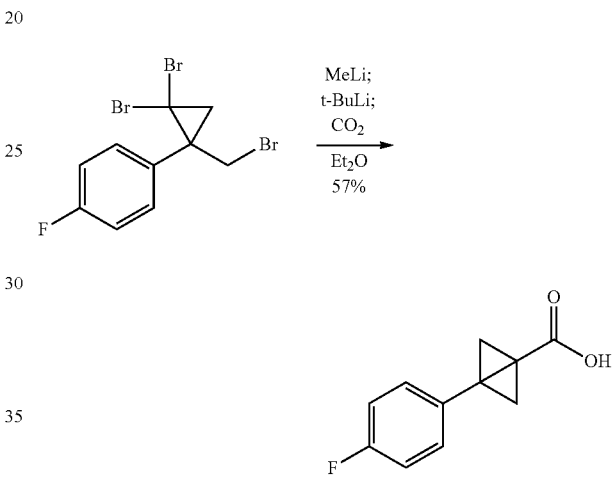

3-(4-Fluorophenyl)bicyclo[1.1.0]butane-1-carboxylic acid. A solution of tribromide (0.880 g, 2.57 mmol) in Et$_2$O (7 mL) and THF (3 mL, necessary for solubility) in a 50 mL round bottom flask was placed under N$_2$ and cooled to −78° C. MeLi (1.6 mL, 2.6 mmol, 1.0 eq, 1.6 M in ether) was added via syringe over 10 min. After 1.75 h at −78° C., t-BuLi (1.5 mL, 2.6 mmol, 1.0 eq, 1.7 M in pentane) was added via syringe over 10 min. After an additional 1 h at −78° C., a balloon of dry CO$_2$ was bubbled through the solution via a needle for 10 min (external bubbler was used, and a continuous stream of CO$_2$ was passed through the flask). The cooling bath was then removed, and the opaque grey reaction mixture was warmed to 0° C. over 20 min. The reaction mixture was then quenched with 1 M NaOH (10 mL), then the material was partitioned between ether and 1 M NaOH (50 mL each). The light brown aqueous layer was acidified with con HCl, forming an opaque solution with a light brown precipitate. This solution was then extracted with ether (2×40 mL). The organic layer was dried (NaSO$_4$) and concentrated to afford the acid (0.228 g, 1.19 mmol, 57%) as a buff solid: Mp 158-160° C.; IR (ATR) 1646, 1527, 1226, 841 cm$^{-1}$; $^1$H NMR (300 MHz, CD$_3$OD) δ 7.41-7.32 (m, 2H), 7.05 (app t, 2H, J=9.0 Hz), 2.88 (t, 2H, J=1.2 Hz), 1.60 (s, 2H); $^{13}$C NMR (100 MHz, CD$_3$OD) δ 172.2, 127.5 ($^3$J$_{CF}$=8 Hz), 114.9 ($^2$J$_{CF}$=21 Hz), 34.9, 31.8, 22.4; $^{19}$F NMR (376 MHz, CD$_3$OD) δ −117.7; HRMS m/z calcd for C$_{11}$H$_{10}$FO$_2$ [M+H] 193.0665, found 193.0660.

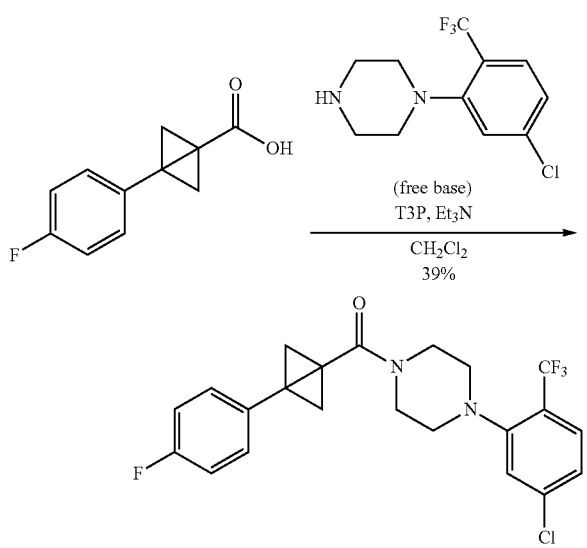

(4-(5-Chloro-2-(trifluoromethyl)phenyl)piperazin-1-yl) (3-(4-fluorophenyl)bicyclo[1.1.0]butan-1-yl)methanone. A solution of bicyclobutane acid (0.018 g, 0.096 mmol, 1.1 eq) and piperazine free base (0.023 g, 0.087 mmol) in $CH_2Cl_2$ (1 mL) was cooled to 0° C. and treated with $Et_3N$ (0.02 mL, 0.2 mmol, 2 eq). The transparent beige solution was then treated with T3P (50% solution in EtOAc) (0.09 mL, 0.13 mmol, 1.5 eq) dropwise via syringe over ~1 min. The reaction was stirred at 0° C. for 30 min, then the ice bath was removed and the reaction was warmed to rt for 19.5 h. The reaction mixture was then directly purified by chromatography on $SiO_2$ (15-25% EtOAc/hexanes) without workup to afford the amide (0.015 g, 0.038 mmol, 39%) as a colorless oil: IR (ATR) 2923, 1620, 1596, 1434, 1307, 1221, 1120, 1027, 906, 933, 725 cm$^{-1}$; $^1$H NMR (400 MHz, $CDCl_3$) δ 7.56 (d, 1H, J=8.4 Hz), 7.34-7.27 (m, 2H), 7.25-7.19 (m, 2H), 7.01 (app t, 2H, J=8.8), 4.1-3.5 (br m, 4H), 2.9-2.7 (br m, 4H), 2.75 (s, 2H), 1.63 (s, 2H); $^{13}$C NMR (100 MHz, $CDCl_3$) δ 167.7, 161.9 (d, $^1J_{CF}$=243 Hz), 152.9, 138.8, 135.1, 129.7 (d, $^4J_{CF}$=3 Hz), 128.6 (q, $^3J_{CF}$=5 Hz), 128.0 (d, $^3J_{CF}$=8 Hz), 126.3 (q, $^1J_{CF}$=272 Hz), 125.4 (q, $^2J_{CF}$=30 Hz), 115.4 (d, $^2J_{CF}$=21 Hz), 36.9, 30.6, 21.0; $^{19}$F NMR (376 MHz, $CDCl_3$) δ -60.3, -115.9; MS (ESI)$^+$ m/z 439 (100), 265 (3), 175 (5), 147 (45); HRMS (ESI)$^+$ m/z cald for $C_{22}H_{20}ClF_4N_2O$ [M+H]439.1195, found 439.1193.

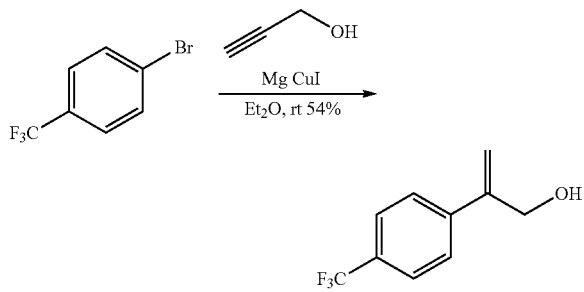

2-(4-(Trifluoromethyl)phenyl)prop-2-en-1-ol (Garzan et al., Chem. Eur. J. 2013, 19:9015-9021). Magnesium turnings (2.71 g, 0.111 mol) were charged to a 500 mL 3-neck round bottomed flask fitted with a reflux condenser, septum, and internal thermometer. After flushing with $N_2$, the turnings were suspended in ether (120 mL). 4-Trifluoromethylbromobenzene (15.8 mL, 0.111 mol) was added by syringe in ~1 mL portions over ~15 min, which caused the formation of a dark brown Gringard solution and spontaneous heating of the reaction to reflux. After ~1 h, the reaction had cooled from reflux back to rt. To the freshly prepared Grignard reagent was added CuI (1.27 g, 6.67 mmol) and the black suspension was stirred for 15 min. A solution of propargyl alcohol (2.60 mL, 44.6 mmol) in ether (50 mL) was added via cannula over 1.75 h, causing an exotherm to 29° C. The reaction was then stirred at rt for 18 h, at which point a quenched aliquot showed consumption of propargyl alcohol by $^1$H NMR. The reaction was then cooled to 0° C. and quenched with sat aq $NH_4Cl$ (100 mL). The layers were separated and the aqueous layer was extracted with ether (2×100 mL). The organic extracts were washed with water (100 mL) and brine (100 mL), then they were dried ($MgSO_4$), filtered, and concentrated. The crude product was purified by chromatography on $SiO_2$ (25% EtOAc/hexanes) to afford the alcohol (4.86 g, 24.0 mmol, 54%) as a red-tinted oil: $^1$H NMR (400 MHz, $CDCl_3$) δ 7.58 (AB q, J=11.2 Hz, $∂_{AB}$=0.05 ppm), 5.55 (s, 1H), 5.46 (s, 1H), 4.56 (s, 2H).

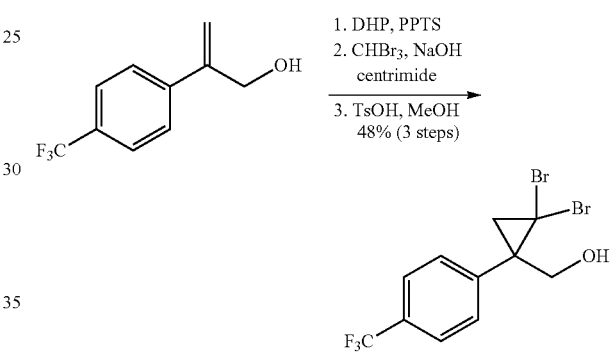

(2,2-Dibromo-1-(4-(trifluoromethyl)phenyl)cyclopropyl) methanol. A solution of alcohol (4.86 g, 24.0 mmol) in $CH_2Cl_2$ (40 mL) was treated with 3,4-dihydro-2H-pyran (3.1 mL, 34 mmol, 1.4 eq) followed by PPTS (0.604 g, 2.40 mmol, 0.10 eq). The resulting solution was stirred at rt for 2.5 h. The reaction mixture was then concentrated on the rotovap. The residue was partitioned between ether and water (75 mL each). The layers were separated, and the organic layer was washed with sat aq $NaHCO_3$ (75 mL). The organic layer was then dried ($Na_2SO_4$) and concentrated to afford the tetrahydropyran (7.11 g) as a red-tinted oil. The material contained residual solvents and was carried on without further purification.

A solution of protected alcohol (7.11 g, 24.8 mmol) and cetyltrimethyl ammonium bromide (0.091 g, 0.25 mmol, 1 mol %) in $CH_2Cl_2$ (12 mL) was placed in a 250 mL 3-neck flask was affixed with an $N_2$ inlet, mechanical stirrer, and septum. Bromoform (6.5 mL, 75 mmol, 3.0 eq) was added, and the solution was cooled to 0° C. Sodium hydroxide (11.9 g, 298 mmol, 12.0 eq) was added as a solution in water (24 mL, ~50 g/100 mL) via syringe over 10 min. The ice bath was removed and the flask stirred at rt for 24 h at 300 rpm. $^1$H NMR of an aliquot showed consumption of the alkene. The reaction mixture was then partitioned between water (50 mL) and $CH_2Cl_2$ (50 mL), the layers were separated, and the aqueous phase was extracted with $CH_2Cl_2$ (50 mL). The combined extracts were washed with water (25 mL), 1:1 water/brine (25 mL), then were dried ($Na_2SO_4$) and concentrated.

This crude dark red oil was dissolved in MeOH (25 mL) and treated with tosic acid monohydrate (0.472 g, 2.48 mmol, 10 mol %). After stirring at rt for 3 h, the reaction mixture was concentrated. The residue was partitioned between water and ether (75 mL each). The layers were separated and the organic layer was washed with water (75 mL), sat aq NaHCO$_3$ (75 mL), and brine (75 mL). The organic layer was then dried (Na$_2$SO$_4$) and concentrated. Purification by chromatography on SiO$_2$ afforded the dibromocyclopropane (4.45 g, 11.9 mmol, 48% over 3 steps) as a colorless oil: $^1$H NMR (400 MHz, CDCl$_3$) δ 7.65 (app d, 2H, J=8.4 Hz), 7.52 (app d, 2H, J=8.0 Hz), 4.01 (AB q, J=12.0 Hz, $\partial_{AB}$=0.04 ppm), 2.11 (AB q, J=7.6 Hz, $\partial_{AB}$=0.03 ppm); $^{13}$C NMR (100 MHz, CDCl$_3$) δ 142.4, 130.2, 125.4 ($^3J_{CF}$=4 Hz), 70.1, 40.7, 31.9, 31.3, 21.1; $^{19}$F NMR (376 MHz, CDCl$_3$) δ −62.6.

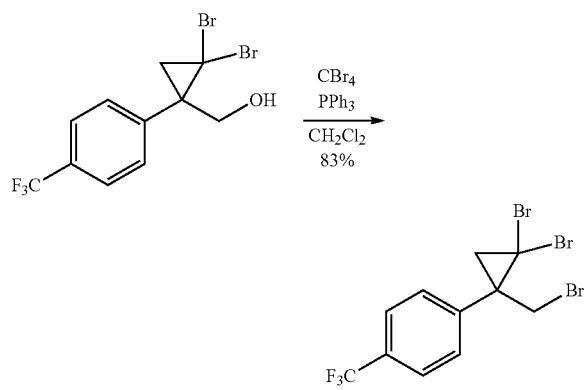

1-(2,2-Dibromo-1-(bromomethyl)cyclopropyl)-4-(trifluoromethyl)benzene. A solution of alcohol (4.45 g, 11.9 mmol) in CH$_2$Cl$_2$ (35 mL) was cooled to 0° C. under N$_2$. PPh$_3$ (3.75 g, 13.1 mmol, 1.20 eq) was then charged, followed by CBr$_4$ (4.34 g, 13.1 mmol, 1.10 eq). The reaction was warmed to rt and stirred for 20 h, then it was concentrated. Purification by chromatography on SiO$_2$ (0-15% EtOAc in hexanes) afforded tribromide (4.31 g, 9.85 mmol, 83%) as a colorless oil: $^1$H NMR (400 MHz, CDCl$_3$) δ 7.66 (d, 2H, J=8.0 Hz), 7.49 (d, 2H, J=8.0 Hz), 3.93 (dd, 1H, J=10.8 Hz, 1.2 Hz), 3.83 (d, 1H, J=10.8 Hz), 2.27 (dd, 1H, J=8.0 Hz, 1.2 Hz), 2.06 (d, 1H, J=8.0 Hz); $^{13}$C NMR (100 MHz, CDCl$_3$) δ 142.0, 130.6, 130.3, 125.4 (q, $^3J_{CF}$=4 Hz), 41.7, 39.8, 34.8, 34.7, 33.4, 31.6, 14.1; $^{19}$F NMR (376 MHz, CDCl$_3$) δ −62.6.

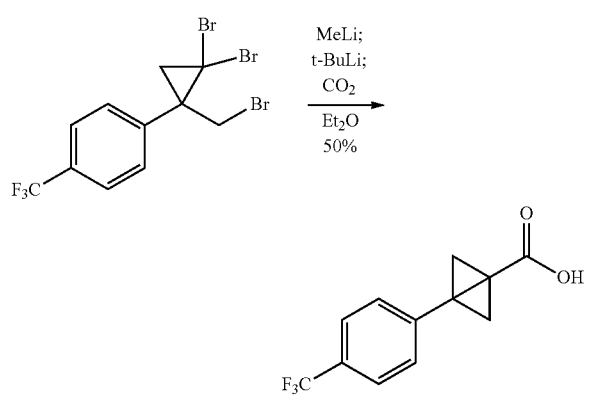

3-(4-(Trifluoromethyl)phenyl)bicyclo[1.1.0]butane-1-carboxylic acid. A solution of tribromide (1.50 g, 3.43 mmol) in Et$_2$O (15 mL) in a 50 mL round bottom flask was placed under N$_2$ and cooled to −78° C. MeLi (2.1 mL, 3.4 mmol, 1.6 M in Et$_2$O) was added via syringe over 5 min. After 1 h at −78° C., t-BuLi (2.0 mL, 3.4 mmol, 1.7 M in pentane, 1.0 eq) was added via syringe over 5 min. After an additional 1 h at −78° C., a balloon of dry CO$_2$ was bubbled through the solution via a needle for 10 min (external bubbler was used and a continuous stream of CO$_2$ was passed through the flask). The cooling bath was then removed, and the opaque grey reaction mixture was warmed to 0° C. over 20 min while maintaining CO$_2$ bubbling. The reaction mixture was then quenched with 1 M NaOH (10 mL), then it was partitioned between ether and 1 M NaOH (50 mL each). The light yellow aqueous layer was acidified with concentrated HCl, forming a colorless precipitate. This suspension was then extracted with ether (2×40 mL). The organic layers were dried (Na$_2$SO$_4$) and concentrated to afford the acid (0.416 g, 1.72 mmol, 50%) as a colorless solid: Mp 146-148° C.; IR (ATR) 2980, 1648, 1616, 1463, 1318, 1167, 1116, 1061, 907, 842, 689 cm$^{-1}$; $^1$H NMR (400 MHz, CD$_3$OD) δ 7.61 (d, 2H, J=8.4 Hz), 7.52 (d, 2H, J=8.4 Hz), 4.88 (s, 1H), 2.99 (t, 2H, J=1.2 Hz), 1.68 (s, 2H); $^{13}$C NMR (100 MHz, CD$_3$OD) δ 171.5, 140.0, 128.4 (q, $^2J_{CF}$=32 Hz), 126.2, 124.9 (q, $^3J_{CF}$=4 Hz), 124.4 (q, $^1J_{CF}$=269 Hz), 35.0, 31.0, 24.2; $^{19}$F NMR (376 MHz, CDCl$_3$) δ −64.0; MS (ESI)$^+$ m/z 243 (80), 233 (50), 231 (50), 197 (60), 177 (40), 155 (100); HRMS (ESI)$^+$ m/z calcd for C$_{12}$H$_{10}$F$_3$O$_2$[M+H] 243.0633, found 243.0626.

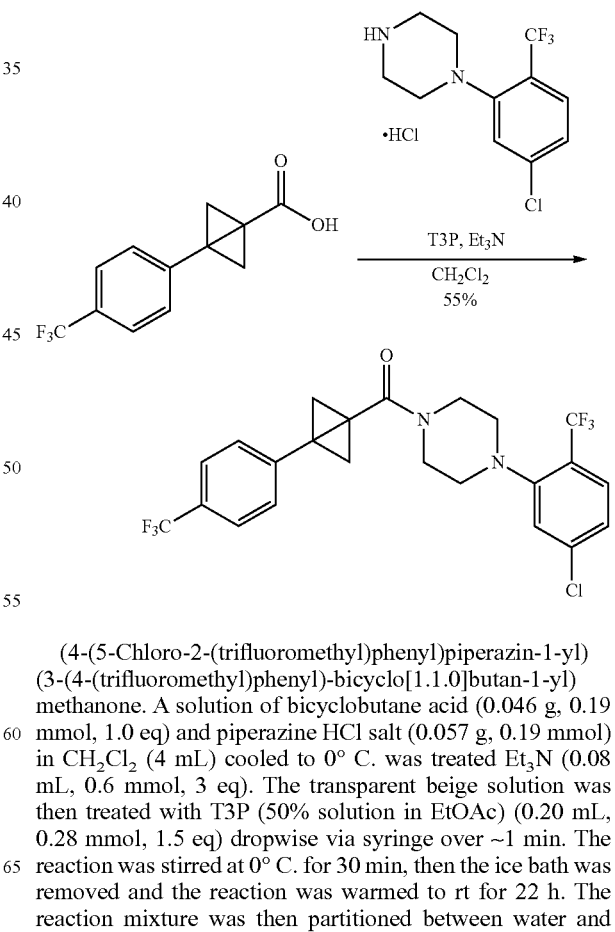

(4-(5-Chloro-2-(trifluoromethyl)phenyl)piperazin-1-yl) (3-(4-(trifluoromethyl)phenyl)-bicyclo[1.1.0]butan-1-yl) methanone. A solution of bicyclobutane acid (0.046 g, 0.19 mmol, 1.0 eq) and piperazine HCl salt (0.057 g, 0.19 mmol) in CH$_2$Cl$_2$ (4 mL) cooled to 0° C. was treated Et$_3$N (0.08 mL, 0.6 mmol, 3 eq). The transparent beige solution was then treated with T3P (50% solution in EtOAc) (0.20 mL, 0.28 mmol, 1.5 eq) dropwise via syringe over ~1 min. The reaction was stirred at 0° C. for 30 min, then the ice bath was removed and the reaction was warmed to rt for 22 h. The reaction mixture was then partitioned between water and CH$_2$Cl$_2$ (30 mL each). The layers were separated, and the aqueous layer was extracted with additional CH$_2$Cl$_2$ (30 mL). The combined extracts were washed with water (30 mL) and sat aq NaHCO$_3$ (30 mL), then were dried (Na$_2$SO$_4$) and concentrated. Purification by chromatography on SiO$_2$ (15-25% EtOAc/hexanes) afforded the amide (0.051 g, 0.10 mmol, 55%) as a colorless solid: Mp 137-139° C.; IR (ATR) 2902, 1604, 1466, 1438, 1312, 1100, 1027, 924, 838, 825 cm$^{-1}$; $^1$H NMR (400 MHz, CDCl$_3$) δ 7.56 (app d, 3H, J=8.4 Hz), 7.43 (app d, 2H, J=8.4 Hz), 7.23 (app q, 2H, J=8.4 Hz), 4.1-3.5 (br, 4H), 3.0-2.7 (br, 4H), 2.83 (s, 2H), 1.69 (s, 2H); $^{13}$C NMR (100 MHz, CDCl$_3$) δ 167.1, 152.8, 138.8, 138.6, 128.5 (q, $^2J_{CF}$=32), 128.5 (q, $^3J_{CF}$=4), 126.6, 125.7 (q, $^2J_{CF}$=29), 125.5, 125.3 (q, $^3J_{CF}$=3), 124.6, 124.3 (q, $^1J_{CF}$=270), 123.6 (q, $^1J_{CF}$=272), 37.0, 30.0, 29.7, 22.7; $^{19}$F NMR (376 MHz, CDCl$_3$) δ −60.3, −62.4; MS (ESI)$^+$ m/z 489, 256 (5); HRMS (ESI)$^+$ m/z calcd for C$_{23}$H$_{20}$F$_6$ClN$_2$O [M+H] 489.1168, found 489.1158.

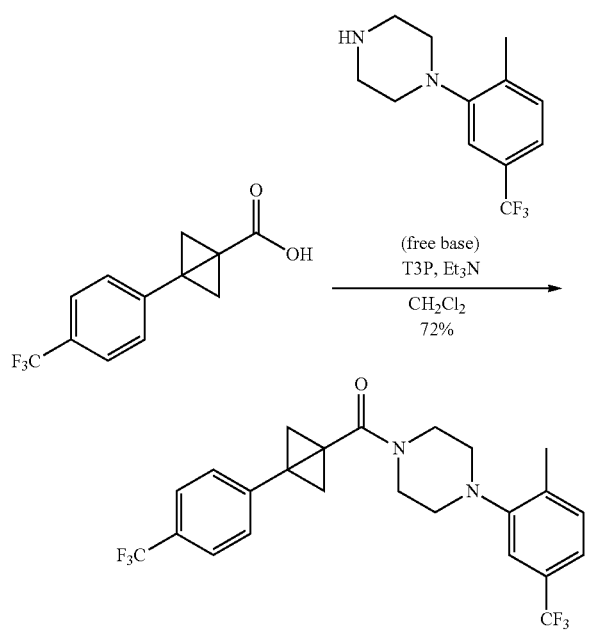

(4-(2-Methyl-5-(trifluoromethyl)phenyl)piperazin-1-yl) (3-(4-(trifluoromethyl)phenyl)-bicyclo[1.1.0]butan-1-yl) methanone. Before this reaction was performed, the piperazine was free-based by shaking a solution of 66 mg (0.24 mmol, 1.1 eq) of HCl salt in CH$_2$Cl$_2$ (30 mL) with 1 M NaOH (2×30 mL). The organic layer was then dried, concentrated, and the free base was used in the following reaction.

A solution of bicyclobutane acid (0.052 g, 0.21 mmol) and piperazine free base in CH$_2$Cl$_2$ (2 mL) cooled to 0° C. and treated with Et$_3$N (0.06 mL, 0.43 mmol, 2.0 eq). The transparent beige solution was treated with T3P (0.23 mL, 0.32 mmol, 1.5 eq, 50% solution in EtOAc) dropwise via syringe. The reaction was stirred at 0° C. for 30 min, then the ice bath was removed and the reaction was warmed to rt for 17 h. The reaction mixture was partitioned between water and CH$_2$Cl$_2$ (50 mL each). The layers were separated, and the aqueous layer was extracted with additional CH$_2$Cl$_2$ (30 mL). The combined extracts were washed with water (50 mL) and sat aq NaHCO$_3$ (40 mL), then were dried (Na$_2$SO$_4$) and concentrated. Purification by chromatography on SiO$_2$ (15-25% EtOAc/hexanes) afforded the amide (0.072 g, 0.154 mmol, 72%) as a colorless oil: IR (ATR) 2821, 1618, 1435, 1418, 1323, 1162, 1114, 1030, 840, 732 cm$^{-1}$; $^1$H NMR (400 MHz, CDCl$_3$) δ 7.56 (d, 2H, J=8.0 Hz), 7.43 (d, 2H, J=8.4 Hz), 7.28 (app q, 2H, J=8.0 Hz), 7.18 (s, 1H), 4.1-3.5 (br, 4H), 3.0-2.7 (br, 4H), 2.84 (s, 2H), 2.36 (s, 3H), 1.70 (s, 2H); $^{13}$C NMR (100 MHz, CDCl$_3$) δ 167.1, 151.2, 138.6, 136.8, 131.6, 129.1 (q, $^2J_{CF}$=32), 128.5 (q, 2J$_{CF}$=32), 126.6, 125.3 (q, 3J$_{CF}$=4), 124.3 (q, J$_{CF}$=270), 124.2 (q, J$_{CF}$=271), 120.4 (q, 3J$_{CF}$ 3), 116.0 (q, 3J$_{CF}$=4), 37.0, 30.0, 22.8, 18.0; $^{19}$F NMR (376 MHz, CDCl$_3$) δ −62.2, −62.4; MS (ESI)$^+$ m/z 469 (100), 197 (5); HRMS (ESI)$^+$ m/z calcd for C$_{24}$H$_{23}$F$_6$N$_2$O [M+H] 469.1709, found 469.1705.

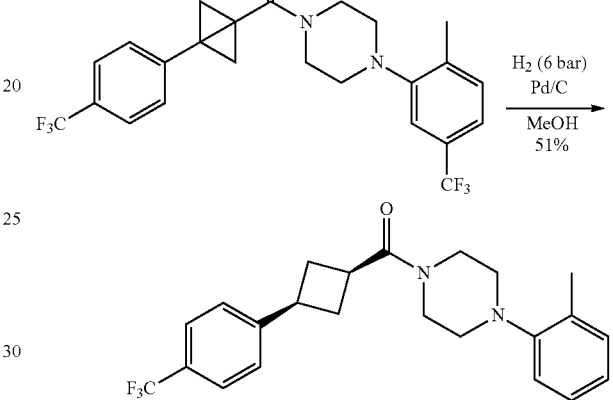

(4-(2-methyl-5-(trifluoromethyl)phenyl)piperazin-1-yl) (3-(4-(trifluoromethyl)phenyl)cyclobutyl)-methanone. A solution of amide (0.072 g, 0.153 mmol) in MeOH (3 mL) was placed under N$_2$ and treated with Pd/C (3 mg, ~20 mol %). A hydrogen atmosphere of 6.43 bar was then established on the Parr hydrogenator. The reaction was stirred at rt for 18 h, at which point the hydrogen was vented and the solution was purified by chromatography on SiO$_2$ (25-40% EtOAc/hexanes) to afford the syn-cyclobutane (0.037 g, 0.079 mmol, 51%) as a colorless oil: IR (ATR) 2939, 1641, 1618, 1417, 1324, 1308, 1161, 1112, 1067, 834, 732 cm$^{-1}$; $^1$H NMR (400 MHz, CDCl$_3$) δ 7.55 (d, 2H, J=8.4 Hz), 7.36 (d, 2H, J=8.4 Hz), 7.32-7.24 (m, 2H, J=8.0 Hz), 7.19 (s, 1H), 3.79 (t, 2H, J=4.8 Hz), 3.60 (t, 2H, J=5.2 Hz), 3.57-3.48 (m, 1H), 3.37-3.26 (m, 1H), 2.95-2.86 (m, 4H), 2.68-2.59 (m, 2H), 2.53 (ddd, 2H, J=19.2 Hz, 9.6 Hz, 2.4 Hz), 2.84 (s, 2H), 2.37 (s, 3H); $^{13}$C NMR (100 MHz, CDCl$_3$) δ 172.4, 151.2, 148.6, 136.8, 131.6, 129.1 (q, $^2J_{CF}$=32), 128.5 (q, $^2J_{CF}$=32), 127.4, 126.9, 126.7, 125.3 (q, $^3J_{CF}$=4), 124.3 (q, $^1J_{CF}$=270), 124.2 (q, $^1J_{CF}$=270), 120.4 (q, $^3J_{CF}$=4), 116.0 (q, $^3J_{CF}$=5), 51.9, 51.7, 45.5, 42.2, 35.5, 33.1, 32.6, 17.6; $^{19}$F NMR (376 MHz, CDCl$_3$) δ −62.3; MS (ESI)$^+$ m/z 471 (100), 355 (1), 246 (3), 179 (3); HRMS (ESI)$^+$ m/z calcd for C$_{24}$H$_{25}$F$_6$N$_2$O [M+H] 471.1871, found 471.1865.

Example 6

Androgen Receptor and Estrogen Receptor Alpha Competitor Assays

The disclosed compounds are assayed for androgen receptor activity using the PolarScreen™ Androgen Receptor Competitor Assay Kit, Green (ThermoFisher Scientific, catalog #A15880). The kit uses rat AR-ligand binding domain tagged with gluthathione-S-transferase (GST) and histidine [AR-LBD(Hist-GST)] to determine the $IC_{50}$ of competitive androgen receptor compounds. AR-LBD(His-GST) is added to fluorescently-tagged androgen ligand (FluormoneAL Green) in the presence of competitor test compounds. Effective competitors prevent the formation of a AL Green/AR-LBD(His-GST) complex, resulting in a decrease of polarization due to ligand displacement by the competitor. The shift in polarization values is used to determine the $IC_{50}$ of test compounds.

The disclosed compounds are assayed for estrogen receptor (ER) alpha activity using the PolarScreen™ ER Alpha Compeitor Asssay Kit, Green (ThermoFisher Scientific, catalog #A15883). The kit uses full length, native (untagged), human estrogen receptor alpha to determine the $IC_{50}$ of competitive estrogen receptor compounds. Full length ER alpha is added to a fluorescent estrogen ligand (Fluormone ES2 Green) to form an ER-Fluormone ES2 complex. An effective ER alpha competitor will displace the Fluormone ES2 ligand from the ER alpha and will result in a decrease in polarization. The shift in fluorescence polarization is used to determine the relative affinity of test compounds for ER alpha.

In view of the many possible embodiments to which the principles of the disclosed compounds, compositions and methods may be applied, it should be recognized that the illustrated embodiments are only preferred examples and should not be taken as limiting the scope of the invention.

What is claimed is:

1. A compound, or a stereoisomer, pharmaceutically acceptable salt, or ester thereof, selected from:
a compound according to formula III

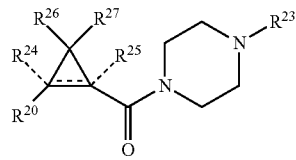

formula III where the bond represented by "-----" is a single or double bond, $R^{20}$ is (a) phenyl substituted with $C_1$-$C_3$ perfluoroalkyl, halo, or pentafluorosulfanyl,
(b) thiophenyl substituted with $C_1$-$C_3$ alkyl, or (c) cycloalkyl substituted with $C_1$-$C_3$ perfluoroalkyl, $R^{23}$ is (a) phenyl mono- or di-substituted with substituents selected from halo, $C_1$-$C_3$ alkyl, $C_1$-$C_3$ perfluoroalkyl, pentafluorosulfanyl, cyano, —C(O)Oalkyl, or —C(O)N(H)alkyl, (b) cycloalkyl, or
(c) heterocycloalkyl, $R^{24}$ and $R^{25}$ are absent if the bond represented by "-----" is a double bond, or $R^{24}$ and $R^{25}$ independently are hydrogen, deuterium, $C_1$-$C_3$ perhaloalkyl, halo, or cyano, or $R^{24}$ and $R^{25}$ together form —$CH_2$—, and $R^{26}$ and $R^{27}$ independently are hydrogen, deuterium, or halo, wherein if $R^{24}$-$R^{27}$ are hydrogen, then $R^{20}$ is not halo-substituted phenyl, and if $R^{24}$-$R^{27}$ are hydrogen and $R^{23}$ is phenyl mono- or di-substituted with substituents selected from halo, $C_1$-$C_3$ alkyl, $C_1$-$C_3$ perfluoroalkyl, pentafluorosulfanyl, cyano, —C(O)Oalkyl, or —C(O)N(H)alkyl, then $R^{20}$ is (a) pentafluorosulfanyl-substituted phenyl, (b) thiophenyl substituted with $C_1$-$C_3$ alkyl, or (c) cycloalkyl substituted with $C_1$-$C_3$ perfluoroalkyl.

2. The compound of claim 1, wherein $R^{20}$ is:
phenyl substituted with —$SF_5$ or —F; or
thiophenyl substituted with —$CH_3$; or
cyclohexyl substituted with —$CF_3$.

3. The compound of claim 2, wherein $R^{20}$ is phenyl or cyclohexyl and is substituted at the C4 position.

4. The compound of claim 1, wherein $R^{23}$ is:
phenyl substituted with —$CF_3$; or
phenyl disubstituted with two halo substituents, halo and —$CF_3$, halo and —$CH_3$, or halo and cyano; or
cyclohexyl; or
heterocyclohexyl.

5. The compound of claim 4, wherein $R^{23}$ is disubstituted phenyl and the two substituents are para to one another.

6. The compound of claim 1, wherein at least one of $R^{24}$-$R^{27}$ is other than hydrogen.

7. The compound of claim 1, wherein the compound is:

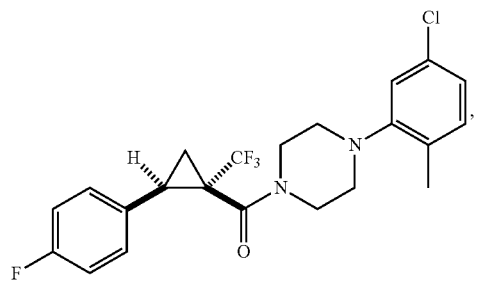

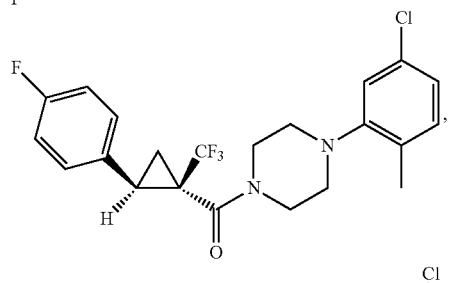

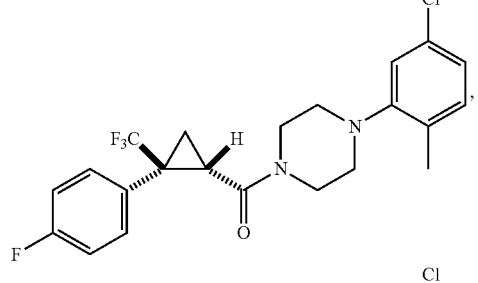

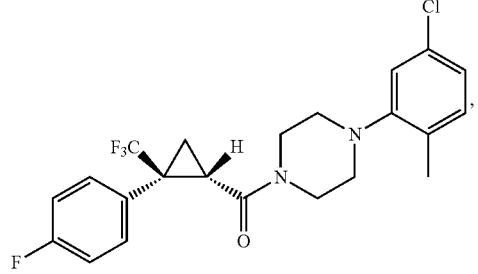

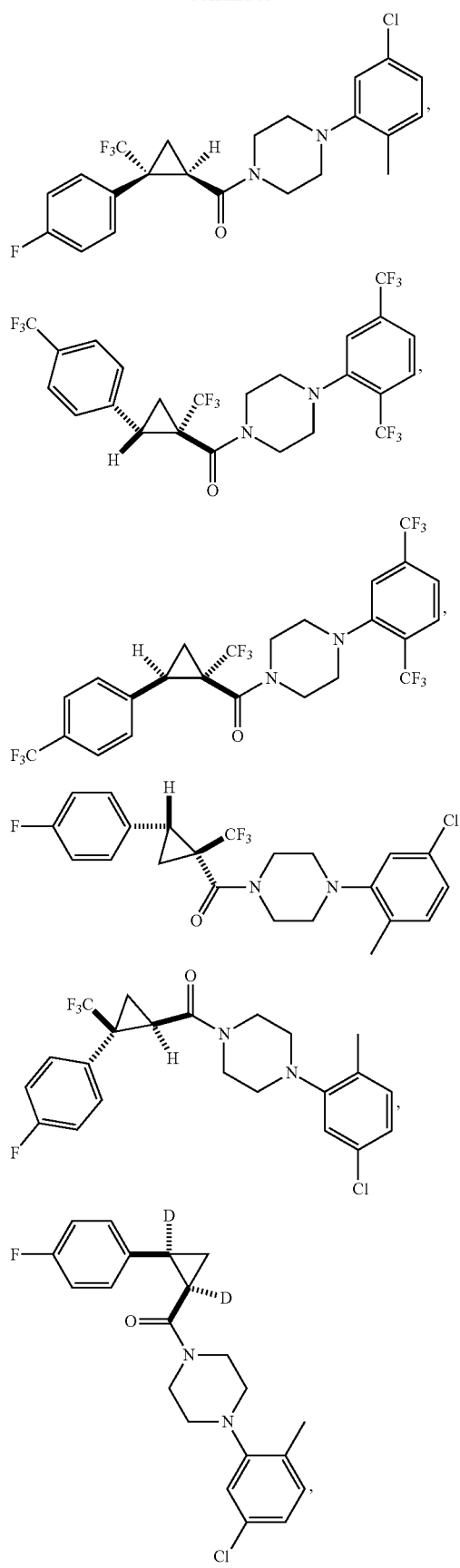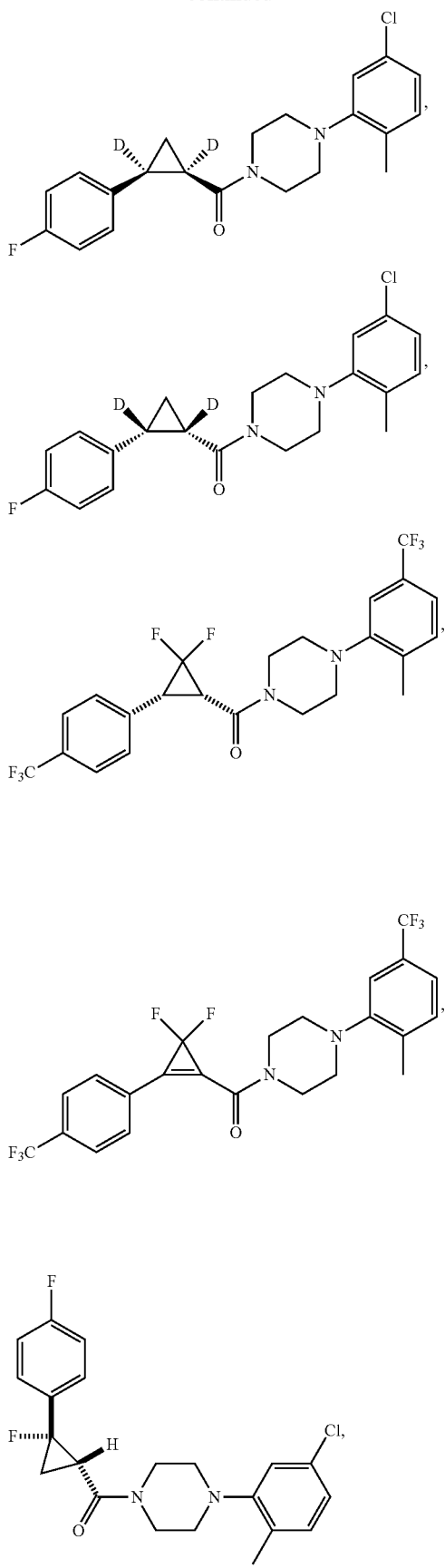

217
-continued
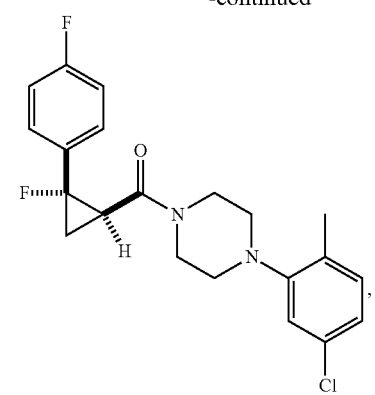
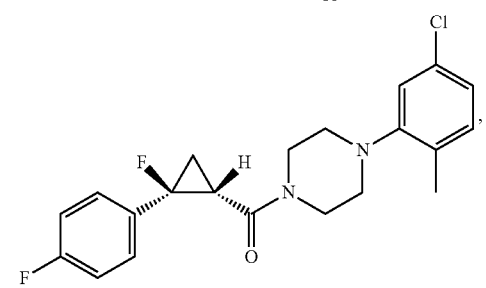
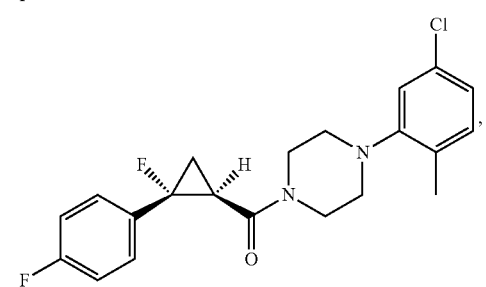
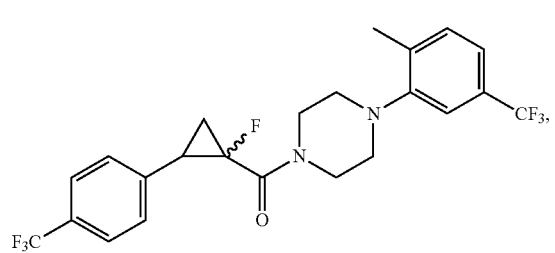
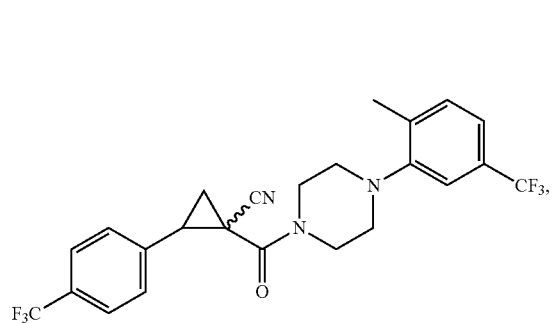
218
-continued
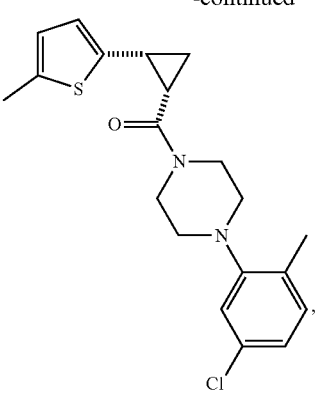
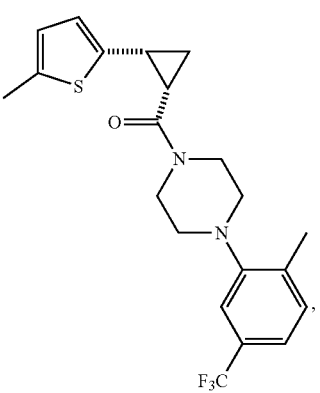
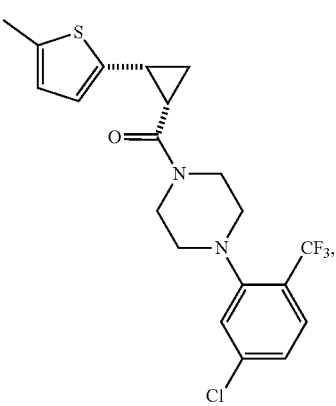
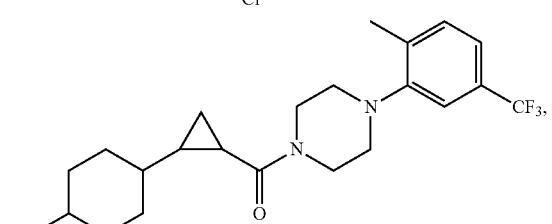
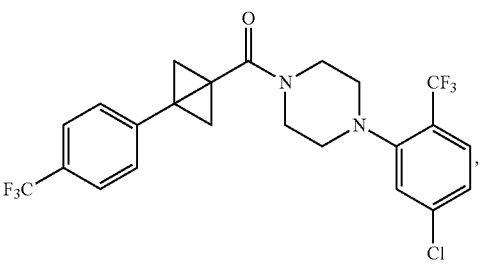

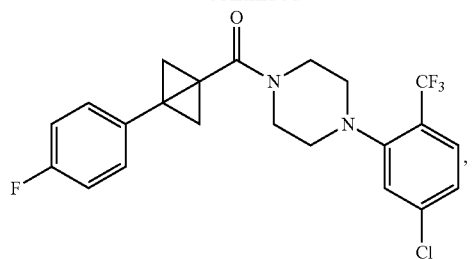
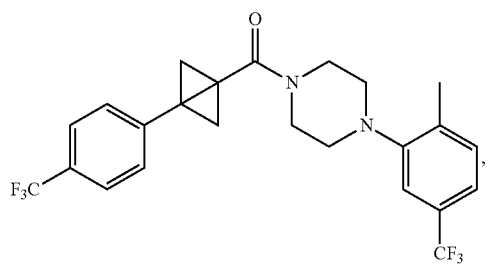
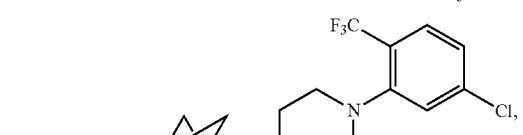
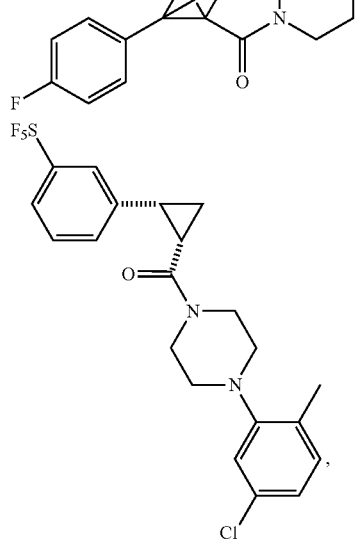
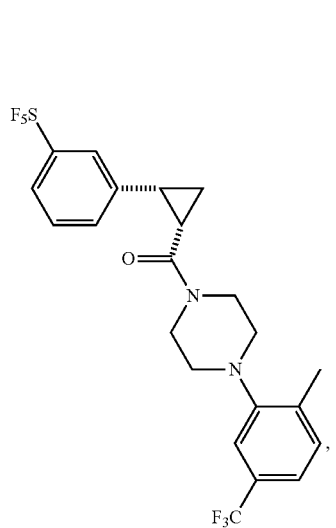
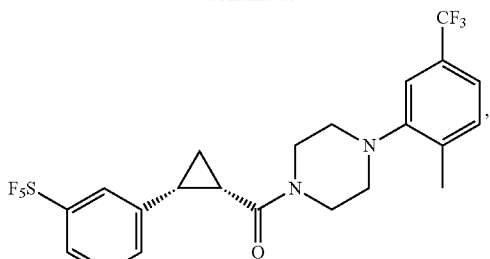
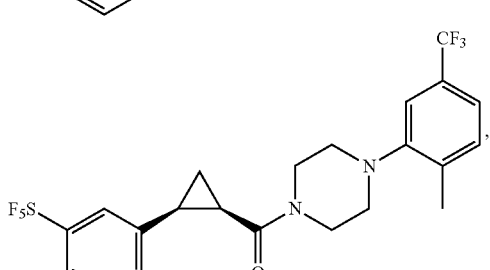
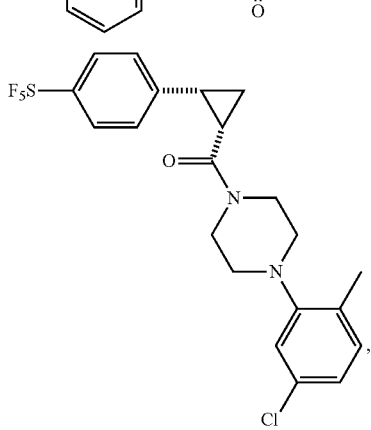
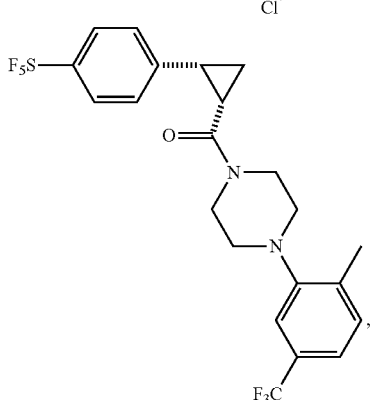
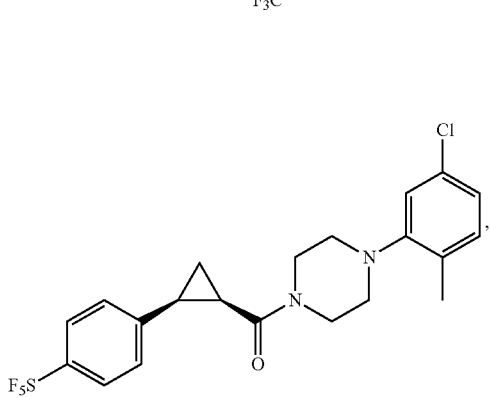

221

-continued

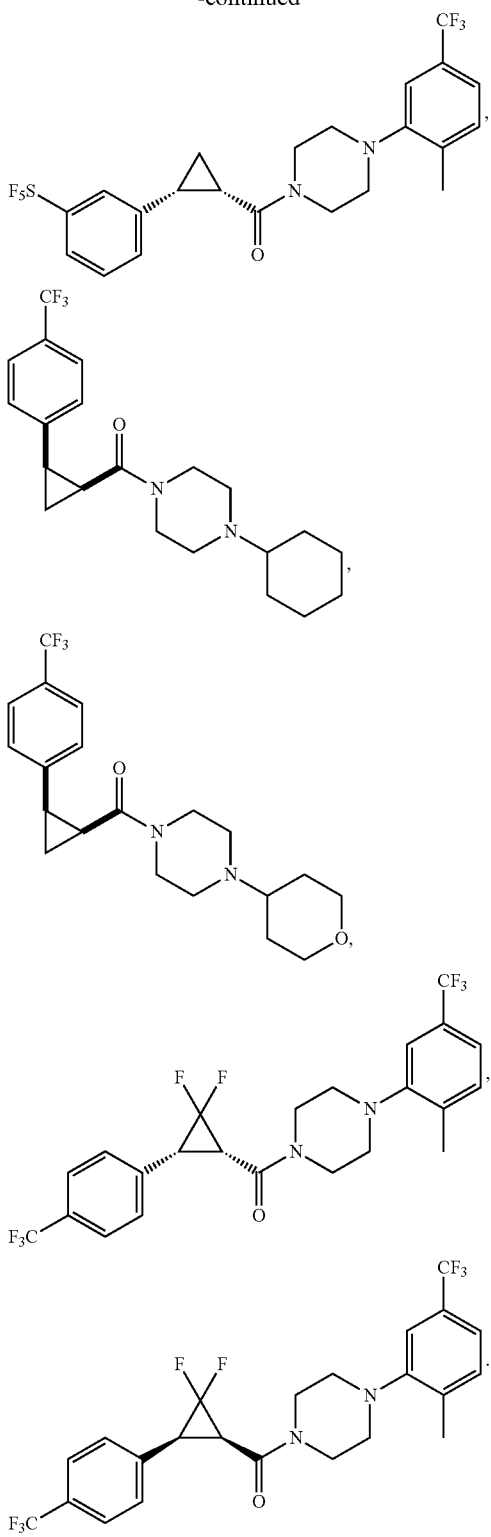

8. A pharmaceutical composition comprising at least one pharmaceutically acceptable additive, and a compound of claim 1.

9. A method for treating prostate cancer in a subject, comprising administering to the subject a therapeutically effective amount of a compound of claim 1.

222

10. The method of claim 9, wherein:
the compound is orally administered; or
the method is used in combination with androgen deprivation therapy; or
the compound is co-administered with abiraterone or enzalutamide.

11. A compound, or a stereoisomer, pharmaceutically acceptable salt, or ester thereof, wherein the compound is:

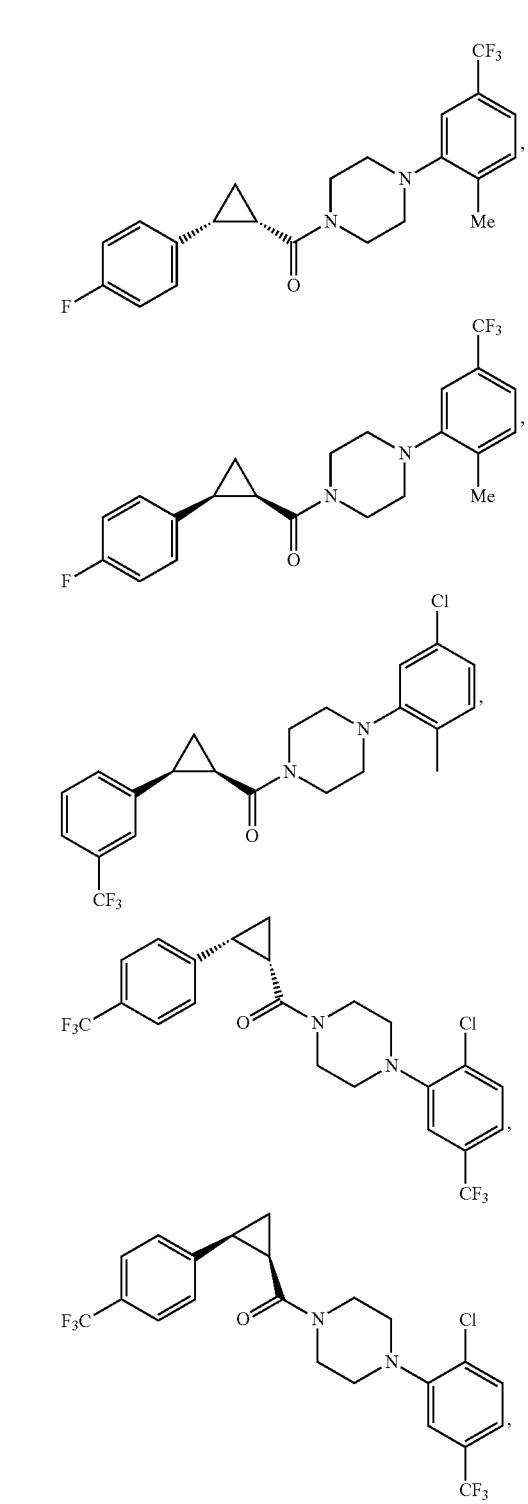

-continued
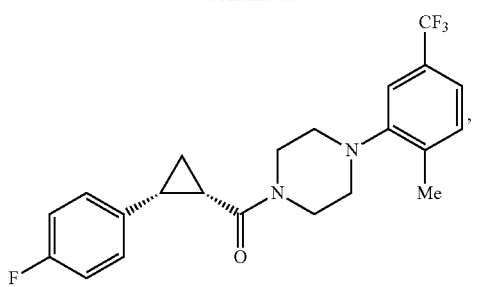
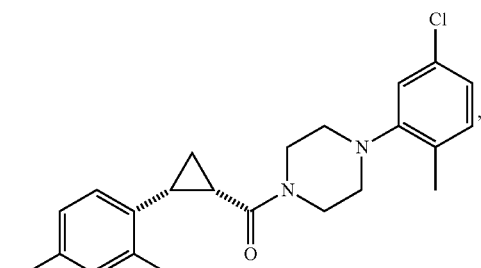
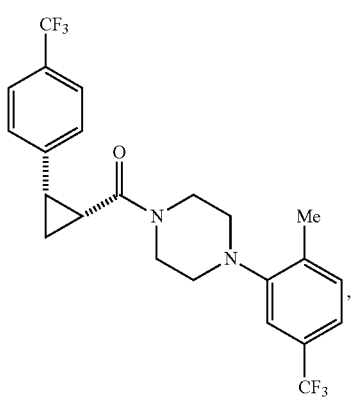
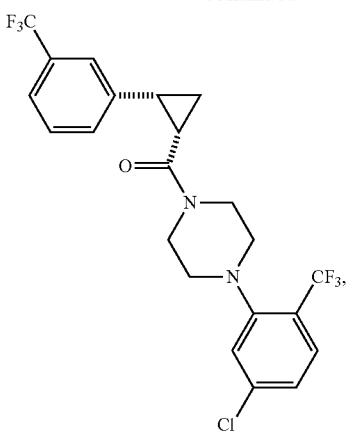
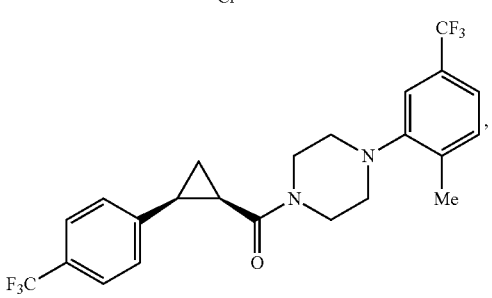
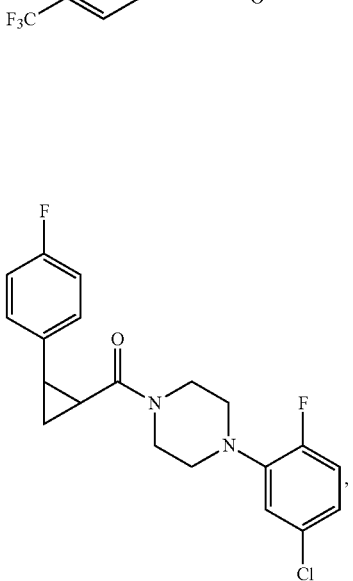

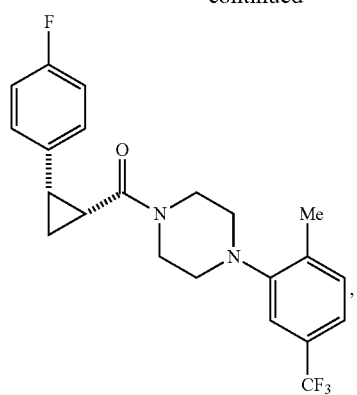
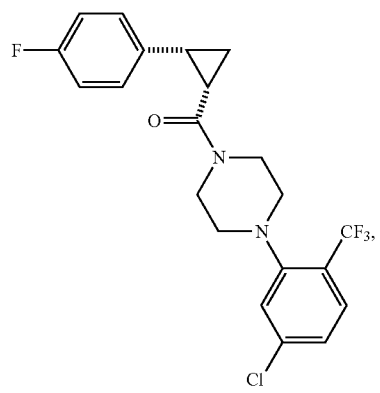
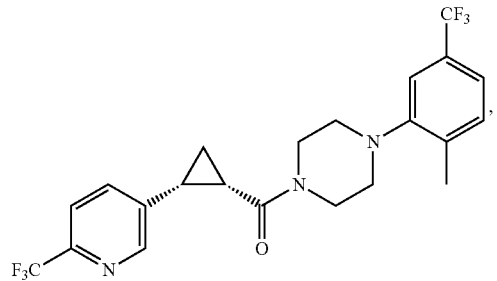
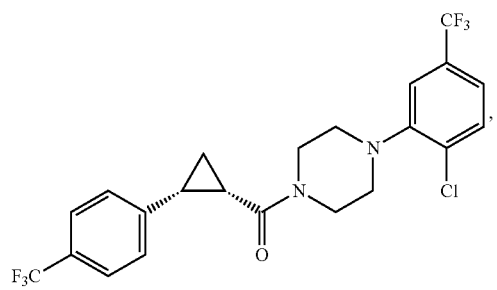
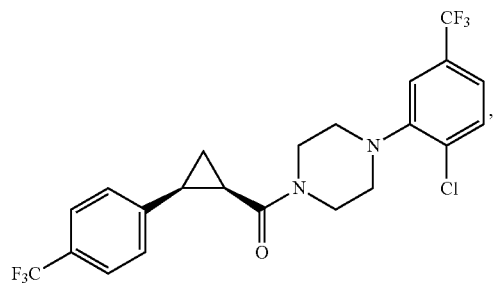
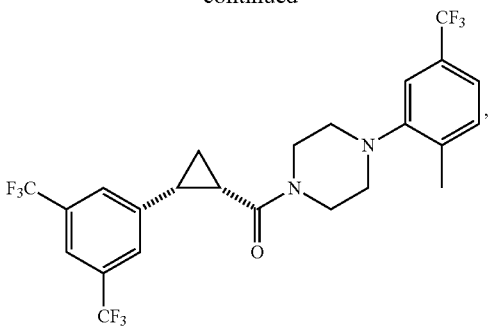
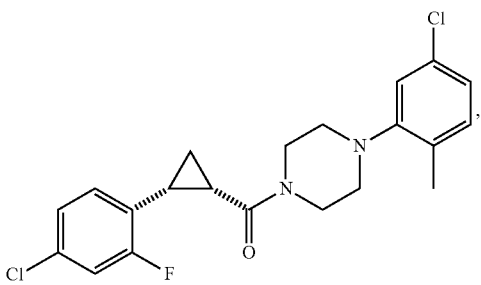
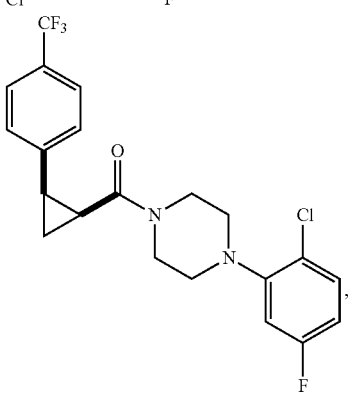
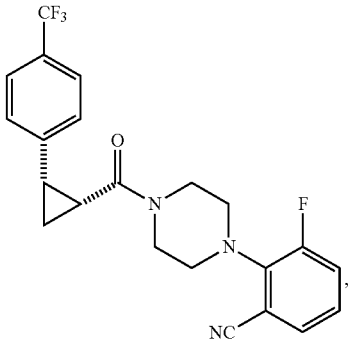
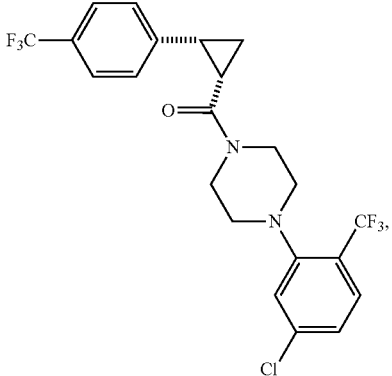

227
-continued
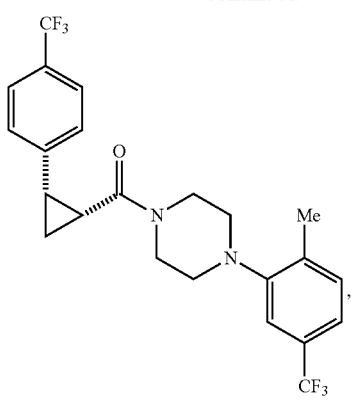
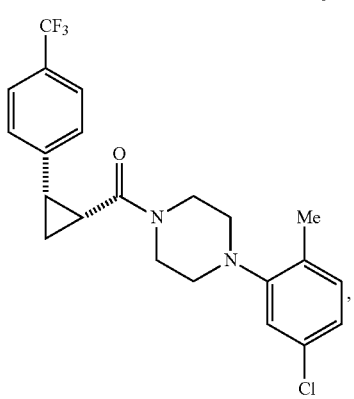
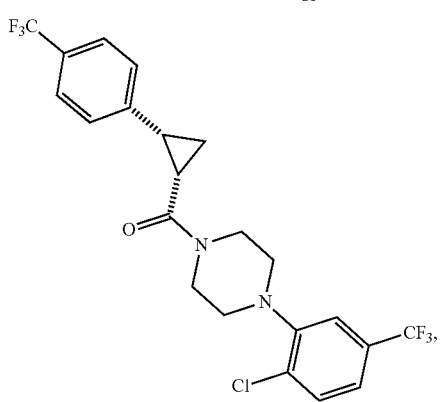
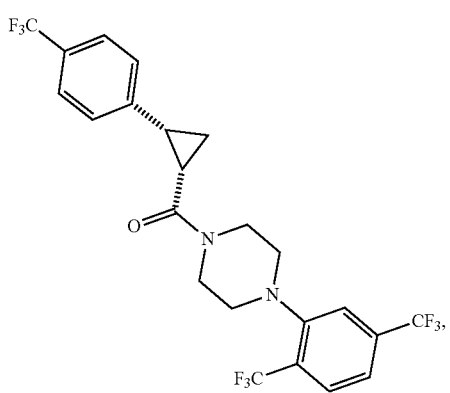
228
-continued
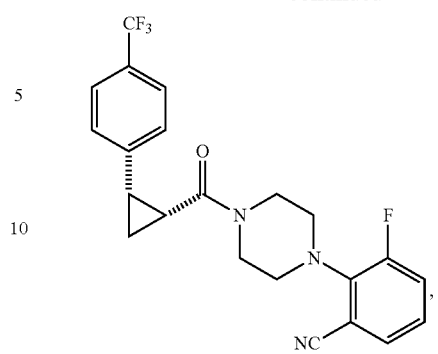
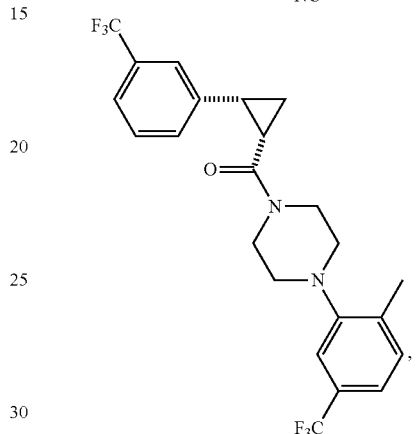
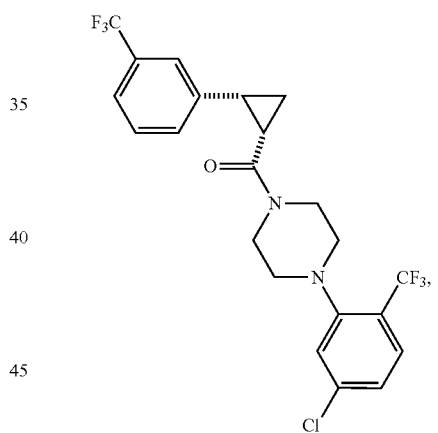
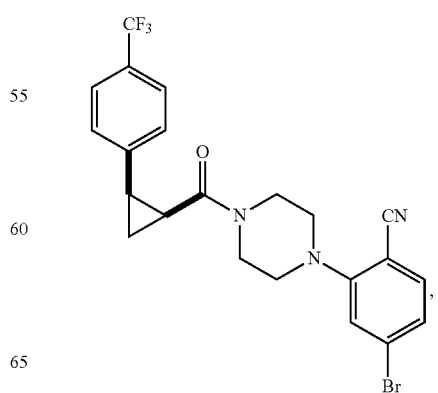

229
-continued
230
-continued
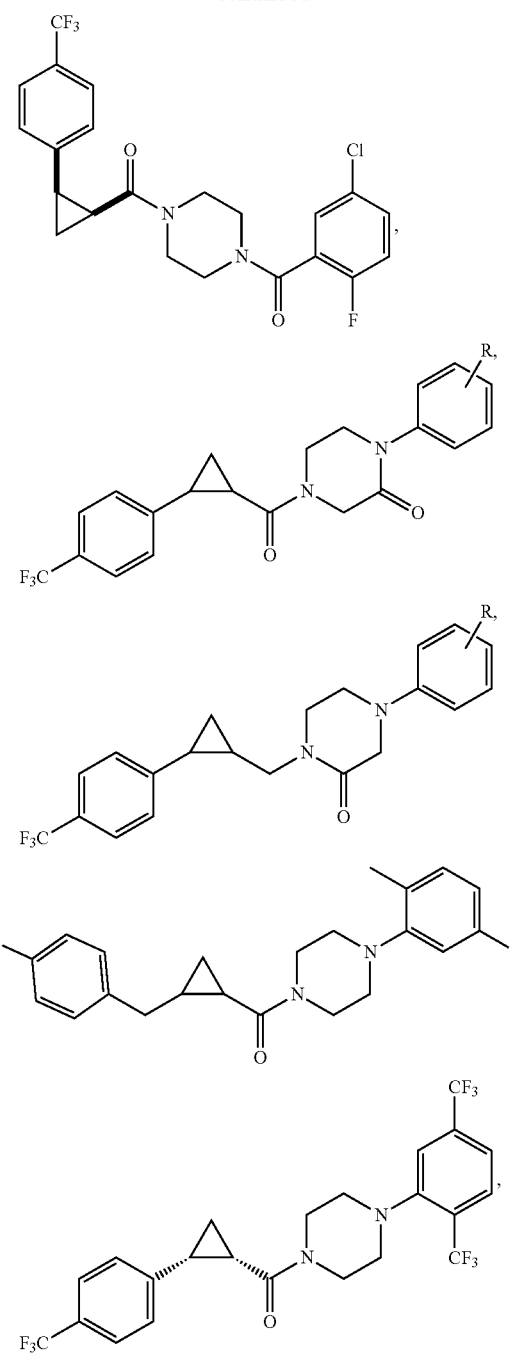
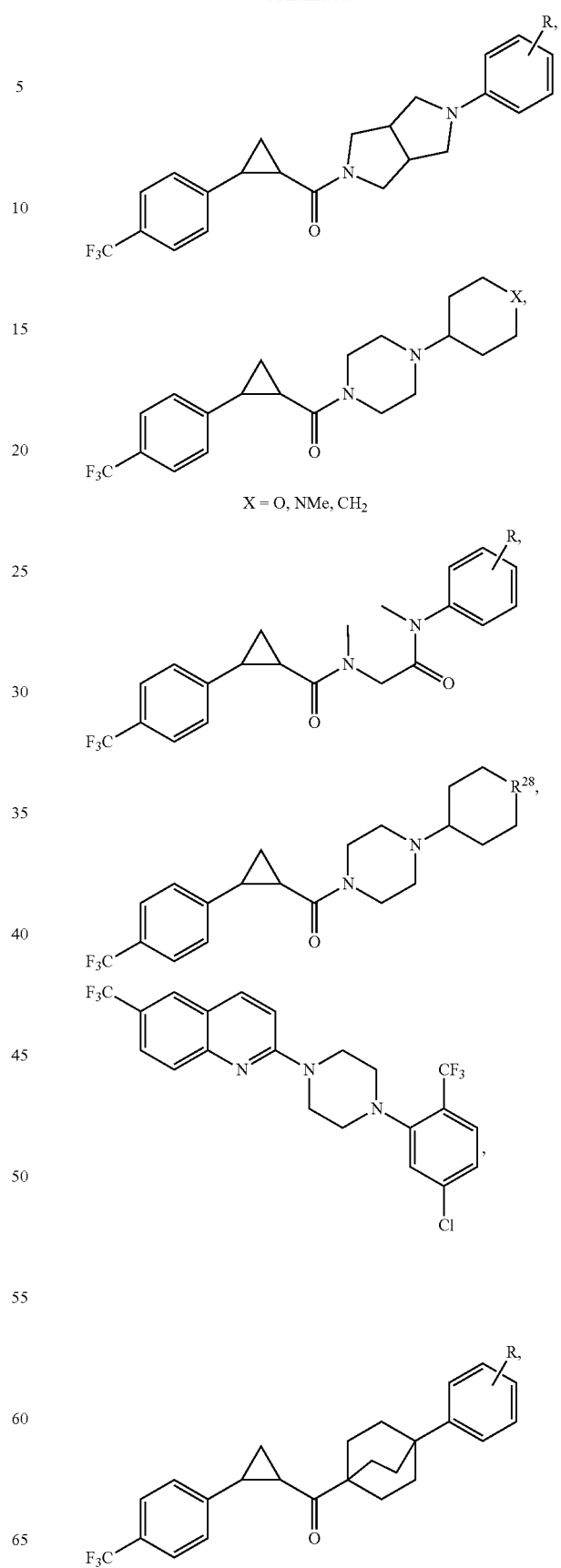
X = O, NMe, CH₂

231
-continued
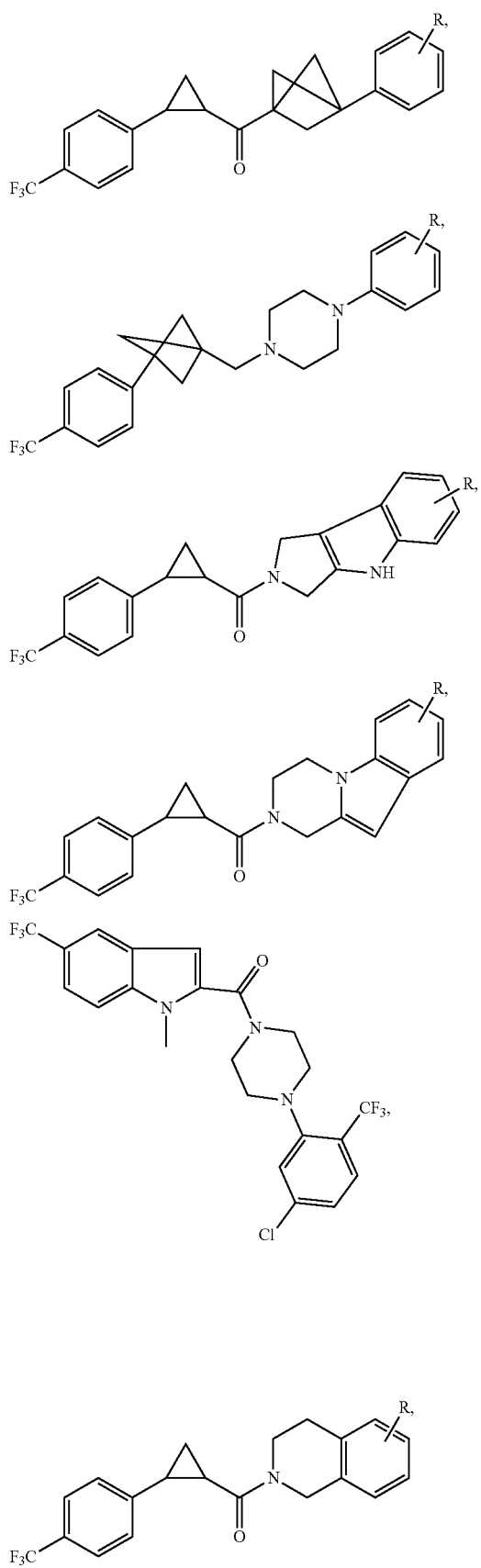
232
-continued
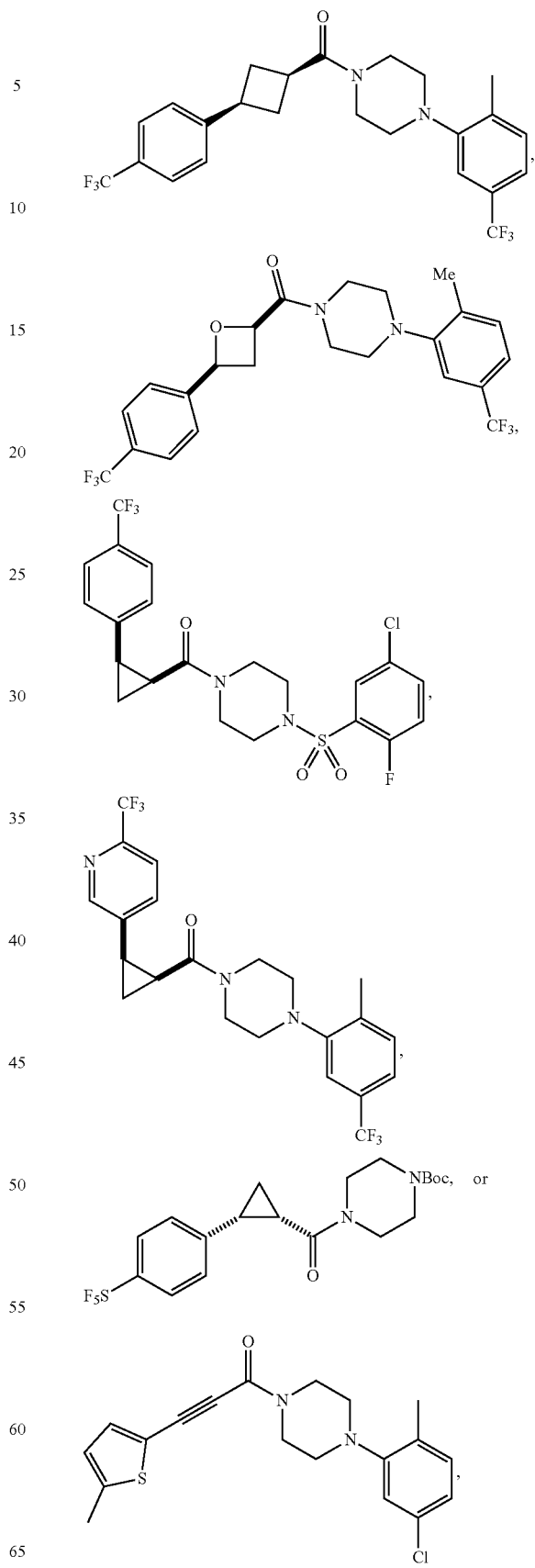

where each R independently is $C_1$-$C_3$ perfluoroalkyl, halo, pentafluorosulfanyl, —C(O)Oalkyl, or C(O)N(H)alkyl; and $R^{28}$ is O, N(CH$_3$), or CH$_2$.

12. A pharmaceutical composition comprising at least one pharmaceutically acceptable additive, and a compound of claim 11.

13. A method for treating prostate cancer in a subject, comprising administering to the subject a therapeutically effective amount of a compound of claim 11.

14. The method of claim 13, wherein:
the compound is orally administered; or
the method is used in combination with androgen deprivation therapy; or
the compound is co-administered with abiraterone or enzalutamide.

15. The compound of claim 1, wherein $R^{23}$ is phenyl disubstituted with halo and —CF$_3$, and the two substituents are para to one another.

16. The compound of claim 1, wherein $R^{20}$ is phenyl substituted at the C3 position.

* * * * *